US010626420B2

(12) United States Patent
Cervin et al.

(10) Patent No.: US 10,626,420 B2
(45) **Date of Patent: *Apr. 21, 2020**

(54) COMPOSITIONS AND METHODS FOR PRODUCING ISOPRENE

(71) Applicants: Danisco US Inc., Palo Alto, CA (US); The Goodyear Tire & Rubber Company, Akron, OH (US)

(72) Inventors: Marguerite A. Cervin, Redwood City, CA (US); Gopal K. Chotani, Cupertino, CA (US); Frank J. Feher, Copley, OH (US); Richard La Duca, Pleasanton, CA (US); Joseph C. McAuliffe, Sunnyvale, CA (US); Andrei Miasnikov, Mountain View, CA (US); Caroline M. Peres, Palo Alto, CA (US); Aaron S. Puhala, Kent, OH (US); Karl J. Sanford, Cupertino, CA (US); Fernando Valle, Burlingame, CA (US); Gregory M. Whited, Belmont, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/873,761

(22) Filed: Jan. 17, 2018

(65) Prior Publication Data

US 2018/0273982 A1 Sep. 27, 2018

Related U.S. Application Data

(60) Continuation of application No. 14/987,681, filed on Jan. 4, 2016, now Pat. No. 9,909,144, which is a continuation of application No. 13/600,132, filed on Aug. 30, 2012, now Pat. No. 9,260,727, which is a division of application No. 12/335,071, filed on Dec. 15, 2008, now Pat. No. 8,288,148.

(60) Provisional application No. 61/013,574, filed on Dec. 13, 2007.

(51) Int. Cl.

| | |
|---|---|
| ***C12P 5/00*** | (2006.01) |
| ***C12N 9/10*** | (2006.01) |
| ***C12N 9/12*** | (2006.01) |
| ***C12N 9/88*** | (2006.01) |
| ***C12N 9/90*** | (2006.01) |
| ***C12N 15/52*** | (2006.01) |

(52) U.S. Cl.

CPC ............ *C12P 5/007* (2013.01); *C12N 9/1022* (2013.01); *C12N 9/1205* (2013.01); *C12N 9/1229* (2013.01); *C12N 9/88* (2013.01); *C12N 9/90* (2013.01); *C12N 15/52* (2013.01); *C12Y 203/01009* (2013.01); *C12Y 207/01036* (2013.01); *C12Y 401/01033* (2013.01); *C12Y 402/03027* (2013.01); *C12Y 503/03002* (2013.01); *Y02E 50/343* (2013.01)

(58) Field of Classification Search

None

See application file for complete search history.

(56) References Cited

U.S. PATENT DOCUMENTS

| | | | |
|---|---|---|---|
| 1,344,713 | A | 6/1920 | Peters |
| 3,686,349 | A | 8/1972 | Schliebs et al. |
| 4,570,029 | A | 2/1986 | Kulprathipanja et al. |
| 4,647,344 | A | 3/1987 | Linder et al. |
| 4,683,195 | A | 7/1987 | Mullis et al. |
| 4,683,202 | A | 7/1987 | Mullis |
| 4,703,007 | A | 10/1987 | Mulholland et al. |
| 4,846,872 | A | 7/1989 | Kamuro et al. |
| 4,965,188 | A | 10/1990 | Mullis et al. |
| 5,322,770 | A | 6/1994 | Gelfand |
| 5,349,126 | A | 9/1994 | Chappell et al. |
| 5,380,831 | A | 1/1995 | Adang et al. |
| 5,436,391 | A | 7/1995 | Fujimoto et al. |
| 5,545,816 | A | 8/1996 | Ausich et al. |
| 5,849,970 | A | 12/1998 | Fall et al. |
| 5,874,276 | A | 2/1999 | Fowler et al. |
| 6,022,725 | A | 2/2000 | Fowler et al. |
| 6,106,888 | A | 8/2000 | Dale et al. |
| 6,176,176 | B1 | 1/2001 | Dale et al. |
| 6,268,328 | B1 | 7/2001 | Mitchinson et al. |
| 6,270,739 | B1 | 8/2001 | Barnicki et al. |
| 6,294,653 | B1 | 9/2001 | Mayfield |
| 6,582,914 | B1 | 6/2003 | Caldwell et al. |
| 6,806,076 | B1 | 10/2004 | Miyake et al. |
| 6,989,257 | B2 | 1/2006 | Berry et al. |
| 6,998,471 | B2 | 2/2006 | Hallahan et al. |

(Continued)

FOREIGN PATENT DOCUMENTS

| | | | |
|---|---|---|---|
| DE | 196 29 568 | C1 | 1/1998 |
| EP | 0 215 594 | A2 | 3/1987 |

(Continued)

OTHER PUBLICATIONS

Morita et al. Isoprene Polymerization by Organometallic Compounds. I, J. Am. Chem. Soc., 1957, 79 (22), pp. 5853-5855.*

Albrecht, M. et al. (Aug. 2000). "Novel Hydroxycarotenoids with Improved Antioxidative Properties Produced by Gene Combination in *Escherichia coli," Nature Biotechnology* 18:843-846.

Alexopoulos, C.J. (1962). Introductory Mycology, Wiley: New York, NY, pp. ix-x, (Table of Contents Only).

Allison, R. et al. (1986). "The Nucleotide Sequence of the Coding Region of Tobacco Etch Virus Genomic RNA: Evidence for the Synthesis of a Single Polyprotein," *Virology* 154:9-20.

(Continued)

*Primary Examiner* — Iqbal H Chowdhury

(74) *Attorney, Agent, or Firm* — Mintz Levin Cohn Ferris Glovsky and Popeo PC

(57) ABSTRACT

The invention features methods for producing isoprene from cultured cells. The invention also provides compositions that include these cultured cells.

19 Claims, 173 Drawing Sheets

Specification includes a Sequence Listing.

(56) References Cited

U.S. PATENT DOCUMENTS

| | | | |
|---|---|---|---|
| 7,129,392 B2 | 10/2006 | Hahn et al. |
| 7,132,268 B2 | 11/2006 | Miyake et al. |
| 7,132,527 B2 | 11/2006 | Payne et al. |
| 7,172,886 B2 | 2/2007 | Keasling et al. |
| 7,183,089 B2 | 2/2007 | Keasling et al. |
| 7,208,298 B2 | 4/2007 | Miyake et al. |
| 7,241,587 B2 | 7/2007 | Dodge et al. |
| 7,262,041 B2 | 8/2007 | Baldwin et al. |
| 7,364,885 B2 | 4/2008 | Miyake et al. |
| 7,531,333 B2 | 5/2009 | Miyake et al. |
| 8,173,410 B2 | 5/2012 | Bott et al. |
| 8,288,148 B2 | 10/2012 | Cervin et al. |
| 8,709,785 B2 | 4/2014 | Cervin et al. |
| 9,260,727 B2 | 2/2016 | Cervin et al. |
| 9,909,144 B2 | 3/2018 | Cervin et al. |
| 2002/0095818 A1 | 7/2002 | Jain et al. |
| 2003/0033626 A1 | 2/2003 | Hahn et al. |
| 2004/0005678 A1 | 1/2004 | Kleasling et al. |
| 2004/0219629 A1 | 11/2004 | Cheng et al. |
| 2005/0287655 A1 | 12/2005 | Tabata et al. |
| 2006/0009647 A1 | 1/2006 | Yeates et al. |
| 2006/0020095 A1 | 1/2006 | Gandon-Pain |
| 2006/0079476 A1 | 4/2006 | Keasling et al. |
| 2008/0038805 A1 | 2/2008 | Melis |
| 2008/0178354 A1 | 7/2008 | Chappell |
| 2009/0155874 A1 | 6/2009 | Clark et al. |
| 2009/0203102 A1 | 8/2009 | Cervin et al. |
| 2010/0003716 A1 | 1/2010 | Cervin et al. |
| 2010/0048964 A1 | 2/2010 | Calabria et al. |
| 2010/0086978 A1 | 4/2010 | Beck et al. |
| 2010/0113846 A1 | 5/2010 | McAuliffe et al. |
| 2010/0196982 A1 | 8/2010 | Anderson |
| 2011/0045563 A1 | 2/2011 | Melis |
| 2011/0076743 A1 | 3/2011 | Beck et al. |

FOREIGN PATENT DOCUMENTS

| | | |
|---|---|---|
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 1 118 855 A2 | 7/2001 |
| EP | 1 118 855 A3 | 7/2001 |
| JP | 2006-271379 A | 10/2006 |
| JP | 2008-035831 A | 2/2008 |
| JP | 2008-182950 A | 8/2008 |
| JP | 2009-207402 A | 9/2009 |
| KR | 2001-0084864 A | 9/2001 |
| RU | 2 197 461 C2 | 1/2003 |
| WO | WO-95/04134 | 2/1995 |
| WO | WO-96/35796 | 11/1996 |
| WO | WO-98/02550 A2 | 1/1998 |
| WO | WO-98/02550 A3 | 1/1998 |
| WO | WO-00/17327 A2 | 3/2000 |
| WO | WO-00/17327 A3 | 3/2000 |
| WO | WO-00/17327 A9 | 3/2000 |
| WO | WO-01/58839 A1 | 8/2001 |
| WO | WO-02/099095 A2 | 12/2002 |
| WO | WO-02/099095 A3 | 12/2002 |
| WO | WO-2004/033646 A2 | 4/2004 |
| WO | WO-2004/033646 A3 | 4/2004 |
| WO | WO-2004/111214 | 12/2004 |
| WO | WO-2005/001036 A2 | 1/2005 |
| WO | WO-2005/001036 C1 | 1/2005 |
| WO | WO-2005/007682 A2 | 1/2005 |
| WO | WO-2005/007682 A3 | 1/2005 |
| WO | WO-2005/078074 A2 | 8/2005 |
| WO | WO-2005/078074 A3 | 8/2005 |
| WO | WO-2006/063752 | 6/2006 |
| WO | WO-2006/085899 A2 | 8/2006 |
| WO | WO-2006-085899 A3 | 8/2006 |
| WO | WO-2007/018062 A1 | 2/2007 |
| WO | WO-2007/136847 A2 | 11/2007 |
| WO | WO-2007/136847 A3 | 11/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/003078 A2 | 1/2008 |
| WO | WO-2008/003078 A3 | 1/2008 |
| WO | WO-2008/003078 A8 | 1/2008 |
| WO | WO-2008/137092 A2 | 11/2008 |
| WO | WO-2008/137092 A3 | 11/2008 |
| WO | WO-2008/153925 A2 | 12/2008 |
| WO | WO-2008/153925 A3 | 12/2008 |
| WO | WO-2008/153925 A9 | 12/2008 |
| WO | WO-2008/153934 A2 | 12/2008 |
| WO | WO-2008/153934 A3 | 12/2008 |
| WO | WO-2008/153935 A2 | 12/2008 |
| WO | WO-2008/153935 A3 | 12/2008 |
| WO | WO-2009/036067 A2 | 3/2009 |
| WO | WO-2009/036067 A3 | 3/2009 |
| WO | WO-2009/064910 A2 | 5/2009 |
| WO | WO-2009/064910 A3 | 5/2009 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/005525 A1 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010-124146 A3 | 10/2010 |

OTHER PUBLICATIONS

Alper, H. et al. (2008). "Uncovering the Gene Knockout Landscape for Improved Lycopene Production in *E. coli*," *Appl Microbiol. Biotechnol.* 10 pages.

Alterthum, F. et al. (Aug. 1989). "Efficient Ethanol Production from Glucose, Lactose, and Xylose by Recombinant *Escherichia coli*," *Applied Environmental Microbiology* 55(8):1943-1948.

Altschul, S.F. et al. (1990). "Basic Local Alignment Search Tool," *J Mol. Biol.* 215:403-410.

Altschul, S.F. et al. (1996). "Local Alignment Statistics," Chapter 27 in Multiple Alignment and Phylogenetic Trees, American Press, Inc. 266:460-480.

Alves, R. et al. (Nov. 2000). "Effect of Overall Feedback Inhibition in Unbranched Biosynthetic Pathways," *Biophysical Journal* 79(5):2290-2304.

Anderson, M.S. et al. (Nov. 15, 1989). "Isopentenyl Diphosphate: Dimethylallyl Diphosphate Isomerase. An Improved Purification of the Enzyme and Isolation of the Gene from *Saccharomyces Cerevisiae*," *J. Biol. Chem.* 264(32):19169-19175.

Andreassi, J.L. et al. (2004, e-pub. Dec. 4, 2004). "*Streptococcus pneumoniae* Isoprenoid Biosynthesis is Downregulated by Diphosphomevalonate: An Antimicrobial Target," *Biochemistry* 43(51):16461-16466.

Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.

Aon, J.C. et al. (Feb. 2008, e-pub. Dec. 14, 2007). "Suppressing Posttranslational Gluconoylation of Heterologous Proteins by Metabolic Engineering of *Escherichia coli*," *Applied and Environmental Microbiology* 74(4):950-958.

(56) References Cited

OTHER PUBLICATIONS

Arai, Y. et al. (2004). "Production of Polyhydroxybutyrate by Polycistronic Expression of Bacterial Genes in Tobacco Plastid," *Plant Cell Physiol.* 45(9):1176-1184.
Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.
Ausubel, F.M. et al. eds. (1987). Current Protocols in Molecular Biology, John Wiley and Sons, Inc., pp. 1-13, (Table of Contents Only).
Baba, T. et al. (Feb. 21, 2006). "Construction of *Escherichia coli* K-12 In-Frame, Single-Gene Knockout Mutants: The Keio Collection," *Molecular Systems Biology* pp. 1-11.
Ballas, N. et al. (1989). "Efficient Functioning of Plant Promoters and Poly(A) Sites in *Xenopus Oocytes," Nucleic Acids Research* 17(19):7891-7903.
Barkovich, R. et al. (2001, e-pub. Dec. 1, 2000). "Metabolic Engineering of Isoprenoids," *Metabolic Engineering* 3:27-29.
Beaucage, S.L. et al. (1981). "Deoxynucleoside Phosphoramidites—A New Class of Key Intermediates for Deoxypolynucleotide Synthesis," *Tetrahedron Letters* 22(20):1859-1862.
Bellion, E. et al. (1993). "Methylamine Utilization in Yeast and Bacteria: Studies Using in vivo NMR," Chapter 32 in *Microbial Growth C1 Compounds*, Muerrell, J.C. et al. eds, Intercept Ltd: Andover, UK, pp. 415-432.
Bennett, J.W. et al. eds. (1991). "Gene Cloning and Analysis," Chapter 3 in *More Gene Manipulations* in Fungi, Academic Press, San Diego, CA pp. 70-76.
Berman, H. et al. (2007, e-pub. Nov. 16, 2006). "The Worldwide Protein Data Bank (wwPDB): Ensuring a Single, Uniform Archive of PDB Data," *Nucleic Acids Research* 35:D301-D303.
Beytia, E. et al. (Oct. 25, 1970). "Purification and Mechanism of Action of Hog Liver Mevalonic Kinase," *The Journal of Biological Chemistry* 245(20):5450-5458.
Bock, R. et al. (2000). "Extranuclear Inheritance: Plastid Genetic: Manipulation of Plastid Genomes and Biotechnological Application," *Progress in Botany* 61:76-90.
Bock, R. (2001). "Transgenic Plastids in Basic Research and Plant Biotechnology," *J. Mol. Biol.* 312:425-438.
Bock, R. et al. (Jun. 2004). "Taming Plastids for a Green Future," *Trends in Biotechnology* 22(6):311-318.
Boel, E. et al. (1984). "Two Different Types of Intervening Sequences in the Glucoamylase Gene from *Aspergillus niger," The EMBO Journal* 3(7):1581-1585.
Bouvier, F. et al. (2005). "Biogenesis, Molecular Regulation and Function of Plant Isoprenoids," *Progress in Lipid Res.* 44:357-429.
Boynton, J.E. et al. (1993). "Chloroplast Transformation in *Chlamydomonas," Methods in Enzymology* 217(37):510.536.
Broun, P. et al. (Nov. 13, 1998). "Catalytic Plasticity of Fatty Acid Modification Enzymes Underlying Chemical Diversity of Plant Lipids," *Science* 282:1315-1317.
Brunger, A.T. et al. (1998). "*Crystallography& NMF? System:* A New Software Suite for Macromolecular Structure Determination," *Acta Cryst.* D54:905-921.
Bubunenko, M. et al. (Apr. 2007). "Essentiality of Ribosomal and Transcription Antitermination Proteins Analyzed by Systematic Gene Replacement in *Escherichia coli," Journal of Bacteriology* 189(7):2844-2853.
Campbell, E.I. et al. (1989). "Improved Transformation Efficiency of *Aspergillus niger* Using the Homologous niaD Gene for Nitrate Reductase," *Curr. Genet.* 16:53-56.
Campbell, J.W. et al. (Oct. 2001). "*Escherichia coli* FadR Positively Regulates Transcription of the fabB Fatty Acid Biosynthetic Gene," *J. Bacteriol.* 183(20):5982-5990.
Campos, N. et al. (2001). "*Escherichia coli* Engineering to Synthesize Isopentenyl Diphosphate and Dimethylallyl Diphosphate from Mevalonate: A Novel System for the Genetic Analysis of the 2-C-Methyl-D-Erythritol 4-Phospate Pathway for Isoprenoid Biosynthesis," *Biochem. J.* 353:59-67.
Cao, Q-N. et al. (2000). "Penicillopepsin-JT2, a Recombinant Enzyme from *Penicillium janthinellum* and the Contribution of a Hydrogen Bond in Subsite $_{s3}$ to $_{kcat}$," *Protein Science* 9:991-1001.
Chamberlin, M. et al. (Oct. 17, 1970). "New RNA Polymerase from *Escherichia coli* Infected with Bacteriophage T7," *Nature* 228:227-231.
Champenoy, S. et al. (1998). "Expression of the Yeast Mevalonate Kinase Gene in Transgenic Tobacco," *Molecular Breeding* 4:291-300.
Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.
Chappell J. et al. (1995). is the Reaction Catalyzed by 3-Hydroxy-3-Methylglutaryl Coenzyme A Reductase a Rate-Limiting Step for Isoprenoid Biosynthesis in Plants? *Plant Physiology* (109):1337-1343.
Chemler, J.A. et al. (May 23, 2006). "Biosynthesis of Isoprenoids, Polyunsaturated Fatty Acids and Flavonoids in *Saccharomyces cerevisiae," Microbial Cell Factories* 5:20, 9 pages.
Chica, R.A. et al. (2005). "Semi-Rational Approaches to Engineering Enzyme Activity: Combining the Benefits of Directed Evolution and Rational Design," *Current Opinion in Biotechnology* 16:378-384.
Cho, H-J. et al. (1995). "Expression Pattern of Bacterial Polycistronic Genes in Tobacco Cells," *Journal of Fermentation and Bioengineering* 80(2):111-117.
Clarke, S. (1992). "Protein Isoprenylation and Methylation at Carboxyl-Terminal Cysteine Residues," *Annu. Rev. Biochem.* 61:355-386.
Clough, S.J. et al. (1998). "Floral Dip: A Simplified Method for *Agrobacterium*-Mediated Transformation of *Arabidopsis thaliana," The Plant Journal* 16(6):735-743.
Collaborative Computational Project, No. 4. (1994). "The CCP4 Suite: Programs for Protein Crystallography," *Acta Cryst.* D50:760-763.
Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.
Crueger, W. et al. (1989). Biotechnology: A Textbook of Industrial Microbiology, Second Edition, Brock, T.D. ed., Sinauer Associates, Inc.: Sunderland, MA, pp. vii-x, (Table of Contents).
Cunningham, F.X. et al. (1998). "Genes and Enzymes of Carotenoid Biosynthesis in Plants," *Ann. Rev. Plant Physiol. Plant Mol. Biol.* 49:557-583.
Cunningham, F.X. et al. (Oct. 2000). "Evidence of a Role for LytB in the Nonmevalonate Pathway of Isoprenoid Biosynthesis," *Journal of Bacteriology* 182(20):5841-5848.
Dale, P.J. (1992). "Spread of Engineered Genes to Wild Relatives," *Plant PhysioL* 100:13-15.
Dale, G.E. et al. (2003). "The Protein as a Variable in Protein Crystallization," *Journal of Structural Biology* 142:88-97.
Daniell, H. (1997). "'Transformation and Foreign Gene Expression in Plants Mediated by *Microprojectile Bombardment,"* Chapter 35 in *Methods in Molecular Biology, Recombinant Gene Expression Protocols*, Tuan, R S. ed., Humana Press: Totowa, NJ, 62:463-489.
Daniell, H. et al. (Apr. 1998) "Containment of Herbicide Resistance Through Genetic Engineering of the Chloroplast Genome," *Nature Biotechnology* 16:345-348.
Datsenko, K.A. et al. (Jun. 6, 2000). "One-Step Inactivation of Chromosomal Genes in *Escherichia coli* K-12 Using PCR Products," *PNAS* 97(12):6640-6645.
Datta, S. et al. (2006). "A Set of Recombineering Plasmids for Gram-Negative Bacteria," *Gene* 379:109-115.
Datukishvili, N. T. et al. (2001). "Isolation and Purification of Protein Responsible for the Conversion of Dimethylallylpyrophosphate from Poplar Leaves into Isoprene," *Russian Journal of Plant Physiology* 48(2):222-225.
Davidson, S. (Oct.-Dec. 2003). "Light Factories," located at <http://www.publish.csiro.au/?act=view_file&file_id=EC117p10.pdf>, last visited on Oct. 2, 2008.

(56) References Cited

OTHER PUBLICATIONS

Davis, I.W. et al. (2007). "MolProbity: All-Atom Contacts and Structure Validation for Proteins and Nucleic Acids," *Nucleic Acids Research* 35:W375-W383.
De Cosa, B. et al. (Jan. 2001). "Overexpression of the Bt cry2Aa2operon in Chloroplasts Leads to Formation of Insecticidal Crystals," *Nature Biotechnology* 19:71-74.
Del Campo, E. M. et al. (1997). "Plastid ndhD Gene of Barley, Sequence and Transcript Editing (Accession No. Y12258) (PGR 97-090)," *Plant Physiol.* 114:747-749.
Della-Cioppa, G. et al. (1987). "Protein Trafficking in Plant Cells," *Plant Physiol.*84:965-968.
Deppenmeier, U. et al. (2002). "The Genome of *Methanosarcina mazei*: Evidence for Lateral Gene Transfer Between Bacteria and Archaea," *J. Mol. Microbiol. Biotechnol.* 4(4):453461.
Deroles, S.C. et al. (1988). "Expression and Inheritance of Kanamycin Resistance in a Large Number of Transgenic Petunias Generated by *Agrobacterium*-Mediated Transformation," *Plant Molecular Biology* 11:355-364.
Dettmer, K. et al. (2000). "Stability of Reactive Low Boiling Hydrocarbons on Carbon Based Adsorbents Typically Used for Adsorptive Enrichment and Thermal Desorption," *Fresenius J. Anal. Chem.* 366:70-78.
Devereux, J. et al. (1984). "A Comprehensive Set of Sequence Analysis Programs for the VAX," *Nucleic Acids Research* 12(1):387-395.
Devos, D. et al. (2000). "Practical Limits of Function Prediction," *Proteins: Structure, Function, and Genetics* 41:98-107.
Dewick, P.M. et al. (2002, e-pub. Jan. 22, 2002). "The Biosynthesis of $_{C5-025}$ Terpenoid Compounds," *Nat. Prod. Rep.* 19:181-222.
Dhe-Paganon, S. et al. (1994). "Mechanism of Mevalonate Pyrophosphate Decarboxylase: Evidence for a Carbocationic Transition State," *Biochemistry* 33(45):13355-13362.
Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.
Doumith, M. et al. (2000, e-pub. Aug. 25, 2000). "Analysis of Genes Involved in 6-Deoxyhexose Biosynthesis and Transfer in *Saccharopolyspora erythraea," Mol. Gen Genet.*264:477-485.
Dynan, W.S. et al. (Aug. 29, 1985). "Control of Eukaryotic Messenger RNA Synthesis by Sequence-Specific DNA-Binding Proteins," *Nature* 316:774-778.
Eisenreich, W. et al. (Sep. 1998). "The Deoxyxylulose Phosphate Pathway of Terpenoid Biosynthesis in Plants and Microorganisms," *Chemistry and Biology* 5(9):R221-R233.
Eisenreich, W. et al, (Feb. 2001). "Deoxyxylulose Phosphate Pathway to Terpenoids," *Trends in Plant Science* 6(2):78-84.
Elroy-Stein, O. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.
EMBL-EBI Accession No. AOPFK2, last updated on Mar. 2, 2010, located at <http://srs.ebi.ac.uk/srsbin/cgi-bin/wgetz?-e+[UNIPROT:AOPFK2_POPNI]+-newld>, last visited on Jun. 2, 2010, 2 pages.
EMBL-EBI Accession No. A9PGR5, last updated on Mar. 2, 2010, located at <http://srs.ebi.ac.uk/srsbin/cgi-bin/wgetz?-e+[UNIPROT:A9PGR5_POPTR]+-newld>, last visited on Jun. 2, 2010, 2 pages.
EMBL-EBI Accession No. AB198180, last updated May 10, 2005, located at <http://www.ebi.ac.uk/cgi-bin/dbfetch?db=embl&id=ab1981808(Subm...>, last visited on Aug. 7, 2009, 2 pages.
EMBL-EBI Accession No. AY341431, last updated Apr. 16, 2005, located at <http://www.ebi.ac.uk/cgi-bin/dbfetch?db=embl&id=AY341431&Sub...>, last visited on Nov. 26, 2009, 2 pages.
Emsley, P. et al. (2004). "Coot: Model-Building Tools for Molecular Graphics," *Acta Crystallographica* D60:2126-2132.
Extended European Search Report dated Jun. 14, 2011, for EP Patent Application No. 08860589.4, filed on Dec. 15, 2008, 10 pages.
Fall, R. (Sep. 12, 2003). "Final Technical Report: DE-FG03-97ER20274, 'Microbial Production of Isoprene'," located at <http://www.osti.gov/bridge/product.biblio.jsp?query_id=1&page=0&Losti_id=814920>, last visited on May 26, 2010, 4 pages.
Farmer, W.R. et al. (May 2000). "Improving Lycopene Production in *Escherichia coli* by Engineering Metabolic Control," *Nature Biotechnology* 18:533-537.
Feng, D-F. et al. (1987). "Progressive Sequence Alignment as a Prerequisite to Correct Phylogenetic Trees," *Journal of Molecular Evolution* 25:351-360.
Finkelstein, D.B. (1992). "*Transformation,*" Chapter 6 in *Biotechnology of Filamentous Fungi,* Butterworth-Heinemann: Boston, MA, pp. 113-156.
Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.
Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.
Gallie, D.R. et al. (1989). "Eukaryotic Viral 5'-Leader Sequences Act as Translational Enhancers in *Eukaryotes and Prokaryotes*," in *Molecular Biology of RNA*, Cech, T.R. ed. Alan. R. Liss, Inc: New York, NY, pp. 237-256.
Garret, T.A. et al. (May 15, 1998). "Accumulation of a Lipid a Precursor Lacking the 4'-Phosphate Following Inactivation of the *Escherichia coli* IpxK Gene," *The Journal of Biological Chemistry* 273(20):12457-12465.
GenBank Accession No. AB198180, last updated on May 10, 2005, located at <http://www.ncbi.nlm.nih.gov/nuccore/63108309>, last visited on Jun. 2, 2010, 2 pages.
GenBank Accession No. AJ294819.1, last updated Apr. 15, 2005, located at < http://www.ncbi.nlm.nih.gov/nuccore/AJ294819.1>, last visited on Dec. 7, 2011, 2 pages.
GenBank Accession No. AJ457070, last updated on Apr. 15, 2005, located at <http://www.ncbi.nlm.nih.gov/nuccore/38092202>, last visited on Jun. 2, 2010, 2 pages.
GenBank Accession No. AM410988.1, last updated Aug. 14, 2008, located at < http://www.ncbi.nlm.nih.gov/nuccore/AM410988.1>, last visited on Dec. 7, 2011, 2 pages.
GenBank Accession No. AY182241, last updated on May 4, 2004, located at <http://www.ncbi.nlm.nih.gov/nuccore/32265057>, last visited on Jun. 2, 2010, 2 pages.
GenBank Accession No. AY279379, last updated on Mar. 11, 2005, located at <http://www.ncbi.nlm.nih.gov/nuccore/30984014>, last visited on Jun. 2, 2010, 2 pages.
GenBank Accession No. AY316691, last updated on Feb. 15, 2005, located at <http://www.ncbi.nlm.nih.gov/nuccore/35187003>, last visited on Jun. 2, 2010, 2 pages.
GenBank Accession No. AY341431, last updated on Feb. 15, 2005, located at <http://www.ncbi.nlm.nih.gov/nuccore/33358228>, last visited on Jun. 2, 2010, 3 pages.
GenBank Accession No. EF147555.1, last updated Mar. 24, 2009, located at <http://www.ncbi.nlm.nih.gov/nuccore/EF147555.1>, last visited on Aug. 25, 2015, 2 pages.
GenBank Accession No. EF638224.1, last updated May 3, 2010, located at <http://www.ncbi.nlm.nih.gov/nuccore/EF638224.1>, last visited on Aug. 25, 2015, 2 pages.
GenBank Accession No. EU693027, last updated on May 27, 2008, located at <http://www.ncbi.nlm.nih.gov/nuccore/189017053>, last visited on Jun. 2, 2010, 2 pages.
GenBank Accession No. CAC35696, last updated Apr. 15, 2005, located at <http://www.ncbi.nlm.nih.gov/protein/CAC35696>, last visited on Apr. 6, 2011, 2 pages.
Geneseq Database Accession No. AFB74822, "Monoterpene synthetase protein SEQ ID No. 4." Retrieved from EBI accession No. GSP:AFB74822 (Apr. 19, 2007.).
Gerhardt, P. et al. eds. (1994). Manual of Methods for General and Molecular Bacteriology, American Society for Microbiology: Washington, D.C., p. v, (Table of Contents Only).
Goedegebuur, F. et al. (2002, e-pub. May 7, 2002). "Cloning and Relational Analysis of 15 Novel Fungal Endoglucanases from Family 12 Glycosyl Hydrolase," *Curr. Genet.* 41:89-98.

(56) References Cited

OTHER PUBLICATIONS

Goldschmidt-Clermont, M. (1991). "Transgenic Expression of Aminoglycoside Adenine Transferase in the Chloroplast: A Selectable Marker for Site-Directed Transformation of Chlamydomonas," *Nucleic Acids Res.* 19(15):4083-4089.
Goodwin, T.W. (1971). "Biosynthesis of Carotenoids and Plant Triterpenes: The Fifth CIBA Medal Lecture," *Biochem. J.* 123(3):293-329.
Gottschalk, G. (1986). Bacterial Metabolism Second Edition, Springer Verlag: New York, NY, pp. xi-xiii, (Table of Contents Only).
Grawert, T. et al. (2004, e-pub. Sep. 21, 2004). "IspH Protein of *Escherichia coli:* Studies on Iron-Sulfur Cluster Implementation and Catalysis," *Journal American Chemistry Society* 126:12847-12855.
Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.
Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.
Guda, C. et al. (2000). "Stable Expression for a Biodegradable Protein-Based Polymer in Tobacco Chloroplasts," *Plant Cell Reports* 19:257-262.
Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet.* 226:141-144.
Guo, D-A. et al. (1995). "Developmental Regulation of Sterol Biosynthesis in *Zea mays,*" *Lipids* 30(3):203-219.
Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli,*" *The Journal of Biological Chemistry* 270(19):11298-11303.
Hahn, F.M. et al. (Feb. 1996). "Open Reading Frame 176 in the Photosynthesis Gene Cluster of *Rhodobacter capsulatus* Encodes idi, a Gene for Isopentenyl Diphosphate Isomerase," *Journal of Bacteriology* 178(3):619-624.
Hahn, F.M. et al. (Aug. 1999). "*Escherichia coli* Open Reading Frame 696 is idi, a Nonessential Gene Encoding Isopentenyl Diphosphate Isomerase," *Journal of Bacteriology* 181(15):4499-4504.
Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus,*" *Journal of Bacteriology* 183(1):1-11.
Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.
Hamilton, C.M. et al. (Sep. 1989). "New Method for Generating Deletions and Gene Replacements in *Escherichia coli,*" *Journal of Bacteriology* 171(9):4617-4622.
Hale, W.G. et al. (1991). The Harper Collins Dictionary of Biology, Ehrlich, E. ed., Harper Perennial: New York, NY, 2 pages.
Hanai, T. et al. (Dec. 2007). "Engineered Synthetic Pathway for Isopropanol Production in *Escherichia coli,*" *Applied and Environmental Microbiology* 73(24):7814-7818.
Harker, M. et al. (1999). "Expression of Prokaryotic 1-Deoxy-D-Xylulose-5-Phosphatases in *Escherichia coli* Increases Carotenoid and Ubiquinone Biosynthesis," *FEBS Letters* 448:115-119.
Harkki, A. et al. (Jun. 1989). "A Novel Fungal Expression System: Secretion of Active Calf Chymosin from the Filamentous Fungus *Trichoderma reesei,*" *Bio. Technol.*7:596-603.
Hedl, M. et al. (Apr. 2002). "*Enterococcus faecalis* Acetoacetyl-Coenzyme A Thiolase/3-Hydroxy-3-Methylglutaryl-Coenzyme A Reductase, a Dual-Function Protein of Isopentenyl Diphosphate Biosynthesis," *J. Bacteriol.* 184(8):2116-2122.
Hedl, M. et al. (Apr. 2004). "Class II 3-Hydroxy-3-Methylglutaryl Coenzyme A Reductases," *Journal of Bacteriology* 186(7):1927-1932.
Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.
Herbers, K. et al. (Jun. 1996). "Manipulating Metabolic Partitioning in Transgenic Plants", *TIBTECH* 14:198-205.
Herz, S. et al. (Mar. 14, 2000). "Biosynthesis of Terpenoids: YgbB Protein Converts 4-Diphosphocytidyl-2C-Methyl-D-Erythritol 2-Phosphate to 2C-Methyl-D-Erythritol 2,4-Cyclodiphosphate," *Proc. Natl. Acad. Sci. USA* 97(6):2486-2490.
Higgins, D.G. et al. (1989). "Fast and Sensitive Multiple Sequence Alignments on a Microcomputer," *Cabios Communications* 5(2):151-153.
Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.
Hoeffler, J-F. et al. (2002). "Isoprenoid Biosynthesis Via the Methylerythritol Phosphate Pathway. Mechanistic Investigations of the 1-Deoxy-D-Xylulose 5-Phosphate Reductoisomerase," *Eur. J. Biochem.* 269:4446-4457.
Huang, K-X. et al. (1999). "Overexpression, Purification, and Characterization of the Thermostable Mevalonate Kinase from *Methanococcus jannaschii,*" *Protein Expression and Purification* 17:33-40.
Hunter, B.K. (1985). "Formaldehyde Metabolism by *Escherichia colL* Carbon and Solvent Deuterium Incorporation into Glycerol, 1,2-Propanediol, and 1,3-Propanediol," *Biochemistry* 24(15):4148-4155.
Hyatt, D.C. et al. (Mar. 27, 2007). "Structure of Limonene Synthase, A Simple Model for Terpenoid Cyclase Catalysis," *PNAS* 104(13):5360-5365.
Ilmen, M. et al. (Apr. 1997). "Regulation of Cellulase Gene Expression in the Filamentous Fungus *Trichoderma reesei,*" *Appl. Environ. MicrobioL* 63(4):1298-1306.
Innis, M.A. et al. (Apr. 5, 1985). "Expression, Glycosylation, and Secretion of an *Aspergillus* Glucoamylase by *Saccharomyces cerevisiae,*" *Science* 228:21-26.
International Search Report dated Jun. 18, 2009, for PCT Patent Application No. PCT/US08/86869, filed on Dec. 15, 2008, one page. (2.40).
International Search Report dated Dec. 8, 2009, for PCT Application No. PCT/US2009/041581, filed on Apr. 23, 2009, nine pages. (5.40).
International Search Report dated Dec. 30, 2010, for PCT Application No. PCT/US2010/032134, filed on Apr. 22, 2010, 15 pages. (15.40).
Jenkins, L.S. et al. (Jan. 1987). "Genetic and Molecular Characterization of the Genes Involved in Short-Chain Fatty Acid Degradation in *Escherichia coli:* the ato System," *Journal of Bacteriology* 169(1):42-52.
Jeong, S.-W. et al. (2004, e-pub. Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.
Jobling, S.A. et al. (Feb. 12, 1987). "Enhanced Translation of Chimaeric Messenger RNAs Containing a Plant Viral Untranslated Leader Sequence," *Nature* 235:622-625.
Jones, K.L. et al. (2000). "Low-Copy Plasmids Can Perform as Well as or Better Than High-Copy Plasmids for Metabolic Engineering of Bacteria," *Metabolic Engineering* 2:238-338.
Jones, E.Y. et al. (1991). "Methodology Employed for the Structure Determination of Tumour Necrosis Factor, a Case of High Non-Crystallographic Symmetry," *Acta Cryst* A47:753-770.
Joshi, C.P. (1987). "Putative Polyadenylation Signals in Nuclear Genes of Higher Plants: A Compilation and Analysis," *Nucleic Acid Research* 15(23):9627-9640.
Julsing, M.K. et al. (2007). "Functional Analysis of Genes Involved in the Biosynthesis of Isoprene in *Bacillus subtilis,*" *Applied MicrobioL BiotechnoL* 75:1377-1384.

(56) References Cited

OTHER PUBLICATIONS

Kacian, D.L. et al. (Oct. 1972). "A Replicating RNA Molecule Suitable for a Detailed Analysis of Extracellular Evolution and Replication," *Proc. Natl. Acad. Sci. USA* 69(10):3038-3042.
Kajiwara, S. et al. (1997). "Expression of an Exogenous Isopentenyl Diphosphate Isomerase Gene Enhances Isoprenoid Biosynthesis in *Escherichia coli," Biochem. J.* 324:421-426.
Kampranis, S.C. et al. (Jun. 2007). "Rational Conversion of Substrate and Product Specificity in a *Salvia* Monoterpene Synthase: Structural Insights into the Evolution of Terpene Synthase Function," *The Plant Cell* 19:1994-2005.
Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.
Karl, T. et al. (2003). "Dynamic Measurements of Partition Coefficients Using Proton-Transfer-Reaction Mass Spectrometry (PTR-MS)," *International Journal of Mass Spectrometry* 223-224:383-295.
Karlin, S. (Jun. 1993). "Applications and Statistics for Multiple High-Scoring Segments in Molecular Sequences," *Proc. Natl. Acad. ScL USA* 90:5873-5787.
Kavanagh, T.A. et al. (Jul. 1999). "Homeologous Plastid DNA Transformation in Tobacco is Mediated by Multiple Recombination Events," *Genetics* 52:1111-1122.
Keasling, J.D. (Mar. 29, 2004). "Genetic Tools for Metabolic Enzyme Production in *Escherichia Coli*," presented at NIGMS 2004 PSI Protein Production & Crystallization Workshop, Bethesda, MD, Mar. 29-31, 2004, located at <http://www-nmr.cabm.rutgers.edu/labdocuments/workshops/psi_ppcw_32904/ppcw_32904.html>, last visited on Jun. 4, 2010, 66 pages.
Keasling, J.D. (May 7, 2005). "Drugs from Bugs: Engineering Microorganisms to Produce New Drugs," presented at Engineering a Better World: *Our Environment, Our Health*, Berkeley, CA, May 7, 2005, 62 pages.
Keasling, J.D. (Sep. 23, 2007). "Engineering Microbes for Production of Low-Cost, Effective, Anti-Malarial Drugs," presented at *Enzyme Engineering XIX*, Harrison Hot Springs, British Columbia, Canada, Sep. 23-28, 2007, 152 pages.
Keegan, R.M. et al. (2007). "Automated Search-Model Discovery and Preparation for Structure Solution by Molecular Replacement," *Acta Crystallographica* D63:447-457.
Keeler, K.H. et al. (1996). "Movement of Crop Transgenes into Wild Plants," Chapter 20 in *Herbicide Resistant Crops: Agricultural, Environmental, Economic, Regulatory, and Technical Aspects*, Duke, S.O. ed., Lewis Publishers: Boca Raton, FL., pp. 303-330.
Kelly, J.M. et al. (1985). "Transformation of *Aspergillus niger* by the amdS Gene of *Aspergillus nidulans," The EMBO Journal* 4(2):475-479.
Khan, M.S. et al. (Sep. 1999). "Fluorescent Antibiotic Resistance Marker for Tracking Plastid Transformation in Higher Plants," *Nature Biotechnology* 17:910-914.
Kieser, T. eds. et al. (Jul. 2000). "Introduction of DNA into *Streptomyces*," Chapter 10 in *Practical Streptomyces Genetics*, pp. 229-252.
Kinghorn, J.R. et al. (1992). Applied Molecular Genetics of Filamentous Fungi, Blackie Academic Professional and Chapman and Hall: London, 3 pages, (Table of Contents Only).
Kisselev, L. (Jan. 2002). "Polypeptide Release Factors in Prokaryotes and Eukaryotes: Same Function, Different Structure," Structure 10:8-9.
Klein-Marcuschamer, D. et al. (2007, e-pub. Aug. 2, 2007). "Engineering Microbial Cell Factories for Biosynthesis of Isoprenoid Molecules: Beyond Lycopene," *TRENDS in Biotechnology* 25(9):417-424.
Klein-Marcuschamer, D. et al. (Feb. 19, 2008). "Assessing the Potential of Mutational Strategies to Elicit New Phenotypes in Industrial Strains," *Proc. Natl. Acad. Sci.* 105(7):2319-2324.
Koga, Y. et al. (Mar. 2007). "Biosynthesis of Ether-Type Polar Lipids in Archaea and Evolutionary Considerations," *Microbiology and Molecular Biology Reviews* 71(1):97-120.
Koksal, M. et al. (2010, e-pub. Jul. 17, 2010). "Structure of Isoprene Synthase Illuminates the Chemical Mechanism of Teragram Atmospheric Carbon Emission," *J. Mol. Biol.* pp. 1-11.
Kooter, J. M., et al. (Sep. 1999). "Listening to the Silent Genes: Transgene Silencing, Gene Regulation and Pathogen Control," *Trends in Plant Science* 4(9):340-347.
Kota, M. et al. (Mar. 1999). "Overexpression of the *Bacillus thuringiensis* (Bt) Cry2Aa2 Protein in Chloroplasts Confers Resistance to Plants Against Susceptible and Bt-Resistant Insects," *Proc. Natl. Acad. Sci. USA* 96:1840-1845.
Kozak, M. (Oct. 25, 1991). "Structural Features in Eukaryotic mRNAs That Modulate the Initiation of Translation," *The Journal of Biological Chemistry* 266(30):19867-19870.
Kozak, M. (1999). "Initiation of Translation in Prokaryotes and Eukaryotes," *Gene* 234:187-208.
Kreigler, M. (1990). Gene Transfer and Expression: A Laboratory Manual, W.H. Freeman and Company: New York, NY, pp. Vii-x, (Table of Contents Only.).
Kunkel, T. A. (Jan. 1985). "Rapid and Efficient Site-Specific Mutagenesis without Phenotypic Selection," *Proc. Natl. Acad. Sci. USA* 82:488-492.
Kuzma, J. et al. (1995). "Bacteria Produce the Volatile Hydrocarbon Isoprene," *Current Microbiology* 30:97-103.
Kuzuyama, T. et al. (1998). "Direct Formation of 2-C Methyl-D-Erythritol 4-Phosphate from 1-Deoxy-D-Xylulose 5-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.
Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.
Lange, B.M. et al. (Nov. 23, 1999). "Isopentenyl Diphosphate Biosynthesis Via a Mevalonate-Independent Pathway: Isopentenyl Monophosphate Kinase Catalyzes the Terminal Enzymatic Step," *PNAS* 96(24):13714-13719.
Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.
Law, C.K. (1984). "Heat and Mass Transfer in Combustion: Fundamental Concepts and Analytical Techniques," *Progress in Energy and Combustion Science* 10:295-318.
Lehning, A. et al. (1999). "Isoprene Synthase Activity and Its Relation to Isoprene Emission in *Quercus robur* L. Leaves," Plant, *Cell and Environment* 22:495-504.
Lerner, C.G. et al. (1990). "Low Copy Number Plasmids for Regulated Low-Level Expression of Cloned Genes in *Escherichia coli*with Blue/White Insert Screening Capability," *Nucleic Acids Research* 18(15):4631.
Li, W. et al. (2010, e-pub. Nov. 1, 2009). "Non-Redundant Patent Sequence Databases with Value-Added Annotations at Two Levels," *Nucleic Acids Research* 38:D52-D56.
Lichtenthaler, H.K. et al. (1997). "Biosynthesis of Isoprenoids in Higher Plant Chloroplasts Proceeds Via a Mevalonate-Independent Pathway," *FEBS Letters* 400:271-274.
Lichtenthaler, H.K. (1999). "The 1-Deoxy-D-Xylulose-5-Phosphate Pathway of Isoprenoid Biosynthesis in Plants," *Annu. Rev. Plant Physiol. Plant Mol. Biol.* 50:47-65.
Lin, X-M. et al. (2008, e-pub. Apr. 26, 2008). "Proteomic Analysis of Nalidixic Acid Resistance in *Escherichia coli*: Identification and Functional Characterization of OM Proteins," *Journal of Proteome Research* pp. A-G.
Lluch, M.A. et al. (2000). "Molecular Cloning and Expression Analysis of the Mevalonate Kinase Gene from *Arabidopsis thaliana," Plant Molecular Biology* 42:365-376.
Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," *Proc. Natl. Acad. Sci. USA* 95:2105-2110.

(56) References Cited

OTHER PUBLICATIONS

Loivamaki, M. et al. (Jun. 2007). "*Arabidopsis*, A Model to Study Biological Functions of Isoprene Emission?" *Plant Physiology* 144:1066-1078.
Lommel, S.A. et al. (1991). "Identification of the Maize Chlorotic Mottle Virus Capsid Protein Cistron and Characterization of its Subgenomic Messenger RNA," *Virology* 181:382-385.
Locker, J. et al. (2002). "Monoterpene Biosynthesis in Lemon (*Citrus Limon*). cDNA Isolation and Functional Analysis of Four Monoterpene Synthases," *European Journal of Biochemistry* 269:3160-3171.
Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.
Lottgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-D-Erythritol," *PNAS* 97(3):1062-1067.
Macejak, D.G. et al. (Sep. 5, 1991). "Internal Initiation of Translation Mediated by the 5' Leader of a Cellular mRNA," *Nature* 353:90-94.
Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.
Maldonado-Mendoza, I.E. et al. (1997). "Molecular Characterization of Three Differentially Expressed Members of the *Camptotheca acuminata* 3-Hydroxy-3-Methylglutaryl CoA Reductase (HMGR) Gene Family," *Plant Molecular Biology*134:781-790.
Mann, V. et al. (Aug. 2000). "Metabolic Engineering of Astaxanthin Production in Tobacco Flowers," *Nature Biotechnology* 18:888-892.
Martin, V.J.J. et al. (Dec. 5, 2001). "The In Vivo Synthesis of Plant Sesquiterpenes by *Escherichia coil," Biotechnology and Bioengineering* 75(5):497-503.
Martin, V.J.J. et al. (Jul. 2003). "Engineering a Mevalonate Pathway in *Escherichia coli* for Production of Terpenoids," *Nature Biotechnology* 21(7):796-802.
Martin, W. et al. (May 14, 1998). "Gene Transfer to the Nucleus and the Evolution of Chloroplasts," *Nature* 393:162-165.
Mash Ego, M.R. et al. (2007, e-pub. Nov. 8, 2006). "Microbial Metabolomics: Past, Present and Future Methodologies," *Biotechnol. Lett.* 29:1-16.
Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.
Matteucci, M.D. et al. (1981). "Synthesis of Deoxyoligonucleotides on a Polymer Support," *J. American Chemical Society* 103(11):3185-3191.
Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl Microbiol Biotechnol* 53:396-400.
Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.
McPherson, A. (2004). "Introduction to Protein Crystallization," *Methods* 34:254-265.
Meinkoth, J. et al. (1984). "Hybridization of Nucleic Acids Immobilized on Solid Supports," *Analytical Biochemistry* 138:267-284.
Meyer, P. et al. (1996). "Homology-Dependent Gene Silencing in Plants," *Ann. Rev. Plant Physiol. Plant Mol. Biol.* 47:23-48.
Millen, R.S. et al. (Mar. 2001). "Many Parallel Losses of infA from Chloroplast DNA During Angiosperm Evolution with Multiple Independent Transfers to the Nucleus," *The Plant Cell* 13:645-658.
Miller, B. (2001). "Erstmalige Isolierung Eines Isoprenysthase-Gens and Heterologe Expression Des Aus Der Pappel Stammenden Gens Sowie Charakterisierung der Eingangsgene des Mevalonat-unabhangigen Isoprenoidbiosyntheseweges aus dem Cyanobakterium Synechococcus leopoliensis," located at <http://kups.ub.uni-koeln.de/883/>, last visited on Jun. 23, 2011, English Translation included, 2 pages.
Miller, B. et al. (2001, e-pub. May 10, 2001). "First Isolation of an Isoprene Synthase Gene from Poplar and Successful Expression of the Gene in *Escherichia coil," Planta* 213:483-487.
Milne, P.J. et al. (1995). "Measurement of Vertical Distribution of Isoprene in Surface Seawater, its Chemical Fate, and its Emission from Several Phytoplankton Monocultures," *Marine Chemistry* 48:237-244.
Mo, H. et al. (2004). "Studies of the Isoprenoid-Mediated Inhibition of Mevalonate Synthesis Applied to Cancer Chemotherapy and Chemoprevention," *Exp. Biol. Med.* 229:567-585.
Mogen, B.D. et al. (Dec. 1990). "Upstream Sequences Other than AAUAAA are Required for Efficient Messenger RNA 3'—End Formation in Plants," *The Plant Cell* 2:1261-1272.
Monson, R.K. et al. (1992). "Relationships Among Isoprene Emission Rate, Photosynthesis, and Isoprene Synthase Activity as Influenced by Temperature," *Plant Physiol.* 98:1175-1180.
Munroe, D. et al. (1990). "Tales of Poly(A): a Review," *Gene* 91:151-158.
Murray, E.E. et al. (1989). "Codon Usage in Plant Genes," *Nucleic Acids Research* 17(2): 477-498.
Nakamura, C.E. et al. (2003). "Metabolic Engineering for the Microbial Production of 1,3-Propanediol," *Current Opinion in Biotechnology* 14:454-459.
Nanchen, A. et al. (Apr. 2008, e-pub. Jan. 25, 2008). "Cyclic AMP-Dependent Catabolite Repression is the Dominant Control Mechanism of Metabolic Fluxes Under Glucose Limitation in *Escherichia coil," Journal of Bacteriology* 190(7):2323-2330.
Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl Acad. Sci.* 91:12760-12764.
Needleman, S. B. et al. (1970). "A General Method Applicable to the Search for Similarities in the Amino Acid Sequence of Two Proteins," *J. Mol Biol.* 48:443-453.
Neidhardt, F.C. et al. (Sep. 1974). "Culture Medium for Enterobacteria," *J. Bacteriology* 119(3):736-747.
Neidhardt, F.C. et al. (1990). "Table 1. Overall Macromolecular Composition of an Average *E. coli B/r Cell*[a]," in Chapter 1 in *Physiology of the Bacterial Cell, : A Molecular Approach*, Sinauer Associates, Inc.: Sunderland, MA, pp. 4.
Nevalainen, K.M.H. et al. (1992). "The Molecular Biology of *Trichoderma* and Its Application to *the Expression of Both Homologous and Heterologous Genes,"* Chapter 6 in *Molecular Industrial Mycology, Systems and Applications for Filamentous Fungi*, Leong, S.A. et al. eds., Marcel Dekker Inc.: New York, NY, pp. 129-148.
Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli," Biotechnology and Bioengineering* 95(4):684-691.
Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.
Nielsen, K.M. et al. (1997). "Analysis and Developmental Profile of Carotenoid Pigments in Petals of Three Yellow Petunia Cultivars," *Scientia Horticulturae* 71:257-266.
Niinemets, O. et al. (Nov. 2002). "Stomatal Constraints May Affect Emission of Oxygenated Monoterpenoids from the Foliage of *Pinus pinea," Plant Physiology* 130:1371-1385.
Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnology and Bioengineering* 68(3):316-327.
Nunberg, J.H. et al. (Nov. 1984). "Molecular Cloning and Characterization of the Glucoamylase Gene of *Aspergillus awamori," Mol. Cell. Biol.* 4(11):2306-2315.
Oh, M-K. et al. (Apr. 12, 2002). "Global Expression Profiling of Acetate-Grown *Escherichia coli," The Journal of Biological Chemistry* 277(15):13175-13183.

(56) References Cited

OTHER PUBLICATIONS

Ondrey, G. et al. (Oct. 2008). "Bio-Based Isoprene," *Chemical Engineering, Access Intelligence Association*, Rockville, MA, 115(1):14.
Oulmouden, A. et al. (1991). "Nucleotide Sequence of the ERG12 Gene of *Saccharomyces cerevisiae* Encoding Mevalonate Kinase," *Curr. Genet.* 19:9-14.
Pachuk, C.J. et al. (2000). "Chain Reaction Cloning: A One-Step Method for Directional Ligation of Multiple DNA Fragments," *Gene* 243:19-25.
Pearson, W.R. et al. (Apr. 1988). "Improved Tools for Biological Sequence Comparison," *Proc. Natl. Acad. Sci. USA* 85:2444-2448.
Pegg, S.C.-H. et al. (2006). "Leveraging Enzyme Structure-Function Relationships for Functional Inference and Experimental Design: The Structure-Function Linkage Database," *Biochemistry* 45:2545-2555.
Penttila, M. et al. (1987). "A Versatile Transformation System for the Cellulolytic Filamentous Fungus *Trichoderma reesei*," *Gene* 61:155-164.
Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., *American Society for Microbiology*: Washington, D.C., pp. 615-624.
Phan, R.M. et al. (2001, e-pub. Sep. 13, 2001). "Synthesis of (S)-Isoprenoid Thiodiphosphates as Substrates and Inhibitors," *J. Org. Chem.* 66(20):6705-6710.
Phillips, T.A. et al. (Jul. 1984). "Ion Gene Product of *Escherichia coli* is a Heat-Shock Protein," *Journal of Bacteriology* 159(1):283-287.
Phue, J-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.
Phue, J-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.
Pilloff, D. et al. (Feb. 14, 2003). "The Kinetic Mechanism of Phosphomevalonate Kinase," *The Journal of Biological Chemistry* 278(7):4510-4515.
Pitera, D.J. et al. (2007, e-pub. Nov. 23, 2006). "Balancing a Heterologous Mevalonate Pathway for Improved Isoprenoid Production in *Escherichia coli*," *Metabolic Engineering* 9:193-207.
Pommer, H. et al. (1975). "Industrial Synthesis of Terpene Compounds," *Pure and Applied Chemistry* 43(3-4):527-551.
Potter, D. et al. (Oct. 10, 1997). "Identification of Catalytic Residues in Human Mevalonate Kinase," *The Journal of Biological Chemistry* 272(41):25449-25454.
Pourquie, J. et al. (1988). "Scale Up of Cellulase Production and Utilization," in *Biochemistry and Genetics of Cellulose Degradation*, Aubert, J.-P. et al. eds., *Academic Press:* San Diego, CA, pp. 71-86.
Proudfoot, N. (Feb. 22, 1991). "Poly(A) Signals," *Cell* 64:671-674.
Ramos-Valdivia, A.C. et al. (1997). "Isopentenyl Diphosphate Isomerase: A Core Enzyme in Isoprenoid Biosynthesis: A Review of its Biochemistry and Function," *Natural Product Reports* 6:591-603.
Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.
Re, E.B. et al. (1995). "Co-Expression of Native and Introduced Genes Reveals Cryptic Regulation of HMG CoA Reductase Expression in *Arabidopsis*," *The Plant Journal* 7(5):771-784.
Reiling, K.K. et al. (Jul. 20, 2004, e-pub. Jun. 18, 2004). "Mono and Diterpene Production in *Escherichia coli*," *Biotechnology and Bioengineering* 87(2):200-212.
Rodr1guez-Concepcion, M. et al. (2000). "Genetic Evidence of Branching in the Isoprenoid Pathway for the Production of Isopentenyl Diphosphate and Dimethylallyl Diphosphate in *Escherichia coll.*," *FEBS Letters* 473:328-332.
Rodr1guez-Concepcion, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.
Rodriguez-Villalon, A. et al. (2008). "Carotenoid Accumulation in Bacteria with Enhanced Supply of Isoprenoid Precursors by Upregulation of Exogenous or Endogenous Pathways," *Journal of Biotechnology* 135:78-84.
Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-C-Methylerythritol," *PNAS* 96(21):11758-11763.
Rohdich, F. et al. (Jun. 6, 2000). "Biosynthesis of Terpenoids: 4-Diphosphocytidyl-2C-Methyl-D-Erythritol Synthase of *Arabidopsis thaliana*," *PNAS* 97(12):6451-6456.
Rohmer, M. (1998). "Isoprenoid Biosynthesis Via the Mevalonate-Independent Route, a Novel Target for Antibacterial Drugs?" *Progress in Drug Research* 50:137-154.
Rohrich, R.C. et al. (2005, e-pub. Nov. 2, 2005). "Reconstitution of an Apicoplast-Localised Electron Transfer Pathway Involved in the Isoprenoid Biosynthesis of Plasmodium falciparum," *FEBS Letters* 579:6433-6438.
Rondon, M.R. et al. (May 1999). "Toward Functional Genomics in Bacteria: Analysis of Gene Expression in *Escherichia coli* from a Bacterial Artificial Chromosome Library of *Bacillus cereus*," *Proc. Natl. Acad. Sci. USA* 96:6451-6455.
Rosenfeld, J. et al. (1992). "In-Gel Digestion of Proteins for Internal Sequence Analysis After One- or Two-Dimensional Gel Electrophoresis," *Analytical Biochemistry* 203:173-179.
Rost, B. et al. (2004). "The PredictProtein Server," *Nucleic Acids Research* 32:W321-W326.
Sambrook, J. et al. (1989). Molecular Cloning: A Laboratory Manual, 2nd edition, Cold Spring Harbor Laboratory Press: New York, NY, pp. xi-xxxviii (Table of Contents Only).
Sanchez, C. et al. (Apr. 2002). "The Biosynthetic Gene Cluster for the Antitumor Rebeccamycin: Characterization and Generation of Indolocarbazole Derivatives," *Chemistry and Biology* 9(4):519-531.
Sander, R. (Apr. 8, 1999). *Compilation of Henry's Law Constants for Inorganic and Organic Species of Potential Importance in Environmental Chemistry*, 3:1-107.
Sanfacon, H. et al. (1991). "A Dissection of the Cauliflower Mosaic Virus Polyadenylation Signal," *Genes & Development* 5:141-149.
Sasaki, K. et al. (2005, e-pub. Apr. 7, 2005). "Gene Expression and Characterization of Isoprene Synthase from Populus alba," *FEBS Letters* 579:2514-2518.
Schneider, D. et al. (Jul. 9, 2002). "Genomic Comparisons Among *Escherichia coli* Strains B, K-12, and 0157:H7 Using IS Elements as Molecular Markers," *BMC Microbiology* 2:18, 8 pages.
Schnitzler, J.-P. et al. (2005, e-pub. Jul. 29, 2005). "Biochemical Properties of Isoprene Synthase in Poplar (*Populus x canescens*)," *Planta* 222(5):777-786.
Scholler, C. et al. (1997). "Volatile Metabolites from some Gram-Negative Bacteria," *Chemosphere* 35(7):1487-1495.
Scott, E. et al. (2007, e-pub. Mar. 27, 2007). "Biomass in the Manufacture of Industrial Products—The Use of Proteins and Amino Acids," *Appl Microbiol. Biotechnol.* 75:751-762.
Sen, S. et al. (2007). "Developments in Directed Evolution for Improving Enzyme Functions," *AppL Biochem. Biotechnol.* 143:212-223.
Serino, G. et al. (1997). "A Negative Selection Scheme Based on the Expression of Cytosine Deaminase in Plastids," *The Plant Journal* 12(3):697-701.
Sharkey, T.D. et al. (Feb. 1, 2005). "Supplemental data for: Evolution of the Isoprene Biosynthetic Pathway in Kudzu," *Plant Physiology* 137(2):700-712.
Sharkey, T.D. et al. (Feb. 2005). "Evolution of the Isoprene Biosynthetic Pathway in Kudzu," *Plant Physiology* 137:700-712.

(56) References Cited

OTHER PUBLICATIONS

Sheir-Neiss, G. et al. (Jul. 1984). "Characterization of the Secreted Cellulases of Trichoderma reesei Wild Type and Mutants During Controlled Fermentations," *Appl. Microbiol. Biotechnol.* 20(1):46-53.
Shelton, D. et al. (2004, e-pub. Nov. 26, 2004). "Isolation and Partial Characterization of a Putative Monoterpene Synthase from *Melaleuca alternifolia," Plant Physiology and Biochemistry* 42:875-882.
Shinozaki, K. et al. (1986). "The Complete Nucleotide Sequence of the Tobacco Chloroplast Genome: its Gene Organization and Expression," *The EMBO Journal* 5(9):2043-2049.
Shirk, M.C. et al. (2002, e-pub. Jul. 27, 2002). "Isoprene Formation in *Bacillus subtilis*: A Barometer of Central Carbon Assimilation in a Bioreactor?" *Biotechnol. Prog.* 18(5):1109-1115.
Silver, G.M. et al. (1991). "Enzymatic Synthesis of Isoprene from Dimethylallyl Diphosphate in Aspen Leaf Extracts," *Plant Physiol.* 97:1588-1591.
Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.
Sivy, T.L. et al. (2002). "Isoprene Synthase Activity Parallels Fluctuations of Isoprene Release During Growth of *Bacillus subtilis," Biochemical and Biophysical Research Communications* 294:71-75.
Siwko, M.E. et al. (2007, e-pub. Oct. 4, 2006). "Does Isoprene Protect Plant Membranes from Thermal Shock? A Molecular Dynamics Study," *Biochimica et Biophysica Acta* 1768:198-206.
Slabinski, L. et al. (2007). "The Challenge of Protein Structure Determination-Lessons from Structural Genomics," *Protein Science* 16:2472-2482.
Slater, S. et al. (Apr. 1992). "Production of Poly-(3-Hydroxybutyrate-Co-3-Hydroxyvalerate) in a Recombinant *Escherichia coli* Strain," *Applied and Environmental Microbiology* 58(4):1089-1094.
Slater, S. et al. (Oct. 1999). "Metabolic Engineering of *Arabidopsis* and *Brassica* for Poly(3-Hydroxybutyrate-co-3-Hydroxyvalerate) Copolymer Production," *Nature Biotechnology* 17:1011-1016.
Smit, A. et al. (2000). "Biosynthesis of Isoprenoids Via Mevalonate in Archaea: The Lost Pathway," *Genome Research* 10:1468-1484.
Smith, T. et al. (1981). "Comparison of Biosequences." *Advances in Applied Mathematics* 2:482-489.
Sprenger, G.A. et al. (Nov. 1997). "Identification of a Thiamin-Dependent Synthase in *Escherichia coli* Required for the Formation of the 1-Deoxy-D-Xylulose 5-Phosphate Precursor to Isoprenoids, Thiamin, and Pyridoxol," *Proc. Natl. Acad. Sci. USA* 94:12857-12862.
Starks, C.M. et al. (Sep. 19, 1997). "Structural Basis for Cyclic Terpene Biosynthesis by Tobacco 5-Epi-Aristolochene Synthase," *Science* 277:1815-1820.
Staub, J. M. et al. (1995). "Expression of a Chimeric uidA Gene Indicates that Polycistronic mRNAs are Efficiently Translated in Tobacco Plastids," *The Plant Journal* 7(5):845-848.
Staub, J. M. et al. (Mar. 2000). "High-Yield Production of a Human Therapeutic Protein in Tobacco Chloroplast," *Nature Biotechnology* 18:333-338.
Steinbuchel, A. (2003). "Production of Rubber-Like Polymers by Microorganisms," *Current Opinion in Microbiology* 6:261-270.
Steller, I. et al. (1997). "An Algorithm for Automatic Indexing of Oscillation Images using Fourier Analysis," *Journal of Applied Crystallography* 30:1036.1040.
Stermer, B.A. et al. (1994). "Regulation of HMG-CoA Reductase Activity in Plants," *Journal of Lipid Research* 35:1133-1140.
Stevens, D.R. et al. (1997). "Genetic Engineering of Eukaryotic Algae: Progress and Prospects," *J. Phycol.* 33:713-722.
Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.
Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *Journal of Bacteriology* 184(15):4065-4070.
Takagi, M. et al. (Aug. 2000). "A Gene Cluster for the Mevalonate Pathway from *Streptomyces* sp. Strain CL190," *Journal of Bacteriology* 182(15):4153-4157.
Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.
Takara Bio Inc. (Feb. 2008). "Chaperon Plasmid Set," Cat. # 3340, pp. 1-8.
Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.
Thomas, F. et al. (1988). "Expression of the rp123, rp12 and rps19 Genes in Spinach Chloroplasts," *Nucleic Acids Research* 16(6):2461-2472.
Thomason, L.C. et al. (2007, e-pub. Apr. 16, 2007). "Multicopy Plasmid Modification with Phage A Red Recombineering," *Plasmid* 58:148-158.
Thouvenot, B. et al. (2004). "The Strong Efficiency of the *Escherichia coli* gapA P1 Promoter Depends on a Complex Combination of Functional Determinants," *Biochem. J.* 383:371-382.
Timberlake, W.E. (1991). "Gene Cloning and Analysis" in Chapter 3 in *More Gene Manipulations in Fungi*, Bennett et al. eds., *Academic Press*: San Diego, CA, pp. 70-76.
Toriyama, K. et al. (1985). "Cell Suspension and Protoplast Culture in Rice," *Plant Science* 41:179-183.
Tsay, Y.H. et al. (Feb. 1991). "Cloning and Characterization of ERG8, an Essential Gene of *Saccharomyces cerevisiae* That Encodes Phosphomevalonate Kinase," *Molecular and Cellular Biology* 11(2):620-631.
Tsudsuki, T. (Apr. 24, 1988) "Direct submission, bases 1-155939", *Data Processing Center*, 1998, Aichi-Gakuin University, Aixhi, Japan, 12 pages.
UniProt Database Accession No. A2XGY9, located at <http://www.uniprot.org/uniprot/A2XGY9.txt>, last visited on Aug. 25, 2015, 2 pages.
UniProt Database Accession No. A5AR04, located at <http://www.uniprot.org/uniprot/A5AR04.txt, last visited on Aug. 25, 2015, 2 pages.
UniProt Database Accession No. A5B7V4, located at <http://www.uniprot.org/uniprot/A5B7V4.txt>, last visited on Aug. 25, 2015, 2 pages.
UniProt Database Accession No. A5BKK1, located at < http://www.uniprot.org/uniprot/A5BKK1.txt>, last visited on Aug. 25, 2015, 2 pages.
UniProt Database Accession No. A5BLS5, located at < http://www.unipro.torg/uniprot/A5BLS5.txt>, last visited on Aug. 25, 2015, 2 pages.
UniProt Database Accession No. A9PGR5, located at <http://www.uniprot.org/uniprot/A9PGR5.txt>, last visited on Aug. 25, 2015 1 page.
UniProt Database Accession No. B1 P189, last updated Jul. 27, 2011, located at <http://www.uniprotorgiobs/201109112CDIFX17BK.txt>, last visited on Sep. 11, 2011, 1 page.
UniProt Database Accession No. B3GEM8, located at <http://www.uniprot.org/uniprot/B3GEM8.txt>, last visited on Aug. 25, 2015, 1 page.
UniProt Database Accession No. B3TPQ7, located at < http://www.uniprot.org/uniprot/B3TPQ7.txt>, last visited Aug. 25, 2015, 2 pages.
UniProt Database Accession No. B7FL16, last updated Jul. 27, 2011, located at <http://www.uniprotorg/jobs/20110911315BAXCRQU.txt>, last visited on Sep. 11, 2011, 1 page.
UniProt Database Accession No. B9HE95, located at <http://www.uniprot.org/uniprot/B9HE95.txt,> last visited on Aug. 25, 2015, 2 pages.

(56) References Cited

OTHER PUBLICATIONS

UniProt Database Accession No. B9MXU1, last updated Jul. 27, 2011, located at <http://www.uniprotorg/jobs/201109112CDIFV8DIC.txt>, last visited on Sep. 11, 2011, 2 pages.

UniProt Database Accession No. B9PAP5, last updated Jul. 27, 2011, located at <http://www.uniprotorg/jobs/201109112CDIG1HNFH.txt>, last visited on Sep. 11, 2011, 2 pages.

UniProt Database Accession No. B9RPM0, located at < http://www.uniprot.org/uniprot/B9RPM0.txt>, last visited Aug. 25, 2015, 2 pages.

UniProt Database Accession No. B9T537, last updated Nov. 30, 2010, located at <http://www.uniprotorg/jobs/20110911315BB065GR.txt>, last visited on Sep. 11, 2011, 1 page.

UniProt Database Accession No. B9T825, located at <http://www.uniprot.org/uniprot/B9T825.txt>, last visited on Aug. 25, 2015, 2 pages.

UniProt Database Accession No. QOPCI3, last updated Jul. 27, 2011, located at <http://www.uniprotorg/jobs/20110911315BAPL92C.txt>, last visited on Sep. 11, 2011, 1 page.

UniProt Database Accession No. QOPCI4, last updated Jul. 27, 2011, located at <http://www.uniprotorg/jobs/20110911315BAQURQ8.txt>, last visited on Sep. 11, 2011, 1 page.

UniProt Database Accession No. Q50L36, located at <http://www.uniprot.org/uniprot/Q50L36.txt>, last visited on Aug. 25, 2015, 2 pages.

UniProt Database Accession No. Q5SBP1, located at <http://www.uniprot.org/uniprot/Q5SBP1.txt>, last visited on Aug. 25, 2015, 2 pages.

UniProt Database Accession No. Q5SBP2, located at <http://www.uniprot.org/uniprot/Q5SBP2.txt>, last visited on Aug. 25, 2015, 2 pages.

UniProt Database Accession No. Q5SBP4, located at < http://www.uniprot.org/uniprot/Q5SBP4.txt>, last visited on Aug. 25, 2015, 2 pages.

UniProt Database Accession No. Q5UB07, located at < http://www.uniprot.org/uniprot/Q5UB07.txt,> last visited on Aug. 25, 2015, 3 pages.

UniProt Database Accession No. 0672F7, located at < http://www.uniprot.org/uniprot/Q672F7.txt>, last visited on Aug. 25, 2015, 2 pages.

UniProt Database Accession No. Q6EJ97, located at < http://www.uniprot.org/uniprot/Q6EJ97.txt>, last visited on Aug. 25, 2015, 2 pages.

UniProt Database Accession No. Q6PWU1, located at < http://www.uniprot.org/uniprot/Q6PWU2.txt>, last visited on Aug. 25, 2015, 2 pages.

UniProt Database Accession No. Q7Y1V1, located at < http://www.uniprot.org/uniprot/Q7Y1V1.txt>, last visited on Aug. 25, 2015, 1 page.

UniProt Database Accession No. 0941 H1, last updated Jul. 27, 2011, located at <http://www.uniprotorg/jobs/201109112CDIG6PW6Y.txt>, last visited on Sep. 11, 2011, 1 page.

UniProt Database Accession No. Q9AR86, located at <http://www.uniprot.org/uniprot/Q9AR86.txt>, last visited on Aug. 25, 2015 2 pages.

UniProt Database Accession No. Q9LIA1; Q84UU7, located at <http://www.uniprot.org/uniprot/Q9LIA1.txt>, last visited on Aug. 25, 2015, 3 pages.

UniProt Database Accession No. Q9LRZ6, located at < http://www.uniprot.org/uniprot/Q9LRZ6.txt>, last visited on Aug. 25, 2015, 3 pages.

UniProt Database Accession No. Q7XAS7, located at <http://www.unipro.torg/uniprot/Q7XAS7.txt>, last visited on Aug. 25, 2015, 2 pages.

UniProt Database Accession No. Q9FQ26, located at <http://www.uniprot.org/uniprot/Q9FQ26.txt>, last visited on Aug. 25, 2015, 1 page.

Vadali, R.V. et al. (2005, e-pub. Sep. 2, 2005). "Enhanced Lycopene Productivity by Manipulation of Carbon Flow to Isopentenyl Diphosphate in *Escherichia coli," Biotechnol. Prog.* 21 (5):1558-1561.

Vagin, A. et al. (1997). "*MOLREP*: An Automated Program for Molecular Replacement," *Journal of Applied Crystallography* 30:1022-1025.

Vandamme, E.J. et al. (2002, e-pub. 2002). "Bioflavours and Fragrances Via Fermentation and Biocatalysis," *Journal of Chemical Technology and Biotechnology* 77:1323-1332.

Van Den Hondel, C.A.M.J.J. et al. (1991). "Heterologous Gene Expression in Filamentous Fungi," Chapter 18 in *More Gene Manipulations in Fungi*, Bennett, J.W. et al. eds., *Academic Press, Inc.*: San Diego, CA, pp. 396-428.

Van De Walle, M. et al. (Jan. 5, 1998). "Proposed Mechanism of Acetate Accumulation in Two Recombinant *Escherichia coli* Strains During High Density Fermentation," *Biotechnology and Bioengineering* 57(1):71-78.

Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.

Vane, L.M. (2005, e-pub. Apr. 21, 2005). "A Review of Pervaporation for Product Recovery from Biomass Fermentation Processes," *Journal of Chemical Technology and Biotechnology* 80:603-629.

Velikova, V. et al. (2005). "Consequences of Inhibition of Isoprene Synthesis in *Phragmites australis* Leaves Exposed to Elevated Temperatures," *Agriculture, Ecosystems & Environment* 106:209-217.

Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.

Voss, S. et al. (1997). "Mutagenesis of a Flexible Loop in Streptavidin Leads to Higher Affinity for the Strep-tag II Peptide and Improved Performance in Recombinant Protein Purification," *Protein Engineering* 10(8):975-982.

Voynova, N. E. et al. (Jan. 2004). "*Staphylococcus aureus* Mevalonate Kinase: Isolation and Characterization of an Enzyme of the Isoprenoid Biosyntheitc Pathway," *Journal of Bacteriology* 186(1):61-67.

Wagner, W.P. et al. (Aug. 1999). "Three Distinct Phases of Isoprene Formation During Growth and Sporulation of *Bacillus subtilis," Journal of Bacteriology* 181(15):4700-4703.

Wagner, W.P. et al. (Jan. 2000, e-pub. Nov. 18, 1999). "Isoprene Biosynthesis in *Bacillus subtilis* Via the Methylerythritol Phosphate Pathway," *J. Nat. Prod.* 63(1):37-40.

Wang, C-W. et al. (Jan. 20, 1999). "Engineered Isoprenoid Pathway Enhances Astaxanthin Production in Escherichia coli," *Biotechnology and Bioengineering* 62(2):235-241.

Ward, M. et al. (Aug. 1993). "Use of *Aspergillus* Overproducing Mutants, Cured for Integrated Plasm id, to Overproduce Heterologous Proteins," *Appl. Microbial. Biotechnol.* 39(6):738-743.

Weissermel, K. et al. (2003). *Industrial Organic Chemistry, 4th, Completely Revised Edition*, translated by Lindley, C.R. et al., Wiley-VCH GmbH & Co. KGaA, Weinheim, Germany, pp. 117-222.

Whisstock, J.C. et al. (2003). "Prediction of Protein Function from Protein Sequence and Structure," *Quarterly Reviews of Biophysics* 36(3):307-340.

Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.

Wildermuth, M.C. et al. (1998). "Biochemical Characterization of Stromal and Thylakoid-Bound Isoforms of Isoprene Synthase in Willow Leaves," *Plant Physiology* 116:1111-1123.

Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.

Wilkins, K. (1996). "Volatile Metabolites from Actinomycetes," *Chemosphere* 32(7):1427-1434.

Williams, D.C. et al. (1998). "Truncation of Limonene Synthase Preprotein Provides a Fully Active 'Pseudomature' Form of This

(56) References Cited

OTHER PUBLICATIONS

Monoterpene Cyclase and Reveals the Function of the Amino-Terminal Arginine Pair," *Biochemistry* 37(35):12213-12220.
Wishart, M.J. et al. (Nov. 10, 1995). "A Single Mutation Converts a Novel Phosphotyrosine Binding Domain into a Dual-Specificity Phosphatase," *The Journal of Biological Chemistry* 270(45):26782-26785.
Withers, S.T. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.
Witkowski, A. et al. (1999, e-pub. Aug. 18, 1999). "Conversion of p-Ketoacyl Synthase to a Malonyl Decarboxylase by Replacement of the Active-Site Cysteine with Glutamine," *Biochemistry* 38(36):11643-11650.
Wolfertz, M. et al. (2003). "Biochemical Regulation of Isoprene Emission," *Plant, Cell and Environment* 26:1357-1364.
Wolfertz, M. et al. (Aug. 2004). "Rapid Regulation of the Methylerythritol 4-Phosphate Pathway During Isoprene Synthesis," *Plant Physiology* 135:1939-1945.
Wu, D.Y. et al. (1989). "The Ligation Amplification Reaction (LAR)-Amplification of Specific DNA Sequences Using Sequential Rounds of Template-Dependent Ligation," *Genomics* 4:560-569.
Xia, X-X. et al. (2008). "Comparison of the Extracellular Proteomes of *Escherichia coli* B and K-12 Strains During High Cell Density Cultivation," *Proteomics* 8:1-15.
Yamada, K. et al. (1989). "Production of Glycerol from Methanol by a Mutant Strain of *Candida boidinii* No. 2201," Agric. Biol. Chem. 53(2):541-543.
Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.
Ye, X. et al. (Jan. 14, 2000). "Engineering the Provitamin A ((3-Carotene) Biosynthetic Pathway into (Carotenoid-Free) Rice Endosperm," *Science* 287:303-305.
Yelton, M.M. et al. (Mar. 1984). "Transformation of *Aspergillus nidulans* by Using a trpC Plasmid," *Proc. Natl. Acad. Sci. USA* 81:1470-1474.
Yoon, S-H. et al. (2007, e-pub. May 15, 2007). "Increased /3-Carotene Production in Recombinant *Escherichia coli* Harboring an Engineered Isoprenoid Precursor Pathway with Mevalonate Addition," *Biotechnol. Prog.* 23(3):599-605.
Yoon, S-H. et al. (2009). "Combinatorial Expression of Bacterial Whole Mevalonate Pathway for the Production of I3-Carotene in *E. coli,*" *Journal of Biotechnology* 140:218-226.
Zepeck, F. et al. (2005, e-pub. Oct. 14, 2005). "Biosynthesis of Isoprenoids. Purification and Properties of IspG Protein from *Escherichia coli,*" *J. Org. Chem.* 70:9168-9174.
Brüggemann, N. et al. (Oct. 2002). "Relationship of isopentenyl diphosphate (IDP) isomerase activity to isoprene emission of oak leaves," *Tree Physiol* 22(14):1011-1018.
Horbach, S. et al. (Aug. 1993). "Isoprenoid biosynthesis in bacteria: two different pathways?" *FEMS Microbiol Lett* 111(2-3):135-140.
Lange, B.M. et al. (Nov. 21, 2000). "Isoprenoid biosynthesis: the evolution of two ancient and distinct pathways across genomes," *PNAS USA* 97(24):13172-13177.
Sivy, T. et al. (May 2002). "Isoprene synthase activity parallels fluctuations of isoprene release during growth of Bacillus subtilis," *Biochemical and Biophysical Research Communications* 294(1):71-75.

* cited by examiner

*atg*tgtgcgacctcttctcaatttactcagattaccgagcataattcccgtcgttccgcaaact
atcagccaaacctgtggaatttcgaattcctgcaatccctggagaacgacctgaaagtggaaaa
gctggaggagaaagcgaccaaactggaggaagaagttcgctgcatgatcaaccgtgtagacacc
cagccgctgtccctgctggagctgatcgacgatgtgcagcgcctgggtctgacctacaaatttg
aaaaagacatcattaaagccctggaaaacatcgtactgctggacgaaaacaaaaagaacaaatc
tgacctgcacgcaaccgctctgtctttccgtctgctgcgtcagcacggtttcgaggtttctcag
gatgttttgagcgtttcaaggataaagaaggtggtttcagcggtgaactgaaaggtgacgtcc
aaggcctgctgagcctgtatgaagcgtcttacctgggtttcgagggtgagaacctgctggagga
ggcgcgtaccttttccatcacccacctgaagaacaacctgaaagaaggcattaataccaaggtt
gcagaacaagtgagccacgccctggaactgccatatcaccagcgtctgcaccgtctggaggcac
gttggttcctggataaatacgaaccgaaagaaccgcatcaccagctgctgctggagctggcgaa
gctggattttaacatggtacagaccctgcaccagaaagagctgcaagatctgtcccgctggtgg
accgagatgggcctggctagcaaactggattttgtacgcgaccgcctgatggaagtttatttct
gggcactgggtatggcgccagacccgcagtttggtgaatgtcgcaaagctgttactaaaatgtt
tggtctggtgacgatcatcgatgacgtgtatgacgtttatggcactctggacgaactgcaactg
ttcaccgatgctgtagagcgctgggacgttaacgctattaacaccctgccggactatatgaaac
tgtgtttcctggcactgtacaacaccgttaacgacacgtcctattctattctgaaagagaaagg
tcataacaacctgtcctatctgacgaaaagctggcgtgaactgtgcaaagcctttctgcaagag
gcgaaatggtccaacaacaaaattatcccggctttctccaagtacctggaaaacgccagcgttt
cctcctccggtgtagcgctgctggcgccgtcttacttttccgtatgccagcagcaggaagacat
ctccgaccacgcgctgcgttccctgaccgacttccatggtctggtgcgttctagctgcgttatc
ttccgcctgtgcaacgatctggccacctctgcggcggagctggaacgtggcgagactaccaatt
ctatcattagctacatgcacgaaaacgatggtaccagcgaggaacaggcccgcgaagaactgcg
taaactgatcgacgccgaatggaaaaagatgaatcgtgaacgcgttagcgactccaccctgctg
cctaaagcgttcatggaaatcgcagttaacatggcacgtgtttcccactgcacctaccagtatg
gcgatggtctgggtcgcccagactacgcgactgaaaaccgcatcaaactgctgctgattgaccc
tttcccgattaaccagctgatgtatgtc
taactgcag
(SEQ ID NO:1)

FIG. 3A

1- gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccATGtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtacctttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtcTAActgca
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg

FIG. 3B agggtggcgggcaggacgcccgccataaactgccaggcatcaaattaagcagaaggccatcctg
acggatggcctttttgcgtttctacaaactctttttgtttatttttctaaatacattcaaatat
gtatccgctcatgagacaataaccctgataaatgcttcaataatattgaaaaaggaagagtatg
agtattcaacatttccgtgtcgcccttattcccttttttgcggcattttgccttcctgtttttg
ctcacccagaaacgctggtgaaagtaaaagatgctgaagatcagttgggtgcacgagtgggtta
catcgaactggatctcaacagcggtaagatccttgagagttttcgccccgaagaacgttttcca
atgatgagcacttttaaagttctgctatgtggcgcggtattatcccgtgttgacgccgggcaag
agcaactcggtcgccgcatacactattctcagaatgacttggttgagtactcaccagtcacaga
aaagcatcttacggatggcatgacagtaagagaattatgcagtgctgccataaccatgagtgat
aacactgcggccaacttacttctgacaacgatcggaggaccgaaggagctaaccgcttttttgc
acaacatgggggatcatgtaactcgccttgatcgttgggaaccggagctgaatgaagccatacc
aaacgacgagcgtgacaccacgatgcctgtagcaatggcaacaacgttgcgcaaactattaact
ggcgaactacttactctagcttcccggcaacaattaatagactggatggaggcggataaagttg
caggaccacttctgcgctcggcccttccggctggctggtttattgctgataaatctggagccgg
tgagcgtgggtctcgcggtatcattgcagcactggggccagatggtaagccctcccgtatcgta
gttatctacacgacggggagtcaggcaactatggatgaacgaaatagacagatcgctgagatag
gtgcctcactgattaagcattggtaactgtcagaccaagtttactcatatatactttagattga
tttaaaacttcatttttaatttaaaaggatctaggtgaagatcctttttgataatctcatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct

FIG. 3C

Gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
(SEQ ID NO:2)

FIG. 5A 1-
ttctcatgtttgacagcttatcatcgataagctttaatgcggtagtttatcacagttaaattgc
taacgcagtcaggcaccgtgtatgaaatctaacaatgcgctcatcgtcatcctcggcaccgtca
ccctggatgctgtaggcataggcttggttatgccggtactgccgggcctcttgcgggatatccg
gatatagttcctcctttcagcaaaaaacccctcaagacccgtttagaggccccaaggggttatg
ctagttattgctcagcggtggcagcagccaactcagcttcctttcgggctttgttagcagccgg
atccctgcagttagacatacatcagctggttaatcgggaaagggtcaatcagcagcagtttgat
gcggttttcagtcgcgtagtctgggcgacccagaccatcgccatactggtaggtgcagtgggaa
acacgtgccatgttaactgcgatttccatgaacgctttaggcagcagggtggagtcgctaacgc
gttcacgattcatctttttccattcggcgtcgatcagtttacgcagttcttcgcgggcctgttc
ctcgctggtaccatcgtttcgtgcatgtagctaatgatagaattggtagtctcgccacgttcc
agctccgccgcagaggtggccagatcgttgcacaggcggaagataacgcagctagaacgcacca
gaccatggaagtcggtcagggaacgcagcgcgtggtcggagatgtcttcctgctgctggcatac
ggaaaagtaagacggcgccagcagcgctacaccggaggaggaaacgctggcgttttccaggtac
ttggagaaagccgggataatttgttgttggaccatttcgcctcttgcagaaaggctttgcaca
gttcacgccagcttttcgtcagataggacaggttgttatgacctttctctttcagaatagaata
ggacgtgtcgttaacggtgttgtacagtgccaggaaacacagtttcatatagtccggcagggtg
ttaatagcgttaacgtcccagcgctctacagcatcggtgaacagttgcagttcgtccagagtgc
cataaacgtcatacacgtcatcgatgatcgtcaccagaccaaacatttagtaacagctttgcg
acattcaccaaactgcgggtctggcgccatacccagtgcccagaaataaacttccatcaggcgg
tcgcgtacaaaatccagtttgctagccaggcccatctcggtccaccagcgggacagatcttgca
gctctttctggtgcagggtctgtaccatgttaaaatccagcttcgccagctccagcagcagctg
gtgatgcggttctttcggttcgtatttatccaggaaccaacgtgcctccagacggtgcagacgc
tggtgatatggcagttccagggcgtggctcacttgttctgcaaccttggtattaatgccttctt
tcaggttgttcttcaggtgggtgatggaaaggtacgcgcctcctccagcaggttctcaccctc
gaaacccaggtaagacgcttcatacaggctcagcaggccttggacgtcacctttcagttcaccg
ctgaaaccaccttctttatccttgaaacgctcaaaaacatcctgagaaacctcgaaaccgtgct
gacgcagcagacggaaagacagagcggttgcgtgcaggtcagatttgttctttttgttttcgtc
cagcagtacgatgttttccagggctttaatgatgtctttttcaaatttgtaggtcagacccagg
cgctgcacatcgtcgatcagctccagcagggacagcggctgggtgtctacacggttgatcatgc
agcgaacttcttcctccagtttggtcgctttctcctccagcttttccactttcaggtcgttctc
cagggattgcaggaattcgaaattccacaggtttggctgatagtttgcggaacgacgggaatta
tgctcggtaatctgagtaaattgagaagaggtcgcacacatatgacgaccttcgatatggccgc
tgctgtgatgatgatgatgatgatgatgatgatggcccatggtatatctccttcttaaagttaa
acaaaattatttctagaggggaattgttatccgctcacaattcccctatagtgagtcgtattaa
tttcgcgggatcgagatctcgatcctctacgccggacgcatcgtggccggcatcaccggcgcca
caggtgcggttgctggcgcctatatcgccgacatcaccgatggggaagatcgggctcgccactt
cgggctcatgagcgcttgtttcggcgtgggtatggtggcaggccccgtggccgggggactgttg
ggcgccatctccttgcatgcaccattccttgcggcggcggtgctcaacggcctcaacctactac
tgggctgcttcctaatgcaggagtcgcataagggagagcgtcgagatcccggacaccatcgaat
ggcgcaaaacctttcgcggtatggcatgatagcgcccggaagagagtcaattcagggtggtgaa
tgtgaaaccagtaacgttatacgatgtcgcagagtatgccggtgtctcttatcagaccgtttcc
cgcgtggtgaaccaggccagccacgtttctgcgaaaacgcgggaaaaagtggaagcggcgatgg
cggagctgaattacattcccaaccgcgtggcacaacaactggcgggcaaacagtcgttgctgat
tggcgttgccacctccagtctggccctgcacgcgccgtcgcaaattgtcgcggcgattaaatct

FIG. 5B cgcgccgatcaactgggtgccagcgtggtggtgtcgatggtagaacgaagcggcgtcgaagcct
gtaaagcggcggtgcacaatcttctcgcgcaacgcgtcagtgggctgatcattaactatccgct
ggatgaccaggatgccattgctgtggaagctgcctgcactaatgttccggcgttatttcttgat
gtctctgaccagacacccatcaacagtattattttctcccatgaagacggtacgcgactgggcg
tggagcatctggtcgcattgggtcaccagcaaatcgcgctgttagcgggcccattaagttctgt
ctcggcgcgtctgcgtctggctggctggcataaatatctcactcgcaatcaaattcagccgata
gcggaacgggaaggcgactggagtgccatgtccggttttcaacaaaccatgcaaatgctgaatg
agggcatcgttcccactgcgatgctggttgccaacgatcagatggcgctgggcgcaatgcgcgc
cattaccgagtccgggctgcgcgttggtgcggatatctcggtagtgggatacgacgataccgaa
gacagctcatgttatatcccgccgttaaccaccatcaaacaggattttcgcctgctggggcaaa
ccagcgtggaccgcttgctgcaactctctcagggccaggcggtgaagggcaatcagctgttgcc
cgtctcactggtgaaaagaaaaaccaccctggcgcccaatacgcaaaccgcctctccccgcgcg
ttggccgattcattaatgcagctggcacgacaggtttcccgactggaaagcgggcagtgagcgc
aacgcaattaatgtaagttagctcactcattaggcaccgggatctcgaccgatgcccttgagag
ccttcaacccagtcagctccttccggtgggcgcggggcatgactatcgtcgccgcacttatgac
tgtcttctttatcatgcaactcgtaggacaggtgccggcagcgctctgggtcattttcggcgag
gaccgctttcgctggagcgcgacgatgatcggcctgtcgcttgcggtattcggaatcttgcacg
ccctcgctcaagccttcgtcactggtcccgccaccaaacgtttcggcgagaagcaggccattat
cgccggcatggcggccgacgcgctgggctacgtcttgctggcgttcgcgacgcgaggctggatg
gccttccccattatgattcttctcgcttccggcggcatcgggatgcccgcgttgcaggccatgc
tgtccaggcaggtagatgacgaccatcagggacagcttcaaggatcgctcgcggctcttaccag
cctaacttcgatcactggaccgctgatcgtcacggcgatttatgccgcctcggcgagcacatgg
aacgggttggcatggattgtaggcgccgccctataccttgtctgcctccccgcgttgcgtcgcg
gtgcatggagccgggccacctcgacctgaatggaagccggcggcacctcgctaacggattcacc
actccaagaattggagccaatcaattcttgcggagaactgtgaatgcgcaaaccaacccttggc
agaacatatccatcgcgtccgccatctccagcagccgcacgcggcgcatctcgggcagcgttgg
gtcctggccacgggtgcgcatgatcgtgctcctgtcgttgaggacccggctaggctggcggggt
tgccttactggttagcagaatgaatcaccgatacgcgagcgaacgtgaagcgactgctgctgca
aaacgtctgcgacctgagcaacaacatgaatggtcttcggtttccgtgtttcgtaaagtctgga
aacgcggaagtcagcgccctgcaccattatgttccggatctgcatcgcaggatgctgctggcta
ccctgtggaacacctacatctgtattaacgaagcgctggcattgaccctgagtgatttttctct
ggtcccgccgcatccataccgccagttgtttaccctcacaacgttccagtaaccgggcatgttc
atcatcagtaacccgtatcgtgagcatcctctctcgtttcatcggtatcattacccccatgaac
agaaatcccccttacacggaggcatcagtgaccaaacaggaaaaaaccgcccttaacatggccc
gctttatcagaagccagacattaacgcttctggagaaactcaacgagctggacgcggatgaaca
ggcagacatctgtgaatcgcttcacgaccacgctgatgagctttaccgcagctgcctcgcgcgt
ttcggtgatgacggtgaaaacctctgacacatgcagctcccggagacggtcacagcttgtctgt
aagcggatgccgggagcagacaagcccgtcagggcgcgtcagcgggtgttggcgggtgtcgggg
cgcagccatgacccagtcacgtagcgatagcggagtgtatactggcttaactatgcggcatcag
agcagattgtactgagagtgcaccatatatgcggtgtgaaataccgcacagatgcgtaaggaga
aaataccgcatcaggcgctcttccgcttcctcgctcactgactcgctgcgctcggtcgttcggc
tgcggcgagcggtatcagctcactcaaaggcggtaatacggttatccacagaatcaggggataa
cgcaggaaagaacatgtgagcaaaaggccagcaaaaggccaggaaccgtaaaaaggccgcgttg
ctggcgtttttccataggctccgcccccctgacgagcatcacaaaaatcgacgctcaagtcaga

FIG. 5C ggtggcgaaacccgacaggactataaagataccaggcgtttccccctggaagctccctcgtgcg
ctctcctgttccgaccctgccgcttaccggatacctgtccgcctttctcccttcgggaagcgtg
gcgctttctcatagctcacgctgtaggtatctcagttcggtgtaggtcgttcgctccaagctgg
gctgtgtgcacgaaccccccgttcagcccgaccgctgcgccttatccggtaactatcgtcttga
gtccaacccggtaagacacgacttatcgccactggcagcagccactggtaacaggattagcaga
gcgaggtatgtaggcggtgctacagagttcttgaagtggtggcctaactacggctacactagaa
ggacagtatttggtatctgcgctctgctgaagccagttaccttcggaaaaagagttggtagctc
ttgatccggcaaacaaaccaccgctggtagcggtggtttttttgtttgcaagcagcagattacg
cgcagaaaaaaaggatctcaagaagatcctttgatcttttctacggggtctgacgctcagtgga
acgaaaactcacgttaagggattttggtcatgagattatcaaaaaggatcttcacctagatcct
tttaaattaaaaatgaagttttaaatcaatctaaagtatatatgagtaaacttggtctgacagt
taccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgga
agggccgagcgcagaagtggtcctgcaactttatccgcctccatccagtctattaattgttgcc
gggaagctagagtaagtagttcgccagttaatagtttgcgcaacgttgttgccattgctgcagg
catcgtggtgtcacgctcgtcgtttggtatggcttcattcagctccggttcccaacgatcaagg
cgagttacatgatcccccatgttgtgcaaaaaagcggttagctccttcggtcctccgatcgttg
tcagaagtaagttggccgcagtgttatcactcatggttatggcagcactgcataattctcttac
tgtcatgccatccgtaagatgcttttctgtgactggtgagtactcaaccaagtcattctgagaa
tagtgtatgcggcgaccgagttgctcttgcccggcgtcaacacgggataataccgcgccacata
gcagaactttaaaagtgctcatcattggaaaacgttcttcggggcgaaaactctcaaggatctt
accgctgttgagatccagttcgatgtaacccactcgtgcacccaactgatcttcagcatctttt
actttcaccagcgtttctgggtgagcaaaaacaggaaggcaaaatgccgcaaaaaagggaataa
gggcgacacggaaatgttgaatactcatactcttcctttttcaatattattgaagcatttatca
gggttattgtctcatgagcggatacatatttgaatgtatttagaaaaataaacaaataggggtt
ccgcgcacatttccccgaaaagtgccacctgacgtctaagaaaccattattatcatgacattaa
cctataaaaataggcgtatcacgaggccctttcgtcttcaagaa
(SEQ ID NO:5)

FIG. 7A 1-
cccgtcttactgtcgggaattcgcgttggccgattcattaatgcagctggcacgacaggtttcc
cgactggaaagcgggcagtgagcgcaacgcaattaatgtgagttagctcactcattaggcaccc
caggctttacactttatgcttccggctcgtatgttgtgtggaattgtgagcggataacaatttc
acacaggaaacagctatgaccatgattacgccaagcttgtatcgattaaataaggaggaataaa
ccatgtgtgcgacctcttctcaatttactcagattaccgagcataattcccgtcgttccgcaaa
ctatcagccaaacctgtggaatttcgaattcctgcaatccctggagaacgacctgaaagtggaa
aagctggaggagaaagcgaccaaactggaggaagaagttcgctgcatgatcaaccgtgtagaca
cccagccgctgtccctgctggagctgatcgacgatgtgcagcgcctgggtctgacctacaaatt
tgaaaaagacatcattaaagccctggaaaacatcgtactgctggacgaaaacaaaaagaacaaa
tctgacctgcacgcaaccgctctgtctttccgtctgctgcgtcagcacggtttcgaggtttctc
aggatgtttttgagcgtttcaaggataaagaaggtggtttcagcggtgaactgaaaggtgacgt
ccaaggcctgctgagcctgtatgaagcgtcttacctgggtttcgagggtgagaacctgctggag
gaggcgcgtacctttttccatcacccacctgaagaacaacctgaaagaaggcattaataccaagg
ttgcagaacaagtgagccacgccctggaactgccatatcaccagcgtctgcaccgtctggaggc
acgttggttcctggataaatacgaaccgaaagaaccgcatcaccagctgctgctggagctggcg
aagctggattttaacatggtacagaccctgcaccagaaagagctgcaagatctgtcccgctggt
ggaccgagatgggcctggctagcaaactggatttgtacgcgaccgcctgatggaagtttattt
ctgggcactgggtatggcgccagacccgcagtttggtgaatgtcgcaaagctgttactaaaatg
tttggtctggtgacgatcatcgatgacgtgtatgacgtttatggcactctggacgaactgcaac
tgttcaccgatgctgtagagcgctgggacgttaacgctattaacaccctgccggactatatgaa
actgtgtttcctggcactgtacaacaccgttaacgacacgtcctattctattctgaaagagaaa
ggtcataacaacctgtcctatctgacgaaaagctggcgtgaactgtgcaaagcctttctgcaag
aggcgaaatggtccaacaacaaaattatcccggctttctccaagtacctggaaaacgccagcgt
ttcctcctccggtgtagcgctgctggcgccgtcttactttttccgtatgccagcagcaggaagac
atctccgaccacgcgctgcgttccctgaccgacttccatggtctggtgcgttctagctgcgtta
tcttccgcctgtgcaacgatctggccacctctgcggcggagctggaacgtggcgagactaccaa
ttctatcattagctacatgcacgaaaacgatggtaccagcgaggaacaggcccgcgaagaactg
cgtaaactgatcgacgccgaatggaaaaagatgaatcgtgaacgcgttagcgactccaccctgc
tgcctaaagcgttcatggaaatcgcagttaacatggcacgtgtttcccactgcacctaccagta
tggcgatggtctgggtcgcccagactacgcgactgaaaaccgcatcaaactgctgctgattgac
cctttcccgattaaccagctgatgtatgtctaactgcaggtcgactctagaggatccccgggta
ccgagctcgaattcactggccgtcgttttacaacgtcgtgactgggaaaaccctggcgttaccc
aacttaatcgccttgcagcacatcccccttcgccagctggcgtaatagcgaagaggcccgcac
cgatcgcccttcccaacagttgcgcagcctgaatggcgaatggcgcctgatgcggtattttctc
cttacgcatctgtgcggtatttcacaccgcatatggtgcactctcagtacaatctgctctgatg
ccgcatagttaagccagccccgacacccgccaacacccgctgacgagcttagtaaagccctcgc
tagattttaatgcggatgttgcgattacttcgccaactattgcgataacaagaaaagccagcc
tttcatgatatatctcccaatttgtgtagggcttattatgcacgcttaaaaataataaaagcag
acttgacctgatagtttggctgtgagcaattatgtgcttagtgcatctaacgcttgagttaagc
cgcgccgcgaagcggcgtcggcttgaacgaattgttagacattatttgccgactaccttggtga
tctcgcctttcacgtagtggacaaattcttccaactgatctgcgcgcgaggccaagcgatcttc
ttcttgtccaagataagcctgtctagcttcaagtatgacgggctgatactgggccggcaggcgc
tccattgcccagtcggcagcgacatccttcggcgcgattttgccggttactgcgctgtaccaaa
tgcgggacaacgtaagcactacatttcgctcatcgccagcccagtcgggcggcgagttccatag

FIG. 7B cgttaaggtttcatttagcgcctcaaatagatcctgttcaggaaccggatcaaagagttcctcc
gccgctggacctaccaaggcaacgctatgttctcttgcttttgtcagcaagatagccagatcaa
tgtcgatcgtggctggctcgaagatacctgcaagaatgtcattgcgctgccattctccaaattg
cagttcgcgcttagctggataacgccacggaatgatgtcgtcgtgcacaacaatggtgacttct
acagcgcggagaatctcgctctctccaggggaagccgaagtttccaaaaggtcgttgatcaaag
ctcgccgcgttgtttcatcaagccttacggtcaccgtaaccagcaaatcaatatcactgtgtgg
cttcaggccgccatccactgcggagccgtacaaatgtacggccagcaacgtcggttcgagatgg
cgctcgatgacgccaactacctctgatagttgagtcgatacttcggcgatcaccgcttccctca
tgatgtttaactttgttttagggcgactgccctgctgcgtaacatcgttgctgctccataacat
caaacatcgacccacggcgtaacgcgcttgctgcttggatgcccgaggcatagactgtacccca
aaaaaacagtcataacaagccatgaaaaccgccactgcgccgttaccaccgctgcgttcggtca
aggttctggaccagttgcgtgagcgcatacgctacttgcattacagcttacgaaccgaacaggc
ttatgtccactgggttcgtgccttcatccgtttccacggtgtgcgtcacccggcaaccttgggc
agcagcgaagtcgaggcatttctgtcctggctggcgaacgagcgcaaggtttcggtctccacgc
atcgtcaggcattggcggccttgctgttcttctacggcaaggtgctgtgcacggatctgccctg
gcttcaggagatcggaagacctcggccgtcgcggcgcttgccggtggtgctgaccccggatgaa
gtggttcgcatcctcggttttctggaaggcgagcatcgtttgttcgcccagcttctgtatggaa
cgggcatgcggatcagtgagggtttgcaactgcgggtcaaggatctggatttcgatcacggcac
gatcatcgtgcgggagggcaagggctccaaggatcgggccttgatgttacccgagagcttggca
cccagcctgcgcgagcaggggaattaattcccacgggttttgctgcccgcaaacgggctgttct
ggtgttgctagtttgttatcagaatcgcagatccggcttcagccggtttgccggctgaaagcgc
tatttcttccagaattgccatgatttttccccacgggaggcgtcactggctcccgtgttgtcg
gcagctttgattcgataagcagcatcgcctgtttcaggctgtctatgtgtgactgttgagctgt
aacaagttgtctcaggtgttcaatttcatgttctagttgctttgttttactggtttcacctgtt
ctattaggtgttacatgctgttcatctgttacattgtcgatctgttcatggtgaacagctttga
atgcaccaaaaactcgtaaaagctctgatgtatctatctttttacaccgttttcatctgtgca
tatggacagttttccctttgatatgtaacggtgaacagttgttctacttttgtttgttagtctt
gatgcttcactgatagatacaagagccataagaacctcagatccttccgtatttagccagtatg
ttctctagtgtggttcgttgttttgcgtgagccatgagaacgaaccattgagatcatacttac
tttgcatgtcactcaaaaattttgcctcaaaactggtgagctgaattttgcagttaaagcatc
gtgtagtgtttttcttagtccgttatgtaggtaggaatctgatgtaatggttgttggtatttg
tcaccattcatttttatctggttgttctcaagttcggttacgagatccatttgtctatctagtt
caacttggaaaatcaacgtatcagtcgggcggcctcgcttatcaaccaccaatttcatattgct
gtaagtgtttaaatctttacttattggtttcaaaacccattggttaagccttttaaactcatgg
tagttattttcaagcattaacatgaacttaaattcatcaaggctaatctctatatttgccttgt
gagttttcttttgtgttagttcttttaataaccactcataaatcctcatagagtatttgttttc
aaaagacttaacatgttccagattatattttatgaatttttttaactggaaaagataaggcaat
atctcttcactaaaaactaattctaatttttcgcttgagaacttggcatagtttgtccactgga
aaatctcaaagcctttaaccaaaggattcctgatttccacagttctcgtcatcagctctctggt
tgctttagctaatacaccataagcattttccctactgatgttcatcatctgagcgtattggtta
taagtgaacgataccgtccgttctttccttgtagggttttcaatcgtggggttgagtagtgcca
cacagcataaaattagcttggtttcatgctccgttaagtcatagcgactaatcgctagttcatt
tgctttgaaaacaactaattcagacatacatctcaattggtctaggtgattttaatcactatac
caattgagatgggctagtcaatgataattactagtcctttcctttgagttgtgggtatctgta

FIG. 7C

Aattctgctagacctttgctggaaaacttgtaaattctgctagaccctctgtaaattccgctag
acctttgtgtgtttttttttgtttatattcaagtggttataatttatagaataaagaaagaataa
aaaaagataaaaagaatagatcccagccctgtgtataactcactactttagtcagttccgcagt
attacaaaaggatgtcgcaaacgctgtttgctcctctacaaaacagaccttaaaaccctaaagg
cttaagtagcaccctcgcaagctcgggcaaatcgctgaatattccttttgtctccgaccatcag
gcacctgagtcgctgtctttttcgtgacattcagttcgctgcgctcacggctctggcagtgaat
gggggtaaatggcactacaggcgccttttatggattcatgcaaggaaactacccataatacaag
aaaagcccgtcacgggcttctcagggcgttttatggcgggtctgctatgtggtgctatctgact
ttttgctgttcagcagttcctgccctctgattttccagtctgaccacttcggattatcccgtga
caggtcattcagactggctaatgcacccagtaaggcagcggtatcatcaacaggctta
(SEQ ID NO:7)

FIG. 12A 1-
gaattgctccattttcttctgctatcaaaataacagactcgtgattttccaaacgagctttcaa
aaaagcctctgccccttgcaaatcggatgcctgtctataaaattcccgatattggttaaacagc
ggcgcaatggcggccgcatctgatgtctttgcttggcgaatgttcatcttatttcttcctccct
ctcaataatttttcattctatcccttttctgtaaagtttattttcagaatacttttatcatc
atgctttgaaaaaatatcacgataatatccattgttctcacggaagcacacgcaggtcatttga
acgaatttttcgacaggaatttgccgggactcaggagcatttaacctaaaaaagcatgacatt
tcagcataatgaacatttactcatgtctattttcgttcttttctgtatgaaaatagttatttcg
agtctctacggaaatagcgagagatgatatacctaaatagagataaaatcatctcaaaaaaatg
ggtctactaaaatattattccatctattacaataaattcacagaatagtcttttaagtaagtct
actctgaatttttttaaaaggagagggtaaagagtgtgtgcgacctcttctcaatttactcaga
ttaccgagcataattcccgtcgttccgcaaactatcagccaaacctgtggaatttcgaattcct
gcaatccctggagaacgacctgaaagtggaaaagctggaggagaaagcgaccaaactggaggaa
gaagttcgctgcatgatcaaccgtgtagacacccagccgctgtccctgctggagctgatcgacg
atgtgcagcgcctgggtctgacctacaaatttgaaaaagacatcattaaagccctggaaaacat
cgtactgctggacgaaaacaaaaagaacaaatctgacctgcacgcaaccgctctgtctttccgt
ctgctgcgtcagcacggtttcgaggtttctcaggatgtttttgagcgtttcaaggataaagaag
gtggtttcagcggtgaactgaaaggtgacgtccaaggcctgctgagcctgtatgaagcgtctta
cctgggtttcgagggtgagaacctgctggaggaggcgcgtacctttttccatcacccacctgaag
aacaacctgaaagaaggcattaataccaaggttgcagaacaagtgagccacgccctggaactgc
catatcaccagcgtctgcaccgtctggaggcacgttggttcctggataaatacgaaccgaaaga
accgcatcaccagctgctgctggagctggcgaagctggattttaacatggtacagaccctgcac
cagaaagagctgcaagatctgtcccgctggtggaccgagatgggcctggctagcaaactggatt
ttgtacgcgaccgcctgatggaagtttatttctgggcactgggtatggcgccagacccgcagtt
tggtgaatgtcgcaaagctgttactaaaatgtttggtctggtgacgatcatcgatgacgtgtat
gacgtttatggcactctggacgaactgcaactgttcaccgatgctgtagagcgctgggacgtta
acgctattaacaccctgccggactatatgaaactgtgtttcctggcactgtacaacaccgttaa
cgacacgtcctattctattctgaaagagaaaggtcataacaacctgtcctatctgacgaaaagc
tggcgtgaactgtgcaaagcctttctgcaagaggcgaaatggtccaacaacaaaattatcccgg
ctttctccaagtacctggaaaacgccagcgtttcctcctccggtgtagcgctgctggcgccgtc
ttacttttccgtatgccagcagcaggaagacatctccgaccacgcgctgcgttccctgaccgac
ttccatggtctggtgcgttctagctgcgttatcttccgcctgtgcaacgatctggccacctctg
cggcggagctggaacgtggcgagactaccaattctatcattagctacatgcacgaaaacgatgg
taccagcgaggaacaggcccgcgaagaactgcgtaaactgatcgacgccgaatggaaaaagatg
aatcgtgaacgcgttagcgactccaccctgctgcctaaagcgttcatggaaatcgcagttaaca
tggcacgtgtttcccactgcacctaccagtatggcgatggtctgggtcgcccagactacgcgac
tgaaaaccgcatcaaactgctgctgattgaccctttcccgattaaccagctgatgtatgtctaa
aaaaaaccggccttggccccgccggtttttttattatttttcttcctccgcatgttcaatccgct
ccataatcgacggatggctccctctgaaaattttaacgagaaacggcgggttgacccggctcag
tcccgtaacggccaagtcctgaaacgtctcaatcgccgcttcccggtttccggtcagctcaatg
ccgtaacggtcggcggcgttttcctgataccgggagacggcattcgtaatcggatcctctagag
tcgacctgcaggcatgcaagctttgcctcgcgcgtttcggtgatgacggtgaaaacctctgaca
catgcagctcccggagacggtcacagcttgtctgtaagcggatgccgggagcagacaagcccgt
cagggcgcgtcagcgggtgttggcgggtgtcggggcgcagccatgacccagtcacgtagcgata

FIG. 12B gcggagtgtatactggcttaactatgcggcatcagagcagattgtactgagagtgcaccatatg
cggtgtgaaataccgcacagatgcgtaaggagaaaataccgcatcaggcgctcttccgcttcct
cgctcactgactcgctgcgctcggtcgttcggctgcggcgagcggtatcagctcactcaaaggc
ggtaatacggttatccacagaatcaggggataacgcaggaaagaacatgtgagcaaaaggccag
caaaaggccaggaaccgtaaaaaggccgcgttgctggcgtttttccataggctccgcccccctg
acgagcatcacaaaaatcgacgctcaagtcagaggtggcgaaacccgacaggactataaagata
ccaggcgtttccccctggaagctccctcgtgcgctctcctgttccgaccctgccgcttaccgga
tacctgtccgcctttctcccttcgggaagcgtggcgctttctcaatgctcacgctgtaggtatc
tcagttcggtgtaggtcgttcgctccaagctgggctgtgtgcacgaaccccccgttcagcccga
ccgctgcgccttatccggtaactatcgtcttgagtccaacccggtaagacacgacttatcgcca
ctggcagcagccactggtaacaggattagcagagcgaggtatgtaggcggtgctacagagttct
tgaagtggtggcctaactacggctacactagaaggacagtatttggtatctgcgctctgctgaa
gccagttaccttcggaaaaagagttggtagctcttgatccggcaaacaaaccaccgctggtagc
ggtggtttttttgtttgcaagcagcagattacgcgcagaaaaaaaggatctcaagaagatcctt
tgatcttttctacggggtctgacgctcagtggaacgaaaactcacgttaagggattttggtcat
gagattatcaaaaaggatcgaagtcggttcagaaaaagaaggatatggatctggagctgtaata
taaaaaccttcttcaactaacggggcaggttagtgacattagaaaaccgactgtaaaaagtaca
gtcggcattatctcatattataaaagccagtcattaggcctatctgacaattcctgaatagagt
tcataaacaatcctgcatgataaccatcacaaacagaatgatgtacctgtaaagatagcggtaa
atatattgaattacctttattaatgaatttcctgctgtaataatgggtagaaggtaattacta
ttattattgatatttaagttaaacccagtaaatgaagtccatggaataatagaaagagaaaaag
cattttcaggtataggtgttttgggaaacaatttaaaagaaccattatatttctctacatcaga
aaggtataaatcataaaactctttgaagtcattctttacaggagtccaaataccagagaatgtt
ttagatacaccatcaaaaattgtataaagtggctctaacttatcccaataacctaactctccgt
cgctattgtaaccagttctaaaagctgtatttgagtttatcacccttgtcactaagaaaataaa
tgcagggtaaatttatatccttcttgttttatgtttcggtataaaacactaatatcaatttct
gtggttatactaaaagtcgtttgttggttcaaataatgattaaatatctcttttctcttccaat
tgtctaaatcaattttattaaagttcatttgatatgcctcctaaattttatctaaagtgaatt
taggaggcttacttgtctgctttcttcattagaatcaatcctttttaaagtcaatattactgt
aacataaatatatattttaaaatatcccactttatccaattttcgtttgttgaactaatgggt
gctttagttgaagaataaagaccacattaaaaatgtggtcttttgtgtttttttaaaggattt
gagcgtacgcgaaaaatcctttttctttctttcttatcttgataataagggtaactattgccggt
tgtccattcatggctgaactctgcttcctctgttgacatgacacacatcatctcaatatccgaa
tagggcccatcagtctgacgaccaagagagccataaacaccaatagccttaacatcatccccat
atttatccaatattcgttccttaatttcatgaacaatcttcattctttcttctctagtcattat
tattggtccattcactattctcattccctttcagataatttagatttgcttttctaaataag
aatatttggagagcaccgttcttattcagctattaataactcgtcttcctaagcatccttcaat
cctttaataacaattatagcatctaatcttcaacaaactggcccgtttgttgaactactcttt
aataaaataatttttccgttcccaattccacattgcaataatagaaaatccatcttcatcggct
ttttcgtcatcatctgtatgaatcaaatcgccttcttctgtgtcatcaaggtttaatttttat
gtatttcttttaacaaaccaccataggagattaacctttacggtgtaaaccttcctccaaatc
agacaaacgtttcaaattcttttcttcatcatcggtcataaaatccgtatcctttacaggatat
tttgcagtttcgtcaattgccgattgtatatccgatttatatttattttcggtcgaatcattt
gaacttttacatttggatcatagtctaatttcattgcctttttccaaaattgaatccattgttt

FIG. 12C ttgattcacgtagttttctgttattctaaaataagttggttccacacataccattacatgcatg
tgctgattataagaattatctttattatttattgtcacatccgttgcacgcataaaaccaacaa
gattttattaatttttttatattgcatcattcggcgaaatccttgagccatatctgtcaaact
cttatttaattcttcgccatcataaacattttaactgttaatgtgagaaacaaccaacgaact
gttggcttttgtttaataacttcagcaacaaccttttgtgactgaatgccatgtttcattgctc
tcctccagttgcacattggacaaagcctggatttgcaaaaccacactcgataccactttctttc
gcctgtttcacgattttgtttatactctaatatttcagcacaatcttttactctttcagccttt
ttaaattcaagaatatgcagaagttcaaagtaatcaacattagcgattttcttttctctccatg
gtctcacttttccacttttgtcttgtccactaaacccttgatttttcatctgaataaatgct
actattaggacacataatattaaaagaaacccccatctatttagttatttgtttagtcacttat
aactttaacagatggggtttttctgtgcaaccaatttaagggtttcaatactttaaaacaca
tacataccaacacttcaacgcacctttcagcaactaaaataaaaatgacgttatttctatatgt
atcaagataagaaagaacaagttcaaaaccatcaaaaaaagacacctttcaggtgcttttttt
attttataaactcattccctgatctcgacttcgttctttttttacctctcggttatgagttagt
tcaaattcgttcttttaggttctaaatcgtgtttttcttggaattgtgctgttttatccttta
ccttgtctacaaaccccttaaaaacgtttttaaaggcttttaagccgtctgtacgttccttaag (SEQ ID NO:57)

FIG. 13

ATGTGTGCAACCTCCTCCCAGTTTACTCAGATTACCGAGCATAATTCTCGACGATCTGCTAACT
ACCAGCCGAACCTTTGGAACTTTGAGTTTCTCCAGTCTCTCGAAAATGACCTGAAGGTGGAAAA
GCTCGAGGAGAAGGCGACCAAACTCGAGGAGGAGGTGCGATGTATGATCAACAGAGTTGACACC
CAACCCCTGTCTTTGCTGGAGCTGATCGACGATGTGCAGCGGTTGGGTTTGACTTATAAATTCG
AGAAGGACATTATCAAGGCACTGGAGAACATTGTGCTCCTCGACGAGAACAAGAAGAACAAGTC
TGATCTTCACGCTACCGCTCTCTCTTTCCGACTTCTTCGACAACACGGCTTCGAGGTGTCGCAG
GACGTCTTCGAGAGATTTAAGGACAAGGAGGGAGGATTTAGCGGCGAGCTGAAGGGAGACGTTC
AGGGTCTTCTCTCCTTGTACGAGGCGTCCTACCTGGGATTCGAGGGAGAGAACCTCCTGGAGGA
AGCTCGTACATTTTCCATCACTCACCTTAAGAATAACCTTAAGGAGGGAATTAACACCAAGGTG
GCCGAGCAGGTTTCTCACGCCCTGGAGCTCCCCTACCACCAACGGCTCCATAGACTGGAGGCTC
GTTGGTTCCTGGACAAATATGAGCCAAAGGAGCCTCATCATCAGTTGCTGTTGGAGTTGGCCAA
GCTGGACTTCAATATGGTTCAGACGCTGCACCAAAAGGAGTTGCAGGACCTGTCTCGATGGTGG
ACCGAGATGGGATTGGCCTCGAAGCTGGATTTTGTCCGTGACCGACTTATGGAGGTCTATTTTT
GGGCCCTTGGAATGGCGCCTGACCCCCAGTTCGGAGAGTGCCGGAAGGCGGTGACGAAGATGTT
CGGTCTTGTGACTATCATCGACGACGTCTACGATGTCTACGGCACACTCGACGAGTTGCAGCTG
TTCACTGACGCCGTCGAGCGATGGGATGTGAACGCCATTAATACTCTCCCTGACTATATGAAGC
TGTGCTTCCTGGCTCTGTACAACACTGTCAACGATACCTCGTACTCTATCCTCAAGGAGAAGGG
ACACAACAATCTCTCCTACTTGACCAAATCCTGGCGAGAACTGTGCAAGGCTTTTCTGCAGGAG
GCTAAATGGTCCAATAACAAGATCATTCCTGCTTTTTCTAAATACCTGGAAAATGCCTCGGTGT
CGAGCTCTGGCGTCGCCCTTCTGGCCCCTTCCTACTTCTCCGTCTGCCAGCAGCAGGAGGATAT
TTCCGATCATGCTCTTAGATCGCTGACCGATTTTCACGGCCTCGTGCGATCTTCCTGCGTGATT
TTTCGGTTGTGTAATGACCTTGCGACCTCTGCTGCTGAGCTGGAACGAGGCGAGACTACAAATT
CCATTATTTCTTACATGCACGAAAACGATGGAACATCTGAAGAACAGGCTAGAGAGGAACTGCG
AAAGTTGATCGACGCCGAGTGGAAGAAGATGAACAGAGAGCGGGTGTCCGACTCTACCCTGCTT
CCCAAGGCCTTCATGGAGATCGCCGTGAACATGGCTCGAGTTTCCCATTGTACTTACCAGTACG
GTGACGGCCTGGGTCGTCCGGACTACGCTACAGAGAACCGAATCAAGCTGCTGCTCATCGACCC
CTTCCCTATCAACCAATTGATGTACGTGTAA
(SEQ ID NO:8)

FIG. 15A

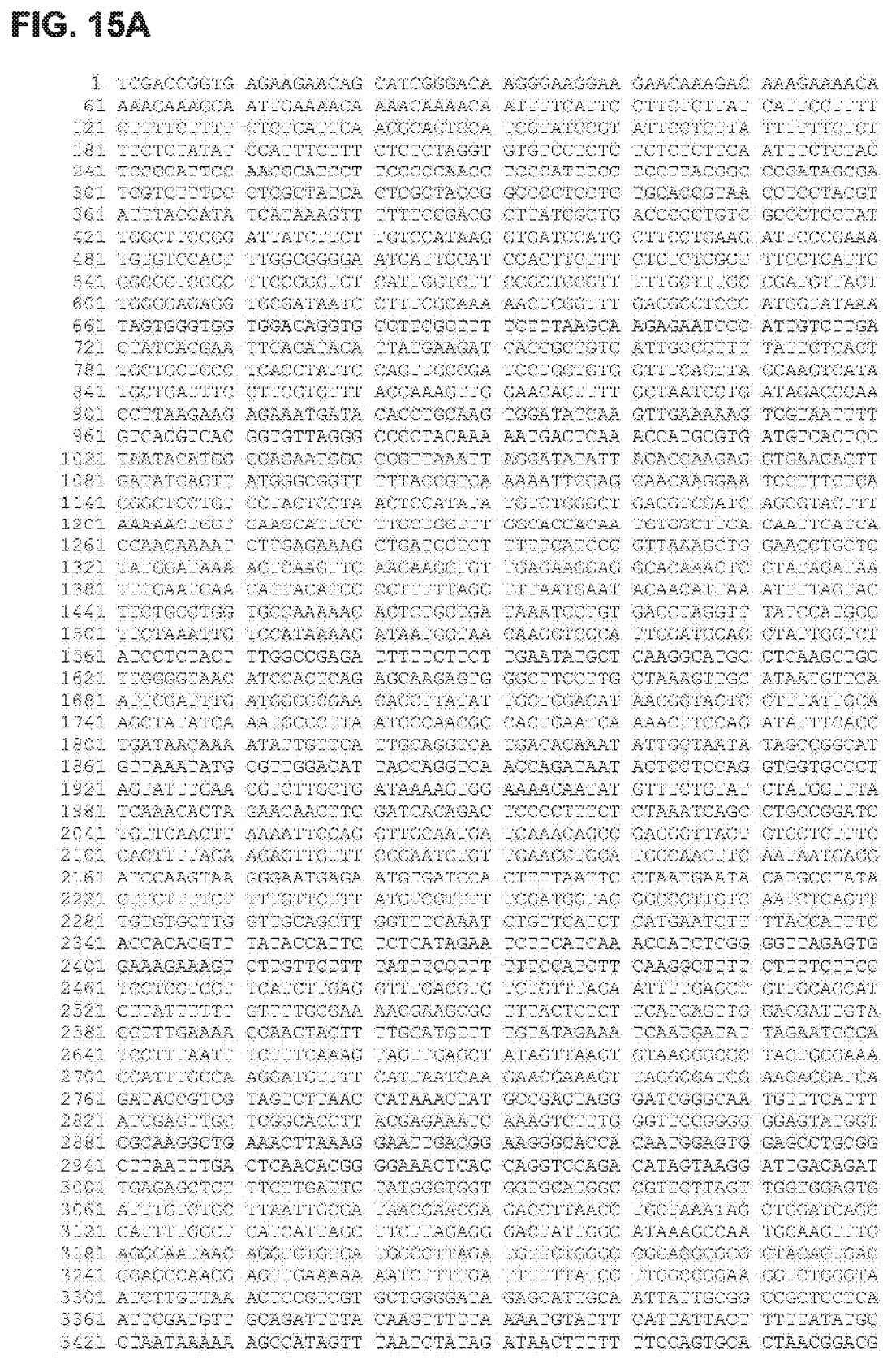

```
   1 TCGACCGGTG AGAAGAACAG CATCGGGACA AGGGAAGGAA GAACAAAGAC AAAGAAAACA
  61 AAACAAAGCA ATTGAAAACA AAACAAAACA ATTTTCATTC CTTGTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCCA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACG CTTATCGCTG ACCCCCTGTC GCCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCCCGTCT CATTGGTCTT CCCCTCCCTT TTTGCTTTCC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG GCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC GTTCGTGTTT ACCAAAGTTG GAACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTCA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCCCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCGGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCGTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCCATGGTAC GGCCGTTCTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCCT TCATCTTGAG GTTTCACGTG TCTGTTTAGA ATTTTGAGCT GTTGCAGCAT
2521 CTTATTTTTT GTTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTCAGCT ATAGTTAAGT GTAACGGCCC TACTGCGAAA
2701 GCATTTGCCA AGGATCTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGAGTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTTGGCT GATCATTAGC TTCTTAGAGG GACTATTGGC ATAAAGCCAA TGGAAGTTTG
3181 AGGCAATAAC AGGTCTGTCA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

FIG. 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCCGTA
3721 GTCTAATATC TACCAAAAAT CTTTTGGCTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTACAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGCGAGTG TTGTAAACAT GAATTGGATT ATGTCAGGAA AAGAACGACA ATTTTGCATC
4561 CAAATTGTCT AAATTTTAGA GTTGCTTGAA AACAATAGAA GCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA GCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGCCCTCCTT TCTAGGTCGG GCTGATTGCT CTTGAAGCTC TCTAGGGGGG
6061 CTCAGACCAT AGCCAGATAA CGTTCCCCAG CGGCTCGCCT CGTAAGCGCA CAAGGACTGC
6121 TCCCAAGATC CCTAGGCGGG ATTTTGCCGA TTTCGGCCTA AAGGAACCGG AACACGTAGA
6181 AAGCCAGTCC GCAGAAACGG TGCTGACCCC GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

FIG. 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAACGT ACCAAGTTTA CTCATATATA CTTTAGATTG ATTTAAAACT
7321 TGATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```

(SEQ ID NO:11)

FIG. 16

1 GAATTCAAAA CAAAATGTGT GCAACCTCCT CCCAGTTTAC TCAGATTACC GAGCATAATT
61 CTCCGACGATC TGCTAACTAC CAGCCGAACC TTTGGAACTT TGAGTTTCTG CAGTCTCTCG
121 AAAATGACCT GAAGGTGGAA AAGCTCGAGG AGAAGGCGAC CAAACTCGAG GAGGAGGTGC
181 GATGTATGAT CAACAGAGTT GACACCCAAC CCCTGTCTTT GCTGGAGCTG ATCGACGATG
241 TGCAGCGGTT GGGTTTGACT TATAAATTCG AGAAGGACAT TATCAAGGCA CTGGAGAACA
301 TTGTGCTCCT CGACGAGAAC AAGAAGAACA AGTCTGATCT TCACGCTACC GCTCTCTCTT
361 TCCGACTTCT TCGACAACAC GGCTTCGAGG TGTCGCAGGA CGTCTTCGAG AGATTTAAGG
421 ACAAGGAGGG AGGATTTAGC GGCGACCTGA AGGGAGACGT TCAGGGTCTT CTCTCCTTGT
481 ACGAGGCGTC GTACCTGGCA TTCGAGGCAG AGAACCTCCT GGAGGAAGCT CGTACATTTT
541 CCATCACTCA CCTTAAGAAT AACCTTAAGG AGGGAATTAA CACCAAGGTG GCCGAGCAGG
601 TTTCTCACGC CCTGGAGCTC CCCTACCACC AACGGCTCCA TAGACTGGAG GCTCGTTGGT
661 TCCTGGACAA ATATGAGCCA AAGGAGCCTC ATCATCAGTT GCTGTTGGAG TTGGCCAAGC
721 TGGACTTCAA TATGGTTCAG ACGCTGCACC AAAAGGAGTT GCAGGACCTG TCTCGATGGT
781 GGACCGAGAT GGGATTGGCC TCGAAGCTGG ATTTTGTCCG TGACCGACTT ATGGAGGTCT
841 ATTTTTGGGC CCTTGGAATG GCGCCTGACC CCCAGTTCGG AGAGTGCCGG AAGGCGGTGA
901 CGAAGATGTT CGGTCTTGTG ACTATCATCG ACGACGTCTA CGATGTCTAC GGCACACTCG
961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGCCGAG
1141 AACTGTGCAA GGCTTTTCTG CAGGAGGCTA AATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC GGTCTGCCAG CAGCAGGAGG ATATTTCCGA TCATGCTCTT AGATCGCTGA
1321 CCGATTTTCA CGGCCTCGTG CGATCTTCCT GCCTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTG ATCGACCCCT
1681 TCCCTATCAA GCAATTGATG TACCTGTAAT AGTCTAGAGG ATCC (SEQ ID NO:12)

FIG. 17

1 GAATTCAACA AAAATGTCCT CTGTTTCCAC TGAGAACCTG TCCTTTACTG AGACTGAGAC
61 TGAAGCACGT AGAAGCGCCA ACTACGAACC CAACTCCTGG GATTATGACT TTCTGCTGTC
121 TTCTGACACC GACGAGTCGA TCGAGGTTTA TAAGGATAAG GCCAAGAAAC TTGAGGCCGA
181 GGTCAGACCA GAGATTAACA ACCAGAAGGC CGAGTTCCTG ACCCTTCTTG ACCTGATCCA
241 CAACGTTGAA CGACTTGGTC TTGGTTACCG TTTCGAATCC GATATCCGAC GTGCATTGGA
301 TCGATTTGTC TCGTCGGGAG GTTTCGATGG TGTGACTAAG ACGTCGCTGC ACCCCACAGC
361 TCTTTCCTTC AGACTGTTGC GGCAGCATGG ATTTGAGGTT TCCCAGGAAG CCTTTTCTGG
421 TTTCAAGGAT CAGAACGGAA ACTTTTTGGA GAATCTCAAG GAGGACACCA AGGCCATCCT
481 GTCCTTGTAT CAGGCGTCCT TCCTGGCTCT TGAGGGCGAG AATATTCTGG ATGAGGCTCG
541 GGTTTTCGCT ATTTCGCACC TGAAGGAGTT GTCGGAGGAA AAGATCGGAA AGGAACTGGC
601 CGAGCAGGTG AACCATGCAC TTGAACTTCC CCTGCATCGA CGTACCCAGC GACTCGAGGC
661 CGTCTGGAGC ATCGAGGCCT ACAGAAAAAA GGAGGATGCT AATCAGGTTC TGCTCGAACT
721 CGCTATCCTC GACTATAACA TGATTCAGAG CGTGTACCAG CGTGACTTGC GAGAGACAAG
781 CCGGTGGTGG CGACGGGTGG GACTGGCCAC GAAGCTCCAC TTTGCTAAAG ATCGATTGAT
841 TGAGTCGTTC TACTGGGCAG TCGGTGTGGC CTTTGAGCCT CAGTACTCCG ACTGCCGAAA
901 CTCGGTTGCA AAGATGTTTT CTTTTGTCAC TATCATCGAC GACATCTACG ATGTTTACGG
961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTCTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCCATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C (SEQ ID NO:13)

FIG. 18A(1)
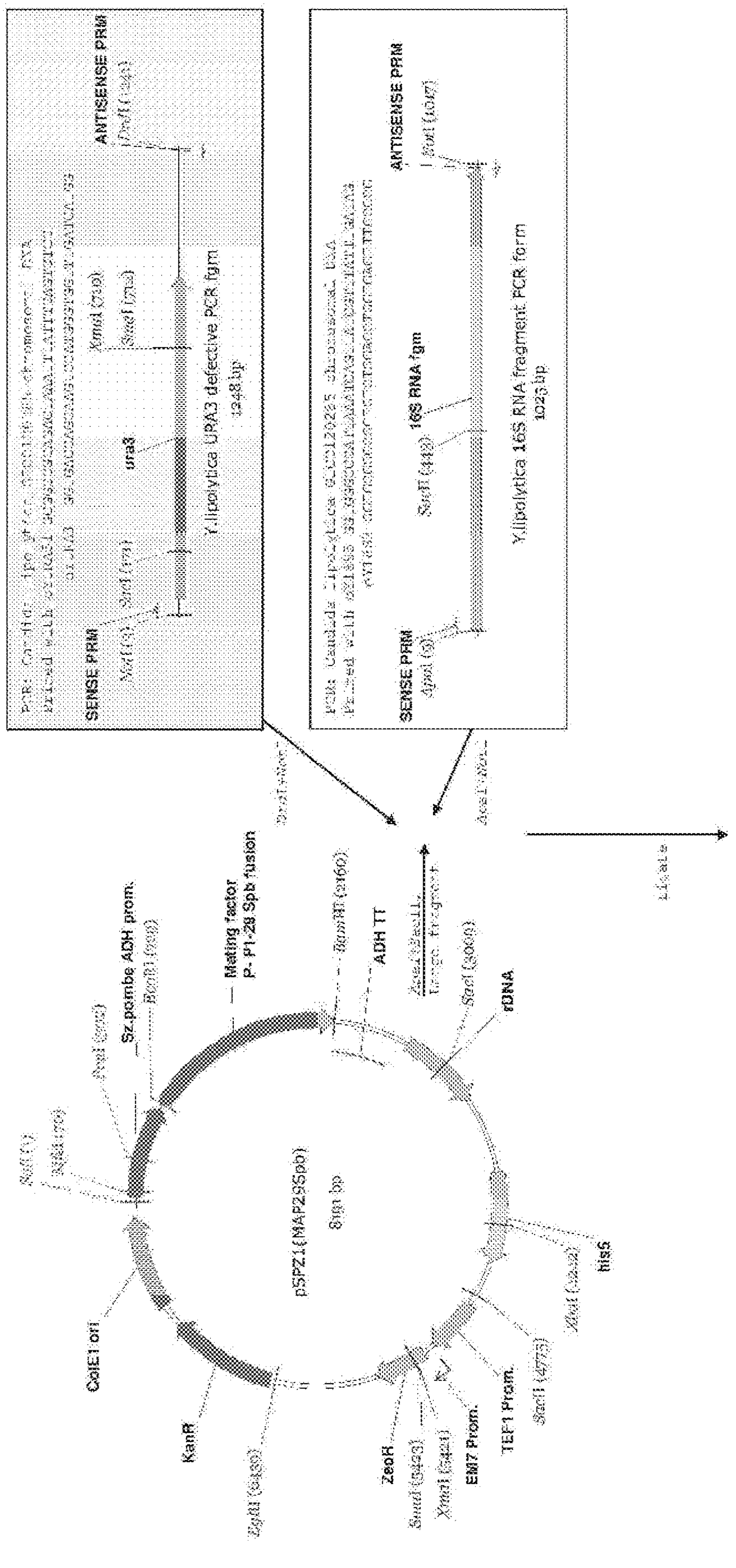

FIG. 18A(2)
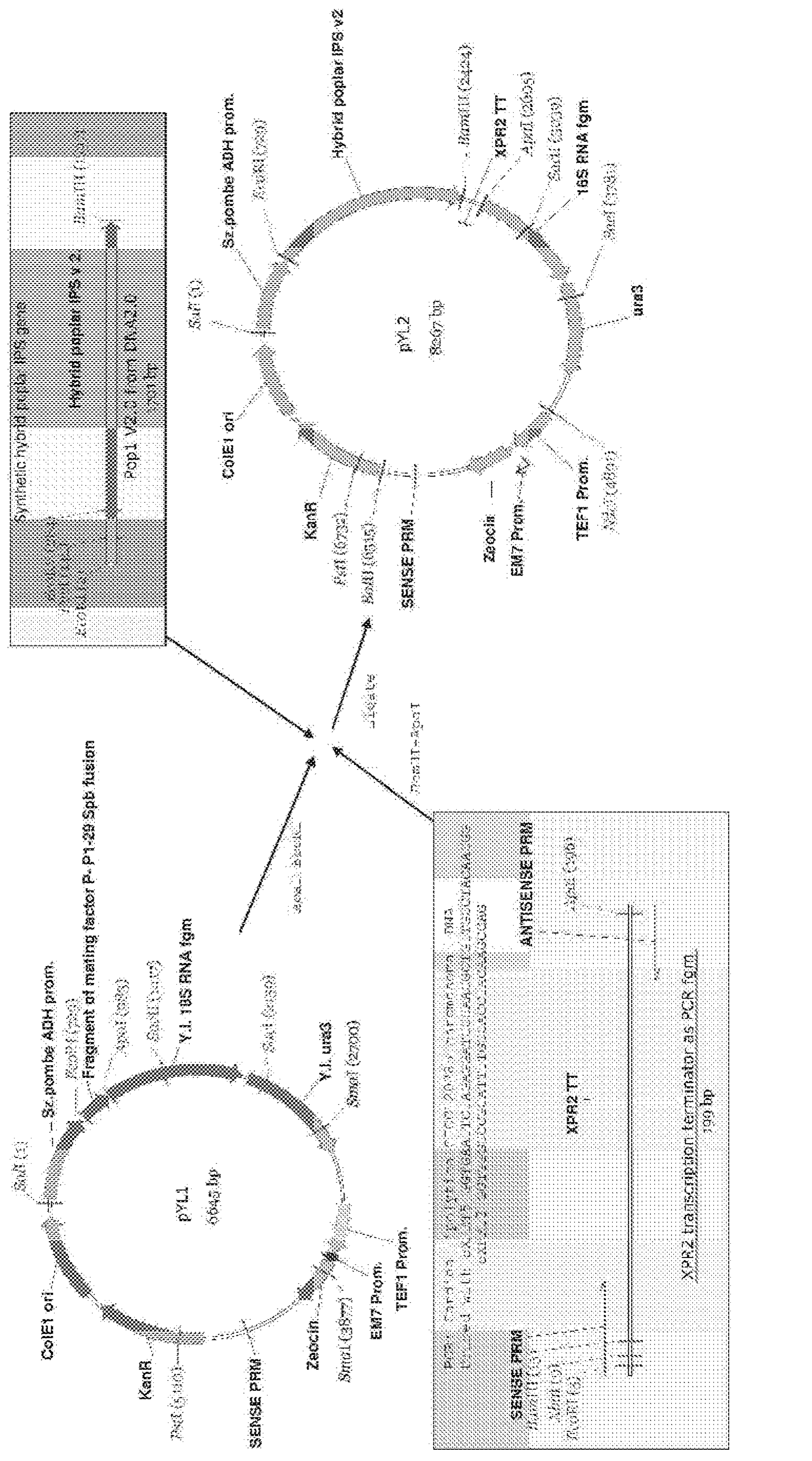

acetyl-CoA acetoacetyl-CoA

HMG-CoA mevalonic acid 5-phosphomevalonic acid isopentenyl-P diphosphomevalonic acid isopentenyl-PP dimethylallyl-PP FIG. 20
Y. *lipolytica* CLIB122:: pYLA(KZ1)
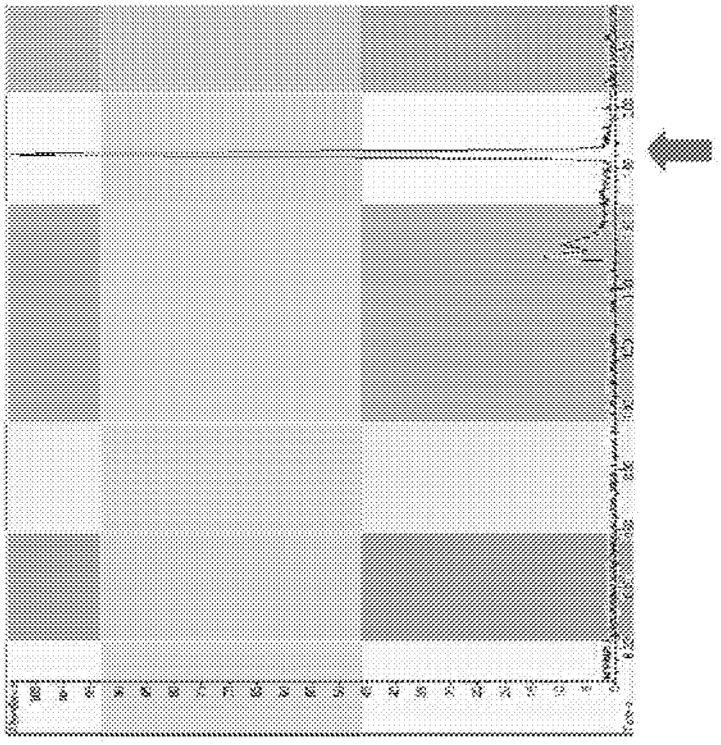
Y. *lipolytica* CLIB122:: pYLA(MAP29)
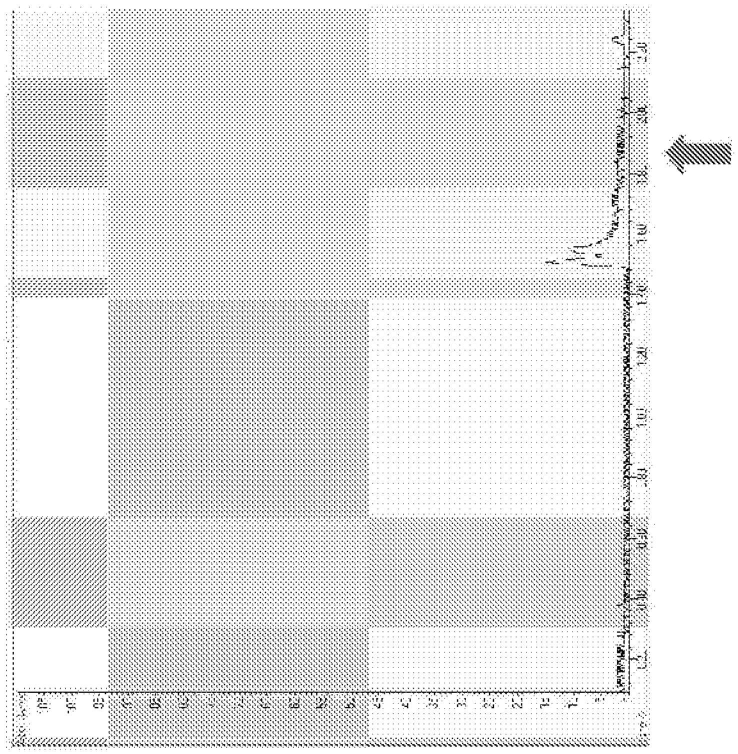

FIG. 22A 1-
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg
agggtggcgggcaggacgcccgccataaactgccaggcatcaaattaagcagaaggccatcctg
acggatggcctttttgcgtttctacaaactctttttgtttatttttctaaatacattcaaatat
gtatccgcttaaccggaattgccagctggggcgccctctggtaaggttgggaagccctgcaaag
taaactggatggctttctcgccgccaaggatctgatggcgcaggggatcaagctctgatcaaga
gacaggatgaggatcgtttcgcatgattgaacaagatggattgcacgcaggttctccggccgct
tgggtggagaggctattcggctatgactgggcacaacagacaatcggctgctctgatgccgccg
tgttccggctgtcagcgcaggggcgcccggttctttttgtcaagaccgacctgtccggtgccct
gaatgaactgcaagacgaggcagcgcggctatcgtggctggccacgacgggcgttccttgcgca
gctgtgctcgacgttgtcactgaagcgggaagggactggctgctattgggcgaagtgccggggc
aggatctcctgtcatctcaccttgctcctgccgagaaagtatccatcatggctgatgcaatgcg
gcggctgcatacgcttgatccggctacctgcccattcgaccaccaagcgaaacatcgcatcgag
cgagcacgtactcggatggaagccggtcttgtcgatcaggatgatctggacgaagagcatcagg
ggctcgcgccagccgaactgttcgccaggctcaaggcgagcatgcccgacggcgaggatctcgt
cgtgacccatggcgatgcctgcttgccgaatatcatggtggaaaatggccgcttttctggattc
atcgactgtggccggctgggtgtggcggaccgctatcaggacatagcgttggctacccgtgata
ttgctgaagagcttggcggcgaatgggctgaccgcttcctcgtgctttacggtatcgccgctcc
cgattcgcagcgcatcgccttctatcgccttcttgacgagttcttctgacatgaccaaaatccc
ttaacgtgagttttcgttccactgagcgtcagaccccgtagaaaagatcaaaggatcttcttga
gatcctttttttctgcgcgtaatctgctgcttgcaaacaaaaaaaccaccgctaccagcggtgg
tttgtttgccggatcaagagctaccaactctttttccgaaggtaactggcttcagcagagcgca
gataccaaatactgtccttctagtgtagccgtagttaggccaccacttcaagaactctgtagca
ccgcctacatacctcgctctgctaatcctgttaccagtggctgctgccagtggcgataagtcgt
gtcttaccgggttggactcaagacgatagttaccggataaggcgcagcggtcgggctgaacggg
gggttcgtgcacacagcccagcttggagcgaacgacctacaccgaactgagatacctacagcgt
gagctatgagaaagcgccacgcttcccgaagggagaaaggcggacaggtatccggtaagcggca
gggtcggaacaggagagcgcacgagggagcttccagggggaaacgcctggtatctttatagtcc
tgtcgggtttcgccacctctgacttgagcgtcgatttttgtgatgctcgtcaggggggcggagc
ctatggaaaaacgccagcaacgcggcctttttacggttcctggccttttgctggccttttgctc
acatgttctttcctgcgttatcccctgattctgtggataaccgtattaccgcctttgagtgagc
tgataccgctcgccgcagccgaacgaccgagcgcagcgagtcagtgagcgaggaagcggaagag
cgcctgatgcggtattttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagcagatcaattcgcgcgcgaaggcgaagcggcatgca
tttacgttgacaccatcgaatggtgcaaaacctttcgcggtatggcatgatagcgcccggaaga

FIG. 22B gagtcaattcagggtggtgaatgtgaaaccagtaacgttatacgatgtcgcagagtatgccggt
gtctcttatcagaccgtttcccgcgtggtgaaccaggccagccacgtttctgcgaaaacgcggg
aaaaagtggaagcggcgatggcggagctgaattacattcccaaccgcgtggcacaacaactggc
gggcaaacagtcgttgctgattggcgttgccacctccagtctggccctgcacgcgccgtcgcaa
attgtcgcggcgattaaatctcgcgccgatcaactgggtgccagcgtggtggtgtcgatggtag
aacgaagcggcgtcgaagcctgtaaagcggcggtgcacaatcttctcgcgcaacgcgtcagtgg
gctgatcattaactatccgctggatgaccaggatgccattgctgtggaagctgcctgcactaat
gttccggcgttatttcttgatgtctctgaccagacacccatcaacagtattattttctcccatg
aagacggtacgcgactgggcgtggagcatctggtcgcattgggtcaccagcaaatcgcgctgtt
agcgggcccattaagttctgtctcggcgcgtctgcgtctggctggctggcataaatatctcact
cgcaatcaaattcagccgatagcggaacgggaaggcgactggagtgccatgtccggttttcaac
aaaccatgcaaatgctgaatgagggcatcgttcccactgcgatgctggttgccaacgatcagat
ggcgctgggcgcaatgcgcgccattaccgagtccgggctgcgcgttggtgcggatatctcggta
gtgggatacgacgataccgaagacagctcatgttatatcccgccgtcaaccaccatcaaacagg
attttcgcctgctggggcaaaccagcgtggaccgcttgctgcaactctctcagggccaggcggt
gaagggcaatcagctgttgcccgtctcactggtgaaaagaaaaaccaccctggcgcccaatacg
caaaccgcctctccccgcgcgttggccgattcattaatgcagctggcacgacaggtttcccgac
tggaaagcgggcagtgagcgcaacgcaattaatgtgagttagcgcgaattgatctggtttgaca
gcttatcatcgactgcacggtgcaccaatgcttctggcgtcaggcagccatcggaagctgtggt
atggctgtgcaggtcgtaaatcactgcataattcgtgtcgctcaaggcgcactcccgttctgga
taatgttttttgcgccgacatcataacggttctggcaaatattctgaaatgagctgttgacaat
taatcatccggctcgtataatgtgtggaattgtgagcggataacaatttcacacaggaaacagc
gccgctgagaaaaagcgaagcggcactgctctttaacaatttatcagacaatctgtgtgggcac
tcgaccggaattatcgattaactttattattaaaaattaaagaggtatatattaatgtatcgat
taaataaggaggaataaaccatgtgtgcgacctcttctcaatttactcagattaccgagcataa
ttcccgtcgttccgcaaactatcagccaaacctgtggaatttcgaattcctgcaatccctggag
aacgacctgaaagtggaaaagctggaggagaaagcgaccaaactggaggaagaagttcgctgca
tgatcaaccgtgtagacacccagccgctgtccctgctggagctgatcgacgatgtgcagcgcct
gggtctgacctacaaatttgaaaaagacatcattaaagccctggaaaacatcgtactgctggac
gaaaacaaaaagaacaaatctgacctgcacgcaaccgctctgtctttccgtctgctgcgtcagc
acggtttcgaggtttctcaggatgtttttgagcgtttcaaggataaagaaggtggtttcagcgg
tgaactgaaaggtgacgtccaaggcctgctgagcctgtatgaagcgtcttacctgggtttcgag
ggtgagaacctgctggaggaggcgcgtacctttttccatcacccacctgaagaacaacctgaaag
aaggcattaataccaaggttgcagaacaagtgagccacgccctggaactgccatatcaccagcg
tctgcaccgtctggaggcacgttggttcctggataaatacgaaccgaaagaaccgcatcaccag
ctgctgctggagctggcgaagctggattttaacatggtacagaccctgcaccagaaagagctgc
aagatctgtcccgctggtggaccgagatgggcctggctagcaaactggattttgtacgcgaccg
cctgatggaagtttatttctgggcactgggtatggcgccagacccgcagtttggtgaatgtcgc
aaagctgttactaaaatgtttggtctggtgacgatcatcgatgacgtgtatgacgtttatggca
ctctggacgaactgcaactgttcaccgatgctgtagagcgctgggacgttaacgctattaacac
cctgccggactatatgaaactgtgtttcctggcactgtacaacaccgttaacgacacgtcctat
tctattctgaaagagaaaggtcataacaacctgtcctatctgacgaaaagctggcgtgaactgt
gcaaagcctttctgcaagaggcgaaatggtccaacaacaaaattatcccggctttctccaagta
cctggaaaacgccagcgtttcctcctccggtgtagcgctgctggcgccgtcttacttttccgta

FIG. 22C tgccagcagcaggaagacatctccgaccacgcgctgcgttccctgaccgacttccatggtctgg
tgcgttctagctgcgttatcttccgcctgtgcaacgatctggccacctctgcggcggagctgga
acgtggcgagactaccaattctatcattagctacatgcacgaaaacgatggtaccagcgaggaa
caggcccgcgaagaactgcgtaaactgatcgacgccgaatggaaaaagatgaatcgtgaacgcg
ttagcgactccaccctgctgcctaaagcgttcatggaaatcgcagttaacatggcacgtgtttc
ccactgcacctaccagtatggcgatggtctgggtcgcccagactacgcgactgaaaaccgcatc
aaactgctgctgattgaccctttcccgattaaccagctgatgtatgtctaactgcatcgccctt
aggaggtaaaaaaaaatgactgccgacaacaatagtatgccccatggtgcagtatctagttacg
ccaaattagtgcaaaaccaaacacctgaagacattttggaagagtttcctgaaattattccatt
acaacaaagacctaatacccgatctagtgagacgtcaaatgacgaaagcggagaaacatgtttt
tctggtcatgatgaggagcaaattaagttaatgaatgaaaattgtattgttttggattgggacg
ataatgctattggtgccggtaccaagaaagtttgtcatttaatggaaaatattgaaaagggttt
actacatcgtgcattctccgtctttattttcaatgaacaaggtgaattacttttacaacaaaga
gccactgaaaaaataactttccctgatctttggactaacacatgctgctctcatccactatgta
ttgatgacgaattaggtttgaagggtaagctagacgataagattaagggcgctattactgcggc
ggtgagaaaactagatcatgaattaggtattccagaagatgaaactaagacaaggggtaagttt
cactttttaaacagaatccattacatggcaccaagcaatgaaccatggggtgaacatgaaattg
attacatcctattttataagatcaacgctaaagaaaacttgactgtcaacccaaacgtcaatga
agttagagacttcaaatgggtttcaccaaatgatttgaaaactatgtttgctgacccaagttac
aagtttacgccttggtttaagattatttgcgagaattacttattcaactggtgggagcaattag
atgacctttctgaagtggaaaatgacaggcaaattcatagaatgctataacaacgcgtcctgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagtttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgctttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg

FIG. 22D cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgca
(SEQ ID NO:20)

FIG. 25A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatggatccgagctcggatccactagtaacggccgcc
agtgtgctggaattcgcccttaggaggtaaaaaaacatgtcattaccgttcttaacttctgcac
cgggaaaggttattatttttggtgaacactctgctgtgtacaacaagcctgccgtcgctgctag
tgtgtctgcgttgagaacctacctgctaataagcgagtcatctgcaccagatactattgaattg
gacttcccggacattagctttaatcataagtggtccatcaatgatttcaatgccatcaccgagg
atcaagtaaactcccaaaaattggccaaggctcaacaagccaccgatggcttgtctcaggaact
cgttagtctttggatccgttgttagctcaactatccgaatccttccactaccatgcagcgttt
tgtttcctgtatatgtttgtttgcctatgcccccatgccaagaatattaagtttctttaaagt
ctactttacccatcggtgctgggttgggctcaagcgcctctatttctgtatcactggccttagc
tatggcctacttgggggggttaataggatctaatgacttggaaaagctgtcagaaaacgataag
catatagtgaatcaatgggccttcataggtgaaaagtgtattcacggtaccccttcaggaatag
ataacgctgtggccacttatggtaatgccctgctatttgaaaaagactcacataatggaacaat
aaacacaaacaattttaagttcttagatgatttcccagccattccaatgatcctaacctatact
agaattccaaggtctacaaaagatcttgttgctcgcgttcgtgtgttggtcaccgagaaatttc
ctgaagttatgaagccaattctagatgccatgggtgaatgtgccctacaaggcttagagatcat
gactaagttaagtaaatgtaaaggcaccgatgacgaggctgtagaaactaataatgaactgtat
gaacaactattggaattgataagaataaatcatggactgcttgtctcaatcggtgtttctcatc
ctggattagaacttattaaaaatctgagcgatgatttgagaattggctccacaaaacttaccgg
tgctggtggcggcggttgctctttgactttgttacgaagagacattactcaagagcaaattgac
agcttcaaaaagaaattgcaagatgattttagttacgagacatttgaaacagacttgggtggga
ctggctgctgtttgttaagcgcaaaaaatttgaataaagatcttaaaatcaaatccctagtatt
ccaattatttgaaaataaaactaccacaaagcaacaaattgacgatctattattgccaggaaac
acgaatttaccatggacttcataagctaatttgcgataggcctgcacccttaaggaggaaaaaa
acatgtcagagttgagagccttcagtgccccagggaaagcgttactagctggtggatatttagt
tttagatacaaaatatgaagcatttgtagtcggattatcggcaagaatgcatgctgtagcccat
ccttacggttcattgcaagggtctgataagtttgaagtgcgtgtgaaaagtaaacaatttaaag
atggggagtggctgtaccatataagtcctaaaagtggcttcattcctgtttcgataggcggatc
taagaaccctttcattgaaaaagttatcgctaacgtatttagctactttaaacctaacatggac
gactactgcaatagaaacttgttcgttattgatattttctctgatgatgcctaccattctcagg
aggatagcgttaccgaacatcgtggcaacagaagattgagttttcattcgcacagaattgaaga
agttcccaaaacagggctgggctcctcggcaggtttagtcacagttttaactacagctttggcc
tcctttttgtatcggacctggaaaataatgtagacaaatatagagaagttattcataatttag
cacaagttgctcattgtcaagctcagggtaaaattggaagcgggtttgatgtagcggcggcagc
atatggatctatcagatatagaagattcccacccgcattaatctctaatttgccagatattgga
agtgctacttacggcagtaaactggcgcatttggttgatgaagaagactggaatattacgatta
aaagtaaccatttaccttcgggattaactttatggatggcgatattaagaatggttcagaaac
agtaaaactggtccagaaggtaaaaaattggtatgattcgcatatgccagaaagcttgaaaata

FIG. 25B tatacagaactcgatcatgcaaattctagatttatggatggactatctaaactagatcgcttac
acgagactcatgacgattacagcgatcagatatttgagtctcttgagaggaatgactgtacctg
tcaaaagtatcctgaaatcacagaagttagagatgcagttgccacaattagacgttcctttaga
aaaataactaaagaatctggtgccgatatcgaacctcccgtacaaactagcttattggatgatt
gccagaccttaaaggagttcttacttgcttaatacctggtgctggtggttatgacgccattgc
agtgattactaagcaagatgttgatcttagggctcaaaccgctaatgacaaaagattttctaag
gttcaatggctggatgtaactcaggctgactggggtgttaggaaagaaaaagatccggaaactt
atcttgataaataacttaaggtagctgcatgcagaattcgcccttaaggaggaaaaaaaaatga
ccgtttacacagcatccgttaccgcacccgtcaacatcgcaacccttaagtattgggggaaaag
ggacacgaagttgaatctgcccaccaattcgtccatatcagtgactttatcgcaagatgacctc
agaacgttgacctctgcggctactgcacctgagtttgaacgcgacactttgtggttaaatggag
aacccacacagcatcgacaatgaaagaactcaaaattgtctgcgcgacctacgccaattaagaaa
ggaaatggaatcgaaggacgcctcattgcccacattatctcaatggaaactccacattgtctcc
gaaaataactttcctacagcagctggtttagcttcctccgctgctggctttgctgcattggtct
ctgcaattgctaagttataccaattaccacagtcaacttcagaaatatctagaatagcaagaaa
ggggtctggttcagcttgtagatcgttgtttggcggatacgtggcctgggaaatgggaaaagct
gaagatggtcatgattccatggcagtacaaatcgcagacagctctgactggcctcagatgaaag
cttgtgtcctagttgtcagcgatattaaaaaggatgtgagttccactcagggtatgcaattgac
cgtggcaacctccgaactatttaaagaaagaattgaacatgtcgtaccaaagagatttgaagtc
atgcgtaaagccattgttgaaaaagatttcgccacctttgcaaaggaaacaatgatggattcca
actctttccatgccacatgtttggactctttccctccaatattctacatgaatgacacttccaa
gcgtatcatcagttggtgccacaccattaatcagttttacggagaaacaatcgttgcatacacg
tttgatgcaggtccaaatgctgtgttgtactacttagctgaaaatgagtcgaaactctttgcat
ttatctataaattgtttggctctgttcctggatgggacaagaaatttactactgagcagcttga
ggctttcaaccatcaatttgaatcatctaactttactgcacgtgaattggatcttgagttgcaa
aaggatgttgccagagtgattttaactcaagtcggttcaggcccacaagaaacaaacgaatctt
tgattgacgcaaagactggtctaccaaaggaataagatcaattcgctgcatcgcccttaggagg
taaaaaaaaatgactgccgacaacaatagtatgccccatggtgcagtatctagttacgccaaat
tagtgcaaaaccaaacacctgaagacattttggaagagtttcctgaaattattccattacaaca
aagacctaatacccgatctagtgagacgtcaaatgacgaaagcggagaaacatgtttttctggt
catgatgaggagcaaattaagttaatgaatgaaaattgtattgttttggattgggacgataatg
ctattggtgccggtaccaagaaagtttgtcatttaatggaaaatattgaaaagggtttactaca
tcgtgcattctccgtctttattttcaatgaacaaggtgaattacttttacaacaaagagccact
gaaaaaataactttccctgatctttggactaacacatgctgctctcatccactatgtattgatg
acgaattaggtttgaagggtaagctagacgataagattaagggcgctattactgcggcggtgag
aaaactagatcatgaattaggtattccagaagatgaaactaagacaaggggtaagtttcacttt
ttaaacagaatccattacatggcaccaagcaatgaaccatggggtgaacatgaaattgattaca
tcctattttataagatcaacgctaaagaaaacttgactgtcaacccaaacgtcaatgaagttag
agacttcaaatgggtttcaccaaatgatttgaaaactatgtttgctgacccaagttacaagttt
acgccttggtttaagattatttgcgagaattacttattcaactggtgggagcaattagatgacc
tttctgaagtggaaaatgacaggcaaattcatagaatgctataacaacgcgtcctgcattcgcc
cttaggaggtaaaaaaacatgtgtgcgacctcttctcaatttactcagattaccgagcataatt
cccgtcgttccgcaaactatcagccaaacctgtggaatttcgaattcctgcaatccctggagaa
cgacctgaaagtggaaaagctggaggagaaagcgaccaaactggaggaagaagttcgctgcatg

FIG. 25C atcaaccgtgtagacacccagccgctgtccctgctggagctgatcgacgatgtgcagcgcctgg
gtctgacctacaaatttgaaaaagacatcattaaagccctggaaaacatcgtactgctggacga
aaacaaaaagaacaaatctgacctgcacgcaaccgctctgtctttccgtctgctgcgtcagcac
ggtttcgaggtttctcaggatgttttgagcgtttcaaggataaagaaggtggtttcagcggtg
aactgaaaggtgacgtccaaggcctgctgagcctgtatgaagcgtcttacctgggtttcgaggg
tgagaacctgctggaggaggcgcgtaccttttccatcacccacctgaagaacaacctgaaagaa
ggcattaataccaaggttgcagaacaagtgagccacgccctggaactgccatatcaccagcgtc
tgcaccgtctggaggcacgttggttcctggataaatacgaaccgaaagaaccgcatcaccagct
gctgctggagctggcgaagctggattttaacatggtacagaccctgcaccagaaagagctgcaa
gatctgtcccgctggtggaccgagatgggcctggctagcaaactggattttgtacgcgaccgcc
tgatggaagtttatttctgggcactgggtatggcgccagacccgcagtttggtgaatgtcgcaa
agctgttactaaaatgtttggtctggtgacgatcatcgatgacgtgtatgacgtttatggcact
ctggacgaactgcaactgttcaccgatgctgtagagcgctgggacgttaacgctattaacaccc
tgccggactatatgaaactgtgtttcctggcactgtacaacaccgttaacgacacgtcctattc
tattctgaaagagaaaggtcataacaacctgtcctatctgacgaaaagctggcgtgaactgtgc
aaagcctttctgcaagaggcgaaatggtccaacaacaaaattatcccggctttctccaagtacc
tggaaaacgccagcgtttcctcctccggtgtagcgctgctggcgccgtcttacttttccgtatg
ccagcagcaggaagacatctccgaccacgcgctgcgttccctgaccgacttccatggtctggtg
cgttctagctgcgttatcttccgcctgtgcaacgatctggccacctctgcggcggagctggaac
gtggcgagactaccaattctatcattagctacatgcacgaaaacgatggtaccagcgaggaaca
ggcccgcgaagaactgcgtaaactgatcgacgccgaatggaaaaagatgaatcgtgaacgcgtt
agcgactccaccctgctgcctaaagcgttcatggaaatcgcagttaacatggcacgtgtttccc
actgcacctaccagtatggcgatggtctgggtcgcccagactacgcgactgaaaaccgcatcaa
actgctgctgattgaccctttcccgattaaccagctgatgtatgtctaactgcagctggtacca
tatgggaattcgaagctttctagaacaaaaactcatctcagaagaggatctgaatagcgccgtc
gaccatcatcatcatcatcattgagtttaaacggtctccagcttggctgttttggcggatgaga
gaagattttcagcctgatacagattaaatcagaacgcagaagcggtctgataaaacagaatttg
cctggcggcagtagcgcggtggtcccacctgaccccatgccgaactcagaagtgaaacgccgta
gcgccgatggtagtgtggggtctccccatgcgagagtagggaactgccaggcatcaaataaaac
gaaaggctcagtcgaaagactgggcctttcgttttatctgttgtttgtcggtgaacgctctcct
gagtaggacaaatccgccgggagcggatttgaacgttgcgaagcaacggcccggagggtggcgg
gcaggacgcccgccataaactgccaggcatcaaattaagcagaaggccatcctgacggatggcc
tttttgcgtttctacaaactctttttgtttatttttctaaatacattcaaatatgtatccgctt
aaccggaattgccagctggggcgccctctggtaaggttgggaagccctgcaaagtaaactggat
ggctttctcgccgccaaggatctgatggcgcaggggatcaagctctgatcaagagacaggatga
ggatcgtttcgcatgattgaacaagatggattgcacgcaggttctccggccgcttgggtggaga
ggctattcggctatgactgggcacaacagacaatcggctgctctgatgccgccgtgttccggct
gtcagcgcaggggcgcccggttctttttgtcaagaccgacctgtccggtgccctgaatgaactg
caagacgaggcagcgcggctatcgtggctggccacgacgggcgttccttgcgcagctgtgctcg
acgttgtcactgaagcgggaagggactggctgctattgggcgaagtgccggggcaggatctcct
gtcatctcaccttgctcctgccgagaaagtatccatcatggctgatgcaatgcggcggctgcat
acgcttgatccggctacctgcccattcgaccaccaagcgaaacatcgcatcgagcgagcacgta
ctcggatggaagccggtcttgtcgatcaggatgatctggacgaagagcatcaggggctcgcgcc
agccgaactgttcgccaggctcaaggcgagcatgcccgacggcgaggatctcgtcgtgaccat

FIG. 25D ggcgatgcctgcttgccgaatatcatggtggaaaatggccgcttttctggattcatcgactgtg
gccggctgggtgtggcggaccgctatcaggacatagcgttggctacccgtgatattgctgaaga
gcttggcggcgaatgggctgaccgcttcctcgtgctttacggtatcgccgctcccgattcgcag
cgcatcgccttctatcgccttcttgacgagttcttctgacgcatgaccaaaatcccttaacgtg
agttttcgttccactgagcgtcagaccccgtagaaaagatcaaaggatcttcttgagatccttt
ttttctgcgcgtaatctgctgcttgcaaacaaaaaaaccaccgctaccagcggtggtttgtttg
ccggatcaagagctaccaactctttttccgaaggtaactggcttcagcagagcgcagataccaa
atactgtccttctagtgtagccgtagttaggccaccacttcaagaactctgtagcaccgcctac
atacctcgctctgctaatcctgttaccagtggctgctgccagtggcgataagtcgtgtcttacc
gggttggactcaagacgatagttaccggataaggcgcagcggtcgggctgaacggggggttcgt
gcacacagcccagcttggagcgaacgacctacaccgaactgagatacctacagcgtgagctatg
agaaagcgccacgcttcccgaagggagaaaggcggacaggtatccggtaagcggcagggtcgga
acaggagagcgcacgagggagcttccagggggaaacgcctggtatctttatagtcctgtcgggt
ttcgccacctctgacttgagcgtcgatttttgtgatgctcgtcaggggggcggagcctatggaa
aaacgccagcaacgcggcctttttacggttcctggccttttgctggccttttgctcacatgttc
tttcctgcgttatcccctgattctgtggataaccgtattaccgcctttgagtgagctgataccg
ctcgccgcagccgaacgaccgagcgcagcgagtcagtgagcgaggaagcggaagagcgcctgat
gcggtattttctccttacgcatctgtgcggtatttcacaccgcatatggtgcactctcagtaca
atctgctctgatgccgcatagttaagccagtatacactccgctatcgctacgtgactgggtcat
ggctgcgccccgacacccgccaacacccgctgacgcgccctgacgggcttgtctgctcccggca
tccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgtt
gacaccatcgaatggtgcaaaacctttcgcggtatggcatgatagcgcccggaagagagtcaat
tcagggtggtgaatgtgaaaccagtaacgttatacgatgtcgcagagtatgccggtgtctctta
tcagaccgtttcccgcgtggtgaaccaggccagccacgtttctgcgaaaacgcgggaaaaagtg
gaagcggcgatggcggagctgaattacattcccaaccgcgtggcacaacaactggcgggcaaac
agtcgttgctgattggcgttgccacctccagtctggccctgcacgcgccgtcgcaaattgtcgc
ggcgattaaatctcgcgccgatcaactgggtgccagcgtggtggtgtcgatggtagaacgaagc
ggcgtcgaagcctgtaaagcggcggtgcacaatcttctcgcgcaacgcgtcagtgggctgatca
ttaactatccgctggatgaccaggatgccattgctgtggaagctgcctgcactaatgttccggc
gttatttcttgatgtctctgaccagacacccatcaacagtattattttctcccatgaagacggt
acgcgactgggcgtggagcatctggtcgcattgggtcaccagcaaatcgcgctgttagcgggcc
cattaagttctgtctcggcgcgtctgcgtctggctggctggcataaatatctcactcgcaatca
aattcagccgatagcggaacgggaaggcgactggagtgccatgtccggttttcaacaaaccatg
caaatgctgaatgagggcatcgttcccactgcgatgctggttgccaacgatcagatggcgctgg
gcgcaatgcgcgccattaccgagtccgggctgcgcgttggtgcggatatctcggtagtgggata
cgacgataccgaagacagctcatgttatatcccgccgtcaaccaccatcaaacaggattttcgc
ctgctggggcaaaccagcgtggaccgcttgctgcaactctctcagggccaggcggtgaagggca
atcagctgttgcccgtctcactggtgaaaagaaaaaccaccctggcgcccaatacgcaaaccgc
ctctccccgcgcgttggccgattcattaatgcagctggcacgacaggtttcccgactggaaagc
gggcagtgagcgcaacgcaattaatgtgagttagcgcgaattgatctg
(SEQ ID NO:33)

FIG. 27A

5'-
cccgtcttactgtcgggaattcgcgttggccgattcattaatgcagattctgaaatgagctgtt
gacaattaatcatccggctcgtataatgtgtggaattgtgagcggataacaatttcacacagga
aacagcgccgctgagaaaaagcgaagcggcactgctctttaacaatttatcagacaatctgtgt
gggcactcgaccggaattatcgattaactttattattaaaaattaaagaggtatatattaatgt
atcgattaaataaggaggaataaaccatggatccgagctcaggaggtaaaaaaacatgaaaaca
gtagttattattgatgcattacgaacaccaattggaaaatataaaggcagcttaagtcaagtaa
gtgccgtagacttaggaacacatgttacaacacaactttaaaaagacattccactatttctga
agaaattgatcaagtaatctttggaaatgttttacaagctggaaatggccaaaatcccgcacga
caaatagcaataaacagcggtttgtctcatgaaattcccgcaatgacggttaatgaggtctgcg
gatcaggaatgaaggccgttattttggcgaaacaattgattcaattaggagaagcggaagtttt
aattgctggcgggattgagaatatgtcccaagcacctaaattacaacgttttaattacgaaaca
gaaagctacgatgcgcctttttctagtatgatgtatgatggattaacggatgcctttagtggtc
aggcaatgggcttaactgctgaaaatgtggccgaaaagtatcatgtaactagagaagagcaaga
tcaattttctgtacattcacaattaaaagcagctcaagcacaagcagaagggatattcgctgac
gaaatagccccattagaagtatcaggaacgcttgtggagaaagatgaagggattcgccctaatt
cgagcgttgagaagctaggaacgcttaaaacagtttttaaagaagacggtactgtaacagcagg
gaatgcatcaaccattaatgatggggcttctgctttgattattgcttcacaagaatatgccgaa
gcacacggtcttccttatttagctattattcgagacagtgtggaagtcggtattgatccagcct
atatgggaatttcgccgattaaagccattcaaaaactgttagcgcgcaatcaacttactacgga
agaaattgatctgtatgaaatcaacgaagcatttgcagcaacttcaatcgtggtccaaagagaa
ctggctttaccagaggaaaaggtcaacatttatggtggcggtatttcattaggtcatgcgattg
gtgccacaggtgctcgtttattaacgagtttaagttatcaattaaatcaaaaagaaaagaaata
tggagtggcttctttatgtatcggcggtggcttaggactcgctatgctactagagagacctcag
caaaaaaaaaacagccgattttatcaaatgagtcctgaggaacgcctggcttctcttcttaatg
aaggccagatttctgctgatacaaaaaaagaatttgaaaatacggctttatcttcgcagattgc
caatcatatgattgaaaatcaaatcagtgaaacagaagtgccgatgggcgttggcttacattta
acagtggacgaaactgattatttggtaccaatggcgacagaagagccctcagttattgcggctt
tgagtaatggtgcaaaaatagcacaaggatttaaaacagtgaatcaacaacgcttaatgcgtgg
acaaatcgtttttacgatgttgcagatcccgagtcattgattgataaactacaagtaagagaa
gcggaagttttcaacaagcagagttaagttatccatctatcgttaaacggggcggcggcttaa
gagatttgcaatatcgtacttttgatgaatcatttgtatctgtcgactttttagtagatgttaa
ggatgcaatgggggcaaatatcgttaacgctatgttggaaggtgtggccgagttgttccgtgaa
tggtttgcggagcaaaagattttattcagtattttaagtaattatgccacggagtcggttgtta
cgatgaaaacggctattccagtttcacgtttaagtaaggggagcaatggccgggaaattgctga
aaaaattgttttagcttcacgctatgcttcattagatccttatcgggcagtcacgcataacaaa
ggaatcatgaatggcattgaagctgtagttttagctacaggaaatgatacacgcgctgttagcg
cttcttgtcatgcttttgcggtgaaggaaggtcgctaccaaggcttgactagttggacgctgga
tggcgaacaactaattggtgaaatttcagttccgcttgctttagccacggttggcggtgccaca
aaagtcttacctaaatctcaagcagctgctgatttgttagcagtgacggatgcaaaagaactaa
gtcgagtagtagcggctgttggtttggcacaaaatttagcggcgttacgggccttagtctctga
aggaattcaaaaaggacacatggctctacaagcacgttctttagcgatgacggtcggagctact
ggtaaagaagttgaggcagtcgctcaacaattaaaacgtcaaaaaacgatgaaccaagaccgag
ccatggctatttaaatgatttaagaaaacaataaaggaggtaaaaaaacatgacaattgggat

FIG. 27B tgataaaattagtttttttgtgccccttattatattgatatgacggcactggctgaagccaga
aatgtagaccctggaaaatttcatattggtattgggcaagaccaaatggcggtgaacccaatca
gccaagatattgtgacatttgcagccaatgccgcagaagcgatcttgaccaaagaagataaaga
ggccattgatatggtgattgtcgggactgagtccagtatcgatgagtcaaaagcggccgcagtt
gtcttacatcgtttaatggggattcaacctttcgctcgctctttcgaaatcaaggaagcttgtt
acggagcaacagcaggcttacagttagctaagaatcacgtagccttacatccagataaaaaagt
cttggtcgtagcggcagatattgcaaaatatggcttaaattctggcggtgagcctacacaagga
gctggggcggttgcaatgttagttgctagtgaaccgcgcatttggctttaaagaggataatg
tgatgctgacgcaagatatctatgacttttggcgtccaacaggccacccgtatcctatggtcga
tggtcctttgtcaaacgaaacctacatccaatcttttgcccaagtctgggatgaacataaaaaa
cgaaccggtcttgattttgcagattatgatgctttagcgttccatattccttacacaaaaatgg
gcaaaaaagccttattagcaaaaatctccgaccaaactgaagcagaacaggaacgaattttagc
ccgttatgaagaaagtatcgtctatagtcgtcgcgtaggaaacttgtatacgggttcactttat
ctgggactcatttccctttagaaaatgcaacgactttaaccgcaggcaatcaaattggtttat
tcagttatggttctggtgctgtcgctgaatttttcactggtgaattagtagctggttatcaaaa
tcatttacaaaaagaaactcatttagcactgctggataatcggacagaactttctatcgctgaa
tatgaagccatgtttgcagaaactttagacacagacattgatcaaacgttagaagatgaattaa
aatatagtatttctgctattaataataccgttcgttcttatcgaaactaagagatctgcagctg
gtaccatatgggaattcgaagcttgggcccgaacaaaaactcatctcagaagaggatctgaata
gcgccgtcgaccatcatcatcatcatcattgagtttaaacggtctccagcttggctgttttggc
ggatgagagaagattttcagcctgatacagattaaatcagaacgcagaagcggtctgataaaac
agaatttgcctggcggcagtagcgcggtggtcccacctgaccccatgccgaactcagaagtgaa
acgccgtagcgccgatggtagtgtggggtctccccatgcgagagtagggaactgccaggcatca
aataaaacgaaaggctcagtcgaaagactgggcctttcgttttatctgttgtttgtcggtgaac
gctctcctgagtaggacaaatccgccgggagcggatttgaacgttgcgaagcaacggcccggag
ggtggcgggcaggacgcccgccataaactgccaggcatcaaattaagcagaaggccatcctgac
ggatggcctttttgcgtttctacaaactctttttgtttatttttctaaatacattcaaatatgt
atccgctcatgagacaataaccctgataaatgcttcaataatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc
tgatgccgcatagttaagccagccccgacacccgccaacacccgctgacgagcttagtaaagcc
ctcgctagattttaatgcggatgttgcgattacttcgccaactattgcgataacaagaaaaagc
cagcctttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat

FIG. 27C caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttccccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttttacaccgttttcatct
gtgcatatggacagttttccctttgatatgtaacggtgaacagttgttctactttttgtttgtta
gtcttgatgcttcactgatagatacaagagccataagaacctcagatccttccgtatttagcca
gtatgttctctagtgtggttcgttgtttttgcgtgagccatgagaacgaaccattgagatcata
cttactttgcatgtcactcaaaaattttgcctcaaaactggtgagctgaattttttgcagttaaa
gcatcgtgtagtgtttttcttagtccgttatgtaggtaggaatctgatgtaatggttgttggta
ttttgtcaccattcatttttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc
cttgtgagttttcttttgtgttagttcttttaataaccactcataaatcctcatagagtatttg
ttttcaaaagacttaacatgttccagattatattttatgaatttttttaactggaaaagataag
gcaatatctcttcactaaaaactaattctaatttttcgcttgagaacttggcatagtttgtcca
ctggaaaatctcaaagcctttaaccaaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtcctttttcctttgagttgtgggtat
ctgtaaattctgctagacctttgctggaaacttgtaaattctgctagaccctctgtaaattcc
gctagacctttgtgtgttttttttgtttatattcaagtggttataatttatagaataaagaaag
aataaaaaaagataaaaagaatagatcccagccctgtgtataactcactactttagtcagttcc
gcagtattacaaaggatgtcgcaaacgctgtttgctcctctacaaaacagaccttaaaaccct
aaaggcttaagtagcaccctcgcaagctcgggcaaatcgctgaatattcctttgtctccgacc

FIG. 27D

Atcaggcacctgagtcgctgtctttttcgtgacattcagttcgctgcgctcacggctctggcag
tgaatgggggtaaatggcactacaggcgcctttttatggattcatgcaaggaaactacccataat
acaagaaaagcccgtcacgggcttctcagggcgttttatggcgggtctgctatgtggtgctatc
tgactttttgctgttcagcagttcctgccctctgattttccagtctgaccacttcggattatcc
cgtgacaggtcattcagactggctaatgcacccagtaaggcagcggtatcatcaacaggctta
(SEQ ID NO:46)

Lower Pathway Bacillus Cassette
9371 bp

FIG. 29A

5'-
tgtaacctttgctttcaaatgagtagaaataatgcacatccatgtttgtatcgtgcaaataaag
tgtttcatccgtaggaaaaaatgactttagtatctgttccgctttttctgatgaaatgtgctcc
ccgacaaaattgaatgaatcatggacatttgctggctttgatacagcgaaagcagccgttccta
tgttatatatcggatttaacagcaggacaaaaaacaccatgacagccatcgtcacccacttatt
cacacgcacataaacctttcctgacttttggaacagatgatagctcatcaaaaatcccgccatt
gccaaataaatcgtatatggcattactgcaccataatcttttgagatttgattgggatatggcg
caagcagcaagacaagcagtccgataatcagcgtataaaataagcctagtaagatcttatccgt
tctccaatacagcttgaaaaacactacattcaacgcaatgggaagagtgatgatgaaaaacaga
aacacgaatgcaatcggctccatcccatccgggtattccttccaatacgaaaagaaactaaaaa
tcatttgtacgatcggcaaactgacaacagcaaggtcgaacgtataaaacttaccctttccgcc
atgatcacgcggcatcagcatatagtgaaaagccgtcagcagcacatatccgtataacaaaaaa
tgcagcagcggcagcagttcttttccgtcctctcttaagtaagcgctggtgaagtttgttgatt
gcacctggtgaataagttcaacagacactcccgccagcagcacaatccgcaatataacacccgc
caagaacattgtgcgctgccggtttattttgggatgatgcaccaaaagatataagcccgccaga
acaacaattgaccattgaatcagcagggtgctttgtctgcttaatataaaataacgttcgaaat
gcaatacataatgactgaataactccaacacgaacaacaactccatttttcttctgctatcaaaa
taacagactcgtgattttccaaacgagctttcaaaaaagcctctgccccttgcaaatcggatgc
ctgtctataaaattcccgatattggttaaacagcggcgcaatggcggccgcatctgatgtcttt
gcttggcgaatgttcatcttatttcttcctccctctcaataatttttttcattctatcccttttc
tgtaaagtttatttttcagaatacttttatcatcatgctttgaaaaaatatcacgataatatcc
attgttctcacggaagcacacgcaggtcatttgaacgaatttttttcgacaggaatttgccggga
ctcaggagcatttaacctaaaaaagcatgacatttcagcataatgaacatttactcatgtctat
tttcgttcttttctgtatgaaaatagttatttcgagtctctacggaaatagcgagagatgatat
acctaaatagagataaaatcatctcaaaaaaatgggtctactaaaatattattccatctattac
aataaattcacagaatagtcttttaagtaagtctactctgaattttttttaaaggagagggtaa
agagtgtcattaccgttcttaacttctgcaccgggaaaggttattatttttggtgaacactctg
ctgtgtacaacaagcctgccgtcgctgctagtgtgtctgcgttgagaacctacctgctaataag
cgagtcatctgcaccagatactattgaattggacttcccggacattagctttaatcataagtgg
tccatcaatgatttcaatgccatcaccgaggatcaagtaaactcccaaaaattggccaaggctc
aacaagccaccgatggcttgtctcaggaactcgttagtcttttggatccgttgttagctcaact
atccgaatccttccactaccatgcagcgttttgtttcctgtatatgtttgtttgcctatgcccc
catgccaagaatattaagtttttctttaaagtctactttacccatcggtgctgggttgggctcaa
gcgcctctatttctgtatcactggccttagctatggcctacttggggggttaataggatctaa
tgacttggaaaagctgtcagaaaacgataagcatatagtgaatcaatgggccttcataggtgaa
aagtgtattcacggtaccccttcaggaatagataacgctgtggccacttatggtaatgccctgc
tatttgaaaaagactcacataatggaacaataaacacaaacaatttaagttcttagatgattt
cccagccattccaatgatcctaacctatactagaattccaaggtctacaaaagatcttgttgct
cgcgttcgtgtgttggtcaccgagaaatttcctgaagttatgaagccaattctagatgccatgg
gtgaatgtgccctacaaggcttagagatcatgactaagttaagtaaatgtaaaggcaccgatga
cgaggctgtagaaactaataatgaactgtatgaacaactattggaattgataagaataaatcat
ggactgcttgtctcaatcggtgtttctcatcctggattagaacttattaaaaatctgagcgatg
atttgagaattggctccacaaaacttaccggtgctggtggcggcggttgctctttgactttgtt
acgaagagacattactcaagagcaaattgacagcttcaaaaagaaattgcaagatgattttagt

FIG. 29B tacgagacatttgaaacagacttgggtgggactggctgctgtttgttaagcgcaaaaaatttga
ataaagatcttaaaatcaaatccctagtattccaattatttgaaaataaaactaccacaaagca
acaaattgacgatctattattgccaggaaacacgaatttaccatggacttcataaaaggagagg
gtgtcagagttgagagccttcagtgccccagggaaagcgttactagctggtggatatttagttt
tagatacaaaatatgaagcatttgtagtcggattatcggcaagaatgcatgctgtagcccatcc
ttacggttcattgcaagggtctgataagtttgaagtgcgtgtgaaaagtaaacaatttaaagat
ggggagtggctgtaccatataagtcctaaaagtggcttcattcctgtttcgataggcggatcta
agaacccttttcattgaaaaagttatcgctaacgtatttagctactttaaacctaacatggacga
ctactgcaatagaaacttgttcgttattgatattttctctgatgatgcctaccattctcaggag
gatagcgttaccgaacatcgtggcaacagaagattgagttttcattcgcacagaattgaagaag
ttcccaaaacagggctgggctcctcggcaggtttagtcacagttttaactacagctttggcctc
ctttttgtatcggacctggaaaataatgtagacaaatatagagaagttattcataatttagca
caagttgctcattgtcaagctcagggtaaaattggaagcgggtttgatgtagcggcggcagcat
atggatctatcagatatagaagattcccacccgcattaatctctaatttgccagatattggaag
tgctacttacggcagtaaactggcgcatttggttgatgaagaagactggaatattacgattaaa
agtaaccatttaccttcgggattaactttatggatgggcgatattaagaatggttcagaaacag
taaaactggtccagaaggtaaaaaattggtatgattcgcatatgccagaaagcttgaaaatata
tacagaactcgatcatgcaaattctagatttatggatggactatctaaactagatcgcttacac
gagactcatgacgattacagcgatcagatatttgagtctcttgagaggaatgactgtacctgtc
aaaagtatcctgaaatcacagaagttagagatgcagttgccacaattagacgttcctttagaaa
aataactaaagaatctggtgccgatatcgaacctcccgtacaaactagcttattggatgattgc
cagaccttaaaaggagttcttacttgcttaatacctggtgctggtggttatgacgccattgcag
tgattactaagcaagatgttgatcttagggctcaaaccgctaatgacaaaagattttctaaggt
tcaatggctggatgtaactcaggctgactggggtgttaggaaagaaaaagatccggaaacttat
cttgataaataaaaggagagggtgaccgtttacacagcatccgttaccgcacccgtcaacatcg
caacccttaagtattgggggaaagggacacgaagttgaatctgcccaccaattcgtccatatc
agtgactttatcgcaagatgacctcagaacgttgacctctgcggctactgcacctgagtttgaa
cgcgacactttgtggttaaatggagaaccacacagcatcgacaatgaaagaactcaaaattgtc
tgcgcgacctacgccaattaagaaaggaaatggaatcgaaggacgcctcattgcccacattatc
tcaatggaaactccacattgtctccgaaaataactttcctacagcagctggtttagcttcctcc
gctgctggctttgctgcattggtctctgcaattgctaagttataccaattaccacagtcaactt
cagaaatatctagaatagcaagaaaggggtctggttcagcttgtagatcgttgtttggcggata
cgtggcctgggaaatgggaaaagctgaagatggtcatgattccatggcagtacaaatcgcagac
agctctgactggcctcagatgaaagcttgtgtcctagttgtcagcgatattaaaaaggatgtga
gttccactcagggtatgcaattgaccgtggcaacctccgaactatttaaagaaagaattgaaca
tgtcgtaccaaagagatttgaagtcatgcgtaaagccattgttgaaaaagatttcgccaccttt
gcaaaggaaacaatgatggattccaactctttccatgccacatgtttggactctttccctccaa
tattctacatgaatgacacttccaagcgtatcatcagttggtgccacaccattaatcagtttta
cggagaaacaatcgttgcatacacgtttgatgcaggtccaaatgctgtgttgtactacttagct
gaaaatgagtcgaaactctttgcatttatctataaattgtttggctctgttcctggatgggaca
agaaatttactactgagcagcttgaggctttcaaccatcaatttgaatcatctaactttactgc
acgtgaattggatcttgagttgcaaaaggatgttgccagagtgattttaactcaagtcggttca
ggcccacaagaaacaaacgaatctttgattgacgcaaagactggtctaccaaaggaataaagg
agagggtgactgccgacaacaatagtatgccccatggtgcagtatctagttacgccaaattagt

FIG. 29C gcaaaaccaaacacctgaagacattttggaagagtttcctgaaattattccattacaacaaaga
cctaatacccgatctagtgagacgtcaaatgacgaaagcggagaaacatgtttttctggtcatg
atgaggagcaaattaagttaatgaatgaaaattgtattgttttggattgggacgataatgctat
tggtgccggtaccaagaaagtttgtcatttaatggaaaatattgaaaagggtttactacatcgt
gcattctccgtctttattttcaatgaacaaggtgaattacttttacaacaaagagccactgaaa
aaataactttccctgatctttggactaacacatgctgctctcatccactatgtattgatgacga
attaggtttgaagggtaagctagacgataagattaagggcgctattactgcggcggtgagaaaa
ctagatcatgaattaggtattccagaagatgaaactaagacaaggggtaagtttcacttttaa
acagaatccattacatggcaccaagcaatgaaccatggggtgaacatgaaattgattacatcct
attttataagatcaacgctaaagaaaacttgactgtcaacccaaacgtcaatgaagttagagac
ttcaaatgggtttcaccaaatgatttgaaaactatgtttgctgacccaagttacaagtttacgc
cttggtttaagattatttgcgagaattacttattcaactggtgggagcaattagatgacctttc
tgaagtggaaaatgacaggcaaattcatagaatgctataaaaaaaccggccttggccccgccg
gtttttattatttttcttcctccgcatgttcaatccgctccataatcgacggatggctccctc
tgaaaatttaacgagaaacggcgggttgacccggctcagtcccgtaacggccaagtcctgaaa
cgtctcaatcgccgcttcccggtttccggtcagctcaatgccgtaacggtcggcggcgttttcc
tgataccgggagacggcattcgtaatttgaatacatacgaacaaattaataaagtgaaaaaat
acttcggaaacatttaaaaataaccttattggtacttacatgtttggatcaggagttgagagt
ggactaaaaccaaatagtgatcttgacttttttagtcgtcgtatctgaaccattgacagatcaaa
gtaaagaaatacttatacaaaaaattagacctatttcaaaaaaaataggagataaaagcaactt
acgatatattgaattaacaattattattcagcaagaaatggtaccgtggaatcatcctcccaaa
caagaatttatttatggagaatggttacaagagctttatgaacaaggatacattcctcagaagg
aattaaattcagatttaaccataatgctttaccaagcaaaacgaaaaaataaaagaatatacgg
aaattatgacttagaggaattactacctgatattccattttctgatgtgagaagagccattatg
gattcgtcagaggaattaatagataattatcaggatgatgaaaccaactctatattaactttat
gccgtatgattttaactatggacacgggtaaaatcataccaaaagatattgcgggaaatgcagt
ggctgaatcttctccattagaacatagggagagaattttgttagcagttcgtagttatcttgga
gagaatattgaatggactaatgaaaatgtaaatttaactataaactatttaaataacagattaa
aaaaattataatgtaacctttgctttcaaatgagtagaaataatgcacatccatgtttgtatcg
tgcaaataaagtgtttcatccgtaggaaaaaatgactttagtatctgttccgcttttctgatg
aaatgtgctccccgacaaaattgaatgaatcatggacatttgctggctttgatacagcgaaagc
agccgttcctatgttatatatcggatttaacagcaggacaaaaaacaccatgacagccatcgtc
acccacttattcacacgcacataaacctttcctgacttttggaacagatgatagctcatcaaaa
atcccgccattgccaaataaatcgtatatggcattactgcaccataatcttttgagatttgatt
gggatatggcgcaagcagcaagacaagcagtccgataatcagcgtataaaataagcctagtaag
atcttatccgttctccaatacagcttgaaaaacactacattcaacgcaatgggaagagtgatga
tgaaaaacagaaacacgaatgcaatcggctccatcccatccgggtattccttccaatacgaaaa
gaaactaaaaatcatttgtacgatcggcaaactgacaacagcaaggtcgaacgtataaaactta
ccctttccgccatgatcacgcggcatcagcatatagtgaaaagccgtcagcagcacatatccgt
ataacaaaaaatgcagcagcggcagcagttcttttccgtcctctcttaagtaagcgctggtgaa
gtttgttgattgcacctggtgaataagttcaacagacactcccgccagcagcacaatccgcaat
ataacacccgccaagaacattgtgcgctgccggtttattttgggatgatgcaccaaaagatata
agcccgccagaacaacaattgaccattgaatcagcagggtgctttgtctgcttaatataaaata
acgttcgaaatgcaatacataatgactgaataactccaacacgaacaacaaaagtgcgcatttt

FIG. 29D

Ataaaagctaatgattcagtccacataattgatagacgaattctgctacaggtcacgtggctat
gtgaaggatcgcgcgtccagttaagagcaaaaacattgacaaaaaaatttatttatgctaaaat
ttactattaatatatttgtatgtataataagattctcctggccaggggaatcttatttttgtg
gaggatcatttcatgaggaaaaatgagtccagcttaacgtctctaatttcagcttttgcccgtg
catatcacagccgatatgacacacctcttattttgatgattttatcgcaaaagatctcattaa
cgaaaaagagtttatcgacatcagtaaaaatatgattcaagaaatatcgtttttcaacaaagag
atcgccgaacgtcttcaaaatgatcctgaaaaaatattaaaatgggttgcacaaatccagctgt
ctccaacgcccctagcacgtgcttcttattgtgaaaaagtcttgcacaacgaattaatcctggg
ggcaaaacagtatgtcattcttggagcgggactggatactttctgctttcggcatccagaatta
gaaaacagcttacaggttttcgaggttgatcatccggccacacagcaattgaaaaaaaataagc
tgaaggatgcaaatctgacaattccgggtcatcttcatttgttcctatggatttcaccaaaac
gttttcgtatgatcctctcttagatgaaggatttaaaaacacaaaaacattcttcagccttctc
ggagtgtcttattatgtaacacgggaagaaaatgcaagcttgatcagcaatttattttctcatg
tcccgcctggaagctctattgtttttgattatgcggacgaaacacttttacagcaaaagggac
gtcgaatcgagttgaacatatggtgaagatggctgccgcaagcggggaaccgatgaaatcatgt
ttcacttatcaagagattgaacatctg
(SEQ ID NO:47)

FIG. 31A

5′-
tagaaaaactcatcgagcatcaaatgaaactgcaatttattcatatcaggattatcaataccat
atttttgaaaaagccgtttctgtaatgaaggagaaaactcaccgaggcagttccataggatggc
aagatcctggtatcggtctgcgattccgactcgtccaacatcaatacaacctattaatttcccc
tcgtcaaaaataaggttatcaagtgagaaatcaccatgagtgacgactgaatccggtgagaatg
gcaaaagtttatgcatttctttccagacttgttcaacaggccagccattacgctcgtcatcaaa
atcactcgcatcaaccaaaccgttattcattcgtgattgcgcctgagcgaggcgaaatacgcga
tcgctgttaaaaggacaattacaaacaggaatcgagtgcaaccggcgcaggaacactgccagcg
catcaacaatattttcacctgaatcaggatattcttctaatacctggaacgctgtttttccggg
gatcgcagtggtgagtaaccatgcatcatcaggagtacggataaaatgcttgatggtcggaagt
ggcataaattccgtcagccagtttagtctgaccatctcatctgtaacatcattggcaacgctac
ctttgccatgtttcagaaacaactctggcgcatcgggcttcccatacaagcgatagattgtcgc
acctgattgcccgacattatcgcgagcccatttatacccatataaatcagcatccatgttggaa
tttaatcgcggcctcgacgtttcccgttgaatatggctcatattcttcctttttcaatattatt
gaagcatttatcagggttattgtctcatgagcggatacatatttgaatgtatttagaaaaataa
acaaataggggtcagtgttacaaccaattaaccaattctgaacattatcgcgagcccatttata
cctgaatatggctcataacaccccttgtttgcctggcggcagtagcgcggtggtcccacctgac
cccatgccgaactcagaagtgaaacgccgtagcgccgatggtagtgtggggactccccatgcga
gagtagggaactgccaggcatcaaataaaacgaaaggctcagtcgaaagactgggcctttcgcc
cgggctaattagggggtgtcgccctttagtcgctgaacatgtgctctgtttctaccgagaacgt
ttccttcactgagacggaaaccgaggcacgtcgtagcgcgaactacgagccgaatagctgggac
tacgatttcctgctgtcttccgatactgacgaatctattgaggtgtacaaagacaaagcaaaga
aactggaggctgaagtgcgccgcgaaattaacaacgagaaagctgaattcctgactctgctgga
gctgatcgataacgtacagcgcctgggtctgggttaccgcttcgaatctgatatccgtcgcgca
ctggatcgtttcgtaagcagcggcggtttcgatggcgtgaccaaaacgagcctgcacgctaccg
cgctgtccttccgtctgctgcgtcagcacggcttcgaagtttctcaggaagcattctccggttt
caaagatcaaaacggtaacttcctggaaaacctgaaagaagacactaaggcgatcctgagcctg
tatgaggcaagctttctggccctggagggtgagaacatcctggatgaggcgcgcgtattcgcca
tctcccatctgaaagagctgtctgaagagaaaatcggtaaggaactggcagagcaggttaatca
cgcactggaactgccgctgcatcgtcgtacccagcgtctggaggcggtttggtccatcgaagcg
taccgcaaaaaggaggatgctaaccaggttctgctggaactggccatcctggactacaacatga
tccagtccgtttaccagcgtgatctgcgtgaaacctcccgttggtggcgccgtgtgggcctggc
gaccaaactgcacttcgctaaggaccgcctgattgagtctttttactgggcagtcggcgttgcg
ttcgaacctcagtattctgactgccgtaacagcgttgcgaaaatgttcagcttcgttactatta
tcgacgacatctacgacgtttacggtactctggacgagctggaactgtttaccgacgctgtcga
acgttgggatgttaacgccatcaacgatctgcctgactacatgaaactgtgcttcctggcactg
tataacacgatcaacgaaattgcatacgacaacctgaaagacaaaggtgaaaacatcctgccgt
acctgactaaagcgtgggcggatctgtgtaacgcttttctgcaagaagcgaaatggctgtataa
caaatccactccgacctttgacgattatttcggcaatgcctggaaatccagctctggcccgctg
caactgatcttcgcttattttgcggttgtccaaaacatcaaaaaggaggaaattgaaaacctgc
aaaaataccacgatatcattagccgtccttctcatatctttcgcctgtgcaacgacctggcaag
cgcgtccgcagagatcgcacgtggcgaaaccgctaactctgtttcctgctacatgcgcaccaag
ggcatttccgaagagctggcaaccgagagcgtaatgaatctgatcgacgaaacctgtaagaaaa
tgaacaaagaaaaactgggtggctccctgttcgctaaaccgttcgtagagactgctattaacct

FIG. 31B ggcacgtcagagccactgcacctaccacaatggtgacgcacatactagcccggatgaactgact
cgtaaacgtgtactgtctgttatcaccgaaccgattctgccgttcgaacgttaactgcagcgtc
aatcgaaagggcgacacaaaatttattctaaatgcataataaatactgataacatcttatagtt
tgtattatattttgtattatcgttgacatgtataattttgatatcaaaaactgattttcccttt
attattttcgagatttattttcttaattctctttaacaaactagaaatattgtatatacaaaaa
atcataaataatagatgaatagtttaattataggtgttcatcaatcgaaaaagcaacgtatctt
atttaaagtgcgttgctttttctcatttataaggttaaataattctcatatatcaagcaaagt
gacaggcgcccttaaatattctgacaaatgctctttccctaaactccccccataaaaaaacccg
ccgaagcgggtttttacgttatttgcggattaacgattactcgttatcagaaccgcccagggg
cccgagcttaagactggccgtcgttttacaacacagaaagagtttgtagaaacgcaaaaaggcc
atccgtcaggggccttctgcttagtttgatgcctggcagttccctactctcgccttccgcttcc
tcgctcactgactcgctgcgctcggtcgttcggctgcggcgagcggtatcagctcactcaaagg
cggtaatacggttatccacagaatcaggggataacgcaggaaagaacatgtgagcaaaaggcca
gcaaaaggccaggaaccgtaaaaaggccgcgttgctggcgtttttccataggctccgcccccct
gacgagcatcacaaaaatcgacgctcaagtcagaggtggcgaaacccgacaggactataaagat
accaggcgtttccccctggaagctccctcgtgcgctctcctgttccgaccctgccgcttaccgg
atacctgtccgcctttctcccttcgggaagcgtggcgctttctcatagctcacgctgtaggtat
ctcagttcggtgtaggtcgttcgctccaagctgggctgtgtgcacgaaccccccgttcagcccg
accgctgcgccttatccggtaactatcgtcttgagtccaacccggtaagacacgacttatcgcc
actggcagcagccactggtaacaggattagcagagcgaggtatgtaggcggtgctacagagttc
ttgaagtggtggcctaactacggctacactagaagaacagtatttggtatctgcgctctgctga
agccagttaccttcggaaaaagagttggtagctcttgatccggcaaacaaaccaccgctggtag
cggtggtttttttgtttgcaagcagcagattacgcgcagaaaaaaaggatctcaagaagatcct
ttgatcttttctacggggtctgacgctcagtggaacgacgcgcgcgtaactcacgttaaggat
tttggtcatgagcttgcgccgtcccgtcaagtcagcgtaatgctctgcttt
(SEQ ID NO:48)

FIG. 33A

5′-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgctctgtttctaccgagaacgtttccttcact
gagacggaaaccgaggcacgtcgtagcgcgaactacgagccgaatagctgggactacgatttcc
tgctgtcttccgatactgacgaatctattgaggtgtacaaagacaaagcaaagaaactggaggc
tgaagtgcgccgcgaaattaacaacgagaaagctgaattcctgactctgctggagctgatcgat
aacgtacagcgcctgggtctgggttaccgcttcgaatctgatatccgtcgcgcactggatcgtt
tcgtaagcagcggcggtttcgatggcgtgaccaaaacgagcctgcacgctaccgcgctgtcctt
ccgtctgctgcgtcagcacggcttcgaagtttctcaggaagcattctccggtttcaaagatcaa
aacggtaacttcctggaaaacctgaaagaagacactaaggcgatcctgagcctgtatgaggcaa
gctttctggccctggagggtgagaacatcctggatgaggcgcgcgtattcgccatctcccatct
gaaagagctgtctgaagagaaaatcggtaaggaactggcagagcaggttaatcacgcactggaa
ctgccgctgcatcgtcgtacccagcgtctggaggcggtttggtccatcgaagcgtaccgcaaaa
aggaggatgctaaccaggttctgctggaactggccatcctggactacaacatgatccagtccgt
ttaccagcgtgatctgcgtgaaacctcccgttggtggcgccgtgtgggcctggcgaccaaactg
cacttcgctaaggaccgcctgattgagtctttttactgggcagtcggcgttgcgttcgaacctc
agtattctgactgccgtaacagcgttgcgaaaatgttcagcttcgttactattatcgacgacat
ctacgacgtttacggtactctggacgagctggaactgtttaccgacgctgtcgaacgttgggat
gttaacgccatcaacgatctgcctgactacatgaaactgtgcttcctggcactgtataacacga
tcaacgaaattgcatacgacaacctgaaagacaaaggtgaaaacatcctgccgtacctgactaa
agcgtgggcggatctgtgtaacgctttctgcaagaagcgaaatggctgtataacaaatccact
ccgacctttgacgattatttcggcaatgcctggaaatccagctctggcccgctgcaactgatct
tcgcttattttgcggttgtccaaaacatcaaaaaggaggaaattgaaaacctgcaaaaatacca
cgatatcattagccgtccttctcatatctttcgcctgtgcaacgacctggcaagcgcgtccgca
gagatcgcacgtggcgaaaccgctaactctgtttcctgctacatgcgcaccaagggcatttccg
aagagctggcaaccgagagcgtaatgaatctgatcgacgaaacctgtaagaaaatgaacaaaga
aaaactgggtggctccctgttcgctaaaccgttcgtagagactgctattaacctggcacgtcag
agccactgcacctaccacaatggtgacgcacatactagcccggatgaactgactcgtaaacgtg
tactgtctgttatcaccgaaccgattctgccgttcgaacgttaactgcagctggtaccatatgg
gaattcgaagctttctagaacaaaaactcatctcagaagaggatctgaatagcgccgtcgacca
tcatcatcatcatcattgagtttaaacggtctccagcttggctgttttggcggatgagagaaga
ttttcagcctgatacagattaaatcagaacgcagaagcggtctgataaaacagaatttgcctgg
cggcagtagcgcggtggtcccacctgaccccatgccgaactcagaagtgaaacgccgtagcgcc
gatggtagtgtggggtctccccatgcgagagtagggaactgccaggcatcaaataaaacgaaag
gctcagtcgaaagactgggcctttcgttttatctgttgtttgtcggtgaacgctctcctgagta
ggacaaatccgccgggagcggatttgaacgttgcgaagcaacggcccggagggtggcgggcagg
acgcccgccataaactgccaggcatcaaattaagcagaaggccatcctgacggatggcctttttt
gcgtttctacaaactctttttgtttatttttctaaatacattcaaatatgtatccgctcatgag
acaataaccctgataaatgcttcaataatattgaaaaaggaagagtatgagtattcaacatttc

FIG. 33B cgtgtcgcccttattcccttttttgcggcattttgccttcctgtttttgctcacccagaaacgc
tggtgaaagtaaaagatgctgaagatcagttgggtgcacgagtgggttacatcgaactggatct
caacagcggtaagatccttgagagttttcgccccgaagaacgttttccaatgatgagcactttt
aaagttctgctatgtggcgcggtattatcccgtgttgacgccgggcaagagcaactcggtcgcc
gcatacactattctcagaatgacttggttgagtactcaccagtcacagaaaagcatcttacgga
tggcatgacagtaagagaattatgcagtgctgccataaccatgagtgataacactgcggccaac
ttacttctgacaacgatcggaggaccgaaggagctaaccgcttttttgcacaacatgggggatc
atgtaactcgccttgatcgttgggaaccggagctgaatgaagccataccaaacgacgagcgtga
caccacgatgcctgtagcaatggcaacaacgttgcgcaaactattaactggcgaactacttact
ctagcttcccggcaacaattaatagactggatggaggcggataaagttgcaggaccacttctgc
gctcggcccttccggctggctggtttattgctgataaatctggagccggtgagcgtgggtctcg
cggtatcattgcagcactggggccagatggtaagccctcccgtatcgtagttatctacacgacg
gggagtcaggcaactatggatgaacgaaatagacagatcgctgagataggtgcctcactgatta
agcattggtaactgtcagaccaagtttactcatatatactttagattgatttaaaacttcattt
ttaatttaaaaggatctaggtgaagatcctttttgataatctcatgaccaaaatcccttaacgt
gagttttcgttccactgagcgtcagaccccgtagaaaagatcaaaggatcttcttgagatcctt
tttttctgcgcgtaatctgctgcttgcaaacaaaaaaaccaccgctaccagcggtggtttgttt
gccggatcaagagctaccaactctttttccgaaggtaactggcttcagcagagcgcagatacca
aatactgtccttctagtgtagccgtagttaggccaccacttcaagaactctgtagcaccgccta
catacctcgctctgctaatcctgttaccagtggctgctgccagtggcgataagtcgtgtcttac
cgggttggactcaagacgatagttaccggataaggcgcagcggtcgggctgaacggggggttcg
tgcacacagcccagcttggagcgaacgacctacaccgaactgagatacctacagcgtgagctat
gagaaagcgccacgcttcccgaagggagaaaggcggacaggtatccggtaagcggcagggtcgg
aacaggagagcgcacgagggagcttccagggggaaacgcctggtatctttatagtcctgtcggg
tttcgccacctctgacttgagcgtcgatttttgtgatgctcgtcaggggggcggagcctatgga
aaaacgccagcaacgcggcctttttacggttcctggccttttgctggccttttgctcacatgtt
ctttcctgcgttatcccctgattctgtggataaccgtattaccgcctttgagtgagctgatacc
gctcgccgcagccgaacgaccgagcgcagcgagtcagtgagcgaggaagcggaagagcgcctga
tgcggtattttctccttacgcatctgtgcggtatttcacaccgcatatggtgcactctcagtac
aatctgctctgatgccgcatagttaagccagtatacactccgctatcgctacgtgactgggtca
tggctgcgccccgacacccgccaacacccgctgacgcgccctgacgggcttgtctgctcccggc
atccgcttacagacaagctgtgaccgtctccgggagctgcatgtgtcagaggttttcaccgtca
tcaccgaaacgcgcgaggcagcagatcaattcgcgcgcgaaggcgaagcggcatgcatttacgt
tgacaccatcgaatggtgcaaaacctttcgcggtatggcatgatagcgcccggaagagagtcaa
ttcagggtggtgaatgtgaaaccagtaacgttatacgatgtcgcagagtatgccggtgtctctt
atcagaccgtttcccgcgtggtgaaccaggccagccacgtttctgcgaaaacgcgggaaaaagt
ggaagcggcgatggcggagctgaattacattcccaaccgcgtggcacaacaactggcgggcaaa
cagtcgttgctgattggcgttgccacctccagtctggccctgcacgcgccgtcgcaaattgtcg
cggcgattaaatctcgcgccgatcaactgggtgccagcgtggtggtgtcgatggtagaacgaag
cggcgtcgaagcctgtaaagcggcggtgcacaatcttctcgcgcaacgcgtcagtgggctgatc
attaactatccgctggatgaccaggatgccattgctgtggaagctgcctgcactaatgttccgg
cgttatttcttgatgtctctgaccagacacccatcaacagtattattttctcccatgaagacgg
tacgcgactgggcgtggagcatctggtcgcattgggtcaccagcaaatcgcgctgttagcgggc
ccattaagttctgtctcggcgcgtctgcgtctggctggctggcataaatatctcactcgcaatc

FIG. 33C aaattcagccgatagcggaacgggaaggcgactggagtgccatgtccggttttcaacaaaccat
gcaaatgctgaatgagggcatcgttcccactgcgatgctggttgccaacgatcagatggcgctg
ggcgcaatgcgcgccattaccgagtccgggctgcgcgttggtgcggatatctcggtagtgggat
acgacgataccgaagacagctcatgttatatcccgccgtcaaccaccatcaaacaggattttcg
cctgctggggcaaaccagcgtggaccgcttgctgcaactctctcagggccaggcggtgaagggc
aatcagctgttgcccgtctcactggtgaaaagaaaaaccaccctggcgcccaatacgcaaaccg
cctctccccgcgcgttggccgattcattaatgcagctggcacgacaggtttcccgactggaaag
cgggcagtgagcgcaacgcaattaatgtgagttagcgcgaattgatctg
(SEQ ID NO:49)

FIG. 35A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt

FIG. 35B ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
tcgcccttaggaggtaaaaaaaaatgactgccgacaacaatagtatgccccatggtgcagtatc
tagttacgccaaattagtgcaaaaccaaacacctgaagacattttggaagagtttcctgaaatt
attccattacaacaaagacctaatacccgatctagtgagacgtcaaatgacgaaagcggagaaa
catgtttttctggtcatgatgaggagcaaattaagttaatgaatgaaaattgtattgttttgga
ttgggacgataatgctattggtgccggtaccaagaaagtttgtcatttaatggaaaatattgaa
aagggtttactacatcgtgcattctccgtctttattttcaatgaacaaggtgaattacttttac
aacaaagagccactgaaaaaataactttccctgatctttggactaacacatgctgctctcatcc
actatgtattgatgacgaattaggtttgaagggtaagctagacgataagattaagggcgctatt
actgcggcggtgagaaaactagatcatgaattaggtattccagaagatgaaactaagacaaggg
gtaagtttcactttttaaacagaatccattacatggcaccaagcaatgaaccatggggtgaaca
tgaaattgattacatcctattttataagatcaacgctaaagaaaacttgactgtcaacccaaac
gtcaatgaagttagagacttcaaatgggtttcaccaaatgatttgaaaactatgtttgctgacc
caagttacaagtttacgccttggtttaagattatttgcgagaattacttattcaactggtggga
gcaattagatgacctttctgaagtggaaaatgacaggcaaattcatagaatgctataacaacgc
gtcctgcagctggtaccatatgggaattcgaagctttctagaacaaaaactcatctcagaagag
gatctgaatagcgccgtcgaccatcatcatcatcatcattgagtttaaacggtctccagcttgg
ctgttttggcggatgagagaagattttcagcctgatacagattaaatcagaacgcagaagcggt
ctgataaaacagaatttgcctggcggcagtagcgcggtggtcccacctgaccccatgccgaact
cagaagtgaaacgccgtagcgccgatggtagtgtggggtctccccatgcgagagtagggaactg
ccaggcatcaaataaaacgaaaggctcagtcgaaagactgggcctttcgttttatctgttgttt
gtcggtgaacgctctcctgagtaggacaaatccgccgggagcggatttgaacgttgcgaagcaa
cggcccggagggtggcgggcaggacgcccgccataaactgccaggcatcaaattaagcagaagg
ccatcctgacggatggcctttttgcgtttctacaaactctttttgtttatttttctaaatacat
tcaaatatgtatccgcttaaccggaattgccagctggggcgccctctggtaaggttgggaagcc
ctgcaaagtaaactggatggctttctcgccgccaaggatctgatggcgcaggggatcaagctct
gatcaagagacaggatgaggatcgtttcgcatgattgaacaagatggattgcacgcaggttctc
cggccgcttgggtggagaggctattcggctatgactgggcacaacagacaatcggctgctctga
tgccgccgtgttccggctgtcagcgcaggggcgcccggttctttttgtcaagaccgacctgtcc
ggtgccctgaatgaactgcaagacgaggcagcgcggctatcgtggctggccacgacgggcgttc
cttgcgcagctgtgctcgacgttgtcactgaagcgggaagggactggctgctattgggcgaagt
gccggggcaggatctcctgtcatctcaccttgctcctgccgagaaagtatccatcatggctgat

FIG. 35C gcaatgcggcggctgcatacgcttgatccggctacctgcccattcgaccaccaagcgaaacatc
gcatcgagcgagcacgtactcggatggaagccggtcttgtcgatcaggatgatctggacgaaga
gcatcaggggctcgcgccagccgaactgttcgccaggctcaaggcgagcatgcccgacggcgag
gatctcgtcgtgacccatggcgatgcctgcttgccgaatatcatggtggaaaatggccgctttt
ctggattcatcgactgtggccggctgggtgtggcggaccgctatcaggacatagcgttggctac
ccgtgatattgctgaagagcttggcggcgaatgggctgaccgcttcctcgtgctttacggtatc
gccgctcccgattcgcagcgcatcgccttctatcgccttcttgacgagttcttctgacatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
(SEQ ID NO:50)

FIG. 37A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtacctttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct

FIG. 37B attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacacccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagtttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgcagctggtaccatatgggaattcgaagctt
tctagaacaaaaactcatctcagaagaggatctgaatagcgccgtcgaccatcatcatcatcat
cattgagtttaaacggtctccagcttggctgttttggcggatgagagaagattttcagcctgat
acagattaaatcagaacgcagaagcggtctgataaaacagaatttgcctggcggcagtagcgcg

FIG. 37C gtggtcccacctgaccccatgccgaactcagaagtgaaacgccgtagcgccgatggtagtgtgg
ggtctccccatgcgagagtagggaactgccaggcatcaaataaaacgaaaggctcagtcgaaag
actgggcctttcgttttatctgttgtttgtcggtgaacgctctcctgagtaggacaaatccgcc
gggagcggatttgaacgttgcgaagcaacggcccggagggtggcgggcaggacgcccgccataa
actgccaggcatcaaattaagcagaaggccatcctgacggatggcctttttgcgtttctacaaa
ctctttttgtttatttttctaaatacattcaaatatgtatccgcttaaccggaattgccagctg
gggcgccctctggtaaggttgggaagccctgcaaagtaaactggatggctttctcgccgccaag
gatctgatggcgcaggggatcaagctctgatcaagagacaggatgaggatcgtttcgcatgatt
gaacaagatggattgcacgcaggttctccggccgcttgggtggagaggctattcggctatgact
gggcacaacagacaatcggctgctctgatgccgccgtgttccggctgtcagcgcaggggcgccc
ggttctttttgtcaagaccgacctgtccggtgccctgaatgaactgcaagacgaggcagcgcgg
ctatcgtggctggccacgacgggcgttccttgcgcagctgtgctcgacgttgtcactgaagcgg
gaagggactggctgctattgggcgaagtgccggggcaggatctcctgtcatctcaccttgctcc
tgccgagaaagtatccatcatggctgatgcaatgcggcggctgcatacgcttgatccggctacc
tgcccattcgaccaccaagcgaaacatcgcatcgagcgagcacgtactcggatggaagccggtc
ttgtcgatcaggatgatctggacgaagagcatcaggggctcgcgccagccgaactgttcgccag
gctcaaggcgagcatgcccgacggcgaggatctcgtcgtgacccatggcgatgcctgcttgccg
aatatcatggtggaaaatggccgcttttctggattcatcgactgtggccggctgggtgtggcgg
accgctatcaggacatagcgttggctacccgtgatattgctgaagagcttggcggcgaatgggc
tgaccgcttcctcgtgctttacggtatcgccgctcccgattcgcagcgcatcgccttctatcgc
cttcttgacgagttcttctgacgcatgaccaaaatcccttaacgtgagttttcgttccactgag
cgtcagaccccgtagaaaagatcaaaggatcttcttgagatcctttttttctgcgcgtaatctg
ctgcttgcaaacaaaaaaaccaccgctaccagcggtggtttgtttgccggatcaagagctacca
actctttttccgaaggtaactggcttcagcagagcgcagataccaaatactgtccttctagtgt
agccgtagttaggccaccacttcaagaactctgtagcaccgcctacatacctcgctctgctaat
cctgttaccagtggctgctgccagtggcgataagtcgtgtcttaccgggttggactcaagacga
tagttaccggataaggcgcagcggtcgggctgaacggggggttcgtgcacacagcccagcttgg
agcgaacgacctacaccgaactgagatacctacagcgtgagctatgagaaagcgccacgcttcc
cgaagggagaaaggcggacaggtatccggtaagcggcagggtcggaacaggagagcgcacgagg
gagcttccagggggaaacgcctggtatctttatagtcctgtcgggtttcgccacctctgacttg
agcgtcgatttttgtgatgctcgtcaggggggcggagcctatggaaaaacgccagcaacgcggc
ctttttacggttcctggccttttgctggccttttgctcacatgttctttcctgcgttatcccct
gattctgtggataaccgtattaccgcctttgagtgagctgataccgctcgccgcagccgaacga
ccgagcgcagcgagtcagtgagcgaggaagcggaagagcgcctgatgcggtattttctccttac
gcatctgtgcggtatttcacaccgcatatggtgcactctcagtacaatctgctctgatgccgca
tagttaagccagtatacactccgctatcgctacgtgactgggtcatggctgcgccccgacaccc
gccaacacccgctgacgcgccctgacgggc
(SEQ ID NO:51)

FIG. 39A

5′-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgatttttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctacttttgtttgttagtcttgatgcttcactgatagatacaagagccataagaacct
cagatccttccgtatttagccagtatgttctctagtgtggttcgttgttttgcgtgagccatg
agaacgaaccattgagatcatacttactttgcatgtcactcaaaatttgcctcaaaactggt
gagctgaatttttgcagttaaagcatcgtgtagtgtttttcttagtccgttatgtaggtaggaa
tctgatgtaatggttgttggtattttgtcaccattcattttttatctggttgttctcaagttcgg

FIG. 39B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
ttttttaactggaaaagataaggcaatatctcttcactaaaaactaattctaatttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgccttttatggattc
atgcaaggaaactacccataatacaagaaaagcccgtcacgggcttctcagggcgttttatggc
gggtctgctatgtggtgctatctgactttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggatttttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

FIG. 39C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcagctggtaccatatgggaattcgaagctttctagaacaaaaactca
tctcagaagaggatctgaatagcgccgtcgaccatcatcatcatcatcattgagtttaaacggt
ctccagcttggctgttttggcggatgagagaagattttcagcctgatacagattaaatcagaac
gcagaagcggtctgataaaacagaatttgcctggcggcagtagcgcggtggtcccacctgaccc
catgccgaactcagaagtgaaacgccgtagcgccgatggtagtgtggggtctccccatgcgaga
gtagggaactgccaggcatcaaataaaacgaaaggctcagtcgaaagactgggcctttcgtttt
atctgttgtttgtcggtgaacgctctcctgagtaggacaaatccgccgggagcggatttgaacg
ttgcgaagcaacggcccggagggtggcgggcaggacgcccgccataaactgccaggcatcaaat
taagcagaaggccatcctgacggatggcctttttgcgtttctacaaactctttttgtttatttt
tctaaatacattcaaatatgtatccgctcatgagacaataaccctgataaatgcttcaataat
(SEQ ID NO:52)

FIG. 41A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttagacatacatcagctggttaatcgggaaagg
gtcaatcagcagcagtttgatgcggttttcagtcgcgtagtctgggcgacccagaccatcgcca
tactggtaggtgcagtgggaaacacgtgccatgttaactgcgatttccatgaacgctttaggca
gcagggtggagtcgctaacgcgttcacgattcatctttttccattcggcgtcgatcagtttacg
cagttcttcgcgggcctgttcctcgctggtaccatcgttttcgtgcatgtagctaatgatagaa
ttggtagtctcgccacgttccagctccgccgcagaggtggccagatcgttgcacaggcggaaga
taacgcagctagaacgcaccagaccatggaagtcggtcagggaacgcagcgcgtggtcggagat
gtcttcctgctgctggcatacggaaaagtaagacggcgccagcagcgctacaccggaggaggaa
acgctggcgtttccaggtacttggagaaagccgggataatttgttgttggaccatttcgcct
cttgcagaaaggctttgcacagttcacgccagcttttcgtcagataggacaggttgttatgacc
tttctctttcagaatagaataggacgtgtcgttaacggtgttgtacagtgccaggaaacacagt
ttcatatagtccggcagggtgttaatagcgttaacgtcccagcgctctacagcatcggtgaaca
gttgcagttcgtccagagtgccataaacgtcatacacgtcatcgatgatcgtcaccagaccaaa
cattttagtaacagctttgcgacattcaccaaactgcgggtctggcgccatacccagtgcccag
aaataaacttccatcaggcggtcgcgtacaaaatccagtttgctagccaggcccatctcggtcc
accagcgggacagatcttgcagctctttctggtgcagggtctgtaccatgttaaaatccagctt
cgccagctccagcagcagctggtgatgcggttctttcggttcgtatttatccaggaaccaacgt
gcctccagacggtgcagacgctggtgatatggcagttccagggcgtggctcacttgttctgcaa
ccttggtattaatgccttctttcaggttgttcttcaggtgggtgatggaaaaggtacgcgcctc
ctccagcaggttctcaccctcgaaacccaggtaagacgcttcatacaggctcagcaggccttgg
acgtcacctttcagttcaccgctgaaaccaccttctttatccttgaaacgctcaaaaacatcct
gagaaacctcgaaaccgtgctgacgcagcagacggaaagacagagcggttgcgtgcaggtcaga
tttgttctttttgttttcgtccagcagtacgatgttttccagggctttaatgatgtctttttca
aatttgtaggtcagacccaggcgctgcacatcgtcgatcagctccagcagggacagcggctggg
tgtctacacggttgatcatgcagcgaacttcttcctccagtttggtcgctttctcctccagctt
ttccactttcaggtcgttctccagggattgcaggaattcgaaattccacaggtttggctgatag
tttgcggaacgacgggaattatgctcggtaatctgagtaaattgagaagaggtcgcacacatgg
tttattcctccttatttaatcgatacattaatatatacctctttaatttttaataataaagtta
atcgataattccggtcgagtgcccacacagattgtctgataaattgttaaagagcagtgccgct
tcgctttttctcagcggcgctgtttcctgtgtgaaattgttatccgctcacaattccacacatt
atacgagccggatgattaattgtcaacagctcatttcagaatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc

FIG. 41B tgatgccgcatagttaagccagccccgacacccgccaacacccgctgacgagcttagtaaagcc
ctcgctagatttaatgcggatgttgcgattacttcgccaactattgcgataacaagaaaaagc
cagcctttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttttccccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttttacaccgttttcatct
gtgcatatggacagttttccctttgatatgtaacggtgaacagttgttctactttgtttgtta
gtcttgatgcttcactgatagatacaagagccataagaacctcagatccttccgtatttagcca
gtatgttctctagtgtggttcgttgttttgcgtgagccatgagaacgaaccattgagatcata
cttactttgcatgtcactcaaaaattttgcctcaaaactggtgagctgaatttttgcagttaaa
gcatcgtgtagtgtttttcttagtccgttatgtaggtaggaatctgatgtaatggttgttggta
ttttgtcaccattcatttttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc

FIG. 41C cttgtgagttttcttttgtgttagttcttttaataaccactcataaatcctcatagagtatttg
ttttcaaaagacttaacatgttccagattatattttatgaatttttttaactggaaaagataag
gcaatatctcttcactaaaaactaattctaatttttcgcttgagaacttggcatagtttgtcca
ctggaaaatctcaaagcctttaaccaaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtcctttcctttgagttgtgggtat
ctgtaaattctgctagacctttgctggaaacttgtaaattctgctagaccctctgtaaattcc
gctagacctttgtgtgtttttttttgtttatattcaagtggttataatttatagaataaagaaag
aataaaaaaagataaaaagaatagatcccagccctgtgtataactcactactttagtcagttcc
gcagtattacaaaaggatgtcgcaaacgctgtttgctcctctacaaaacagaccttaaaccct
aaaggcttaagtagcaccctcgcaagctcgggcaaatcgctgaatattccttttgtctccgacc
atcaggcacctgagtcgctgtctttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgttttatggcgggtctgctatgtggtgctatc
tgactttttgctgttcagcagttcctgccctctgattttccagtctgaccacttcggattatcc
cgtgacaggtcattcagactggctaatgcacccagtaaggcagcggtatcatcaacaggctta
(SEQ ID NO:53)

FIG. 43A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagatttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgatttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctacttttgtttgttagtcttgatgcttcactgatagatacaagagccataagaacct
cagatccttccgtatttagccagtatgttctctagtgtggttcgttgttttgcgtgagccatg
agaacgaaccattgagatcatacttactttgcatgtcactcaaaaattttgcctcaaaactggt
gagctgaatttttgcagttaaagcatcgtgtagtgtttttcttagtccgttatgtaggtagga
tctgatgtaatggttgttggtattttgtcaccattcatttttatctggttgttctcaagttcgg

FIG. 43B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
ttttttaactggaaaagataaggcaatatctcttcactaaaaactaattctaatttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgccttttatggattc
atgcaaggaaactacccataatacaagaaaagcccgtcacgggcttctcagggcgttttatggc
gggtctgctatgtggtgctatctgactttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggatttttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

FIG. 43C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcatcgcccttaggaggtaaaaaaaaatgactgccgacaacaatagta
tgccccatggtgcagtatctagttacgccaaattagtgcaaaaccaaacacctgaagacatttt
ggaagagtttcctgaaattattccattacaacaaagacctaatacccgatctagtgagacgtca
aatgacgaaagcggagaaacatgtttttctggtcatgatgaggagcaaattaagttaatgaatg
aaaattgtattgttttggattgggacgataatgctattggtgccggtaccaagaaagtttgtca
tttaatggaaaatattgaaaagggtttactacatcgtgcattctccgtctttattttcaatgaa
caaggtgaattacttttacaacaaagagccactgaaaaaataactttccctgatctttggacta
acacatgctgctctcatccactatgtattgatgacgaattaggtttgaagggtaagctagacga
taagattaagggcgctattactgcggcggtgagaaaactagatcatgaattaggtattccagaa
gatgaaactaagacaaggggtaagtttcactttttaaacagaatccattacatggcaccaagca
atgaaccatggggtgaacatgaaattgattacatcctattttataagatcaacgctaaagaaaa
cttgactgtcaacccaaacgtcaatgaagttagagacttcaaatgggtttcaccaaatgatttg
aaaactatgtttgctgacccaagttacaagtttacgccttggtttaagattatttgcgagaatt
acttattcaactggtgggagcaattagatgacctttctgaagtggaaaatgacaggcaaattca
tagaatgctataacgacgcgtcctgcagctggtaccatatgggaattcgaagctttctagaacg
aaaactcatctcagaagaggatctgaatagcgccgtcgaccatcatcatcatcatcattgagtt
taaacggtctccagcttggctgttttggcggatgagagaagattttcagcctgatacagattaa
atcagaacgcagaagcggtctgataaaacagaatttgcctggcggcagtagcgcggtggtccca
cctgaccccatgccgaactcagaagtgaaacgccgtagcgccgatggtagtgtggggtctcccc
atgcgagagtagggaactgccaggcatcaaataaaacgaaaggctcagtcgaaagactgggcct
ttcgttttatctgttgtttgtcggtgaacgctctcctgagtaggacaaatccgccgggagcgga
tttgaacgttgcgaagcaacggcccggagggtggcgggcaggacgcccgccataaactgccagg
catcaaattaagcagaaggccatcctgacggatggcctttttgcgtttctacaaactcttttg
tttatttttctaaatacattcaaatatgtatccgctcatgagacaataaccctgataaatgctt
caataat
(SEQ ID NO:54)

FIG. 45A

5′-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttatgccagccaggccttgattttggcttccat
accagcggcatcgaggccgagttcggcgcgcatttcttcctgagttccttgcggaataaagaag
tccggcaggccaatgttcagcacgggtactggtttacgatgggccatcagcacttcgttcacgc
cgctgcctgcgccgcccataatggcgtttcttctacggtgaccagcgcttcatggctggcggc
catttccagaattaacgcttcatcaagcggtttcacaaaacgcatatcgaccagcgtggcgttc
agcgattcggcgactttcgccgcttctggcatcagcgtaccaaagttaaggatcgccagtttct
cgccacgacgcttcacaatgcctttgccaattggtagtttttccagcggcgtcagttccacgcc
gaccgcgttgccacgcgggtagcgcaccgctgacgggccatcgttatagtgatagccggtatag
agcatctggcgacattcgttttcatcgctcggggtcataatgaccatttccggtatgcagcgca
ggtaagagagatcaaaagcaccctgatgggtttgaccgtcagcaccaacaatgcccgcgcggtc
gatggcgaacaggaccggaagcttttgaatcgccacgtcatgcagcacctgatcataggcgcgt
tgcaggaaagtggagtaaatcgcgacaatgggtttgtacccaccaatcgccagacccgcagcaa
aggtcaccgcgtgttgctcggcaattgccacgtcgaagtagcgatccgggaatttacgtgaaaa
ctcgaccatgccggaaccttcacgcatcgccggagtaatcgccatcagcttgttgtctttcgct
gccgtttcgcacaaccagtcgccaaagattttgaatagctcggcaaaccgccgctacttttcg
gcaaacaaccgctggagggatcaaatttaggcacggcgtggaaagtgatcgggtctttttctgc
cggttcataaccacgacctttttggtcatgatatgcaggaactgcgggcctttcaggtcgcgc
atgttctttagcgtggtgataagccccagcacatcgtgaccgtccaccgggccgatgtagttaa
agcccagctcttcaaacaacgtgccaggcactaccatgcctttaatatgttcttcggtgcgttt
gagcagctctttaattggcggcacgccagagaaactttttcccgccttcgcgcagtgaagag
taaagcttaccggaaagcagctgtgccagatggttgttgagcgcgccgacatttcggaaatcg
acatttcattgtcgttgagaatcaccagcatatcaggacggatatcgcccgcgtgattcatcgc
ttcaaacgccatgcctgcggtaatcgcgccatcgccaatgacacagacggtgcggcgattttg
ccttctttttcggcagcaaccgcaataccaattccggcactgatggaggttgatgaatgcccga
cgcttaatacgtcatattcgctttcgccgcgccacgggaacgggtgcagaccgcctttctgacg
gatggtgccgatttgtcgcggcgtccggtcaaaatttatgcggataagcctgatgccccaca
tcccaaatcaattggtcaaacggggtgttgtagacatagtgcagcgccacggtcagttcgaccg
tgcccagcccggaggcgaagtgcccgctggaacggctcacgctgtcgagtaaatagcggcgcag
ttcgtcgcagagtttcggtaaactctctttcggcaacagtcgtaactcctgggtggagtcgacc
agtgccagggtcgggtatttggcaatatcaaaactcatgtttttttacctcctaagggcgaatg
cagttagacatacatcagctggttaatcgggaaagggtcaatcagcagcagtttgatgcggttt
tcagtcgcgtagtctgggcgacccagaccatcgccatactggtaggtgcagtgggaaacacgtg
ccatgttaactgcgatttccatgaacgctttaggcagcagggtggagtcgctaacgcgttcacg

FIG. 45B attcatctttttccattcggcgtcgatcagtttacgcagttcttcgcgggcctgttcctcgctg
gtaccatcgtttcgtgcatgtagctaatgatagaattggtagtctcgccacgttccagctccg
ccgcagaggtggccagatcgttgcacaggcggaagataacgcagctagaacgcaccagaccatg
gaagtcggtcagggaacgcagcgcgtggtcggagatgtcttcctgctgctggcatacggaaaag
taagacggcgccagcagcgctacaccggaggaggaaacgctggcgtttttccaggtacttggaga
aagccgggataattttgttgttggaccatttcgcctcttgcagaaaggctttgcacagttcacg
ccagcttttcgtcagataggacaggttgttatgacctttctctttcagaatagaataggacgtg
tcgttaacggtgttgtacagtgccaggaaacacagtttcatatagtccggcagggtgttaatag
cgttaacgtcccagcgctctacagcatcggtgaacagttgcagttcgtccagagtgccataaac
gtcatacacgtcatcgatgatcgtcaccagaccaaacattttagtaacagctttgcgacattca
ccaaactgcgggtctggcgccatacccagtgcccagaaataaacttccatcaggcggtcgcgta
caaaatccagtttgctagccaggcccatctcggtccaccagcgggacagatcttgcagctcttt
ctggtgcagggtctgtaccatgttaaaatccagcttcgccagctccagcagcagctggtgatgc
ggttctttcggttcgtatttatccaggaaccaacgtgcctccagacggtgcagacgctggtgat
atggcagttccagggcgtggctcacttgttctgcaaccttggtattaatgccttctttcaggtt
gttcttcaggtgggtgatggaaaaggtacgcgcctcctccagcaggttctcaccctcgaaaccc
aggtaagacgcttcatacaggctcagcaggccttggacgtcacctttcagttcaccgctgaaac
caccttctttatccttgaaacgctcaaaaacatcctgagaaacctcgaaaccgtgctgacgcag
cagacggaaagacagagcggttgcgtgcaggtcagatttgttcttttttgttttcgtccagcagt
acgatgttttccagggctttaatgatgtctttttcaaatttgtaggtcagacccaggcgctgca
catcgtcgatcagctccagcagggacagcggctgggtgtctacacggttgatcatgcagcgaac
ttcttcctccagtttggtcgctttctcctccagcttttccactttcaggtcgttctccagggat
tgcaggaattcgaaattccacaggtttggctgatagtttgcggaacgacgggaattatgctcgg
taatctgagtaaattgagaagaggtcgcacacatggtttattcctccttatttaatcgatacat
taatatatacctctttaatttttaataataaagttaatcgataattccggtcgagtgcccacac
agattgtctgataaattgttaaagagcagtgccgcttcgcttttctcagcggcgctgtttcct
gtgtgaaattgttatccgctcacaattccacacattatacgagccggatgattaattgtcaaca
gctcatttcagaatctggcgtaatagcgaagaggcccgcaccgatcgcccttcccaacagttgc
gcagcctgaatggcgaatggcgcctgatgcggtattttctccttacgcatctgtgcggtatttc
acaccgcatatggtgcactctcagtacaatctgctctgatgccgcatagttaagccagccccga
cacccgccaacacccgctgacgagcttagtaaagccctcgctagatttaatgcggatgttgcg
attacttcgccaactattgcgataacaagaaaaagccagcctttcatgatatatctcccaattt
gtgtagggcttattatgcacgcttaaaaataataaaagcagacttgacctgatagtttggctgt
gagcaattatgtgcttagtgcatctaacgcttgagttaagccgcgccgcgaagcggcgtcggct
tgaacgaattgttagacattatttgccgactaccttggtgatctcgcctttcacgtagtggaca
aattcttccaactgatctgcgcgcgaggccaagcgatcttcttcttgtccaagataagcctgtc
tagcttcaagtatgacgggctgatactgggccggcaggcgctccattgcccagtcggcagcgac
atccttcggcgcgattttgccggttactgcgctgtaccaaatgcgggacaacgtaagcactaca
tttcgctcatcgccagcccagtcgggcggcgagttccatagcgttaaggtttcatttagcgcct
caaatagatcctgttcaggaaccggatcaaagagttcctccgccgctggacctaccaaggcaac
gctatgttctcttgcttttgtcagcaagatagccagatcaatgtcgatcgtggctggctcgaag
atacctgcaagaatgtcattgcgctgccattctccaaattgcagttcgcgcttagctggataac
gccacggaatgatgtcgtcgtgcacaacaatggtgacttctacagcgcggagaatctcgctctc
tccaggggaagccgaagtttccaaaaggtcgttgatcaaagctcgccgcgttgtttcatcaagc

FIG. 45C cttacggtcaccgtaaccagcaaatcaatatcactgtgtggcttcaggccgccatccactgcgg
agccgtacaaatgtacggccagcaacgtcggttcgagatggcgctcgatgacgccaactacctc
tgatagttgagtcgatacttcggcgatcaccgcttccctcatgatgtttaactttgttttaggg
cgactgccctgctgcgtaacatcgttgctgctccataacatcaaacatcgacccacggcgtaac
gcgcttgctgcttggatgcccgaggcatagactgtaccccaaaaaaacagtcataacaagccat
gaaaaccgccactgcgccgttaccaccgctgcgttcggtcaaggttctggaccagttgcgtgag
cgcatacgctacttgcattacagcttacgaaccgaacaggcttatgtccactgggttcgtgcct
tcatccgtttccacggtgtgcgtcacccggcaaccttgggcagcagcgaagtcgaggcatttct
gtcctggctggcgaacgagcgcaaggtttcggtctccacgcatcgtcaggcattggcggccttg
ctgttcttctacggcaaggtgctgtgcacggatctgccctggcttcaggagatcggaagacctc
ggccgtcgcggcgcttgccggtggtgctgaccccggatgaagtggttcgcatcctcggttttct
ggaaggcgagcatcgtttgttcgcccagcttctgtatggaacgggcatgcggatcagtgagggt
ttgcaactgcgggtcaaggatctggatttcgatcacggcacgatcatcgtgcgggagggcaagg
gctccaaggatcgggccttgatgttacccgagagcttggcacccagcctgcgcgagcaggggaa
ttaattcccacgggttttgctgcccgcaaacgggctgttctggtgttgctagtttgttatcaga
atcgcagatccggcttcagccggtttgccggctgaaagcgctatttcttccagaattgccatga
tttttccccacgggaggcgtcactggctcccgtgttgtcggcagctttgattcgataagcagc
atcgcctgtttcaggctgtctatgtgtgactgttgagctgtaacaagttgtctcaggtgttcaa
tttcatgttctagttgctttgttttactggtttcacctgttctattaggtgttacatgctgttc
atctgttacattgtcgatctgttcatggtgaacagctttgaatgcaccaaaaactcgtaaaagc
tctgatgtatctatctttttacaccgttttcatctgtgcatatggacagttttccctttgata
tgtaacggtgaacagttgttctactttgtttgttagtcttgatgcttcactgatagatacaag
agccataagaacctcagatccttccgtatttagccagtatgttctctagtgtggttcgttgttt
ttgcgtgagccatgagaacgaaccattgagatcatacttactttgcatgtcactcaaaaatttt
gcctcaaaactggtgagctgaatttttgcagttaaagcatcgtgtagtgtttttcttagtccgt
tatgtaggtaggaatctgatgtaatggttgttggtatttgtcaccattcatttttatctggtt
gttctcaagttcggttacgagatccatttgtctatctagttcaacttggaaaatcaacgtatca
gtcgggcggcctcgcttatcaaccaccaatttcatattgctgtaagtgtttaaatctttactta
ttggtttcaaaacccattggttaagccttttaaactcatggtagttattttcaagcattaacat
gaacttaaattcatcaaggctaatctctatatttgccttgtgagttttcttttgtgttagttct
tttaataaccactcataaatcctcatagagtatttgttttcaaaagacttaacatgttccagat
tatattttatgaatttttttaactggaaaagataaggcaatatctcttcactaaaaactaattc
taatttttcgcttgagaacttggcatagtttgtccactggaaaatctcaaagcctttaaccaaa
ggattcctgatttccacagttctcgtcatcagctctctggttgctttagctaatacaccataag
cattttccctactgatgttcatcatctgagcgtattggttataagtgaacgataccgtccgttc
tttccttgtagggttttcaatcgtggggttgagtagtgccacacagcataaaattagcttggtt
tcatgctccgttaagtcatagcgactaatcgctagttcatttgctttgaaaacaactaattcag
acatacatctcaattggtctaggtgattttaatcactataccaattgagatgggctagtcaatg
ataattactagtcctttttcctttgagttgtgggtatctgtaaattctgctagacctttgctgga
aaacttgtaaattctgctagaccctctgtaaattccgctagacctttgtgtgttttttttgttt
atattcaagtggttataatttatagaataaagaaagaataaaaaaagataaaaagaatagatcc
cagccctgtgtataactcactactttagtcagttccgcagtattacaaaggatgtcgcaaacg
ctgtttgctcctctacaaaacagaccttaaaccctaaaggcttaagtagcaccctcgcaagct
cgggcaaatcgctgaatattccttttgtctccgaccatcaggcacctgagtcgctgtctttttc

FIG. 45D

Gtgacattcagttcgctgcgctcacggctctggcagtgaatgggggtaaatggcactacaggcg
cctttttatggattcatgcaaggaaactacccataatacaagaaaagcccgtcacgggcttctca
gggcgttttatggcgggtctgctatgtggtgctatctgacttttttgctgttcagcagttcctgc
cctctgattttccagtctgaccacttcggattatcccgtgacaggtcattcagactggctaatg
cacccagtaaggcagcggtatcatcaacaggctta
(SEQ ID NO:55)

5'-
tcgctgcgctcggtcgttcggctgcggcgagcggtatcagctcactcaaaggcggtaatacggt
tatccacagaatcaggggataacgcaggaaagaacatgtgagcaaaaggccagcaaaaggccag
gaaccgtaaaaaggccgcgttgctggcgtttttccataggctccgcccccctgacgagcatcac
aaaaatcgacgctcaagtcagaggtggcgaaacccgacaggactataaagataccaggcgtttc
cccctggaagctccctcgtgcgctctcctgttccgaccctgccgcttaccggatacctgtccgc
ctttctcccttcgggaagcgtggcgctttctcatagctcacgctgtaggtatctcagttcggtg
taggtcgttcgctccaagctgggctgtgtgcacgaaccccccgttcagcccgaccgctgcgcct
tatccggtaactatcgtcttgagtccaacccggtaagacacgacttatcgccactggcagcagc
cactggtaacaggattagcagagcgaggtatgtaggcggtgctacagagttcttgaagtggtgg
cctaactacggctacactagaagaacagtatttggtatctgcgctctgctgaagccagttacct
tcggaaaaagagttggtagctcttgatccggcaaacaaaccaccgctggtagcggtggtttttt
tgtttgcaagcagcagattacgcgcagaaaaaaaggatctcaagaagatcctttgatcttttct
acggggtctgacgctcagtggaacgaaaactcacgttaagggattttggtcatgagattatcaa
aaaggatcttcacctagatccttttaaattaaaaatgaagttttaaatcaatctaaagtatata
tgagtaaacttggtctgacagttaccaatgcttaatcagtgaggcacctatctcagcgatctgt
ctatttcgttcatccatagttgcctgactccccgtcgtgtagataactacgatacgggagggct
taccatctggccccagtgctgcaatgataccgcgagacccacgctcaccggctccagatttatc
agcaataaaccagccagccggaagggccgagcgcagaagtggtcctgcaactttatccgcctcc
atccagtctattaattgttgccgggaagctagagtaagtagttcgccagttaatagtttgcgca
acgttgttgccattgctacaggcatcgtggtgtcacgctcgtcgtttggtatggcttcattcag
ctccggttcccaacgatcaaggcgagttacatgatcccccatgttgtgcaaaaaagcggttagc
tccttcggtcctccgatcgttgtcagaagtaagttggccgcagtgttatcactcatggttatgg
cagcactgcataattctcttactgtcatgccatccgtaagatgcttttctgtgactggtgagta
ctcaaccaagtcattctgagaatagtgtatgcggcgaccgagttgctcttgcccggcgtcaata
cgggataataccgcgccacatagcagaactttaaaagtgctcatcattggaaaacgttcttcgg
ggcgaaaactctcaaggatcttaccgctgttgagatccagttcgatgtaacccactcgtgcacc
caactgatcttcagcatcttttactttcaccagcgtttctgggtgagcaaaaacaggaaggcaa
aatgccgcaaaaaagggaataagggcgacacggaaatgttgaatactcatactcttcctttttc
aatattattgaagcatttatcagggttattgtctcatgagcggatacatatttgaatgtattta
gaaaaataaacaaataggggttccgcgcacatttccccgaaaagtgccacctgacgtctaagaa
accattattatcatgacattaacctataaaaataggcgtatcacgaggccctttcgtctcgcgc
gtttcggtgatgacggtgaaaacctctgacacatgcagctcccggagacggtcacagcttgtct
gtaagcggatgccgggagcagacaagcccgtcagggcgcgtcagcgggtgttggcgggtgtcgg
ggctggcttaactatgcggcatcagagcagattgtactgagagtgcaccatagatctggagctg
taatataaaaaccttcttcaactaacggggcaggttagtgacattagaaaaccgactgtaaaaa
gtacagtcggcattatctcatattataaaagccagtcattaggcctatctgacaattcctgaat
agagttcataaacaatcctgcatgataaccatcacaaacagaatgatgtacctgtaaagatagc
ggtaaatatattgaattacctttattaatgaattttcctgctgtaataatgggtagaaggtaat
tactattattattgatatttaagttaaacccagtaaatgaagtccatggaataatagaaagaga
aaaagcatttcaggtataggtgttttgggaaacaatttccccgaaccattatatttctctaca
tcagaaaggtataaatcataaaactctttgaagtcattctttacaggagtccaaataccagaga
atgttttagatacaccatcaaaaattgtataaagtggctctaacttatcccaataacctaactc
tccgtcgctattgtaaccagttctaaaagctgtatttgagtttatcacccttgtcactaagaaa
ataaatgcagggtaaaatttatatccttcttgttttatgtttc

FIG. 51B ggtataaaacactaatatcaatttctgtggttatactaaaagtcgtttgttggttcaaataatg
attaaatatctcttttctcttccaattgtctaaatcaattttattaaagttcatttgatatgcc
tcctaaatttttatctaaagtgaatttaggaggcttacttgtctgctttcttcattagaatcaa
tcctttttaaaagtcaatattactgtaacataaatatatatttaaaaatatcccactttatc
caatttcgtttgttgaactaatgggtgctttagttgaagaataaaagacctatgcggtgtgaa
ataccgcacagatgcgtaaggagaaaataccgcatcaggcgccattcgccattcaggctgcgca
actgttgggaagggcgatcggtgcgggcctcttcgctattacgccagctggcgaaagggggatg
tgctgcaaggcgattaagttgggtaacgccagggttttcccagtcacgacgttgtaaaacgacg
gccagtgccaagcttgcatgcctgcactccatttcttctgctatcaaaataacagactcgtga
ttttccaaacgagctttcaaaaaagcctctgccccttgcaaatcggatgcctgtctataaaatt
cccgatattggttaaacagcggcgcaatggcggccgcatctgatgtctttgcttggcgaatgtt
catcttatttcttcctccctctcaataatttttttcattctatccctttctgtaaagtttattt
ttcagaatacttttatcatcatgctttgaaaaaatatcacgataatatccattgttctcacgga
agcacacgcaggtcatttgaacgaatttttcgacaggaatttgccgggactcaggagcattta
acctaaaaaagcatgacatttcagcataatgaacatttactcatgtctattttcgttcttttct
gtatgaaaatagttatttcgagtctctacggaaatagcgagagatgatatacctaaatagagat
aaaatcatctcaaaaaaatgggtctactaaaatattattccatctattacaataaattcacaga
atagtcttttaagtaagtctactctgaatttttttaaaaggagagggtaaagagtgaaaacagt
agttattattgatgcattacgaacaccaattggaaaatataaaggcagcttaagtcaagtaagt
gccgtagacttaggaacacatgttacaacacaacttttaaaaagacattccactatttctgaag
aaattgatcaagtaatctttggaaatgttttacaagctggaaatggccaaaatcccgcacgaca
aatagcaataaacagcggtttgtctcatgaaattcccgcaatgacggttaatgaggtctgcgga
tcaggaatgaaggccgttattttggcgaaacaattgattcaattaggagaagcggaagttttaa
ttgctggcgggattgagaatatgtcccaagcacctaaattacaacgttttaattacgaaacaga
aagctacgatgcgcctttttctagtatgatgtatgatggattaacggatgcctttagtggtcag
gcaatgggcttaactgctgaaaatgtggccgaaaagtatcatgtaactagagaagagcaagatc
aattttctgtacattcacaattaaaagcagctcaagcacaagcagaagggatattcgctgacga
aatagccccattagaagtatcaggaacgcttgtggagaaagatgaagggattcgccctaattcg
agcgttgagaagctaggaacgcttaaaacagttttaaagaagacggtactgtaacagcaggga
atgcatcaaccattaatgatggggcttctgctttgattattgcttcacaagaatatgccgaagc
acacggtcttccttatttagctattattcgagacagtgtggaagtcggtattgatccagcctat
atgggaatttcgccgattaaagccattcaaaaactgttagcgcgcaatcaacttactacggaag
aaattgatctgtatgaaatcaacgaagcatttgcagcaacttcaatcgtggtccaaagagaact
ggctttaccagaggaaaaggtcaacatttatggtggcggtatttcattaggtcatgcgattggt
gccacaggtgctcgtttattaacgagtttaagttatcaattaaatcaaaaagaaaagaaatatg
gagtggcttctttatgtatcggcggtggcttaggactcgctatgctactagagagacctcagca
aaaaaaaaacagccgattttatcaaatgagtcctgaggaacgcctggcttctcttcttaatgaa
ggccagatttctgctgatacaaaaaaagaatttgaaaatacggctttatcttcgcagattgcca
atcatatgattgaaaatcaaatcagtgaaacagaagtgccgatgggcgttggcttacatttaac
agtggacgaaactgattatttggtaccaatggcgacagaagagccctcagttattgcggctttg
agtaatggtgcaaaaatagcacaaggatttaaaacagtgaatcaacaacgcttaatgcgtggac
aaatcgtttttacgatgttgcagatcccgagtcattgattgataaactacaagtaagagaagc
ggaagtttttcaacaagcagagttaagttatccatctatcgttaaacggggcggcggcttaaga
gatttgcaatatcgtacttttgatgaatcatttgtatctgtcgacttttagtagatgttaagg
atgcaatgggggcaaatatcgttaacgctatgttggaaggtgtg

FIG. 51C gccgagttgttccgtgaatggtttgcggagcaaaagatttttattcagtattttaagtaattatg
ccacggagtcggttgttacgatgaaaacggctattccagtttcacgtttaagtaaggggagcaa
tggccgggaaattgctgaaaaattgttttagcttcacgctatgcttcattagatccttatcgg
gcagtcacgcataacaaaggaatcatgaatggcattgaagctgtagttttagctacaggaaatg
atacacgcgctgttagcgcttcttgtcatgcttttgcggtgaaggaaggtcgctaccaaggctt
gactagttggacgctggatggcgaacaactaattggtgaaatttcagttccgcttgctttagcc
acggttggcggtgccacaaaagtcttacctaaatctcaagcagctgctgatttgttagcagtga
cggatgcaaaagaactaagtcgagtagtagcggctgttggtttggcacaaaatttagcggcgtt
acgggccttagtctctgaaggaattcaaaaaggacacatggctctacaagcacgttctttagcg
atgacggtcggagctactggtaaagaagttgaggcagtcgctcaacaattaaaacgtcaaaaa
cgatgaaccaagaccgagccatggctattttaaatgatttaagaaaacaataaaaggagagggt
gacaattgggattgataaaattagtttttttgtgccccttattatattgatatgacggcactg
gctgaagccagaaatgtagaccctggaaaatttcatattggtattgggcaagaccaaatggcgg
tgaacccaatcagccaagatattgtgacatttgcagccaatgccgcagaagcgatcttgaccaa
agaagataaagaggccattgatatggtgattgtcgggactgagtccagtatcgatgagtcaaaa
gcggccgcagttgtcttacatcgtttaatggggattcaacctttcgctcgctctttcgaaatca
aggaagcttgttacggagcaacagcaggcttacagttagctaagaatcacgtagccttacatcc
agataaaaaagtcttggtcgtagcggcagatattgcaaaatatggcttaaattctggcggtgag
cctacacaaggagctggggcggttgcaatgttagttgctagtgaaccgcgcatttttggcttaa
aagaggataatgtgatgctgacgcaagatatctatgacttttggcgtccaacaggccacccgta
tcctatggtcgatggtcctttgtcaaacgaaacctacatccaatcttttgcccaagtctgggat
gaacataaaaaacgaaccggtcttgattttgcagattatgatgctttagcgttccatattcctt
acacaaaaatgggcaaaaaagccttattagcaaaaatctccgaccaaactgaagcagaacagga
acgaattttagcccgttatgaagaaagtatcgtctatagtcgtcgcgtaggaaacttgtatacg
ggttcactttatctgggactcatttccccttttagaaaatgcaacgactttaaccgcaggcaatc
aaattggtttattcagttatggttctggtgctgtcgctgaatttttcactggtgaattagtagc
tggttatcaaaatcatttacaaaaagaaactcatttagcactgctggataatcggacagaactt
tctatcgctgaatatgaagccatgtttgcagaaactttagacacagacattgatcaaacgttag
aagatgaattaaaatatagtatttctgctattaataataccgttcgttcttatcgaaactaaaa
aaaaccggccttggccccgccggtttttttattatttttcttcctccgcatgttcaatccgctcc
ataatcgacggatggctccctctgaaaattttaacgagaaacggcgggttgacccggctcagtc
ccgtaacggccaagtcctgaaacgtctcaatcgccgcttcccggtttccggtcagctcaatgcc
gtaacggtcggcggcgttttcctgataccgggagacggcattcgtaatcgggatccccgggtac
cgagctcgaattcgtaatcatgtcatagctgtttcctgtgtgaaattgttatccgctcacaatt
ccacacaacatacgagccggaagcataaagtgtaaagcctggggtgcctaatgagtgagctaac
tcacattaattgcgttgcgctcactgcccgctttccagtcgggaaacctgtcgtgccagctgca
ttaatgaatcggccaacgcgcggggagaggcggtttgcgtattgggcgctcttccgcttcctcg
ctcactgac
(SEQ ID NO:56)

FIG. 55A 1-
tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctccctttagggttcc
gatttagtgctttacggcacctcgaccccaaaaaacttgattagggtgatggttcacgtagtgggccatcgccctgatagacggtttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaacccctatttgtttatttttctaaatacattcaaatatgtatccgctcatgaattaattcttagaaaaactcatcg
agcatcaaatgaaactgcaatttattcatatcaggattatcaataccatatttttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccagggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag

FIG. 55B ccagccagacgcagacgcgccgagacagaacttaatgggcccgctaacagcgcgatttgctggtgacccaatgcgaccagatgctccac
gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccactttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatgcgttgtagcgtgtccaccg
aaaatgtgtctttcaccgaaactgaaaccgaagctcgtcgttctgcgaactacgaacctaacagctgggactatgattacctgctgtcctccga
cacggacgagtccatcgaagtatacaaagacaaagcgaaaaagctggaagccgaagttcgtcgcgagattaataacgaaaaagcagaat
ttctgaccctgctggaactgattgacaacgtccagcgcctgggcctgggttaccgtttcgagtctgatatccgtggtgcgctggatcgcttcgt
ttcctccggcggcttcgatgcggtaaccaagacttccctgcacggtacggcactgtctttccgtctgctgcgtcaacacggttttgaggtttctc
aggaagcgttcagcggcttcaaagaccaaaacggcaacttcctggagaacctgaaggaagatatcaaagctatcctgagcctgtacgagg
ccagcttcctggctctggaaggcgaaaacatcctggacgaggcgaaggttttcgcaatctctcatctgaaagaactgtctgaagaaaagatc
ggtaaagagctggcagaacaggtgaaccatgcactggaactgccactgcatcgccgtactcagcgtctggaagcagtatggtctatcgag
gcctaccgtaaaaaggaggacgcgaatcaggttctgctggagctggcaattctggattacaacatgatccagtctgtataccagcgtgatct
gcgtgaaacgtcccgttggtggcgtcgtgtgggtctggcgaccaaactgcactttgctcgtgaccgcctgattgagagcttctactgggccg
tgggtgtagcattcgaaccgcaatactccgactgccgtaactccgtcgcaaaaatgtttctttcgtaaccattatcgacgatatctacgatgtat
acggcaccctggacgaactggagctgtttactgatgcagttgagcgttgggacgtaaacgccatcaacgacctgccggattacatgaaact
gtgctttctggctctgtataacactattaacgaaatcgcctacgacaacctgaaagataaaggtgagaacatcctgccgtatctgaccaaagc
ctgggctgacctgtgcaacgctttcctgcaagaagccaagtggctgtacaacaaatctactccgacctttgacgactacttcggcaacgcatg
gaaatcctcttctggcccgctgcaactggtgttcgcttacttcgctgtcgtgcagaacattaaaaaggaagagatcgaaaacctgcaaaaata
ccatgacaccatctctcgtccttcccatatcttccgtctgtgcaatgacctggctagcgcgtctgcggaaattgcgcgtggtgaaaccgcaaat
agcgtttcttgttacatgcgcactaaaggtatctccgaagaactggctaccgaaagcgtgatgaatctgatcgatgaaacctggaaaaagatg
aacaaggaaaaactgggtggtagcctgttcgcgaaaccgttcgtggaaaccgcgatcaacctggcacgtcaatctcactgcacttatcataa
cggcgacgcgcatacctctccggatgagctgacccgcaaacgcgttctgtctgtaatcactgaaccgattctgccgtttgaacgctaaggat
ccgaattcgagctccgtcgacaagcttgcggccgcactcgagcaccaccaccaccaccactgagatccggctgctaacaaagcccgaaa
ggaagctgagttggctgctgccaccgctgagcaataactagcataaccccttggggcctctaaacgggtcttgaggggttttttgctgaaag
gaggaactatatccggat (SEQ ID NO:87)

FIG. 58A

1- gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgtttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgtttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcagctggtaccatatgggaattcgaagctttctagaac
aaaaactcatctcagaagaggatctgaatagcgccgtcgaccatcatcatcatcatcattgagtttaaacggtctccagcttggctgttttggcg
gatgagagaagattttcagcctgatacagattaaatcagaacgcagaagcggtctgataaaacagaatttgcctggcggcagtagcgcggt
ggtcccacctgaccccatgccgaactcagaagtgaaacgccgtagcgccgatggtagtgtggggtctccccatgcgagagtagggaact
gccaggcatcaaataaaacgaaaggctcagtcgaaagactgggcctttcgttttatctgttgtttgtcggtgaacgctctcctgagtaggacaa
atccgccgggagcggatttgaacgttgcgaagcaacggcccggagggtggcgggcaggacgcccgccataaactgccaggcatcaaat
taagcagaaggccatcctgacggatggcctttttgcgtttctacaaactcttttgtttatttttctaaatacattcaaatatgtatccgctcatgaga
caataaccctgataaatgcttcaataatattgaaaaaggaagagtatgagtattcaacatttccgtgtcgcccttattcccttttttgcggcattttg
ccttcctgtttttgctcacccagaaacgctggtgaaagtaaaagatgctgaagatcagttgggtgcacgagtgggttacatcgaactggatctc
aacagcggtaagatccttgagagttttcgccccgaagaacgttttccaatgatgagcacttttaaagttctgctatgtggcgcggtattatcccg
tgttgacgccgggcaagagcaactcggtcgccgcatacactattctcagaatgacttggttgagtactcaccagtcacagaaaagcatcttac
ggatggcatgacagtaagagaattatgcagtgctgccataaccatgagtgataacactgcggccaacttacttctgacaacgatcggagga
ccgaaggagctaaccgcttttttgcacaacatgggggatcatgtaactcgccttgatcgttgggaaccggagctgaatgaagccataccaaa
cgacgagcgtgacaccacgatgcctgtagcaatggcaacaacgttgcgcaaactattaactggcgaactacttactctagcttcccggcaac
aattaatagactggatggaggcggataaagttgcaggaccacttctgcgctcggcccttccggctggctggtttattgctgataaatctggag
ccggtgagcgtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagtttactcatata
ctttagattgatttaaaacttcatttttaatttaaaaggatctaggtgaagatcctttttgataatctcatgaccaaaatcccttaacgtgagttttcgtt
ccactgagcgtcagaccccgtagaaaagatcaaaggatcttcttgagatcctttttttctgcgcgtaatctgctgcttgcaaacaaaaaaacca
ccgctaccagcggtggtttgtttgccggatcaagagctaccaactctttttccgaaggtaactggcttcagcagagcgcagataccaaatact
gtccttctagtgtagccgtagttaggccaccacttcaagaactctgtagcaccgcctacatacctcgctctgctaatcctgttaccagtggctgc

FIG. 58B tgccagtggcgataagtcgtgtcttaccgggttggactcaagacgatagttaccggataaggcgcagcggtcgggctgaacggggggttc
gtgcacacagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccagggggaaacgcctggtat
ctttatagtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgtattaccgcct
ttgagtgagctgataccgctcgccgcagccgaacgaccgagcgcagcgagtcagtgagcgaggaagcggaagagcgcctgatgcggt
attttctccttacgcatctgtgcggtatttcacaccgcatatggtgcactctcagtacaatctgctctgatgccgcatagttaagccagtatacact
ccgctatcgctacgtgactgggtcatggctgcgccccgacacccgccaacacccgctgacgcgccctgacgggcttgtctgctcccggca
tccgcttacagacaagctgtgaccgtctccgggagctgcatgtgtcagaggttttcaccgtcatcaccgaaacgcgcgaggcagcagatca
attcgcgcgcgaaggcgaagcggcatgcatttacgttgacaccatcgaatggtgcaaaacctttcgcggtatggcatgatagcgcccggaa
gagagtcaattcagggtggtgaatgtgaaaccagtaacgttatacgatgtcgcagagtatgccggtgtctcttatcagaccgtttcccgcgtg
gtgaaccaggccagccacgtttctgcgaaaacgcgggaaaaagtggaagcggcgatggcggagctgaattacattcccaaccgcgtggc
acaacaactggcgggcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagcggcggtgcacaa
tcttctcgcgcaacgcgtcagtgggctgatcattaactatccgctggatgaccaggatgccattgctgtggaagctgcctgcactaatgttccg
gcgttatttcttgatgtctctgaccagacacccatcaacagtattattttctcccatgaagacggtacgcgactgggcgtggagcatctggtcgc
attgggtcaccagcaaatcgcgctgttagcgggcccattaagttctgtctcggcgcgtctgcgtctggctggctggcataaatatctcactcg
caatcaaattcagccgatagcggaacgggaaggcgactggagtgccatgtccggttttcaacaaaccatgcaaatgctgaatgagggcatc
gttcccactgcgatgctggttgccaacgatcagatggcgctgggcgcaatgcgcgccattaccgagtccgggctgcgcgttggtgcggat
atctcggtagtgggatacgacgataccgaagacagctcatgttatatcccgccgtcaaccaccatcaaacaggattttcgcctgctggggca
aaccagcgtggaccgcttgctgcaactctctcagggccaggcggtgaagggcaatcagctgttgcccgtctcactggtgaaaagaaaaac
caccctggcgcccaatacgcaaaccgcctctccccgcgcgttggccgattcattaatgcagctggcacgacaggtttcccgactggaaagc
gggcagtgagcgcaacgcaattaatgtgagttagcgcgaattgatctg (SEQ ID NO:88)

FIG. 61A

1- gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgtttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgtttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttccccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcataaaggaggtaaaaaaacatggtatcctgttctgcg
ccgggtaagatttacctgttcggtgaacacgccgtagtttatggcgaaactgcaattgcgtgtgcggtggaactgcgtacccgtgttcgcgcg
gaactcaatgactctatcactattcagagccagatcggccgcaccggtctggatttcgaaaagcacccttatgtgtctgcggtaattgagaaa
atgcgcaaatctattcctattaacggtgtttttcttgaccgtcgattccgacatcccggtgggctccggtctgggtagcagcgcagccgttactat
cgcgtctattggtgcgctgaacgagctgttcggctttggcctcagcctgcaagaaatcgctaaactgggccacgaaatcgaaattaaagtac
agggtgccgcgtccccaaccgatacgtatgtttctaccttcggcggcgtggttaccatcccggaacgtcgcaaactgaaaactccggactg
cggcattgtgattggcgataccggcgttttctcctccaccaaagagttagtagctaacgtacgtcagctgcgcgaaagctacccggatttgat
cgaaccgctgatgacctctattggcaaaatctctcgtatcggcgaacaactggttctgtctggcgactacgcatccatcggccgcctgatgaa
cgtcaaccagggtctcctggacgccctgggcgttaacatcttagaactgagccagctgatctattccgctcgtgcggcaggtgcgtttggcg
ctaaaatcacgggcgctggcggcggtggctgtatggttgcgctgaccgctccggaaaaatgcaaccaagtggcagaagcggtagcaggc
gctggcggtaaagtgactatcactaaaccgaccgagcaaggtctgaaagtagattaaagtctagttaaagtttaaacggtctccagcttggct
gttttggcggatgagagaagattttcagcctgatacagattaaatcagaacgcagaagcggtctgataaaacagaatttgcctggcggcagt
agcgcggtggtcccacctgaccccatgccgaactcagaagtgaaacgccgtagcgccgatggtagtgtggggtctccccatgcgagagt
agggaactgccaggcatcaaataaaacgaaaggctcagtcgaaagactgggcctttcgttttatctgttgtttgtcggtgaacgctctcctgag
taggacaaatccgccgggagcggatttgaacgttgcgaagcaacggcccggagggtggcgggcaggacgcccgccataaactgccag
gcatcaaattaagcagaaggccatcctgacggatggcctttttgcgtttctacaaactctttttgtttatttttctaaatacattcaaatatgtatccg
ctcatgagacaataaccctgataaatgcttcaataatattgaaaaaggaagagtatgagtattcaacatttccgtgtcgcccttattcccttttttg
cggcattttgccttcctgtttttgctcacccagaaacgctggtgaaagtaaaagatgctgaagatcagttgggtgcacgagtgggttacatcga
actggatctcaacagcggtaagatccttgagagttttcgccccgaagaacgttttccaatgatgagcacttttaaagttctgctatgtggcgcg
gtattatcccgtgttgacgccgggcaagagcaactcggtcgccgcatacactattctcagaatgacttggttgagtactcaccagtcacagaa
aagcatcttacggatggcatgacagtaagagaattatgcagtgctgccataaccatgagtgataacactgcggccaacttacttctgacaacg

FIG. 61B atcggaggaccgaaggagctaaccgcttttttgcacaacatgggggatcatgtaactcgccttgatcgttgggaaccggagctgaatgaag
ccataccaaacgacgagcgtgacaccacgatgcctgtagcaatggcaacaacgttgcgcaaactattaactggcgaactacttactctagct
tcccggcaacaattaatagactggatggaggcggataaagttgcaggaccacttctgcgctcggcccttccggctggctggtttattgctgat
aaatctggagccggtgagcgtgggtctcgcggtatcattgcagcactggggccagatggtaagccctcccgtatcgtagttatctacacgac
ggggagtcaggcaactatggatgaacgaaatagacagatcgctgagataggtgcctcactgattaagcattggtaactgtcagaccaagttt
actcatatatactttagattgatttaaaacttcatttttaatttaaaaggatctaggtgaagatcctttttgataatctcatgaccaaaatcccttaacgt
gagttttcgttccactgagcgtcagaccccgtagaaaagatcaaaggatcttcttgagatcctttttttctgcgcgtaatctgctgcttgcaaaca
aaaaaaccaccgctaccagcggtggtttgtttgccggatcaagagctaccaactctttttccgaaggtaactggcttcagcagagcgcagat
accaaatactgtccttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgggctgaa
cggggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccagggggaa
acgcctggtatctttatagtcctgtcgggtttcgccacctctgacttgagcgtcgatttttgtgatgctcgtcaggggggcggagcctatggaaa
aacgccagcaacgcggcctttttacggttcctggccttttgctggccttttgctcacatgttctttcctgcgttatcccctgattctgtggataacc
gtattaccgcctttgagtgagctgataccgctcgccgcagccgaacgaccgagcgcagcgagtcagtgagcgaggaagcggaagagcg
cctgatgcggtattttctccttacgcatctgtgcggtatttcacaccgcatatggtgcactctcagtacaatctgctctgatgccgcatagttaag
ccagtatacactccgctatcgctacgtgactgggtcatggctgcgccccgacacccgccaacacccgctgacgcgccctgacgggcttgt
ctgctcccggcatccgcttacagacaagctgtgaccgtctccgggagctgcatgtgtcagaggttttcaccgtcatcaccgaaacgcgcga
ggcagcagatcaattcgcgcgcgaaggcgaagcggcatgcatttacgttgacaccatcgaatggtgcaaaacctttcgcggtatggcatga
tagcgcccggaagagagtcaattcagggtggtgaatgtgaaaccagtaacgttatacgatgtcgcagagtatgccggtgtctcttatcagac
cgtttcccgcgtggtgaaccaggccagccacgtttctgcgaaaacgcgggaaaaagtggaagcggcgatggcggagctgaattacattcc
caaccgcgtggcacaacaactggcgggcaaacagtcgttgctgattggcgttgccacctccagtctggccctgcacgcgccgtcgcaaatt
gtcgcggcgattaaatctcgcgccgatcaactgggtgccagcgtggtggtgtcgatggtagaacgaagcggcgtcgaagcctgtaaagcg
gcggtgcacaatcttctcgcgcaacgcgtcagtgggctgatcattaactatccgctggatgaccaggatgccattgctgtggaagctgcctg
cactaatgttccggcgttatttcttgatgtctctgaccagacacccatcaacagtattattttctcccatgaagacggtacgcgactgggcgtgg
agcatctggtcgcattgggtcaccagcaaatcgcgctgttagcgggcccattaagttctgtctcggcgcgtctgcgtctggctggctggcata
aatatctcactcgcaatcaaattcagccgatagcggaacgggaaggcgactggagtgccatgtccggttttcaacaaaccatgcaaatgctg
aatgagggcatcgttcccactgcgatgctggttgccaacgatcagatggcgctgggcgcaatgcgcgccattaccgagtccgggctgcgc
gttggtgcggatatctcggtagtgggatacgacgataccgaagacagctcatgttatatcccgccgtcaaccaccatcaaacaggattttcgc
ctgctggggcaaaccagcgtggaccgcttgctgcaactctctcagggccaggcggtgaagggcaatcagctgttgcccgtctcactggtg
aaaagaaaaaccaccctggcgcccaatacgcaaaccgcctctccccgcgcgttggccgattcattaatgcagctggcacgacaggtttccc
gactggaaagcgggcagtgagcgcaacgcaattaatgtgagttagcgcgaattgatctg (SEQ ID NO:89)

MCM484-487 - GB-cmr gi1.x MVKmazei
8123 bp

FIG. 63A

1- aagggcgagctcaacgatccggctgctaacaaagcccgaaaggaagctgagttggctgctgccaccgctgagcaataactagcataacc
ccttggggcctctaaacgggtcttgaggggttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcacttttcggggaaatgtgcgcggaacccctatttgttt
atttttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttctttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

FIG. 63B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggtttttcttttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtggccccttcgcgccaccttccactcctcc
cctagtcaggaagttcccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaaggggtgggtccgggggcgggctcaggggcgggctcaggggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggcctttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttattttcatgatctgtgtgttggtttttgtgtgcggcgcggaagttcctattctctag
aaagtataggaacttcctcgagccctatagtgagtcgtattagatcgcggccgcgcccttgacaatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgtttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtccccaaccgatacgtatgtttctacc
ttcggcggcgtggttaccatcccggaacgtcgcaaactgaaaactccggactgcggcattgtgattggcgataccggcgtttttctcctccac
caaagagttagtagctaacgtacgtcagctgcgcgaaagctacccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

FIG. 63C tgcgctgaccgctccggaaaaatgcaaccaagtggcagaagcggtagcaggcgctggcggtaaagtgactatcactaaaccgaccgag
caaggtctgaaagtagattaa (SEQ ID NO:90)

FIG. 64A

1-
aagggcgagctcaacgatccggctgctaacaaagcccgaaaggaagctgagttggctgctgccaccgctgagcaataactagcataacc
ccttggggcctctaaacgggtcttgaggggttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcacttttcggggaaatgtgcgcggaacccctatttgttt
atttttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaacagacaatcggctgctctgatgccg
ccgtgttccggctgtcagcgcaggggcgcccggttctttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgagcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

FIG. 64B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggtttttcttttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtggccccttcgcgccaccttccactcctcc
cctagtcaggaagttcccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaaggggtgggtccgggggcgggctcaggggcgggctcaggggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggcctttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttattttcatgatctgtgtgttggtttttgtgtgcggcgcggaagttcctattctctag
aaagtataggaacttcctcgagccctatagtgagtcgtattagatcgcggccgcgccccttgaccatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgtttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtccccaaccgatacgtatgtttctacc
ttcggcggcgtggttaccatcccggaacgtcgcaaactgaaaactccggactgcggcattgtgattggcgataccggcgttttctcctccac
caaagagttagtagctaacgtacgtcagctgcgcgaaagctacccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

FIG. 64C tgcgctgaccgctccggaaaaatgcaaccaagtggcagaagcggtagcaggcgctggcggtaaagtgactatcactaaaccgaccgag
caaggtctgaaagtagattaa (SEQ ID NO:91)

FIG. 65A

1- aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcacttttcggggaaatgtgcgcggaacccctatttgttt
atttttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttctttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

FIG. 65B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggtttttcttttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtggccccttcgcgccaccttccactcctcc
cctagtcaggaagttcccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaaggggtgggtccgggggcgggctcaggggcgggctcaggggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggcctttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttattttcatgatctgtgtgttggtttttgtgtgcggcgcggaagttcctattctctag
aaagtataggaacttcctcgagccctatagtgagtcgtattagatcgcggccgcgcccttgacgatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgtttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtccccaaccgatacgtatgtttctacc
ttcggcggcgtggttaccatcccggaacgtcgcaaactgaaaactccggactgcggcattgtgattggcgataccggcgtttttctcctccac
caaagagttagtagctaacgtacgtcagctgcgcgaaagctacccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

FIG. 65C tgcgctgaccgctccggaaaaatgcaaccaagtggcagaagcggtagcaggcgctggcggtaaagtgactatcactaaaccgaccgag
caaggtctgaaagtagattaa (SEQ ID NO:92)

FIG. 66A

1- aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaattaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcacttttcggggaaatgtgcgcggaacccctatttgttt
atttttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttctttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

FIG. 66B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggtttttcttttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtggccccttcgcgccaccttccactcctcc
cctagtcaggaagttcccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaaggggtgggtccgggggcgggctcaggggcgggctcaggggcggggcgggcgcccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggcctttttaaag
accgtaaagaaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagctttattttcatgatctgtgtgttggtttttgtgtgcggcgcggaagttcctattctctag
aaagtataggaacttcctcgagccctatagtgagtcgtattagatcgcggccgcgccccttgactatgccacatcctgagcaaataattcaacc
actaattgtgagcggataacaaaggaggtaaaaaaacatggtatcctgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgtttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaaattaaagtacagggtgccgcgtccccaaccgatacgtatgtttctacc
ttcggcggcgtggttaccatcccggaacgtcgcaaactgaaaactccggactgcggcattgtgattggcgataccggcgtttttctcctccac
caaagagttagtagctaacgtacgtcagctgcgcgaaagctacccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

FIG. 66C tgcgctgaccgctccggaaaaatgcaaccaagtggcagaagcggtagcaggcgctggcggtaaagtgactatcactaaaccgaccgag
caaggtctgaaagtagattaa (SEQ ID NO:93)

FIG. 73B(1)

gcggccgcgccccttgacgatgccacatcctgagcaaataattcaaccactaattgtgagcggataacacaaggaggaaacagc
catggtatcctgttctgcgccgggtaagatttacctgttcggtgaacacgccgtagtttatggcgaaactgcaattgcgtgtgcggt
ggaactgcgtacccgtgttcgcgcggaactcaatgactctatcactattcagagccagatcggccgcaccggtctggatttcgaa
aagcaccccttatgtgtctgcggtaattgagaaaatgcgcaaatctattcctattaacggtgttttcttgaccgtcgattccgacatccc
ggtgggctccggtctgggtagcagcgcagccgttactatcgcgtctattggtgcgctgaacgagctgttcggctttggcctcagc
ctgcaagaaatcgctaaactgggccacgaaatcgaaattaaagtacagggtgccgcgtccccaaccgatacgtatgtttctacct
tcggcggcgtggttaccatcccggaacgtcgcaaactgaaaactccggactgcggcattgtgattggcgataccggcgttttctc
ctccaccaaagagttagtagctaacgtacgtcagctgcgcgaaagctacccggatttgatcgaaccgctgatgacctctattggc
aaaatctctcgtatcggcgaacaactggttctgtctggcgactacgcatccatcggccgcctgatgaacgtcaaccagggtctcct
ggacgccctgggcgttaacatcttagaactgagccagctgatctattccgctcgtgcggcaggtgcgtttggcgctaaaatcacg
ggcgctggcggcggtggctgtatggttgcgctgaccgctccggaaaaatgcaaccaagtggcagaagcggtagcaggcgct
ggcggtaaagtgactatcactaaaccgaccgagcaaggtctgaaagtagattaagccttgacttaatagctgcttatttcgccctta
tggtacctagtaggaggaaaaaaacatggaaatgcgtcaaccggctgtcgcaggtcaattctacccactgcgttgcgagaacct
ggaaaacgaactgaaacgctgcttcgaaggcctggagatccgcgaacaagaagtgctgggcgcagtctgtccgcacgccggt
tatatgtactctggcaaagttgcggcgcacgtctatgccactctgccggaagctgatacctacgtaatcttcggcccgaaccacac
cggctacggtagccctgtctctgtgagccgtgaaacttggaagaccccgttgggcaatatcgatgttgacctggaactggcgga
cggcttcctgggttccatcgtagatgcggatgaactcggtcacaaatacgaacactctatcgaagttcagctgccgtttctgcaata
ccgttttgaacgcgatttcaaaattctgccaatctgcatgggtatgcaagacgaagaaaccgcggtcgaagtaggtaacctgctg
gcggatctgatcagcgagtccggtaaacgtgctgtgatcatcgcaagctctgatttcacccactatgagacggctgaacgtgcca
aagaaatcgattccgaagttattgattctatcctgaactttgacatctctggcatgtacgatcgcctgtatcgccgtaacgcctctgttt
gcggttacggcccgatcaccgctatgctgacggcaagcaaaaagctgggcggctctcgtgcgactttgctgaaatacgcaaac
agcggtgacgtgtccggtgataaagacgctgtggtgggctacgccgccatcatcgttgagtaagctgattaaaggttgaacagat
aggatttcgtcatggatcctacaaggaggaaaaaaacatgaatgcttctaatgaaccggtgattctgaaactgggtggctctgcta
ttaccgacaaaggtgcctacgaaggcgtagttaaggaagctgatttgctgcgcatcgcacaggaagttagcggtttccgtggca
agatgatcgtggttcatggtgctggtagcttcggccatacgtacgcgaagaaatacggcctggaccgtaccttcgacccagagg
gcgcaattgttactcatgaatctgttaaaaagctcgcctccaaagttgtaggtgctctgaatagcttcggcgtgcgtgctatcgcgg
tgcatcctatggactgcgcagtatgccgtaacggtcgtatcgaaacgatgtatctggactccatcaagttaatgctggaaaaaggt
ctggtgccggttctgcacggcgacgtcgcaatggatattgaactgggcacttgtatcctgtccggtgatcaaatcgttccttacctg
gccaaagaactgggtatctcccgcctcggcctgggcagcgcagaggatggtgtgctggatatggagggcaaacctgtaccgg
aaatcaccccagaaactttcgaagagttccgccactgcatcggtggttctggttctactgatgtaaccggtggcatgctgggcaaa
gtgctggaacttctggaattgagcaaaaattcttccattactagctacattttcaacgctggtaaagcagacaacatctaccgctttct
gaatggtgagtccatcggcactcgcatcagcccggacaagcgtgtttaagctagttattaacctaaatgctctaaaccagttatga
gctctacaaggaggaaaaaaacatgattaacactaccagccgccgcaaaattgaacacctgaaactctgcgcagaatccccgg
ttgaagcgcgtcaggtatctgccggctttgaagacgttactctgatccaccgcgctttaccggagctgaacatggatgaactgga
cctcagcgttgatttcctgggtaaacgcatcaaagcgccgttcctgattgcgtctatcacgggtggtcacccagataccatcccgg
ttaacgctgcgctggcagctgctgctgaggagctgggtgttggcatcggcgttggctctcagcgcgcggccattgatgatccga
gccaggaagacagcttccgtgtagtgcgtgatgaagccccagatgcgtttgtttatggcaacgtcggcgcagcacagatccgtc
agtatggtgttgaaggtgttgaaaaactgatcgaaatgattgacgcagatgccttggcaatccacctgaactttctgcaagaagcg
gtccaaccggaaggtgaccgcgacgcgaccggttgcctggacatgattaccgaaatttgctctcagattaaaactccggtaatcg
tgaaagaaaccggtgcaggcattagccgtgaagatgcgattctgttccagaaagctggcgtgagcgcaatcgacgttggcggc
gcgggcggcacctcctgggctggcgtcgaggtctaccgtgctaaagaaagccgtgactctgttagcgagcgtttaggtgagct
gttttgggatttcggcattccgacggtagcttctctgattgaatcccgcgtttccttgccgctgatcgcaaccggcggtatccgtaac
ggtctggacattgctaaaagcattgctctcggcgcaagcgctgccagcgccgctctgccgttcgttggtccgtccctggagggc
aaagaatccgttgtacgtgtgctgagctgcatgctggaagaatttaaagcagcaatgtttttgtgcggttgcggcaacatcaaaga

FIG. 73B(2)

cctgcacaactctccagtagtggtaactggttggacccgcgaatacctggagcagcgcggttttaacgttaaggacctctccctg
ccgggcaacgctctgtaagcttcaacgcgtctacaaataaaaaaggcacgtcagatgacgtgcctttttcttgtctaga
(SEQ ID NO:113)

MCM376 - MVK from M. mazei archeal Lowerin pET200D
6647bp

FIG. 74B(1)

aagggcgagctcaacgatccggctgctaacaaagcccgaaaggaagctgagttggctgctgccaccgctgagcaataactag
cataaccccttggggcctctaaacgggtcttgaggagttttttgctgaaaggaggaactatatccggatatcccgcaagaggccc
ggcagtaccggcataaccaagcctatgcctacagcatccagggtgacggtgccgaggatgacgatgagcgcattgttagatttc
atacacggtgcctgactgcgttagcaatttaactgtgataaactaccgcattaaagcttatcgatgataagctgtcaaacatgagaa
ttaattcttgaagacgaaagggcctcgtgatacgcctatttttataggttaatgtcatgataataatggtttcttagacgtcaggtggca
cttttcggggaaatgtgcgcggaacccctatttgtttatttttctaaatacattcaaatatgtatccgctcatgagacaataaccctgat
aaatgcttcaataatattgaaaaaggaagagtatgattgaacaagatggattgcacgcaggttctccggccgcttgggtggagag
gctattcggctatgactgggcacaactgacaatcggctgctctgatgccgccgtgttccggctgtcagcgcaggggcgcccggt
tctttttgtcaagaccgacctgtccggtgccctgaatgaactgcaggacgaggcagcgcggctatcgtggctggccacgacgg
gcgttccttgcgcagctgtgctcgacgttgtcactgaagcgggaagggactggctgctattgggcgaagtgccggggcaggat
ctcctgtcatctcaccttgctcctgccgagaaagtatccatcatggctgatgcaatgcggcggctgcatacgcttgatccggctac
ctgcccattcgaccaccaagcgaaacatcgcatcgagcgggcacgtactcggatggaagccggtcttgtcgatcaggatgatct
ggacgaagagcatcaggggctcgcgccagccgaactgttcgccaggctcaaggcgcgcatgcccgacggcgaggatctcgt
cgtgacacatggcgatgcctgcttgccgaatatcatggtggaaaatggccgcttttctggattcatcgactgtggccggctgggtg
tggcggaccgctatcaggacatagcgttggctacccgtgatattgctgaagagcttggcggcgaatgggctgaccgcttcctcgt
gctttacggtatcgccgctcccgattcgcagcgcatcgccttctatcgccttcttgacgagttcttctgagcgggactctggggttc
gaaatgaccgaccaagcgacgcctaactgtcagaccaagtttactcatatatactttagattgatttaaaacttcatttttaatttaaaa
ggatctaggtgaagatcctttttgataatctcatgaccaaaatcccttaacgtgagttttcgttccactgagcgtcagaccccgtaga
aaagatcaaaggatcttcttgagatcctttttttctgcgcgtaatctgctgcttgcaaacaaaaaaaccaccgctaccagcggtggtt
tgtttgccggatcaagagctaccaactctttttccgaaggtaactggcttcagcagagcgcagataccaaatactgtccttctagtgt
agccgtagttaggccaccacttcaagaactctgtagcaccgcctacatacctcgctctgctaatcctgttaccagtggctgctgcc
agtggcgataagtcgtgtcttaccgggttggactcaagacgatagttaccggataaggcgcagcggtcgggctgaacggggg
gttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttctttcctgcgtt
atcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcaatggtgca
ctctcagtacaatctgctctgatgccgcatagttaagccagtatacactccgctatcgctacgtgactgggtcatggctgcgcccc
gacacccgccaacacccgctgacgcgccctgacgggcttgtctgctcccggcatccgcttacagacaagctgtgaccgtctcc
gggagctgcatgtgtcagaggttttcaccgtcatcaccgaaacgcgcgaggcagctgcggtaaagctcatcagcgtggtcgtg
aagcgattcacagatgtctgcctgttcatccgcgtccagctcgttgagtttctccagaagcgttaatgtctggcttctgataaagcgg
gccatgttaagggcggttttttcctgtttggtcactgatgcctccgtgtaagggggatttctgttcatgggggtaatgataccgatga
aacgagagaggatgctcacgatacgggttactgatgatgaacatgcccggttactggaacgttgtgagggtaaacaactggcg
gtatggatgcggcgggaccagagaaaaatcactcagggtcaatgccagcgcttcgttaatacagatgtaggtgttccacagggt
agccagcagcatcctgcgatgcagatccggaacataatggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaaccccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcagg
tcgaggtggcccggctccatgcaccgcgacgcaacgcggggaggcagacaaggtatagggcggcgcctacaatccatgcc
aacccgttccatgtgctcgccgaggcggcataaatcgccgtgacgatcagcggtccaatgatcgaagttaggctggtaagagc
cgcgagcgatccttgaagctgtccctgatggtcgtcatctacctgcctggacagcatggcctgcaacgcgggcatcccgatgcc
gccggaagcgagaagaatcataatggggaaggccatccagcctcgcgtcgcgaacgccagcaagacgtagcccagcgcgt

FIG. 74B(2)

cggccgccatgccggcgataatggcctgcttctcgccgaaacgtttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccca
ccggaaggagctgactgggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctga
gagagttgcagcaagcggtccacgctggtttgccccagcaggcgaaaatcctgtttgatggtggttaacggcgggatataacat
gagctgtcttcggtatcgtcgtatcccactaccgagatatccgcaccaacgcgcagcccggactcggtaatggcgcgcattgcg
cccagcgccatctgatcgttggcaaccagcatcgcagtgggaacgatgccctcattcagcatttgcatggtttgttgaaaaccgg
acatggcactccagtcgccttcccgttccgctatcggctgaatttgattgcgagtgagatatttatgccagccagccagacgcaga
cgcgccgagacagaacttaatgggcccgctaacagcgcgatttgctggtgacccaatgcgaccagatgctccacgcccagtcg
cgtaccgtcttcatgggagaaaataatactgttgatgggtgtctggtcagagacatcaagaaataacgccggaacattagtgcag
gcagcttccacagcaatggcatcctggtcatccagcggatagttaatgatcagcccactgacgcgttgcgcgagaagattgtgc
accgccgctttacaggcttcgacgccgcttcgttctaccatcgacaccaccacgctggcacccagttgatcggcgcgagatttaa
tcgccgcgacaatttgcgacggcgcgtgcagggccagactggaggtggcaacgccaatcagcaacgactgtttgcccgccag
ttgttgtgccacgcggttgggaatgtaattcagctccgccatcgccgcttccactttttcccgcgttttcgcagaaacgtggctggc
ctggttcaccacgcgggaaacggtctgataagagacaccggcatactctgcgacatcgtataacgttactggtttcacattcacca
ccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatg
caaggagatggcgcccaacagtcccccggccacggggcctgccaccatacccacgccgaaacaagcgctcatgagcccga
agtggcgagcccgatcttccccatcggtgatgtcggcgatataggcgccagcaaccgcacctgtggcgccggtgatgccggc
cacgatgcgtccggcgtagaggatcgagatctcgatcccgcgaaattaatacgactcactataggggaattgtgagcggataac
aattcccctctagaaataattttgtttaactttaagaaggagatatacatatgcggggttctcatcatcatcatcatcatggtatggcta
gcatgactggtggacagcaaatgggtcgggatctgtacgacgatgacgataaggatcatcccttcaccatggtatcctgttctgc
gccgggtaagatttacctgttcggtgaacacgccgtagtttatggcgaaactgcaattgcgtgtgcggtggaactgcgtacccgt
gttcgcgcggaactcaatgactctatcactattcagagccagatcggccgcaccggtctggatttcgaaaagcacccttatgtgtc
tgcggtaattgagaaaatgcgcaaatctattcctattaacggtgttttcttgaccgtcgattccgacatcccggtgggctccggtctg
ggtagcagcgcagccgttactatcgcgtctattggtgcgctgaacgagctgttcggctttggcctcagcctgcaagaaatcgcta
aactgggccacgaaatcgaaattaaagtacagggtgccgcgtccccaaccgatacgtatgtttctaccttcggcggcgtggttac
catcccggaacgtcgcaaactgaaaactccggactgcggcattgtgattggcgataccggcgttttctcctccaccaaagagtta
gtagctaacgtacgtcagctgcgcgaaagctacccggatttgatcgaaccgctgatgacctctattggcaaaatctctcgtatcgg
cgaacaactggttctgtctggcgactacgcatccatcggccgcctgatgaacgtcaaccagggtctcctggacgccctgggcgt
taacatcttagaactgagccagctgatctattccgctcgtgcggcaggtgcgtttggcgctaaaatcacgggcgctggcggcggt
ggctgtatggttgcgctgaccgctccggaaaaatgcaaccaagtggcagaagcggtagcaggcgctggcggtaaagtgactat
cactaaaccgaccgagcaaggtctgaaagtagattaa
(SEQ ID NO:114)

Figure 74C cggccgccatgccggcgataatggcctgcttctcgccgaaacgtttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccca
ccggaaggagctgactgggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctga
gagagttgcagcaagcggtccacgctggtttgccccagcaggcgaaaatcctgtttgatggtggttaacggcgggatataacat
gagctgtcttcggtatcgtcgtatcccactaccgagatatccgcaccaacgcgcagcccggactcggtaatggcgcgcattgcg
cccagcgccatctgatcgttggcaaccagcatcgcagtgggaacgatgccctcattcagcatttgcatggtttgttgaaaaccgg
acatggcactccagtcgccttcccgttccgctatcggctgaatttgattgcgagtgagatatttatgccagccagccagacgcaga
cgcgccgagacagaacttaatgggcccgctaacagcgcgatttgctggtgacccaatgcgaccagatgctccacgcccagtcg
cgtaccgtcttcatgggagaaaataatactgttgatgggtgtctggtcagagacatcaagaaataacgccggaacattagtgcag
gcagcttccacagcaatggcatcctggtcatccagcggatagttaatgatcagcccactgacgcgttgcgcgagaagattgtgc
accgccgctttacaggcttcgacgccgcttcgttctaccatcgacaccaccacgctggcacccagttgatcggcgcgagatttaa
tcgccgcgacaatttgcgacggcgcgtgcagggccagactggaggtggcaacgccaatcagcaacgactgtttgcccgccag
ttgttgtgccacgcggttgggaatgtaattcagctccgccatcgccgcttccactttttcccgcgttttcgcagaaacgtggctggc
ctggttcaccacgcgggaaacggtctgataagagacaccggcatactctgcgacatcgtataacgttactggtttcacattcacca
ccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatg
caaggagatggcgcccaacagtcccccggccacggggcctgccaccatacccacgccgaaacaagcgctcatgagcccga
agtggcgagcccgatcttccccatcggtgatgtcggcgatataggcgccagcaaccgcacctgtggcgccggtgatgccggc
cacgatgcgtccggcgtagaggatcgagatctcgatcccgcgaaattaatacgactcactataggggaattgtgagcggataac
aattcccctctagaaataattttgtttaactttaagaaggagatatacatatgcggggttctcatcatcatcatcatcatggtatggcta
gcatgactggtggacagcaaatgggtcgggatctgtacgacgatgacgataaggatcatcccttcaccatggtatcctgttctgc
gccgggtaagatttacctgttcggtgaacacgccgtagtttatggcgaaactgcaattgcgtgtgcggtggaactgcgtacccgt
gttcgcgcggaactcaatgactctatcactattcagagccagatcggccgcaccggtctggatttcgaaaagcacccttatgtgtc
tgcggtaattgagaaaatgcgcaaatctattcctattaacggtgttttcttgaccgtcgattccgacatcccggtgggctccggtctg
ggtagcagcgcagccgttactatcgcgtctattggtgcgctgaacgagctgttcggctttggcctcagcctgcaagaaatcgcta
aactgggccacgaaatcgaaattaaagtacagggtgccgcgtccccaaccgatacgtatgtttctaccttcggcggcgtggttac
catcccggaacgtcgcaaactgaaaactccggactgcggcattgtgattggcgataccggcgttttctcctccaccaaagagtta
gtagctaacgtacgtcagctgcgcgaaagctacccggatttgatcgaaccgctgatgacctctattggcaaaatctctcgtatcgg
cgaacaactggttctgtctggcgactacgcatccatcggccgcctgatgaacgtcaaccagggtctcctggacgccctgggcgt
taacatcttagaactgagccagctgatctattccgctcgtgcggcaggtgcgtttggcgctaaaatcacgggcgctggcggcggt
ggctgtatggttgcgctgaccgctccggaaaaatgcaaccaagtggcagaagcggtagcaggcgctggcggtaaagtgactat
cactaaaccgaccgagcaaggtctgaaagtagattaa
(SEQ ID NO:114)

CDS 2: Gentamycin resistance gene; CDS1: E. coli replication protein.

FIG. 77A 1-
ctcgggccgtctcttgggcttgatcggccttcttgcgcatctcacgcgctcctgcggcggcctgtagggcaggctcatacccctgccgaacc
gcttttgtcagccggtcggccacggcttccggcgtctcaacgcgctttgagattcccagcttttcggccaatccctgcggtgcataggcgcgt
ggctcgaccgcttgcgggctgatggtgacgtggcccactggtggccgctccagggcctcgtagaacgcctgaatgcgcgtgtgacgtgc
cttgctgccctcgatgccccgttgcagccctagatcggccacagcggccgcaaacgtggtctggtcgcgggtcatctgcgctttgttgccga
tgaactccttggccgacagcctgccgtcctgcgtcagcggcaccacgaacgcggtcatgtgcgggctggtttcgtcacggtggatgctggc
cgtcacgatgcgatccgccccgtacttgtccgccagccacttgtgcgccttctcgaagaacgccgcctgctgttcttggctggccgacttcca
ccattccgggctggccgtcatgacgtactcgaccgccaacacagcgtccttgcgccgcttctctggcagcaactcgcgcagtcggcccatc
gcttcatcggtgctgctggccgcccagtgctcgttctctggcgtcctgctggcgtcagcgttgggcgtctcgcgctcgcggtaggcgtgctt
gagactggccgccacgttgcccattttcgccagcttcttgcatcgcatgatcgcgtatgccgccatgcctgcccctcccttttggtgtccaacc
ggctcgacgggggcagcgcaaggcggtgcctccggcgggccactcaatgcttgagtatactcactagactttgcttcgcaaagtcgtgac
cgcctacggcggctgcggcgccctacgggcttgctctccgggcttcgccctgcgcggtcgctgcgctcccttgccagcccgtggatatgtg
gacgatggccgcgagcggccaccggctggctcgcttcgctcggcccgtggacaaccctgctggacaagctgatggacaggctgcgcct
gcccacgagcttgaccacagggattgcccaccggctacccagccttcgaccacatacccaccggctccaactgcgcggcctgcggcctt
gccccatcaatttttttaatttttctctggggaaaagcctccggcctgcggcctgcgcgcttcgcttgccggttggacaccaagtggaaggcgg
gtcaaggctcgcgcagcgaccgcgcagcggcttggccttgacgcgcctggaacgacccaagcctatgcgagtgggggcagtcgaagg
cgaagcccgcccgcctgccccccgagcctcacggcggcgagtgcgggggttccaagggggcagcgccaccttgggcaaggccgaag
gccgcgcagtcgatcaacaagccccggaggggccactttttgccggagggggagccgcgccgaaggcgtgggggaacccccgcaggg
gtgcccttctttgggcaccaaagaactagatatagggcgaaatgcgaaagacttaaaaatcaacaacttaaaaaaggggggtacgcaacag
ctcattgcggcacccccgcaatagctcattgcgtaggttaaagaaaatctgtaattgactgccacttttacgcaacgcataattgttgtcgcgc
tgccgaaaagttgcagctgattgcgcatggtgccgcaaccgtgcggcacccctaccgcatggagataagcatggccacgcagtccagaga
aatcggcattcaagccaagaacaagcccggtcactgggtgcaaacggaacgcaaagcgcatgaggcgtgggccgggcttattgcgagg
aaacccacggcggcaatgctgctgcatcacctcgtggcgcagatgggccaccagaacgccgtggtggtcagccagaagacactttccaa
gctcatcggacgttctttgcggacggtccaatacgcagtcaaggacttggtggccgagcgctggatctccgtcgtgaagctcaacggcccc
ggcaccgtgtcggcctacgtggtcaatgaccgcgtggcgtggggccagccccgcgaccagttgcgcctgtcggtgttcagtgccgccgt
ggtggttgatcacgacgaccaggacgaatcgctgttggggcatggcgacctgcgccgcatcccgaccctgtatccgggcgagcagcaac
taccgaccggccccggcgaggagccgcccagccagcccggcattccgggcatggaaccagacctgccagccttgaccgaaacggag
gaatgggaacggcgcgggcagcagcgcctgccgatgcccgatgagccgtgttttctggacgatggcgagccgttggagccgccgacac
gggtcacgctgccgcgccggtagcacttgggttgcgcagcaacccgtaagtgcgctgttccagactatcggctgtagccgcctcgccgcc
ctataccttgtctgcctccccgcgttgcgtcgcggtgcatggagccgggccacctcgacctgaatggaagccggcggcacctcgctaacg
gattcaccgtttttatcaggctctgggaggcagaataaatgatcatatcgtcaattattacctccacggggagagcctgagcaaactggcctca
ggcatttgagaagcacacggtcacactgcttccggtagtcaataaaccggtaaaccagcaatagacataagcggctatttaacgaccctgcc
ctgaaccgacgaccgggtcgaatttgctttcgaatttctgccattcatccgcttattatcacttattcaggcgtagcaccaggcgtttaagggca
ccaataactgccttaaaaaaattacgccccgccctgccactcatcgcagtcggcctattggttaaaaaatgagctgatttaacaaaaatttaac
gcgaattttaacaaaatattaacgcttacaatttccattcgccattcaggctgcgcaactgttgggaagggcgatcggtgcgggcctcttcgct
attacgccagctggcgaaagggggatgtgctgcaaggcgattaagttgggtaacgccagggttttcccagtcacgacgttgtaaaacgacg
gccagtgagcgcgcgtaatacgactcactatagggcgaattggagctccaccgcggtggcggccgctctagaactagtggatcccccgg
gctgcatgctcgagcggccgccagtgtgatggatatctgcagaattcgcccttcttgatatcttagtgtgcgttaaccaccacccacattggtc
cctgcccgaccgcatagcggcctttttcatgcagtagcccctgctcgccaacaatttcgtataccgagatgtggtgagatttttgcccggcgg
caatcagatacttgccgctgtgatcaacattgaagccgcgcggctgggtttccgttggctggaagccttctttactcaacacgctgccatcttc
cgaaacgctgaaaacggtaatcaggctggcggtacggtcgcaggcgtataaatggcgaccatccggggtgatatgaatatcagccgccc
aacgggtgtcggagaagttttccggcatcatatccagcgtctggacacattcgatattaccgtgcggatctttcagttcccagacatccactga
gctgtttaactcattgacgcaatacgcatattgttcgtttggatggaataccatatgacgcgggccggcccccttcaacggtggtcacttccgca
gggtcctgcgccacgagatgaccatcatcgctgaccgtaaacaggcaaatgcgatcctgctttaatgccggaacccacagcgtacggttgt

FIG. 77B ccggtgagatattggcggaatggcaaccgtccagcccctcgaccacatcgacgacgcccactggcaggccatcttccagacgcgttacgc
tcacgttacccgcattgtaagaacctacaaagacaaactgcccctggtgatcggtggaaatatgcgtcggactacccggcagcgcagactc
tgcggcaaaggtcagtgcgccatcgtccggggcgatacgatacgccaggacgcgaaactcagggcgaacaccaacatagagataacgt
ttgtccgggctgaccaccatcggctgcacctgccccggcacatcgacaacctgtgtcagcgtcagtgcgccttcatgattcagattccagac
gtgaatttgctggctctcagggctggcgatataaactgtttgcttcatgaatgctcctttgggttacctccgggaaacgcggttgatttgtttagtg
gttgaattatttgctcaggatgtggcatagtcaagggcgtgacggctcgctaatacaactcactatagggctcgaggaagttcctatactttcta
gagaataggaacttccgcgccgcacacaaaaaccaacacacagatcatgaaaataaagctcttttattggtaccgaattcgccagggagct
ctcagacgtcgcttggtcggtctttattcgaaccccagagtcccgcttacgccccgccctgccactcatcgcagtactgttgtaattcattaagc
attctgccgacatggaagccatcacaaacggcatgatgaacctgaatcgccagcggcatcagcaccttgtcgccttgcgtataatatttgccc
atggtgaaaacgggggcgaagaagttgtccatattggccacgtttaaatcaaaactggtgaaactcacccagggattggctgagacgaaaa
acatattctcaataaaccctttagggaaataggccaggttttcaccgtaacacgccacatcttgcgaatatatgtgtagaaactgccggaaatc
gtcgtggtattcactccagagcgatgaaaacgtttcagtttgctcatggaaaacggtgtaacaagggtgaacactatcccatatcaccagctc
accgtctttcattgccatacggaattccggatgagcattcatcaggcgggcaagaatgtgaataaaggccggataaaacttgtgcttatttttct
ttacggtctttaaaaaggccgtaatatccagctgaacggtctggttataggtacattgagcaactgactgaaatgcctcaaaatgttctttacgat
gccattgggatatatcaacggtggtatatccagtgatttttttctccatggtttagttcctcaccttgtcgtattatactatgccgatatactatgccg
atgattaattgtcaacacgtgctgctgcaggtcgaaaggcccggagatgaggaagaggagaacagcgcggcagacgtgcgcttttgaag
cgtgcagaatgccgggcctccggaggaccttcgggcgcccgccccgcccctgagcccgcccctgagcccgcccccggacccacccctt
cccagcctctgagcccagaaagcgaaggagcaaagctgctattggccgctgccccaaaggcctacccgcttccattgctcagcggtgctg
tccatctgcacgagactagtgagacgtgctacttccatttgtcacgtcctgcacgacgcgagctgcggggcgggggggaacttcctgacta
ggggaggagtggaaggtggcgcgaaggggccaccaaagaacggagccggttggcgcctaccggtggatgtggaatgtgtgcgaggc
cagaggccacttgtgtagcgccaagtgcccagcggggctgctaaagcgcatgctccagactgccttgggaaaagcgcctcccctacccg
gtagaatgaagttcctatactttctagagaataggaacttcgcggccgcccctttagtgagggttaattcaactgactgtaacagctaaaattagt
cgcttttggcggtaagggcgaattccagcacactggcggccgttactagtggatccgagctcggtaccaagcttgatgcaggaattcgatat
caagcttatcgataccgtcgacctcgagggggggcccggtacccagcttttgttccctttagtgagggttaattgcgcgcttggcgtaatcatg
gtcatagctgtttcctgtgtgaaattgttatccgctcacaattccacacaacatacgagccggaagcataaagtgtaaagcctggggtgcctaa
tgagtgagctaactcacattaattgcgttgcgctcactgcccgctttccagtcgggaaacctgtcgtgccagctgcattaatgaatcggccaac
gcgcggggagaggcggtttgcgtattgggcgcatgcataaaaactgttgtaattcattaagcattctgccgacatggaagccatcacaaacg
gcatgatgaacctgaatcgccagcggcatcagcaccttgtcgccttgcgtataatatttgcccatggacgcacaccgtggaaacggatgaa
ggcacgaacccagttgacataagcctgttcggttcgtaaactgtaatgcaagtagcgtatgcgctcacgcaactggtccagaaccttgaccg
aacgcagcggtggtaacggcgcagtggcggttttcatggcttgttatgactgtttttttgtacagtctatgcctcgggcatccaagcagcaagc
gcgttacgccgtgggtcgatgtttgatgttatggagcagcaacgatgttacgcagcagcaacgatgttacgcagcagggcagtcgccctaa
aacaaagttaggtggctcaagtatgggcatcattcgcacatgtaggctcggccctgaccaagtcaaatccatgcgggctgctcttgatctttc
ggtcgtgagttcggagacgtagccacctactcccaacatcagccggactccgattacctcgggaacttgctccgtagtaagacattcatcgc
gcttgctgccttcgaccaagaagcggttgttggcgctctcgcggcttacgttctgcccaggtttgagcagccgcgtagtgagatctatatctat
gatctcgcagtctccggcgagcaccggaggcagggcattgccaccgcgctcatcaatctcctcaagcatgaggccaacgcgcttggtgct
tatgtgatctacgtgcaagcagattacggtgacgatcccgcagtggctctctatacaaagttgggcatacgggaagaagtgatgcactttgat
atcgacccaagtaccgccacctaacaattcgttcaagccgagatcggcttcccggccgcggagttgttcggtaaattgtcacaacgccgcc
aggtggcactttcggggaaatgtgcgcgcccgcgttcctgctggcgctgggcctgtttctggcgctggacttcccgctgttccgtcagcag
cttttcgcccacggccttgatgatcgcggcggccttggcctgcatatcccgattcaacggccccagggcgtccagaacgggcttcaggcgc
tcccgaaggt (SEQ ID NO:122).

FIG. 79B(1)

5'-
tagaaaaactcatcgagcatcaaatgaaactgcaatttattcatatcaggattatcaataccatatttttgaaaaagccgtttctgtaatgaagga
gaaaactcaccgaggcagttccataggatggcaagatcctggtatcggtctgcgattccgactcgtccaacatcaatacaacctattaatttcc
cctcgtcaaaaataaggttatcaagtgagaaatcaccatgagtgacgactgaatccggtgagaatggcaaaagtttatgcatttctttccagac
ttgttcaacaggccagccattacgctcgtcatcaaaatcactcgcatcaaccaaaccgttattcattcgtgattgcgcctgagcgaggcgaaat
acgcgatcgctgttaaaaggacaattacaaacaggaatcgagtgcaaccggcgcaggaacactgccagcgcatcaacaatattttcacctg
aatcaggatattcttctaatacctggaacgctgtttttccggggatcgcagtggtgagtaaccatgcatcatcaggagtacggataaaatgctt
gatggtcggaagtggcataaattccgtcagccagtttagtctgaccatctcatctgtaacatcattggcaacgctacctttgccatgtttcagaa
acaactctggcgcatcgggcttcccatacaagcgatagattgtcgcacctgattgcccgacattatcgcgagcccatttatacccatataaatc
agcatccatgttggaatttaatcgcggcctcgacgtttcccgttgaatatggctcatattcttcctttttcaatattattgaagcatttatcagggttat
tgtctcatgagcggatacatatttgaatgtatttagaaaaataaacaaataggggtcagtgttacaaccaattaaccaattctgaacattatcgcg
agcccatttatacctgaatatggctcataacaccccttgtttgcctggcggcagtagcgcggtggtcccacctgaccccatgccgaactcaga
agtgaaacgccgtagcgccgatggtagtgtggggactccccatgcgagagtagggaactgccaggcatcaaataaaacgaaaggctcag
tcgaaagactgggcctttcgcccgggctaattagggggtgtcgcccttcgattgacggttacgggatcctcacacgtacatcagctggttgat
ggggaacgggtcgatgagcagcagcttgatgcggttctcggtggcgtaatccgggcggcccagcccgtccccatattggtaggtgcagtg
gctcacgcgggccatgttcacggcgatctccatgaacgccttcggcagcagggtgctgtccgacacgcgctcgcggttcatttcttccact
cggcgtcgatcagcttgcgcagctcttcgcgggcctgttcctcgctcgtgccgtcgttctcgtgcatgtagctgatgatgctgttggtggtttcg
ccgcgttcgagttccgccgccgaggtcgccagatcgttgcacagccgaaagatcacgcaggacgagcgcaccaggccgtggaagtcgg
tcagggagcggagggcgtggtccgagatatcttcctgctgctggcagaccgagaagtagctcggcgccagcagcgcgaccccgctgga
ggacacgctggcgttctccaggtacttgctgaaggcggggatgatcttgttattgctccacttggcttcttgcaggaaggccttgcacagttcg
cgccagcttttggtcagatagctcaggttattgtggcccttctccttcaggatggagtaggacgtgtcgttcacggtgttgtacagggccagga
agcacagcttcatatagtcgggcagcgtgttgatggcgttcacgtcccagcgttccaccgcgtcggtgaagagctgcagttcgtccagggta
ccgtacacgtcatagacgtcatcgataatggtgaccagaccgaacatcttggtgacggccttgcggcattcgccgaactgcgggtccggcg
ccatgcccagcgcccagaagtacacttccatcaggcggtcccgcacgaaatccagcttgctggcgaggcccatctcggtccaccaccgg
ctcaggtcctgcagctcttttggtgcagggtctggaccatgttgaaatcgagtttggccagttccagcagcagctggtgatgcggctccttgg
gttcgtacttgtccagaaaccaccgcgcctccaggcggtgcaggcgttgatgatacggcagctccagcgcgtgggacacctgctcggcca
ccttcgtgttgatcccctccttgaggttgttcttcagatgggtgatgctgaaggtacgggcctcctccagcagatttcgccttcgaaaccgaga
tagctggcctcgtacaggctcagcaggccctgcacgtcacccttcagttccccggagaagccccccttctttgtccttgaagcgctcgaacac
gtcctggctcacctcaaagccatgctgccgcagcaggcggaagctcagggcggtcgcgtgcagatcgcttttgttcttcttattctcgtccag
caggacgatgttctccagcgccttgatgatatctttctcaaacttgtaggtcaggcccaggcgctgcacgtcgtcgatgagctccagcaggct
caggggctgggtgtccacccggttgatcatgcaacgcacctcctcctccagcttggtggccttctcttcgagcttctccaccttcaggtcgtttt
ccaggctctgcaggaactcgaagttccacaggttgggctggtagttcgcggaccgacggctattatgctcggtgatctgggtgaactggctg
ctggtggcgcacatatgtatatctccttcttaaagttaaacaagcttaagatgttcagcgacaagggcgacacaaaatttattctaaatgcataat
aaatactgataacatcttatagtttgtattatattttgtattatcgttgacatgtataattttgatatcaaaaactgattttccctttattattttcgagattta
ttttcttaattctctttaacaaactagaaatattgtatatacaaaaaatcataaataatagatgaatagtttaattataggtgttcatcaatcgaaaaag
caacgtatcttatttaaagtgcgttgctttttctcatttataaggttaaataattctcatatatcaagcaaagtgacaggcgcccttaaatattctga
caaatgctctttccctaaactccccccataaaaaaacccgccgaagcgggtttttacgttatttgcggattaacgattactcgttatcagaaccg
cccagggggcccgagcttaagactggccgtcgttttacaacacagaaagagtttgtagaaacgcaaaaaggccatccgtcaggggccttct
gcttagtttgatgcctggcagttccctactctcgccttccgcttcctcgctcactgactcgctgcgctcggtcgttcggctgcggcgagcggtat
cagctcactcaaaggcggtaatacggttatccacagaatcaggggataacgcaggaaagaacatgtgagcaaaaggccagcaaaaggc
caggaaccgtaaaaaggccgcgttgctggcgtttttccataggctccgcccccctgacgagcatcacaaaaatcgacgctcaagtcagag
gtggcgaaacccgacaggactataaagataccaggcgtttccccctggaagctccctcgtgcgctctcctgttccgaccctgccgcttaccg
gatacctgtccgcctttctcccttcgggaagcgtggcgctttctcatagctcacgctgtaggtatctcagttcggtgtaggtcgttcgctccaag
ctgggctgtgtgcacgaaccccccgttcagcccgaccgctgcgccttatccggtaactatcgtcttgagtccaacccggtaagacacgactt

FIG. 79B(2)

atcgccactggcagcagccactggtaacaggattagcagagcgaggtatgtaggcggtgctacagagttcttgaagtggtgggctaactac
ggctacactagaagaacagtatttggtatctgcgctctgctgaagccagttaccttcggaaaaagagttggtagctcttgatccggcaaacaa
accaccgctggtagcggtggtttttttgtttgcaagcagcagattacgcgcagaaaaaaaggatctcaagaagatcctttgatcttttctacgg
ggtctgacgctcagtggaacgacgcgcgcgtaactcacgttaagggattttggtcatgagcttgcgccgtcccgtcaagtcagcgtaatgct
ctgcttt (SEQ ID NO:123)

Figure 79C atcgccactggcagcagccactggtaacaggattagcagagcgaggtatgtaggcggtgctacagagttcttgaagtggtgggctaactac
ggctacactagaagaacagtatttggtatctgcgctctgctgaagccagttaccttcggaaaaagagttggtagctcttgatccggcaaacaa
accaccgctggtagcggtggtttttttgtttgcaagcagcagattacgcgcagaaaaaaaggatctcaagaagatcctttgatcttttctacgg
ggtctgacgctcagtggaacgacgcgcgcgtaactcacgttaagggattttggtcatgagcttgcgccgtcccgtcaagtcagcgtaatgct
ctgcttt (SEQ ID NO:123)

COMPOSITIONS AND METHODS FOR PRODUCING ISOPRENE

CROSS-REFERENCE TO RELATED APPLICATIONS

This application is a continuation application of U.S. patent application Ser. No. 14/987,681, filed Jan. 4, 2016, now U.S. Pat. No. 9,909,144, which is a continuation of U.S. patent application Ser. No. 13/600,132, filed Aug. 30, 2012, now U.S. Pat. No. 9,260,727, which is a divisional application of U.S. patent application Ser. No. 12/335,071, filed Dec. 15, 2008, now U.S. Pat. No. 8,288,148, which claims priority benefit of U.S. Provisional Patent Application No. 61/013,574, filed Dec. 13, 2007, the disclosures of which are herein incorporated by reference in their entireties.

INCORPORATION BY REFERENCE

The content of the following submission on ASCII text file is incorporated herein by reference in its entirety: a computer readable form (CFR) of the Sequence Listing (file name: 48768_501D02US_Sub_Seq_Listing_032016.txt, dated created Mar. 23, 2016, size 282,884 bytes.

FIELD OF THE INVENTION

The present invention relates generally to methods for producing isoprene from cultured cells and compositions that include these cultured cells.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway (FIGS. 19A and 19B). However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

BRIEF SUMMARY OF THE INVENTION

In one aspect, the invention features cells in culture that produce isoprene. In some embodiments, the invention provides cells in culture that produce greater than about 400 nmole of isoprene/gram of cells for the wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that have an average volumetric productivity of isoprene greater than about 0.1 mg/$L_{broth}$/hr. In some embodiments, the invention provides cells in culture that have a peak volumetric productivity of isoprene greater than about 0.5 mg/$L_{broth}$/hr. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that convert more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In one aspect, the invention features methods of producing isoprene, such as methods of using any of the cells described herein to produce isoprene. In some embodiments, the method involves culturing cells under conditions sufficient to produce greater than about 400 nmole/$g_{wcm}$/hr of isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In one aspect, the invention features methods of producing isoprene, such as methods of using any of the cells described herein to produce isoprene. In some embodiments, the method involves culturing cells under conditions resulting in an average volumetric productivity of isoprene greater than about 0.1 mg/$L_{broth}$/hr. In some embodiments, the method involves culturing cells under conditions resulting in a peak volumetric productivity of isoprene greater than about 0.5 mg/$L_{broth}$/hr. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the method includes culturing cells under conditions sufficient to convert more than about 0.002% of the carbon in a cell culture medium into isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole/$g_{wcm}$/hr isoprene. In some embodiments, the cells in culture have an average volumetric productivity of isoprene at greater than or about 0.1, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, or more mg of isoprene/L of broth/hr (mg/$L_{broth}$/hr, wherein the volume of broth includes the volume of the cells and the cell medium). In some embodiments, the cells in culture have a peak volumetric productivity of isoprene at greater than or about 0.5, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 12,500, 15,000, or more mg of isoprene/L of broth/hr (mg/$L_{broth}$/hr, wherein the volume of broth includes the volume of the cells and the cell medium). In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 2.0, 2.2, 2.4, 2.6, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 23.2, 23.4, 23.6, 23.8, 24.0, 25.0, 30.0, 31.0, 32.0, 33.0, 35.0, 37.5, 40.0, 45.0, 47.5, 50.0, 55.0, 60.0, 65.0, 70.0, 75.0, 80.0, 85.0, 90.0 molar %, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the heterologous isoprene synthase nucleic acid is operably linked to a T7 promoter, such as a T7 promoter contained in a medium or high copy plasmid. In some embodiments of any of the aspects of the invention, the heterologous isoprene synthase nucleic acid is operably linked to a Trc promoter, such as a Trc promoter contained in a medium or high copy plasmid. In some embodiments of any of the aspects of the invention, the heterologous isoprene synthase nucleic acid is operably linked to a Lac promoter, such as a Lac promoter contained in a low copy plasmid. In some embodiments of any of the aspects of the invention, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments of any of the aspects of the invention, at least a portion of the cells maintain the heterologous isoprene synthase nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, IDI, or DXS nucleic acid also comprises a selective marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisi, Methanosarcina mazei*, or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia, Methanosarcina mazei*, or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid).

In some embodiments of any of the aspects of the invention, the isoprene synthase polypeptide is a naturally-occurring polypeptide from a plant such as *Pueraria* (e.g., *Pueraria montana*) or *Populus* (e.g., *Populus tremuloides, Populus alba* (*P. alba*), *Populus nigra, Populus trichocarpa*, or the hybrid, *Populus alba* x *Populus tremula*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor, Streptomyces coelicolor, Streptomyces albus*, or *Streptomyces griseus* cells). In some embodiments of any of the aspects of the invention, the cells are gram-negative bacterial cells (e.g., *Escherichia* cells such as *Escherichia coli* cells or *Pantoea* cells such as *Pantoea citrea* cells). In some embodiments, the *E. coli* cells are *E. coli* FadR atoC mutant cells. In some embodiments, the *E. coli* cells express (such as constitutively express) ybhE (also known as pgl). In some embodiments of any of the aspects of the invention, the cells are fungal, cells such as filamentous funal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention provides a tire comprising polyisoprene. In some embodiments, the polyisoprene is produced by (i) polymerizing isoprene from any of the compositions or methods described herein or (ii) polymerizing isoprene recovered from any of the compositions or methods described herein. In some embodiments, the polyisoprene comprises cis-1,4-polyisoprene.

In one aspect, the invention features a product (such as a tire) produced by any of the compositions or methods of the invention.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIGS. 3A, 3B and 3C are the nucleotide sequences of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIGS. 5A, 5B and 5C are the nucleotide sequences of pETNHisKudzu (SEQ ID NO:5).

FIGS. 7A, 7B and 7C are the nucleotide sequences of pCL-lac-Kudzu (SEQ ID NO:7).

FIGS. 12A, 12B and 12C are the nucleotide sequences of pBS Kudzu #2 (SEQ ID NO:57).

FIG. 13 is the nucleotide sequence of kudzu isoprene synthase codon-optimized for expression in *Yarrowia* (SEQ ID NO:8).

FIGS. 15A, 15B and 15C are the nucleotide sequences of vector pSPZ1(MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba* x *Populus tremula*) isoprene synthase gene (SEQ ID NO:13). The ATG start codon is in bold and the stop codon is underlined.

FIGS. 18A(1) and 18A(2) show schematic outlining constructions of vectors pYLA 1, pYL1 and pYL2.

FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.

FIGS. 22A, 22B, 22C and 22D are the nucleotide sequences of pTrcKudzu yIDI DXS Kan (SEQ ID NO:20).

FIGS. 25A, 25B, 25C and 25D are the nucleotide sequences of pTrcKKDyIkIS kan (SEQ ID NO:33).

FIGS. 27A, 27B, 27C and 27D are the nucleotide sequences of pCL PtrcUpperPathway (SEQ ID NO:46).

FIGS. 29A, 29B, 29C and 29D are the nucleotide sequences of cassette containing the lower MVA pathway and yeast idi for integration into the *B. subtilis* chromosome at the nprE locus (SEQ ID NO:47).

FIGS. 31A and 31B are the nucleotide sequences of p9796-poplar (SEQ ID NO:48).

FIGS. 33A, 33B and 33C are the nucleotide sequences of pTrcPoplar (SEQ ID NO:49).

FIGS. 35A, 35B and 35C are nucleotide sequences of pTrcKudzu yIDI Kan (SEQ ID NO:50).

FIGS. 37A, 37B and 37C are the nucleotide sequences of pTrcKudzuDXS Kan (SEQ ID NO:51).

FIGS. 39A, 39B and 39C are the nucleotide sequence of pCL PtrcKudzu (SEQ ID NO:52).

FIGS. 41A, 41B and 41C are the nucleotide sequences of pCL PtrcKudzu A3 (SEQ ID NO:53).

FIGS. 43A, 43B and 43C are the nucleotide sequences of pCL PtrcKudzu yIDI (SEQ ID NO:54).

FIGS. 45A, 45B, 45C and 45D are the nucleotide sequences of pCL PtrcKudzu DXS (SEQ ID NO:55).

FIG. 46A shows isoprene production from corn stover, FIG. 46B shows isoprene production from bagasse, FIG. 46C shows isoprene production from softwood pulp, FIG. 46D shows isoprene production from glucose, and FIG. 46E shows isoprene production from cells with no additional feedstock. Grey squares represent $OD_{600}$ measurements of the cultures at the indicated times post-inoculation and black triangles represent isoprene production at the indicated times post-inoculation.

FIG. 48A shows the time course of optical density within fermentors fed with varying amounts of yeast extract. FIG. 48B shows the time course of isoprene titer within fermentors fed with varying amounts of yeast extract. The titer is defined as the amount of isoprene produced per liter of fermentation broth. FIG. 48C shows the effect of yeast extract on isoprene production in *E. coli* grown in fed-batch culture.

FIG. 49A shows the time course of optical density within the 500-L bioreactor fed with glucose and yeast extract. FIG. 49B shows the time course of isoprene titer within the 500-L bioreactor fed with glucose and yeast extract. The titer is defined as the amount of isoprene produced per liter of fermentation broth. FIG. 49C shows the time course of total isoprene produced from the 500-L bioreactor fed with glucose and yeast extract.

FIGS. 51A, 51B and 51C are the nucleotide sequences of pJMupperpathway2 (SEQ ID NO:56).

FIGS. 55A and 55B are the nucleotide sequences of plasmid pET24 *P. alba* HGS (SEQ ID NO:87).

FIGS. 58A and 58B are the nucleotide sequences of plasmid EWL230 (SEQ ID NO:88).

FIGS. 61A and 61B are the nucleotide sequences of plasmid EWL244 (SEQ ID NO:89).

FIGS. 63A, 63B and 63C are the nucleotide sequences of plasmid MCM484 (SEQ ID NO:90).

FIGS. 64A, 64B and 64C are the nucleotide sequences of plasmid MCM485 (SEQ ID NO:91).

FIGS. 65A, 65B and 65C are the nucleotide sequences of plasmid MCM486 (SEQ ID NO:92).

FIGS. 66A, 66B and 66C are the nucleotide sequences of plasmid MCM487 (SEQ ID NO:93).

FIG. 67A shows the time course of optical density within the 15-L bioreactor fed with glucose. FIG. 67B shows the time course of isoprene titer within the 15-L bioreactor fed with glucose. The titer is defined as the amount of isoprene produced per liter of fermentation broth. FIG. 67C shows the time course of total isoprene produced from the 15-L bioreactor fed with glucose. FIG. 67D shows the total carbon dioxide evolution rate (TCER), or metabolic activity profile, within the 15-L bioreactor fed with glucose.

FIG. 68A shows the time course of optical density within the 15-L bioreactor fed with glucose. FIG. 68B shows the time course of isoprene titer within the 15-L bioreactor fed with glucose. The titer is defined as the amount of isoprene produced per liter of fermentation broth. FIG. 68C shows the time course of total isoprene produced from the 15-L bioreactor fed with glucose. FIG. 68D shows the volumetric productivity within the 15-L bioreactor fed with glucose. An average value of 1.1 g/L/hr was maintained for a 40-hour period (23-63 hours) with yeast extract feeding. FIG. 68E shows the carbon dioxide evolution rate (CER), or metabolic activity profile, within the 15-L bioreactor fed with glucose.

FIG. 69A shows growth of *E. coli* EWL256, which contains both the MVA pathway and isoprene synthase, on either glucose, biomass hydrolysate, glycerol, or acetate as the only carbon source. The different carbon sources were added to a concentration of 1% in the media. A negative control with no added carbon source was included. Growth was measured as optical density at 600 nM. FIG. 69B shows specific productivity of isoprene from *E. coli* EWL256 containing both the MVA pathway and isoprene synthase when grown on either glucose, biomass hydrolysate, glycerol, or acetate as only carbon source. The different carbon sources were added to a concentration of 1% in the media. A negative control with no added carbon source was included. Samples were taken 190 minutes, 255 minutes and 317 minutes after inoculation and isoprene produced by the bacteria was measured using GC-MS. FIG. 69C shows growth of *E. coli* EWL256 on either glucose or xylose as the only carbon source. The different carbon sources were added to a concentration of 1% in the media. A negative control with no added carbon source was included. Growth was measured as optical density at 600 nM. FIG. 69D shows specific productivity of isoprene from *E. coli* EWL256 when grown on either glucose or xylose as only carbon source. The carbon sources were added to a concentration of 1% in the media. A negative control with no added carbon source was included. Samples were taken 260 minutes, 322 minutes and 383 minutes after inoculation and isoprene produced by the bacteria was measured using GC-MS.

FIGS. 73B(1) and 73B(2) are the nucleotide sequences of the *M. mazei* archaeal lower Pathway operon (SEQ ID NO:113).

FIGS. 74B(1), 74B(2) and 74C are the nucleotide sequences of MCM376-MVK from *M. mazei* archaeal Lowerin pET200D (SEQ ID NO:114).

FIGS. 77A and 77B are the nucleotide sequences of plasmid pBBRCMPGI1.5-pgl (SEQ ID NO:122).

FIG. 78A shows the time course of optical density within the 15-L bioreactor fed with glucose. FIG. 78B shows the time course of isoprene titer within the 15-L bioreactor fed with glucose. The titer is defined as the amount of isoprene produced per liter of fermentation broth. Method for calculating isoprene: cumulative isoprene produced in 59 hrs, g/Fermentor volume at 59 hrs, L [=] g/L broth. FIG. 78C also shows the time course of isoprene titer within the 15-L bioreactor fed with glucose. Method for calculating isoprene: ∫(Instantaneous isoprene production rate, g/L/hr)dt from t=0 to 59 hours [=] g/L broth. FIG. 78D shows the time course of total isoprene produced from the 15-L bioreactor fed with glucose. FIG. 78E shows volumetric productivity within the 15-L bioreactor fed with glucose. FIG. 78F shows carbon dioxide evolution rate (CER), or metabolic activity profile, within the 15-L bioreactor fed with glucose.

FIGS. 79B(1), 79B(2) and 79C are the nucleotide sequences of pJ201:19813 (SEQ ID NO:123).

DETAILED DESCRIPTION OF THE INVENTION

Figure 2:
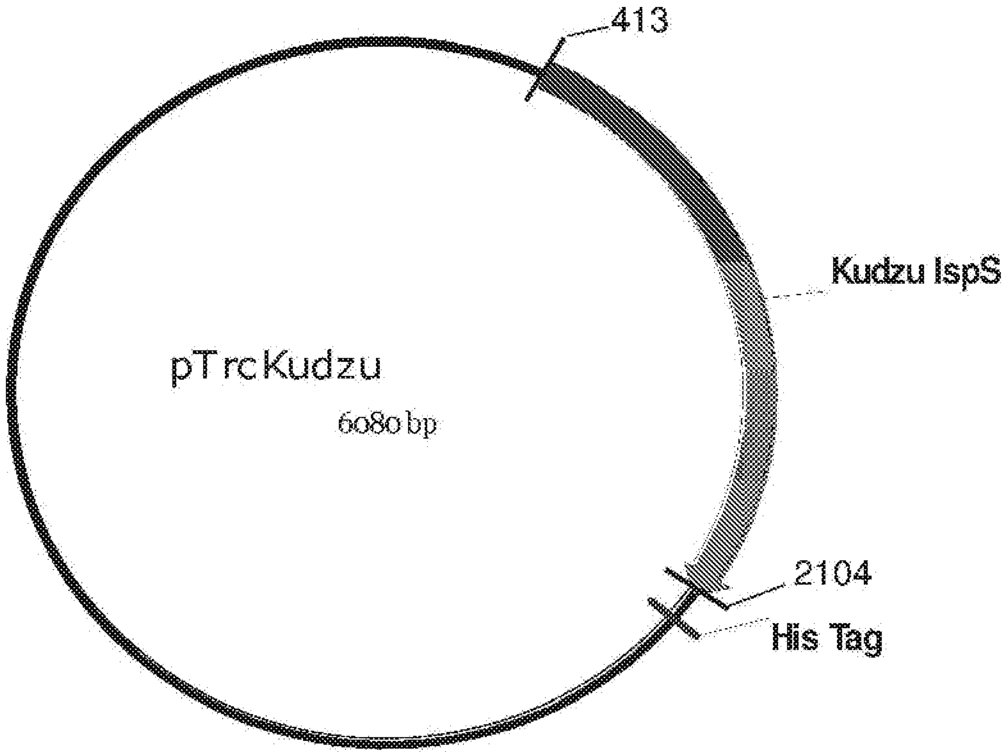
FIG. 2 is a map of pTrcKudzu.

The invention features compositions and methods for the production of increased amounts of isoprene. In particular, these compositions and methods increase the rate of isoprene production and increase the total amount of isoprene that is produced. For example, cell culture systems that generate $4.8\times10^4$ nmole/$g_{wcm}$/hr of isoprene have been produced (Table 1). The efficiency of these systems is demonstrated by the conversion of ~23.6 molar % yield (10.7 weight % yield) of the carbon that the cells consume from a cell culture medium into isoprene (% carbon yield). As shown in the Examples and Table 2, approximately 60.5 g of isoprene per liter of broth was generated. Isoprene was produced at a peak specific rate of $1.88\times10^5$ nmol/OD/hr ($1.88\times10^5$ nmole/$g_{wcm}$/hr). If desired, even greater amounts of isoprene can be obtained using other conditions, such as those described herein. In some embodiments, a renewable carbon source is used for the production of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) or *Populus alba* (Poplar) isoprene synthase polypeptide was expressed in a variety of host cells, such as *Escherichia coli, Panteoa citrea, Bacillus subtilis, Yarrowia lipolytica*, and *Trichoderma reesei*. As also shown in the Examples, a heterologous *Methanosarcina mazei* (*M. mazei*) mevalonate kinase (MVK) was expressed in host cells such as *Escherichia coli* to increase isoprene production. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 60.5 g of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

Table 1: Exemplary yields of isoprene from a shake flask using the cell cultures and methods of the invention. The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

| Strain | Isoprene Production in a Headspace vial* Headspace concentration $\mu g/L_{gas}$ | Specific Rate $\mu g/L_{broth}/hr/OD$ ($nmol/g_{wcm}/hr$) |
|---|---|---|
| *E. coli* BL21/pTrcKudzu IS | 1.40 | 53.2 (781.2) |
| *E. coli* BL21/Pcl DXS yidi Kudzu IS | 7.61 | 289.1 ($4.25 \times 10^3$) |
| *E. coli* BL21/MCM127 with kudzu IS and entire MVA pathway | 23.0 | 874.1 ($1.28 \times 10^4$) |
| *E. coli* BL21/Pet N-HisKudzu IS | 1.49 | 56.6 (831.1) |
| *Pantoea citrea*/pTrcKudzu IS | 0.66 | 25.1 (368.6) |
| *E. coli* w/Poplar IS [Miller (2001)] | — | 5.6 (82.2) |
| *Bacillis licheniformis* Fall U.S. Pat. No. 5,849,970 | — | 4.2 (61.4) |
| *Yarrowia lipolytica* with kudzu isoprene synthase | ~0.05 μg/L | ~2 (~30) |
| *Trichoderma reesei* with kudzu isoprene synthase | ~0.05 μg/L | ~2 (~30) |
| *E. coli* BL21/ pTrcKKD$_y$I$_k$IS with kudzu IS and lower MVA pathway | 85.9 | $3.2 \times 10^3$ ($4.8 \times 10^4$) |

*Normalized to 1 mL of 1 $OD_{600}$, cultured for 1 hour in a sealed headspace vial with a liquid to headspace volume ratio of 1:19.

Table 2: Exemplary yields of isoprene in a fermentor using the cell cultures and methods of the invention. The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| Strain | Isoprene Production in Fermentors Peak Headspace concentration** ($ug/L_{gas}$) | Titer ($mg/L_{broth}$) | Peak Specific rate $\mu g/L_{broth}/hr/OD$ ($nmol/g_{wcm}/hr$) |
|---|---|---|---|
| *E. coli* BL21/ pTrcKudzu with Kudzu IS | 52 | 41.2 | 37 (543.3) |
| *E. coli* FM5/pTrcKudzu IS | 3 | 3.5 | 21.4 (308.1) |
| *E. coli* BL21/triple strain (DXS, yidi, IS) | 285 | 300 | 240 ($3.52 \times 10^3$) |
| *E. coli* FM5/triple strain (DXS, yidi, IS) | 50.8 | 29 | 180.8 ($2.65 \times 10^3$) |
| *E. coli*/MCM127 with Kudzu IS and entire MVA pathway | 1094 | 250 | 875 ($1.28 \times 10^4$) |
| *Bacillus subtilis* wild-type | 1.5 | 2.5 | 0.8 (11.7) |
| *Bacillus* pBS Kudzu IS | 16.6 | ~30 (over 100 hours) | 5 (73.4) |
| *Bacillus* Marburg 6051 [Wagner and Fall (1999)] | 2.04 | 0.61 | 24.5 (359.8) |
| *Bacillus* Marburg 6051 Fall U.S. Pat. No. 5,849,970 | 0.7 | 0.15 | 6.8 (100) |
| *E. coli* BL21/pCLPtrcUpper Pathway and gil.2KKDyI and pTrcAlba-mMVK | $2.03 \times 10^4$ | $3.22 \times 10^4$ | $5.9 \times 10^3$ ($8.66 \times 10^4$) |
| *E. coli* BL21/pCLPtrcUpper Pathway and gi1.2KKDyI and pTrcAlba-mMVK plus pBBRCMPGI1.5pgl | $3.22 \times 10^4$ | $6.05 \times 10^4$ | $1.28 \times 10^4$ ($1.88 \times 10^5$) |

**Normalized to an off-gas flow rate of 1 vvm (1 volume off-gas per 1 $L_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 19A:
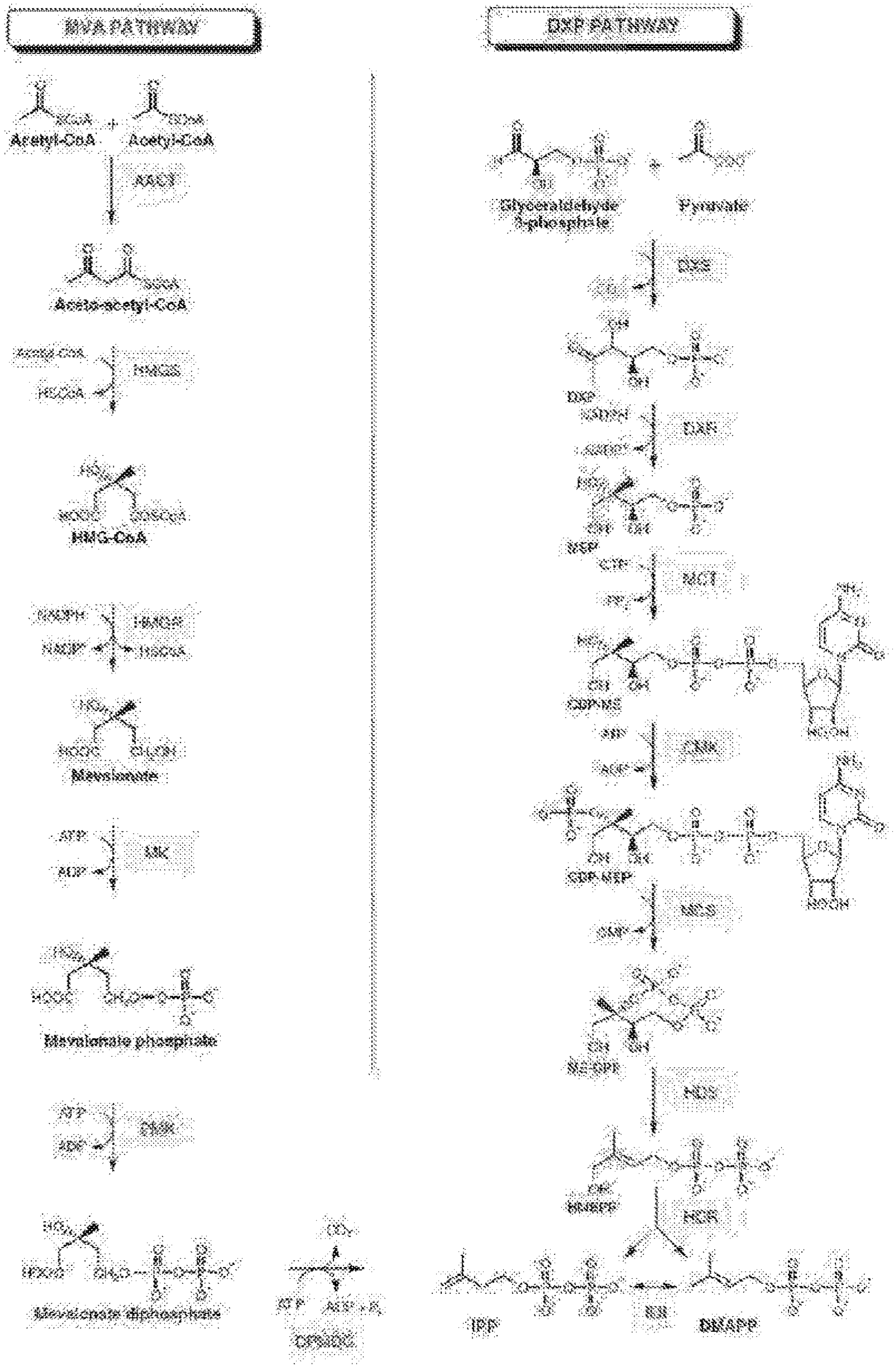
FIG. 19A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: *J. Bacteriol.,* 184: 2116-2122, 2002; HMGS; Hydroxymethylglutaryl-CoA synthase, MvaS, EC 2.3.3.10. Assay: *J. Bacteriol.,* 184: 4065-4070, 2002; HMGR; 3-Hydroxy-3-methylglutaryl-CoA reductase, MvaE, EC 1.1.1.34. Assay: *J. Bacteriol.,* 184: 2116-2122, 2002; MVK; Mevalonate kinase, ERG12, EC 2.7.1.36. Assay: *Curr Genet* 19:9-14, 1991. PMK; Phosphomevalonate kinase, ERGS, EC 2.7.4.2, Assay: *Mol Cell Biol.,* 11:620-631, 1991; DPMDC; Diphosphomevalonate decarboxylase, MVD1, EC 4.1.1.33. Assay: *Biochemistry,* 33:13355-13362, 1994; IDI; Isopentenyl-diphosphate delta-isomerase, IDI1, EC 5.3.3.2. Assay: *J. Biol. Chem.* 264: 19169-19175, 1989. DXP Pathway: DXS; 1-Deoxyxylulose-5-phosphate synthase, dxs, EC 2.2.1.7. Assay: *PNAS,* 94:12857-62, 1997; DXR; 1-Deoxy-D-xylulose 5-phosphate reductoisomerase, dxr, EC 2.2.1.7. Assay: *Eur. J. Biochem.* 269:4446-4457, 2002; MCT; 4-Diphosphocytidyl-2C-methyl-D-erythritol synthase, IspD, EC 2.7.7.60. Assay: *PNAS,* 97: 6451-6456, 2000; CMK; 4-Diphosphocytidyl-2-C-methyl-D-erythritol kinase, IspE, EC 2.7.1.148. Assay: *PNAS,* 97:1062-1067, 2000; MCS; 2C-Methyl-D-erythritol 2,4-cyclodiphosphate synthase, IspF, EC 4.6.1.12. Assay: *PNAS,* 96:11758-11763, 1999; HDS; 1-Hydroxy-2-methyl-2-(E)-butenyl 4-diphosphate synthase, ispG, EC 1.17.4.3. Assay: *J. Org. Chem.,* 70:9168-9174, 2005; HDR; 1-Hydroxy-2-methyl-2-(E)-butenyl 4-diphosphate reductase, IspH, EC 1.17.1.2. Assay: *JACS,* 126:12847-12855, 2004.

The encoded DXS and IDI polypeptides are part of the DXP pathway for the biosynthesis of isoprene (FIG. 19A). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

For example, fermentation of *E. coli* cells with a kudzu isoprene synthase, *S. cerevisia* IDI, and *E. coli* DXS nucleic acids was used to produce isoprene. The levels of isoprene varied from 50 to 300 μg/L over a time period of 15 hours (Example 7, part VII). As another example, fermentation of *E. coli* with *M. mazei* mevalonate kinase (MVK), *P. alba* isoprene synthase, the upper MVA pathway, and the integrated lower MVA pathway was used to produce isoprene. The levels of isoprene varied from 32 to 35.6 g/L over a time period of 67 hours (Example 10, part III).

In yet another example, fermentation of *E. coli* with *M. mazei* mevalonate kinase (MVK), *P. alba* isoprene synthase, pgl over-expression (RHM111608-2), the upper MVA pathway, and the integrated lower MVA pathway were used to produce isoprene. The levels of isoprene vary from 33.2 g/L to 40.0 g/L over a time period of 40 hours or 48.6 g/L to 60.5 g/L over a time period of 59 hours (Example 13, part (ii)).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by *E. coli* cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

Figure 19B:
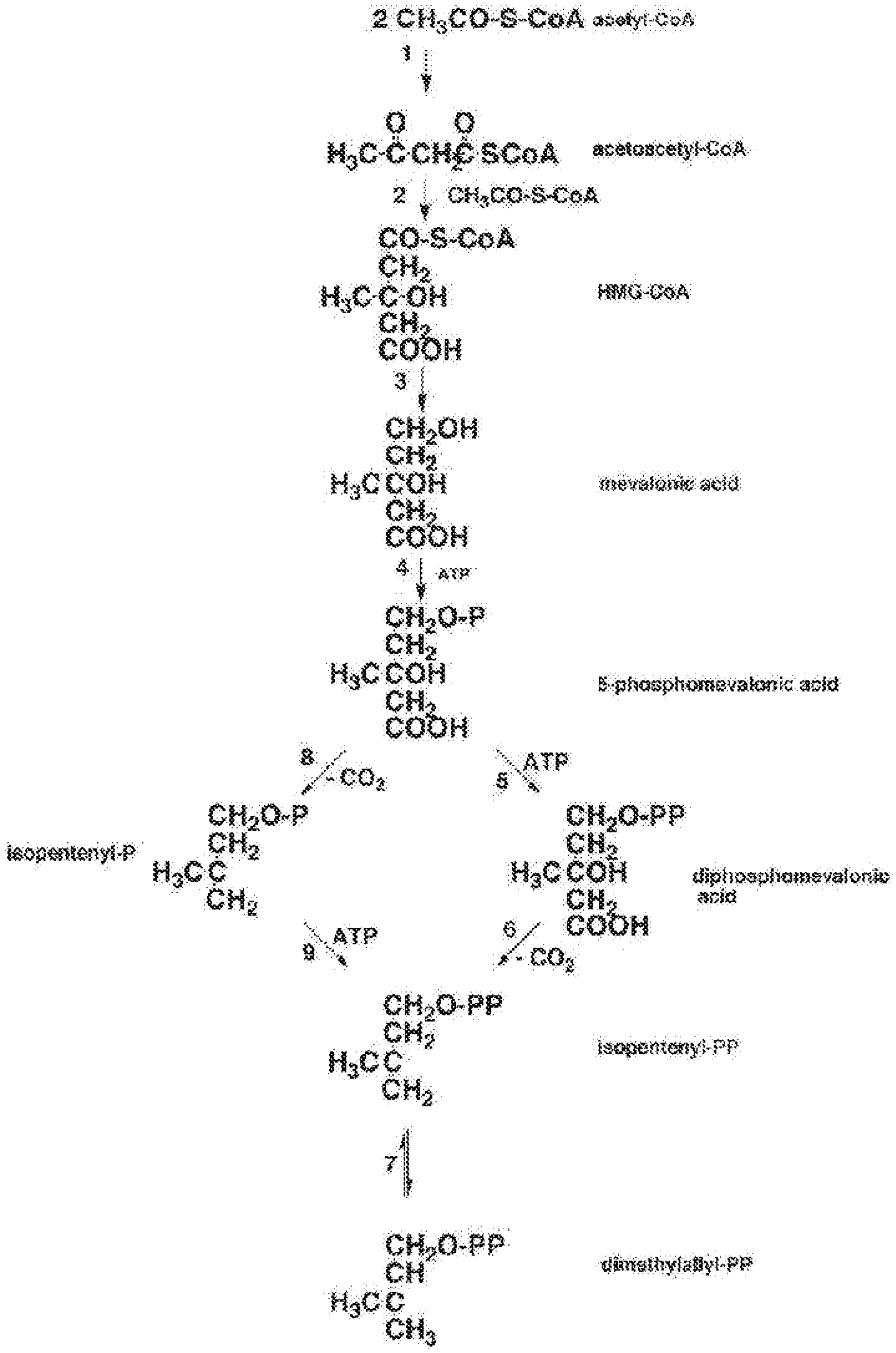
FIG. 19B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews,* 71:97-120, 2007, which is incorporated by reference in its entirety, particularly with respect to nucleic acids and polypeptides of the modified MVA pathway. The modified MVA pathway is present, for example, in some archaeal organisms, such as *Methanosarcina mazei.*

In some embodiments, the production of isoprene by cells that contain a heterologous isoprene synthase nucleic acid is augmented by increasing the amount of a MVA polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. In some embodiments, the cells contain an entire MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, *E. coli* cells containing a nucleic acid encoding a kudzu isoprene synthase polypeptide and nucleic acids encoding *Saccharomyces cerevisia* MVK, PMK, MVD, and IDI polypeptides generated isoprene at a rate of $6.67\times10^4$ nmol/$L_{broth}$/$OD_{600}$/hr (see Example 8). Additionally, a 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in *E. coli*. *E. coli* cells that contain nucleic acids for both the upper MVA pathway and the lower MVA pathway as well as a kudzu isoprene synthase (strain MCM 127) produced significantly more isoprene (874 ⊠ g/$L_{broth}$/hr/OD) compared to *E. coli* cells with nucleic acids for only the lower MVA pathway and the kudzu isoprene synthase (strain MCM 131) (see Table 3 and Example 8, part VIII).

As another example, *E. coli* cells containing a nucleic acid encoding a *P. alba* isoprene synthase polypeptide and a nucleic acid encoding *M. mazei* MVK polypeptide generated 320.6 g (at a peak specific rate of $9.54\times10^4$ nmol/$L_{broth}$/$OD_{600}$/hr (i.e. $9.5\times10^{-5}$ mol/$L_{broth}$/$OD_{600}$/hr)) of isoprene during a 67 hour fermentation in the absence of yeast extract feeding or 395.5 g (at a peak specific rate of $8.66\times10^4$ nmol/$L_{broth}$/$OD_{600}$/hr) during a 68 hour fermentation in the presence of yeast extract feeding (see Example 10).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Figure 48A:
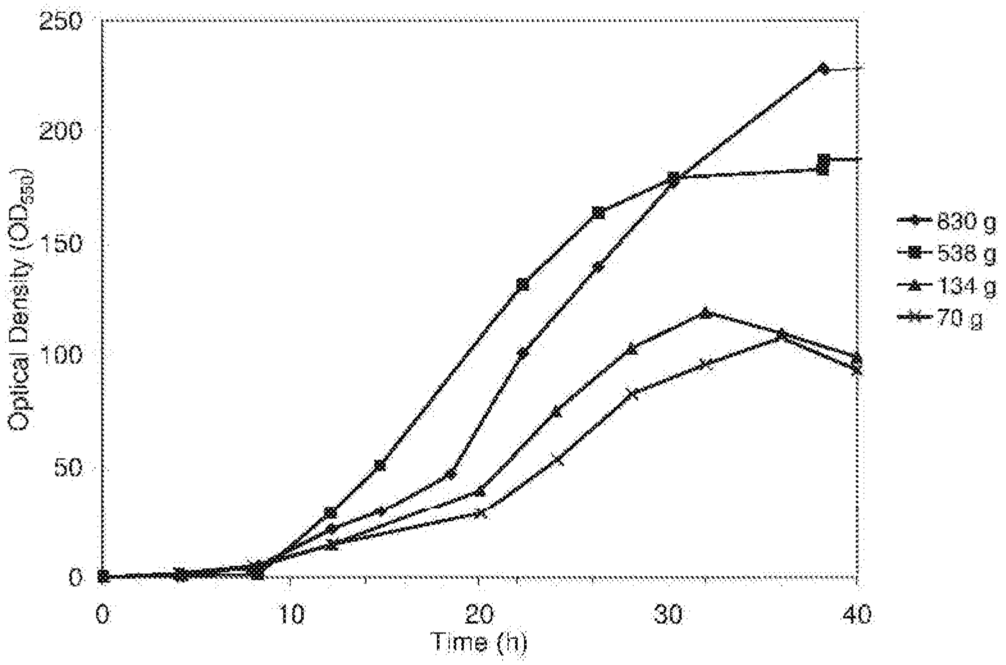
FIGS. 48A, 48B, and 48C show graphs demonstrating the effect of yeast extract of isoprene production.
Figure 48B:
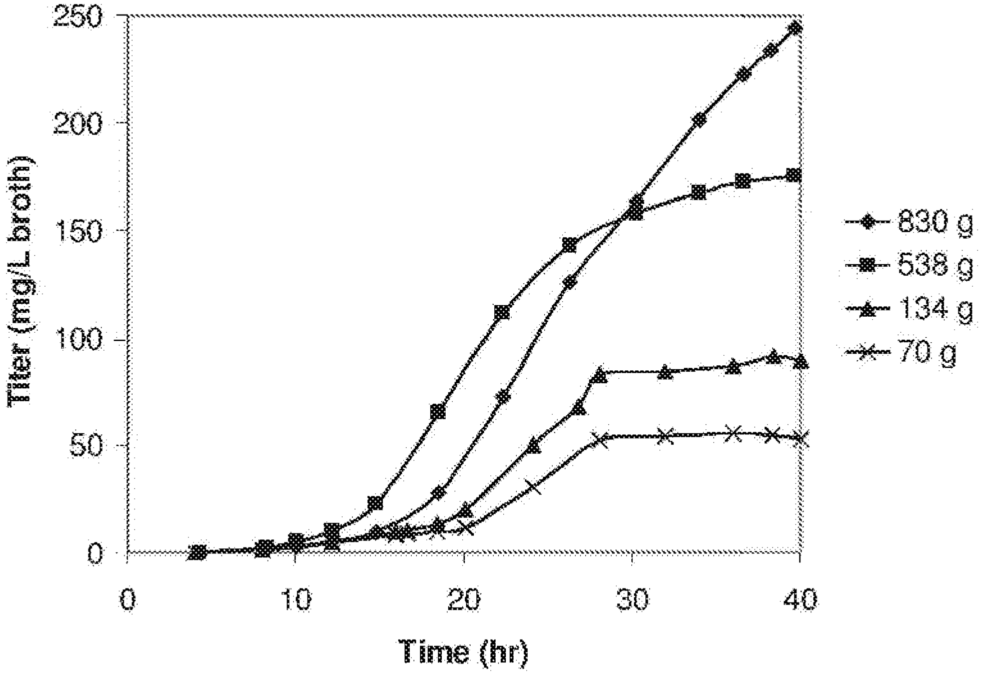
Figure 48C:
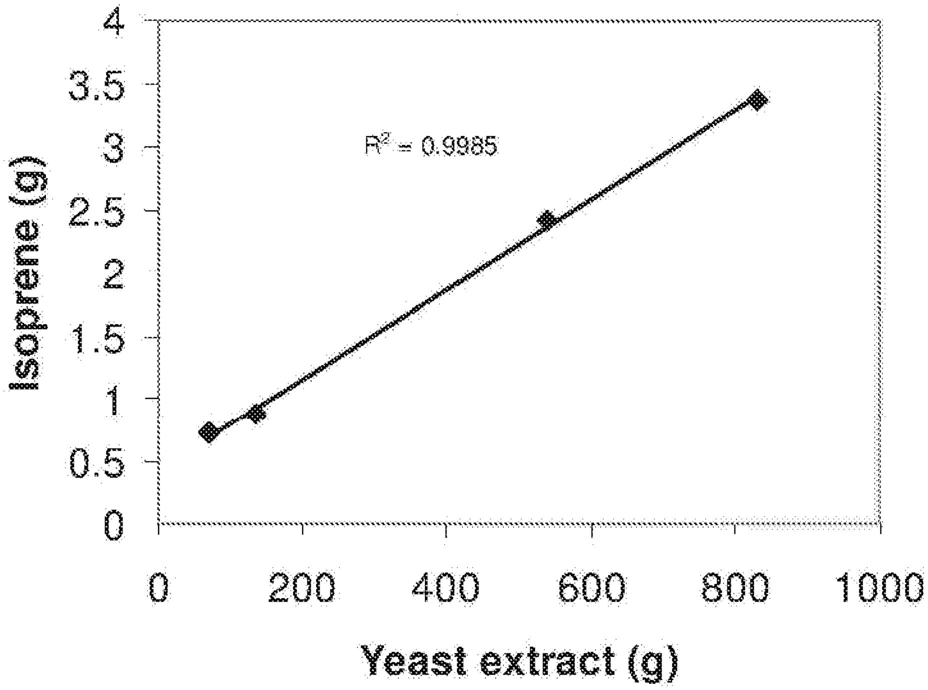

As indicated in Example 7, part VI, the amount of isoprene produced can be further increased by adding yeast extract to the cell culture medium using *E. coli* cells with kudzu isoprene synthase, *S. cerevisia* IDI, and *E. coli* DXS nucleic acids to produce isoprene. In particular, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Figure 69A:
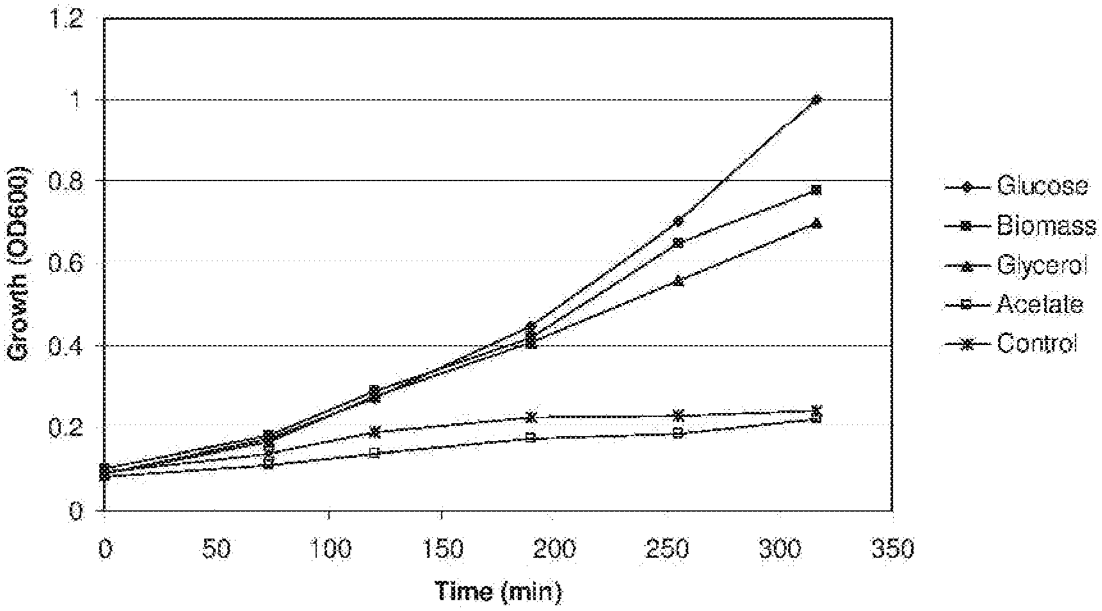
FIGS. 69A, 69B, 69C and 69D show production of isoprene from different carbon sources via the MVA (pathway).
Figure 69B:
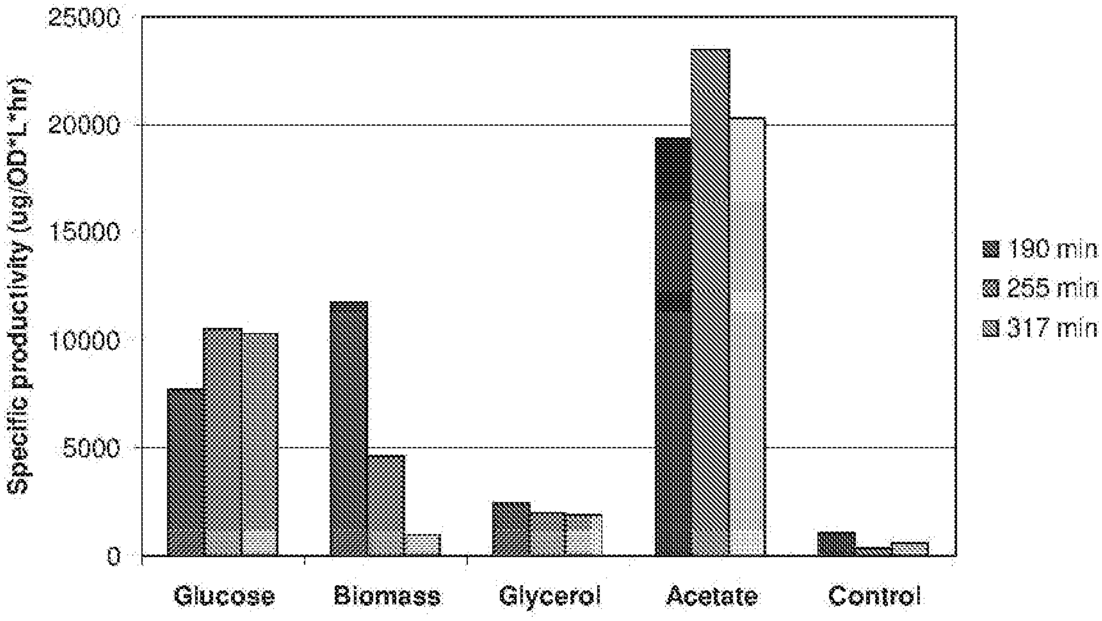
Figure 69C:
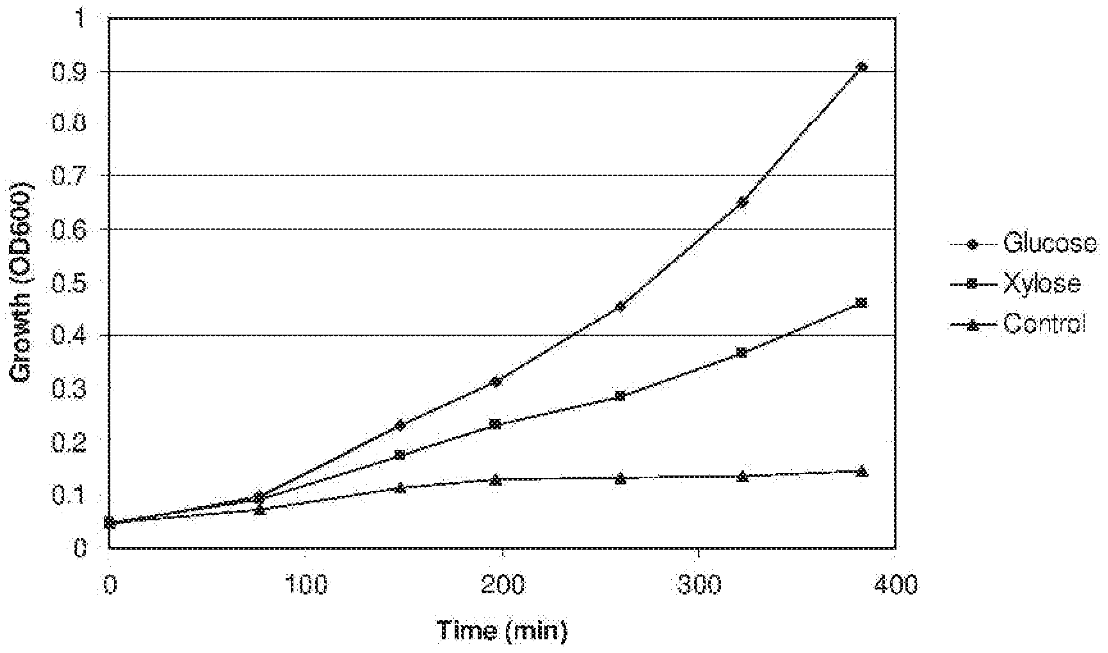

Isoprene production was also demonstrated using three types of hydrolyzed biomass (bagasse, corn stover, and soft wood pulp) as the carbon source (FIGS. 46A-46C and 69A-69B). *E. coli* cells with kudzu isoprene synthase, *S. cerevisia* IDI, and *E. coli* DXS nucleic acids produced as much isoprene from these hydrolyzed biomass carbon sources as from the equivalent amount of glucose (e.g., 1% glucose, w/v). *E. coli* cells expressing *P. alba* isoprene synthase and the MVA pathway produced isoprene at a higher initial growth rate from ammonia fiber expansion (AFEX) pretreated corn stover than from the equivalent amount of glucose. (FIGS. 69A and 69B). If desired, any other biomass carbon source can be used in the compositions and methods of the invention. Biomass carbon sources are desirable because they are cheaper than many conventional cell mediums, thereby facilitating the economical production of isoprene.

Figure 47A:
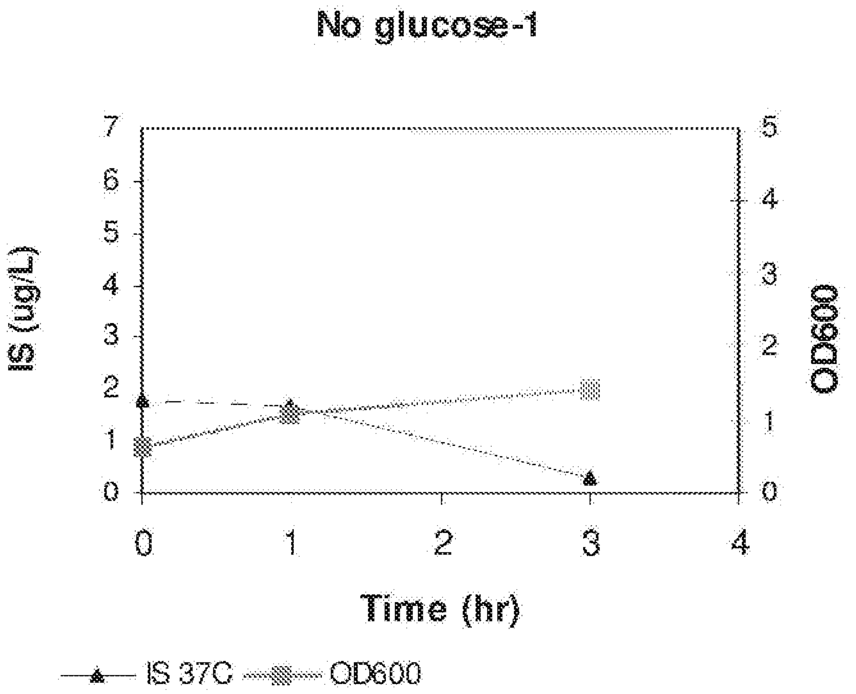
FIG. 47A shows a graph representing isoprene production by BL21 (λDE3) pTrcKudzu yIDI DXS (kan) in a culture with no glucose added. Squares represent $OD_{600}$, and triangles represent isoprene produced (μg/ml).
Figure 47B:
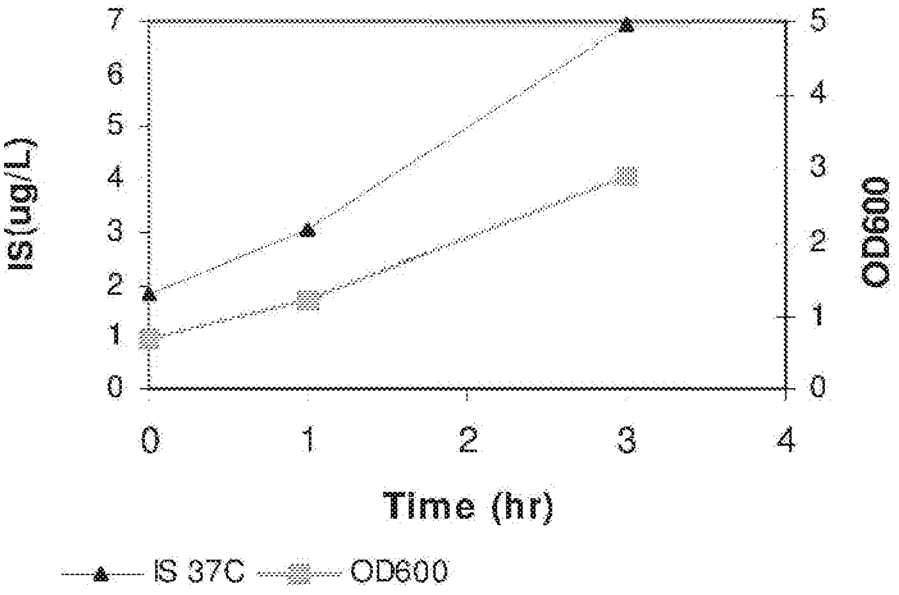
FIG. 47B shows a graph representing isoprene production from 1% glucose feedstock invert sugar by BL21 (λDE3) pTrcKudzu yIDI DXS (kan). Squares represent $OD_{600}$, and triangles represent isoprene produced (μg/ml).
Figure 47C:
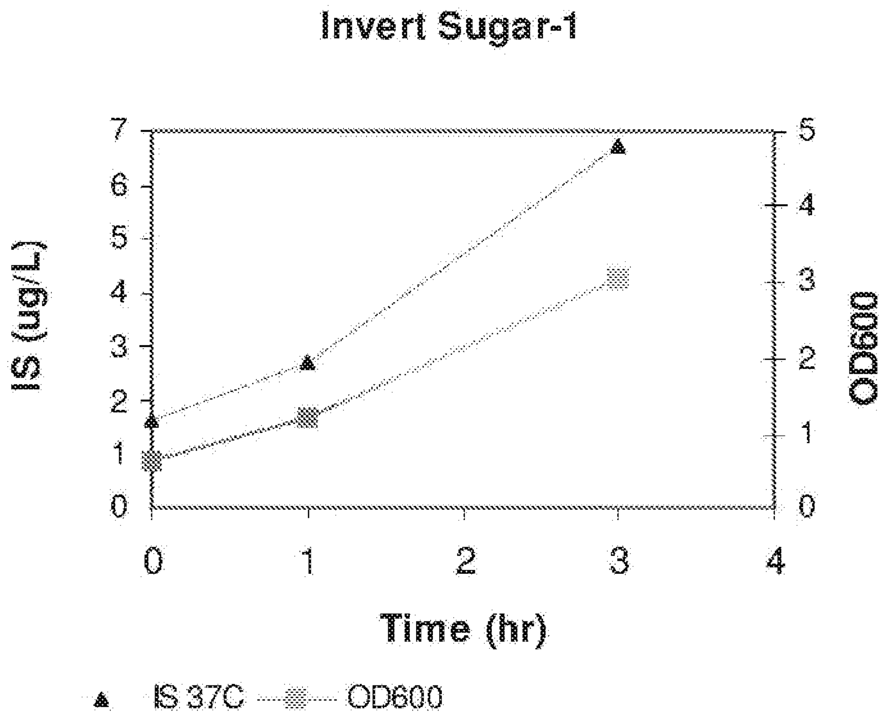
FIG. 47C shows a graph representing isoprene production from 1% invert sugar feedstock by BL21 (λDE3) pTrcKudzu yIDI DXS (kan). Squares represent $OD_{600}$, and triangles represent isoprene produced (μg/ml).
Figure 47D:
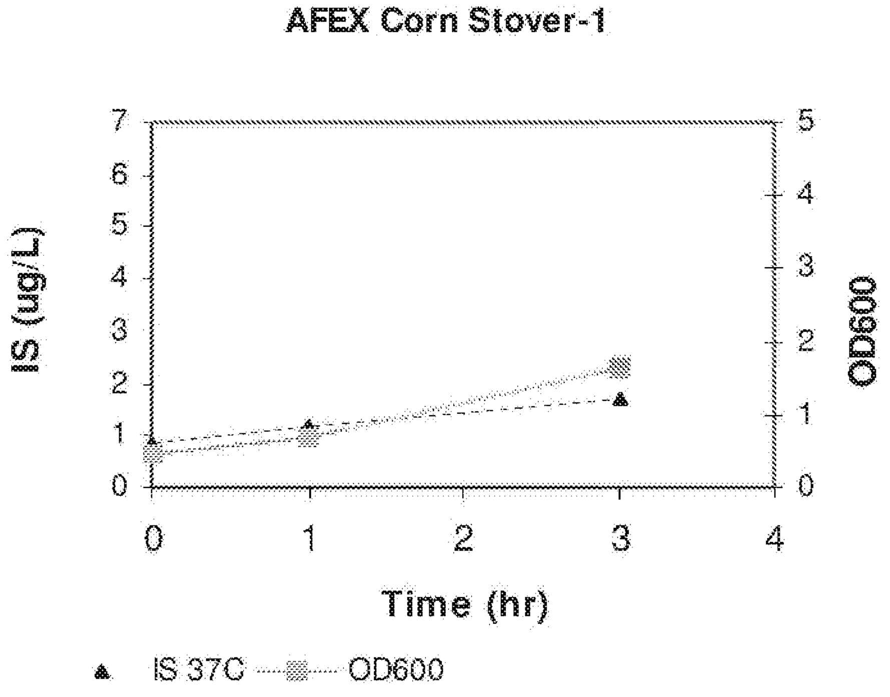
FIG. 47D shows a graph representing isoprene production from 1% AFEX corn stover feedstock by BL21 (λDE3) pTrcKudzu yIDI DXS (kan). Squares represent $OD_{600}$, and triangles represent isoprene produced (μg/ml).

Additionally, invert sugar was shown to function as a carbon source for the generation of isoprene (FIG. 47D).

Additionally, xylose, acetate, and glycerol were also shown to function as a carbon source for the generation of isoprene (FIGS. 69A-69D). For example, *E. coli* cells with *P. alba* isoprene synthase and the MVA pathway grown on acetate as the only carbon source had a specific productivity of isoprene about twice as high as during growth on glucose (Example 10, Part IV; FIGS. 69A and 69B).

In some embodiments, an oil is included in the cell medium. For example, *B. subtilis* cells containing a kudzu isoprene synthase nucleic acid produced isoprene when cultured in a cell medium containing an oil and a source of glucose (Example 4, part III). As another example, *E. coli* fadR atoC mutant cells containing the upper and lower MVA pathway plus kudzu isoprene synthase produced isoprene when cultured in a cell medium containing palm oil and a source of glucose (Example 12, part II). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides that include part or all of a first polypeptide (e.g., an isoprene synthase, DXS, IDI, or MVA pathway polypeptide) and part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments, the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the world-wide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Dec. 11, 2008, such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mLs of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., *J. Biol. Chem.* 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µl of 1M $MgCl_2$, 1 mM (250 ⊠g/ml) DMAPP, 65 ⊠l of Plant Extract Buffer (PEB) (50 mM Tris-HCl, pH 8.0, 20 mM $MgCl_2$, 5% glycerol, and 2 mM DTT) is added to 25 ⊠l of cell extract in a 20 ml Headspace vial with a metal screw cap and teflon coated silicon septum (Agilent Technologies) and cultured at 37° C. for 15 minutes with shaking. The reaction is quenched by adding 200 ⊠l of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa, Populus alba* x *tremula* (CAC35696), or *Populus alba*) (Sasaki et al., FEBS Letters 579(11): 2514-2518, 2005; Miller et al., *Planta* 213: 483-487, 2001), aspen (such as *Populus tremuloides*) (Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptide phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, $2^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (world-wide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., *EMBO J.* 4:475-479, 1985 and Penttila et al., *Gene* 61:155-164, 1987 (which are each hereby incorporated by reference in their entireties, particularly with respect to selective markers). In some embodiments, an isoprene synthase, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, 2$^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and lac, trp, ⊠ $P_L$, ⊠ $P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132,527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia, Panteoa, Bacillus, Yarrowia, Streptomyces*, or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, 2$^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable nonlimiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei* cellobiohydrolase 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh 1 derived from a *Trichoderma* strain (such as *T. reesei*).

Other useful fungal terminators include the terminator from an *A. niger* or *A. awamori* glucoamylase nucleic acid (Nunberg et al., *Mol. Cell Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh 1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIG. 19). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens, H. lanuginose*, or *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, or *A. awamori*) (Ward et al., Appl. Microbiol. Biotechnol. 39: 7380743, 1993 and Goedegebuur et al., Genet 41: 89-98, 2002), *Fusarium* sp., (e.g., *F. roseum, F. graminum F. cerealis, F. oxysporuim*, or *F. venenatum*), *Neurospora* sp., (e.g., *N.*

*crassa*), *Hypocrea* sp., *Mucor* sp., (e.g., *M. miehei*), *Rhizopus* sp. and *Emericella* sp. (see also, Innis et al., Sci. 228: 21-26, 1985). The term "*Trichoderma*" or "*Trichoderma* sp." or "*Trichoderma* spp." refer to any fungal genus previously or currently classified as *Trichoderma.*

In some embodiments, the fungus is *A. nidulans, A. awamori, A. oryzae, A. aculeatus, A. niger, A. japonicus, T. reesei, T. viride, F. oxysporum*, or *F. solani. Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei.*

In some embodiments, the source organism is a yeast, such as *Saccharomyces* sp., *Schizosaccharomyces* sp., *Pichia* sp., or *Candida* sp.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. albus, S. lividans*, or *S. rubiginosus*, or strains of *Escherichia* such as *E. coli.*

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus.*

In some embodiments, the source organism is a gram-positive bacterium. Non-limiting examples include strains of *Streptomyces* (e.g., *S. albus, S. lividans, S. coelicolor*, or *S. griseus*) and *Bacillus*. In some embodiments, the source organism is a gram-negative bacterium, such as *E. coli* or *Pseudomonas* sp.

In some embodiments, the source organism is a plant, such as a plant from the family Fabaceae, such as the Faboideae subfamily. In some embodiments, the source organism is kudzu, poplar (such as *Populus alba* x *tremula* CAC35696 or *Populus alba*) (Sasaki et al., *FEBS Letters* 579(11): 2514-2518, 2005), aspen (such as *Populus tremuloides*), or *Quercus robur.*

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: *Chroococcales, Pleurocapsales, Oscillatoriales, Nostocales*, or *Stigonematales.*

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. Nos. 6,022,725; 6,268,328; 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes*," in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (Sci. 9:991-1001, 2000; EP 238023; and Yelton et al., *Proceedings. Natl. Acad. Sci.* USA 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2\times10^6$/mL) are used in the transformation. A volume of 100 μL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), acetate, animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose. In some embodiment, the carbohydrate is xylose or glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include acetate, glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. Nos. 6,176,176; 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.,* 53(2) 541-543, 1989, which is hereby incorporated by reference in its entirety, particularly with respect to carbon sources) and in bacteria (Hunter et. al., *Biochemistry,* 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, Bacterial Metabolism, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.*, [Int. Symp.], $7^{th}$ ed., 415-32. Editors: Murrell et al., Publisher: Intercept, Andover, U K, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell media). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: A Textbook of Industrial Microbiology, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: A Textbook of Industrial Microbiology, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid(s) operably linked to the promoter.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The peak specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "peak volumetric productivity" is meant the maximum amount of isoprene produced per volume of broth (including the volume of the cells and the cell medium) during the culturing of cells for a particular period of time (e.g., the culturing of cells during a particular fermentation run). By "peak specific volumetric productivity time point" is meant the time point during the culturing of cells for a particular period of time (e.g., the culturing of cells during a particular fermentation run) when the amount of isoprene produced per volume of broth is at a maximum. The peak specific volumetric productivity is determined by dividing the total productivity by the volume of broth and amount of time. In some embodiments, the isoprene amount is measured at the peak specific volumetric productivity time point. In some embodiments, the peak specific volumetric productivity for the cells is about any of the isoprene amounts per volume per time disclosed herein.

By "peak concentration" is meant the maximum amount of isoprene produced during the culturing of cells for a particular period of time (e.g., the culturing of cells during a particular fermentation run). By "peak concentration time point" is meant the time point during the culturing of cells for a particular period of time (e.g., the culturing of cells during a particular fermentation run) when the amount of isoprene produced per cell is at a maximum. In some embodiments, the isoprene amount is measured at the peak concentration time point. In some embodiments, the peak concentration for the cells is about any of the isoprene amounts disclosed herein.

By "average volumetric productivity" is meant the average amount of isoprene produced per volume of broth (including the volume of the cells and the cell medium) during the culturing of cells for a particular period of time (e.g., the culturing of cells during a particular fermentation run). The average volumetric productivity is determined by dividing the total productivity by the volume of broth and amount of time. In some embodiments, the average specific volumetric productivity for the cells is about any of the isoprene amounts per volume per time disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole of isoprene/gram of cells for the wet weight of the cells/hour (nmole/$g_{wcm}$/hr). In some embodiments, the amount of isoprene is between about 2 to about 200,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, about 2,000 to about 5,000 nmole/$g_{wcm}$/hr, about 5,000 to about 10,000 nmole/$g_{wcm}$/hr, about 10,000 to about 50,000 nmole/$g_{wcm}$/hr, about 50,000 to about 100,000 nmole/$g_{wcm}$/hr, about 100,000 to about 150,000 nmole/$g_{wcm}$/hr, or about 150,000 to about 200,000 nmole/$g_{wcm}$/hr. In some embodiments, the amount of isoprene is between about 20 to about 200,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, about 400 to about 1,000 nmole/$g_{wcm}$/hr, about 1,000 to about 5,000 nmole/$g_{wcm}$/hr, about 2,000 to about 20,000 nmole/$g_{wcm}$/hr, about 5,000 to about 50,000 nmole/$g_{wcm}$/hr, about 10,000 to about 100,000 nmole/$g_{wcm}$/hr, about 20,000 to about 150,000 nmole/$g_{wcm}$/hr, or about 20,000 to about 200,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

In some embodiments, the cells in culture have an average volumetric productivity of isoprene at greater than or about 0.1, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, or more mg of isoprene/L of broth/hr (mg/$L_{broth}$/hr, wherein the volume of broth includes the volume of the cells and the cell medium). In some embodiments, the average volumetric productivity of isoprene is between about 0.1 to about 3,500 mg/$L_{broth}$/hr, such as between about 0.1 to about 100 mg/$L_{broth}$/hr, about 100 to about 500 mg/$L_{broth}$/hr, about 500 to about 1,000 mg/$L_{broth}$/hr, about 1,000 to about 1,500 mg/$L_{broth}$/hr, about 1,500 to about 2,000 mg/$L_{broth}$/hr, about 2,000 to about 2,500 mg/$L_{broth}$/hr, about 2,500 to about 3,000 mg/$L_{broth}$/hr, or about 3,000 to about 3,500 mg/$L_{broth}$/hr. In some embodiments, the average volumetric productivity of isoprene is between about 10 to about 3,500 mg/$L_{broth}$/hr, about 100 to about 3,500 mg/$L_{broth}$/hr, about 200 to about 1,000 mg/$L_{broth}$/hr, about 200 to about 1,500 mg/$L_{broth}$/hr, about 1,000 to about 3,000 mg/$L_{broth}$/hr, or about 1,500 to about 3,000 mg/$L_{broth}$/hr.

In some embodiments, the cells in culture have a peak volumetric productivity of isoprene at greater than or about 0.5, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 12,500, 15,000, or more mg of isoprene/L of broth/hr (mg/$L_{broth}$/hr, wherein the volume of broth includes the volume of the cells and the cell medium). In some embodiments, the peak volumetric productivity of isoprene is between about 0.5 to about 15,000 mg/$L_{broth}$/hr, such as between about 0.5 to about 10 mg/$L_{broth}$/hr, about 1.0 to about 100 mg/$L_{broth}$/hr, about 100 to about 500 mg/$L_{broth}$/hr, about 500 to about 1,000 mg/$L_{broth}$/hr, about 1,000 to about 1,500 mg/$L_{broth}$/hr, about 1,500 to about 2,000 mg/$L_{broth}$/hr, about 2,000 to about 2,500 mg/$L_{broth}$/hr, about 2,500 to about 3,000 mg/$L_{broth}$/hr, about 3,000 to about 3,500 mg/$L_{broth}$/hr, about 3,500 to about 5,000 mg/$L_{broth}$/hr, about 5,000 to about 7,500 mg/$L_{broth}$/hr, about 7,500 to about 10,000 mg/$L_{broth}$/hr, about 10,000 to about 12,500 mg/$L_{broth}$/h, or about 12,500 to about 15,000 mg/$L_{broth}$/hr. In some embodiments, the peak volumetric productivity of isoprene is between about 10 to about 15,000 mg/$L_{broth}$/hr, about 100 to about 2,500 mg/$L_{broth}$/hr, about 1,000 to about 5,000 mg/$L_{broth}$/hr, about 2,500 to about 7,500 mg/$L_{broth}$/hr, about 5,000 to about 10,000 mg/$L_{broth}$/hr, about 7,500 to about 12,500 mg/$L_{broth}$/hr, or about 10,000 to about 15,000 mg/$L_{broth}$/hr.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 2.0, 2.2, 2.4, 2.6, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 23.2, 23.4, 23.6, 23.8, 24.0, 25.0, 30.0, 31.0, 32.0, 33.0, 35.0, 37.5, 40.0, 45.0, 47.5, 50.0, 55.0, 60.0, 65.0, 70.0, 75.0, 80.0, 85.0, or 90.0 molar % of the carbon in the cell culture medium into isoprene. In some embodiments, the percent conversion of carbon into isoprene is between about 0.002 to about 90.0 molar %, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, about 1.0 to about 1.6%, about 1.6 to about 3.0%, about 3.0 to about 5.0%, about 5.0 to about 8.0%, about 8.0 to about 10.0%, about 10.0 to about 15.0%, about 15.0 to about 20.0%, about 20.0 to about 25.0%, about 25.0% to 30.0%, about 30.0% to 35.0%, about 35.0% to 40.0%, about 45.0% to 50.0%, about 50.0% to 55.0%, about 55.0% to 60.0%, about 60.0% to 65.0%, about 65.0% to 70.0%, about 75.0% to 80.0%, about 80.0% to 85.0%, or about 85.0% to 90.0%. In some embodiments, the percent conversion of carbon into isoprene is between about 0.002 to about 0.4 molar %, 0.002 to about 0.16 molar %, 0.04 to about 0.16 molar %, about 0.005 to about 0.3 molar %, about 0.01 to about 0.3 molar %, about 0.05 to about 0.3 molar %, about 0.1 to 0.3 molar %, about 0.3 to about 1.0 molar %, about 1.0 to about 5.0 molar %, about 2 to about 5.0 molar %, about 5.0 to about 10.0 molar %, about 7 to about 10.0 molar %, about 10.0 to about 20.0 molar %, about 12 to about 20.0 molar %, about 16 to about 20.0 molar %, about 18 to about 20.0 molar %, about 18 to 23.2 molar %, about 18 to 23.6 molar %, about 18 to about 23.8 molar %, about 18 to about 24.0 molar %, about 18 to about 25.0 molar %, about 20 to about 30.0 molar %, about 30 to about 40.0 molar %, about 30 to about 50.0 molar %, about 30 to about 60.0 molar %, about 30 to about 70.0 molar %, about 30 to about 80.0 molar %, or about 30 to about 90.0 molar %

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100 Equation 1

For this calculation, yeast extract can be assumed to contain 50% w/w carbon. As an example, for the 500 liter described in Example 7, part VIII, the percent conversion of carbon into isoprene can be calculated as shown in Equation 2.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)] *100=0.042% Equation 2

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein.

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate) Equation 3

1 nmol isoprene/$g_{wcm}$/hr=1 nmol isoprene/$L_{broth}$/hr/$OD_{600}$ (This conversion assumes that one liter of broth with an $OD_{600}$ value of 1 has a wet cell weight of 1 gram.) Equation 4

1 nmol isoprene/$g_{wcm}$/hr=68.1 ng isoprene/$g_{wcm}$/hr (given the molecular weight of isoprene) Equation 5

1 nmol isoprene/$L_{gas}$ $O_2$/hr=90 nmol isoprene/$L_{broth}$/hr(at an $O_2$ flow rate of 90 L/hr per L of culture broth) Equation 6

1 ug isoprene/$L_{gas}$ isoprene in off-gas=60 ug isoprene/$L_{broth}$/hr at a flow rate of 60 $L_{gas}$ per $L_{broth}$ (1 vvm) Equation 7

Units for Titer (Total and Specific)

1 nmol isoprene/mg cell protein=150 nmol isoprene/$L_{broth}$/$OD_{600}$ (This conversion assumes that one liter of broth with an $OD_{600}$ value of 1 has a total cell protein of approximately 150 mg) (specific productivity) Equation 8

1 g isoprene/$L_{broth}$=14.7 mmol isoprene/$L_{broth}$ (total titer) Equation 9

If desired, Equation 10 can be used to convert any of the units that include the wet weight of the cells into the corresponding units that include the dry weight of the cells.

Dry weight of cells=(wet weight of cells)/3.3 Equation 10

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, any of the methods described herein further include polymerizing the isoprene. For example, standard methods can be used to polymerize the purified isoprene to form cis-polyisoprene or other down stream products using standard methods.

Additional methods and compositions are described in U.S. Provisional patent application No. 61/097,186, filed on Sep. 15, 2008, U.S. Provisional patent application No. 61/097,189, filed on Sep. 15, 2008, and U.S. Provisional patent application No. 61/097,163, filed on Sep. 15, 2008, all of which are incorporated by reference in their entireties, particular with respect to compositions and methods for producing isoprene.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1: Production of Isoprene in *E. coli* Expressing Recombinant Kudzu Isoprene Synthase I. Construction of Vectors for Expression of the Kudzu Isoprene Synthase in *E. coli*

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
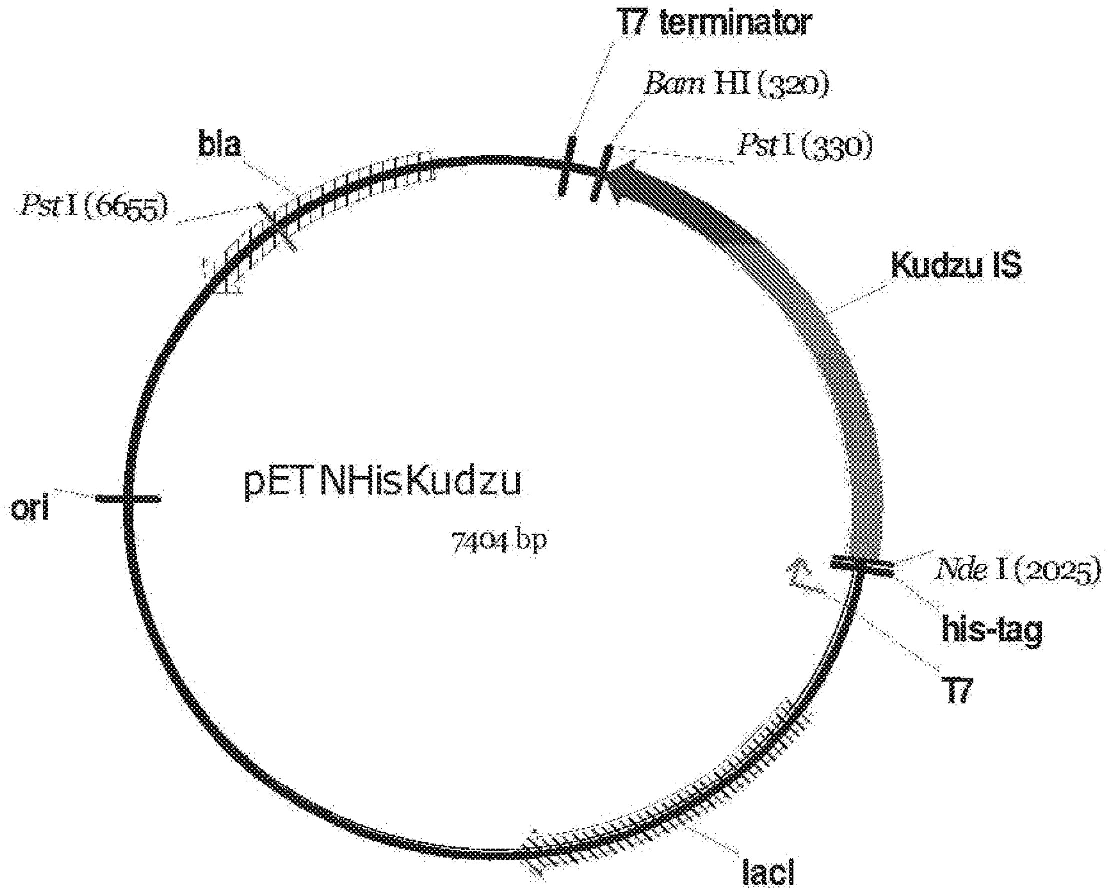
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGATCATATGTGTGCGACCTCTTCTCAATTTAC (SEQ ID NO:3) and pET-His-Kudzu-R: 5'-CGGTCGACGGATCCCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 μl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid, in which the kudzu isoprene synthase gene was expressed from the T7 promoter, was designated pETNHisKudzu (FIGS. 4 and 5).

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAGCTTGTATCGATTAAATAAGGAGGAATAAACC (SEQ ID NO:6) and BamH1-Kudzu R:

5'-CGGTCGACGGATCCCTGCAGTTAGACATACATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E.*

Figure 6:
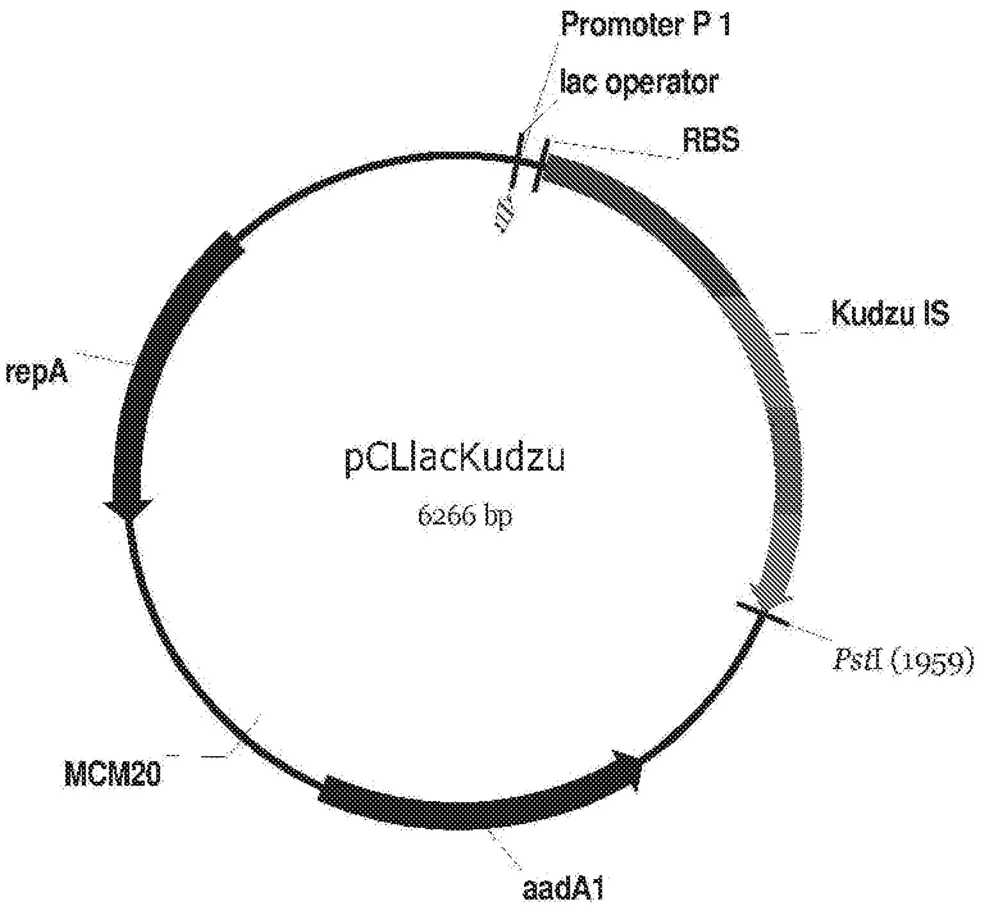
FIG. 6 is a map of pCL-lac-Kudzu.
Figure 8A:
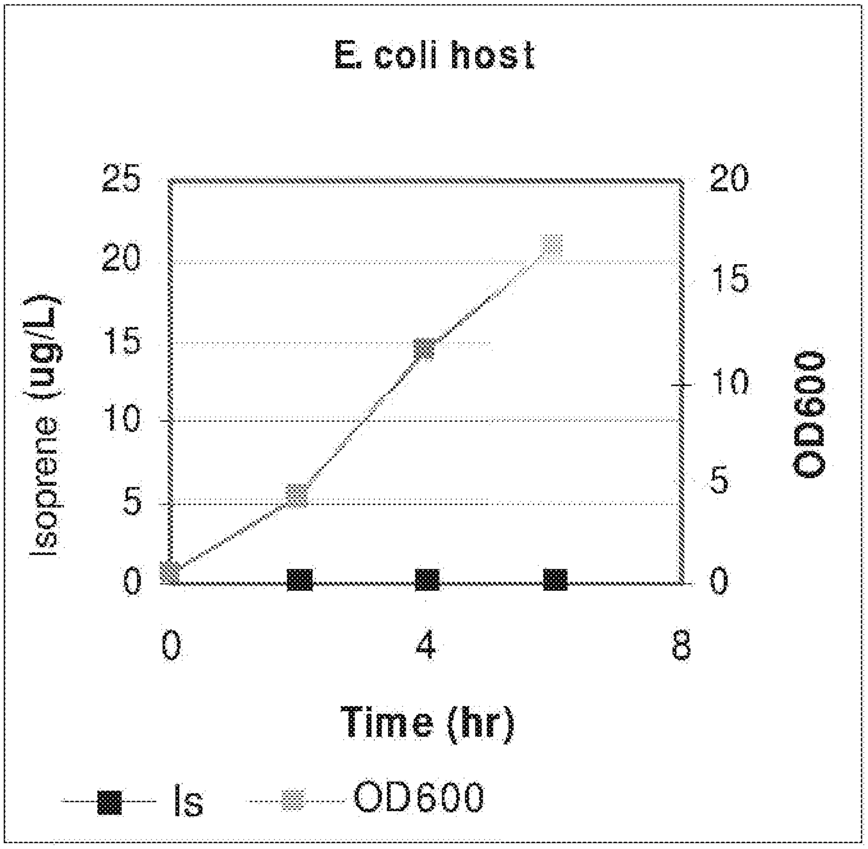
FIG. 8A is a graph showing the production of isoprene in *E. coli* BL21 cells with no vector.
Figure 8B:
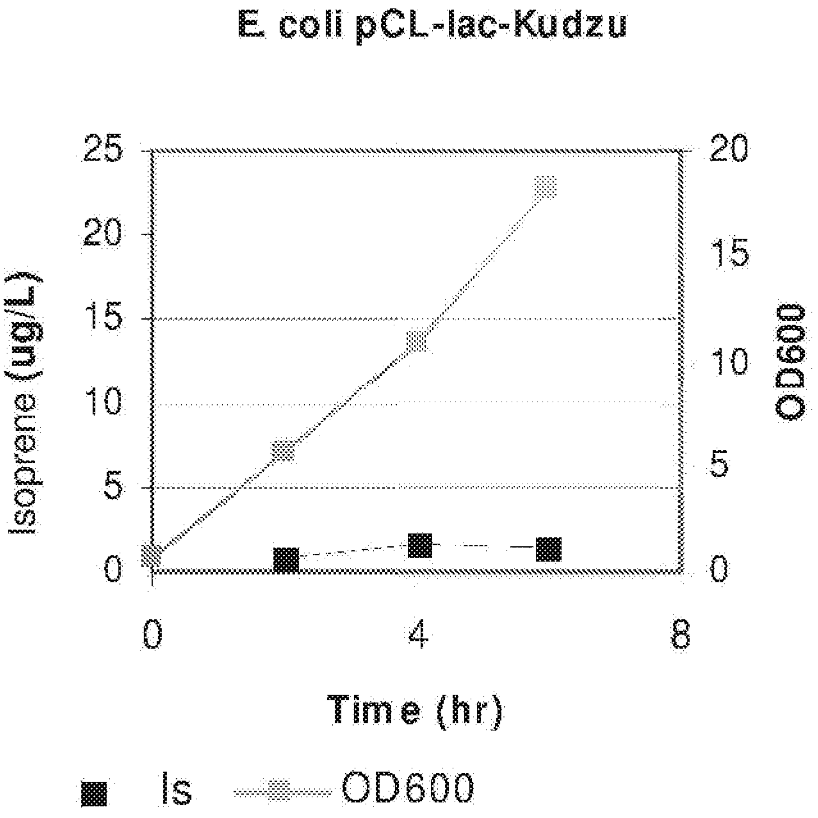
FIG. 8B is a graph showing the production of isoprene in *E. coli* BL21 cells with pCL-lac-Kudzu
Figure 8C:
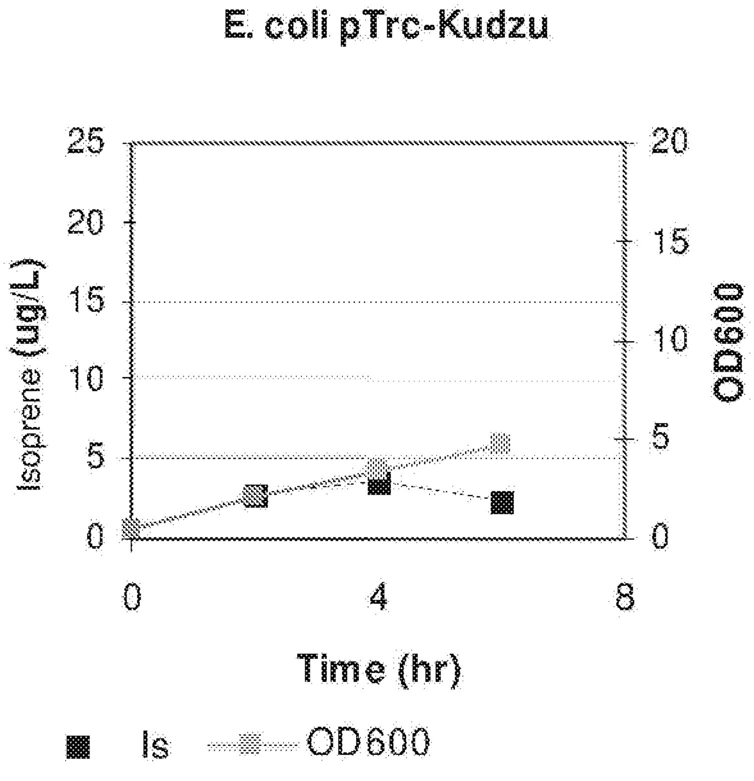
FIG. 8C is a graph showing the production of isoprene in *E. coli* BL21 cells with pTrcKudzu.
Figure 8D:
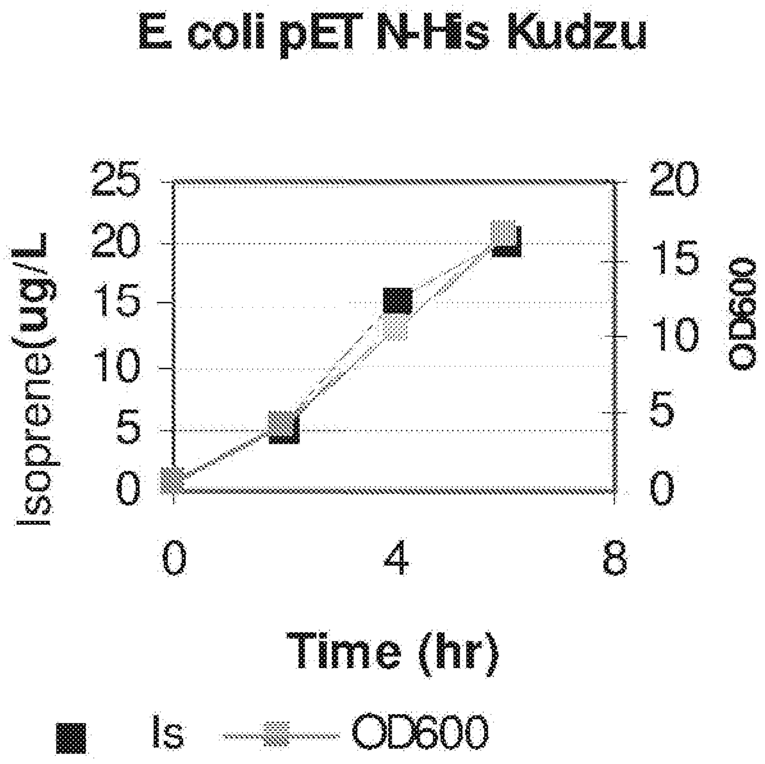
FIG. 8D is a graph showing the production of isoprene in *E. coli* BL21 cells with pETNHisKudzu.

*coli* Top10. Several transformants were checked by sequencing. The resulting plasmid was designated pCL-lac-Kudzu (FIGS. 6 and 7).

II. Determination of Isoprene Production

For the shake flask cultures, one ml of a culture was transferred from shake flasks to 20 ml CTC headspace vials (Agilent vial cat #5188 2753; cap cat #5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/minutes The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 200 μg/l. The limit of detection was estimated to be 50 to 100 ng/L using this method.

III. Production of Isoprene in Shake Flasks Containing *E. coli* Cells Expressing Recombinant Isoprene Synthase The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar) and carbenicillin (50 μg/ml) and incubated overnight at 37° C. Single colonies were inoculated into 250 ml baffled shake flasks containing 20 ml Luria Bertani broth (LB) and carbenicillin (100 μg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen) and carbenicillin (100 μg/ml) to an $OD_{600 \sim 0.05}$. The culture was incubated at 30° C. with shaking at 200 rpm. When the $OD_{600}$~0.5-0.8, 400 μM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, MgSO4* $7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in $diH_2O$. The pH was adjusted to 6.8 with potassium hydroxide (KOH) and q.s. to volume. The final product was filter sterilized with 0.22μ filter (only, do not autoclave). The recipe for 1000× Modified Trace Metal Solution was as follows: Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, ZnSO*$7H_2O$ 1 g, $CuSO_4$* $5H_2O$ 100 mg, $H_3BO_3$ 100 mg, $NaMoO_4$*$2H_2O$ 100 mg. Each component was dissolved one at a time in $diH_2O$, pH to 3.0 with HCl/NaOH, then q.s. to volume and filter sterilized with a 0.22μ filter.

Figure 9A:
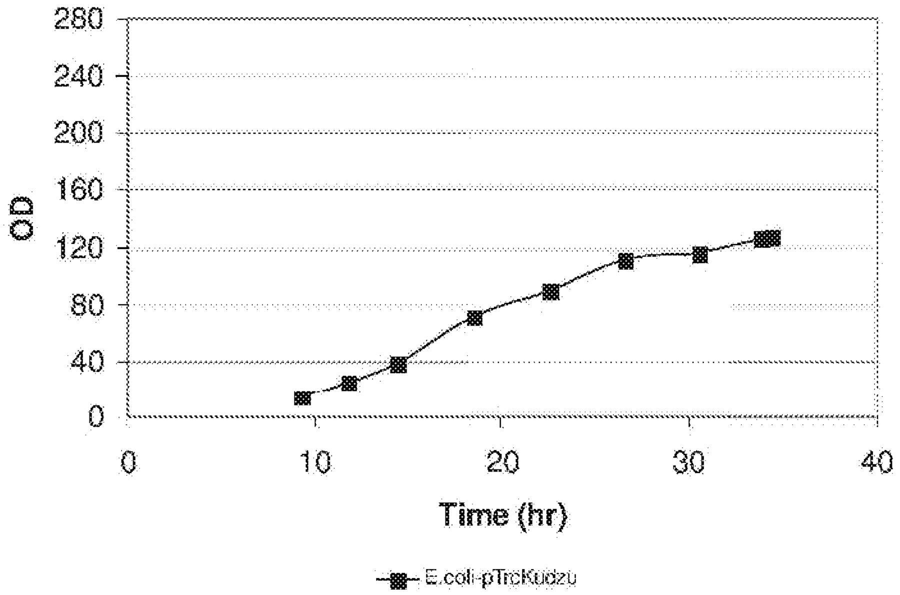
FIG. 9A is a graph showing OD over time of fermentation of *E. coli* BL21/pTrcKudzu in a 14 liter fed batch fermentation.
Figure 9B:
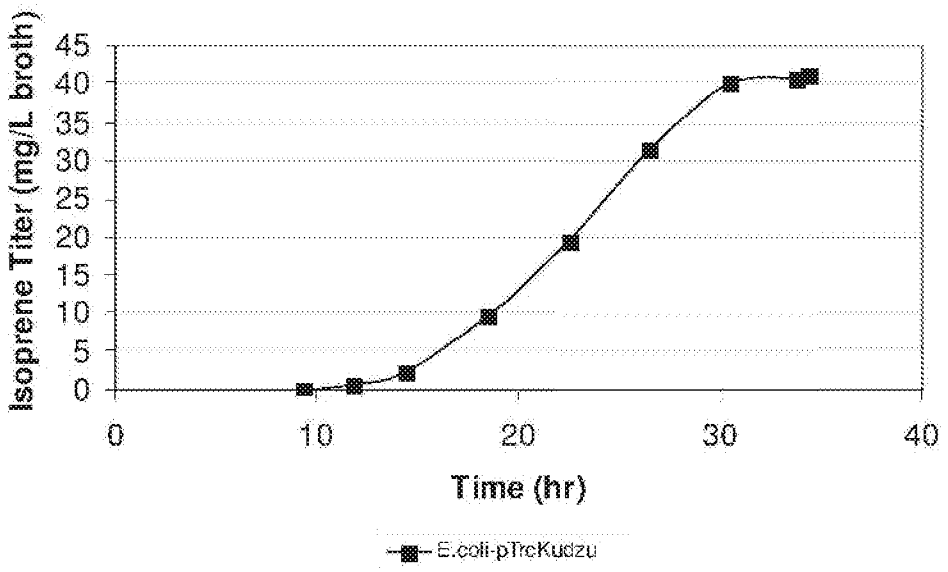
FIG. 9B is a graph showing isoprene production over time of fermentation of *E. coli* BL21/pTrcKudzu in a 14 liter fed batch fermentation.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Figure 30:
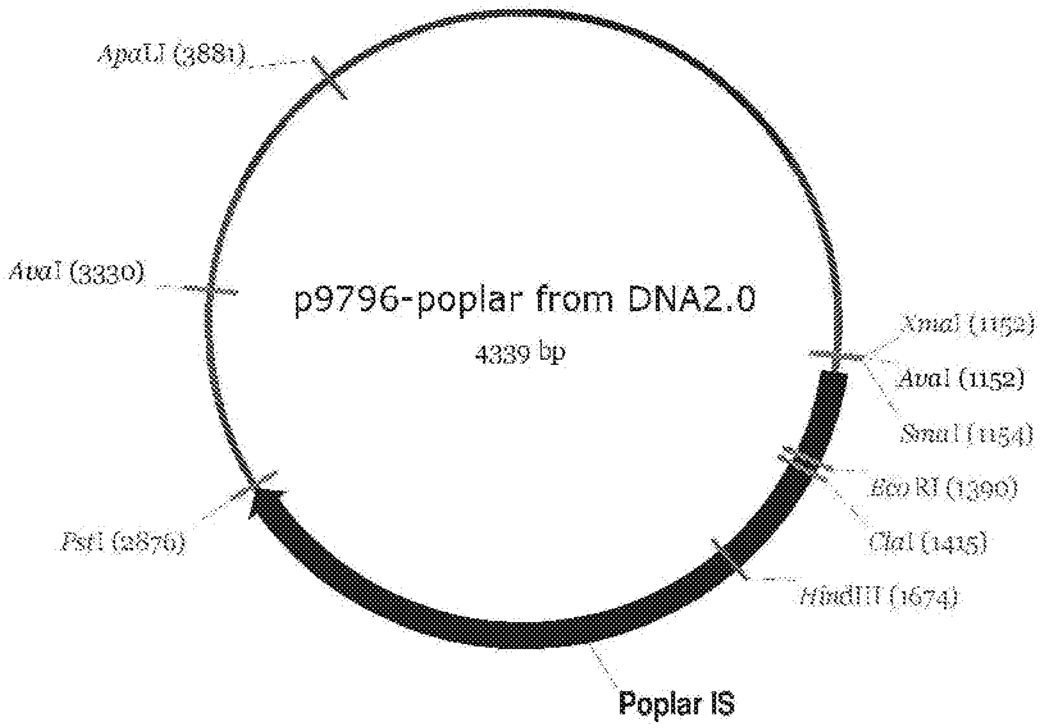
FIG. 30 is a map of p9796-poplar.
Figure 32:
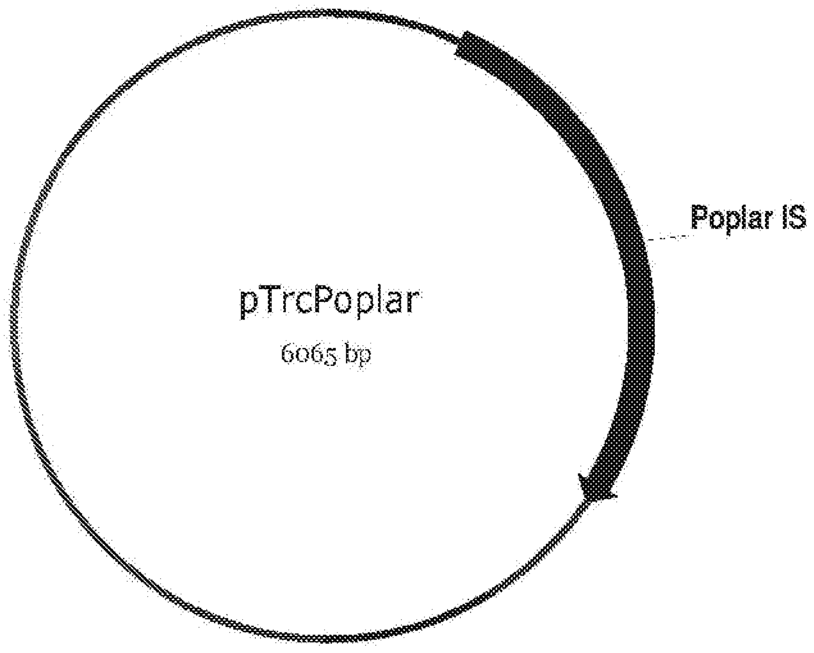
FIG. 32 is a map of pTrcPoplar.

Example 2: Production of Isoprene in *E. coli* Expressing Recombinant Poplar Isoprene Synthase The protein sequence for the poplar (*Populus alba* x *Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33), was verified by sequencing.

Figure 10A:
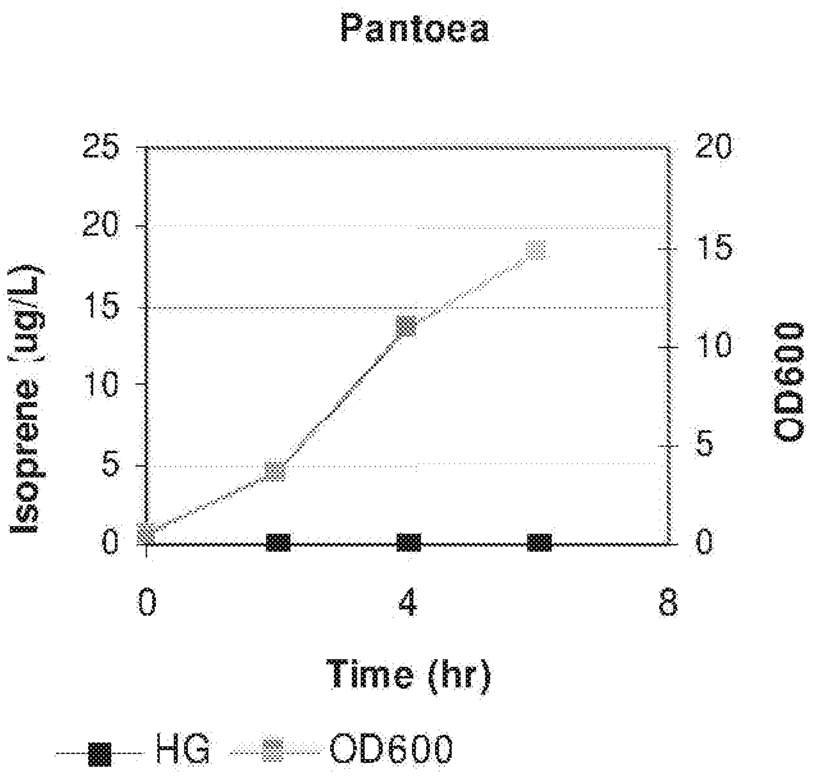
FIG. 10A is a graph showing the production of isoprene in *Panteoa citrea*. Control cells without recombinant kudzu isoprene synthase. Grey diamonds represent isoprene synthesis, black squares represent $OD_{600}$.
Figure 10B:
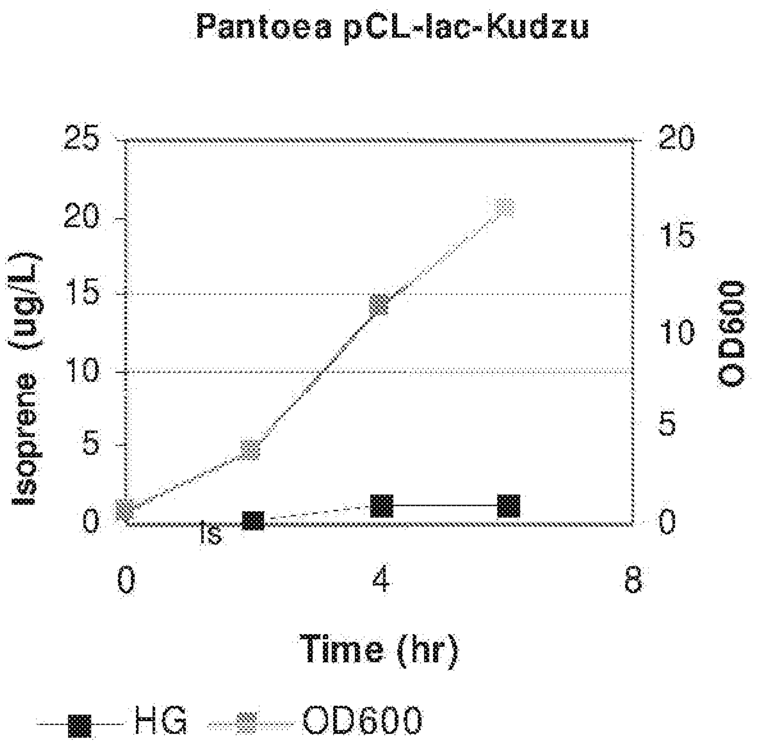
FIG. 10B is a graph showing the production of isoprene in *Panteoa citrea* expressing pCL-lac Kudzu. Grey diamonds represent isoprene synthesis, black squares represent $OD_{600}$.
Figure 10C:
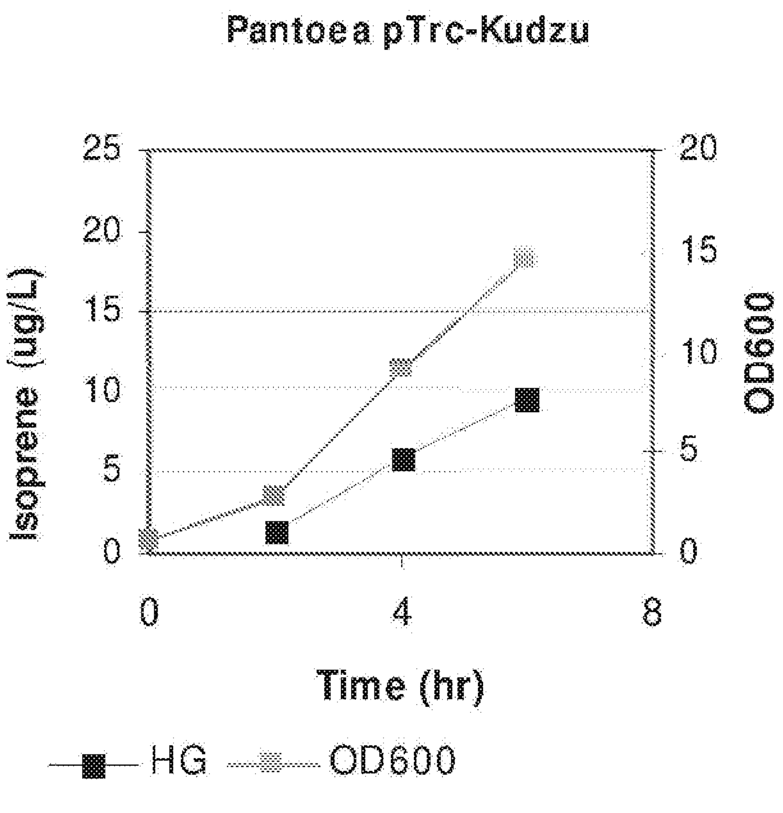
FIG. 10C is a graph showing the production of isoprene in *Panteoa citrea* expressing pTrcKudzu. Grey diamonds represent isoprene synthesis, black squares represent $OD_{600}$.

Example 3: Production of Isoprene in *Panteoa citrea* Expressing Recombinant Kudzu Isoprene Synthase The pTrcKudzu and pCL-lac Kudzu plasmids described in Example 1 were electroporated into *P. citrea* (U.S. Pat. No. 7,241,587). Transformants were selected on LA containing carbenicillin (200 μg/ml) or spectinomycin (50 μg/ml) respectively. Production of isoprene from shake flasks and determination of the amount of isoprene produced was performed as described in Example 1 for *E. coli* strains expressing recombinant kudzu isoprene synthase. Results are shown in FIG. 10.

Example 4: Production of Isoprene in *Bacillus subtilis* Expressing Recombinant Kudzu Isoprene Synthase I. Construction of a *B. subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS19 and transformed into *B. subtilis*.

a) Amplification of the aprE Promoter

The aprE promoter was amplified from chromosomal DNA from *Bacillus subtilis* using the following primers:

CF 797 (+) Start aprE promoter MfeI (SEQ ID NO: 58)
5'-GACATCAATTGCTCCATTTTCTTCTGCTATC CF 07-43 (−) Fuse aprE promoter to Kudzu ispS (SEQ ID NO: 59)
5'-ATTGAGAAGAGGTCGCACACACTCTTTACCCTCTCCTTTTA b) Amplification of the Isoprene Synthase Gene The kudzu isoprene synthase gene was amplified from plasmid pTrcKudzu (SEQ ID NO:2). The gene had been codon optimized for *E. coli* and synthesized by DNA 2.0. The following primers were used:

CF 07-42 (+) Fuse the aprE promoter to kudzu isoprene synthase gene (GTG start codon)

(SEQ ID NO: 60)
5'-TAAAAGGAGAGGGTAAAGAGTGTGTGCGACCTCTTCTCAAT

CF 07-45 (−) Fuse the 3' end of kudzu isoprene synthase gene to the terminator (SEQ ID NO: 61)
5'-CCAAGGCCGGTTTTTTTTAGACATACATCAGCTGGTTAATC c) Amplification of the Transcription Terminator The terminator from the alkaline serine protease of *Bacillus amyliquefaciens* was amplified from a previously sequenced plasmid pJHPms382 using the following primers:

CF 07-44 (+) Fuse the 3' end of kudzu isoprene synthase to the terminator (SEQ ID NO: 62)
5'-GATTAACCAGCTGATGTATGTCTAAAAAAAACCGGCCTTGG CF 07-46 (−) End of *B. amyliquefaciens* terminator (BamHI)

(SEQ ID NO: 63)
5'-GACATGACGGATCCGATTACGAATGCCGTCTC

The kudzu fragment was fused to the terminator fragment using PCR with the following primers:

CF 07-42 (+) Fuse the aprE promoter to kudzu isoprene synthase gene (GTG start codon)

(SEQ ID NO: 61)
5'-TAAAAGGAGAGGGTAAAGAGTGTGTGCGACCTCTTCTCAAT

CF 07-46 (−) End of *B. amyliquefaciens* terminator (BamHI)

(SEQ ID NO: 63)
5'-GACATGACGGATCCGATTACGAATGCCGTCTC

The kudzu-terminator fragment was fused to the promoter fragment using PCR with the following primers:

CF 797 (+) Start aprE promoter MfeI (SEQ ID NO: 64)
5'-GACATCAATTGCTCCATTTTCTTCTGCTATC CF 07-46 (−) End of *B. amyliquefaciens* terminator (BamHI)

(SEQ ID NO: 63)
5'-GACATGACGGATCCGATTACGAATGCCGTCTC

The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA and 50 carbenicillin plates. A total of six colonies were chosen and grown overnight in LB and 50 carbenicillin and then plasmids were isolated using a Qiagen kit. The plasmids were digested with EcoRI and BamHI to check for inserts and three of the correct plasmids were sent in for sequencing with the following primers:

CF 149 (+) EcoRI start of aprE promoter (SEQ ID NO: 65)
5'-GACATGAATTCCTCCATTTTCTTCTGC CF 847 (+) Sequence in pXX 049 (end of aprE promoter)

(SEQ ID NO: 66)
5'-AGGAGAGGGTAAAGAGTGAG

Figure 52:
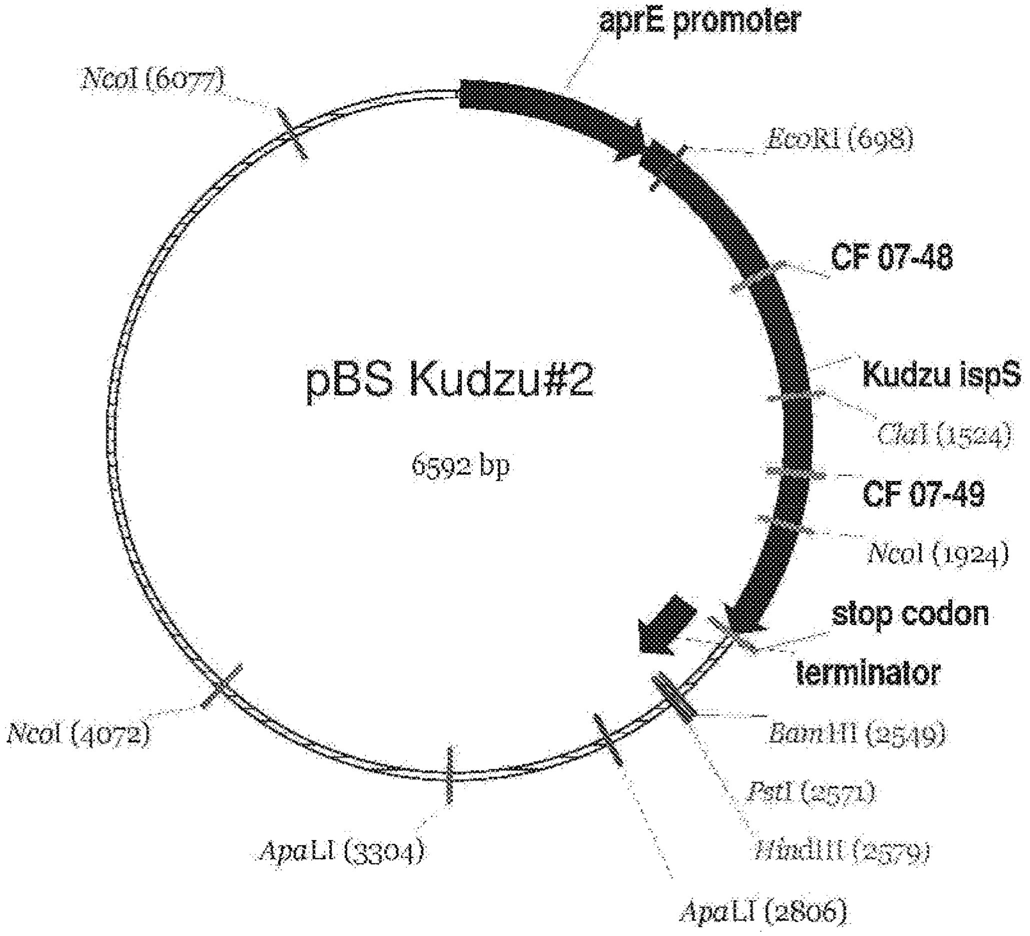
FIG. 52 is a map of pBS Kudzu #2.

CF 07-45 (−) Fuse the 3' end of kudzu isoprene synthase to the terminator (SEQ ID NO: 61)
5'-CCAAGGCCGGTTTTTTTTAGACATACATCAGCTGGTTAATC CF 07-48 (+) Sequencing primer for kudzu isoprene synthase (SEQ ID NO: 67)
5'-CTTTTCCATCACCCACCTGAAG CF 07-49 (+) Sequencing in kudzu isoprene synthase (SEQ ID NO: 68)
5'-GGCGAAATGGTCCAACAACAAAATTATC The plasmid designated pBS Kudzu #2 (FIGS. 52 and 12) was correct by sequencing and was transformed into BG 3594 comK, a *Bacillus subtilis* host strain. Selection was done on LA and 5 chloramphenicol plates. A transformant was chosen and struck to single colonies on LA and 5 chloramphenicol, then grown in LB and 5 chloramphenicol until it reached an $OD_{600}$ of 1.5. It was stored frozen in a vial at −80° C. in the presence of glycerol. The resulting strain was designated CF 443.

Figure 11:
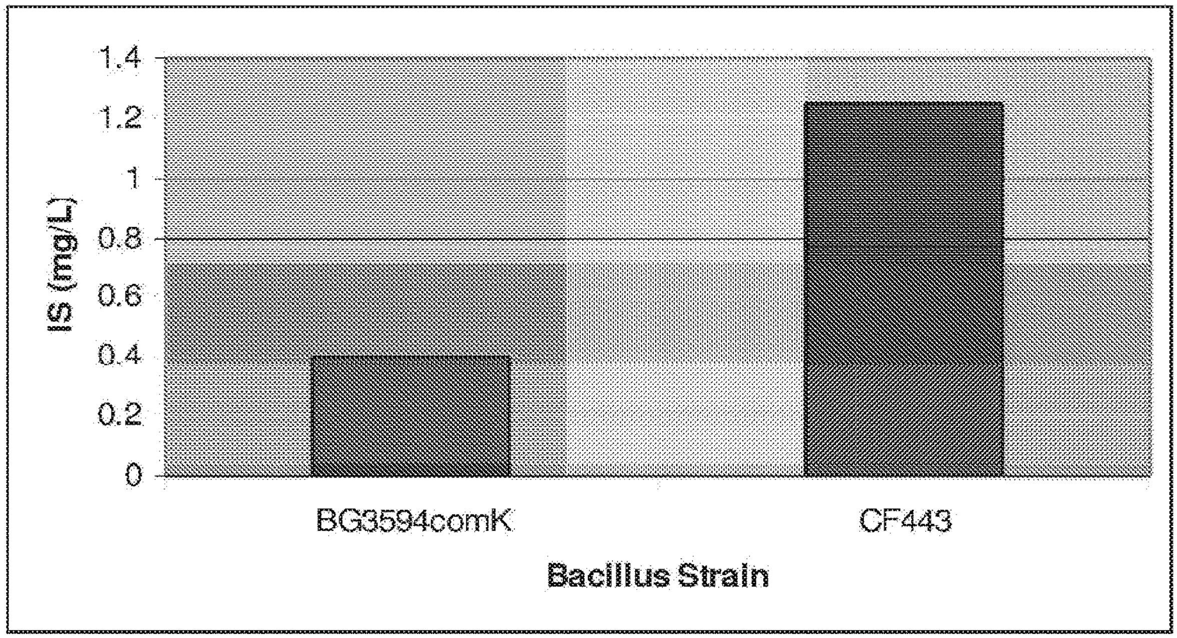
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

II. Production of Isoprene in Shake Flasks Containing *B. subtilis* Cells Expressing Recombinant Isoprene Synthase Overnight cultures were inoculated with a single colony of CF 443 from a LA and Chloramphenicol (Cm, 25 µg/ml). Cultures were grown in LB and Cm at 37° C. with shaking at 200 rpm. These overnight cultures (1 ml) were used to inoculate 250 ml baffled shake flasks containing 25 ml Grants II media and chloramphenicol at a final concentration of 25 μg/ml. Grants II Media recipe was 10 g soytone, 3 ml 1M $K_2HPO_4$, 75 g glucose, 3.6 g urea, 100 ml 10× MOPS, q.s. to 1 L with $H_2O$, pH 7.2; 10× MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2$*$2H_2O$, 0.4 g $FeSO_4$*$7H_2O$, 0.1 g $MnSO_4$*$H_2O$, 0.1 g $ZnSO_4$*$H_2O$, 0.05 g $CuCl_2$*$2H_2O$, 0.1 g $CoCl_2$*$6H_2O$, 0.1 g $Na_2MoO_4$*$2H_2O$, q.s. to 1 L with $H_2O$. Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation

Figure 53A:
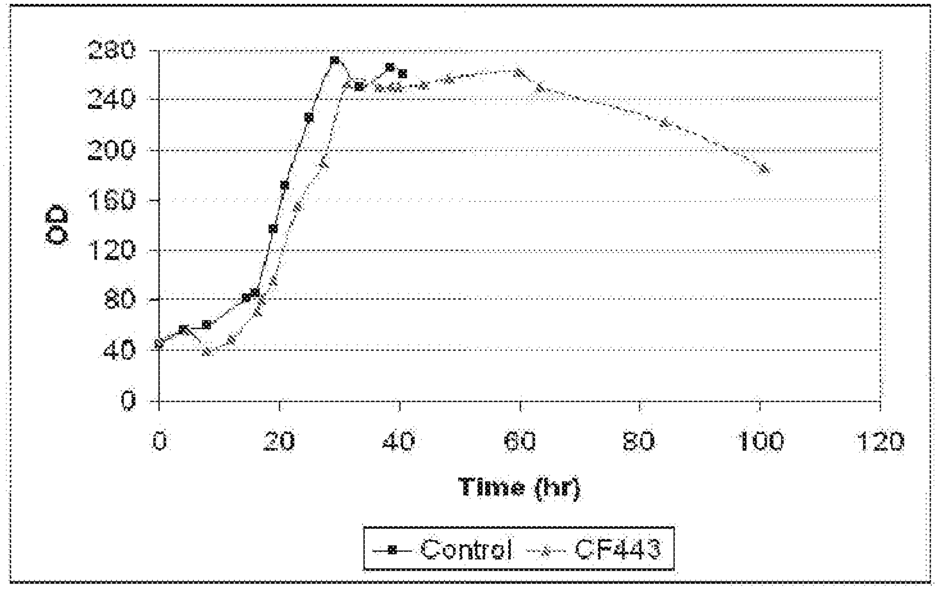
FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).
Figure 53B:
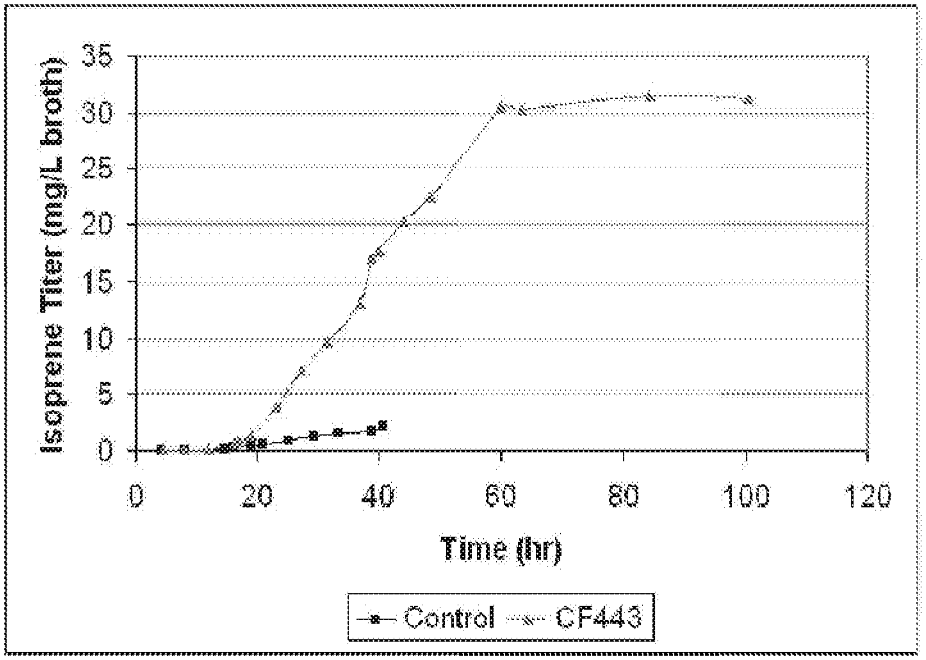
FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, DO %, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. subtilis.*

The kudzu isoprene synthase gene was cloned in an integrating plasmid (pJH101-cmpR) under the control of the aprE promoter. Under the conditions tested, no isoprene was detected.

Example 5: Production of Isoprene in *Trichoderma*

I. Construction of Vectors for Expression of the Kudzu Isoprene Synthase in *Trichoderma reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 μl plasmid template (20 ng/ul), 1 μl Primer EL-945 (10 uM) 5'-GCTTATGGATCCTCTAGACTATTACACGTACATCAATTGG (SEQ ID NO:9), 1 μl Primer EL-965 (10 uM) 5'-CACCATGTGTGCAACCTCCTCCCAGTTTAC (SEQ ID NO:10), 1 μl dNTP (10 mM), 5 μl 10× PfuUltra II Fusion HS DNA Polymerase Buffer, 1 μl PfuUltra II Fusion HS DNA Polymerase, 40 μl water in a total reaction volume of 50 μl. The forward primer contained an additional 4 nucleotides at the 5'-end that did not correspond to the E *lipolytica* codon-optimized kudzu isoprene synthase gene, but was required for cloning into the pENTR/D-TOPO vector. The reverse primer contained an additional 21 nucleotides at the 5'-end that did not correspond to the E *lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the E *lipolytica* codon-optimized kudzu isoprene synthase gene.

The PCR product was then cloned using the TOPO pENTR/D-TOPO Cloning Kit following manufacturer's protocol: 1 μl PCR reaction, 1 μl Salt solution, 1 μl TOPO pENTR/D-TOPO vector and 3 μl water in a total reaction volume of 6 μl. The reaction was incubated at room temperature for 5 minutes. One microliter of TOPO reaction was transformed into TOP10 chemically competent *E. coli* cells. The transformants were selected on LA and 50 μg/ml kanamycin plates. Several colonies were picked and each was inoculated into a 5 ml tube containing LB and 50 μg/mlkanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a E *lipolytica* codon-optimized kudzu isoprene synthase gene, was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 μl *Y. lipolytica* codon-optimized kudzu isoprene synthase gene pENTR/D-TOPO donor vector, 1 μl pTrex3g destination vector, 6 μl TE buffer, pH 8.0 in a total reaction volume of 8 μl. The reaction was incubated at room temperature for 1 hour and then 1 μl proteinase K solution was added and the incubation continued at 37° C. for 10 minutes. Then 1 μl of reaction was transformed into TOP10 chemically competent *E. coli* cells. The transformants were selected on LA and 50 μg/ml carbenicillin plates. Several colonies were picked and each was inoculated into a 5 ml tube containing LB and 50 μlg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
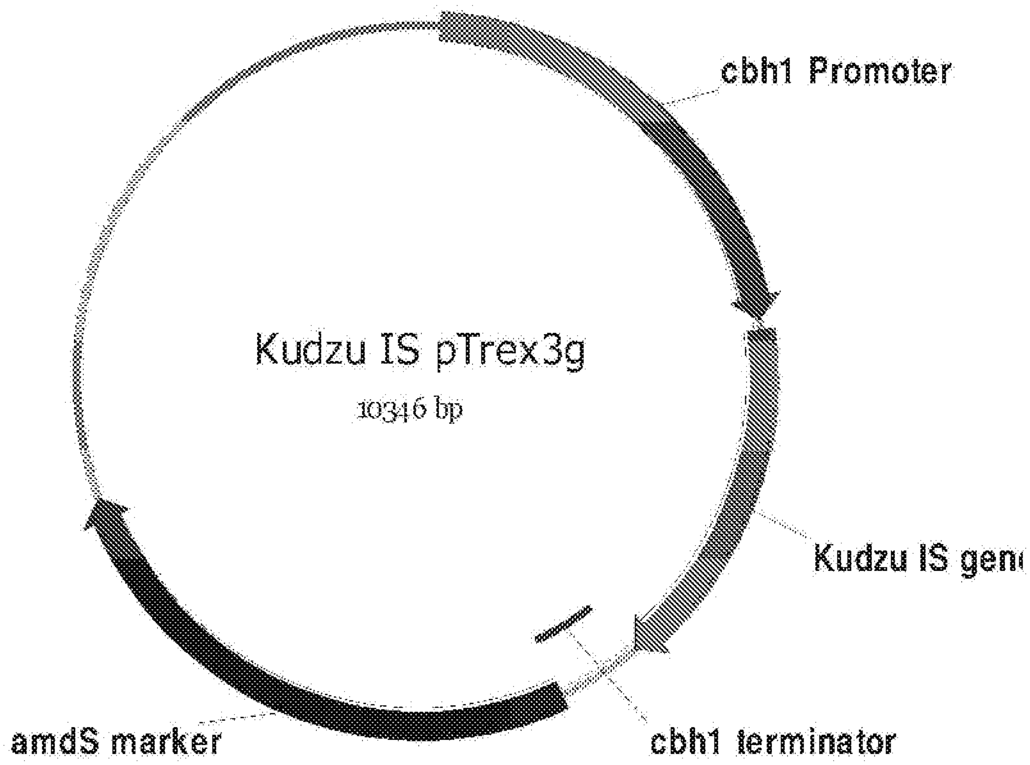
FIG. 14 is a map of pTrex3g comprising a kudzu isoprene synthase gene codon-optimized for expression in *Yarrowia.*

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 μg/L for the 14 hour incubation. The untransformed control showed no detectable levels of isoprene. This experiment shows that *T. reesei* is capable of producing isoprene from endogenous precursor when supplied with an exogenous isoprene synthase.

Example 6: Production of Isoprene in *Yarrowia*

I. Construction of Vectors for Expression of the Kudzu Isoprene Synthase in *Yarrowia lipolytica.*

The starting point for the construction of vectors for the expression of the kudzu isoprene synthase gene in *Yarrowia lipolytica* was the vector pSPZ1(MAP29Spb). The complete sequence of this vector (SEQ ID No:11) is shown in FIG. 15.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

```
ICL1 3
                                       (SEQ ID NO: 69)
5'-GGTGAATTCAGTCTACTGGGGATTCCCAAATCTATATATACTGCAG

GTGAC

ICL1 5
                                       (SEQ ID NO: 70)
5'-GCAGGTGGGAAACTATGCACTCC

XPR 3
                                       (SEQ ID NO: 71)
5'-CCTGAATTCTGTTGGATTGGAGGATTGGATAGTGGG

XPR5
                                       (SEQ ID NO: 72)
5'-GGTGTCGACGTACGGTCGAGCTTATTGACC

XPRT3
                                       (SEQ ID NO: 73)
5'-GGTGGGCCCGCATTTTGCCACCTACAAGCCAG

XPRT 5
                                       (SEQ ID NO: 74)
5'-GGTGAATTCTAGAGGATCCCAACGCTGTTGCCTACAACGG

Y18S3
                                       (SEQ ID NO: 75)
5'-GGTGCGGCCGCTGTCTGGACCTGGTGAGTTTCCCCG

Y18S 5
                                       (SEQ ID NO: 76)
5'-GGTGGGCCCATTAAATCAGTTATCGTTTATTTGATAG

YURA3
                                       (SEQ ID NO: 77)
5'-GGTGACCAGCAAGTCCATGGGTGGTTTGATCATGG

YURA 50
                                       (SEQ ID NO: 78)
5'-GGTGCGGCCGCCTTTGGAGTACGACTCCAACTATG

YURA 51
                                       (SEQ ID NO: 79)
5'-GCGGCCGCAGACTAAATTTATTTCAGTCTCC
```

For PCR amplification the PfuUltraII polymerase (Stratagene), supplier-provided buffer and dNTPs, 2.5 μM primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
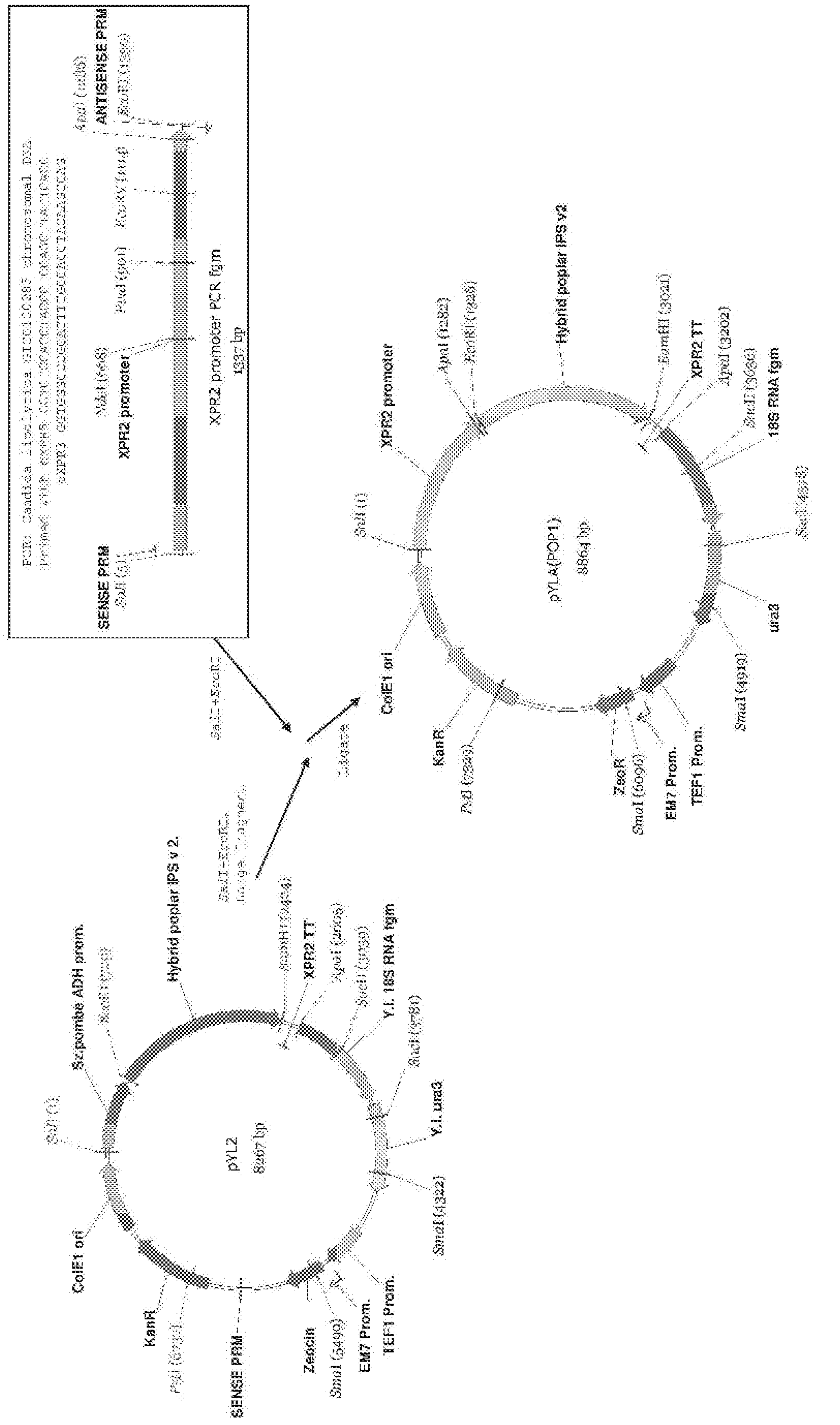
FIG. 18B shows a schematic outlining construction of the vector pYLA(POP1).
Figure 18C:
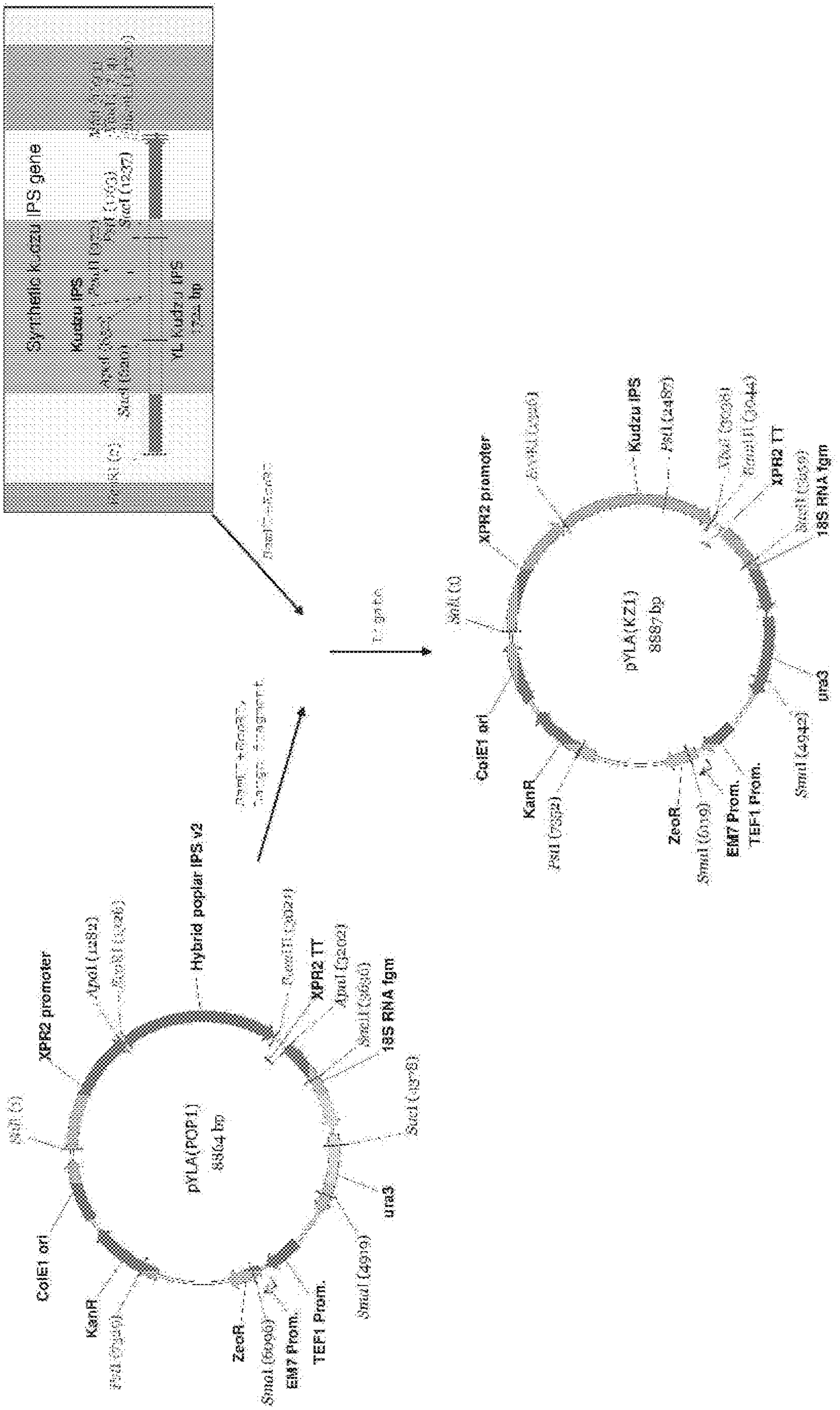
FIG. 18C shows a schematic outlining construction of the vector pYLA(KZ1)
Figure 18D:
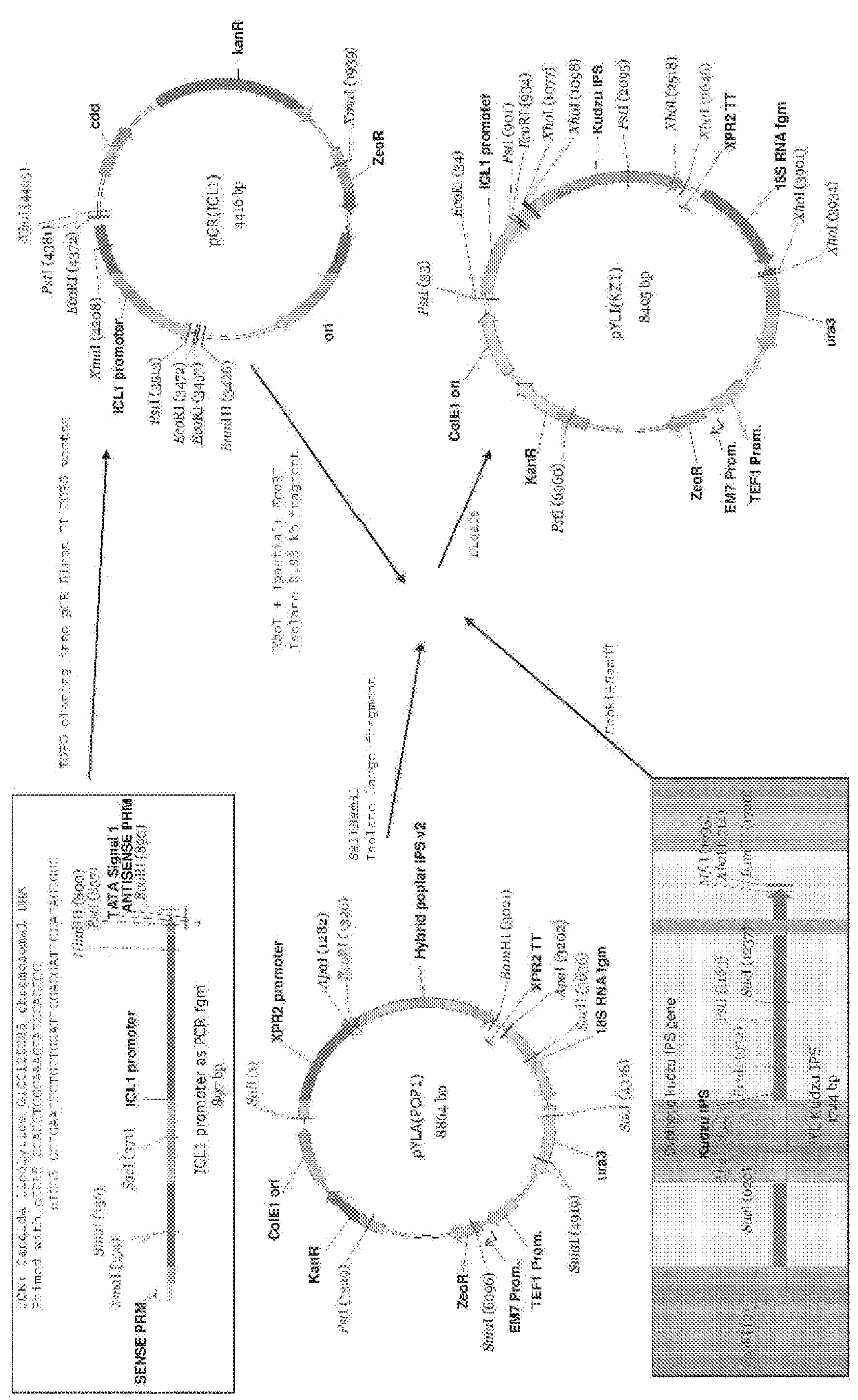
FIG. 18D shows a schematic outlining construction of the vector pYLI(KZ1)
Figure 18E:
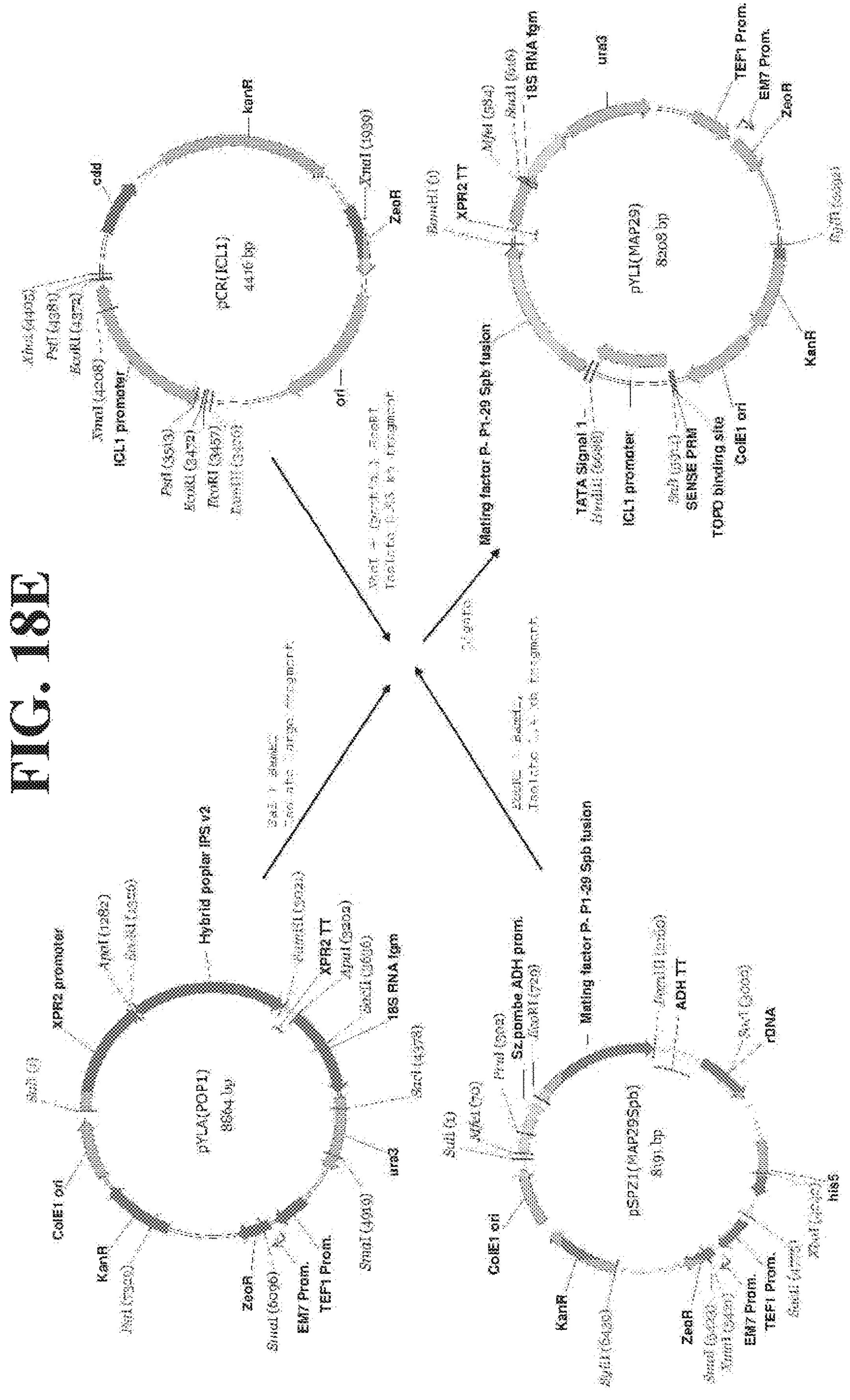
FIG. 18E shows a schematic outlining construction of the vector pYLI(MAP29)
Figure 18F:
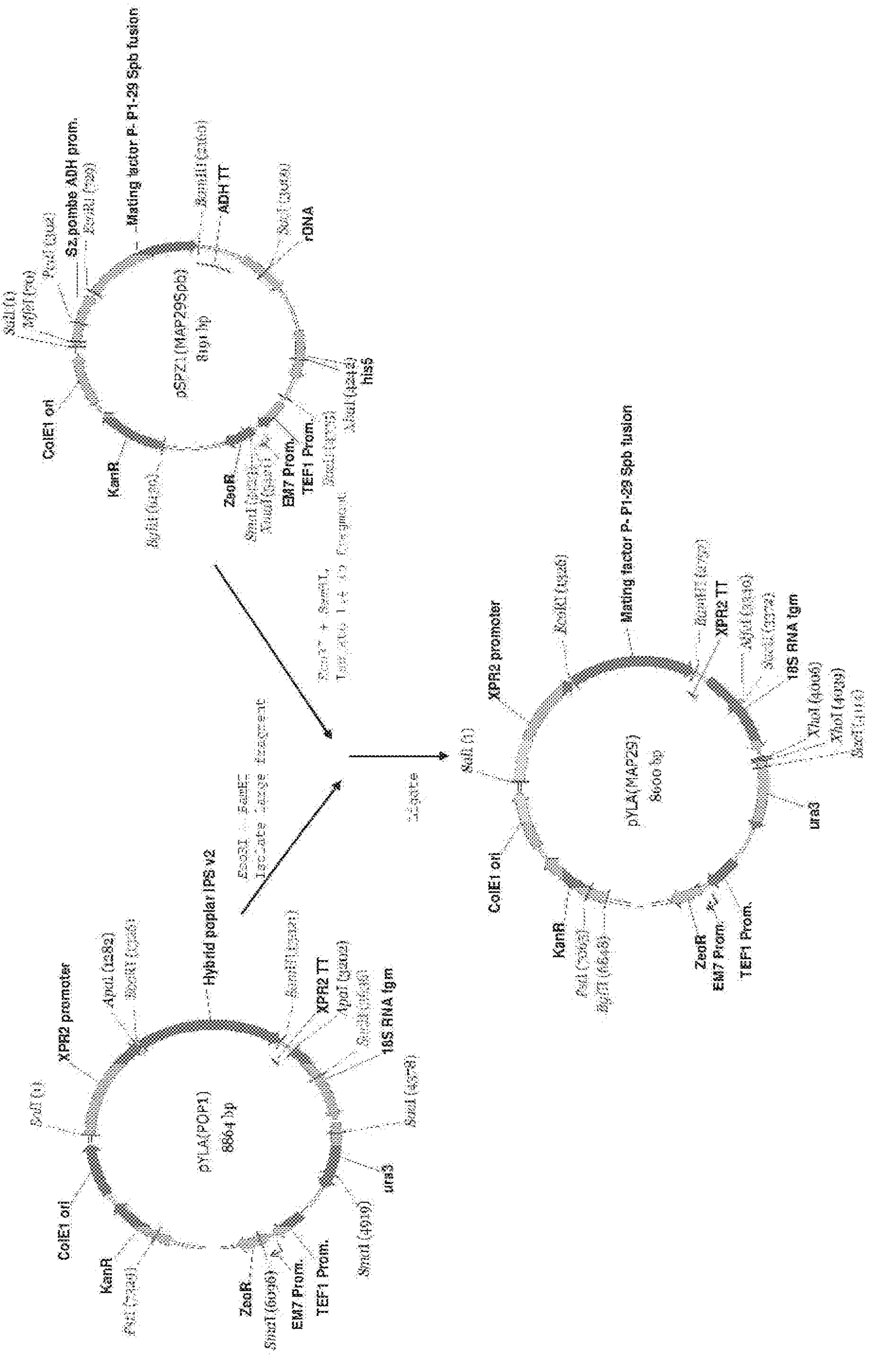
FIG. 18F shows a schematic outlining construction of the vector pYLA(MAP29)

Synthetic DNA molecules encoding the kudzu isoprene synthase gene, codon-optimized for expression in *Yarrowia*, was obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene were also constructed (FIGS. 18E and 18F).

A similar cloning procedure can be used to express a poplar (*Populus alba* x *Populus tremula*) isoprene synthase gene. The sequence of the poplar isoprene is described in Miller B. et al. (2001) *Planta* 213, 483-487 and shown in FIG. 17 (SEQ ID NO:13). A construction scheme for the generation the plasmids pYLA(POP1) and pYLI(POP1) carrying synthetic poplar isoprene synthase gene under control of XPR2 and ICL1 promoters respectively is presented in FIGS. 18A and 18B.

II. Production of Isoprene by Recombinant Strains of *Y. lipolytica.*

Vectors pYLA(KZ1), pYLI(KZ1), pYLA(MAP29) and pYLI(MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred μl aliquots of the cell suspension were mixed with linearized plasmid DNA solution (10-20 μg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 μg/L to 1 μg/l, FIG. 20). No isoprene was detected in the headspace of the control strains carrying phytase gene instead of an isoprene synthase gene.

Example 7: Production of Isoprene in *E. coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli* i) Construction of pTrcKudzuKan

Figure 34:
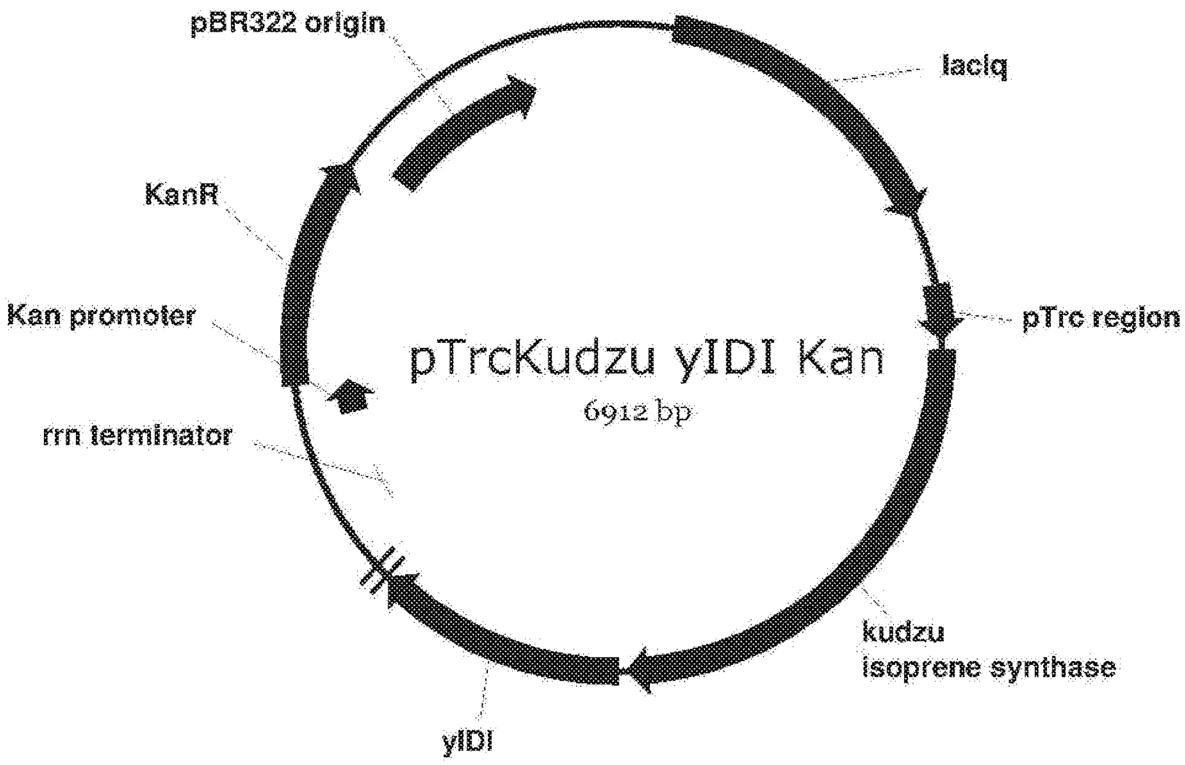
FIG. 34 is a map of pTrcKudzu yIDI Kan.

The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the $kan^r$ gene which had been PCR amplified from pCR-Blunt-II-TOPO using primers MCM22 5'-GATCAAGCTTAACCGGAATTGCCAGCTG (SEQ ID NO:14) and MCM23 5'-GATCCGATCGTCAGAAGAACTCGTCAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 μg/ml.

ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATGCATCGCCCTTAGGAGGTAAAAAAAAATGAC (SEQ ID NO:16) and PstI-YIDI 1 R 5'-CCTTCTGCAGGACGCGTTGTTATAGC (SEQ ID NO:17); and the template was *S. cerevisiae* genomic DNA. The PCR product was digested with NsiI and PstI and gel purified prior to ligation. The ligation mixture was transformed into chemically competent TOP10 cells and selected on LA containing 50 μg/mlkanamycin. Several transformants were isolated and sequenced and the resulting plasmid was called pTrcKudzu-yIDI(kan) (FIGS. 34 and 35).

iii) Construction of pTrcKudzu DXS Kan

Figure 21:
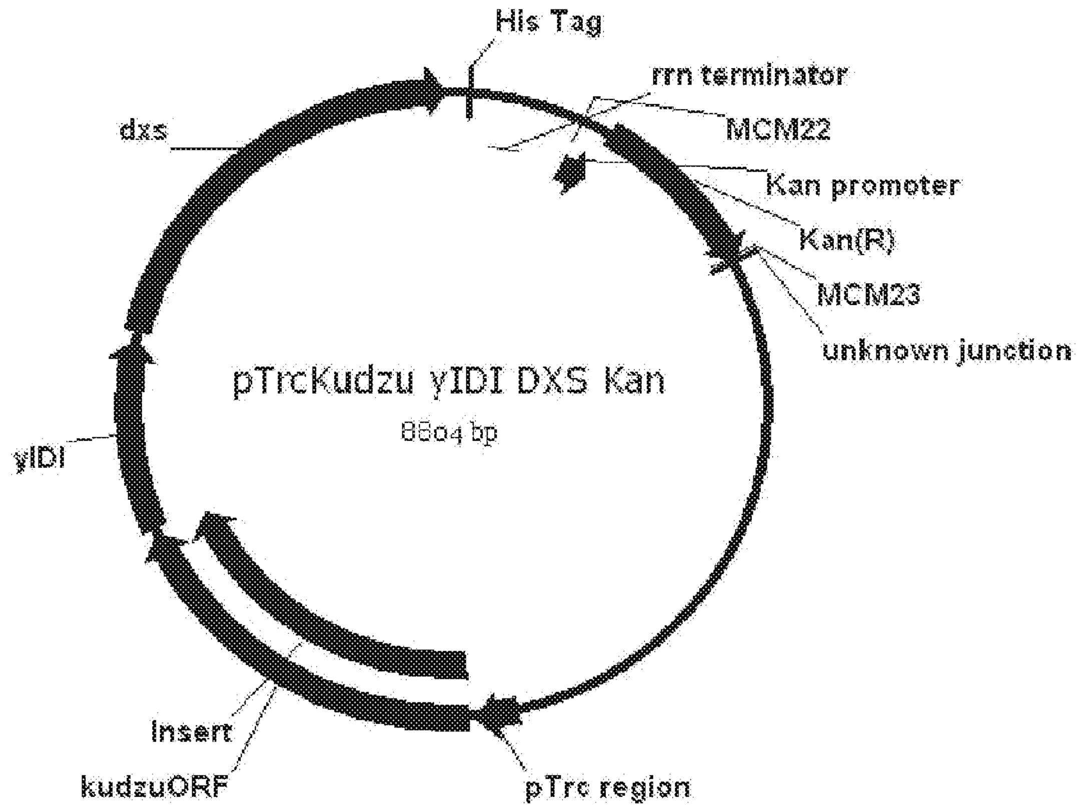
FIG. 21 is a map of pTrcKudzu yIDI DXS Kan.
Figure 36:
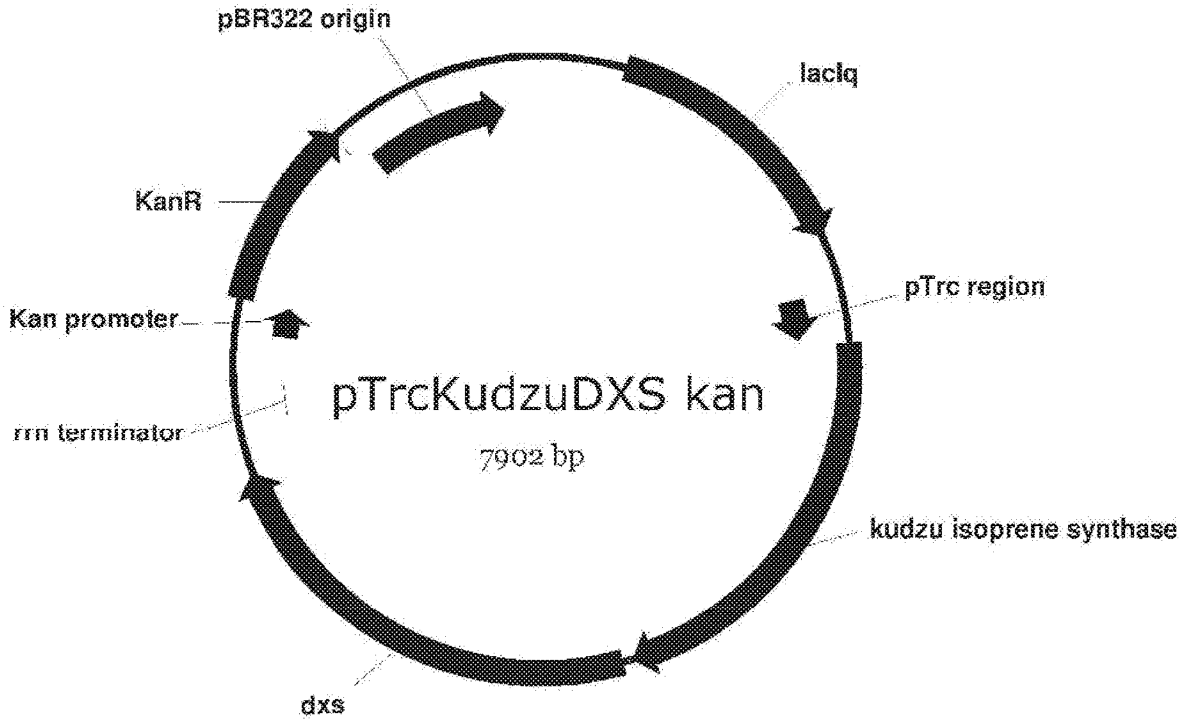
FIG. 36 is a map of pTrcKudzuDXS Kan.
Figure 38:
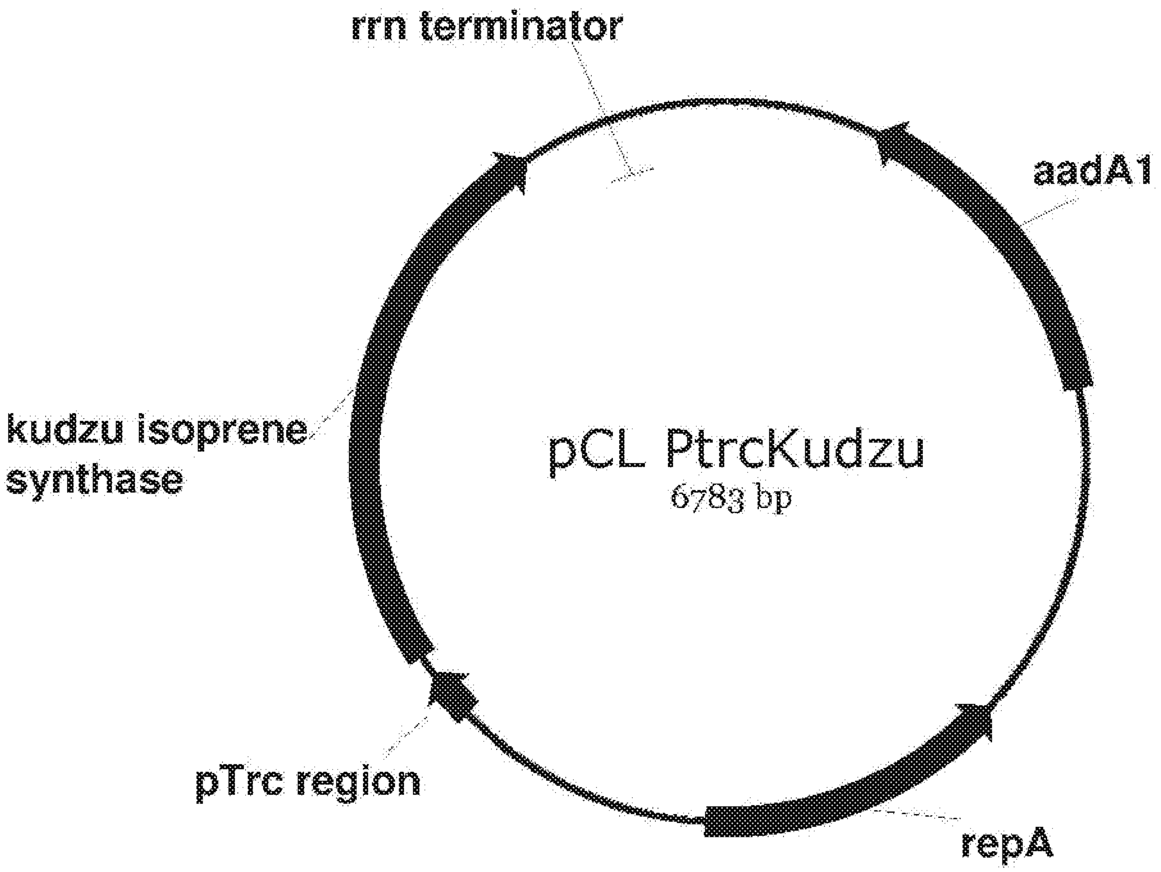
FIG. 38 is a map of pCL PtrcKudzu.
Figure 40:
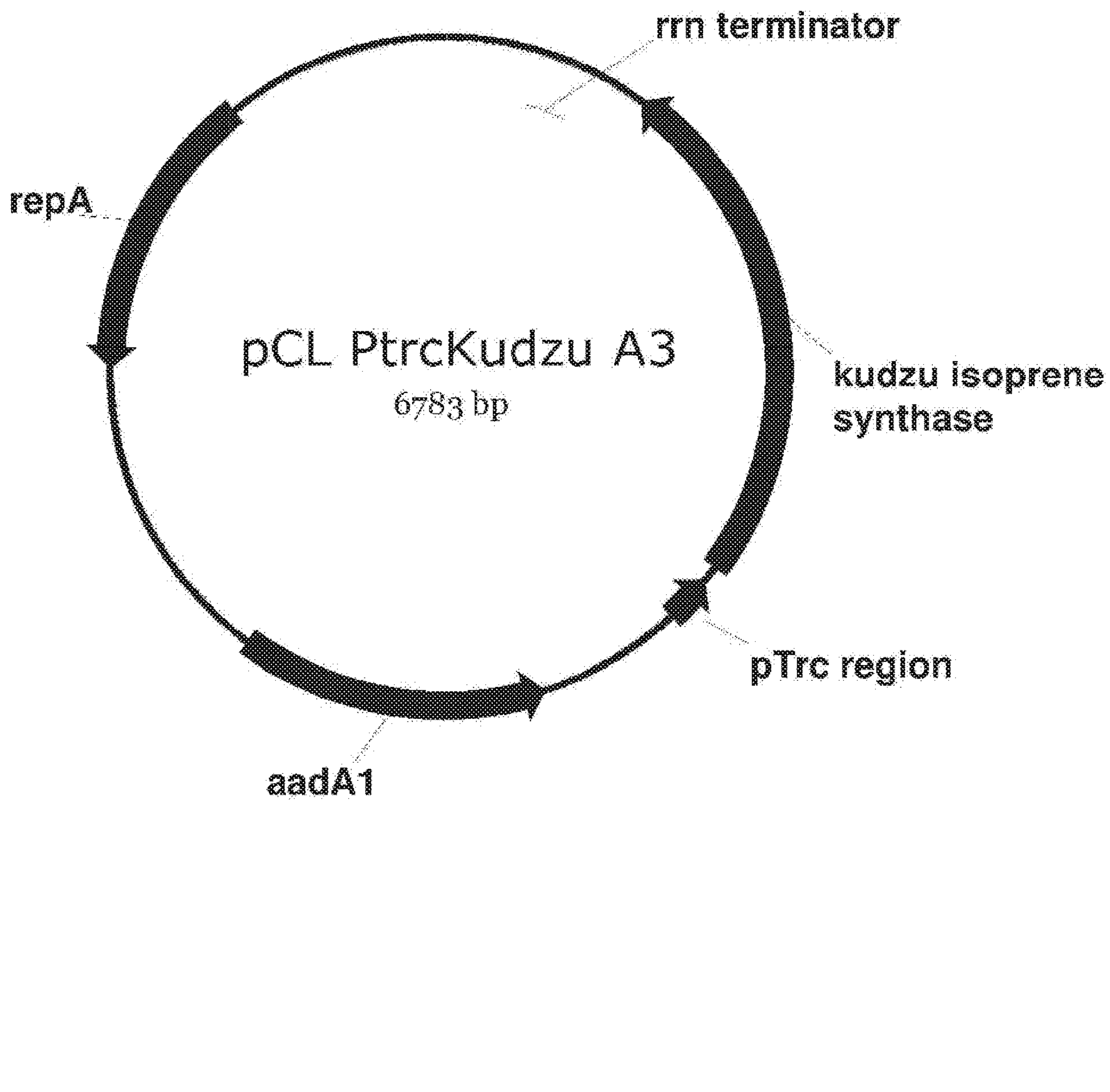
FIG. 40 is a map of pCL PtrcKudzu A3.

Plasmid pTrcKudzuKan was digested with PstI, treated with SAP, heat killed and gel purified. It was ligated to a PCR product encoding dxs from *E. coli* with a synthetic RBS. The primers for PCR were MCM13 5'-GATCATGCATTCGCCCTTAGGAGGTAAAAAAACATGAGTTTTGATATTGCCAAATACCCG (SEQ ID NO:18) and MCM14 5'-CATGCTGCAGTTATGCCAGCCAGGCCTTGAT (SEQ ID NO:19); and the template was *E. coli* genomic DNA. The PCR product was digested with NsiI and PstI and gel purified prior to ligation. The resulting transformation reaction was transformed into TOP10 cells and selected on LA with kanamycin 50 μg/ml. Several transformants were isolated and sequenced and the resulting plasmid was called pTrcKudzu-DXS(kan) (FIGS. 36 and 37).

iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAGGTAAAAAAACATGAGTTTTGATATTGCCAAATACCCG (SEQ ID NO:18) and MCM14 5'-CATGCTGCAGTTATGCCAGCCAGGCCTTGAT (SEQ ID NO:19); template TOP10 cells) which had been digested with NsiI and PstI and gel purified. The final plasmid was called pTrcKudzu-yIDI-dxs (kan) (FIGS. 21 and 22).

v) Construction of pCL PtrcKudzu

A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 μg/ml. Several clones were isolated and sequenced and two were selected. pCL PtrcKudzu and pCL PtrcKudzu (A3) have the insert in opposite orientations (FIGS. 38-41).

vi) Construction of pCL PtrcKudzu yIDI

Figure 42:
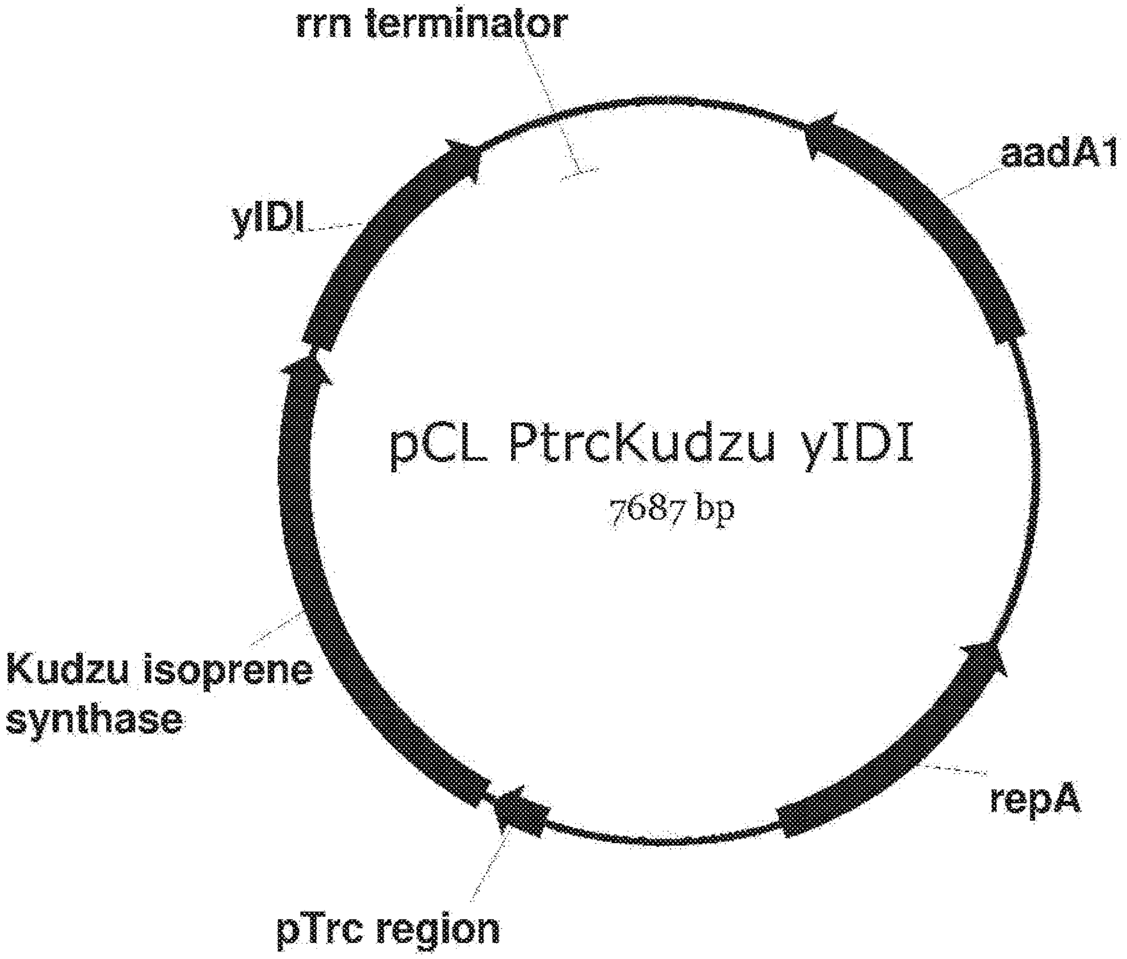
FIG. 42 is a map of pCL PtrcKudzu yIDI.

The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu yIDI (FIGS. 42 and 43).

vii) Construction of pCL PtrcKudzu DXS

Figure 44:
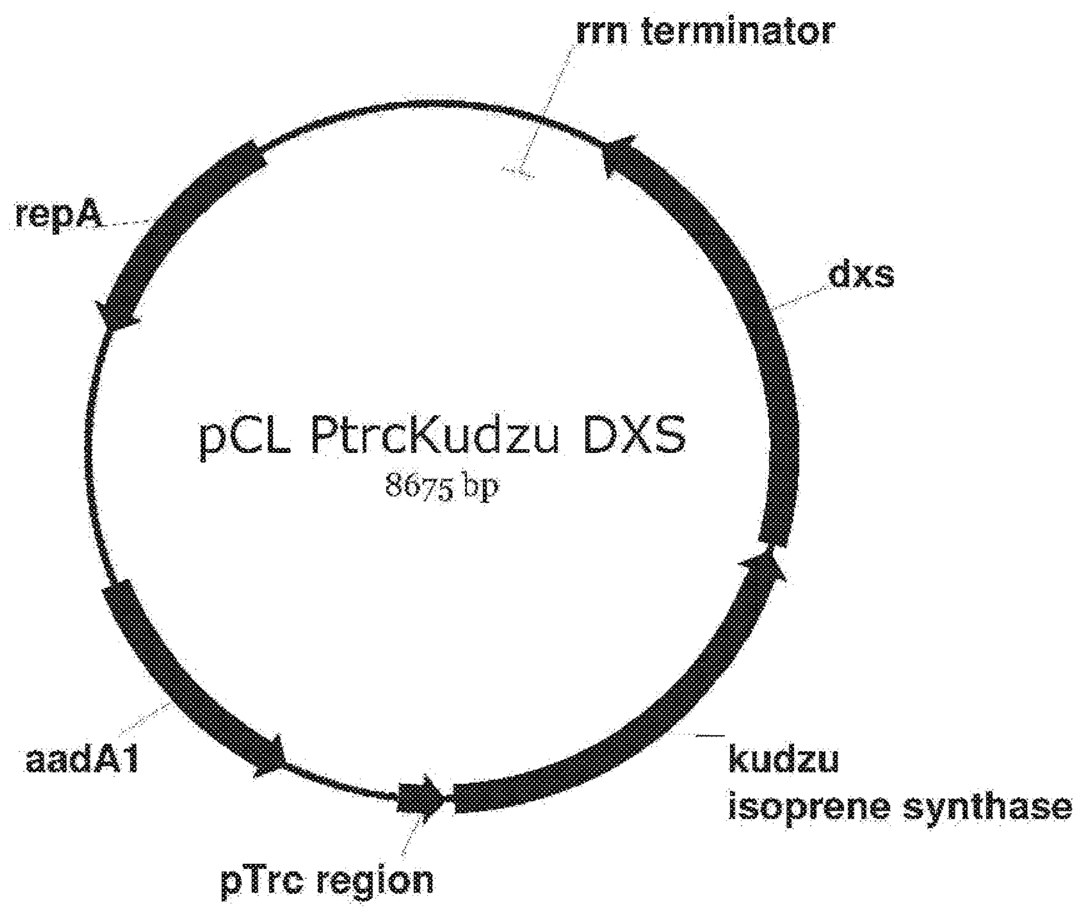
FIG. 44 is a map of pCL PtrcKudzu DXS.
Figure 46A:
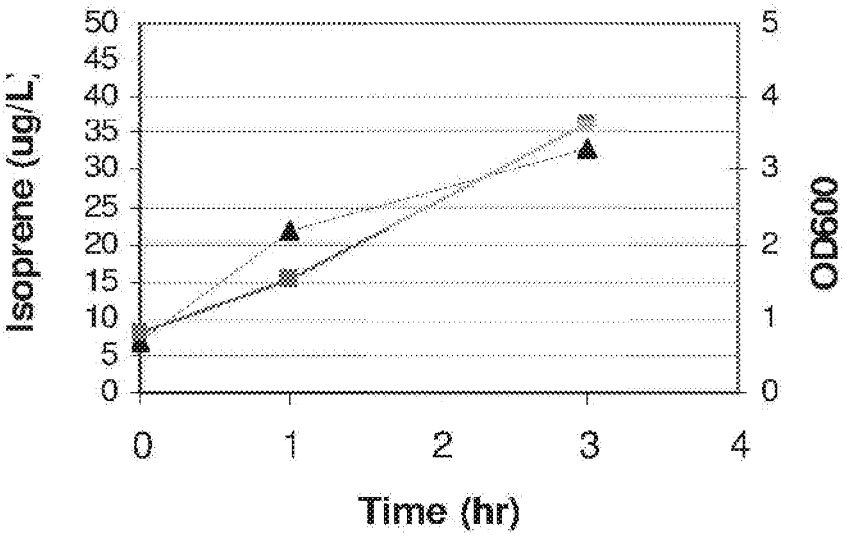
FIG. 46A, FIG. 46B, FIG. 46C, FIG. 46D, and FIG. 46E show graphs representing isoprene production from biomass feedstocks.
Figure 46B:
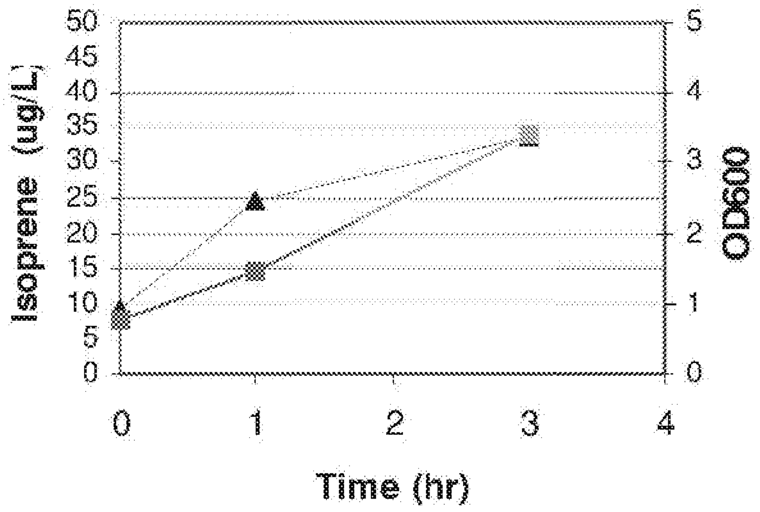
Figure 46C:
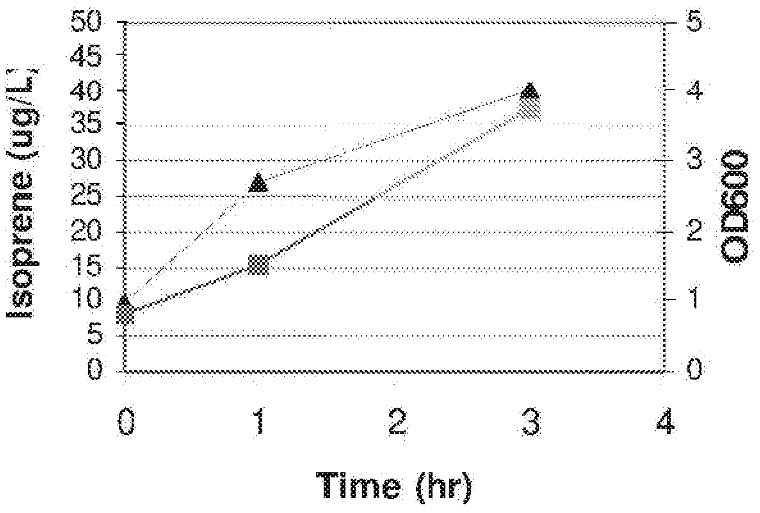
Figure 46D:
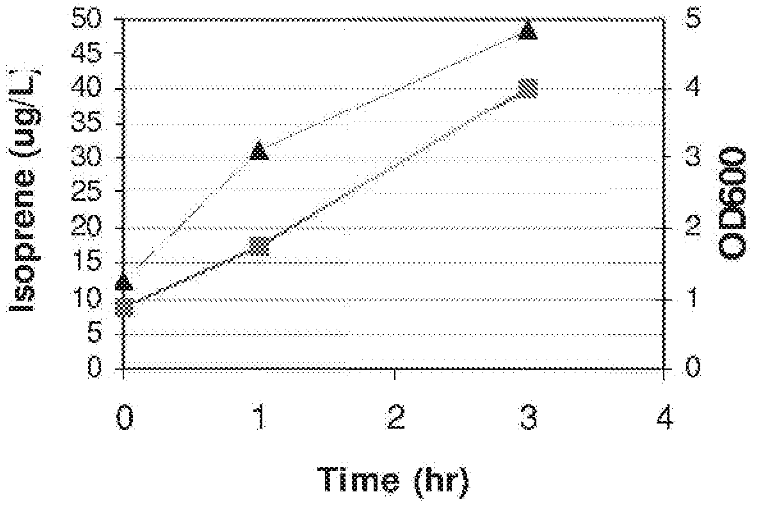
Figure 46E:
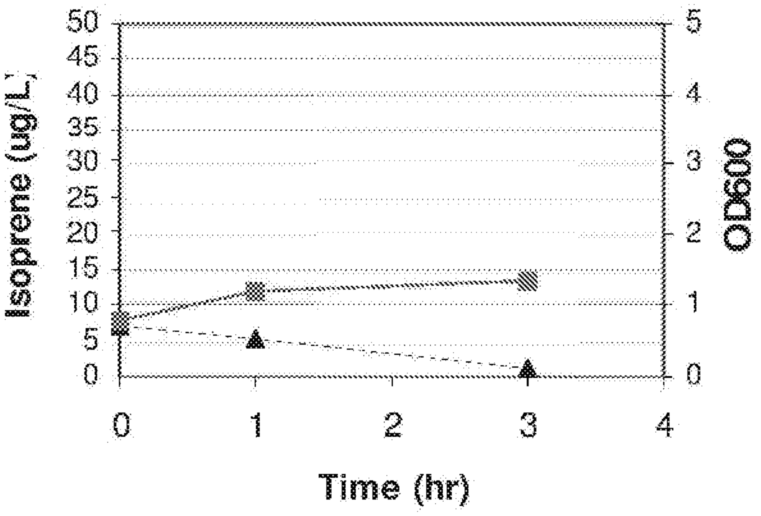

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu DXS (FIGS. 44 and 45).

II. Measurement of Isoprene in Headspace from Cultures Expressing Kudzu Isoprene Synthase, idi, and/or dxs at Different Copy Numbers.

Cultures of *E. coli* BL21(λDE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 μg/mL. Cultures of pCL PtrcKudzu (E), pCL PtrcKudzu, pCL PtrcKudzu-yIDI (F) and pCL PtrcKudzu-DXS (G) were grown in LB spectinomycin 50 μg/ml. Cultures were induced with 400 μM IPTG at time 0 ($OD_{600}$ approximately 0.5) and samples taken for isoprene headspace measurement (see Example 1). Results are shown in FIGS. 23A-23G.

Figure 23A:
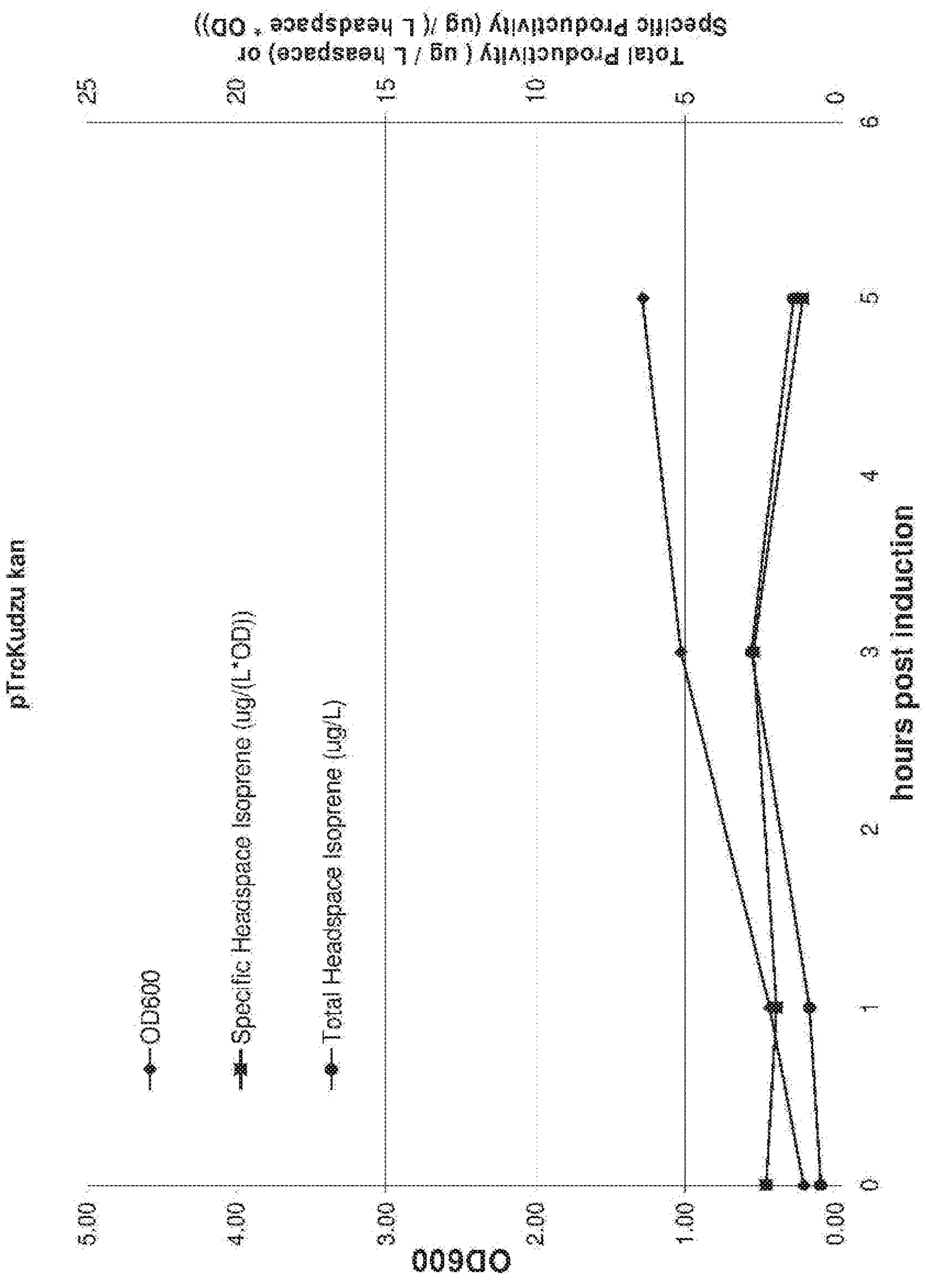
FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23B:
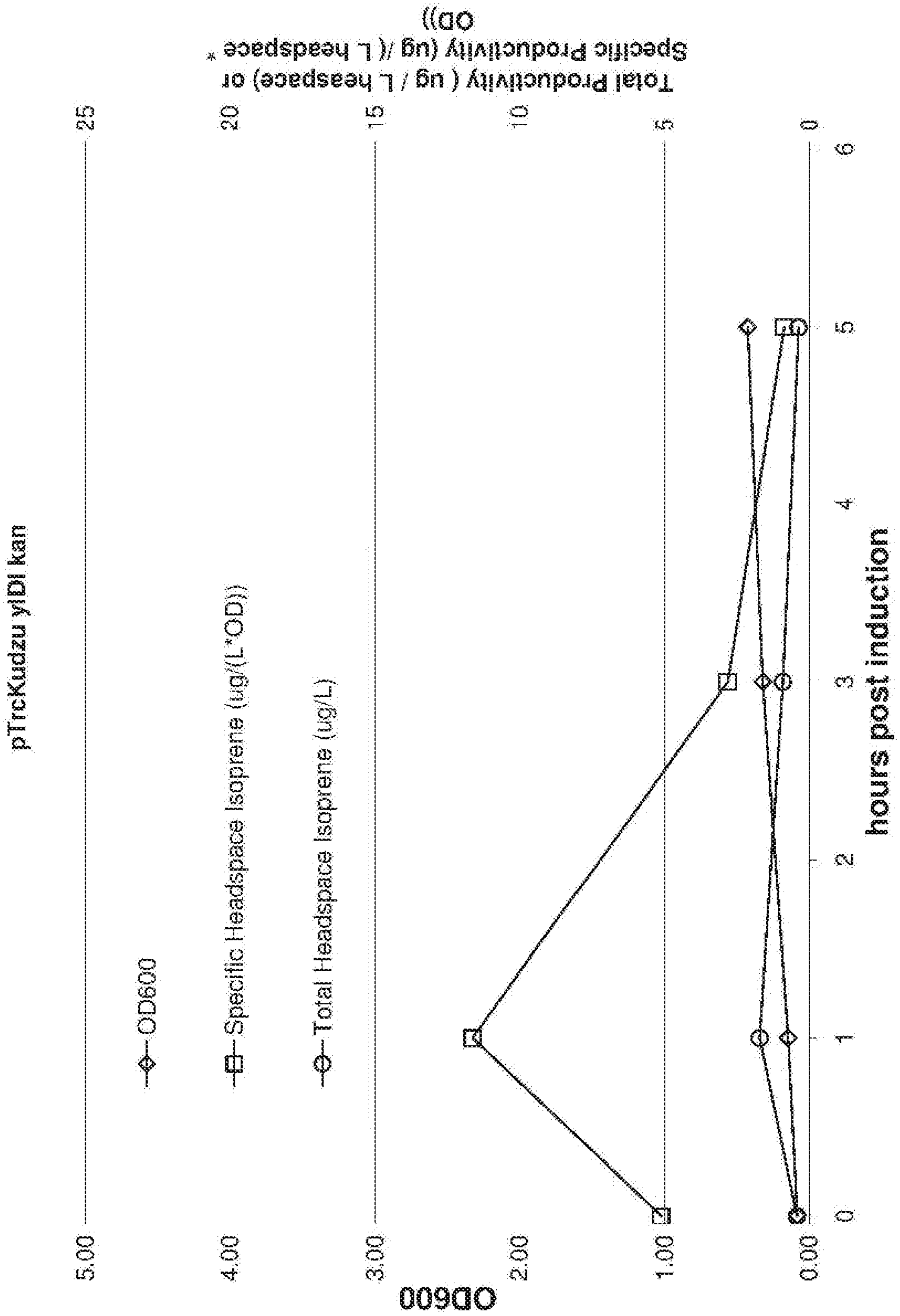
FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23C:
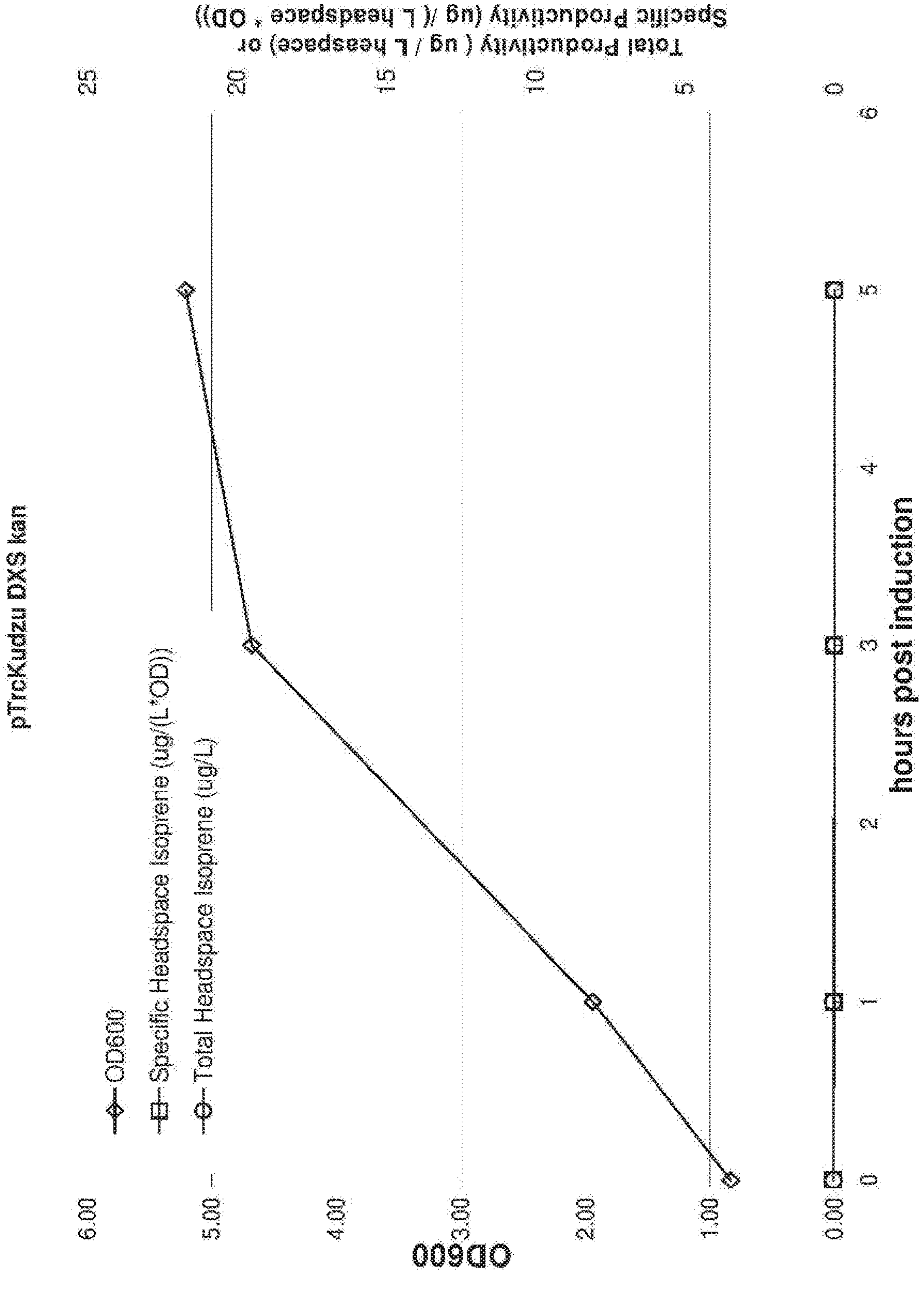
FIG. 23C is a graph showing production of isoprene from glucose in BL21/pTrcKudzu DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23D:
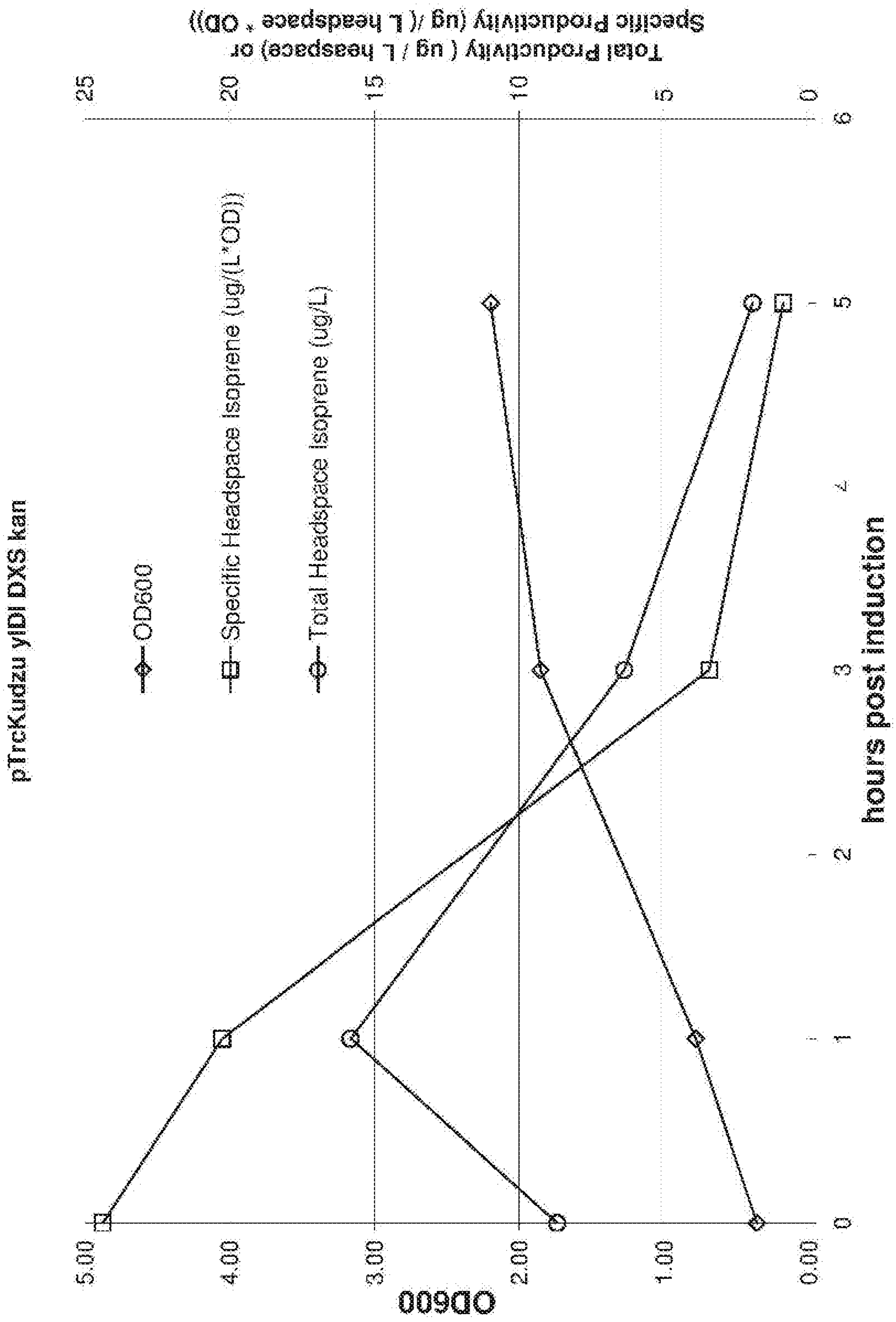
FIG. 23D is a graph showing production of isoprene from glucose in BL21/pTrcKudzu yIDI DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23E:
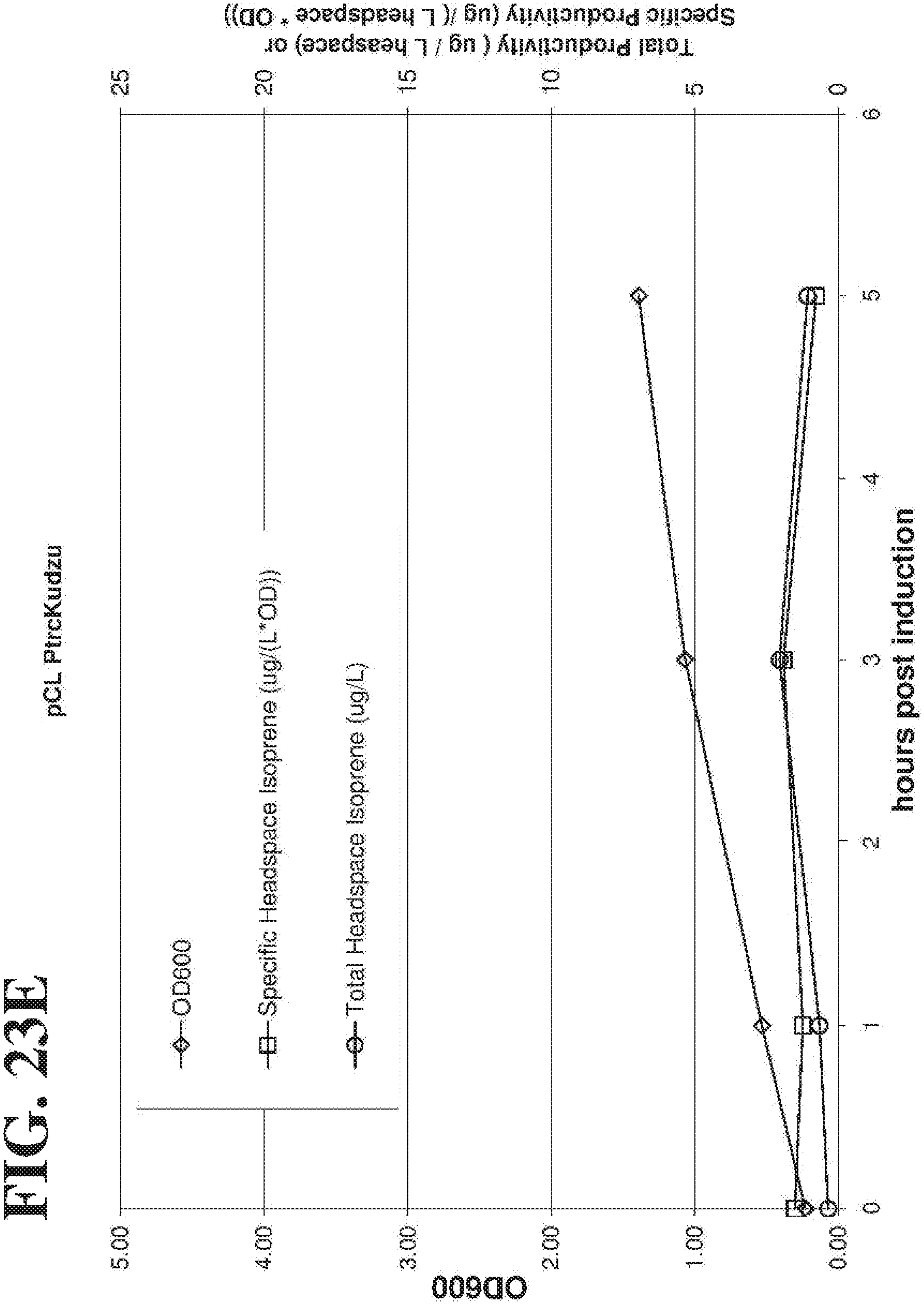
FIG. 23E is a graph showing production of isoprene from glucose in BL21/pCL PtrcKudzu. Time 0 is the time of induction with IPTG (400 μmol). The x-axis is time after induction; the y-axis is $OD_{600}$ and the y2-axis is total productivity of isoprene (μg/l headspace or specific productivity (μg/L headspace/OD). Diamonds represent $OD_{600}$, circles represent total isoprene productivity (μg/L) and squares represent specific productivity of isoprene (μg/L/OD).
Figure 23F:
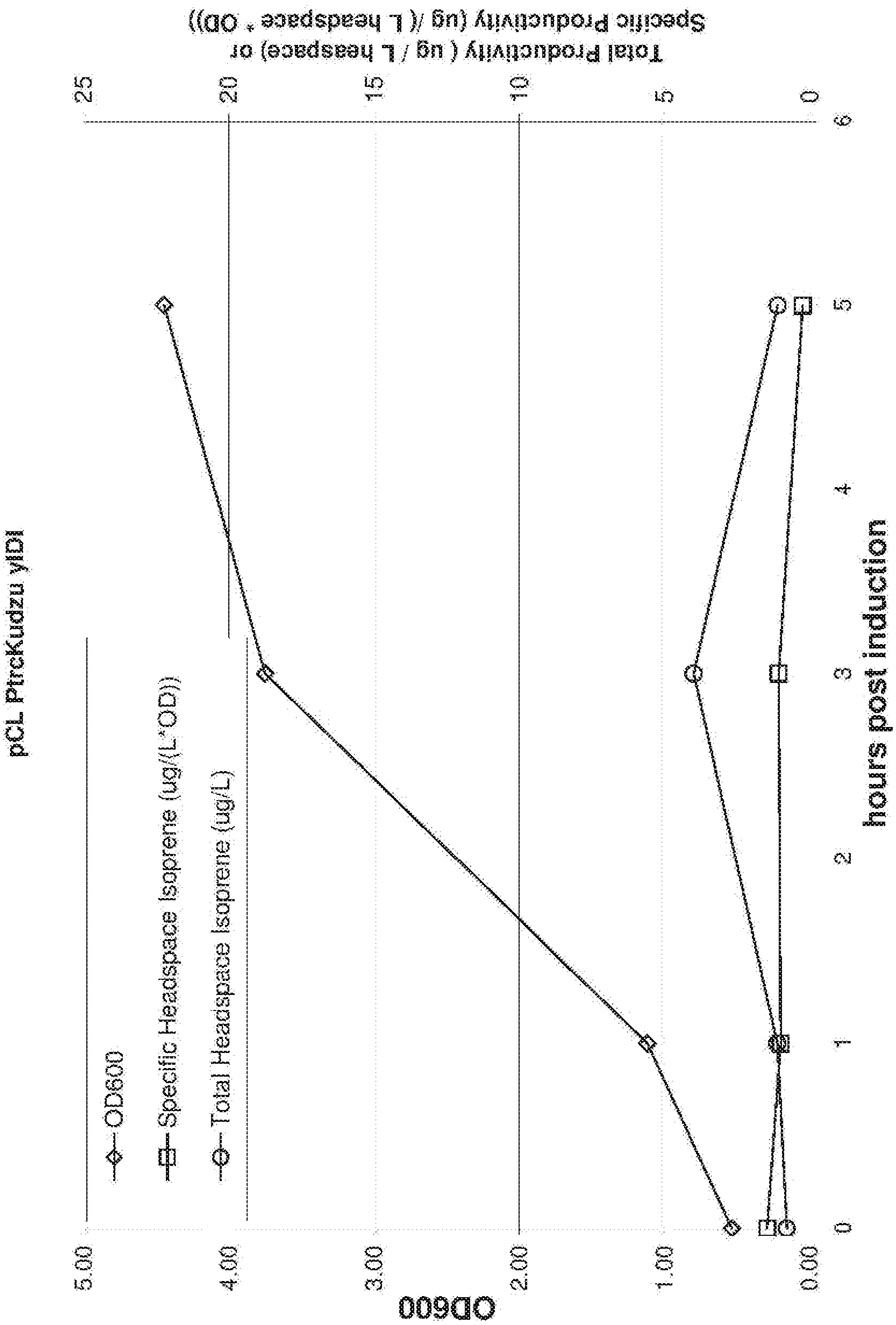
FIG. 23F is a graph showing production of isoprene from glucose in BL21/pCL PtrcKudzu yIDI. Time 0 is the time of induction with IPTG (400 μmol). The x-axis is time after induction; the y-axis is $OD_{600}$ and the y2-axis is total productivity of isoprene (μg/l headspace or specific productivity (μg/L headspace/OD). Diamonds represent $OD_{600}$, circles represent total isoprene productivity (μg/L) and squares represent specific productivity of isoprene (μg/l/OD).
Figure 23G:
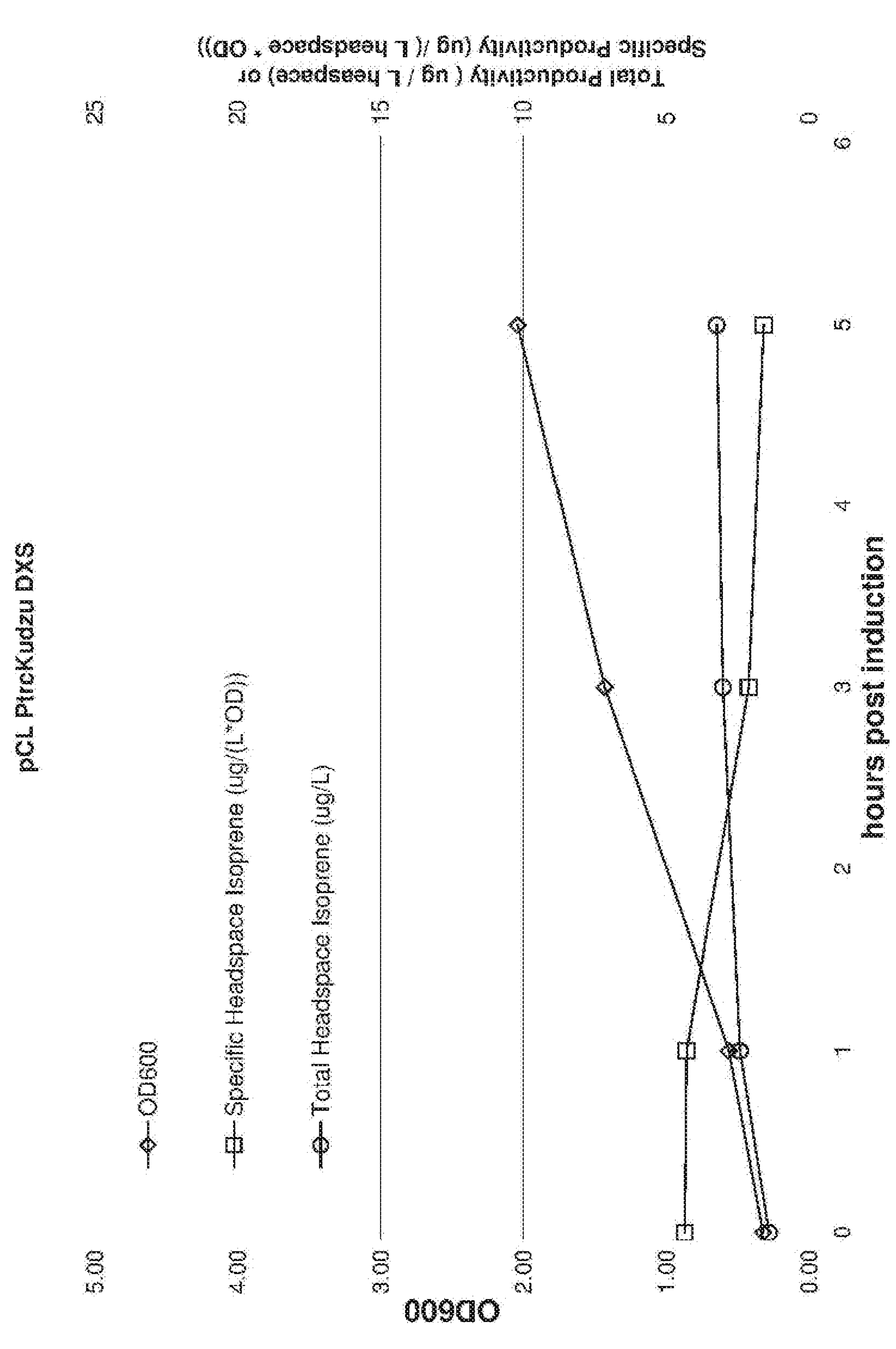
FIG. 23G is a graph showing production of isoprene from glucose in BL21/pCL PtrcKudzu DXS. Time 0 is the time of induction with IPTG (400 μmol). The x-axis is time after induction; the y-axis is $OD_{600}$ and the y2-axis is total productivity of isoprene (μg/l headspace or specific productivity (μg/L headspace/OD). Diamonds represent $OD_{600}$, circles represent total isoprene productivity (μg/L) and squares represent specific productivity of isoprene (μg/L/OD).
Figure 23H:
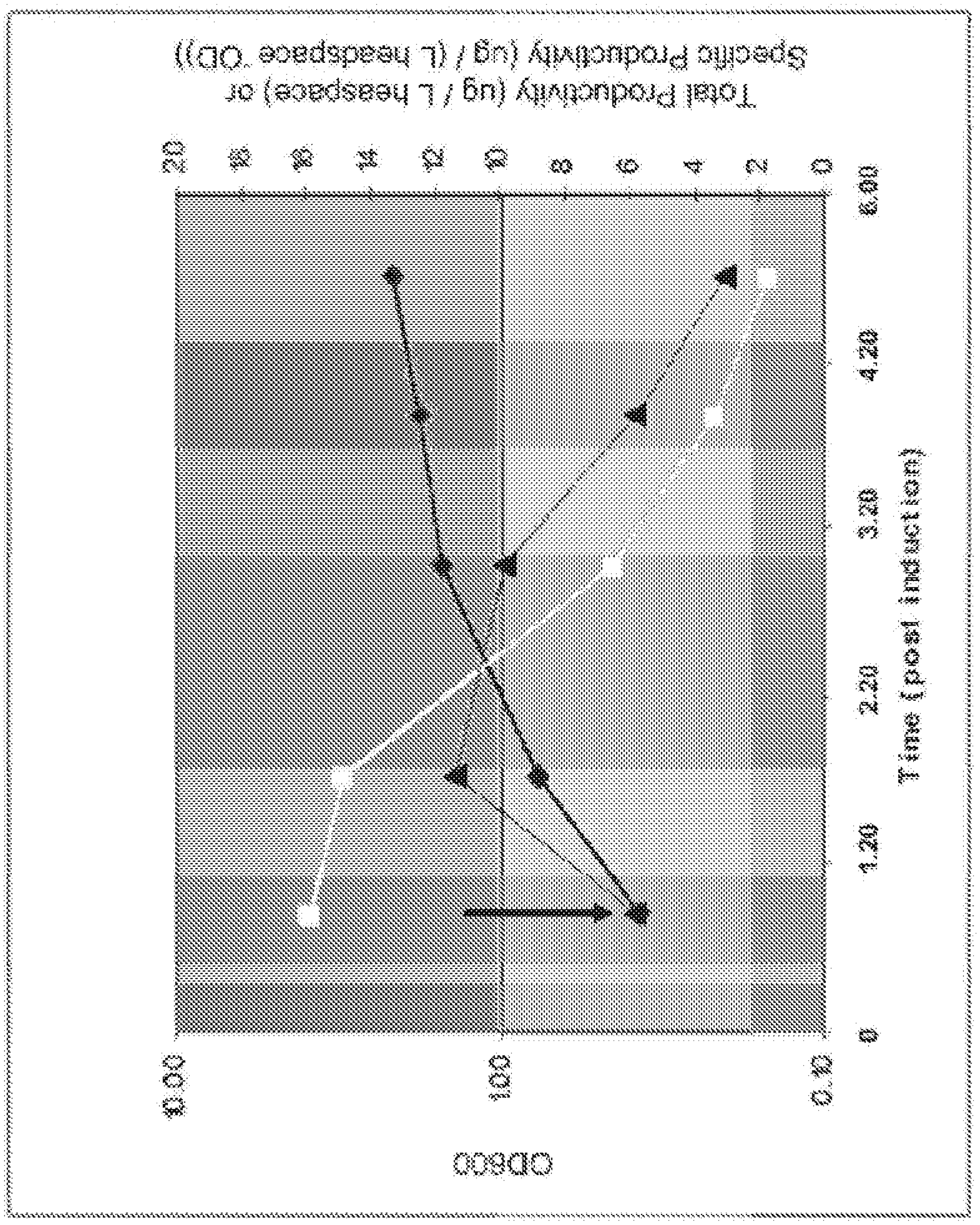
FIG. 23H is a graph showing production of isoprene from glucose in BL21/pTrcKudzuIDIDXSkan. The arrow indicates the time of induction with IPTG (400 μmol). The x-axis is time after induction; the y-axis is $OD_{600}$ and the y2-axis is total productivity of isoprene (μg/L headspace or specific productivity (μg/l headspace/OD). Black diamonds represent $OD_{600}$, black triangles represent isoprene productivity (μg/l) and white squares represent specific productivity of isoprene (μg/l/OD).

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 μg/ml) at 20° C. and used to inoculate shake flasks of TM3 (13.6 g $K_2PO_4$, 13.6 g $KH_2PO_4$, 2.0 g $MgSO_4{*}7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 μM IPTG. Samples were taken at various times after induction and the amount of isoprene in the head space was measured as described in Example 1. Results are shown in FIG. 23H.

III. Production of Isoprene from Biomass in *E. coli*/pTrcKudzu yIDI DXS

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 μg/ml). The culture was incubated overnight at 25° C. with shaking. The following day the overnight culture was diluted to an $OD_{600}$ of 0.05 in 25 ml of TM3 and 0.2% YE and 1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 46.

IV. Production of Isoprene from Invert Sugar in *E. coli*/pTrcKudzuIDIDXS

A single colony from a plate freshly transformed cells of BL21 (λDE3)/pTrcKudzu yIDI DXS (kan) was used to inoculate 5 mL of LB and kanamycin (50 μg/ml). The culture was incubated overnight at 25° C. with shaking. The following day the overnight culture was diluted to an $OD_{600}$ of 0.05 in 25 ml of TM3 and 0.2% YE and 1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$~0.8-1.0 (0 hour). The cultures were analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. coli* Grown in Fed-batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

VII. Production of Isoprene in 500 L Fermentation of pTrcKudzu DXS yIDI

A 500 liter fermentation of *E. coli* cells with a kudzu isoprene synthase, *S. cerevisiae* IDI, and *E. coli* DXS nucleic acids (*E. coli* BL21 (λDE3) pTrc Kudzu dxs yidi) was used to produce isoprene. The levels of isoprene varied from 50 to 300 μg/l over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of *E. coli* Grown in Fed-batch Culture Medium Recipe (Per Liter Fermentation Medium):

$K_2HPO_4$ 7.5 g, $MgSO_4$*7$H_2O$ 2 g, citric acid monohydrate 2 g, ferric ammonium citrate 0.3 g, yeast extract 0.5 g, 1000× Modified Trace Metal Solution 1 ml. All of the components were added together and dissolved in di$H_2O$. This solution was autoclaved. The pH was adjusted to 7.0 with ammonium gas ($NH_3$) and q.s. to volume. Glucose 10 g, thiamine*HCl 0.1 g, and antibiotic were added after sterilization and pH adjustment.

1000× Modified Trace Metal Solution:

Citric Acids*$H_2O$ 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BO_3$ 100 mg, $NaMoO_4$*2$H_2O$ 100 mg. Each component is dissolved one at a time in DI $H_2O$, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 49A:
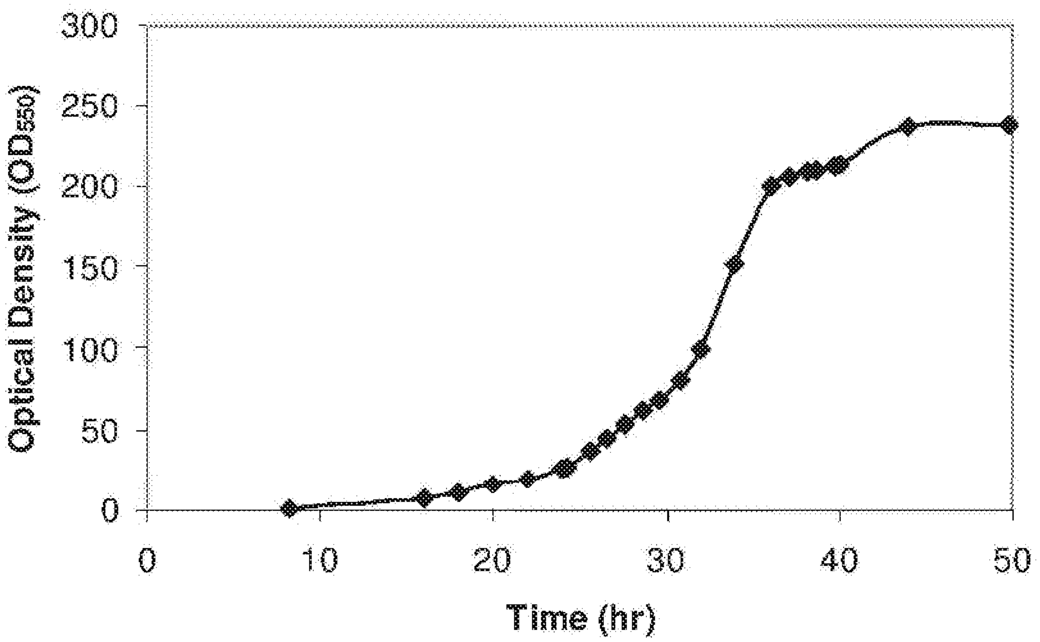
FIGS. 49A, 49B, and 49C show graphs demonstrating isoprene production from a 500 L bioreactor with *E. coli* cells containing the pTrcKudzu and yIDI and DXS plasmid.
Figure 49B:
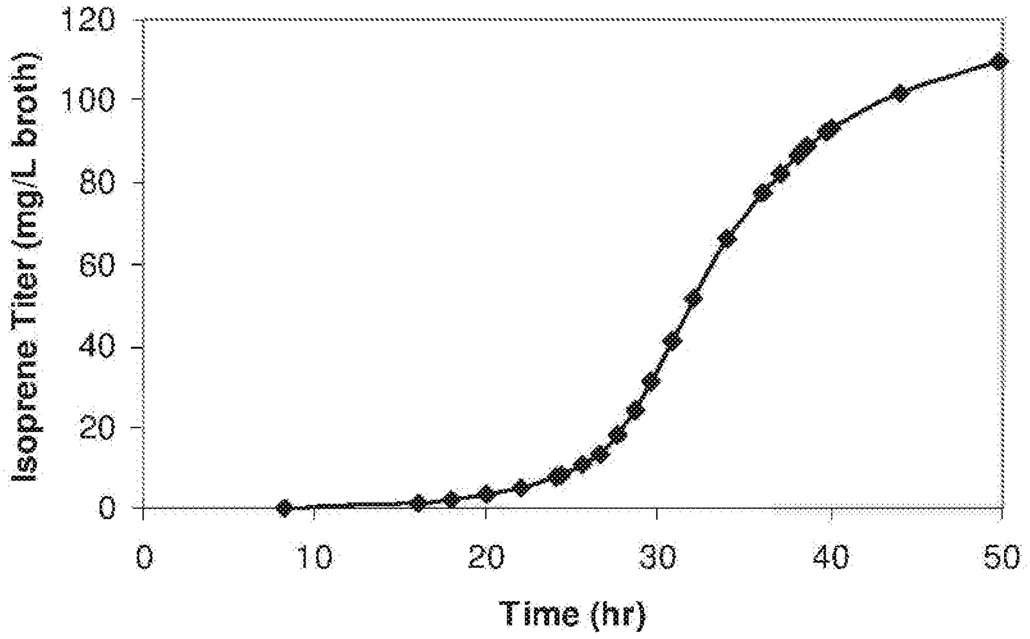
Figure 49C:
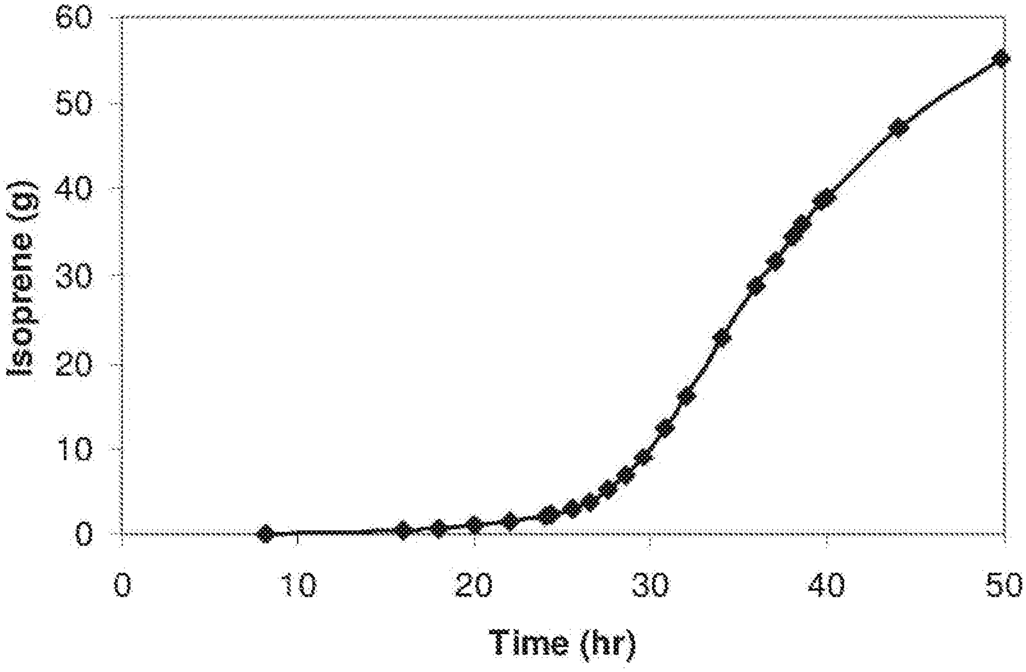

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described. The isoprene titer increased over the course of the fermentation (FIG. 49B). The total amount of isoprene produced during the 50 hour fermentation was 55.1 g and the time course of production is shown in FIG. 49C.

Example 8: Production of Isoprene in *E. coli* Expressing Kudzu Isoprene Synthase and Recombinant Mevalonic Acid Pathway Genes I. Cloning the Lower MVA Pathway The strategy for cloning the lower mevalonic pathway was as follows. Four genes of the mevalonic acid biosynthesis pathway; mevalonate kinase (MVK), phosphomevalonate kinase (PMK), diphosphomevalonte decarboxylase (MVD) and isopentenyl diphosphate isomerase genes were amplified by PCR from *S. cerevisiae* chromosomal DNA and cloned individually into the pCR BluntII TOPO plasmid (Invitrogen). In some cases, the idi gene was amplified from *E. coli* chromosomal DNA. The primers were designed such that an *E. coli* consensus RBS (AGGAGGT (SEQ ID NO:80) or AAGGAGG (SEQ ID NO:81)) was inserted at the 5' end, 8 bp upstream of the start codon and a PstI site was added at the 3' end. The genes were then cloned one by one into the pTrcHis2B vector until the entire pathway was assembled.

Chromosomal DNA from *S. cerevisiae* S288C was obtained from ATCC (ATCC 204508D). The MVK gene was amplified from the chromosome of *S. cerevisiae* using primers MVKF (5'-AGGAGGTAAAAAAACATGTCATTACCGTTCTTAACTTCTGC, SEQ ID NO:21) and MVK-PstI-R (5'-ATGGCTGCAGGCCTATCGCAAATTAGCT- TATGAAGTCCATGGTAAATTCGTG, SEQ ID NO:22) using PfuTurbo as per manufacturer's instructions. The correct sized PCR product (1370 bp) was identified by electrophoresis through a 1.2% E-gel (Invitrogen) and cloned into pZeroBLUNT TOPO. The resulting plasmid was designated pMVK1. The plasmid pMVK1 was digested with SacI and Taq1 restriction endonucleases and the fragment was gel purified and ligated into pTrcHis2B digested with SacI and BstBI. The resulting plasmid was named pTrc-MVK1.

The second gene in the mevalonic acid biosynthesis pathway, PMK, was amplified by PCR using primers: PstI-PMK1 R (5'-GAATTCGCCCTTCTGCAGCTACC, SEQ ID NO:23) and BsiHKA I-PMK1 F (5'-CGACTGGTGCAC-CCTTAAGGAGGAAAAAAACATGTCAG, SEQ ID NO:24). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK. The MVD and the idi genes were cloned in the same manner. PCR was carried out using the primer pairs PstI-MVD 1 R (5'-GTGCTGGAATTCGCCCTTCTGCAGC, SEQ ID NO:25) and NsiI-MVD 1 F (5'-GTAGATGCATGCAGAATTCGC-CCTTAAGGAGG, SEQ ID NO:26) to amplify the MVD gene and PstI-YIDI 1 R (5'-CCTTCTGCAGGACGCGTT-GTTATAGC, SEQ ID NO:27) and NsiI-YIDI 1 F (5'-CATCAATGCATCGCCCTTAGGAGGTAAAAAAAAAT-GAC, SEQ ID NO:28) to amplify the yIDI gene. In some cases the IPP isomerase gene, idi from *E. coli* was used. To amplify idi from *E. coli* chromosomal DNA, the following primer set was used: PstI-CIDI 1 R (5'-GTGTGATGGA-TATCTGCAGAATTCG, SEQ ID NO:29) and NsiI-CIDI 1 F (5'-CATCAATGCATCGCCCTTAGGAGGTAAAA-AAACATG, SEQ ID NO:30). Template DNA was chromosomal DNA isolated by standard methods from *E. coli* FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the *E. coli* idi gene. The plasmids were transformed into *E. coli* hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 bp fragment was separated on a 1.2% agarose E-gel and purified using the Qiagen Gel Purification kit according to the manufacturer's instructions. The plasmid pTrcKudzuKan, described in Example 7, was digested with restriction endonucleases ApaI and PstI, and the 3338 bp fragment containing the vector was purified from a 1.2% E-gel using the Qiagen Gel Purification kit. The 3338 bp vector fragment and the 5930 bp lower MVA pathway fragment were ligated using the Roche Quick Ligation kit. The ligation mix was transformed into *E. coli* TOP10 cells and tranformants were grown at 37° C. overnight with selection on LA containing kanamycin (50 μg/ml). The transformants were verified by restriction enzyme digestion and one was frozen as a stock. The plasmid was designated pTrcKanKKDIy.

II. Cloning a Kudzu Isoprene Synthase Gene into pTrcK-anKKDIy

The kudzu isoprene synthase gene was amplified by PCR from pTrcKudzu, described in Example 1, using primers MCM50 5'-GATCATGCATTCGCCCTTAGGAGG-TAAAAAAACATGTGTGCGACCTCTTCTCAATTTACT (SEQ ID NO:31) and MCM53 5'-CGGTCGACGGATC-CCTGCAGTTAGACATACATCAGCTG (SEQ ID NO:32). The resulting PCR fragment was cloned into pCR2.1 and transformed into *E. coli* TOP10. This fragment contains the coding sequence for kudzu isoprene synthase and an upstream region containing a RBS from *E. coli*. Transformants were incubated overnight at 37° C. with selection on LA containing carbenicillin (50 μg/ml). The correct insertion of the fragment was verified by sequencing and this strain was designated MCM93.

Figure 24:
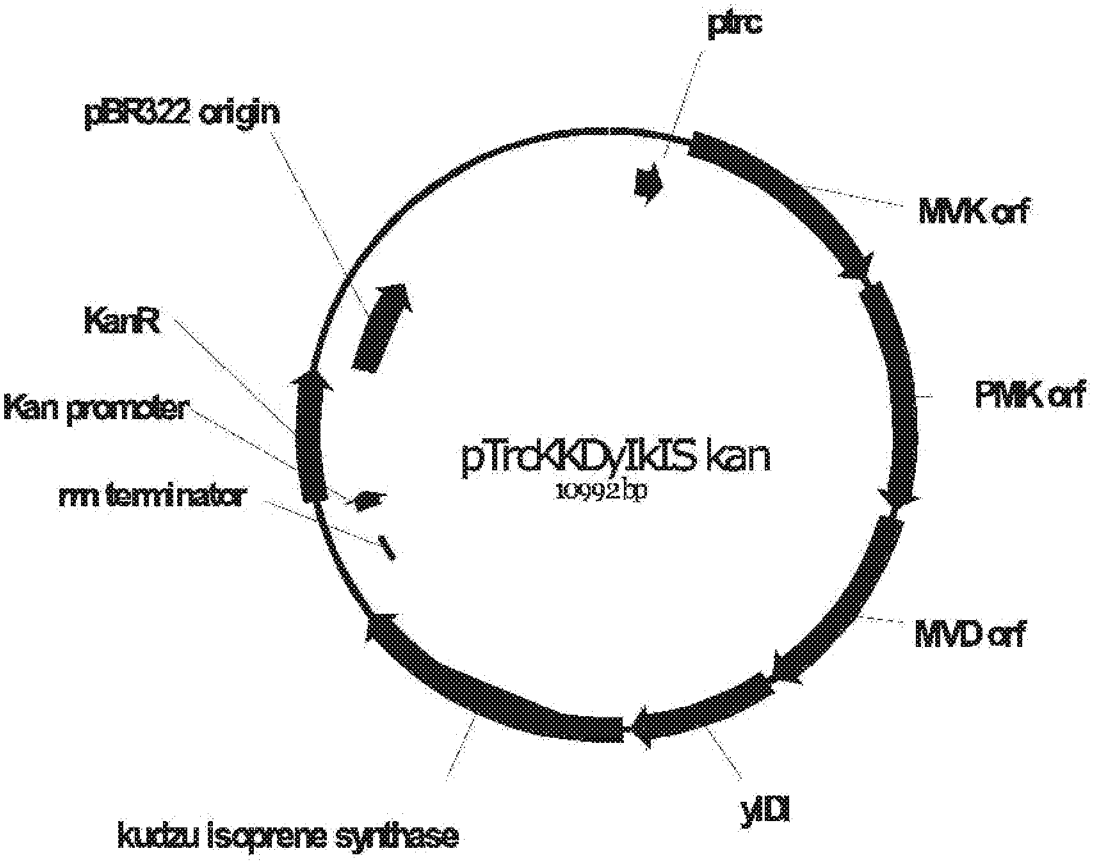
FIG. 24 is a map of pTrcKKDyIkIS kan.

The plasmid from strain MCM93 was digested with restriction endonucleases NsiI and PstI to liberate a 1724 bp insert containing the RBS and kudzu isoprene synthase. The 1724 bp fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into *E. coli* TOP10 cells and transformants were grown overnight at 37° C. with selection on LA containing Kanamycin at 50 μg/ml. The correct transformant was verified by restriction digestion and the plasmid was designated pTrcKKDyIkISKan (FIGS. 24 and 25). This plasmid was transformed into BL21(λDE3) cells (Invitrogen).

III. Isoprene Production from Mevalonate in *E. coli* Expressing the Recombinant Lower Mevalonate Pathway and Isoprene Synthase from Kudzu.

Strain BL21/pTrcKKDyIkISKan was cultured in MOPS medium (Neidhardt et al., (1974) *J. Bacteriology* 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 μM IPTG when the culture had reached an $OD_{600}$ of 0.3 to 0.5. The cultures were grown at 30° C. with shaking at 250 rpm. The production of isoprene was analyzed 3 hours after induction by using the head space assay described in Example 1. Maximum production of isoprene was $6.67\times10^4$ nmol/$L_{broth}$/$OD_{600}$/hr where $L_{broth}$ is the volume of broth and includes both the volume of the cell medium and the volume of the cells. The control culture not supplemented with mevalonic acid did not produce measurable isoprene.

IV. Cloning the Upper MVA Pathway

The upper mevalonate biosynthetic pathway, comprising two genes encoding three enzymatic activities, was cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from *E. faecalis* genomic DNA (ATCC 700802D-5) with an *E. coli* ribosome binding site and a spacer in front using the following primers:

CF 07-60 (+) Start of mvaE w/RBS+ATG start codon SacI (SEQ ID NO: 34)
5'-GAGACATGAGCTCAGGAGGTAAAAAAACATGAAAACAGTAGTTATT

ATTG

CF 07-62 (−) Fuse mvaE to mvaS with RBS in between (SEQ ID NO: 35)
5'-TTTATCAATCCCAATTGTCATGTTTTTTTACCTCCTTTATTGTTTT

CTTAAATC

The mvaS gene was amplified from *E. faecalis* genomic DNA (ATCC 700802D-5) with a RBS and spacer from *E. coli* in front using the following primers:

CF 07-61 (+) Fuse mvaE to mvaS with RBS in between (SEQ ID NO: 36)
5'-GATTTAAGAAAACAATAAAGGAGGTAAAAAAACATGACAATTGGGA

TTGATAAA

CF 07-102 (−) End of mvaS gene BglII (SEQ ID NO: 37)
5'-GACATGACATAGATCTTTAGTTTCGATAAGAACGAACGGT The PCR fragments were fused together with PCR using the following primers:

CF 07-60 (+) Start of mvaE w/RBS+ATG start codon SacI (SEQ ID NO: 34)
5'-GAGACATGAGCTCAGGAGGTAAAAAAACATGAAAACAGTAGTTATT

ATTG

CF 07-102 (−) End of mvaS gene BglII (SEQ ID NO: 37)
5'-GACATGACATAGATCTTTAGTTTCGATAAGAACGAACGGT The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into *E. coli* Top 10 cells and colonies were selected on LA and 50 μg/ml carbenicillin plates. A total of six colonies were chosen and grown overnight in LB and 50 μg/ml carbenicillin and plasmids were isolated using a Qiagen kit. The plasmids were digested with SacI and BglII to check for inserts and one correct plasmid was sequenced with the following primers:

CF 07-58 (+) Start of mvaE gene (SEQ ID NO: 38)
5'-ATGAAAACAGTAGTTATTATTGATGC

CF 07-59 (−) End of mvaE gene (SEQ ID NO: 39)
5'-ATGTTATTGTTTTCTTAAATCATTTAAAATAGC CF 07-82 (+) Start of mvaS gene (SEQ ID NO: 40)
5'-ATGACAATTGGGATTGATAAAATTAG CF 07-83 (−) End of mvaS gene (SEQ ID NO: 41)
5'-TTAGTTTCGATAAGAACGAACGGT CF 07-86 (+) Sequence in mvaE (SEQ ID NO: 42)
5'-GAAATAGCCCCATTAGAAGTATC CF 07-87 (+) Sequence in mvaE (SEQ ID NO: 43)
5'-TTGCCAATCATATGATTGAAAATC CF 07-88 (+) Sequence in mvaE (SEQ ID NO: 44)
5'-GCTATGCTTCATTAGATCCTTATCG CF 07-89 (+) Sequence mvaS (SEQ ID NO: 45)
5'-GAAACCTACATCCAATCTTTTGCCC The plasmid called pTrcHis2AUpperPathway #1 was correct by sequencing and was transformed into the commercially available *E. coli* strain BL21. Selection was done on LA and 50 μg/ml carbenicillin. Two transformants were chosen and grown in LB and 50 μg/ml carbenicillin until they reached an $OD_{600}$ of 1.5. Both strains were frozen in a vial at −80° C. in the presence of glycerol. Strains were designated CF 449 for pTrcHis2AUpperPathway #1 in BL21, isolate #1 and CF 450 for pTrcHis2AUpperPathway #1 in BL21, isolate #2. Both clones were found to behave identically when analyzed.

V. Cloning of UpperMVA Pathway into pCL1920

Figure 26:
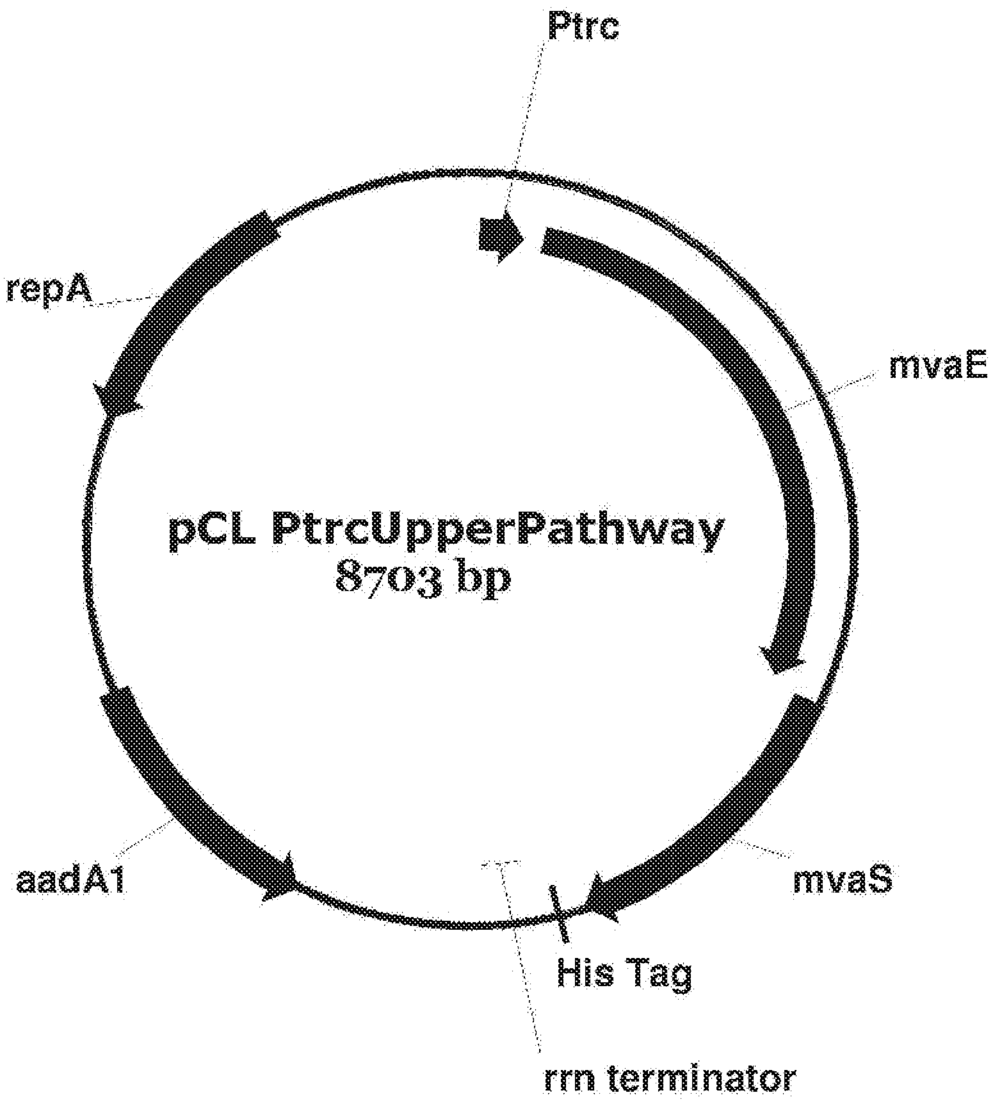
FIG. 26 is a map of pCL PtrcUpperPathway.

The plasmid pTrcHis2AUpperPathway was digested with the restriction endonuclease SspI to release a fragment containing pTrc-mvaE-mvaS-(His tag)-terminator. In this fragment, the his tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP10 chemically competent cells. Transformants were selected on LA containing spectinomycin (50 μg/ml). A correct colony was identified by screening for the presence of the insert by PCR. The plasmid was designated pCL PtrcUpperPathway (FIGS. 26 and 27).

VI. Strains Expressing the Combined Upper and Lower Mevalonic Acid Pathways

To obtain a strain with a complete mevalonic acid pathway plus kudzu isoprene synthase, plasmids pTrcKKDyIkI-Skan and pCLpTrcUpperPathway were both transformed into BL21(λDE3) competent cells (Invitrogen) and transformants were selected on LA containing kanamycin (50

μg/ml) and Spectinomycin (50m/ml). The transformants were checked by plasmid prep to ensure that both plasmids were retained in the host. The strain was designated MCM127.

VII. Production of Mevalonic Acid from Glucose in *E. coli*/pUpperpathway

Single colonies of the BL21/pTrcHis2A-mvaE/mvaS or FM5/p pTrcHis2A-mvaE/mvaS are inoculated into LB and carbenicillin (100 μg/ml) and are grown overnight at 37° C. with shaking at 200 rpm. These cultures were diluted into 50 ml medium in 250 ml baffled flasks to an $OD_{600}$ of 0.1. The medium was TM3, 1 or 2% glucose, carbenicillin (100 ug/ml) or TM3, 1% glucose. hydrolyzed soy oil, and carbenicillin (100 ug/ml) or TM3 and biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 μM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in *E. coli.*

VIII. Production of Isoprene from *E. coli* BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 7. The host cells used were chemically competent BL21 (λDE3) and the transformations were done by standard methods. Transformants were selected on L agar containing kanamycin (50 μg/ml) or kanamycin plus spectinomycin (both at a concentration of 50 μg/ml). Plates were grown at 37° C. The resulting strains were designated as follows:

Grown on Kanamycin plus Spectinomycin (50 μg/ml each)

MCM127—pCL Upper MVA and pTrcKKDyIkIS (kan) in BL21(λDE3)

MCM131—pCL1920 and pTrcKKDyIkIS (kan) in BL21 (λDE3)

MCM125—pCL Upper MVA and pTrcHis2B (kan) in BL21 (λDE3)

Grown on Kanamycin (50 μg/ml)

MCM64—pTrcKudzu yIDI DXS (kan) in BL21(λDE3)

MCM50—pTrcKudzu (kan) in BL21(λDE3)

MCM123—pTrcKudzu yIDI DXS DXR (kan) in BL21 (λDE3)

The above strains were streaked from freezer stocks to LA and appropriate antibiotic and grown overnight at 37° C. A single colony from each plate was used to inoculate shake flasks (25 ml LB and the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB and the appropriate antibiotic. The cultures were then diluted into 25 ml LB, % glucose, and the appropriate antibiotic to an $OD_{600}$ of 0.1. Two flasks for each strain were set up, one set for induction with IPTG (800 μM) the second set was not induced. The cultures were incubated at 37° C. with shaking at 250 rpm. One set of the cultures were induced after 1.50 hours (immediately following sampling time point 1). At each sampling time point, the $OD_{600}$ was measured and the amount of isoprene determined as described in Example 1. Results are presented in Table 3. The amount of isoprene made is presented as the amount at the peak production for the particular strain.

TABLE 3

Production of isoprene in *E. coli* strains

| Strain | Isoprene (μg/$L_{broth}$/hr/OD |
|---|---|
| MCM50 | 23.8 |
| MCM64 | 289 |
| MCM125 | ND |
| MCM131 | Trace |
| MCM127 | 874 |

ND: not detected

Trace: peak present but not integrable.

IX. Analysis of Mevalonic Acid

Mevalonolactone (1.0 g, 7.7 mmol) (CAS #503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1H$ NMR analysis. Samples for HPLC analysis were prepared by centrifugation at 14,000 rpm for 5 minutes to remove cells, followed by the addition of a 300 μl aliquot of supernatant to 900 μl of $H_2O$. Perchloric acid (36 μl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+ column (300 mm by 7.0 mm) eluted with 5 mM sulfuric acid at 0.6 mL/min with refractive index (RI) detection. Under these conditions mevalonic acid eluted as the lactone form at 18.5 minutes.

Example 9. Construction of the Upper and Lower MVA Pathway for Integration into *Bacillus subtilis*

I. Construction of the Upper MVA Pathway in *Bacillus subtilis*

The upper pathway from *Enterococcus faecalis* is integrated into *B. subtilis* under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allow them to be fused together by a PCR reaction. PCR amplifications are carried out using Herculase polymerase according to manufacturer's instructions.

1: PaprE

CF 07-134 (+) Start of aprE promoter PstI (SEQ ID NO: 82)
5'-GACATCTGCAGCTCCATTTTCTTCTGC CF 07-94 (–) Fuse PaprE to mvaE (SEQ ID NO: 83)
5'-CAATAATAACTACTGTTTTCACTCTTTACCCTCTCCTTTTAA Template: *Bacillus subtilis* chromosomal DNA 2: mvaE CF 07-93 (+) fuse mvaE to the aprE promoter (GTG start codon)

(SEQ ID NO: 84)
5'-TTAAAAGGAGAGGGTAAAGAGTGAAAACAGTAGTTATTATTG

CF 07-62 (–) Fuse mvaE to mvaS with RBS in between (SEQ ID NO: 35)
5'-TTTATCAATCCCAATTGTCATGTTTTTTTACCTCCTTTATTGTTTTC

TTAAATC

Template: *Enterococcus faecalis* chromosomal DNA (from ATCC)

3. mvaS

CF 07-61 (+) Fuse mvaE to mvaS with RBS in between (SEQ ID NO: 36)
5'-GATTTAAGAAAACAATAAAGGAGGTAAAAAAACATGACAATTGGGAT

TGATAAA

CF 07-124 (–) Fuse the end of mvaS to the terminator (SEQ ID NO: 85)
5'-CGGGGCCAAGGCCGGTTTTTTTTAGTTTCGATAAGAACGAACGGT Template: *Enterococcus faecalis* chromosomal DNA 4. *B. amyliquefaciens* Alkaline Serine Protease Terminator CF 07-123 (+) Fuse the end of mvaS to the terminator (SEQ ID NO: 86)
5'-ACCGTTCGTTCTTATCGAAACTAAAAAAAACCGGCCTTGGCCCCG CF 07-46 (–) End of *B. amyliquefaciens* terminator BamHI (SEQ ID NO: 63)
5'-GACATGACGGATCCGATTACGAATGCCGTCTC Template: *Bacillus* amyliquefaciens chromosomal DNA PCR Fusion Reactions 5. Fuse mvaE to mvaS CF 07-93 (+) fuse mvaE to the aprE promoter (GTG start codon)

(SEQ ID NO: 84)
5'-TTAAAAGGAGAGGGTAAAGAGTGAAAACAGTAGTTATTATTG

CF 07-124 (–) Fuse the end of mvaS to the terminator (SEQ ID NO: 85)
5'-CGGGGCCAAGGCCGGTTTTTTTTAGTTTCGATAAGAACGAACGGT Template: #2 and 3 from above 6. Fuse mvaE-mvaS to aprE Promoter CF 07-134 (+) Start of aprE promoter PstI (SEQ ID NO: 82)
5'-GACATCTGCAGCTCCATTTTCTTCTGC CF 07-124 (–) Fuse the end of mvaS to the terminator (SEQ ID NO: 85)
5'-CGGGGCCAAGGCCGGTTTTTTTTAGTTTCGATAAGAACGAACGGT Template #1 and #4 from above 7. Fuse PaprE-mvaE-mvaS to Terminator CF 07-134 (+) Start of aprE promoter PstI (SEQ ID NO: 82)
5'-GACATCTGCAGCTCCATTTTCTTCTGC CF 07-46 (–) End of *B. amyliquefaciens* terminator BamHI (SEQ ID NO: 63)
5'-GACATGACGGATCCGATTACGAATGCCGTCTC Template: #4 and #6

Figure 50:
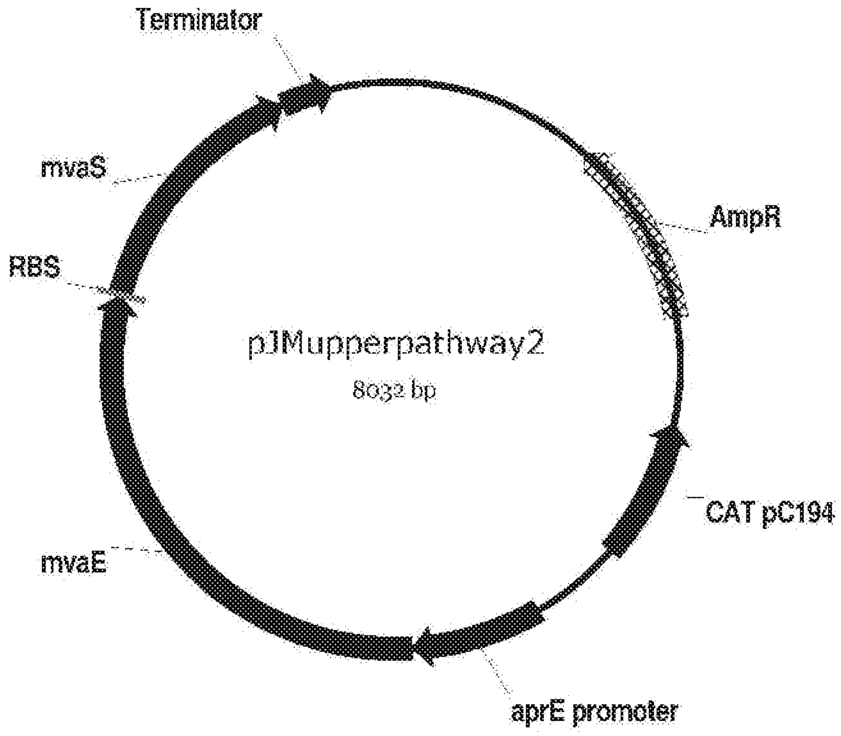
FIG. 50 is a map of pJMupperpathway2.

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), *Bacillus subtilis* and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 μg/ml). The correct plasmid is identified by sequencing and is designated pJMUpperpathway2 (FIGS. 50 and 51). Purified plasmid DNA is transformed into *Bacillus subtilis* aprEnprE Pxyl-comK and transformants are selected on L agar containing chloramphenicol (5 μg/ml). A correct colony is selected and is plated sequentially on L agar containing chloramphenicol 10, 15 and 25 μg/ml to amplify the number of copies of the cassette containing the upper pathway.

The resulting strain is tested for mevalonic acid production by growing in LB containing 1% glucose and 1%. Cultures are analyzed by GC for the production of mevalonic acid.

This strain is used subsequently as a host for the integration of the lower mevalonic acid pathway.

The following primers are used to sequence the various constructs above.

Sequencing Primers:

CF 07-134 (+) Start of aprE promoter PstI (SEQ ID NO: 82)
5'-GACATCTGCAGCTCCATTTTCTTCTGC CF 07-58 (+) Start of mvaE gene (SEQ ID NO: 38)
5'-ATGAAAACAGTAGTTATTATTGATGC CF 07-59 (−) End of mvaE gene (SEQ ID NO: 39)
5'-ATGTTATTGTTTTCTTAAATCATTTAAAATAGC CF 07-82 (+) Start of mvaS gene (SEQ ID NO: 40)
5'-ATGACAATTGGGATTGATAAAATTAG CF 07-83 (−) End of mvaS gene (SEQ ID NO: 41)
5'-TTAGTTTCGATAAGAACGAACGGT CF 07-86 (+) Sequence in mvaE (SEQ ID NO: 42)
5'-GAAATAGCCCCATTAGAAGTATC CF 07-87 (+) Sequence in mvaE (SEQ ID NO: 43)
5'-TTGCCAATCATATGATTGAAAATC CF 07-88 (+) Sequence in mvaE (SEQ ID NO: 44)
5'-GCTATGCTTCATTAGATCCTTATCG CF 07-89 (+) Sequence mvaS (SEQ ID NO: 45)
5'- GAAACCTACATCCAATCTTTTGCCC Transformants are selected on LA containing chloramphenicol at a concentration of 5 μg/ml. One colony is confirmed to have the correct integration by sequencing and is plated on LA containing increasing concentrations of chloramphenicol over several days, to a final level of 25 μg/ml. This results in amplification of the cassette containing the genes of interest. The resulting strain is designated CF 455: pJMupperpathway #1 X *Bacillus subtilis* aprEnprE Pxyl comK (amplified to grow on LA containing chloramphenicol 25 μg/ml).

II. Construction of the Lower MVA Pathway in *Bacillus subtilis*

Figure 28:
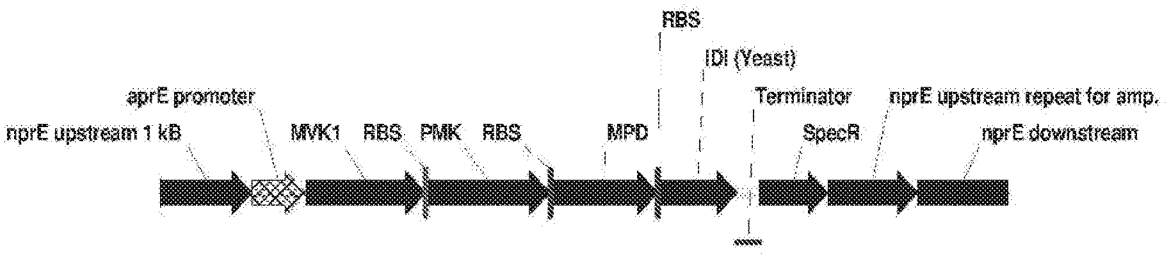
FIG. 28 shows a map of the cassette containing the lower MVA pathway and yeast idi for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonte kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast idi gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

The lower MVA pathway, consisting of the genes mvk1, pmk, mpd and idi are combined in a cassette consisting of flanking DNA regions from the nprE region of the *B. subtilis* chromosome (site of integration), the aprE promoter, and the spectinomycin resistance marker (see FIGS. 28 and 29). This cassette is synthesized by DNA2.0 and is integrated into the chromosome of *B. subtilis* containing the upper MVA pathway integrated at the aprE locus. The kudzu isoprene synthase gene is expressed from the replicating plasmid described in Example 4 and is transformed into the strain with both upper and lower pathways integrated.

Example 10: Production of Isoprene in *E. coli* Expressing *M. mazei* Mevalonate Kinase and *P. alba* Isoprene Synthase I. Construction of Vectors and Strains Encoding *M. mazei* Mevalonate Kinase (MVK) and *P. alba* Isoprene Synthase (i) Construction of Strain EWL201 (BL21, Cm-GI1.2-KKDyI)

*E. coli* BL21 (Novagen brand, EMD Biosciences, Inc.) was a recipient strain, transduced with MCM331 P1 lysate (lysate prepared according to the method described in Ausubel, et al., *Current Protocols in Molecular Biology*. John Wiley and Sons, Inc.). Transductants were selected for by spreading cells onto L Agar and 20 μg/μl chloramphenicol. The plates were incubated overnight at 30° C. Analysis of transductants showed no colonies on control plates (water+cells control plate for reversion and water and P1 lysate control plate for lysate contamination.

Four transductants were picked and used to inoculate 5 mL L Broth and 20 μg/μl chloramphenicol. The cultures were grown overnight at 30° C. with shaking at 200 rpm. To make genomic DNA preps of each transductant for PCR analysis, 1.5 mL of overnight cell culture were centrifuged. The cell pellet was resuspended with 400 μl Resuspension Buffer (20 mM Tris, 1 mM EDTA, 50 mM NaCl, pH 7.5) and 4 μl RNase, DNase-free (Roche) was added. The tubes were incubated at 37° C. for 30 minutes followed by the addition of 4 μl 10% SDS and 4 μl of 10 mg/ml Proteinase K stock solution (Sigma-Aldrich). The tubes were incubated at 37° C. for 1 hour. The cell lysate was transferred into 2 ml Phase Lock Light Gel tubes (Eppendorf) and 200 μl each of saturated phenol pH7.9 (Ambion Inc.) and chloroform were added. The tubes were mixed well and microcentrifuged for 5 minutes. A second extraction was done with 400 μl chloroform and the aqueous layer was transferred to a new eppendorf tube. The genomic DNA was precipitated by the addition of 1 ml of 100% ethanol and centrifugation for 5 minutes. The genomic DNA pellet was washed with 1 ml 70% ethanol. The ethanol was removed and the genomic DNA pellet was allowed to air dry briefly. The genomic DNA pellet was resuspended with 200 μl TE.

Using Pfu Ultra II DNA polymerase (Stratagene) and 200 ng/μl of genomic DNA as template, 2 different sets of PCR reaction tubes were prepared according to manufacturer's protocol. For set 1, primers MCM130 and GB Cm-Rev (Table 4) were used to ensure transductants were successfully integrated into the attTn7 locus. PCR parameters for set 1 were 95° C. for 2 minutes (first cycle only), 95° C. for 25 seconds, 55° C. for 25 seconds, 72° C. for 25 seconds (repeat steps 2-4 for 28 cycles), 72° C. for 1 minute. For set 2, primers MVD For and MVD Rev (Table 4) were used to ensure that the gi1.2-KKDyI operon integrated properly. PCR parameters for set 2 were 95° C. for 2 minutes (first cycle only), 95° C. for 25 seconds, 55° C. for 25 seconds, 72° C. for 10 seconds (repeat steps 2-4 for 28 cycles), 72° C. for 1 minute. Analysis of PCR amplicons on a 1.2% E-gel (Invitrogen Corp.) showed that all 4 transductant clones were correct (picked one and designated as strain EWL201).

ii) Construction of Strain EWL204 (BL21, Loopout-GI1.2-KKDyI)

The chloramphenicol marker was looped out of strain EWL201 using plasmid pCP20 as described by Datsenko and Wanner (2000) (Datsenko et al., *Proc Natl. Acad. Sci* USA 97:6640-6645, 2000). One-step inactivation of chromosomal genes in *Escherichia coli* K-12 using PCR products. (Datsenko et al., *PNAS,* 97: 6640-6645, 2000). EWL201 cells were grown in L Broth to midlog phase and then washed three times in ice-cold, sterile water. An aliquot of 50 μl of cell suspension was mixed with 1 μl of pCP20 and the cell suspension mixture was electroporated in a 2 mm cuvette (Invitrogen Corp.) at 2.5 Volts and 25uFd using a Gene Pulser Electroporator (Bio-Rad Inc.). 1 ml of LB was immediately added to the cells, then transferred to a 14 ml polypropylene tube (Sarstedt) with a metal cap. Cells were allowed to recover by growing for 1 hour at 30° C. Transformants were selected on L Agar and 20 μg/μl chloramphenicol and 50 μg/μl carbenicillin and incubated at 30° C. overnight. The next day, a single clone was grown in 10 ml L Broth and 50 μg/μl carbenicillin at 30° C. until early log phase. The temperature of the growing culture was then shifted to 42° C. for 2 hours. Serial dilutions were made, the cells were then spread onto LA plates (no antibiotic selection), and incubated overnight at 30° C. The next day, 20 colonies were picked and patched onto L Agar (no antibiotics) and LA and 20 μg/μl chloramphenicol plates. Plates were then incubated overnight at 30° C. Cells able to grow on LA plates, but not LA and 20 μg/μl chloramphenicol plates, were deemed to have the chloramphenicol marker looped out (picked one and designated as strain EWL204).

iii) Construction of Plasmid pEWL230 (pTrc *P. alba*)

Figure 54:
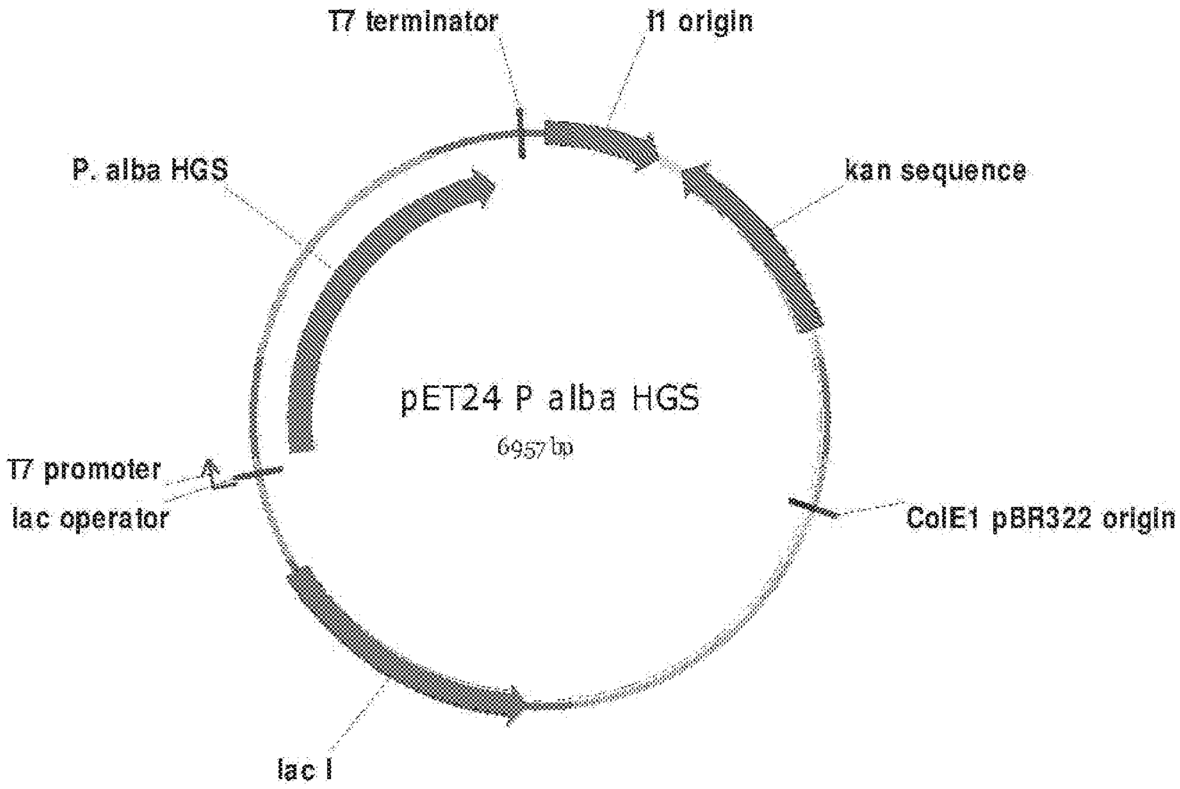
FIG. 54 is a map of plasmid pET24 *P. alba* HGS.

Generation of a synthetic gene encoding *Populus alba* isoprene synthase (*P. alba* HGS) was outsourced to DNA2.0 Inc. (Menlo Park, Calif.) based on their codon optimization method for *E. coli* expression. The synthetic gene was custom cloned into plasmid pET24a (Novagen brand, EMD Biosciences, Inc.) and delivered lyophilized (FIGS. 54, 55A and 55B).

A PCR reaction was performed to amplify the *P. alba* isoprene synthase (*P. alba* HGS) gene using pET24 *P. alba* HGS as the template, primers MCM182 and MCM192, and Herculase II Fusion DNA polymerase (Stratagene) according to manufacturer's protocol. PCR conditions were as follows: 95° C. for 2 minutes (first cycle only), 95° C. for 25 seconds, 55° C. for 20 seconds, 72° C. for 1 minute, repeat for 25 cycles, with final extension at 72° C. for 3 minutes. The *P. alba* isoprene synthase PCR product was purified using QIAquick PCR Purification Kit (Qiagen Inc.).

Figure 56:
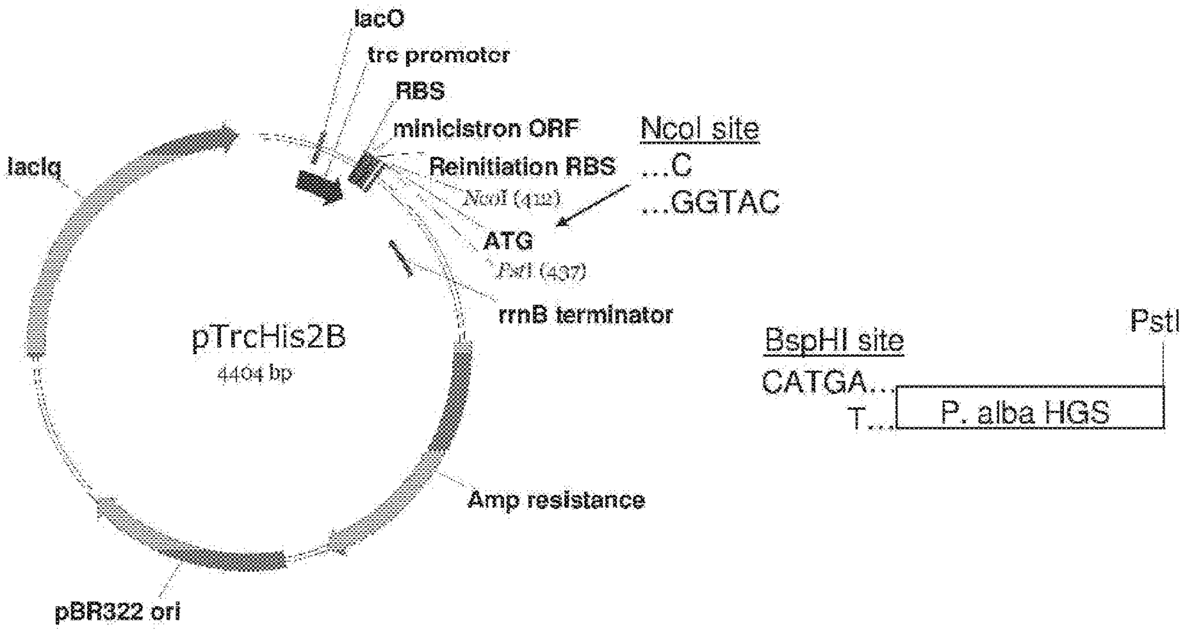
FIG. 56 is a schematic diagram showing restriction sites used for endonuclease digestion to construct plasmid EWL230 and compatible cohesive ends between BspHI and NcoI sites.
Figure 57:
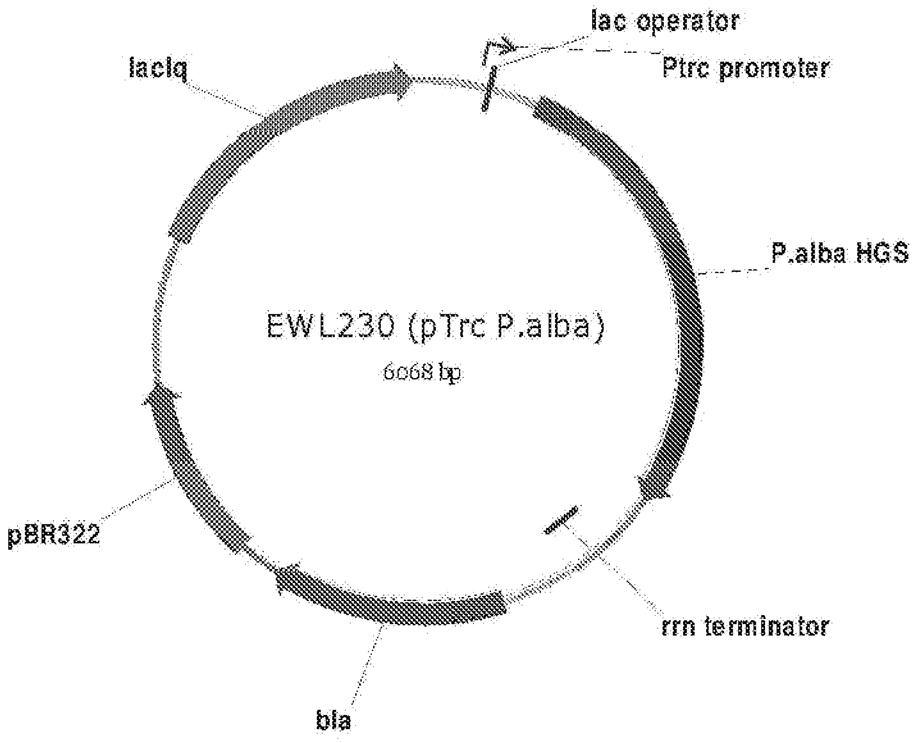
FIG. 57 is a map of plasmid EWL230.

*P. alba* isoprene synthase PCR product was then digested in a 20 μl reaction containing 1 μl BspHI endonuclease (New England Biolabs) with 2 μl 10× NEB Buffer 4. The reaction was incubated for 2 hours at 37° C. The digested PCR fragment was then purified using the QIAquick PCR Purification Kit. A secondary restriction digest was performed in a 20 μl reaction containing 1 μl PstI endonuclease (Roche) with 2 μl 10× Buffer H. The reaction was incubated for 2 hours at 37° C. The digested PCR fragment was then purified using the QIAquick PCR Purification Kit. Plasmid pTrcHis2B (Invitrogen Corp.) was digested in a 20 μl reaction containing 1 μl NcoI endonuclease (Roche), 1 μl PstI endonuclease, and 2 μl 10× Buffer H. The reaction was incubated for 2 hours at 37° C. The digested pTrcHis2B vector was gel purified using a 1.2% E-gel (Invitrogen Corp.) and extracted using the QIAquick Gel Extraction Kit (Qiagen) (FIG. 56). Using the compatible cohesive ends of BspHI and NcoI sites, a 20 μl ligation reaction was prepared containing 5 μl *P. alba* isoprene synthase insert, 2 μl pTrc vector, 1 μl T4 DNA ligase (New England Biolabs), 2 μl 10× ligase buffer, and 10 μl $ddH_2O$. The ligation mixture was incubated at room temperature for 40 minutes. The ligation mixture was desalted by floating a 0.025 μm nitrocellulose membrane filter (Millipore) in a petri dish of $ddH_2O$ and applying the ligation mixture gently on top of the nitrocellulose membrane filter for 30 minutes at room temperature. MCM446 cells (See section II) were grown in LB to midlog phase and then washed three times in ice-cold, sterile water. An aliquot of 50 μl of cell suspension was mixed with 5 μl of desalted pTrc *P. alba* HGS ligation mix. The cell suspension mixture was electroporated in a 2 mm cuvette at 2.5 Volts and 25uFd using a Gene Pulser Electroporator. 1 ml of LB is immediately added to the cells, then transferred to a 14 ml polypropylene tube (Sarstedt) with a metal cap. Cells were allowed to recover by growing for 2 hour at 30° C. Transformants were selected on L Agar and 50 μg/μl carbenicillin and 10 mM mevalonic acid and incubated at 30° C. The next day, 6 transformants were picked and grown in 5 ml L Broth and 50 μg/μl carbenicillin tubes overnight at 30° C. Plasmid preps were performed on the overnight cultures using QIAquick Spin Miniprep Kit (Qiagen). Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 μl reaction to ensure the correct sized linear fragment. All 6 plasmids were the correct size and shipped to Quintara Biosciences (Berkeley, Calif.) for sequencing with primers MCM65, MCM66, EL1000 (Table 4). DNA sequencing results showed all 6 plasmids were correct. Picked one and designated plasmid as EWL230 (FIGS. 57, 58A and 58B).

iv) Construction of Plasmid pEWL244 (pTrc *P. alba*-mMVK)

A PCR reaction was performed to amplify the *Methanosarcina mazei* (*M. mazei*) MVK gene using MCM376 as the template (see section v), primers MCM165 and MCM177 (see Table 4), and Pfu Ultra II Fusion DNA polymerase (Stratagene) according to manufacturer's protocol. PCR conditions were as follows: 95° C. for 2 minutes (first cycle only), 95° C. for 25 seconds, 55° C. for 25 seconds, 72° C. for 18 seconds, repeat for 28 cycles, with final extension at 72° C. for 1 minute. The *M. mazei* MVK PCR product was purified using QIAquick PCR Purification Kit (Qiagen Inc.,)

Figure 59:
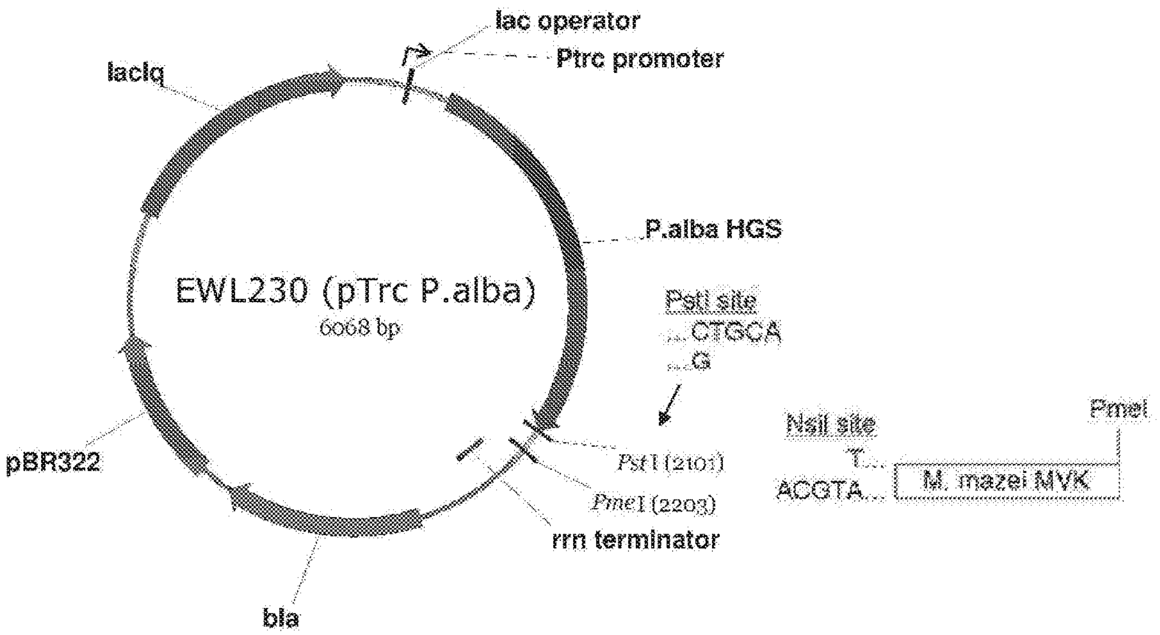
FIG. 59 is a schematic diagram showing restriction sites used for endonuclease digestion to construct plasmid EWL244 and compatible cohesive ends between NsiI and PstI sites.
Figure 60:
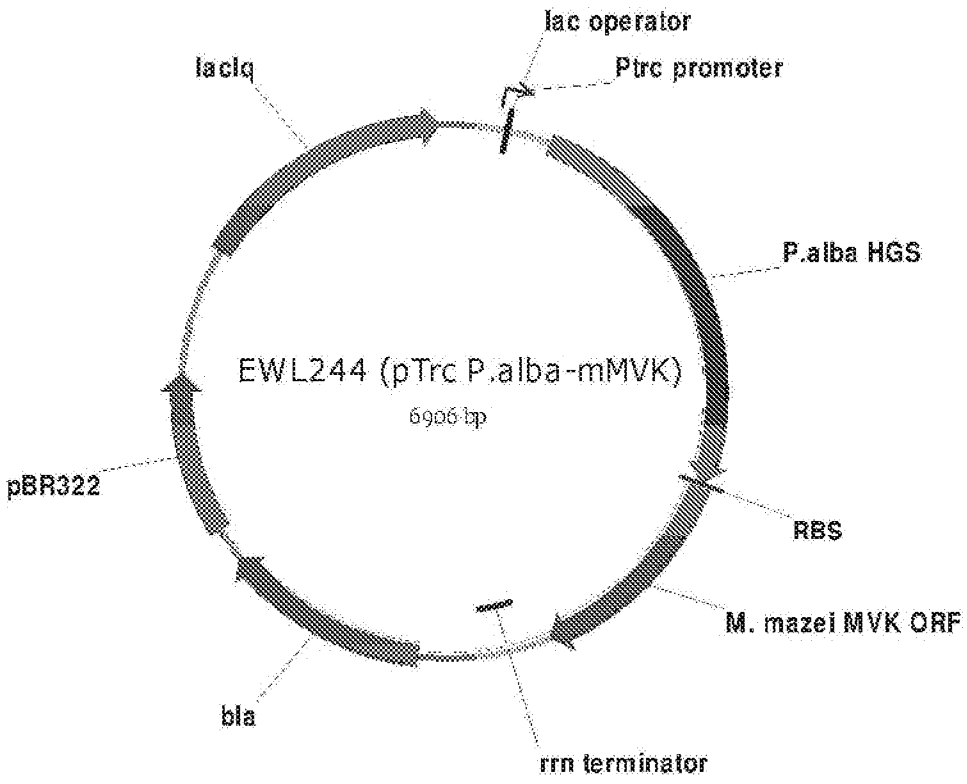
FIG. 60 is a map of EWL244.
Figure 62:
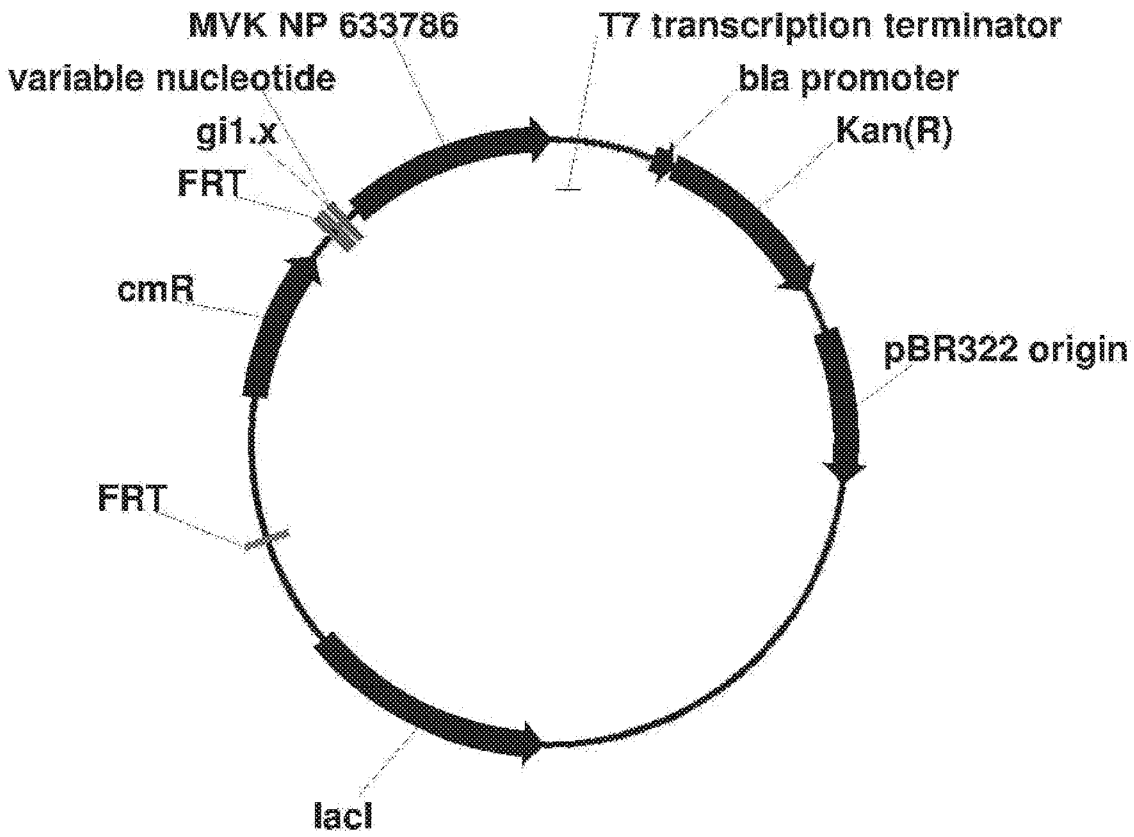
FIG. 62 is a map of plasmids MCM484-487.

The *M. mazei* MVK PCR product was then digested in a 40 μl reaction containing 8 μl PCR product, 2 μl PmeI endonuclease (New England Biolabs), 4 μl 10× NEB Buffer 4, 4 μl 10× NEB BSA, and 22 μl of $ddH_2O$. The reaction was incubated for 3 hours at 37° C. The digested PCR fragment was then purified using the QIAquick PCR Purification Kit. A secondary restriction digest was performed in a 47 μl reaction containing 2 μl NsiI endonuclease (Roche), 4.7 μl 10× Buffer H, and 40 μl of PmeI digested *M. mazei* MVK fragment. The reaction was incubated for 3 hours at 37° C. The digested PCR fragment was then gel purified using a 1.2% E-gel and extracted using the QIAquick Gel Extraction Kit. Plasmid EWL230 was digested in a 40 μl reaction containing 10 μl plasmid, 2 μl PmeI endonuclease, 4 μl 10× NEB Buffer 4, 4 μl 10× NEB BSA, and 20 μl of $ddH_2O$. The reaction was incubated for 3 hours at 37° C. The digested PCR fragment was then purified using the QIAquick PCR Purification Kit. A secondary restriction digest was performed in a 47 μl reaction containing 2 μl PstI endonuclease, 4.7 μl 10× Buffer H, and 40 μl of PmeI digested EWL230 linear fragment. The reaction was incubated for 3 hours at 37° C. The digested PCR fragment was then gel purified using a 1.2% E-gel and extracted using the QIAquick Gel Extraction Kit (FIG. 59). Using the compatible cohesive ends of NsiI and PstI sites, a 20 μl ligation reaction was prepared containing 8 μl *M. mazei* MVK insert, 3 μl EWL230 plasmid, 1 μl T4 DNA ligase, 2 μl 10× ligase buffer, and 6 μl $ddH_2O$. The ligation mixture was incubated at overnight at 16° C. The next day, the ligation mixture was desalted by floating a 0.025 μm nitrocellulose membrane filter in a petri dish of $ddH_2O$ and applying the ligation mixture gently on top of the nitrocellulose membrane filter for 30 minutes at room temperature. MCM446 cells were grown in LB to midlog phase and then washed three times in ice-cold, sterile water. An aliquot of 50 μl of cell suspension was mixed with 5 μl of desalted pTrc *P. alba*-mMVK ligation mix. The cell suspension mixture was electroporated in a 2 mm cuvette at 2.5 Volts and 25uFd using a Gene Pulser Electroporator. 1 ml of LB is immediately added to the cells, then the cells are transferred to a 14 ml polypropylene tube with a metal cap. Cells were allowed to recover by growing for 2 hour at 30° C. Transformants were selected on LA and 50 μg/μl carbenicillin and 5 mM mevalonic acid plates and incubated at 30° C. The next day, 6 transformants were picked and grown in 5 ml LB and 50 μg/μl carbenicillin tubes overnight at 30° C. Plasmid preps were performed on the overnight cultures using QIAquick Spin Miniprep Kit. Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 μl reaction to ensure the correct sized linear fragment. Three of the 6 plasmids were the correct size and shipped to Quintara Biosciences for sequencing with primers MCM65, MCM66, EL1000, EL1003, and EL1006 (Table 4). DNA sequencing results showed all 3 plasmids were correct. Picked one and designated plasmid as EWL244 (FIGS. 60 and 61A-61B).

v) Construction of Plasmid MCM376—MVK from *M. mazei* Archaeal Lower in pET200D.

Figure 73A:
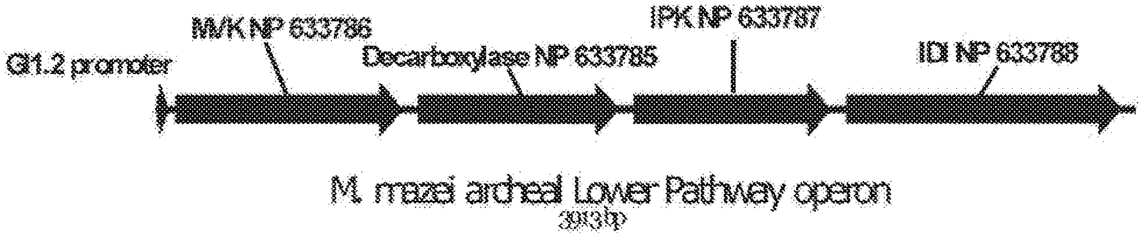
FIG. 73A is a map of the *M. mazei* archaeal Lower Pathway operon.
Figure 74A:
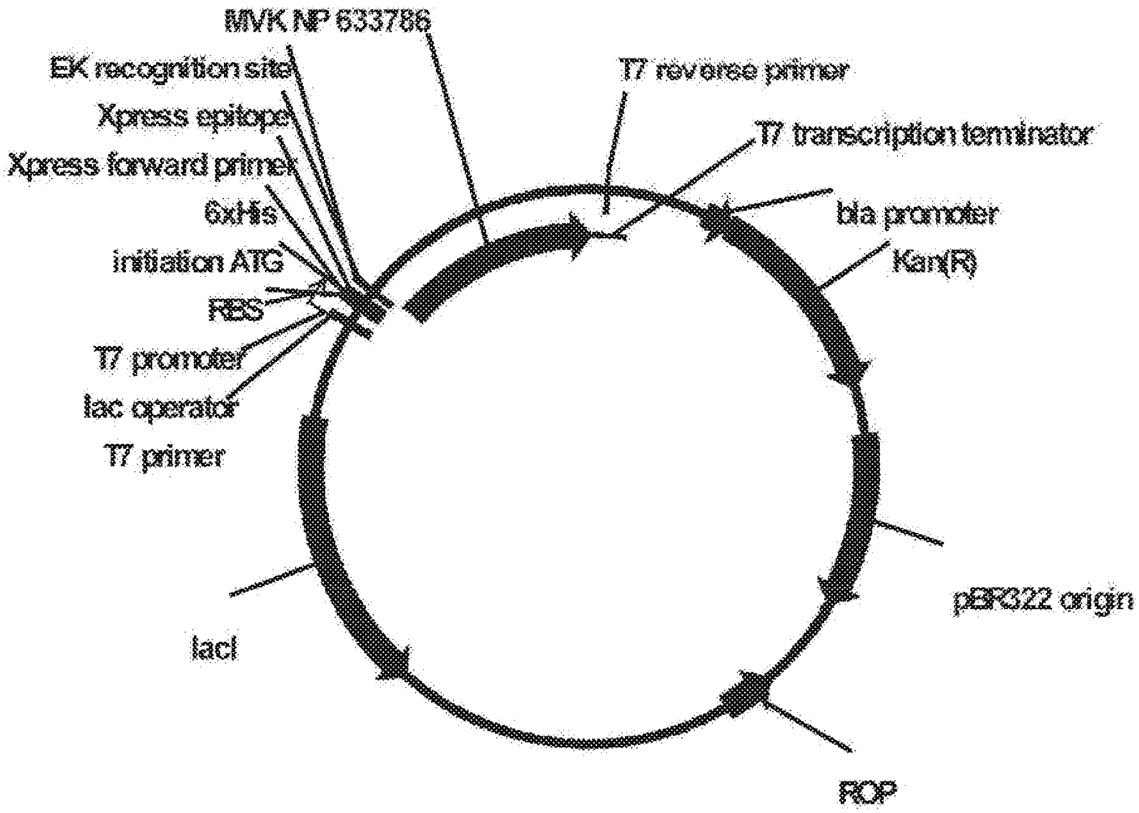
FIG. 74A is a map of MCM376-MVK from *M. mazei* archaeal Lowerin pET200D.
Figure 75A:
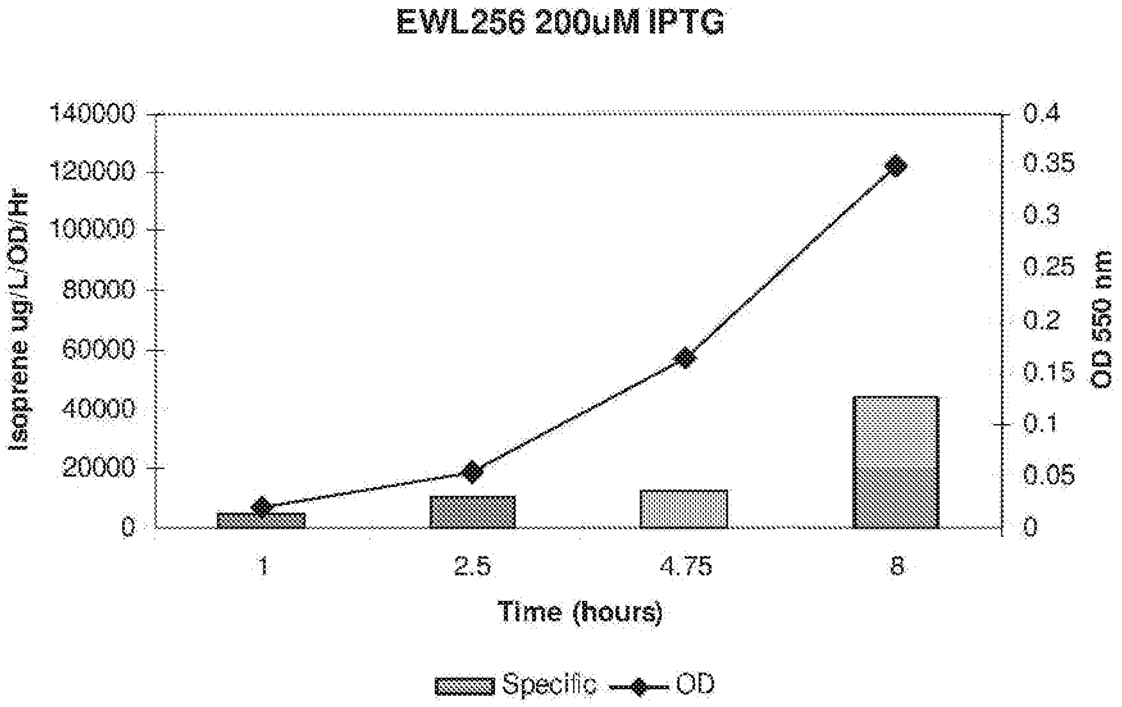
FIGS. 75A, 75B, 75C and 75D show growth and specific productivity of isoprene production for EWL256 compared to RM11608-2. Growth (OD550) is represented by the white diamonds; specific productivity of isoprene is represented by the solid bars. The x-axis is time (hours) post-induction with either 200 (FIG. 75A and FIG. 75B) or 400 (FIG. 75C and FIG. 75D) uM IPTG. Y-1 axis is productivity of isoprene (ug/L/OD/hr) and Y-2 is arbitrary units of optical density at a wavelength of 550. These values for the OD550 must be multiplied by 6.66 to obtain the actual OD of the culture.
Figure 75B:
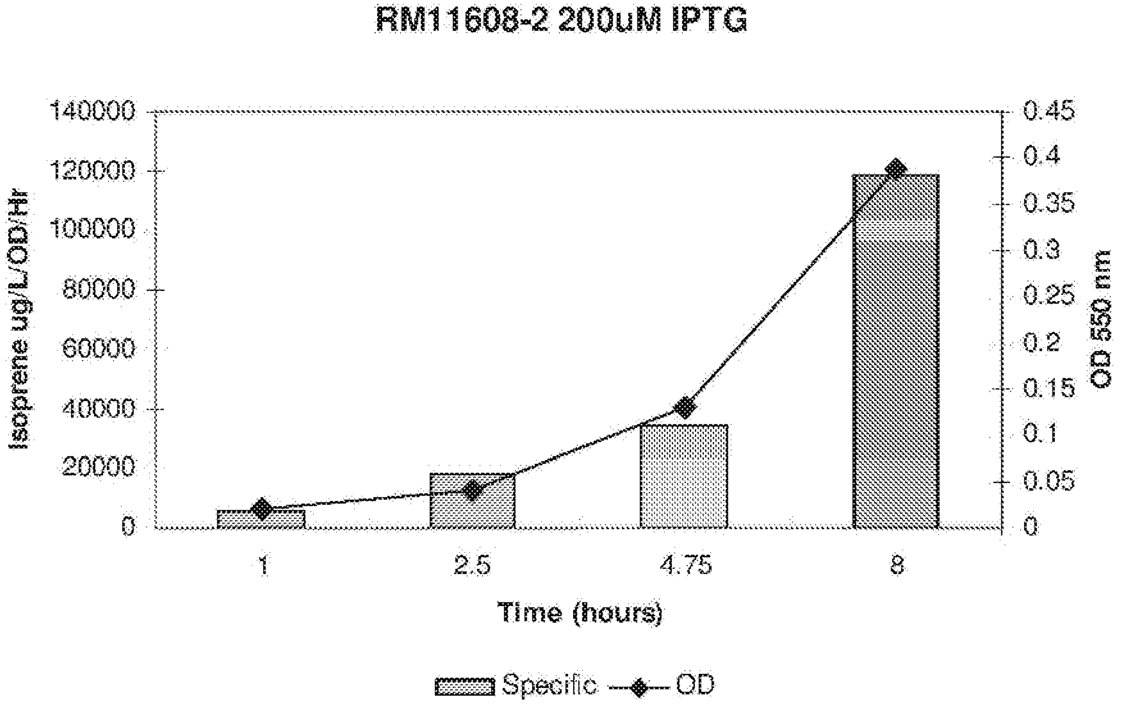
Figure 75C:
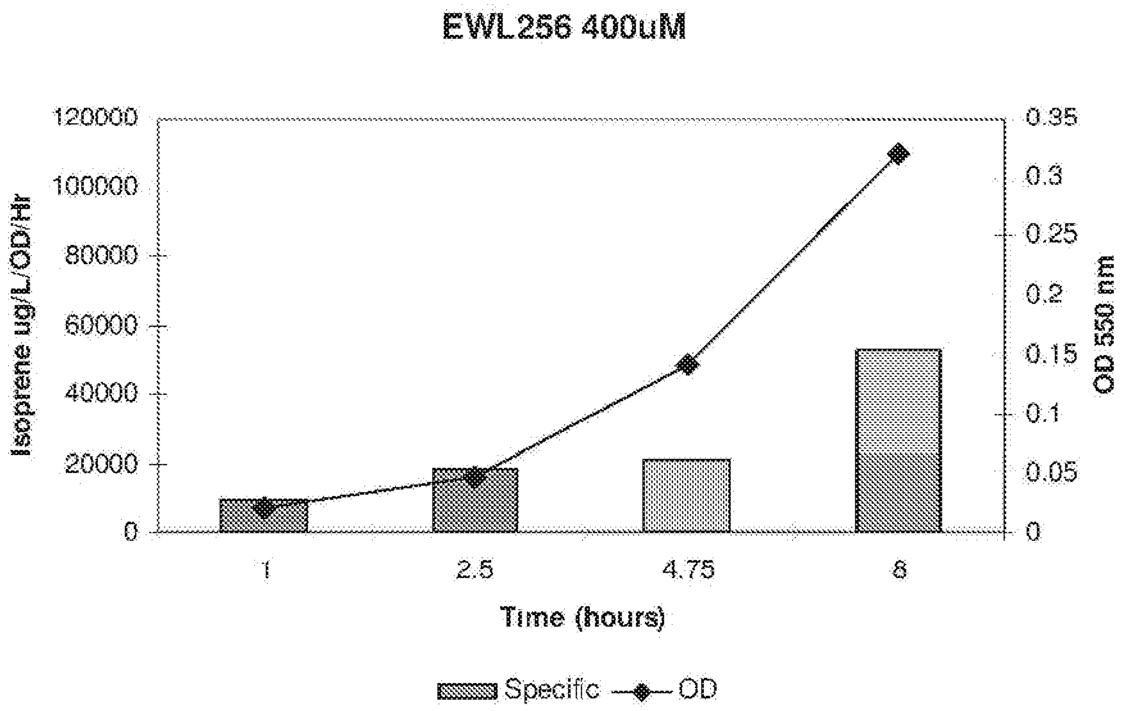
Figure 75D:
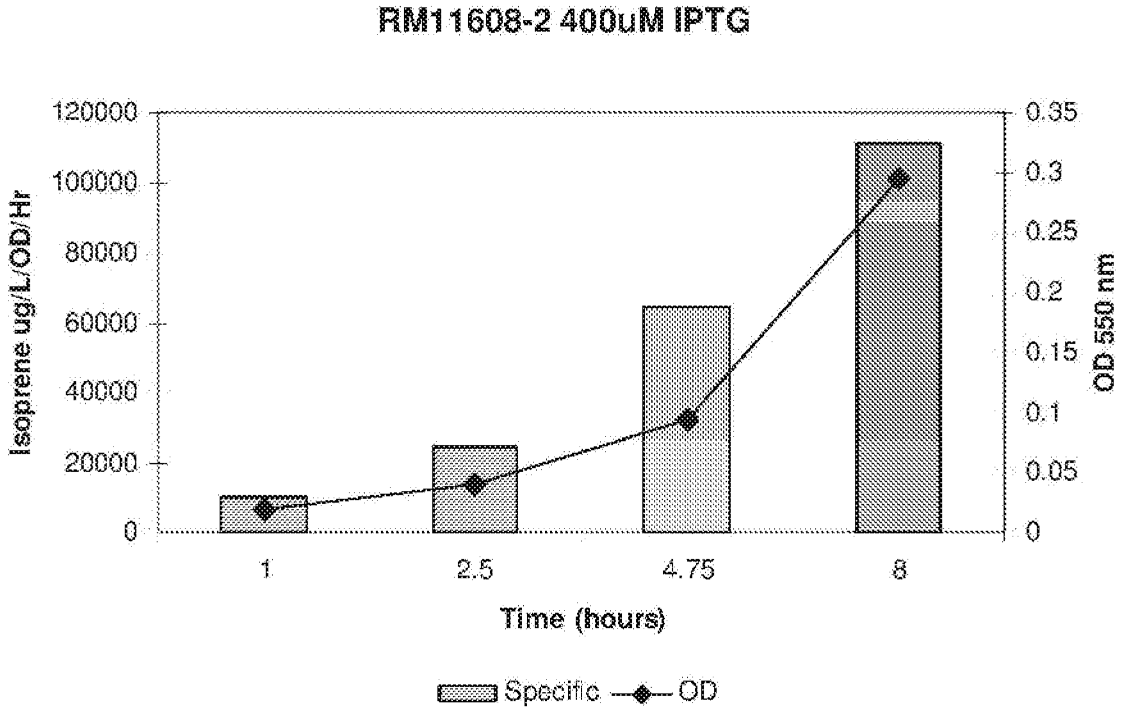
Figure 76:
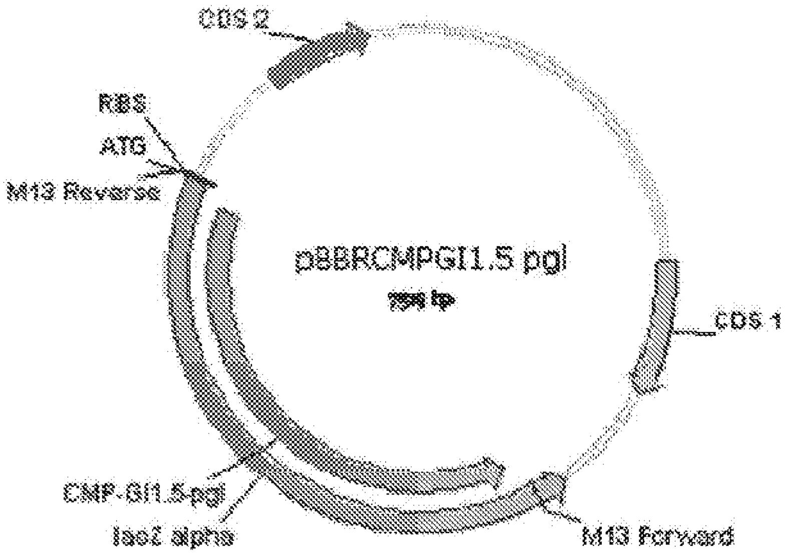
FIG. 76 is a map of plasmid pBBRCMPGI1.5-pgl.

The MVK ORF from the *M. mazei* archaeal Lower Pathway operon (FIGS. 73A-73C) was PCR amplified using primers MCM161 and MCM162 (Table 4) using the Invitrogen Platinum HiFi PCR mix. 45 uL of PCR mix was combined with 1 uL template, 1 uL of each primer at 10 uM, and 2 uL water. The reaction was cycled as follows: 94° C. for 2:00 minutes; 30 cycles of 94° C. for 0:30 minutes, 55° C. for 0:30 minutes and 68° C. for 1:15 minutes; and then 72° C. for 7:00 minutes, and 4° C. until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIGS. 74A-C).

vi) Construction of Strain EWL251 (BL21(DE3), Cm-GI1.2-KKDyI, pTrc *P. alba*-mMVK)

MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) were grown in LB to midlog phase and then washed three times in ice-cold, sterile water. Mixed 50 μl of cell suspension with 1 μl of plasmid EWL244. The cell suspension mixture was electroporated in a 2 mm cuvette at 2.5 Volts and 25uFd using a Gene Pulser Electroporator. 1 ml of LB is immediately added to the cells, then the cells were transferred to a 14 ml polypropylene tube with a metal cap. Cells were allowed to recover by growing for 2 hours at 30° C. Transformants were selected on LA and 50 μg/μl carbenicillin and 5 mM mevalonic acid plates and incubated at 37° C. One colony was selected and designated as strain EWL251.

vii) Construction of Strain EWL256 (BL21(DE3), Cm-GI1.2-KKDyI, pTrc *P. alba*-mMVK, pCL Upper MVA)

EWL251 cells were grown in LB to midlog phase and then washed three times in ice-cold, sterile water. Mixed 50 μl of cell suspension with 1 μl of plasmid MCM82 (which is pCL PtrcUpperPathway encoding *E. faecalis* mvaE and mvaS). The cell suspension mixture was electroporated in a 2 mm cuvette at 2.5 Volts and 25uFd using a Gene Pulser Electroporator. 1 ml of LB was immediately added to the cells, then transferred to a 14 ml polypropylene tube with a metal cap. Cells were allowed to recover by growing for 2 hour at 30° C. Transformants were selected on LA and 50 μg/μl carbenicillin and 50 μg/μl spectinomycin plates and incubated at 37° C. Picked one colony and designated as strain EWL256.

TABLE 4

Primer Sequences

| Primer name | Primer sequence |
|---|---|
| MCM130 | ACCAATTGCACCCGGCAGA (SEQ ID NO: 94) |
| GB Cm Rev | GCTAAAGCGCATGCTCCAGAC (SEQ ID NO: 95) |
| MVD For | GACTGGCCTCAGATGAAAGC (SEQ ID NO: 96) |
| MVD Rev | CAAACATGTGGCATGGAAAG (SEQ ID NO: 97) |
| MCM182 | GGGCCCGTTTAAACTTTAACTAGACTCTGCAGTTAGCGTTCAAACGGCAGAA (SEQ ID NO: 98) |
| MCM192 | CGCATGCATGTCATGAGATGTAGCGTGTCCACCGAAAA (SEQ ID NO: 99 |
| MCM65 | ACAATTTCACACAGGAAACAGC (SEQ ID NO: 100) |
| MCM66 | CCAGGCAAATTCTGTTTTATCAG (SEQ ID NO: 101) |
| EL1000 | GCACTGTCTTTCCGTCTGCTGC (SEQ ID NO: 102) |
| MCM165 | GCGAACGATGCATAAAGGAGGTAAAAAAACATGGTATCCTGTTCTGCGCCGGG TAAGATTTACCTG (SEQ ID NO: 103) |

TABLE 4-continued

| Primer Sequences | |
|---|---|
| Primer name | Primer sequence |
| MCM177 | GGGCCCGTTTAAACTTTAACTAGACTTTAATCTACTTTCAGACCTTGC (SEQ ID NO: 104) |
| EL1003 | GATAGTAACGGCTGCGCTGCTACC (SEQ ID NO: 105) |
| EL1006 | GACAGCTTATCATCGACTGCACG (SEQ ID NO: 106) |
| MCM161 | CACCATGGTATCCTGTTCTGCG (SEQ ID NO: 107) |
| MCM162 | TTAATCTACTTTCAGACCTTGC (SEQ ID NO: 108) |

II. Construction of MCM442-449: BL21 and BL21(DE3) with FRT-cmR-FRT-gi1.x-mKKDyI i) Construction of Template for Recombination FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers MCM193 and MCM195 were used to amplify the resistance cassette from the FRT-gb2-Cm-FRT template using Stratagene Herculase II Fusion kit according to the manufacturer's protocol. The 50 uL reaction was cycled as follows: 95° C., 2 minutes; (95° C., 20 seconds, 55° C., 20 seconds, 72° C., 1 minute)×5, (95° C., 20 seconds, 60° C., 20 seconds, 72° C., 1 minute)×25; 72° C., 3 minutes; 4° C. until cool. The amplicon was purified by a Qiagen PCR column according to the manufacturer's protocol and eluted in 30 uL EB (Elution Buffer). DNA was digested with NdeI and PciI in a 20 uL reaction with 1× Roche H buffer and 0.5 uL BSA. Plasmid MCM376 was digested in a 10 uL reaction containing 1 uL each of NdeI, NcoI, and Roche H buffer. Reactions proceeded overnight at 37° C., and then cut DNA was purified on Qiagen PCR columns and eluted in 30 uL EB. The PCR product was ligated into MCM376 in a reaction containing 1 uL vector, 3 uL PCR product, 1 uL Roche Quick Ligase Buffer 2, 5 uL Buffer1, and 1 uL Ligase. The reaction proceeded at room temperature for 3 hours and then 5 uL was transformed into Invitrogen TOP10 cells according to the manufacturer's protocol. Transformants were selected on L agar (LA) and chloramphenicol (10 ug/mLO) at 37° C. overnight.

Transformant colonies were patched onto LA containing chloramphenicol (30 ug/mL) and kanamycin (50 ug/ml) for storage and sent to Quintara (Berkeley, Calif.) for sequencing. Four clones, one each with the four different nucleotides at the "N" in primer MCM195, were found to have the correct sequence for the inserted promoter. Clones were grown in 5 mL LB containing chloramphenicol (30 ug/mL) and kanamycin (50 ug/mL) and used for the preparation of plasmid DNA. This plasmid was retransformed into TOP10 cells and strains were frozen as:

TABLE 5

| MCM484-487 | |
|---|---|
| MCM484 | cmR-gi1.6-MVK(*mazei*) in pET (clone A1-3, variable nt A) |
| MCM485 | cmR-gi1.0-MVK(*mazei*) in pET (clone B4-6, variable nt C) |
| MCM486 | cmR-gi1.2-MVK(*mazei*) in pET (clone C1-5, variable nt G) |
| MCM487 | cmR-gi1.5-MVK(*mazei*) in pET (clone C3-3, variable nt T) |

ii) Creation of Recombination Target Strains MCM349 and MCM441

The chloramphenicol resistance (cmR) marker was looped out of strain MCM331 using plasmid pGB706 (GeneBridges) according to Manufacturer's instructions. MCM331 cells were grown to mid-log in LB and washed three times in iced, sterile water. A 1 uL aliquot of pGB706 DNA was added to 50 uL of cell suspension and this mixture was electroporated in a 2 mm cuvette at 2.5 volts, 25uFd followed immediately by recovery in 500 uL LB for one hour at 30 C. Transformants were selected on LB containing tetracycline (5 ug/ml) at 30° C. The following day, a clone was grown up at 30° C. in LB containing tetracycline (5 ug/ml) until visibly turbid (OD600~0.5-0.8). This culture was streaked onto LB and grown overnight at 37° C. A clone that was unable to grow on LB containing chloramphenicol (10 ug/mL) or LB containing tetracycline (5 ug/mL) was frozen as MCM348. Plasmid MCM356 (pRedET carbencillin; GeneBridges) was electroporated in as described above and transformants were selected on LB containing carbenicillin (50 ug/mL) at 30° C. A clone was grown in LB carbenicillin (50 ug/mL) at 30° C. and frozen as MCM349.

Strain MCM441 was created by electrotransforming plasmid MCM356 into EWL204 as above.

iii) Recombination of FRT-cmR-FRT-gi1.x-mMVK into MCM349 and MCM441

Plasmids MCM484-487 were used as template for PCR amplification with primers MCM120 and MCM196 and Herculase II Fusion kit, according to the manufacturer's protocol. Three reactions per template were carried out, with 0, 1, or 3 uL DMSO. The 50 uL reactions were cycled as follows: 95° C., 2 minutes; (95° C., 20 seconds; 55° C. 20 seconds; 72° C., 1.5 minutes) for five cycles; (95° C., 20 seconds; 60° C. 20 seconds; 72° C., 1.5 minutes) for 25 cycles; 72° C. for 3 minutes; 4° C., overnight.] The three reactions from a given template were pooled and purified on Qiagen PCR columns and eluted with 30 uL EB at 60° C. 5 uL DNA was digested with 1 uL DpnI in 1× Roche Buffer A for 3 hours at 37° C. This DNA was then microdialyzed against excess water for 30 minutes.

Strains were grown in 5 mL LB containing carbenicillin (50 ug/mL) from fresh streaks at 30 C to an OD600 of ~0.5. 40 mM L-arabinose was added and cultures were incubated at 37 C for 1.5 hours. Cells were harvested and electroporated with 3 uL dialyzed amplicons above, and then recovered in 500 uL SOC at 37 C for 1.5-3 hours. Transformants were selected on LA plates containing chloramphenicol (5 ug/mL) at 37° C.

Kanamycin sensitive clones were screened by PCR for insertion of the amplicon. PCR products from positive clones were sequenced to verify the sequence of inserted DNA. Amplicons were consistent with the FRT-gi1.2-yK-KDyI at attTn7 in MCM441 and 348 being replaced by FRT-cmR-FRT-gi1.x-mKKDyI (The yK and mK designations refer to the mevalonate kinase from *Saccharomyces cerevisiae* and *Methanosarcina mazei* respectively).

TABLE 6A

The following strains were grown in LB containing chloramphenicol (5 ug/mL) and frozen.

| Strain ID | Name | Parent | Recombination Amplicon Template |
|---|---|---|---|
| MCM442 | BL21(DE3) cmR-gi1.6mKKDyI A1, clone37 (A) | MCM349 | MCM484 |
| MCM443 | BL21(DE3) cmR-gi1.0mKKDyI B4, clone27 (C) | MCM349 | MCM485 |
| MCM444 | BL21(DE3) cmR-gi1.2mKKDyI C1, clone16 (G) | MCM349 | MCM486 |
| MCM445 | BL21(DE3) cmR-gi1.5mKKDyI C3, clone7 (T) | MCM349 | MCM487 |
| MCM446 | BL21 cmR-gi1.6mKKDyI A1-3 (A) | MCM441 | MCM484 |
| MCM447 | BL21 cmR-gi1.0mKKDyI B4-6 (C) | MCM441 | MCM485 |
| MCM448 | BL21 cmR-gi1.2mKKDyI C1-5 (G) | MCM441 | MCM486 |
| MCM449 | BL21 cmR-gi1.5mKKDyI C3-3 (T) | MCM441 | MCM487 |

TABLE 6B

| Primers | |
|---|---|
| MCM120 | AAAGTAGCCGAAGATGACGGTTTGTCACATGGAGTTGGCAGGATGTTTGATTAAAAGCAATTAACCCTCACTAAAGGGCGG (SEQ ID NO: 109) |
| MCM193 | GATATACATATGAATTAACCCTCACTAAAGG (SEQ ID NO: 110) |
| MCM195 | GCATGCATGACATGTTTTTTTACCTCCTTTGTTATCCGCTCACAATTAGTGGTTGAATTATTTGCTCAGGATGTGGCATNGTCAAGGGCGCGGCCGCGATCTAATACGACTCACTATAGGGCTCG (SEQ ID NO: 111) |
| MCM196 | AGGCTCTCAACTCTGACATGTTTTTTTCCTCCTTAAGGGTGCAGGCCTATCGCAAATTAGCTTAATCTACTTTCAGACCTTGCTCGG (SEQ ID NO: 112) |

III. The Effect of Yeast Extract on Isoprene Production in *E. coli* Expressing Genes from the Mevalonic Acid Pathway and Grown in Fed-Batch Culture at the 15-L Scale Medium Recipe (per liter fermentation medium):

$K_2HPO_4$ 7.5 g, $MgSO_4$*$7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4$*$H_2O$ 30 g, NaCl 10 g, $FeSO_4$*$7H_2O$ 1 g, $CoCl_2$* $6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in Di $H_2O$, pH to 3.0 with HCl/NaOH, then q.s. to volume and filter sterilized with a 0.22 micron filter.

Figure 67A:
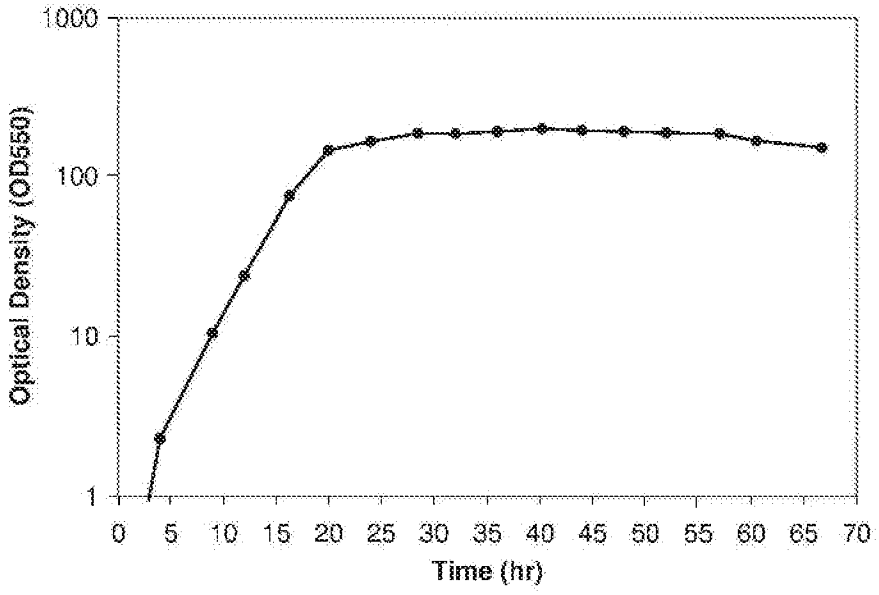
FIGS. 67A, 67B, 67C and 67D are graphs of isoprene production by *E. coli* strain (EWL256) expressing genes from the MVA pathway and grown in fed-batch culture at the 15-L scale without yeast extract feeding.
Figure 67B:
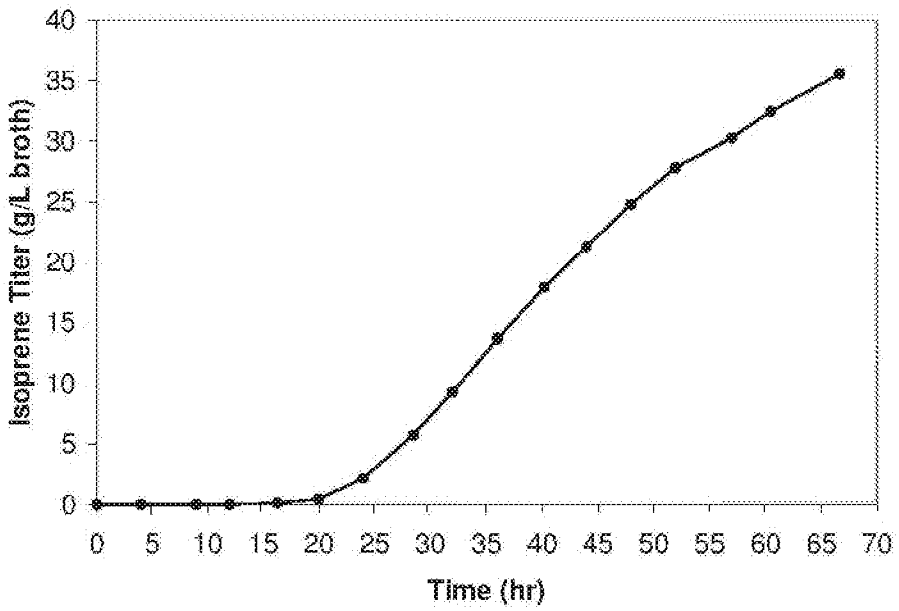
Figure 67C:
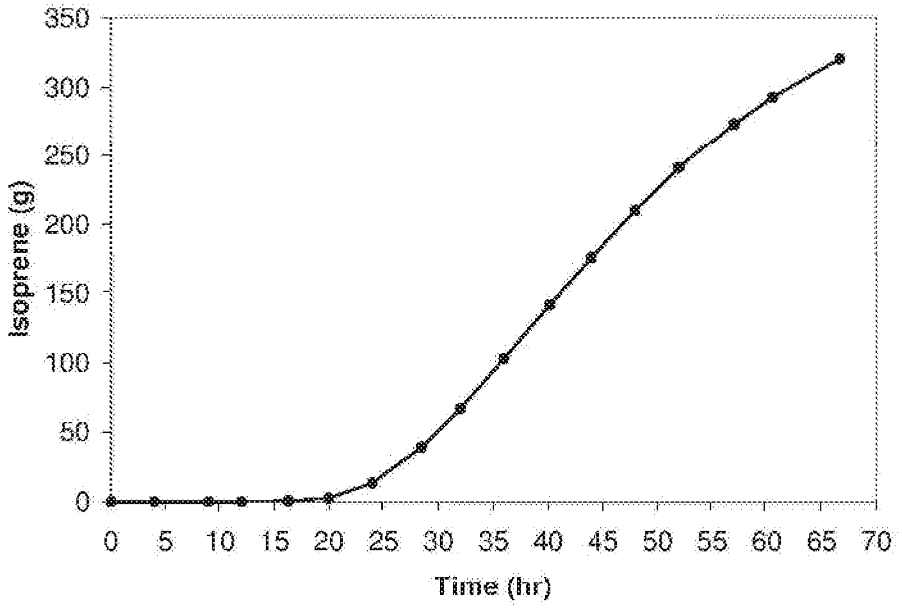
Figure 67D:
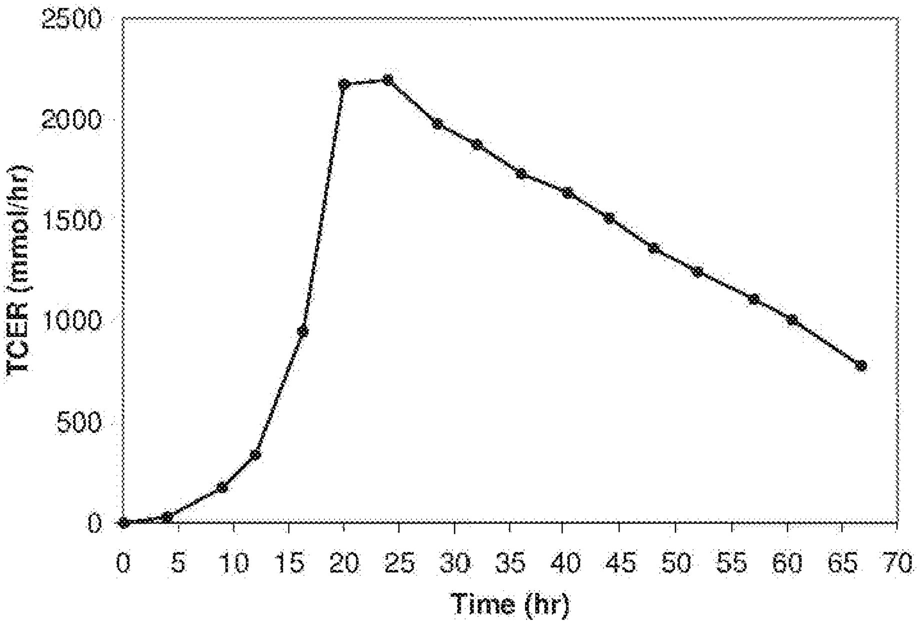

Fermentation was performed in a 15-L bioreactor with BL21 (DE3) *E. coli* cells containing the upper mevalonic acid (MVA) pathway (pCL Upper), the integrated lower MVA pathway (gi1.2KKDyI), and high expression of mevalonate kinase from *M. mazei* and isoprene synthase from *P. alba* (pTrcAlba-mMVK). This experiment was carried out to monitor isoprene formation from glucose at the desired fermentation pH 7.0 and temperature 30° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

i) Production of Isoprene in *E. coli* Cells (EL256) Grown in Fed-batch Culture without Yeast Extract Feeding Glucose was fed at an exponential rate until cells reached the stationary phase. After this time the glucose feed was decreased to meet metabolic demands. The total amount of glucose delivered to the bioreactor during the 67 hour fermentation was 3.9 kg. Induction was achieved by adding isopropyl-beta-D-1-thiogalactopyranoside (IPTG). The IPTG concentration was brought to 102 uM when the optical density at 550 nm ($OD_{550}$) reached a value of 9. The IPTG concentration was raised to 192 uM when $OD_{550}$ reached 140. The $OD_{550}$ profile within the bioreactor over time is shown in FIG. 67A. The isoprene level in the off gas from the bioreactor was determined using a Hiden mass spectrometer. The isoprene titer increased over the course of the fermentation to a final value of 35.6 g/L (FIG. 67B). The total amount of isoprene produced during the 67 hour fermentation was 320.6 g and the time course of production is shown in FIG. 67C. The metabolic activity profile, as measured by TCER, is shown in FIG. 67D. The molar yield of utilized carbon that went into producing isoprene during fermentation was 17.9%. The weight percent yield of isoprene from glucose was 8.1%.

Figure 68A:
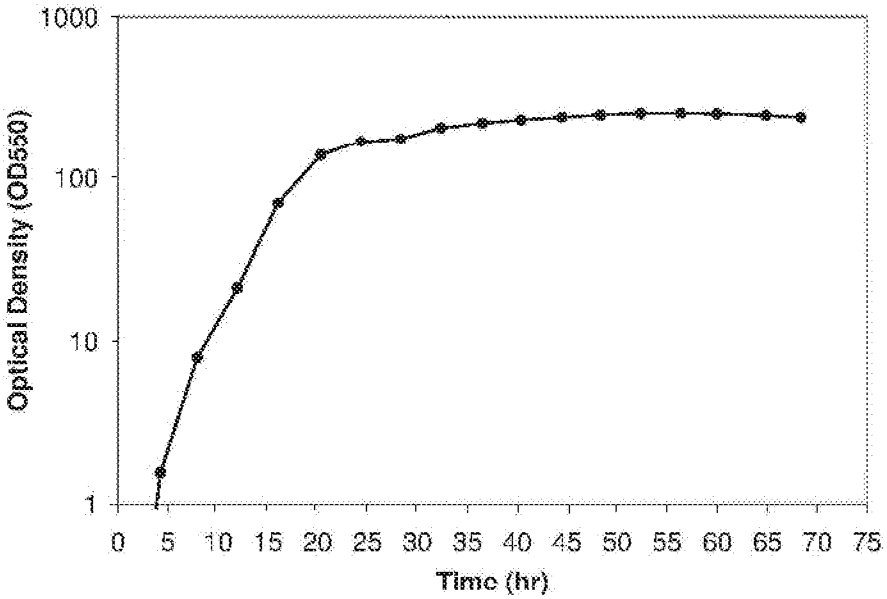
FIGS. 68A, 68B, 68C, 68D and 68E are graphs of isoprene production by *E. coli* strain (EWL256) expressing genes from the MVA pathway and grown in fed-batch culture at the 15-L scale with yeast extract feeding.
Figure 68B:
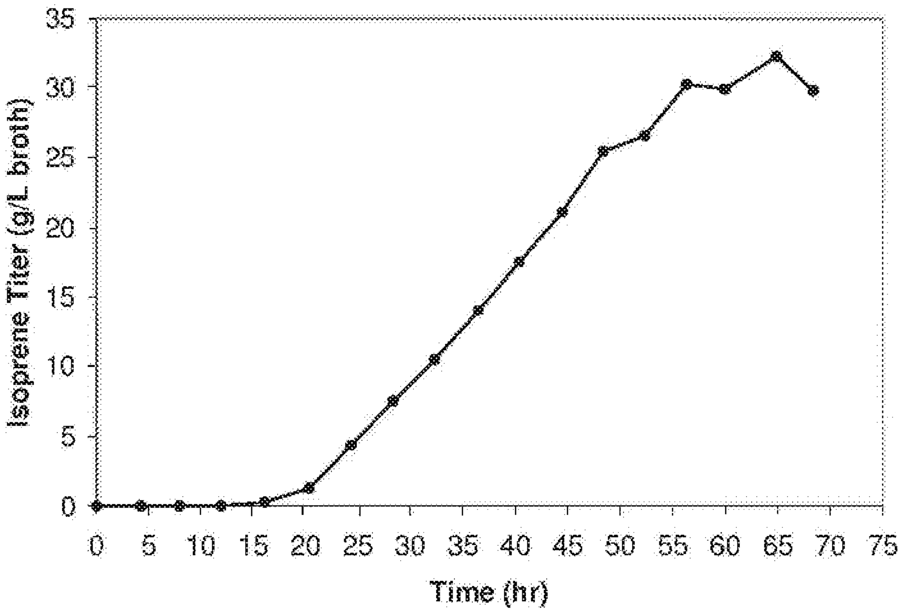
Figure 68C:
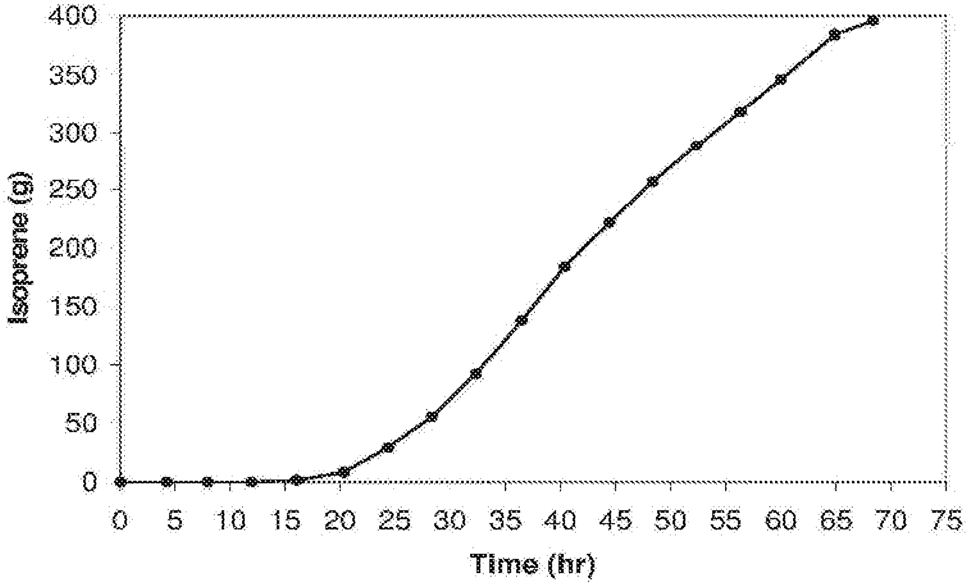
Figure 68D:
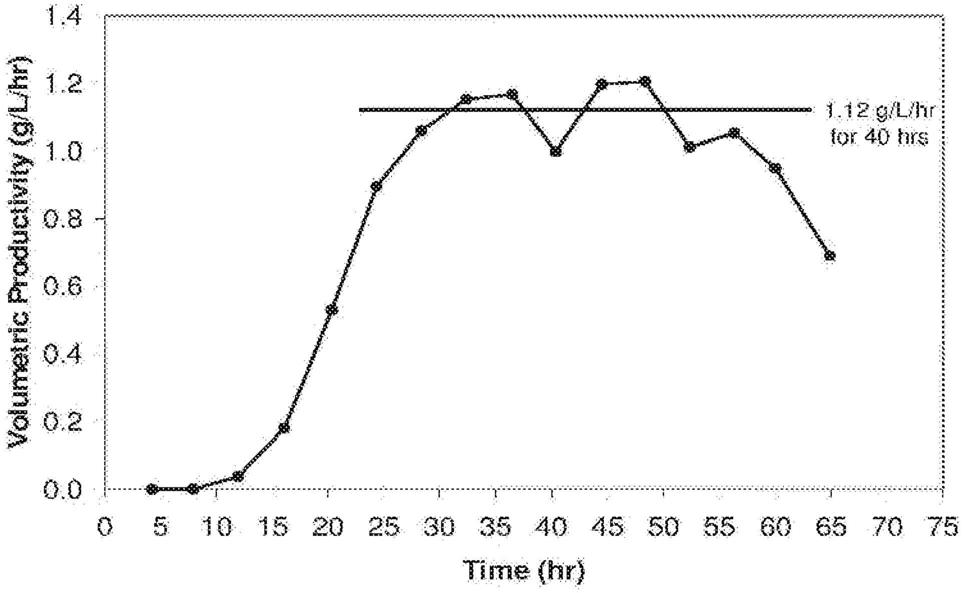
Figure 68E:
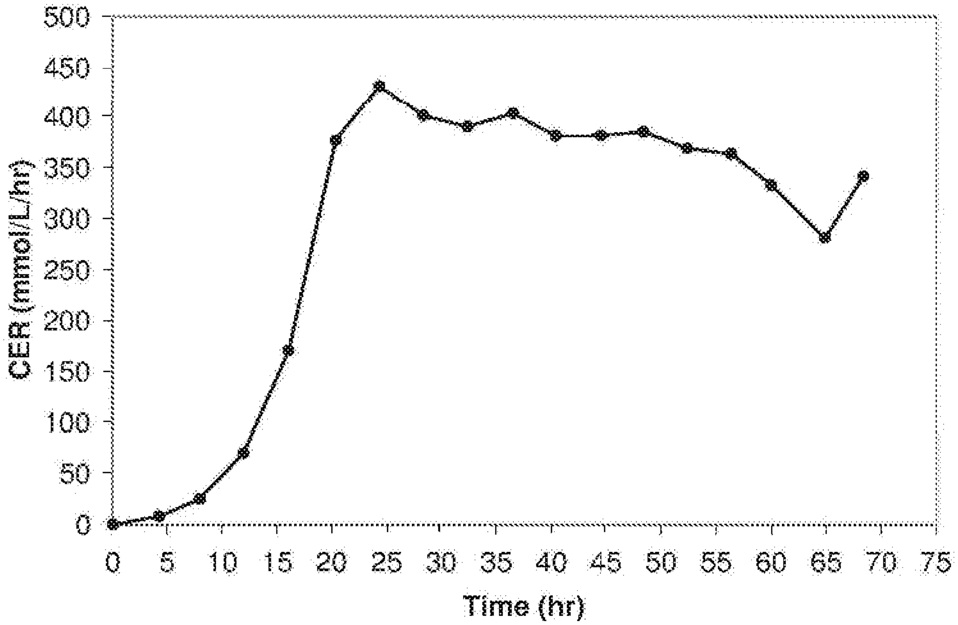

Production of Isoprene in *E. coli* Cells (EL256) Grown in Fed-batch Culture with Yeast Extract Feeding Glucose was fed at an exponential rate until cells reached the stationary phase. After this time the glucose feed was decreased to meet metabolic demands. The total amount of glucose delivered to the bioreactor during the 68 hour fermentation was 7.1 kg. A total of 1.06 kg of yeast extract was also fed during the fermentation. Induction was achieved by adding IPTG. The IPTG concentration was brought to 208 uM when the optical density at 550 nm ($OD_{550}$) reached a value of 7. The IPTG concentration was raised to 193 uM when $OD_{550}$ reached 180. The $OD_{550}$ profile within the bioreactor over time is shown in FIG. 68A. The isoprene level in the off gas from the bioreactor was determined using a Hiden mass spectrometer. The isoprene titer increased over the course of the fermentation to a maximum value of 32.2 g/L (FIG. 68B). The total amount of isoprene produced during the 68 hour fermentation was 395.5 g and the time course of production is shown in FIG. 68C. The time course of volumetric productivity is shown in FIG. 68D and shows that an average rate of 1.1 g/L/hr was maintained for between 23 and 63 hours. The metabolic activity profile, as measured by CER, is shown in FIG. 68E. The molar yield of utilized carbon that went into producing isoprene during fermentation was 10.3%. The weight percent yield of isoprene from glucose was 5.2%.

IV. Production of Isoprene from Different Carbon Sources in *E. coli* Harboring the Mevalonic Acid (MVA) Pathway and Isoprene Synthase (EWL256)

Media Recipe (Per Liter Fermentation Media):

$K_2HPO_4$ 13.6 g, $KH_2PO_4$ 13.6g, $MgSO_4$*$7H_2O$ 2 g, citric acid monohydrate 2 g, ferric ammonium citrate 0.3 g, $(NH_4)_2SO_4$ 3.2 g, yeast extract 0.2 g, 1000× Modified Trace Metal Solution 1 ml. All of the components were dissolved sequentially in $diH_2O$. The pH was adjusted to 6.8 with ammonium hydroxide (30%) and brought to volume. Media was filter sterilized with a 0.22 micron filter. Carbon source was added to a final concentration of 1%. Required antibiotics were added after sterilization and pH adjustment.

1000× Trace Metal Solution (Per Liter Fermentation Media):

Citric Acids*$H_2O$ 40 g, $MnSO_4$*$H_2O$ 30 g, NaCl 10 g, $FeSO_4$*$7H_2O$ 1 g, $CoCl_2$* $6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in di$H_2O$, pH to 3.0 with HCl/NaOH, and then brought to volume and filter sterilized with a 0.22 micron filter.

i) Preparation of AFEX Biomass Hydrolysate

AFEX pretreated corn stover was hydrolyzed to prepare biomass hydrolysate containing both xylose, glucose and acetate.

AFEX pretreated corn stover, received from Michigan Biotechnology Institute, was used. The pretreatment conditions were, 60% moisture, 1:1 ammonia loading, and 90° C. for 30 minutes, then air dried. The moisture content in the AFEX pretreated corn stover was 21.27%. Content of glucan and xylan in the AFEX pretreated corn stover were 31.7% and 19.1% (dry basis) respectively. The enzyme used was accellerase 1000, Grindamyl H121 (Danisco xylanase product from *Aspergillus niger* for bread-making industry).

For saccharification, 20 g of AFEX pretreated corn stover was added into a 500 ml flask, together with 5 ml of 1 M pH 4.8 sodium citrate buffer, 2.25 ml of Accellerase 1000, 0.1 ml of Grindamyl H121, and 72.65 ml of DI water. The flask was put in an orbital shaker, and incubated at 50° C. for 96 hours.

For analysis, one sample was taken from the shaker, and analyzed using HPLC. The hydrolysate contained 37.2 g/l of glucose and 24.3 g/L of xylose, and 7.6 g/L of oligomers of glucose and/or xylose. Additionally, the hydrolysate also contains 1.17 g/L acetate.

ii) Experimental Procedure

An inoculum of the *E. coli* strain EWL256 containing the MVA pathway and isoprene synthase was taken from a frozen vial and streaked onto an LB broth agar plate containing spectinomycin (50 ug/mL) and carbinicllin (50 ug/mL) and incubated at 30° C. overnight. A single colony was inoculated into TM3 media containing glucose, xylose, glycerol, acetate or biomass as only carbon source and grown overnight at 30° C. Cells grow on acetate reached a significantly lower optical density. Cells grown on glucose, glycerol, biomass hydrolysate or acetate were diluted into 20 mL of TM3 media containing the respective carbon sources to reach an optical density of between 0.1 measured at 600 nM. A negative control not containing any carbon source was prepared from the glucose overnight culture. A separate experiment was performed with glucose and xylose, where the cultures were diluted to an optical density of 0.05. All culture conditions (except for acetate and glycerol) were tested in duplicates and the presented results are averaged between these cultures. Production of isoprene was induced with 200 μM IPTG from the beginning of the experiment. The flasks were incubated at 30° C. in an orbital shaker (200 rpm) and growth was followed by measuring optical density. After the glucose fed cultures had reached an optical density of approximately 0.4, samples were analyzed for isoprene production from all the tested carbon sources every hour for three hours. Samples of 100 μL were transferred in duplicates to 2 mL glass vials, sealed and incubated for 30 min at 30° C. The bacteria were then heat killed by incubation at 80° C. for 8 minutes. The amount of produced isoprene was measured using GC-MS and specific productivity (μg/L*hr) was calculated.

iii) Results

Significant production of isoprene could be demonstrated during growth on all the tested carbon sources. These carbon sources are examples of common alcohols, organic acids, sugars containing 5 or 6 carbon units (C5 or C6), and biomass hydrolysate.

Figure 69D:
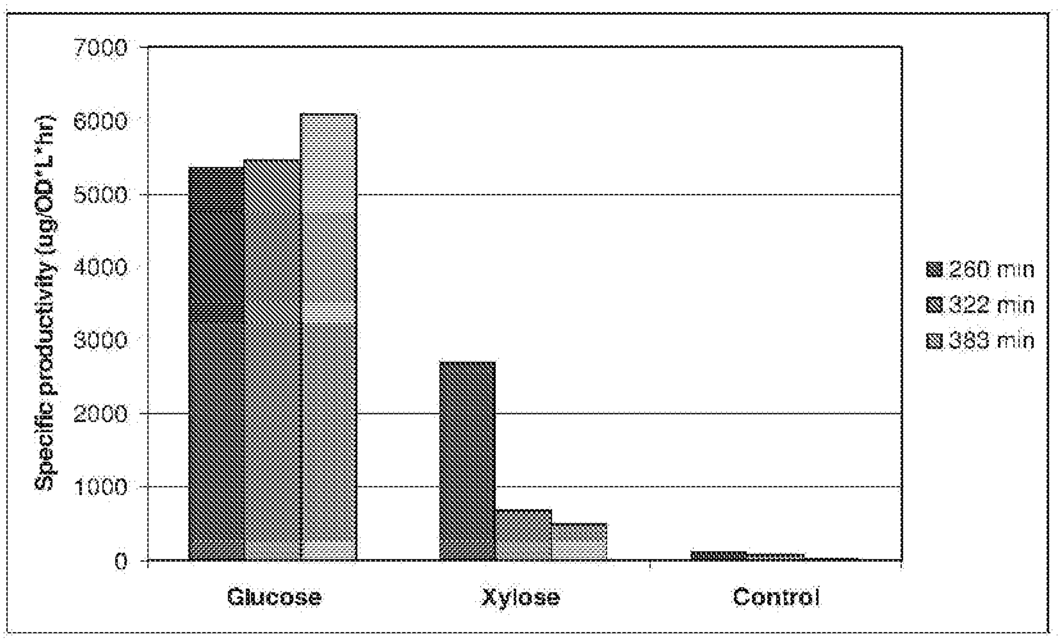

The initial growth rate on biomass hydrolysate was comparable to the growth rate on glucose (FIG. 69A). The initial specific productivity during growth on biomass hydrolysate was significantly higher than during growth on glucose. This demonstrates that biomass hydrolysate can be used as an efficient source of carbon for the production of isoprene. The specific productivity declined after 255 minutes of growth on biomass hydrolysate (FIG. 69B). The bacteria had a slower growth rate with xylose as only carbon source when compared to glucose (FIG. 69C), but a significant specific isoprene productivity was measured (FIG. 69D). This shows that both C5 and C6 sugars can be utilized for the production of isoprene via the mevalonate acid pathway.

Surprisingly, bacteria grown on acetate as the only carbon source had a specific productivity of isoprene approximately twice as high as during growth on glucose (FIG. 69A). The bacteria grew slower on acetate when compared to glucose (FIG. 69B), but the performed experiment demonstrates that acetate can also be used as a carbon source for the production of isoprene. Acetate was also present in the biomass hydrolysate as measured by HPLC.

The bacteria grew well with glycerol as only carbon source (FIG. 69A) and significant production of isoprene was demonstrated (FIG. 69B). This shows that common alcohols may also be used as carbon sources for production of isoprene via the mevalonate acid pathway.

Example 11: Expression of Isoprene-synthase from Plant in *Streptomyces* sp.

Figure 71:
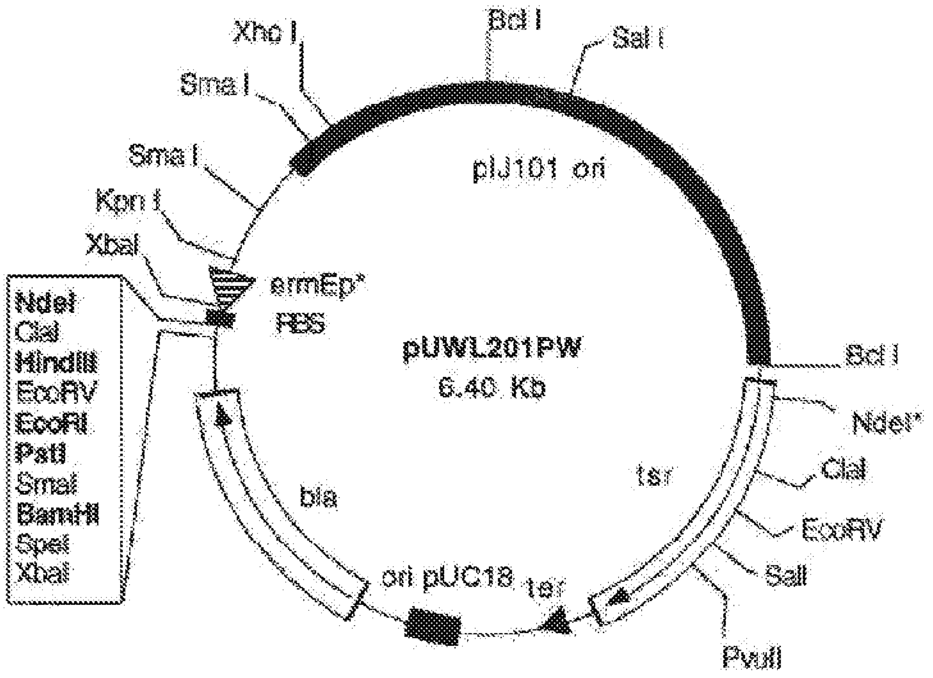
FIG. 71 is a map of the *E. coli-Streptomyces* shuttle vector pUWL201PW (6400 bp) used for cloning isoprene synthase from Kudzu. Tsr, thiostrepton resistance gene. Picture is taken from Doumith et al., Mol. Gen. Genet. 264: 477-485, 2000.
Figure 79A:
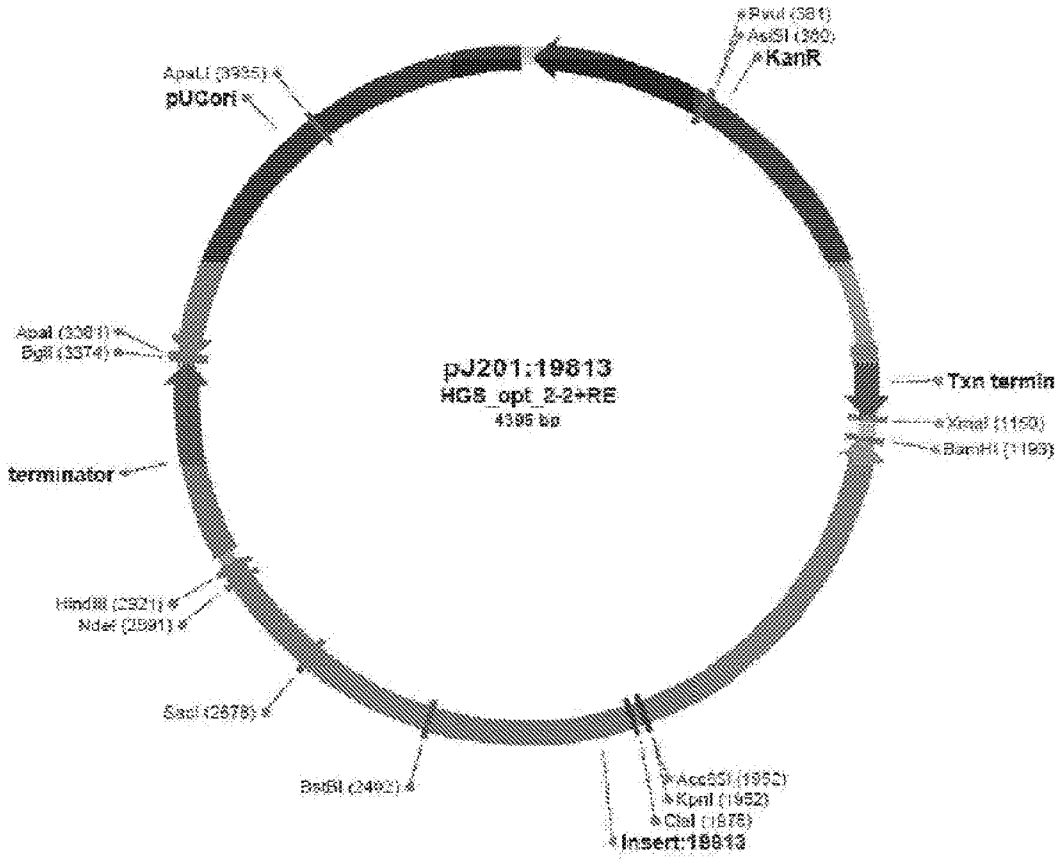
FIG. 79A is a map of plasmid pJ201:19813.

The gene for isoprene synthase Kudzu was obtained from plasmid pJ201:19813. Plasmid pJ201:19813 encodes isoprene synthase from *Pueraia lobata* (Kudzu plant) and was codon-optimized for *Pseudomonas fluorescens, Pseudomonas putida, Rhodopseudomonas palustris* and *Corynebacterium* (FIGS. 79A-79C (SEQ ID NO:123)). Digestion of plasmid pJ201:19813 with restriction enzymes NdeI and BamHI liberated gene iso19813 that was ligated into the *Streptomyces-E. coli* shuttle vector pUWL201PW (Doumith et al., *Mol. Gen. Genet.* 264: 477-485, 2000; FIG. 71) to generate pUWL201_iso. Successful cloning was verified by restriction analysis of pUWL201_iso. Expression of isoprene synthase iso19813 was under control of the erm-promoter which allows for constitutive expression in *Streptomycetes* species, but not for expression in *E. coli.*

PUWL201PW (no insert) and pUWL201_iso were introduced in *Streptomyces albus* J1074 (Sanchez et al., *Chem. Biol.* 9:519-531, 2002) by transformation of protoplasts as described by Hopwood et al., *The John innes foundation, Norwich,* 1985.

A 200 μl aliquot of protoplast suspensions was transformed with 1.9 μg pUWL201PW or 2.9 μg pUWL201_iso. After incubation overnight at 28° C. on non-selective R5-agarplates, positive transformants were selected by further incubation for 4 days in R3-overlay agar containing thiostrepton (250 μg/ml). Thiostrepton resistant transformants were examined for presence of the pUWL-plasmids by plasmid preparation using Plasmid Mini Kit (Qiagen). Prepared plasmid DNA was reintroduced in *E. coli* DH5α to generate sufficient amounts of plasmid DNA to be analyzed by restriction analysis. Positive transformants were selected on ampicillin-containing L-agar plates and insert analysis was done by digestion of plasmid DNA with NdeI and BamHI endonucleases. Isoprene synthase was identified as a 1.7 kb fragment in positive pUWL201 iso clones while in the control strains (pUWL201PW) no such fragment was observed.

Figure 72:
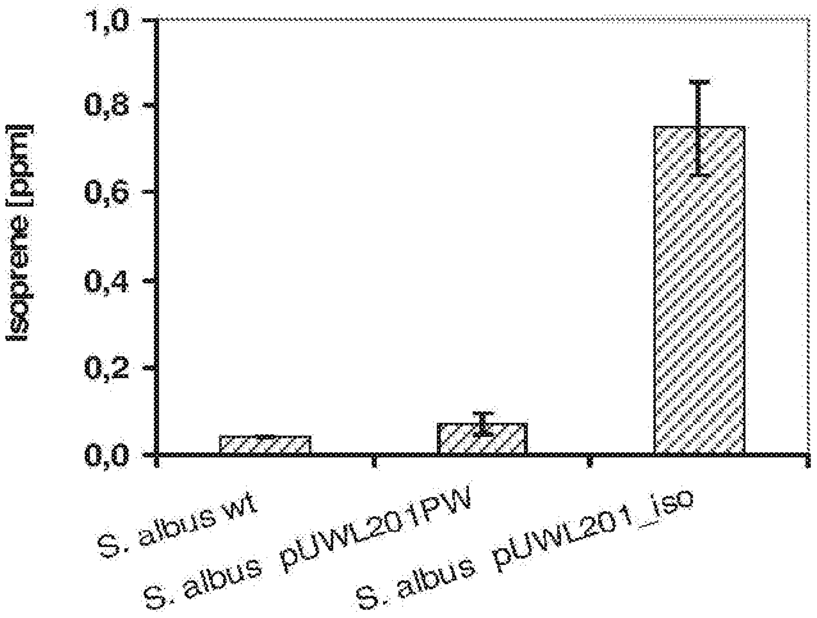
FIG. 72 shows isoprene formation by *Streptomyces albus* wild type strain ("wt") and strains harboring plasmid pUWL201PW (negative control) or pUWL201_iso (encoding isoprene synthase from Kudzu).

Wild type strain and transformants of *S. albus* containing control plasmid pUWL201PW or isoprene synthase encoding pUWL201_iso were analyzed for isoprene formation. Strains were cultivated in duplicate on solid media (tryptic soy broth agar, TSB; 2.5 ml) in presence or absence of thiostrepton (200 μg/ml) and incubated for 4 days at 28° C. in sealed head-space vials (total volume 20 ml). 500 μl head-space samples (end point measurements) were analyzed by GC-MS in SIM-mode and isoprene was identified according to reference retention times and molecular masses (67 m/z). Isoprene present in head-space samples was quantified by previously generated calibration curves. While wild-type *S. albus* and control strains harboring pUWL201PW produced isoprene in concentrations slightly higher than the detection limit (0.04-0.07 ppm), *S. albus* harboring pUWL201_iso produced isoprene in at least ten-fold excess compared to controls (0.75 ppm; FIG. 72). The results demonstrate successful expression of plant-derived isoprene synthase in a prokaryotic organism of the Actinomycetes group.

Example 12: Production of Isoprene or Mevalonate from Fatty Acid or Palm Oil in *E. coli* fadR atoC L55218 Containing the Upper or Upper and Lower Mevalonic Acid Pathway Plus Kudzu Isoprene Synthase

*Escherichia coli* fadR atoC strain LS5218 (#6966) was obtained from the Coli Genetic Stock Center. FadR encodes a transcription repressor that negatively regulates expression of the genes encoding fatty acid degradation enzymes (Campbell et al., *J. Bacteriol.* 183: 5982-5990, 2001). AtoC is a response regulator in a two-component regulatory system with AtoS, regulates acetolactate metabolism. The fadR atoC strain allows constitutive expression of the fatty acid degradation genes and incorporates long chain fatty acids into long-chain-length polyhydroxyalkanoates. When palm oil is used as a carbon source for either mevalonate or isoprene production, the palm oil was converted to glycerol plus fatty acid. Methods for this are well known in the art, and it can be done either enzymatically by incubation with a lipase (for example Porcine pancreatic lipase, *Candida rugosa* lipase, or other similar lipases) or chemically by saponification with a base such as sodium hydroxide.

i) *E. coli* fadR atoC Strain Expressing the Upper Mevalonic Acid Pathway

Strain WW4 was created by electroporating pCLPtrcUpperPathway into LS5218 using standard methods (Sambrooke et al., Molecular Cloning: A Laboratory Manual, 2$^{nd}$ ed., Cold Spring Harbor, 1989). Incorporation of the plasmid was demonstrated by the production of mevalonic acid (MVA) when cells were cultured in TM3 medium supplemented with either C12 fatty acid (FA) or palm oil as the carbon source. To demonstrate production of MVA by WW4 from fatty acid, cells from an overnight culture were diluted 1 to 100 into 5 mL of modified TM3 medium (TM3 without yeast extract) supplemented with 0.25% C12 FA (Sigma cat # L9755). The first sign of MVA production (24 mg/L) was apparent after overnight incubation at 30° C. of the IPTG induced culture. Production increased over three days with the final level of 194 mg/L of MVA produced. To demonstrate production of MVA by WW4 from oil, cells from an overnight culture were diluted 1 to 100 into modified TM3 medium supplemented with 200 mg of digested palm oil per 5 mL of TM3 medium. The first sign of MVA production (50 mg/L) was apparent after overnight incubation of the IPTG induced culture at 30° C. Production increased over three days with a final level of 500 mg/L of MVA produced.

ii) *E. coli* fadR atoC Strain Expressing the Upper and Lower MVA Pathway Plus Kudzu Isoprene Synthase

Figure 70A:
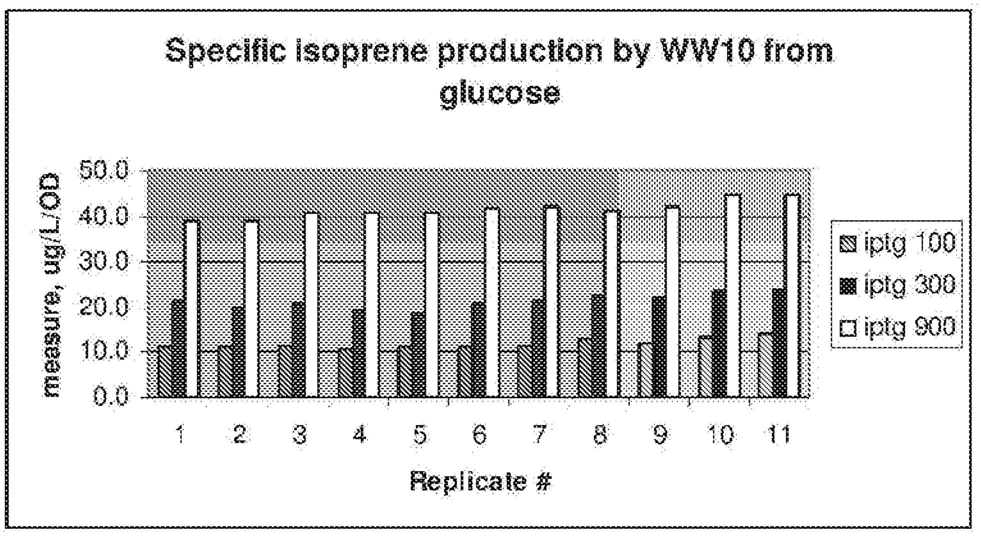
FIGS. 70A and 70B show the production of isoprene by *E. coli* strains from glucose and from fatty acid, respectively. For FIG. 70A, eleven colonies from the transformation of WW4 with pMCM118, the plasmid bearing the lower mevalonic acid pathway, were picked to verify the presence of the lower pathway. Cell from the colonies were cultured in TM3 medium containing 0.1% yeast extract and 2% glucose. Aliquots of induced culture were assayed for isoprene production after 4 hours of induction. All colonies showed the production of isoprene. The inducer IPTG had a strong growth inhibitory effect as was evident from the 3 to 4.6-fold reduced cell density in going from 50 to 900 uM concentration of the inducer (data not shown). The graph shows that higher induction, yields a higher specific titer of isoprene. For FIG. 70B, the production culture was inoculated from a washed overnight culture at 1 to 10 dilution. The culture was grown for several hours and induced with 50 uM IPTG. The left bar shows isoprene assay results four hours after induction followed by a one hour isoprene accumulation assay. The middle bar shows the one hour normalized value for the same culture with the same induction period but analyzed by a 12 hour isoprene accumulation assay. The right bar shows the value for a one hour isoprene accumulation assay of the culture that was induced for 13 hours.

*Escherichia coli* strain WW4 (LS5218 fadR atoC pCLPtrcUpperPathway) was transformed with pMCM118 [pTrcKKDyIkIS] to yield WW10. The incorporation of the plasmid was demonstrated by evidence of production of isoprene when the strain was cultured in TM3 and glucose and induced with IPTG (100, 300, or 900 uM). The strain was relatively sensitive to IPTG and showed a significant growth defect even at 100 uM IPTG. These results are shown in FIG. 70A.

To test isoprene production from dodecanoic acid, WW10 was cultured overnight in L broth containing spectinomycin (50 ug/ml), and kanamycin (50 ug/ml) at 37 C with shaking at 200 rpm. The cells were washed with modified TM3 medium by centrifugation and resuspension in their original culture volume with this medium. The washed and resuspended cells from this starter culture were diluted 1 to 100 and 1 to 10 into 5 mL of modified TM3 medium containing 0.125% C12 Fatty Acid (Sigma cat # L9755).

To demonstrate production of mevalonate from palm oil, the oil was predigested with lipase at 37° C. and 250 rpm for several days to release the fatty acids (evidence of hydrolysis was judged by the foam formed when tubes were shaken).

Figure 70B:
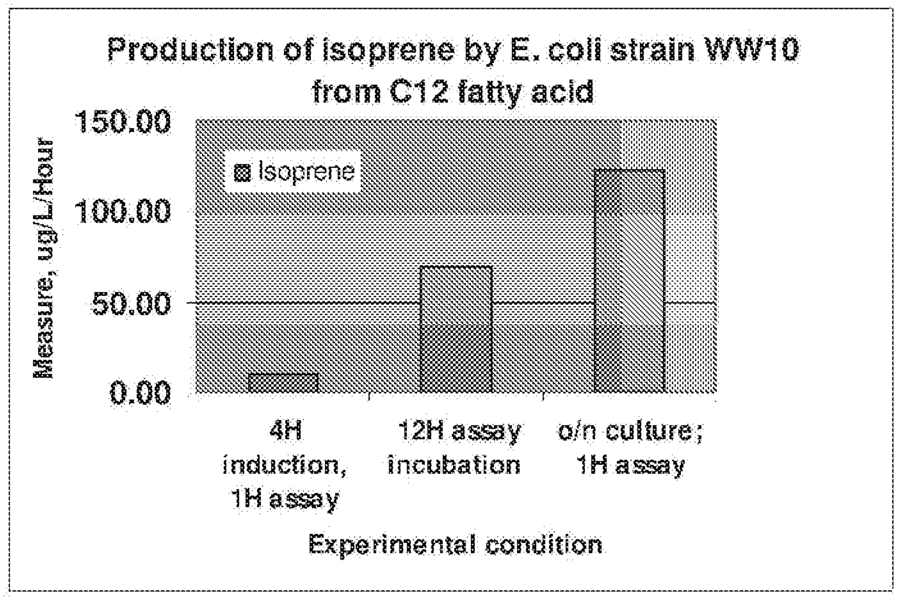

In addition, a culture was set up by diluting the washed cells at 1 to 10 into modified TM3 medium contained in test tubes with palm oil. A further tube was set up by the addition of 0.125% C12FA to the remainder (2.5 mL) of the washed cells without further dilution (bioconversion). After 3.75 hours of growth at 30° C. with shaking at 250 rpm all of the cultures were induced by the addition of 50 uM IPTG. Incubation was continued for 4 hours after which time 200 uL of each of the cultures was assayed for isoprene accumulation with a modified head space assay (1 hour accumulation at 30° C. with shaking at 500 rpm). An additional isoprene assay was conducted by a 12 hour incubation of the assay glass block prior to GCMS analysis. Incubation of the induced cultures was continued overnight and 200 uL aliquots were again assayed for isoprene production (1 hour, 30 deg, 500 rpm Shel-Lab shaker) the following morning. Analysis of these cultures showed the production of significant levels of isoprene. The highest levels of isoprene were observed in the culture which was seeded at 1/10 dilution from the overnight starter culture after it had been incubated and induced overnight. This result suggests that this culture continued to grow and increase in cell density. These results are shown in FIG. 70B. Cell density could not be measured directly because the fatty acid suspension had a turbid appearance. Cell density of this culture was therefore determined by plating an aliquot of the culture and showed $8\times10^7$ colony forming units. This corresponds approximately to an $OD_{600}$ of 0.1. Nevertheless, this culture provided significant isoprene production; no isoprene is observed for similar strains without the pathway described in this example.

Example 13: Improvement of Isoprene Production by Constitutive Expression of ybhE in *E. coli*

This example shows production of isoprene in a strain constitutively expressing ybhE (pgl) compared to a control strain with wild type ybhE. The gene ybhE (pgl) encodes a 6-phosphogluconolactonase that suppresses posttranslational gluconylation of heterologously expressed proteins and improves product solubility and yield while also improving biomass yield and flux through the pentose phosphate pathway (Aon et al. *Applied and Environmental Microbiology,* 74(4): 950-958, 2008).

The BL21 strain of *E. coli* producing isoprene (EWL256) was constructed with constitutive expression of the ybhE gene on a replicating plasmid pBBR1MCS5(Gentamycin) (obtained from Dr. K. Peterson, Louisiana State University).

FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers Pgl-F and PglGI1.5-R were used to amplify the resistance cassette from the FRT-gb2-Cm-FRT template using Stratagene Herculase II Fusion kit according to the manufacturer's protocol. The PCR reaction (50 uL final volume) contained: 5 uL buffer, 1 uL template DNA (FRT-gb2-Cm-F from Gene Bridges), 10 pmols of each primer, and 1.5 uL 25 mM dNTP mix, made to 50 uL with $dH_2O$. The reaction was cycled as follows: 1×2 minutes, 95° C. then 30 cycles of (30 seconds at 95° C.; 30 seconds at 63° C.; 3 minutes at 72° C.).

The resulting PCR product was purified using the QiaQick PCR purification kit (Qiagen) and electroporated into electrocompetent MG1655 cells harboring the pRed-ET recombinase-containing plasmid as follows. Cells were prepared by growing in 5 mLs of L broth to and OD600~0.6 at 30° C. The cells were induced for recombinase expression by the addition of 4% arabinose and allowed to grow for 30 minutes at 30° C. followed by 30 minutes of growth at 37° C. An aliquot of 1.5 mLs of the cells was washed 3-4 times in ice cold $dH_2O$. The final cell pellet was resuspended in 40 uL of ice cold $dH_2O$ and 2-5 uL of the PCR product was added. The electroporation was carried out in 1-mm gap cuvettes, at 1.3 kV in a Gene Pulser Electroporator (Bio-Rad Inc.). Cells were recovered for 1-2 hours at 30° C. and plated on L agar containing chloramphenicol (5 ug/mL). Five transformants were analyzed by PCR and sequencing using primers flanking the integration site (2 primer sets: pgl and 49 rev and 3' EcoRV-pglstop; Bottom Pgb2 and Top GB's CMP (946)). A correct transformant was selected and this strain was designated MG1655 GI1.5-pgl::CMP.

The chromosomal DNA of MG1655 GI1.5-pgl::CMP was used as template to generate a PCR fragment containing the FRT-CMP-FRT-GI1.5-ybhE construct. This construct was cloned into pBBR1MCS5(Gentamycin) as follows. The fragment, here on referred to as CMP-GI1.5-pgl, was amplified using the 5' primer Pglconfirm-F and 3' primer 3' EcoRV-pglstop. The resulting fragment was cloned using the Invitrogen TOPO-Blunt cloning kit into the plasmid vector pCR-Blunt II-TOPO as suggested from the manufacturer. The NsiI fragment harboring the CMP-GI1.5-pgl fragment was cloned into the PstI site of pBBR1MCS5(Gentamycin). A 20 µl ligation reaction was prepared containing 5 µl CMP-GI1.5-pgl insert, 2 µl pBBR1MCS5(Gentamycin) vector, 1 µl T4 DNA ligase (New England Biolabs), 2 µl 10× ligase buffer, and 10 µl $ddH_2O$. The ligation mixture was incubated at room temperature for 40 minutes then 2-4 uL were electroporated into electrocompetent Top10 cells (Invitrogen) using the parameters disclosed above. Transformants were selected on L agar containing 10 ug/ml chloramphenicol and 5 ug/ml Gentamycin. The sequence of the selected clone was determined using a number of the primers described above as well as with the in-house T3 and Reverse primers provided by Sequetech, CA. This plasmid was designated pBBRCMPGI1.5-pgl (FIGS. 77A-B and SEQ ID NO:122).

Plasmid pBBRCMPGI1.5-pgl was electroporated into EWL256, as described above in Example 10 and transformants were plated on L agar containing Chloramphenicol (10 ug/mL), Gentamycin (5 ug/mL), spectinomycin (50 ug/mL), and carbenicillin (50 ug/mL). One transformant was selected and designated RM11608-2.

```
Pgl-F
                                          (SEQ ID NO: 115)
5'-ACCGCCAAAAGCGACTAATTTTAGCTGTTACAGTCAGTTGAAT

TAACCCTCACTAAAGGGCGGCCGC-3'

PglGI1.5-R
                                          (SEQ ID NO: 116)
5'-GCTGGCGATATAAACTGTTTGCTTCATGAATGCTCCTTTGGGT

TACCTCCGGGAAACGCGGTTGATTTGTTTAGTGGTTGAATTATTTGCTC

AGGATGTGGCATAGTCAAGGGCGTGACGGCTCGCTAATACGACTCACTA

TAGGGCTCGAG-3'

3'EcoRV-pglstop:
                                          (SEQ ID NO: 117)
5'-CTT GAT ATC TTA GTG TGC GTT AAC CAC CAC

pgl + 49 rev:
                                          (SEQ ID NO: 118)
CGTGAATTTGCTGGCTCTCAG

Bottom Pgb2:
                                          (SEQ ID NO: 119)
GGTTTAGTTCCTCACCTTGTC

Top GB's CMP (946):
                                          (SEQ ID NO: 120)
ACTGAAACGTTTTCATCGCTC

Pglconfirm-F
                                          (SEQ ID NO: 121)
5'-ACCGCCAAAAGCGACTAATTTTAGCT-3'
```

i) Small Scale Analysis

Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, 1000× Trace Metals Solution 1 ml. All of the components were added together and dissolved in $diH_2O$. The pH was adjusted to 6.8 with ammonium hydroxide (30%) and brought to volume. Media was filter-sterilized with a 0.22 micron filter. Glucose 5.0 g and antibiotics were added after sterilization and pH adjustment.

1000× Trace Metal Solution (Per Liter Fermentation Media):

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

a) Experimental Procedure

Isoprene production was analyzed by growing the strains in a Cellerator™ from MicroReactor Technologies, Inc. The working volume in each of the 24 wells was 4.5 mL. The temperature was maintained at 30° C., the pH setpoint was 7.0, the oxygen flow setpoint was 20 sccm and the agitation rate was 800 rpm. An inoculum of *E. coli* strain taken from a frozen vial was streaked onto an LB broth agar plate (with antibiotics) and incubated at 30° C. A single colony was inoculated into media with antibiotics and grown overnight. The bacteria were diluted into 4.5 mL of media with antibiotics to reach an optical density of 0.05 measured at 550 nm.

Off-gas analysis of isoprene was performed using a gas chromatograph-mass spectrometer (GC-MS) (Agilent) headspace assay. Sample preparation was as follows: 100 μL of whole broth was placed in a sealed GC vial and incubated at 30° C. for a fixed time of 30 minutes. Following a heat kill step, consisting of incubation at 70° C. for 5 minutes, the sample was loaded on the GC.

Optical density (OD) at a wavelength of 550 nm was obtained using a microplate reader (Spectramax) during the course of the run. Specific productivity was obtained by dividing the isoprene concentration (μg/L) by the OD reading and the time (hour).

The two strains EWL256 and RM11608-2 were assessed at 200 and 400 uM IPTG induction levels. Samples were analyzed for isoprene production and cell growth (OD550) at 1, 2.5, 4.75, and 8 hours post-induction. Samples were done in duplicate.

b) Results

The experiment demonstrated that at 2 different concentrations of IPTG the strain expressing the ybhE (pgl) had a dramatic 2-3 fold increase in specific productivity of isoprene compared to the control strain.

ii) Isoprene Fermentation from *E. coli* Expressing *M. mazei* Mevalonate Kinase, *P. alba* Isoprene Synthase, and pgl Over-expression (RHM111608-2) and Grown in Fed-batch Culture at the 15-L Scale Medium Recipe (Per Liter Fermentation Medium)

$K_2HPO_4$ 7.5 g, $MgSO_4$*$7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in di$H_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4$*$H_2O$ 30 g, NaCl 10 g, $FeSO_4$*$7H_2O$ 1 g, $CoCl_2$* $6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in Di $H_2O$, pH to 3.0 with HCl/NaOH, then q.s. to volume and filter sterilized with a 0.22 micron filter Fermentation was performed in a 15-L bioreactor with BL21 (DE3) *E. coli* cells containing the upper mevalonic acid (MVA) pathway (pCL Upper), the integrated lower MVA pathway (gi1.2KKDyI), high expression of mevalonate kinase from *M. mazei* and isoprene synthase from *P. alba* (pTrcAlba-mMVK), and high expression of pgl (pBBR-pgl). This experiment was carried out to monitor isoprene formation from glucose at the desired fermentation pH 7.0 and temperature 34° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

Figure 78A:
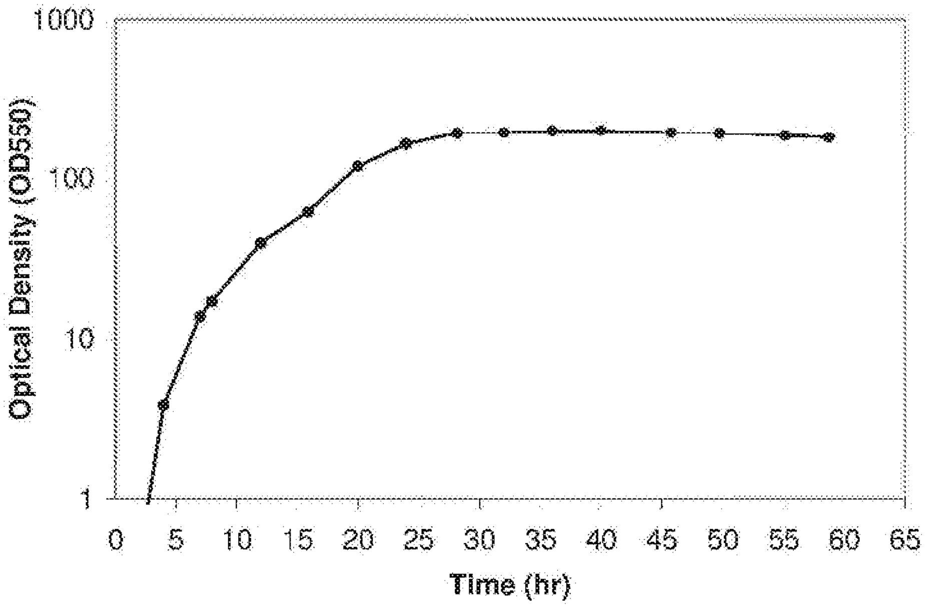
FIGS. 78A, 78B, 78C, 78D, 78E, and 78F are graphs of isoprene production by *E. coli* strain expressing *M. mazei* mevalonate kinase, *P. alba* isoprene synthase, and pgl (RHM111608-2), and grown in fed-batch culture at the 15-L scale.
Figure 78B:
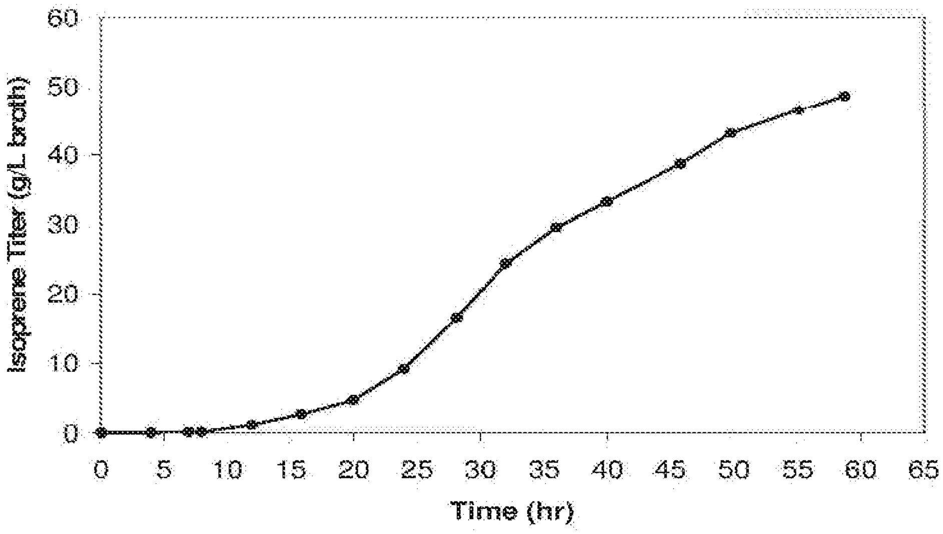
Figure 78C:
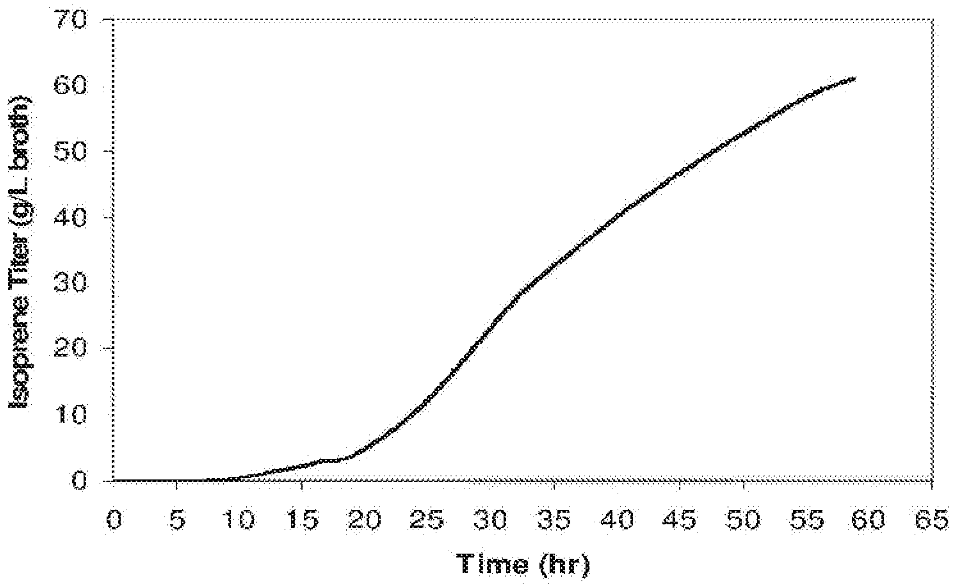
Figure 78D:
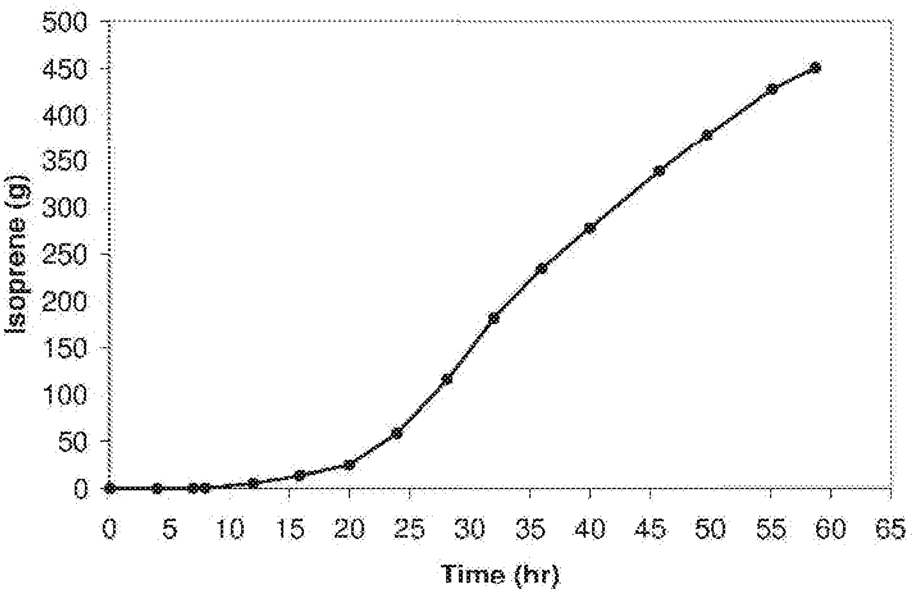
Figure 78E:
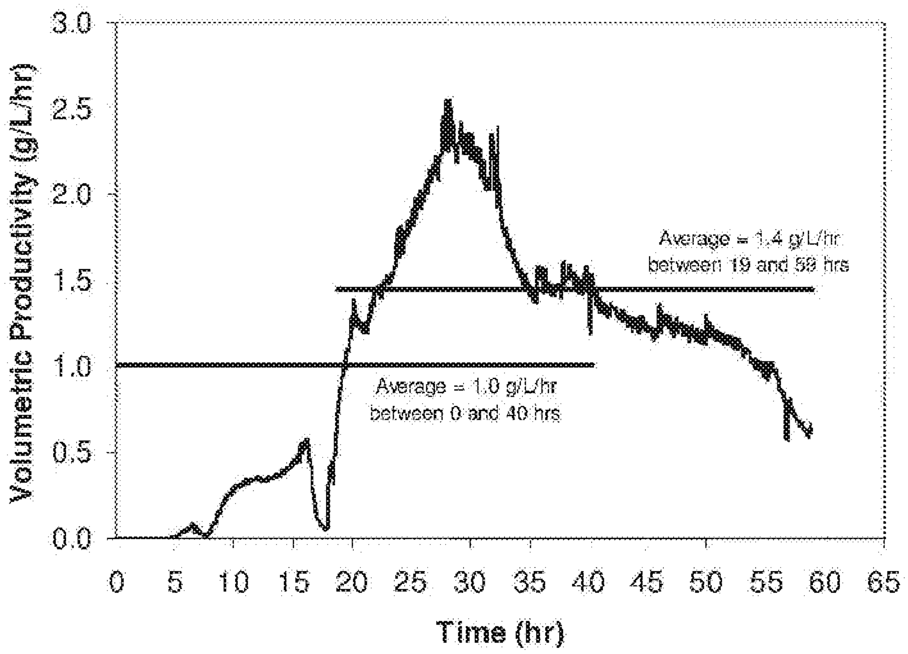
Figure 78F:
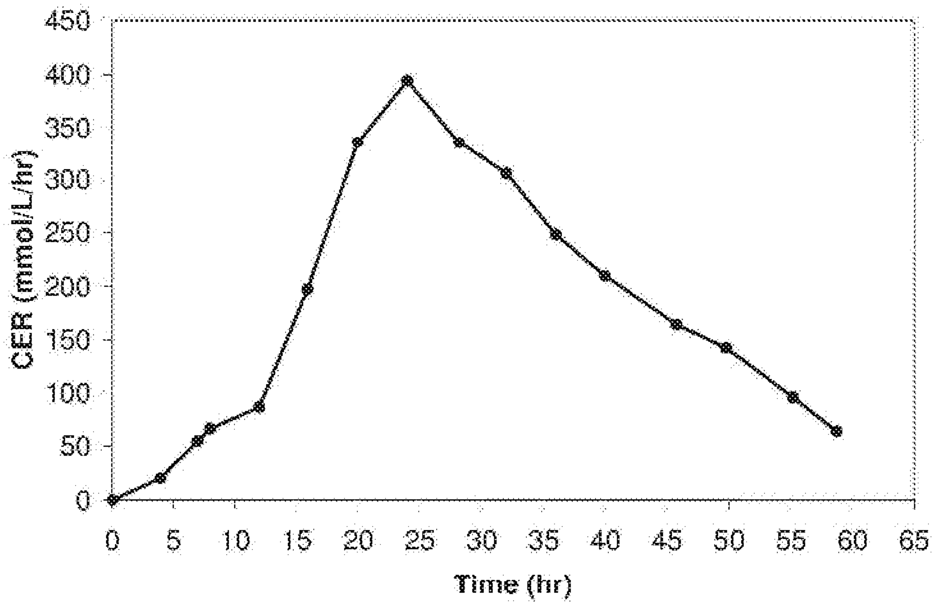

Glucose was fed at an exponential rate until cells reached the stationary phase. After this time the glucose feed was decreased to meet metabolic demands. The total amount of glucose delivered to the bioreactor during the 40 hour (59 hour) fermentation was 3.1 kg (4.2 kg at 59 hour). Induction was achieved by adding IPTG. The IPTG concentration was brought to 110 uM when the optical density at 550 nm ($OD_{550}$) reached a value of 4. The IPTG concentration was raised to 192 uM when $OD_{550}$ reached 150. The $OD_{550}$ profile within the bioreactor over time is shown in FIG. 78A. The isoprene level in the off gas from the bioreactor was determined using a Hiden mass spectrometer. The isoprene titer increased over the course of the fermentation to a maximum value of 33.2 g/L at 40 hours (48.6 g/L at 59 hours) (FIG. 78B). The isoprene titer increased over the course of the fermentation to a maximum value of 40.0 g/L at 40 hours (60.5 g/L at 59 hours) (FIG. 78C). The total amount of isoprene produced during the 40-hour (59-hour) fermentation was 281.3 g (451.0 g at 59 hours) and the time course of production is shown in FIG. 78D. The time course of volumetric productivity is shown in FIG. 78E and shows that an average rate of 1.0 g/L/hr was maintained between 0 and 40 hours (1.4 g/L/hour between 19 and 59 hour). The metabolic activity profile, as measured by CER, is shown in FIG. 78F. The molar yield of utilized carbon that went into producing isoprene during fermentation was 19.6% at 40 hours (23.6% at 59 hours). The weight percent yield of isoprene from glucose was 8.9% at 40 hours (10.7% at 59 hours).

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

APPENDIX 1

Exemplary 1-deoxy-D-xylulose-5-phosphate Synthase Nucleic Acids and Polypeptides

ATH: AT3G21500(DXPS1) AT4G15560(CLA1) AT5G11380(DXPS3)

OSA: 4338768 4340090 4342614

CME: CMF089C
PFA: MAL13P1.186
TAN: TA20470
TPV: TP01_0516
ECO: b0420(dxs)
ECJ: JW0410(dxs)
ECE: Z0523(dxs)
ECS: ECs0474
ECC: c0531(dxs)
ECI: UTI89_C0443(dxs)
ECP: ECP_0479
ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YPO3177(dxs)
YPK: y1008(dxs)
YPM: YP_0754(dxs)
YPA: YPA_2671
YPN: YPN_0911
YPP: YPDSF_2812
YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
MSU: MS1059(dxs)
APL: APL_0207(dxs)
XFA: XF2249
XFT: PD1293(dxs)
XCC: XCC2434(dxs)
XCB: XC_1678
XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
PCR: Pcryo_0245
ACI: ACIAD3247(dxs)
SON: SO_1525(dxs)
SDN: Sden_2571
SFR: Sfri_2790
SAZ: Sama_2436
SBL: Sbal_1357
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Patl_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381
HCH: HCH_05866(dxs)
CSA: Csal_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NMC: NMC0352(dxs)
NGO: NG00036
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10299_1706(dxs)
BMN: BMA10247_A0364(dxs)
BXE: Bxe_B2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)

BPD: BURPS668_A2534(dxs)
BTE: BTH_II0614(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)
MMS: mma_0331
NEU: NE1161(dxs)
NET: Neut_1501
NMU: Nmul_A0236
EBA: ebA4439(dxs)
AZO: azo1198(dxs)
DAR: Daro_3061
TBD: Tbd_0879
MFA: Mfla_2133
HPY: HP0354(dxs)
HPJ: jhp0328(dxs)
HPA: HPAG1_0349
HHE: HH0608(dxs)
HAC: Hac_0968(dxs)
WSU: WS1996
TDN: Tmden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs) CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
PPD: Ppro_1191 Ppro_2403
DVU: DVU1350(dxs)
DVL: Dvul_1718
DDE: Dde_2200
LIP: LI0408(dsx)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735
SME: SMc00972(dxs)
ATU: Atu0745(dxs)
ATC: AGR_C_1351
RET: RHE_CH00913(dxs)
RLE: RL0973(dxs)
BME: BMEI1498
BMF: BAB1_0462(dxs)
BMS: BR0436(dxs)
BMB: BruAb1_0458(dxs)
BOV: BOV_0443(dxs)
BJA: bll2651(dxs)
BRA: BRADO2161(dxs)
BBT: BBta_2479(dxs)
RPA: RPA0952(dxs)
RPB: RPB_4460
RPC: RPC_1149
RPD: RPD_4305
RPE: RPE_1067
NWI: Nwi_0633
NHA: Nham_0778
BHE: BH04350(dxs)
BQU: BQ03540(dxs)
BBK: BARBAKC583_0400(dxs)
CCR: CC_2068
SIL: SPO0247(dxs)
SIT: TM1040_2920
RSP: RSP_0254(dxsA) RSP_1134(dxs)
JAN: Jann_0088 Jann_0170
RDE: RD1_0101(dxs) RD1_0548(dxs)
MMR: Mmar10_0849
HNE: HNE_1838(dxs)
ZMO: ZMO1234(dxs) ZMO1598(dxs)
NAR: Saro_0161
SAL: Sala_2354
ELI: ELI_12520
GOX: GOX0252
GBE: GbCGDNIH1_0221 GbCGDNIH1_2404
RRU: Rru_A0054 Rru_A2619
MAG: amb2904
MGM: Mmcl_1048
SUS: Acid_1783
BSU: BG11715(dxs)
BHA: BH2779
BAN: BA4400(dxs)
BAR: GBAA4400(dxs)
BAA: BA_4853
BAT: BAS4081
BCE: BC4176(dxs)
BCA: BCE_4249(dxs)
BCZ: BCZK3930(dxs)
BTK: BT9727_3919(dxs)
BTL: BALH_3785(dxs)
BLI: BL01523(dxs)
BLD: BLi02598(dxs)
BCL: ABC2462(dxs)
BAY: RBAM_022600
BPU: BPUM_2159
GKA: GK2392
GTN: GTNG_2322
LMO: lmo1365(tktB)
LMF: LMOf2365_1382(dxs)
LIN: lin1402(tktB)
LWE: lwe1380(tktB)
LLA: L108911(dxsA) L123365(dxsB)
LLC: LACR_1572 LACR_1843
LLM: llmg_0749(dxsB)
SAK: SAK_0263
LPL: lp_2610(dxs)
LJO: LJ0406
LAC: LBA0356
LSL: LSL_0209(dxs)
LGA: LGAS_0350
STH: STH1842
CAC: CAC2077 CA_P0106(dxs)
CPE: CPE1819
CPF: CPF_2073(dxs)
CPR: CPR_1787(dxs)
CTC: CTC01575
CNO: NT01CX_1983

CTH: Cthe_0828
CDF: CD1207(dxs)
CBO: CBO1881(dxs)
CBA: CLB_1818(dxs)
CBH: CLC_1825(dxs)
CBF: CLI_1945(dxs)
CKL: CKL_1231(dxs)
CHY: CHY_1985(dxs)
DSY: DSY2348
DRM: Dred_1078
PTH: PTH_1196(dxs)
SWO: Swol_0582
CSC: Csac_1853
TTE: TTE1298(dxs)
MTA: Moth_1511
MPE: MYPE730
MGA: MGA_1268(dxs)
MTU: Rv2682c(dxs1) Rv3379c(dxs2)
MTC: MT2756(dxs)
MBO: Mb2701c(dxs1) Mb3413c(dxs2)
MLE: ML1038(dxs)
MPA: MAP2803c(dxs)
MAV: MAV_3577(dxs)
MSM: MSMEG_2776(dxs)
MMC: Mmcs_2208
CGL: NCgl1827(cgl1902)
CGB: cg2083(dxs)
CEF: CE1796
CDI: DIP1397(dxs)
CJK: jk1078(dxs)
NFA: nfa37410(dxs)
RHA: RHA1_ro06843
SCO: SCO6013(SC1C3.01) SCO6768(SC6A5.17)
SMA: SAV1646(dxs1) SAV2244(dxs2)
TWH: TWT484
TWS: TW280(Dxs)
LXX: Lxx10450(dxs)
CMI: CMM_1660(dxsA)
AAU: AAur_1790(dxs)
PAC: PPA1062
TFU: Tfu_1917
FRA: Francci3_1326
FAL: FRAAL2088(dxs)
ACE: Acel_1393
SEN: SACE_1815(dxs) SACE_4351
BLO: BL1132(dxs)
BAD: BAD_0513(dxs)
FNU: FN1208 FN1464
RBA: RB2143(dxs)
CTR: CT331(dxs)
CTA: CTA_0359(dxs)
CMU: TC0608
CPN: CPn1060(tktB_2)
CPA: CP0790
CPJ: CPj1060(tktB_2)
CPT: CpB1102
CCA: CCA00304(dxs)
CAB: CAB301(dxs)
CFE: CF0699(dxs)
PCU: pc0619(dxs)
TPA: TP0824
TDE: TDE1910(dxs)
LIL: LA3285(dxs)
LIC: LIC10863(dxs)
LBJ: LBJ_0917(dxs)
LBL: LBL_0932(dxs)
SYN: sll1945(dxs)
SYW: SYNW1292(Dxs)
SYC: syc1087_c(dxs)
SYF: Synpcc7942_0430
SYD: Syncc9605_1430
SYE: Syncc9902_1069
SYG: sync_1410(dxs)
SYR: SynRCC307_1390(dxs)
SYX: SynWH7803_1223(dxs)
CYA: CYA_1701(dxs)
CYB: CYB_1983(dxs)
TEL: tll0623
GVI: gll0194
ANA: alr0599
AVA: Ava_4532
PMA: Pro0928(dxs)
PMM: PMM0907(Dxs)
PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521
PME: NATL1_09721(dxs)
TER: Tery_3042
BTH: BT_1403 BT_4099
BFR: BF0873 BF4306
BFS: BF0796(dxs) BF4114
PGI: PG2217(dxs)
CHU: CHU_3643(dxs)
GFO: GFO_3470(dxs)
FPS: FP0279(dxs)
CTE: CT0337(dxs)
CPH: Cpha266_0671
PVI: Cvib_0498
PLT: Plut_0450
DET: DET0745(dxs)
DEH: cbdb_A720(dxs)
DRA: DR_1475
DGE: Dgeo_0994
TTH: TTC1614
TTJ: TTHA0006
AAE: aq_881
TMA: TM1770
PMO: Pmob_1001

Exemplary Acetyl-CoA-Acetyltransferase Nucleic Acids and Polypeptides

HSA: 38(ACAT1) 39(ACAT2)
PTR: 451528(ACAT1)
MCC: 707653(ACAT1) 708750(ACAT2)
MMU: 110446(Acat1) 110460(Acat2)
RNO: 25014(Acat1)
CFA: 484063(ACAT2) 489421(ACAT1)
GGA: 418968(ACAT1) 421587(RCJMB04_34i5)
XLA: 379569(MGC69098) 414622(MGC81403) 414639 (MGC81256) 444457(MGC83664)
XTR: 394562(acat2)
DRE: 30643(acat2)
SPU: 759502(LOC759502)
DME: Dmel_CG10932 Dmel_CG9149
CEL: T02G5.4 T02G5.7 T02G5.8(kat-1)
ATH: AT5G48230(ACAT2/EMB1276)
OSA: 4326136 4346520
CME: CMA042C CME087C
SCE: YPL028W(ERG10)

AGO: AGOS_ADR165C
PIC: PICST_31707(ERG10)
CAL: CaO19.1591(erg10)
CGR: CAGL0L12364g
SPO: SPBC215.09c
MGR: MGG_01755 MGG_13499
ANI: AN1409.2
AFM: AFUA_6G14200 AFUA_8G04000
AOR: AO090103000012 AO090103000406
CNE: CNC05280
UMA: UM03571.1
DDI: DDB_0231621
PFA: PF14_0484
TET: TTHERM_00091590 TTHERM_00277470 TTHERM_00926980
TCR: 511003.60
ECO: b2224(atoB)
ECJ: JW2218(atoB) JW5453(yqeF)
ECE: Z4164(yqeF)
ECS: ECs3701
ECC: c2767(atoB) c3441(yqeF)
ECI: UTI89_C2506(atoB) UTI89_C3247(yqeF)
ECP: ECP_2268 ECP 2857
ECV: APECO1_3662(yqeF) APECO1_4335(atoB) APECO1_43352(atoB)
ECX: EcHS_A2365
STY: STY3164(yqeF)
STT: t2929(yqeF)
SPT: SPA2886(yqeF)
SEC: SC2958(yqeF)
STM: STM3019(yqeF)
SFL: SF2854(yqeF)
SFX: 53052(yqeF)
SFV: SFV_2922(yqeF)
SSN: SSON_2283(atoB) SSON_3004(yqeF)
SBO: SBO_2736(yqeF)
ECA: ECA1282(atoB)
ENT: Ent638_3299
SPE: Spro_0592
HIT: NTHI0932(atoB)
XCC: XCC1297(atoB)
XCB: XC_2943
XCV: XCV1401(thlA)
XAC: XAC1348(atoB)
XOO: XOO_1881(atoB)
XOM: XOO_1778(XOO1778)
VCH: VCA0690
VCO: VC0395_0630
VVU: VV2_0494 VV2_0741
VVY: VVA1043 VVA1210
VPA: VPA0620 VPA1123 VPA1204
PPR: PBPRB1112 PBPRB1840
PAE: PA2001(atoB) PA2553 PA3454 PA3589 PA3925
PAU: PA14_38630(atoB)
PPU: PP_2051(atoB) PP_2215(fadAx) PP_3754 PP_4636
PPF: Pput_2009 Pput_2403 Pput_3523 Pput_4498
PST: PSPTO_0957(phbA-1) PSPTO_3164(phbA-2)
PSB: Psyr_0824 Psyr_3031
PSP: PSPPH_0850(phbA1) PSPPH_2209(phbA2)
PFL: PFL_1478(atoB-2) PFL_2321 PFL_3066 PFL_4330 (atoB-2) PFL_5283
PFO: Pfl_1269 Pfl_1739 Pfl_2074 Pfl_2868
PEN: PSEEN3197 PSEEN3547(fadAx) PSEEN4635(phbA)
PMY: Pmen_1138 Pmen_2036 Pmen_3597 Pmen_3662 Pmen_3820
PAR: Psyc_0252 Psyc_1169
PCR: Pcryo_0278 Pcryo_1236 Pcryo_1260
PRW: PsycPRwf_2011
ACI: ACIAD0694 ACIAD1612 ACIAD2516(atoB)
SON: SO_1677(atoB)
SDN: Sden 1943
SFR: Sfri_1338 Sfri_2063
SAZ: Sama_1375
SBL: Sbal_1495
SBM: Shew185_1489
SBN: Sbal195_1525
SLO: Shew_1667 Shew_2858
SPC: Sputcn32_1397
SSE: Ssed_1473 Ssed_3533
SPL: Spea_2783
SHE: Shewmr4_2597
SHM: Shewmr7_2664
SHN: Shewana3_2771
SHW: Sputw3181_2704
ILO: IL0872
CPS: CPS_1605 CPS_2626
PHA: PSHAa0908 PSHAa1454(atoB) PSHAa1586(atoB)
PAT: Patl_2923
SDE: Sde_3149
PIN: Ping_0659 Ping_2401
MAQ: Maqu_2117 Maqu_2489 Maqu_2696 Maqu_3162
CBU: CBU_0974
LPN: lpg1825(atoB)
LPF: lpl1789
LPP: lpp1788
NOC: Noc_1891
AEH: Mlg_0688 Mlg_2706
HHA: Hhal_1685
HCH: HCH_05299
CSA: Csal_0301 Csal_3068
ABO: ABO_0648(fadAx)
MMW: Mmwyl1_0073 Mmwyl1_3021 Mmwyl1_3053 Mmwyl1_3097 Mmwyl1_4182
AHA: AHA_2143(atoB)
CVI: CV_2088(atoB) CV_2790(phaA)
RSO: RSc0276(atoB) RSc1632(phbA) RSc1637(bktB) RSc1761(RS02948)
REU: Reut_A0138 Reut_A1348 Reut_A1353 Reut_B4561 Reut_B4738 Reut_B5587 Reut_C5943 Reut_C6062
REH: H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771
RME: Rmet_0106 Rmet_1357 Rmet_1362 Rmet_5156
BMA: BMA1316 BMA1321(phbA) BMA1436
BMV: BMASAVP1_A1805(bktB) BMASAVP1_A1810 (phbA)
BML: BMA10299_A0086(phbA) BMA10299_A0091
BMN: BMA10247_1076(bktB) BMA10247_1081(phbA)
BXE: Bxe_A2273 Bxe_A2335 Bxe_A2342 Bxe_A4255 Bxe_B0377 Bxe_B0739 Bxe_C0332 Bxe_C0574 Bxe_C0915
BVI: Bcep1808_0519 Bcep1808_1717 Bcep1808_2877 Bcep1808_3594 Bcep1808_4015 Bcep1808_5507 Bcep1808_5644
BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332

BCN: Bcen_1553 Bcen_1599 Bcen_2158 Bcen_2563 Bcen_2998 Bcen_6289
BCH: Bcen2424_0542 Bcen2424_1790 Bcen2424_2772 Bcen2424_5368 Bcen2424_6232 Bcen2424_6276
BAM: Bamb_0447 Bamb_1728 Bamb_2824 Bamb_4717 Bamb_5771 Bamb_5969
BPS: BPSL1426 BPSL1535(phbA) BPSL1540
BPM: BURPS1710b_2325(bktB) BURPS1710b_2330 (phbA) BURPS 1710b_2453(atoB-2)
BPL: BURPS1106A_2197(bktB) BURPS1106A_2202 (phbA)
BPD: BURPS668_2160(bktB) BURPS668_2165(phbA)
BTE: BTH_I2144 BTH_I2256 BTH_I2261
PNU: Pnuc_0927
BPE: BP0447 BP0668 BP2059
BPA: BPP0608 BPP1744 BPP3805 BPP4216 BPP4361
BBR: BB0614 BB3364 BB4250 BB4804 BB4947
RFR: Rfer_0272 Rfer_1000 Rfer_1871 Rfer_2273 Rfer_2561 Rfer_2594 Rfer_3839
POL: Bpro_1577 Bpro_2140 Bpro_3113 Bpro_4187
PNA: Pnap_0060 Pnap_0458 Pnap_0867 Pnap_1159 Pnap_2136 Pnap_2804
AAV: Aave_0031 Aave_2478 Aave_3944 Aave_4368
AJS: Ajs_0014 Ajs_0124 Ajs_1931 Ajs_2073 Ajs_2317 Ajs_3548 Ajs_3738 Ajs_3776
VEI: Veis_1331 Veis_3818 Veis_4193
DAC: Daci_0025 Daci_0192 Daci_3601 Daci_5988
MPT: Mpe_A1536 Mpe_A1776 Mpe_A1869 Mpe_A3367
HAR: HEAR0577(phbA)
MMS: mma_0555
NEU: NE2262(bktB)
NET: Neut_0610
EBA: ebA5202 p2A409(tioL)
AZO: azo0464(fadA1) azo0469(fadA2) azo2172(thlA)
DAR: Daro_0098 Daro_3022
HPA: HPAG1_0675
HAC: Hac_0958(atoB)
GME: Gmet_1719 Gmet_2074 Gmet_2213 Gmet_2268 Gmet_3302
GUR: Gura_3043
BBA: Bd0404(atoB) Bd2095
DOL: Dole_0671 Dole_1778 Dole_2160 Dole_2187
ADE: Adeh_0062 Adeh_2365
AFW: Anae109_0064 Anae109_1504
MXA: MXAN_3791
SAT: SYN_02642
SFU: Sfum_2280 Sfum_3582
RPR: RP737
RCO: RC1134 RC1135
RFE: RF_0163(paaJ)
RBE: RBE_0139(paaJ)
RAK: A1C_05820
RBO: A1I_07215
RCM: A1E_04760
PUB: SAR11_0428(thlA)
MLO: mlr3847
MES: Meso_3374
PLA: Plav_1573 Plav_2783
SME: SMa1450 SMc03879(phbA)
SMD: Smed_0499 Smed_3117 Smed_5094 Smed_5096
ATU: Atu2769(atoB) Atu3475
ATC: AGR_C_5022(phbA) AGR_L_2713
RET: RHE_CH04018(phbAch) RHE_PC00068(ypc00040) RHE_PF00014(phbAf)
RLE: RL4621(phaA) pRL100301 pRL120369
BME: BMEI0274 BMEII0817
BMF: BAB1_1783(phbA-1) BAB2_0790(phbA-2)
BMS: BR1772(phbA-1) BRA0448(phbA-2)
BMB: BruAb1_1756(phbA-1) BruAb2_0774(phbA-2)
BOV: BOV_1707(phbA-1)
OAN: Oant_1130 Oant_3107 Oant_3718 Oant_4020
BJA: bll0226(atoB) bll3949 bll7400 bll7819 blr3724(phbA)
BRA: BRADO0562(phbA) BRADO0983(pimB) BRADO3110 BRADO3134(atoB)
BBT: BBta_3558 BBta_3575(atoB) BBta_5147(pimB) BBta_7072(pimB) BBta_7614(phbA)
RPA: RPA0513(pcaF) RPA0531 RPA3715(pimB)
RPB: RPB_0509 RPB_0525 RPB_1748
RPC: RPC_0504 RPC_0636 RPC_0641 RPC_0832 RPC_1050 RPC_2005 RPC_2194 RPC_2228
RPD: RPD_0306 RPD_0320 RPD_3105 RPD_3306
RPE: RPE_0168 RPE_0248 RPE_3827
NWI: Nwi_3060
XAU: Xaut_3108 Xaut_4665
CCR: CC_0510 CC_0894 CC_3462
SIL: SPO0142(bktB) SPO0326(phbA) SPO0773 SPO3408
SIT: TM1040_0067 TM1040_2790 TM1040_3026 TM1040_3735
RSP: RSP_0745 RSP_1354 RSP_3184
RSH: Rsph17029_0022 Rsph17029_2401 Rsph17029_3179 Rsph17029_3921
RSQ: Rsph17025_0012 Rsph17025_2466 Rsph17025_2833
JAN: Jann_0262 Jann_0493 Jann_4050
RDE: RD1_0025 RD1_0201(bktB) RD1_3394(phbA)
PDE: Pden_2026 Pden_2663 Pden_2870 Pden_2907 Pden_4811 Pden_5022
DSH: Dshi_0074 Dshi_3066 Dshi_3331
MMR: Mmar10_0697
HNE: HNE_2706 HNE_3065 HNE_3133
NAR: Saro_0809 Saro_1069 Saro_1222 Saro_2306 Saro_2349
SAL: Sala_0781 Sala_1244 Sala_2896 Sala_3158
SWI: Swit_0632 Swit_0752 Swit_2893 Swit_3602 Swit_4887 Swit_5019 Swit_5309
ELI: ELI_01475 ELI_06705 ELI_12035
GBE: GbCGDNIH1_0447
ACR: Acry_1847 Acry_2256
RRU: Rru_A0274 Rru_A1380 Rru_A1469 Rru_A1946 Rru_A3387
MAG: amb0842
MGM: Mmcl_1165
ABA: Acid345_3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA_0445 BA_4172 BA_4700
BAT: BAS3418 BAS3932 BAS5193
BCE: BC3627 BC4023 BC5344
BCA: BCE_3646 BCE_4076 BCE_5475
BCZ: BCZK3329(mmgA) BCZK3780(thl) BCZK5044 (atoB)
BCY: Bcer98_2722 Bcer98_3865
BTK: BT9727_3379(mmgA) BT9727_3765(thl) BT9727_5028(atoB)
BTL: BALH_3262(mmgA) BALH_3642(fadA) BALH_4843(atoB)
BLI: BL03925(mmgA)
BLD: BLi03968(mmgA)
BCL: ABC0345 ABC2989 ABC3617 ABC3891(mmgA)
BAY: RBAM_022450
BPU: BPUM_2374(yhfS) BPUM_2941 BPUM_3373
OIH: OB0676 OB0689 OB2632 OB3013
GKA: GK1658 GK3397

SAU: SA0342 SA0534(vraB)
SAV: SAV0354 SAV0576(vraB)
SAM: MW0330 MW0531(vraB)
SAR: SAR0351(thl) SAR0581
SAS: SAS0330 SAS0534
SAC: SACOL0426 SACOL0622(atoB)
SAB: SAB0304(thl) SAB0526
SAA: SAUSA300_0355 SAUSA300_0560(vraB)
SAO: SAOUHSC_00336 SAOUHSC_00558
SAJ: SaurJH9_0402
SAH: SaurJH1_0412
SEP: SE0346 SE2384
SER: SERP0032 SERP0220
SHA: SH0510(mvaC) SH2417
SSP: SSP0325 SSP2145
LMO: lmo1414
LMF: LMOf2365_1433
LIN: lin1453
LWE: lwe1431
LLA: L11745(thiL) L25946(fadA)
LLC: LACR_1665 LACR_1956
LLM: llmg_0930(thiL)
SPY: SPy_0140 SPy_1637(atoB)
SPZ: M5005_Spy_0119 M5005_Spy_0432 M5005_Spy_1344(atoB)
SPM: spyM18_0136 spyM18_1645(atoB)
SPG: SpyM3_0108 SpyM3_1378(atoB)
SPS: SPs0110 SPs0484
SPH: MGAS10270_Spy0121 MGAS10270_Spy0433 MGAS10270_Spy1461(atoB)
SPI: MGAS10750_Spy0124 MGAS10750_Spy0452 MGAS10750_Spy1453(atoB)
SPJ: MGAS2096_Spy0123 MGAS2096_Spy0451 MGAS2096_Spy1365(atoB)
SPK: MGAS9429_Spy0121 MGAS9429_Spy0431 MGAS9429_Spy1339(atoB)
SPF: SpyM50447(atoB2)
SPA: M6_Spy0166 M6_Spy0466 M6_Spy1390
SPB: M28_Spy0117 M28_Spy0420 M28_Spy1385(atoB)
SAK: SAK_0568
LJO: 111609
LAC: LBA0626(thiL)
LSA: LSA1486
LDB: Ldb0879
LBU: LBUL_0804
LBR: LVIS_2218
LCA: LSEI_1787
LGA: LGAS_1374
LRE: Lreu_0052
EFA: EF1364
OOE: OEOE_0529
STH: STH2913 STH725 STH804
CAC: CAC2873 CA_P0078(thiL)
CPE: CPE2195(atoB)
CPF: CPF_2460
CPR: CPR_2170
CTC: CTC00312
CNO: NT01CX_0538 NT01CX_0603
CDF: CD1059(thlA1) CD2676(thlA2)
CBO: CBO3200(thl)
CBE: Cbei_0411 Cbei_3630
CKL: CKL_3696(thlA1) CKL_3697(thlA2) CKL_3698 (thlA3)
AMT: Amet_4630
AOE: Clos_0084 Clos_0258
CHY: CHY_1288 CHY_1355(atoB) CHY_1604 CHY_1738
DSY: DSY0632 DSY0639 DSY1567 DSY1710 DSY2402 DSY3302
DRM: Dred_0400 Dred_1491 Dred_1784 Dred_1892
SWO: Swol_0308 Swol_0675 Swol_0789 Swol_1486 Swol_1934 Swol_2051
TTE: TTE0549(paaJ)
MTA: Moth_1260
MTU: Rv1135A Rv1323(fadA4) Rv3546(fadA5)
MTC: MT1365(phbA)
MBO: Mb1167 Mb1358(fadA4) Mb3576(fadA5) Mb3586c (fadA6)
MBB: BCG_1197 BCG_1385(fadA4) BCG_3610(fadA5) BCG_3620c(fadA6)
MLE: ML1158(fadA4)
MPA: MAP2407c(fadA3) MAP2436c(fadA4)
MAV: MAV_1544 MAV_1573 MAV_1863 MAV_5081
MSM: MSMEG_2224 MSMEG_4920
MUL: MUL_0357
MVA: Mvan_1976 Mvan_1988 Mvan_4305 Mvan_4677 Mvan_4891
MGI: Mflv_1347 Mflv_1484 Mflv_2040 Mflv_2340 Mflv_4356 Mflv_4368
MMC: Mmcs_1758 Mmcs_1769 Mmcs_3796 Mmcs_3864
MKM: Mkms_0251 Mkms_1540 Mkms_1805 Mkms_1816 Mkms_2836 Mkms_3159 Mkms_3286 Mkms_3869 Mkms_3938 Mkms_4227 Mkms_4411 Mkms_4580 Mkms_4724 Mkms_4764 Mkms_4776
MJL: Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075
CGL: NCg12309(cg12392)
CGB: cg2625(pcaF)
CEF: CE0731 CE2295
CJK: jk1543(fadA3)
NFA: nfa10750(fadA4)
RHA: RHA1_ro01455 RHA1_ro01623 RHA1_ro01876 RHA1_ro02517(catF) RHA1_ro03022 RHA1_ro03024 RHA1_ro03391 RHA1_ro03892 RHA1_ro04599 RHA1_ro05257 RHA1_ro08871
SCO: SC05399(SC8F4.03)
SMA: SAV1384(fadA5) SAV2856(fadA1)
ART: Arth_1160 Arth_2986 Arth_3268 Arth_4073
NCA: Noca_1371 Noca_1797 Noca_1828 Noca_2764 Noca_4142
TFU: Tfu_1520 Tfu_2394
FRA: Francci3_3687
FRE: Franean1_1044 Franean1_2711 Franean1_2726 Franean1_3929 Franean1_4037 Franean1_4577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxyl_1582 Rxyl_1842 Rxyl_2389 Rxyl_2530
FNU: FN0495
BGA: BG0110(fadA)
BAF: BAPKO_0110(fadA)
LIL: LA0457(thiL1) LA0828(thiL2) LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)

FJO: Fjoh_4612
FPS: FP0770 FP1586 FP1725
RRS: RoseRS_3911 RoseRS_4348
RCA: Rcas_0702 Rcas_3206
HAU: Haur_0522
DRA: DR_1072 DR_1428 DR_1960 DR_2480 DR_A0053
DGE: Dgeo_0755 Dgeo_1305 Dgeo_1441 Dgeo_1883
TTH: TTC0191 TTC0330
TTJ: TTHA0559
TME: Tmel_1134
FNO: Fnod_0314
PMO: Pmob_0515
HMA: rrnAC0896(acaB3) rrnAC2815(aca2) rrnAC3497 (yqeF) rrnB0240(aca1) rrnB0242(acaB2) rrnB0309 (acaB1)
TAC: Ta0582
TVO: TVN0649
PTO: PTO1505
APE: APE_2108
SSO: SSO2377(acaB-4)
STO: ST0514
SAI: Saci_0963 Saci_1361(acaB1)
MSE: Msed_0656
PAI: PAE1220
PIS: Pisl_0029 Pisl_1301
PCL: Pcal_0781
PAS: Pars_0309 Pars_1071
CMA: Cmaq_1941

Exemplary HMG-CoA Synthase Nucleic Acids and Polypeptides

HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS1)
SSC: 397673(CH242-38B5.1)
GGA: 396379(HMGCS1)
XLA: 380091(hmgcs1) 447204(MGC80816)
DRE: 394060(hmgcs1)
SPU: 578259(LOC578259)
DME: Dmel_CG4311(Hmgs)
CEL: F25B4.6
ATH: AT4G11820(BAP1)
OSA: 4331418 4347614
CME: CMM189C
SCE: YML126C(ERG13)
AGO: AGOS_ADL356C
PIC: PICST_83020
CAL: CaO19_7312(CaO19.7312)
CGR: CAGL0H04081g
SPO: SPAC4F8.14c(hcs)
MGR: MGG_01026
ANI: AN4923.2
AFM: AFUA_3G10660 AFUA_8G07210
AOR: AO090003000611 AO090010000487
CNE: CNC05080 CNG02670
UMA: UM05362.1
ECU: ECU10_0510
DDI: DDBDRAFT_0217522 DDB_0219924(hgsA)
TET: TTHERM_00691190
TBR: Tb927.8.6110
YPE: YPO1457
YPK: y2712(pksG)
YPM: YP_1349(pksG)
YPA: YPA_0750
YPN: YPN_2521
YPP: YPDSF_1517
YPS: YPTB1475
CBD: COXBU7E912_1931
TCX: Tcr_1719
DNO: DNO_0799
BMA: BMAA1212
BPS: BPSS1002
BPM: BURPS1710b_A2613
BPL: BURPS1106A_A1384
BPD: BURPS668_A1470
BTE: BTH_II1670
MXA: MXAN_3948(tac) MXAN_4267(mvaS)
BSU: BG10926(pksG)
OIH: OB2248
SAU: SA2334(mvaS)
SAV: SAV2546(mvaS)
SAM: MW2467(mvaS)
SAR: SAR2626(mvaS)
SAS: SAS2432
SAC: SACOL2561
SAB: SAB2420(mvaS)
SAA: SAUSA300_2484
SAO: SAOUHSC_02860
SAJ: SaurJH9_2569
SAH: SaurJH1_2622
SEP: SE2110
SER: SERP2122
SHA: SH0508(mvaS)
SSP: SSP0324
LMO: lmo1415
LMF: LMOf2365_1434(mvaS)
LIN: lin1454
LWE: lwe1432(mvaS)
LLA: L13187(hmcM)
LLC: LACR_1666
LLM: llmg_0929(hmcM)
SPY: SPy_0881(mvaS.2)
SPZ: M5005_Spy_0687(mvaS.1)
SPM: spyM18_0942(mvaS2)
SPG: SpyM3_0600(mvaS.2)
SPS: SPs1253
SPH: MGAS10270_Spy0745(mvaS1)
SPI: MGAS10750_Spy0779(mvaS1)
SPJ: MGAS2096_Spy0759(mvaS1)
SPK: MGAS9429_Spy0743(mvaS1)
SPF: SpyM51121(mvaS)
SPA: M6_Spy0704
SPB: M28_Spy0667(mvaS.1)
SPN: SP_1727
SPR: spr1571(mvaS)
SPD: SPD_1537(mvaS)
SAG: SAG1316
SAN: gbs1386
SAK: SAK_1347
SMU: SMU.943c
STC: str0577(mvaS)
STL: stu0577(mvaS)
STE: STER_0621
SSA: SSA_0338(mvaS)
SSU: SSU05_1641
SSV: SSU98_1652
SGO: SGO_0244
LPL: lp_2067(mvaS)
LJO: LJ1607
LAC: LBA0628(hmcS)
LSA: LSA1484(mvaS)

LSL: LSL_0526
LDB: Ldb0881(mvaS)
LBU: LBUL_0806
LBR: LVIS_1363
LCA: LSEI_1785
LGA: LGAS_1372
LRE: Lreu_0676
PPE: PEPE_0868
EFA: EF1363
OOE: OEOE_0968
LME: LEUM_1184
NFA: nfa22120
SEN: SACE_4570(pksG)
BBU: BB0683
BGA: BG0706
BAF: BAPKO_0727
FJO: Fjoh_0678
HAL: VNG1615G(mvaB)
HMA: rrnAC1740(mvaS)
HWA: HQ2868A(mvaB)
NPH: NP2608A(mvaB_1) NP4836A(mvaB_2)

Exemplary Hydroxymethylglutaryl-CoA Reductase Nucleic Acids and Polypeptides

HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04_14m24)
SPU: 373355(LOC373355)
DME: Dmel_CG10367(Hmgcr)
CEL: F08F8.2
OSA: 4347443
SCE: YLR450W(HMG2) YML075C(HMG1)
AGO: AGOS_AER152W
CGR: CAGL0L11506g
SPO: SPCC162.09c(hmg1)
ANI: AN3817.2
AFM: AFUA_1G11230 AFUA_2G03700
AOR: AO090103000311 AO090120000217
CNE: CNF04830
UMA: UM03014.1
ECU: ECU10_1720
DDI: DDB_0191125(hmgA) DDB_0215357(hmgB)
TBR: Tb927.6.4540
TCR: 506831.40 509167.20
LMA: LmjF30.3190
VCH: VCA0723
VCO: VC0395_0662
VVU: VV2_0117
VVY: VVA0625
VPA: VPA0968
VFI: VFA0841
PAT: Patl_0427
CBU: CBU_0030 CBU_0610
CBD: COXBU7E912_0151 COXBU7E912_0622(hmgA)
TCX: Tcr_1717
DNO: DNO_0797
CVI: CV_1806
SUS: Acid_5728 Acid 6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR_1664
LLM: llmg_0931(mvaA)
SPY: SPy_0880(mvaS.1)
SPM: spyM18_0941(mvaS1)
SPG: SpyM3_0599(mvaS.1)
SPS: SPs1254
SPH: MGAS10270_Spy0744
SPI: MGAS10750_Spy0778
SPJ: MGAS2096_Spy0758
SPK: MGAS9429_Spy0742
SPA: M6_Spy0703
SPN: SP_1726
SAG: SAG1317
SAN: gbs1387
STC: str0576(mvaA)
STL: stu0576(mvaA)
STE: STER_0620
SSA: SSA_0337(mvaA)
LPL: lp_0447(mvaA)
LJO: LJ1608
LSL: LSL_0224
LBR: LVIS_0450
LGA: LGAS_1373
EFA: EF1364
NFA: nfa22110
BGA: BG0708(mvaA)
SRU: SRU_2422
FPS: FP2341
MMP: MMP0087(hmgA)
MMQ: MmarC5_1589
MAC: MA3073(hmgA)
MBA: Mbar_A1972
MMA: MM_0335
MBU: Mbur_1098
MHU: Mhun_3004
MEM: Memar_2365
MBN: Mboo_0137
MTH: MTH562
MST: Msp_0584(hmgA)
MSI: Msm_0227
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA_2) NP2422A(mvaA_1)
TAC: Ta0406m
TVO: TVN1168
PTO: PTO1143
PAB: PAB2106(mvaA)
PFU: PF1848
TKO: TK0914
RCI: RCIX1027(hmgA) RCIX376(hmgA)
APE: APE_1869
IHO: Igni_0476
HBU: Hbut_1531
SSO: SSO0531
STO: ST1352
SAI: Saci_1359
PAI: PAE2182
PIS: Pisl_0814
PCL: Pcal_1085
PAS: Pars_0796

Exemplary Mevalonate Kinase Nucleic Acids and Polypeptides
HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc:103473)
SPU: 585785(L00585785)
DME: Dmel_CG33671
OSA: 4348331
SCE: YMR208W(ERG12)
AGO: AGOS_AER335W
PIC: PICST_40742(ERG12)
CGR: CAGL0F03861g
SPO: SPAC13G6.11c
MGR: MGG_06946
ANI: AN3869.2
AFM: AFUA_4G07780
AOR: A0090023000793
CNE: CNK01740
ECU: ECU09_1780
DDI: DDBDRAFT_0168621
TET: TTHERM_00637680
TBR: Tb927.4.4070
TCR: 436521.9 509237.10
LMA: LmjF31.0560
CBU: CBU_0608 CBU_0609
CBD: COXBU7E912_0620(mvk)
LPN: lpg2039
LPF: lp12017
LPP: lpp2022
BBA: Bd1027(1mbP) Bd1630(mvk)
MXA: MXAN_5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)
SAB: SAB0540(mvaK1)
SAA: SAUSA300_0572(mvk)
SAO: SAOUHSC_00577
SEP: SE0361
SER: SERP0238(mvk)
SHA: SH2402(mvaK1)
SSP: SSP2122
LMO: lmo0010
LMF: LMOf2365_0011
LIN: lin0010
LWE: lwe0011(mvk)
LLA: L7866(yeaG)
LLC: LACR_0454
LLM: llmg_0425(mvk)
SPY: SPy_0876(mvaK1)
SPZ: M5005_Spy_0682(mvaK1)
SPM: spyM18_0937(mvaK1)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP_0381
SPR: spr0338(mvk)
SPD: SPD_0346(mvk)
SAG: SAG1326
SAN: gbs1396
SAK: SAK_1357(mvk)
SMU: SMU.181
STC: str0559(mvaK1)
STL: stu0559(mvaK1)
STE: STER_0598
SSA: SSA_0333(mvaK1)
SSU: SSU05_0289
SSV: SSU98_0285
SGO: SGO_0239(mvk)
LPL: lp_1735(mvaK1)
LJO: LJ1205
LAC: LBA1167(mvaK)
LSA: LSA0908(mvaK1)
LSL: LSL_0685(eRG)
LDB: Ldb0999(mvk)
LBU: LBUL_0906
LBR: LVIS_0858
LCA: LSEI_1491
LGA: LGAS_1033
LRE: Lreu_0915
PPE: PEPE_0927
EFA: EF0904(mvk)
OOE: OEOE_1100
LME: LEUM_1385
NFA: nfa22070
BGA: BG0711
BAF: BAPKO_0732
FPS: FP0313
MMP: MMP1335
MAE: Maeo 0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)
HAL: VNG1145G(mvk)
HMA: rrnAC0077(mvk)
HWA: HQ2925A(mvk)
NPH: NP2850A(mvk)
PTO: PTO1352
PHO: PH1625
PAB: PAB0372(mvk)
PFU: PF1637(mvk)
TKO: TK1474
RCI: LRC399(mvk)
APE: APE_2439
HBU: Hbut_0877
SSO: SS00383
STO: ST2185
SAI: Saci_2365(mvk)
MSE: Msed_1602
PAI: PAE3108
PIS: Pisl_0467
PCL: Pcal_1835

Exemplary Phosphomevalonate Kinase Nucleic Acids and Polypeptides

HSA: 10654(PMVK)
PTR: 457350(PMVK)
MCC: 717014(PMVK)
MMU: 68603(Pmvk)
CFA: 612251(PMVK)
BTA: 513533(PMVK)
DME: Dmel_CG10268
ATH: AT1G31910
OSA: 4332275
SCE: YMR220W(ERG8)
AGO: AGOS_AER354W
PIC: PICST_52257(ERG8)
CGR: CAGL0F03993g
SPO: SPAC343.01c
MGR: MGG_05812
ANI: AN2311.2
AFM: AFUA_5G10680
AOR: AO090010000471
CNE: CNM00100
UMA: UM00760.1
DDI: DDBDRAFT_0184512
TBR: Tb09.160.3690
TCR: 507913.20 508277.140
LMA: LmjF15.1460
MXA: MXAN_5017
OIH: OB0227
SAU: SA0549(mvaK2)
SAV: SAV0592(mvaK2)
SAM: MW0547(mvaK2)
SAR: SAR0598(mvaK2)
SAS: SAS0551
SAC: SACOL0638
SAB: SAB0542(mvaK2)
SAA: SAUSA300_0574
SAO: SAOUHSC_00579
SAJ: SaurJH9_0615
SEP: SE0363
SER: SERP0240
SHA: SH2400(mvaK2)
SSP: SSP2120
LMO: lmo0012
LMF: LMOf2365_0013
LIN: lin0012
LWE: lwe0013
LLA: L10014(yebA)
LLC: LACR_0456
LLM: llmg_0427
SPY: SPy_0878(mvaK2)
SPZ: M5005_Spy_0684(mvaK2)
SPM: spyM18_0939
SPG: SpyM3_0597(mvaK2)
SPS: SPs1256
SPH: MGAS10270_Spy0742(mvaK2)
SPI: MGAS10750_Spy0776(mvaK2)
SPJ: MGAS2096_Spy0755(mvaK2)
SPK: MGAS9429_Spy0739(mvaK2)
SPF: SpyM51124(mvaK2)
SPA: M6_Spy0701
SPB: M28_Spy0664(mvaK2)
SPN: SP_0383
SPR: spr0340(mvaK2)
SPD: SPD_0348(mvaK2)
SAG: SAG1324
SAN: gbs1394
SAK: SAK_1355
SMU: SMU.938
STC: str0561(mvaK2)
STL: stu0561(mvaK2)
STE: STER_0600
SSA: SSA_0335(mvaK2)
SSU: SSU05_0291
SSV: SSU98_0287
SGO: SGO_0241
LPL: lp_1733(mvaK2)
LJO: LJ1207
LAC: LBA1169
LSA: LSA0906(mvaK2)
LSL: LSL_0683
LDB: Ldb0997(mvaK)
LBU: LBUL_0904
LBR: LVIS_0860
LCA: LSEI_1092
LGA: LGAS_1035
LRE: Lreu_0913
PPE: PEPE_0925
EFA: EF0902
NFA: nfa22090
BGA: BG0710
BAF: BAPKO_0731
NPH: NP2852A
SSO: SS02988
STO: ST0978
SAT: Saci_1244

Exemplary Diphosphomevalonate Decarboxylase Nucleic Acids and Polypeptides

HSA: 4597(MVD)
PTR: 468069(MVD)
MCC: 696865(MVD)
MMU: 192156(Mvd)
RNO: 81726(Mvd)
CFA: 489663(MVD)
GGA: 425359(MVD)
DME: Dmel_CG8239
SCE: YNR043W(MVD1)
AGO: AGOS_AGL232C
PIC: PICST_90752
CGR: CAGL0C03630g
SPO: SPAC24C9.03
MGR: MGG_09750
ANI: AN4414.2
AFM: AFUA_4G07130
AOR: A0090023000862
CNE: CNL04950
UMA: UM05179.1
DDI: DDBDRAFT_0218058
TET: TTHERM_00849200
TBR: Tb10.05.0010 Tb10.61.2745
TCR: 507993.330 511281.40
LMA: LmjF18.0020
CBU: CBU_0607(mvaD)
CBD: COXBU7E912_0619(mvaD)
LPN: lpg2040
LPF: lp12018
LPP: lpp2023
TCX: Tcr_1734
DNO: DNO_0504(mvaD)
BBA: Bd1629
MXA: MXAN_5018(mvaD)
OIH: OB0226
SAU: SA0548(mvaD)
SAV: SAV0591(mvaD)
SAM: MW0546(mvaD)

SAR: SAR0597(mvaD)
SAS: SAS0550
SAC: SACOL0637(mvaD)
SAB: SAB0541(mvaD)
SAA: SAUSA300_0573(mvaD)
SAO: SAOUHSC_00578
SAJ: SaurJH9_0614
SAH: SaurJH1_0629
SEP: SE0362
SER: SERP0239(mvaD)
SHA: SH2401(mvaD)
SSP: SSP2121
LMO: lmo0011
LMF: LMOf2365_0012(mvaD)
LIN: lin0011
LWE: lwe0012(mvaD)
LLA: L9089(yeaH)
LLC: LACR_0455
LLM: llmg_0426(mvaD)
SPY: SPy_0877(mvaD)
SPZ: M5005_Spy_0683(mvaD)
SPM: spyM18_0938(mvd)
SPG: SpyM3_0596(mvaD)
SPS: SPs1257
SPH: MGAS10270_Spy0741(mvaD)
SPI: MGAS10750_Spy0775(mvaD)
SPJ: MGAS2096_Spy0754(mvaD)
SPK: MGAS9429_Spy0738(mvaD)
SPF: SpyM51125(mvaD)
SPA: M6_Spy0700
SPB: M28_Spy0663(mvaD)
SPN: SP_0382
SPR: spr0339(mvd1)
SPD: SPD_0347(mvaD)
SAG: SAG1325(mvaD)
SAN: gbs1395
SAK: SAK_1356(mvaD)
SMU: SMU.937
STC: str0560(mvaD)
STL: stu0560(mvaD)
STE: STER_0599
SSA: SSA_0334(mvaD)
SSU: SSU05_0290
SSV: SSU98_0286
SGO: SGO_0240(mvaD)
LPL: lp_1734(mvaD)
LJO: LJ1206
LAC: LBA1168(mvaD)
LSA: LSA0907(mvaD)
LSL: LSL_0684
LDB: Ldb0998(mvaD)
LBU: LBUL_0905
LBR: LVIS_0859
LCA: LSEI_1492
LGA: LGAS_1034
LRE: Lreu_0914
PPE: PEPE_0926
EFA: EF0903(mvaD)
LME: LEUM_1386
NFA: nfa22080
BBU: BB0686
BGA: BG0709
BAF: BAPKO_0730
GFO: GFO_3632
FPS: FP0310(mvaD)
HAU: Haur_1612
HAL: VNG0593G(dmd)

HMA: rrnAC1489(dmd)
HWA: HQ1525A(mvaD)
NPH: NP1580A(mvaD)
PTO: PTO0478 PTO1356
SSO: SSO2989
STO: ST0977
SAI: Saci_1245(mvd)
MSE: Msed_1576

Exemplary Isopentenyl Phosphate Kinases (IPK) Nucleic Acids and Polypeptides

*Methanobacterium thermoautotrophicum* gil2621082
*Methanococcus jannaschii* DSM 2661 gil1590842;
*Methanocaldococcus jannaschii* gil1590842
*Methanothermobacter thermautotrophicus* gil2621082
*Picrophilus torridus* DSM9790 (IG-57) gil48477569
*Pyrococcus abyssi* gil14520758
*Pyrococcus horikoshii* OT3 gil3258052
*Archaeoglobus fulgidus* DSM4304 gil2648231

Exemplary Isopentenyl-diphosphate Delta-isomerase (IDI) Nucleic Acids and Polypeptides HSA: 3422(IDI1) 91734(IDI2)
PTR: 450262(IDI2) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(L00586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
ECU: ECU02_0230
DDI: DDB_0191342(ipi)
TET: TTHERM_00237280 TTHERM_00438860
TBR: Tb09.211.0700
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048
STY: STY3195
STT: t2957
SPT: SPA2907(idi)
SEC: SC2979(idi)
STM: STM3039(idi)
SFL: SF2875(idi)
SFX: S3074

SFV: SFV_2937
SSN: SSON_3042 SSON_3489(yhfK)
SBO: SBO_3103
SDY: SDY 3193
ECA: ECA2789
PLU: plu3987
ENT: Ent638_3307
SPE: Spro_2201
VPA: VPA0278
VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lp12029
LPP: lpp2034
TCX: Tcr_1718
HHA: Hhal_1623
DNO: DNO_0798
EBA: ebA5678 p2A143
DVU: DVU1679(idi)
DDE: Dde_1991
LIP: LI1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
RBO: A1I_04755
RCM: A1E_02555
RRI: A1G_04195
MLO: mlr6371
RET: RHE_PD00245(ypd00046)
XAU: Xaut_4134
SIL: SPO0131
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520
BAA: BA_2041
BAT: BAS1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
OIH: OB0537
SAU: SA2136(fni)
SAV: SAV2346(fni)
SAM: MW2267(fni)
SAR: SAR2431(fni)
SAS: SAS2237
SAC: SACOL2341(fni)
SAB: SAB2225c(fni)
SAA: SAUSA300_2292(fni)
SAO: SAOUHSC_02623
SEP: SE1925
SER: SERP1937(fni-2)
SHA: SH0712(fni)
SSP: SSP0556
LMO: lmo1383
LMF: LMOf2365_1402(fni)
LIN: lin1420
LWE: lwe1399(fni)
LLA: L11083(yebB)
LLC: LACR_0457
LLM: llmg_0428(fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
STC: str0562(idi)
STL: stu0562(idi)
STE: STER_0601
SSA: SSA_0336
SGO: SGO_0242
LPL: lp_1732(idi1)
LJO: LJ1208
LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
STH: STH1674
CBE: Cbei_3081
DRM: Dred_0474
SWO: Swol_1341
MTA: Moth_1328
MTU: Rv1745c(idi)
MTC: MT1787(idi)
MBO: Mb1774c(idi)
MBB: BCG_1784c(idi)
MPA: MAP3079c
MAV: MAV_3894(fni)
MSM: MSMEG_1057(fni) MSMEG_2337(fni)
MUL: MUL_0380(idi2)
MVA: Mvan_1582 Mvan_2176

MGI: Mflv_1842 Mflv_4187
MMC: Mmcs_1954
MKM: Mkms_2000
MJL: Mjls_1934
CGL: NCg12223(cg12305)
CGB: cg2531(idi)
CEF: CE2207
CDI: DIP1730(idi)
NFA: nfa19790 nfa22100
RHA: RHA1_ro00239
SCO: SC06750(SC5F2A.33c)
SMA: SAV1663(idi)
LXX: Lxx23810(idi)
CMI: CMM_2889(idiA)
AAU: AAur_0321(idi)
PAC: PPA2115
FRA: Francci3_4188
FRE: Franean1_5570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxyl_0400
BBU: BB0684
BGA: BG0707
SYN: sll1556
SYC: syc2161 c
SYF: Synpcc7942_1933
CYA: CYA_2395(fni)
CYB: CYB_2691(fni)
TEL: tll1403
ANA: all4591
AVA: Ava_2461 Ava B0346
TER: Tery_1589
SRU: SRU_1900(idi)
CHU: CHU_0674(idi)
GFO: GFO_2363(idi)
FJO: Fjoh_0269
FPS: FP1792(idi)
CTE: CT0257
CCH: Cag_1445
CPH: Cpha266_0385
PVI: Cvib_1545
PLT: Plut_1764
RRS: RoseRS_2437
RCA: Rcas_2215
HAU: Haur_4687
DRA: DR_1087
DGE: Dgeo_1381
TTH: TT_P0067
TTJ: TTHB110
MJA: MJ0862
MMP: MMP0043
MMQ: MmarC5_1637
MMX: MmarC6_0906
MMZ: MmarC7_1040
MAE: Maeo_1184
MVN: Mevan_1058
MAC: MA0604(idi)
MBA: Mbar_A1419
MMA: MM_1764
MBU: Mbur_2397
MTP: Mthe_0474
MHU: Mhun_2888
MLA: Mlab_1665
MEM: Memar_1814
MBN: Mboo_2211
MTH: MTH48
MST: Msp_0856(fni)
MSI: Msm_1441
MKA: MK0776(11dD)
AFU: AF2287
HAL: VNG1818G(idi) VNG6081G(crt_1) VNG6445G (crt_2) VNG7060 VNG7149
HMA: rrnAC3484(idi)
HWA: HQ2772A(idiA) HQ2847A(idiB)
NPH: NP0360A(idiB_1) NP4826A(idiA) NP5124A (idiB_2)
TAC: Ta0102
TVO: TVN0179
PTO: PT00496
PHO: PH1202
PAB: PAB1662
PFU: PF0856
TKO: TK1470
RCI: LRC397(fni)
APE: APE_1765.1
SMR: Smar_0822
IHO: Igni_0804
HBU: Hbut_0539
SSO: SS00063
STO: ST2059
SAI: Saci_0091
MSE: Msed_2136
PAI: PAE0801
PIS: Pisl_1093
PCL: Pcal_0017
PAS: Pars_0051
TPE: Tpen_0272

Exemplary Isoprene Synthase Nucleic Acids and Polypeptides

Genbank Accession Nos.

AY341431
AY316691
AY279379
AJ457070
AY182241

What is claimed as new and desired to be protected by Letters Patent of the United States is:

1. A method of producing cis-polyisoprene, the method comprising:

(a) culturing recombinant cells under suitable culture conditions for the production of isoprene, wherein the cells comprise nucleic acids encoding (i) a heterologous isoprene synthase polypeptide; and (ii) two or more heterologous mevalonate (MVA) pathway polypeptides, and wherein the cells (1) produce greater than 400 nmole/gwcm/hr of isoprene, (2) convert more than 0.002 molar percent of the carbon that the cells consume from a cell culture medium into isoprene, (3) have an average volumetric productivity of isoprene greater than 0.1 mg/Lbroth/hr of isoprene, or (4) produce at least 0.0037 grams of isoprene per gram of dry cell mass (gdcm);

(b) producing isoprene; and (c) polymerizing the isoprene to produce cis-polyisoprene.

2. The method of claim 1, wherein the cells further comprise an endogenous nucleic acid encoding an isoprene synthase polypeptide.

3. The method of claim 1, wherein the isoprene synthase polypeptide is a plant isoprene synthase polypeptide.

4. The method of claim 3, wherein the plant isoprene synthase polypeptide is a poplar isoprene synthase polypeptide or a kudzu isoprene synthase polypeptide.

5. The method of claim 1, wherein the cells further comprise nucleic acids encoding: (a) an isopentenyl-diphosphate delta-isomerase (IDI) polypeptide or (b) a 1-Deoxyxylulose-5-phosphate synthase (DXS) polypeptide.

6. The method of claim 1, wherein the cells comprise polypeptides of the entire MVA pathway.

7. The method of claim 1, wherein the cells are fungal, bacterial, plant, or algal cells.

8. The method of claim 7, wherein the cells are fungal cells.

9. The method of claim 8, wherein the cells are *Aspergillus*, yeast, or *Trichoderma* cells.

10. The method of claim 9, wherein the yeast cells are *Saccharomyces* sp., *Schizosaccharomyces* sp., *Pichia* sp., *Yarrowia* sp., or *Candida* sp. cells.

11. The method of claim 8, where the cells are selected from the group consisting of *A. oryzae, A. niger, S. cerevisiae, S. pombe, T. reesei, H. insolens, H. lanuginose, H. grisea, C. lucknowense, A. sojae, A. japonicus, A. nidulans, A. aculeatus, A. awamori, F. roseum, F. graminum, F. cerealis, F. oxysporuim, F. venenatum, N. crassa, M. miehei, T. viride, F. oxysporum*, and *F. solan* cells.

12. The method of claim 7, wherein the cells are bacterial cells.

13. The method of claim 12, wherein the cells are gram-positive bacterial cells or gram-negative bacterial cells.

14. The method of claim 13, wherein the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *Corynebacteria* sp., and *P. alcaligenes* cells.

15. The method of claim 7, wherein the cells are plant cells.

16. The method of claim 15, wherein the plant cells are selected from the group consisting of: the family Fabaceae, the Faboideae subfamily, kudzu, poplar, *Populus alba* x *tremula, Populus alba*, aspen, *Populus tremuloides*, and *Quercus robur* cells.

17. The method of claim 7, wherein the cells are algal cells.

18. The method of claim 17, wherein the algal cells are selected from the group consisting of: green algae, red algae, glaucophytes, chlorarachniophytes, euglenids, chromista, and dinoflagellates.

19. The method of claim 1, further comprising (d) producing a tire from the cis-polyisoprene.

* * * * *

SEQUENCE LISTING

```
<160> NUMBER OF SEQ ID NOS: 123

<210> SEQ ID NO 1
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 1
```

-continued

```
atgtgtgcga cctcttctca atttactcag attaccgagc ataattcccg tcgttccgca      60

aactatcagc caaacctgtg gaatttcgaa ttcctgcaat ccctggagaa cgacctgaaa     120

gtggaaaagc tggaggagaa agcgaccaaa ctggaggaag aagttcgctg catgatcaac     180

cgtgtagaca cccagccgct gtccctgctg gagctgatcg acgatgtgca gcgcctgggt     240

ctgacctaca aatttgaaaa agacatcatt aaagccctgg aaaacatcgt actgctggac     300

gaaaacaaaa agaacaaatc tgacctgcac gcaaccgctc tgtctttccg tctgctgcgt     360

cagcacggtt tcgaggtttc tcaggatgtt tttgagcgtt tcaaggataa agaaggtggt     420

ttcagcggtg aactgaaagg tgacgtccaa ggcctgctga gcctgtatga agcgtcttac     480

ctgggtttcg agggtgagaa cctgctggag gaggcgcgta ccttttccat cacccacctg     540

aagaacaacc tgaaagaagg cattaatacc aaggttgcag aacaagtgag ccacgccctg     600

gaactgccat atcaccagcg tctgcaccgt ctggaggcac gttggttcct ggataaatac     660

gaaccgaaag aaccgcatca ccagctgctg ctggagctgg cgaagctgga ttttaacatg     720

gtacagaccc tgcaccagaa agagctgcaa gatctgtccc gctggtggac cgagatgggc     780

ctggctagca aactggattt tgtacgcgac cgcctgatgg aagtttattt ctgggcactg     840

ggtatggcgc cagacccgca gtttggtgaa tgtcgcaaag ctgttactaa aatgtttggt     900

ctggtgacga tcatcgatga cgtgtatgac gtttatggca ctctggacga actgcaactg     960

ttcaccgatg ctgtagagcg ctgggacgtt aacgctatta acaccctgcc ggactatatg    1020

aaactgtgtt tcctggcact gtacaacacc gttaacgaca cgtcctattc tattctgaaa    1080

gagaaaggtc ataacaacct gtcctatctg acgaaaagct ggcgtgaact gtgcaaagcc    1140

tttctgcaag aggcgaaatg gtccaacaac aaaattatcc cggctttctc caagtacctg    1200

gaaaacgcca gcgtttcctc ctccggtgta gcgctgctgg cgccgtctta cttttccgta    1260

tgccagcagc aggaagacat ctccgaccac gcgctgcgtt ccctgaccga cttccatggt    1320

ctggtgcgtt ctagctgcgt tatcttccgc ctgtgcaacg atctggccac ctctgcggcg    1380

gagctggaac gtggcgagac taccaattct atcattagct acatgcacga aaacgatggt    1440

accagcgagg aacaggcccg cgaagaactg cgtaaactga tcgacgccga atggaaaaag    1500

atgaatcgtg aacgcgttag cgactccacc ctgctgccta aagcgttcat ggaaatcgca    1560

gttaacatgg cacgtgtttc ccactgcacc taccagtatg gcgatggtct gggtcgccca    1620

gactacgcga ctgaaaaccg catcaaactg ctgctgattg acccttaccc gattaaccag    1680

ctgatgtatg tctaactgca g                                              1701
```

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2

```
gtttgacagc ttatcatcga ctgcacggtg caccaatgct tctggcgtca ggcagccatc      60

ggaagctgtg gtatggctgt gcaggtcgta aatcactgca taattcgtgt cgctcaaggc     120

gcactcccgt tctggataat gtttttttgcg ccgacatcat aacggttctg gcaaatattc     180

tgaaatgagc tgttgacaat taatcatccg gctcgtataa tgtgtggaat tgtgagcgga     240

taacaatttc acacaggaaa cagcgccgct gagaaaaagc gaagcggcac tgctctttaa     300
```

-continued

```
caatttatca gacaatctgt gtgggcactc gaccggaatt atcgattaac tttattatta    360
aaaattaaag aggtatatat taatgtatcg attaaataag gaggaataaa ccatgtgtgc    420
gacctcttct caatttactc agattaccga gcataattcc cgtcgttccg caaactatca    480
gccaaacctg tggaatttcg aattcctgca atccctggag aacgacctga aagtggaaaa    540
gctggaggag aaagcgacca aactggagga agaagttcgc tgcatgatca accgtgtaga    600
cacccagccg ctgtccctgc tggagctgat cgacgatgtg cagcgcctgg gtctgaccta    660
caaatttgaa aaagacatca ttaaagccct ggaaaacatc gtactgctgg acgaaaacaa    720
aaagaacaaa tctgacctgc acgcaaccgc tctgtctttc cgtctgctgc gtcagcacgg    780
tttcgaggtt tctcaggatg tttttgagcg tttcaaggat aaagaaggtg gtttcagcgg    840
tgaactgaaa ggtgacgtcc aaggcctgct gagcctgtat gaagcgtctt acctgggttt    900
cgagggtgag aacctgctgg aggaggcgcg taccttttcc atcacccacc tgaagaacaa    960
cctgaaagaa ggcattaata ccaaggttgc agaacaagtg agccacgccc tggaactgcc   1020
atatcaccag cgtctgcacc gtctggaggc acgttggttc ctggataaat acgaaccgaa   1080
agaaccgcat caccagctgc tgctggagct ggcgaagctg gattttaaca tggtacagac   1140
cctgcaccag aaagagctgc aagatctgtc ccgctggtgg accgagatgg gcctggctag   1200
caaactggat tttgtacgcg accgcctgat ggaagtttat ttctgggcac tgggtatggc   1260
gccagacccg cagtttggtg aatgtcgcaa agctgttact aaaatgtttg gtctggtgac   1320
gatcatcgat gacgtgtatg acgtttatgg cactctggac gaactgcaac tgttcaccga   1380
tgctgtagag cgctgggacg ttaacgctat taacaccctg ccggactata tgaaactgtg   1440
tttcctggca ctgtacaaca ccgttaacga cacgtcctat tctattctga aagagaaagg   1500
tcataacaac ctgtcctatc tgacgaaaag ctggcgtgaa ctgtgcaaag cctttctgca   1560
agaggcgaaa tggtccaaca acaaaattat cccggctttc tccaagtacc tggaaaacgc   1620
cagcgtttcc tcctccggtg tagcgctgct ggcgccgtct tacttttccg tatgccagca   1680
gcaggaagac atctccgacc acgcgctgcg ttccctgacc gacttccatg gtctggtgcg   1740
ttctagctgc gttatcttcc gcctgtgcaa cgatctggcc acctctgcgg cggagctgga   1800
acgtggcgag actaccaatt ctatcattag ctacatgcac gaaaacgatg gtaccagcga   1860
ggaacaggcc cgcgaagaac tgcgtaaact gatcgacgcc gaatggaaaa agatgaatcg   1920
tgaacgcgtt agcgactcca ccctgctgcc taaagcgttc atggaaatcg cagttaacat   1980
ggcacgtgtt tcccactgca cctaccagta tggcgatggt ctgggtcgcc cagactacgc   2040
gactgaaaac cgcatcaaac tgctgctgat tgaccctttc ccgattaacc agctgatgta   2100
tgtctaactg cagctggtac catatgggaa ttcgaagctt tctagaacaa aaactcatct   2160
cagaagagga tctgaatagc gccgtcgacc atcatcatca tcatcattga gtttaaacgg   2220
tctccagctt ggctgttttg gcggatgaga gaagattttc agcctgatac agattaaatc   2280
agaacgcaga agcggtctga taaaacagaa tttgcctggc ggcagtagcg cggtggtccc   2340
acctgacccc atgccgaact cagaagtgaa acgccgtagc gccgatggta gtgtggggtc   2400
tccccatgcg agagtaggga actgccaggc atcaaataaa acgaaaggct cagtcgaaag   2460
actgggcctt tcgttttatc tgttgtttgt cggtgaacgc tctcctgagt aggacaaatc   2520
cgccgggagc ggatttgaac gttgcgaagc aacggcccgg agggtggcgg gcaggacgcc   2580
cgccataaac tgccaggcat caaattaagc agaaggccat cctgacggat ggcctttttg   2640
cgtttctaca aactcttttt gtttattttt ctaaatacat tcaaatatgt atccgctcat   2700
```

gagacaataa ccctgataaa tgcttcaata atattgaaaa aggaagagta tgagtattca 2760
acatttccgt gtcgccctta ttcccttttt tgcggcattt tgccttcctg tttttgctca 2820
cccagaaacg ctggtgaaag taaaagatgc tgaagatcag ttgggtgcac gagtgggtta 2880
catcgaactg gatctcaaca gcggtaagat ccttgagagt tttcgccccg aagaacgttt 2940
tccaatgatg agcactttta aagttctgct atgtggcgcg gtattatccc gtgttgacgc 3000
cgggcaagag caactcggtc gccgcataca ctattctcag aatgacttgg ttgagtactc 3060
accagtcaca gaaaagcatc ttacggatgg catgacagta agagaattat gcagtgctgc 3120
cataaccatg agtgataaca ctgcggccaa cttacttctg acaacgatcg gaggaccgaa 3180
ggagctaacc gcttttttgc acaacatggg ggatcatgta actcgccttg atcgttggga 3240
accggagctg aatgaagcca taccaaacga cgagcgtgac accacgatgc ctgtagcaat 3300
ggcaacaacg ttgcgcaaac tattaactgg cgaactactt actctagctt cccggcaaca 3360
attaatagac tggatggagg cggataaagt tgcaggacca cttctgcgct cggcccttcc 3420
ggctggctgg tttattgctg ataaatctgg agccggtgag cgtgggtctc gcggtatcat 3480
tgcagcactg gggccagatg gtaagccctc ccgtatcgta gttatctaca cgacggggag 3540
tcaggcaact atggatgaac gaaatagaca gatcgctgag ataggtgcct cactgattaa 3600
gcattggtaa ctgtcagacc aagtttactc atatatactt tagattgatt taaaacttca 3660
tttttaattt aaaaggatct aggtgaagat cctttttgat aatctcatga ccaaaatccc 3720
ttaacgtgag ttttcgttcc actgagcgtc agaccccgta gaaaagatca aaggatcttc 3780
ttgagatcct ttttttctgc gcgtaatctg ctgcttgcaa acaaaaaaac caccgctacc 3840
agcggtggtt tgtttgccgg atcaagagct accaactctt tttccgaagg taactggctt 3900
cagcagagcg cagataccaa atactgtcct tctagtgtag ccgtagttag gccaccactt 3960
caagaactct gtagcaccgc ctacatacct cgctctgcta atcctgttac cagtggctgc 4020
tgccagtggc gataagtcgt gtcttaccgg gttggactca agacgatagt taccggataa 4080
ggcgcagcgg tcgggctgaa cggggggttc gtgcacacag cccagcttgg agcgaacgac 4140
ctacaccgaa ctgagatacc tacagcgtga gctatgagaa agcgccacgc ttcccgaagg 4200
gagaaaggcg gacaggtatc cggtaagcgg cagggtcgga acaggagagc gcacgaggga 4260
gcttccaggg ggaaacgcct ggtatcttta tagtcctgtc gggtttcgcc acctctgact 4320
tgagcgtcga tttttgtgat gctcgtcagg ggggcggagc ctatggaaaa acgccagcaa 4380
cgcggccttt ttacggttcc tggccttttg ctggcctttt gctcacatgt tctttcctgc 4440
gttatcccct gattctgtgg ataaccgtat taccgccttt gagtgagctg ataccgctcg 4500
ccgcagccga acgaccgagc gcagcgagtc agtgagcgag gaagcggaag agcgcctgat 4560
gcggtatttt ctccttacgc atctgtgcgg tatttcacac cgcatatggt gcactctcag 4620
tacaatctgc tctgatgccg catagttaag ccagtataca ctccgctatc gctacgtgac 4680
tgggtcatgg ctgcgccccg acacccgcca acacccgctg acgcgccctg acgggcttgt 4740
ctgctcccgg catccgctta cagacaagct gtgaccgtct ccgggagctg catgtgtcag 4800
aggttttcac cgtcatcacc gaaacgcgcg aggcagcaga tcaattcgcg cgcgaaggcg 4860
aagcggcatg catttacgtt gacaccatcg aatggtgcaa aacctttcgc ggtatggcat 4920
gatagcgccc ggaagagagt caattcaggg tggtgaatgt gaaaccagta acgttatacg 4980
atgtcgcaga gtatgccggt gtctcttatc agaccgtttc ccgcgtggtg aaccaggcca 5040

-continued gccacgtttc tgcgaaaacg cgggaaaaag tggaagcggc gatggcggag ctgaattaca 5100
ttcccaaccg cgtggcacaa caactggcgg gcaaacagtc gttgctgatt ggcgttgcca 5160
cctccagtct ggccctgcac gcgccgtcgc aaattgtcgc ggcgattaaa tctcgcgccg 5220
atcaactggg tgccagcgtg gtggtgtcga tggtagaacg aagcggcgtc gaagcctgta 5280
aagcggcggt gcacaatctt ctcgcgcaac gcgtcagtgg gctgatcatt aactatccgc 5340
tggatgacca ggatgccatt gctgtggaag ctgcctgcac taatgttccg gcgttatttc 5400
ttgatgtctc tgaccagaca cccatcaaca gtattatttt ctcccatgaa gacggtacgc 5460
gactgggcgt ggagcatctg gtcgcattgg gtcaccagca aatcgcgctg ttagcgggcc 5520
cattaagttc tgtctcggcg cgtctgcgtc tggctggctg gcataaatat ctcactcgca 5580
atcaaattca gccgatagcg gaacgggaag gcgactggag tgccatgtcc ggttttcaac 5640
aaaccatgca aatgctgaat gagggcatcg ttcccactgc gatgctggtt gccaacgatc 5700
agatggcgct gggcgcaatg cgcgccatta ccgagtccgg gctgcgcgtt ggtgcggata 5760
tctcggtagt gggatacgac gataccgaag acagctcatg ttatatcccg ccgtcaacca 5820
ccatcaaaca ggattttcgc ctgctggggc aaaccagcgt ggaccgcttg ctgcaactct 5880
ctcagggcca ggcggtgaag ggcaatcagc tgttgcccgt ctcactggtg aaaagaaaaa 5940
ccaccctggc gcccaatacg caaaccgcct ctccccgcgc gttggccgat tcattaatgc 6000
agctggcacg acaggtttcc cgactggaaa gcgggcagtg agcgcaacgc aattaatgtg 6060
agttagcgcg aattgatctg 6080

<210> SEQ ID NO 3
<211> LENGTH: 37
<212> TYPE: DNA
<213> ORGANISM: Artificial Sequence
<220> FEATURE:
<223> OTHER INFORMATION: Synthetic Construct

<400> SEQUENCE: 3
cgtgagatca tatgtgtgcg acctcttctc aatttac 37

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
cggtcgacgg atccctgcag ttagacatac atcagctg 38

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5
ttctcatgtt tgacagctta tcatcgataa gctttaatgc ggtagtttat cacagttaaa 60
ttgctaacgc agtcaggcac cgtgtatgaa atctaacaat gcgctcatcg tcatcctcgg 120
caccgtcacc ctggatgctg taggcatagg cttggttatg ccggtactgc cgggcctctt 180
gcgggatatc cggatatagt tcctcctttc agcaaaaaac ccctcaagac ccgtttagag 240
gccccaaggg gttatgctag ttattgctca gcggtggcag cagccaactc agcttccttt 300

-continued

```
cgggctttgt tagcagccgg atccctgcag ttagacatac atcagctggt taatcgggaa    360
agggtcaatc agcagcagtt tgatgcggtt ttcagtcgcg tagtctgggc gacccagacc    420
atcgccatac tggtaggtgc agtgggaaac acgtgccatg ttaactgcga tttccatgaa    480
cgctttaggc agcagggtgg agtcgctaac gcgttcacga ttcatctttt tccattcggc    540
gtcgatcagt ttacgcagtt cttcgcgggc ctgttcctcg ctggtaccat cgttttcgtg    600
catgtagcta atgatagaat tggtagtctc gccacgttcc agctccgccg cagaggtggc    660
cagatcgttg cacaggcgga agataacgca gctagaacgc accagaccat ggaagtcggt    720
cagggaacgc agcgcgtggt cggagatgtc ttcctgctgc tggcatacgg aaaagtaaga    780
cggcgccagc agcgctacac cggaggagga aacgctggcg ttttccaggt acttggagaa    840
agccgggata attttgttgt tggaccattt cgcctcttgc agaaaggctt tgcacagttc    900
acgccagctt ttcgtcagat aggacaggtt gttatgacct ttctctttca gaatagaata    960
ggacgtgtcg ttaacggtgt tgtacagtgc caggaaacac agtttcatat agtccggcag   1020
ggtgttaata gcgttaacgt cccagcgctc tacagcatcg gtgaacagtt gcagttcgtc   1080
cagagtgcca taaacgtcat acacgtcatc gatgatcgtc accagaccaa acattttagt   1140
aacagctttg cgacattcac caaactgcgg gtctggcgcc atacccagtg cccagaaata   1200
aacttccatc aggcggtcgc gtacaaaatc cagtttgcta gccaggccca tctcggtcca   1260
ccagcgggac agatcttgca gctctttctg gtgcagggtc tgtaccatgt taaaatccag   1320
cttcgccagc tccagcagca gctggtgatg cggttctttc ggttcgtatt tatccaggaa   1380
ccaacgtgcc tccagacggt gcagacgctg gtgatatggc agttccaggg cgtggctcac   1440
ttgttctgca accttggtat taatgccttc tttcaggttg ttcttcaggt gggtgatgga   1500
aaaggtacgc gcctcctcca gcaggttctc accctcgaaa cccaggtaag acgcttcata   1560
caggctcagc aggccttgga cgtcaccttt cagttcaccg ctgaaaccac cttctttatc   1620
cttgaaacgc tcaaaaacat cctgagaaac ctcgaaaccg tgctgacgca gcagacggaa   1680
agacagagcg gttgcgtgca ggtcagattt gttctttttg ttttcgtcca gcagtacgat   1740
gttttccagg gctttaatga tgtctttttc aaatttgtag gtcagaccca ggcgctgcac   1800
atcgtcgatc agctccagca gggacagcgg ctgggtgtct acacggttga tcatgcagcg   1860
aacttcttcc tccagtttgg tcgctttctc ctccagcttt tccactttca ggtcgttctc   1920
cagggattgc aggaattcga aattccacag gtttggctga tagtttgcgg aacgacggga   1980
attatgctcg gtaatctgag taaattgaga agaggtcgca cacatatgac gaccttcgat   2040
atggccgctg ctgtgatgat gatgatgatg atgatgatga tggcccatgg tatatctcct   2100
tcttaaagtt aaacaaaatt atttctagag gggaattgtt atccgctcac aattccccta   2160
tagtgagtcg tattaatttc gcgggatcga gatctcgatc ctctacgccg gacgcatcgt   2220
ggccggcatc accggcgcca caggtgcggt tgctggcgcc tatatcgccg acatcaccga   2280
tggggaagat cgggctcgcc acttcgggct catgagcgct tgtttcggcg tgggtatggt   2340
ggcaggcccc gtggccgggg gactgttggg cgccatctcc ttgcatgcac cattccttgc   2400
ggcggcggtg ctcaacggcc tcaacctact actgggctgc ttcctaatgc aggagtcgca   2460
taagggagag cgtcgagatc ccggacacca tcgaatggcg caaaaccttt cgcggtatgg   2520
catgatagcg cccggaagag agtcaattca gggtggtgaa tgtgaaacca gtaacgttat   2580
acgatgtcgc agagtatgcc ggtgtctctt atcagaccgt ttcccgcgtg gtgaaccagg   2640
```

-continued

```
ccagccacgt ttctgcgaaa acgcgggaaa aagtggaagc ggcgatggcg gagctgaatt   2700
acattcccaa ccgcgtggca caacaactgg cgggcaaaca gtcgttgctg attggcgttg   2760
ccacctccag tctggccctg cacgcgccgt cgcaaattgt cgcggcgatt aaatctcgcg   2820
ccgatcaact gggtgccagc gtggtggtgt cgatggtaga acgaagcggc gtcgaagcct   2880
gtaaagcggc ggtgcacaat cttctcgcgc aacgcgtcag tgggctgatc attaactatc   2940
cgctggatga ccaggatgcc attgctgtgg aagctgcctg cactaatgtt ccggcgttat   3000
ttcttgatgt ctctgaccag acacccatca acagtattat tttctcccat gaagacggta   3060
cgcgactggg cgtggagcat ctggtcgcat tgggtcacca gcaaatcgcg ctgttagcgg   3120
gcccattaag ttctgtctcg gcgcgtctgc gtctggctgg ctggcataaa tatctcactc   3180
gcaatcaaat tcagccgata gcggaacggg aaggcgactg gagtgccatg tccggttttc   3240
aacaaaccat gcaaatgctg aatgagggca tcgttcccac tgcgatgctg gttgccaacg   3300
atcagatggc gctgggcgca atgcgcgcca ttaccgagtc cgggctgcgc gttggtgcgg   3360
atatctcggt agtgggatac gacgataccg aagacagctc atgttatatc ccgccgttaa   3420
ccaccatcaa acaggatttt cgcctgctgg ggcaaaccag cgtggaccgc ttgctgcaac   3480
tctctcaggg ccaggcggtg aagggcaatc agctgttgcc cgtctcactg gtgaaaagaa   3540
aaaccaccct ggcgcccaat acgcaaaccg cctctccccg cgcgttggcc gattcattaa   3600
tgcagctggc acgacaggtt tcccgactgg aaagcgggca gtgagcgcaa cgcaattaat   3660
gtaagttagc tcactcatta ggcaccggga tctcgaccga tgcccttgag agccttcaac   3720
ccagtcagct ccttccggtg ggcgcggggc atgactatcg tcgccgcact tatgactgtc   3780
ttctttatca tgcaactcgt aggacaggtg ccggcagcgc tctgggtcat tttcggcgag   3840
gaccgctttc gctggagcgc gacgatgatc ggcctgtcgc ttgcggtatt cggaatcttg   3900
cacgccctcg ctcaagcctt cgtcactggt cccgccacca aacgtttcgg cgagaagcag   3960
gccattatcg ccggcatggc ggccgacgcg ctgggctacg tcttgctggc gttcgcgacg   4020
cgaggctgga tggccttccc cattatgatt cttctcgctt ccggcggcat cgggatgccc   4080
gcgttgcagg ccatgctgtc caggcaggta gatgacgacc atcagggaca gcttcaagga   4140
tcgctcgcgg ctcttaccag cctaacttcg atcactggac cgctgatcgt cacggcgatt   4200
tatgccgcct cggcgagcac atggaacggg ttggcatgga ttgtaggcgc cgccctatac   4260
cttgtctgcc tccccgcgtt gcgtcgcggt gcatggagcc gggccacctc gacctgaatg   4320
gaagccggcg gcacctcgct aacggattca ccactccaag aattggagcc aatcaattct   4380
tgcggagaac tgtgaatgcg caaaccaacc cttggcagaa catatccatc gcgtccgcca   4440
tctccagcag ccgcacgcgg cgcatctcgg gcagcgttgg gtcctggcca cgggtgcgca   4500
tgatcgtgct cctgtcgttg aggacccggc taggctggcg gggttgcctt actggttagc   4560
agaatgaatc accgatacgc gagcgaacgt gaagcgactg ctgctgcaaa acgtctgcga   4620
cctgagcaac aacatgaatg gtcttcggtt tccgtgtttc gtaaagtctg gaaacgcgga   4680
agtcagcgcc ctgcaccatt atgttccgga tctgcatcgc aggatgctgc tggctaccct   4740
gtggaacacc tacatctgta ttaacgaagc gctggcattg accctgagtg atttttctct   4800
ggtcccgccg catccatacc gccagttgtt taccctcaca acgttccagt aaccgggcat   4860
gttcatcatc agtaacccgt atcgtgagca tcctctctcg tttcatcggt atcattaccc   4920
ccatgaacag aaatccccct tacacggagg catcagtgac caaacaggaa aaaaccgccc   4980
ttaacatggc ccgctttatc agaagccaga cattaacgct tctggagaaa ctcaacgagc   5040
```

```
tggacgcgga tgaacaggca gacatctgtg aatcgcttca cgaccacgct gatgagcttt   5100
accgcagctg cctcgcgcgt ttcggtgatg acggtgaaaa cctctgacac atgcagctcc   5160
cggagacggt cacagcttgt ctgtaagcgg atgccgggag cagacaagcc cgtcagggcg   5220
cgtcagcggg tgttggcggg tgtcggggcg cagccatgac ccagtcacgt agcgatagcg   5280
gagtgtatac tggcttaact atgcggcatc agagcagatt gtactgagag tgcaccatat   5340
atgcggtgtg aaataccgca cagatgcgta aggagaaaat accgcatcag gcgctcttcc   5400
gcttcctcgc tcactgactc gctgcgctcg gtcgttcggc tgcggcgagc ggtatcagct   5460
cactcaaagg cggtaatacg gttatccaca gaatcagggg ataacgcagg aaagaacatg   5520
tgagcaaaag gccagcaaaa ggccaggaac cgtaaaaagg ccgcgttgct ggcgtttttc   5580
cataggctcc gcccccctga cgagcatcac aaaaatcgac gctcaagtca gaggtggcga   5640
aacccgacag gactataaag ataccaggcg tttccccctg gaagctccct cgtgcgctct   5700
cctgttccga ccctgccgct taccggatac ctgtccgcct ttctcccttc gggaagcgtg   5760
gcgctttctc atagctcacg ctgtaggtat ctcagttcgg tgtaggtcgt tcgctccaag   5820
ctgggctgtg tgcacgaacc ccccgttcag cccgaccgct gcgccttatc cggtaactat   5880
cgtcttgagt ccaacccggt aagacacgac ttatcgccac tggcagcagc cactggtaac   5940
aggattagca gagcgaggta tgtaggcggt gctacagagt tcttgaagtg gtggcctaac   6000
tacggctaca ctagaaggac agtatttggt atctgcgctc tgctgaagcc agttaccttc   6060
ggaaaaagag ttggtagctc ttgatccggc aaacaaacca ccgctggtag cggtggtttt   6120
tttgtttgca agcagcagat tacgcgcaga aaaaaaggat ctcaagaaga tcctttgatc   6180
ttttctacgg ggtctgacgc tcagtggaac gaaaactcac gttaagggat tttggtcatg   6240
agattatcaa aaaggatctt cacctagatc cttttaaatt aaaaatgaag ttttaaatca   6300
atctaaagta tatatgagta aacttggtct gacagttacc aatgcttaat cagtgaggca   6360
cctatctcag cgatctgtct atttcgttca tccatagttg cctgactccc cgtcgtgtag   6420
ataactacga tacgggaggg cttaccatct ggccccagtg ctgcaatgat accgcgagac   6480
ccacgctcac cggctccaga tttatcagca ataaaccagc cagccggaag ggccgagcgc   6540
agaagtggtc ctgcaacttt atccgcctcc atccagtcta ttaattgttg ccgggaagct   6600
agagtaagta gttcgccagt taatagtttg cgcaacgttg ttgccattgc tgcaggcatc   6660
gtggtgtcac gctcgtcgtt tggtatggct tcattcagct ccggttccca acgatcaagg   6720
cgagttacat gatcccccat gttgtgcaaa aaagcggtta gctccttcgg tcctccgatc   6780
gttgtcagaa gtaagttggc cgcagtgtta tcactcatgg ttatggcagc actgcataat   6840
tctcttactg tcatgccatc cgtaagatgc ttttctgtga ctggtgagta ctcaaccaag   6900
tcattctgag aatagtgtat gcggcgaccg agttgctctt gcccggcgtc aacacgggat   6960
aataccgcgc cacatagcag aactttaaaa gtgctcatca ttggaaaacg ttcttcgggg   7020
cgaaaactct caaggatctt accgctgttg agatccagtt cgatgtaacc cactcgtgca   7080
cccaactgat cttcagcatc ttttactttc accagcgttt ctgggtgagc aaaaacagga   7140
aggcaaaatg ccgcaaaaaa gggaataagg gcgacacgga aatgttgaat actcatactc   7200
ttcctttttc aatattattg aagcatttat cagggttatt gtctcatgag cggatacata   7260
tttgaatgta tttagaaaaa taaacaaata ggggttccgc gcacatttcc ccgaaaagtg   7320
ccacctgacg tctaagaaac cattattatc atgacattaa cctataaaaa taggcgtatc   7380
```

-continued acgaggccct ttcgtcttca agaa 7404

<210> SEQ ID NO 6
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6
catatgaaag cttgtatcga ttaaataagg aggaataaac c 41

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7
cccgtcttac tgtcgggaat tcgcgttggc cgattcatta atgcagctgg cacgacaggt 60
ttcccgactg gaaagcgggc agtgagcgca acgcaattaa tgtgagttag ctcactcatt 120
aggcacccca ggctttacac tttatgcttc cggctcgtat gttgtgtgga attgtgagcg 180
gataacaatt tcacacagga aacagctatg accatgatta cgccaagctt gtatcgatta 240
aataaggagg aataaaccat gtgtgcgacc tcttctcaat ttactcagat taccgagcat 300
aattcccgtc gttccgcaaa ctatcagcca aacctgtgga atttcgaatt cctgcaatcc 360
ctggagaacg acctgaaagt ggaaaagctg gaggagaaag cgaccaaact ggaggaagaa 420
gttcgctgca tgatcaaccg tgtagacacc cagccgctgt ccctgctgga gctgatcgac 480
gatgtgcagc gcctgggtct gacctacaaa tttgaaaaag acatcattaa agccctggaa 540
aacatcgtac tgctggacga aaacaaaaag aacaaatctg acctgcacgc aaccgctctg 600
tctttccgtc tgctgcgtca gcacggtttc gaggtttctc aggatgtttt tgagcgtttc 660
aaggataaag aaggtggttt cagcggtgaa ctgaaaggtg acgtccaagg cctgctgagc 720
ctgtatgaag cgtcttacct gggtttcgag ggtgagaacc tgctggagga ggcgcgtacc 780
ttttccatca cccacctgaa gaacaacctg aaagaaggca ttaataccaa ggttgcagaa 840
caagtgagcc acgccctgga actgccatat caccagcgtc tgcaccgtct ggaggcacgt 900
tggttcctgg ataaatacga accgaaagaa ccgcatcacc agctgctgct ggagctggcg 960
aagctggatt ttaacatggt acagaccctg caccagaaag agctgcaaga tctgtcccgc 1020
tggtggaccg agatgggcct ggctagcaaa ctggattttg tacgcgaccg cctgatggaa 1080
gtttatttct gggcactggg tatggcgcca gacccgcagt ttggtgaatg tcgcaaagct 1140
gttactaaaa tgtttggtct ggtgacgatc atcgatgacg tgtatgacgt ttatggcact 1200
ctggacgaac tgcaactgtt caccgatgct gtagagcgct gggacgttaa cgctattaac 1260
accctgccgg actatatgaa actgtgtttc ctggcactgt acaacaccgt taacgacacg 1320
tcctattcta ttctgaaaga gaaaggtcat aacaacctgt cctatctgac gaaaagctgg 1380
cgtgaactgt gcaaagcctt tctgcaagag gcgaaatggt ccaacaacaa aattatcccg 1440
gctttctcca agtacctgga aaacgccagc gtttcctcct ccggtgtagc gctgctggcg 1500
ccgtcttact tttccgtatg ccagcagcag gaagacatct ccgaccacgc gctgcgttcc 1560
ctgaccgact tccatggtct ggtgcgttct agctgcgtta tcttccgcct gtgcaacgat 1620
ctggccacct ctgcggcgga gctggaacgt ggcgagacta ccaattctat cattagctac 1680

```
atgcacgaaa acgatggtac cagcgaggaa caggcccgcg aagaactgcg taaactgatc   1740
gacgccgaat ggaaaaagat gaatcgtgaa cgcgttagcg actccaccct gctgcctaaa   1800
gcgttcatgg aaatcgcagt taacatggca cgtgtttccc actgcaccta ccagtatggc   1860
gatggtctgg gtcgcccaga ctacgcgact gaaaaccgca tcaaactgct gctgattgac   1920
cctttcccga ttaaccagct gatgtatgtc taactgcagg tcgactctag aggatccccg   1980
ggtaccgagc tcgaattcac tggccgtcgt tttacaacgt cgtgactggg aaaaccctgg   2040
cgttacccaa cttaatcgcc ttgcagcaca tccccctttc gccagctggc gtaatagcga   2100
agaggcccgc accgatcgcc cttcccaaca gttgcgcagc ctgaatggcg aatggcgcct   2160
gatgcggtat tttctcctta cgcatctgtg cggtatttca caccgcatat ggtgcactct   2220
cagtacaatc tgctctgatg ccgcatagtt aagccagccc cgacacccgc caacacccgc   2280
tgacgagctt agtaaagccc tcgctagatt ttaatgcgga tgttgcgatt acttcgccaa   2340
ctattgcgat aacaagaaaa agccagcctt tcatgatata tctcccaatt tgtgtagggc   2400
ttattatgca cgcttaaaaa taataaaagc agacttgacc tgatagtttg gctgtgagca   2460
attatgtgct tagtgcatct aacgcttgag ttaagccgcg ccgcgaagcg gcgtcggctt   2520
gaacgaattg ttagacatta tttgccgact accttggtga tctcgccttt cacgtagtgg   2580
acaaattctt ccaactgatc tgcgcgcgag gccaagcgat cttcttcttg tccaagataa   2640
gcctgtctag cttcaagtat gacgggctga tactgggccg gcaggcgctc cattgcccag   2700
tcggcagcga catccttcgg cgcgattttg ccggttactg cgctgtacca aatgcgggac   2760
aacgtaagca ctacatttcg ctcatcgcca gcccagtcgg gcggcgagtt ccatagcgtt   2820
aaggtttcat ttagcgcctc aaatagatcc tgttcaggaa ccggatcaaa gagttcctcc   2880
gccgctggac ctaccaaggc aacgctatgt tctcttgctt ttgtcagcaa gatagccaga   2940
tcaatgtcga tcgtggctgg ctcgaagata cctgcaagaa tgtcattgcg ctgccattct   3000
ccaaattgca gttcgcgctt agctggataa cgccacggaa tgatgtcgtc gtgcacaaca   3060
atggtgactt ctacagcgcg gagaatctcg ctctctccag gggaagccga agtttccaaa   3120
aggtcgttga tcaaagctcg ccgcgttgtt tcatcaagcc ttacggtcac cgtaaccagc   3180
aaatcaatat cactgtgtgg cttcaggccg ccatccactg cggagccgta caaatgtacg   3240
gccagcaacg tcggttcgag atggcgctcg atgacgccaa ctacctctga tagttgagtc   3300
gatacttcgg cgatcaccgc ttccctcatg atgtttaact ttgttttagg gcgactgccc   3360
tgctgcgtaa catcgttgct gctccataac atcaaacatc gacccacggc gtaacgcgct   3420
tgctgcttgg atgcccgagg catagactgt accccaaaaa aacagtcata acaagccatg   3480
aaaaccgcca ctgcgccgtt accaccgctg cgttcggtca aggttctgga ccagttgcgt   3540
gagcgcatac gctacttgca ttacagctta cgaaccgaac aggcttatgt ccactgggtt   3600
cgtgccttca tccgtttcca cggtgtgcgt cacccggcaa ccttgggcag cagcgaagtc   3660
gaggcatttc tgtcctggct ggcgaacgag cgcaaggttt cggtctccac gcatcgtcag   3720
gcattggcgg ccttgctgtt cttctacggc aaggtgctgt gcacggatct gccctggctt   3780
caggagatcg gaagacctcg gccgtcgcgg cgcttgccgg tggtgctgac cccggatgaa   3840
gtggttcgca tcctcggttt tctggaaggc gagcatcgtt tgttcgccca gcttctgtat   3900
ggaacgggca tgcggatcag tgagggtttg caactgcggg tcaaggatct ggatttcgat   3960
cacggcacga tcatcgtgcg ggagggcaag ggctccaagg atcgggcctt gatgttaccc   4020
```

```
gagagcttgg cacccagcct gcgcgagcag gggaattaat tcccacgggt tttgctgccc   4080
gcaaacgggc tgttctggtg ttgctagttt gttatcagaa tcgcagatcc ggcttcagcc   4140
ggtttgccgg ctgaaagcgc tatttcttcc agaattgcca tgatttttc cccacgggag   4200
gcgtcactgg ctcccgtgtt gtcggcagct ttgattcgat aagcagcatc gcctgtttca   4260
ggctgtctat gtgtgactgt tgagctgtaa caagttgtct caggtgttca atttcatgtt   4320
ctagttgctt tgttttactg gtttcacctg ttctattagg tgttacatgc tgttcatctg   4380
ttacattgtc gatctgttca tggtgaacag ctttgaatgc accaaaaact cgtaaaagct   4440
ctgatgtatc tatcttttt acaccgtttt catctgtgca tatggacagt tttccctttg   4500
atatgtaacg gtgaacagtt gttctacttt tgtttgttag tcttgatgct tcactgatag   4560
atacaagagc cataagaacc tcagatcctt ccgtatttag ccagtatgtt ctctagtgtg   4620
gttcgttgtt tttgcgtgag ccatgagaac gaaccattga gatcatactt actttgcatg   4680
tcactcaaaa attttgcctc aaaactggtg agctgaattt ttgcagttaa agcatcgtgt   4740
agtgtttttc ttagtccgtt atgtaggtag gaatctgatg taatggttgt tggtattttg   4800
tcaccattca tttttatctg gttgttctca agttcggtta cgagatccat ttgtctatct   4860
agttcaactt ggaaaatcaa cgtatcagtc gggcggcctc gcttatcaac caccaatttc   4920
atattgctgt aagtgtttaa atctttactt attggtttca aaacccattg gttaagcctt   4980
ttaaactcat ggtagttatt ttcaagcatt aacatgaact taaattcatc aaggctaatc   5040
tctatatttg ccttgtgagt tttcttttgt gttagttctt ttaataacca ctcataaatc   5100
ctcatagagt atttgttttc aaaagactta acatgttcca gattatattt tatgaatttt   5160
tttaactgga aaagataagg caatatctct tcactaaaaa ctaattctaa tttttcgctt   5220
gagaacttgg catagtttgt ccactggaaa atctcaaagc ctttaaccaa aggattcctg   5280
atttccacag ttctcgtcat cagctctctg gttgctttag ctaatacacc ataagcattt   5340
tccctactga tgttcatcat ctgagcgtat tggttataag tgaacgatac cgtccgttct   5400
ttccttgtag ggttttcaat cgtggggttg agtagtgcca cacagcataa aattagcttg   5460
gtttcatgct ccgttaagtc atagcgacta atcgctagtt catttgcttt gaaaacaact   5520
aattcagaca tacatctcaa ttggtctagg tgattttaat cactatacca attgagatgg   5580
gctagtcaat gataattact agtccttttc ctttgagttg tgggtatctg taaattctgc   5640
tagacctttg ctggaaaact tgtaaattct gctagaccct ctgtaaattc cgctagacct   5700
ttgtgtgttt tttttgttta tattcaagtg gttataattt atagaataaa gaaagaataa   5760
aaaaagataa aaagaataga tcccagccct gtgtataact cactacttta gtcagttccg   5820
cagtattaca aaaggatgtc gcaaacgctg tttgctcctc tacaaaacag accttaaaac   5880
cctaaaggct taagtagcac cctcgcaagc tcgggcaaat cgctgaatat tccttttgtc   5940
tccgaccatc aggcacctga gtcgctgtct ttttcgtgac attcagttcg ctgcgctcac   6000
ggctctggca gtgaatgggg gtaaatggca ctacaggcgc cttttatgga ttcatgcaag   6060
gaaactaccc ataatacaag aaaagcccgt cacgggcttc tcagggcgtt ttatggcggg   6120
tctgctatgt ggtgctatct gactttttgc tgttcagcag ttcctgccct ctgattttcc   6180
agtctgacca cttcggatta tcccgtgaca ggtcattcag actggctaat gcacccagta   6240
aggcagcggt atcatcaaca ggctta                                        6266
```

<210> SEQ ID NO 8
<211> LENGTH: 1695

-continued

<212> TYPE: DNA
<213> ORGANISM: Artificial Sequence
<220> FEATURE:
<223> OTHER INFORMATION: Synthetic Construct

<400> SEQUENCE: 8

```
atgtgtgcaa cctcctccca gtttactcag attaccgagc ataattctcg acgatctgct     60

aactaccagc cgaacctttg gaactttgag tttctccagt ctctcgaaaa tgacctgaag    120

gtggaaaagc tcgaggagaa ggcgaccaaa ctcgaggagg aggtgcgatg tatgatcaac    180

agagttgaca cccaacccct gtctttgctg gagctgatcg acgatgtgca gcggttgggt    240

ttgacttata aattcgagaa ggacattatc aaggcactgg agaacattgt gctcctcgac    300

gagaacaaga agaacaagtc tgatcttcac gctaccgctc tctctttccg acttcttcga    360

caacacggct tcgaggtgtc gcaggacgtc ttcgagagat ttaaggacaa ggagggagga    420

tttagcggcg agctgaaggg agacgttcag ggtcttctct ccttgtacga ggcgtcctac    480

ctgggattcg agggagagaa cctcctggag gaagctcgta cattttccat cactcacctt    540

aagaataacc ttaaggaggg aattaacacc aaggtggccg agcaggtttc tcacgccctg    600

gagctcccct accaccaacg gctccataga ctggaggctc gttggttcct ggacaaatat    660

gagccaaagg agcctcatca tcagttgctg ttggagttgg ccaagctgga cttcaatatg    720

gttcagacgc tgcaccaaaa ggagttgcag gacctgtctc gatggtggac cgagatggga    780

ttggcctcga agctggattt tgtccgtgac cgacttatgg aggtctattt ttgggccctt    840

ggaatggcgc ctgaccccca gttcggagag tgccggaagg cggtgacgaa gatgttcggt    900

cttgtgacta tcatcgacga cgtctacgat gtctacggca cactcgacga gttgcagctg    960

ttcactgacg ccgtcgagcg atgggatgtg aacgccatta atactctccc tgactatatg   1020

aagctgtgct tcctggctct gtacaacact gtcaacgata cctcgtactc tatcctcaag   1080

gagaagggac acaacaatct ctcctacttg accaaatcct ggcgagaact gtgcaaggct   1140

tttctgcagg aggctaaatg gtccaataac aagatcattc ctgctttttc taaatacctg   1200

gaaaatgcct cggtgtcgag ctctggcgtc gcccttctgg ccccttccta cttctccgtc   1260

tgccagcagc aggaggatat ttccgatcat gctcttagat cgctgaccga ttttcacggc   1320

ctcgtgcgat cttcctgcgt gatttttcgg ttgtgtaatg accttgcgac ctctgctgct   1380

gagctggaac gaggcgagac tacaaattcc attatttctt acatgcacga aaacgatgga   1440

acatctgaag aacaggctag agaggaactg cgaaagttga tcgacgccga gtggaagaag   1500

atgaacagag agcgggtgtc cgactctacc ctgcttccca aggccttcat ggagatcgcc   1560

gtgaacatgg ctcgagtttc ccattgtact taccagtacg gtgacggcct gggtcgtccg   1620

gactacgcta cagagaaccg aatcaagctg ctgctcatcg accccttccc tatcaaccaa   1680

ttgatgtacg tgtaa                                                      1695
```

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9

```
gcttatggat cctctagact attacacgta catcaattgg                           40
```

<210> SEQ ID NO 10

-continued

<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
caccatgtgt gcaacctcct cccagtttac 30

<210> SEQ ID NO 11
<211> LENGTH: 8191
<212> TYPE: DNA
<213> ORGANISM: Artificial Sequence
<220> FEATURE:
<223> OTHER INFORMATION: Synthetic Construct

<400> SEQUENCE: 11
tcgaccggtg agaagaacag catcgggaca agggaaggaa gaacaaagac aaagaaaaca 60
aaagaaagca attgaaaaca aaacaaaaca attttcattc cttctcttat cattcctttt 120
cttttctttt ctctcattca acgcactcca tcgtatccgt attcctctta ttttttctct 180
ttctctatat ccatttcttt ctctctaggt gtgtcctctc tctctcttca atttctctac 240
tccgcattcc aacgcatcct tcccccaacc tcccatttcc tccttacggc ccgatagcga 300
tcgtctttcc ctcgctatca ctcgctaccg gcccctcctc tgcaccgtaa cctcctacgt 360
atttaccata tcataaagtt ttttccgacg cttatcgctg accccctgtc gccctcctat 420
tggcttccgg attatcttct tgtccataag gtgatccatg cttcctgaag attcccgaaa 480
tgtgtccact ttggcgggga atcattccat ccacttcttt ctctctcgct ttcctcattc 540
ggcgctcccc ttccgcgtct cattggtctt ccgctccgtt tttgctttgc cgatgttact 600
tggggagagg tgcgataatc ctttcgcaaa aactcggttt gacgcctccc atggtataaa 660
tagtgggtgg tggacaggtg ccttcgcttt tctttaagca agagaatccc attgtcttga 720
ctatcacgaa ttcacataca ttatgaagat caccgctgtc attgcccttt tattctcact 780
tgctgctgcc tcacctattc cagttgccga tcctggtgtg gtttcagtta gcaagtcata 840
tgctgatttc cttcgtgttt accaaagttg gaacactttt gctaatcctg atagacccaa 900
ccttaagaag agaaatgata cacctgcaag tggatatcaa gttgaaaaag tcgtaatttt 960
gtcacgtcac ggtgttaggg cccctacaaa aatgactcaa accatgcgtg atgtcactcc 1020
taatacatgg ccagaatggc ccgttaaatt aggatatatt acaccaagag gtgaacactt 1080
gatatcactt atgggcggtt tttaccgtca aaaattccag caacaaggaa tcctttctca 1140
gggctcctgt cctactccta actccatata tgtctgggct gacgtcgatc agcgtacttt 1200
aaaaactggt gaagcattcc ttgctggttt ggcaccacaa tgtggcttga caattcatca 1260
ccaacaaaat cttgagaaag ctgatcctct ttttcatccc gttaaagctg gaacctgctc 1320
tatggataaa actcaagttc aacaagctgt tgagaaggag gcacaaactc ctatagataa 1380
tttgaatcaa cattacatcc cctttttagc tttaatgaat acaacattaa attttagtac 1440
ttctgcctgg tgccaaaaac actctgctga taaatcctgt gacctaggtt tatccatgcc 1500
ttctaaattg tccataaaag ataatggtaa caaggtcgca ttggatggag ctattggtct 1560
atcctctact ttggccgaga tttttcttct tgaatatgct caaggcatgc ctcaagctgc 1620
ttggggtaac atccactcag agcaagagtg ggcttccttg ctaaagttgc ataatgttca 1680
attcgatttg atggcccgaa caccttatat tgctcgacat aacggtactc ctttattgca 1740
agctatatca aatgccctta atcccaacgc cactgaatca aaacttccag atatttcacc 1800
tgataacaaa atattgttca ttgcaggtca tgacacaaat attgctaata tagccggcat 1860
gttaaatatg cgttggacat taccaggtca accagataat actcctccag gtggtgccct 1920
agtatttgaa cgtcttgctg ataaaagtgg aaaacaatat gtttctgtat ctatggttta 1980
tcaaacacta gaacaacttc gatcacagac tccccttttct ctaaatcagc ctgccggatc 2040
tgttcaactt aaaattccag gttgcaatga tcaaacagcc gagggttact gtcctctttc 2100
cacttttaca agagttgttt cccaatctgt tgaacctgga tgccaacttc aataatgagg 2160
atccaagtaa gggaatgaga atgtgatcca cttttaattc ctaatgaata catgcctata 2220
gttcttttct tttgttcttt atgtcgtttt tcgatggtac ggccgttgtc aatctcagtt 2280
tgtgtgcttg gttgcagctt ggtttcaaat ctgttcatct catgaatctt ttaccatttc 2340
accacacgtt tataccattc tctcatagaa tcttcatcaa accatctcgg ggttagagtg 2400
gaaagaaagt cttgttcttt tatttccttt tttccatctt caaggctttt cttttcttcc 2460
tcctcctcgt tcatcttgag gtttgacgtg tctgtttaga attttgagct gttgcagcat 2520
cttatttttt gttttgcgaa aacgaagcgc tttactctct tcatcagttg gacgattgta 2580
cctttgaaaa ccaactactt ttgcatgttt tgtatagaaa tcaatgatat tagaatccca 2640
tcctttaatt tctttcaaag tagttgagct atagttaagt gtaagggccc tactgcgaaa 2700
gcatttgcca aggatgtttt cattaatcaa gaacgaaagt taggggatcg aagacgatca 2760
gataccgtcg tagtcttaac cataaactat gccgactagg gatcgggcaa tgtttcattt 2820
atcgacttgc tcggcacctt acgagaaatc aaagtctttg ggttccgggg ggagtatggt 2880
cgcaaggctg aaacttaaag gaattgacgg aagggcacca caatggagtg gagcctgcgg 2940
cttaatttga ctcaacacgg ggaaactcac caggtccaga catagtaagg attgacagat 3000
tgagagctct ttcttgattc tatgggtggt ggtgcatggc cgttcttagt tggtggagtg 3060
atttgtctgc ttaattgcga taacgaacga gaccttaacc tgctaaatag ctggatcagc 3120
cattttggct gatcattagc ttcttagagg gactattggc ataaagccaa tggaagtttg 3180
aggcaataac aggtctgtga tgcccttaga tgttctgggc cgcacgcgcg ctacactgac 3240
ggagccaacg agttgaaaaa aatcttttga ttttttatcc ttggccggaa ggtctgggta 3300
atcttgttaa actccgtcgt gctggggata gagcattgca attattgcgg ccgctcctca 3360
attcgatgtt gcagatttta caagttttta aaatgtattt cattattact ttttatatgc 3420
ctaataaaaa agccatagtt taatctatag ataacttttt ttccagtgca ctaacggacg 3480
ttacattccc atacaaaact gcgtagttaa agctaaggaa aagttaatat catgttaatt 3540
aaatacgcta tttacaataa gacattgaac tcatttatat cgttgaatat gaataaccaa 3600
tttcagcgaa tttttaacaa acatcgttca cctcgtttaa ggatatcttg tgtatggggt 3660
gttgacttgc tttatcgaat aattaccgta cctgtaattg gcttgctgga tatagcggta 3720
gtctaatatc tagcaaaaat cttttgggtg aaaaggcttg caatttcacg acaccgaact 3780
atttgtcatt ttttaataag gaagttttcc ataaattcct gtaattctcg gttgatctaa 3840
ttgaaaagag tagttttgca tcacgatgag gagggctttt gtagaaagaa atacgaacga 3900
aacgaaaatc agcgttgcca tcgctttgga caaagctccc ttacctgaag agtcgaattt 3960
tattgatgaa cttataactt ccaagcatgc aaaccaaaag ggagaacaag taatccaagt 4020
agacacggga attggattct tggatcacat gtatcatgca ctggctaaac atgcaggctg 4080
gagcttacga ctttactcaa gaggtgattt aatcatcgat gatcatcaca ctgcagaaga 4140

-continued

```
tactgctatt gcacttggta ttgcattcaa gcaggctatg ggtaactttg ccggcgttaa   4200
aagatttgga catgcttatt gtccacttga cgaagctctt tctagaagcg tagttgactt   4260
gtcgggacgg ccctatgctg ttatcgattt gggattaaag cgtgaaaagg ttggggaatt   4320
gtcctgtgaa atgatccctc acttactata ttcctttttcg gtagcagctg gaattacttt   4380
gcatgttacc tgcttatatg gtagtaatga ccatcatcgt gctgaaagcg cttttaaatc   4440
tctggctgtt gccatgcgcg cggctactag tcttactgga agttctgaag tcccaagcac   4500
gaagggagtg ttgtaaagat gaattggatt atgtcaggaa aagaacgaca attttgcatc   4560
caaattgtct aaattttaga gttgcttgaa aacaatagaa ccttacttgc tttataatta   4620
cgttaattag aagcgttatc tcgtgaagga atatagtacg tagccgtata aattgaattg   4680
aatgttcagc ttatagaata gagacacttt gctgttcaat gcgtcgtcac ttaccatact   4740
cactttatta tacgacttta agtataaact ccgcggttat ggtaaaatta atgatgcaca   4800
aacgtccgat tccatatggg tacactacaa ttaaatactt ttaagctgat cccccacaca   4860
ccatagcttc aaaatgtttc tactcctttt ttactcttcc agattttctc ggactccgcg   4920
catcgccgta ccacttcaaa acacccaagc acagcatact aaatttcccc tctttcttcc   4980
tctagggtgt cgttaattac ccgtactaaa ggtttggaaa agaaaaaaga gaccgcctcg   5040
tttcttttc ttcgtcgaaa aaggcaataa aaatttttat cacgtttctt tttcttgaaa   5100
ttttttttt tagtttttt ctctttcagt gacctccatt gatatttaag ttaataaacg   5160
gtcttcaatt tctcaagttt cagtttcatt tttcttgttc tattacaact tttttttactt   5220
cttgttcatt agaaagaaag catagcaatc taatctaagg gcggtgttga caattaatca   5280
tcggcatagt atatcggcat agtataatac gacaaggtga ggaactaaac catggccaag   5340
ttgaccagtg ccgttccggt gctcaccgcg cgcgacgtcg ccggagcggt cgagttctgg   5400
accgaccggc tcgggttctc ccgggacttc gtggaggacg acttcgccgg tgtggtccgg   5460
gacgacgtga ccctgttcat cagcgcggtc caggaccagg tggtgccgga caacaccctg   5520
gcctgggtgt gggtgcgcgg cctggacgag ctgtacgccg agtggtcgga ggtcgtgtcc   5580
acgaacttcc gggacgcctc cgggccggcc atgaccgaga tcggcgagca gccgtggggg   5640
cgggagttcg ccctgcgcga cccggccggc aactgcgtgc acttcgtggc cgaggagcag   5700
gactgacacg tccgacggcg gcccacgggt cccaggcctc ggagatccgt ccccctttc   5760
ctttgtcgat atcatgtaat tagttatgtc acgcttacat tcacgccctc cccccacatc   5820
cgctctaacc gaaaaggaag gagttagaca acctgaagtc taggtcccta tttattttt   5880
tatagttatg ttagtattaa gaacgttatt tatatttcaa atttttcttt tttttctgta   5940
cagacgcgag cttcccagta aatgtgccat ctcgtaggca gaaaacggtt cccccgtagg   6000
gtctctctct tggcctcctt tctaggtcgg gctgattgct cttgaagctc tctagggggg   6060
ctcacaccat aggcagataa cgttccccac cggctcgcct cgtaagcgca caaggactgc   6120
tcccaaagat cctaggcggg attttgccga tttcggccta aaggaaccgg aacacgtaga   6180
aagccagtcc gcagaaacgg tgctgacccc ggatgaatgt cagctactgg gctatctgga   6240
caagggaaaa cgcaagcgca aagagaaagc aggtagcttg cagtgggctt acatggcgat   6300
agctagactg ggcggtttta tggacagcaa gcgaaccgga attgccagct ggggcgccct   6360
ctggtaaggt tgggaagccc tgcaaagtaa actggatggc tttcttgccg ccaaggatct   6420
gatggcgcag gggatcaaga tctgatcaag agacaggatg aggatcgttt cgcatgattg   6480
aacaagatgg attgcacgca ggttctccgg ccgcttgggt ggagaggcta ttcggctatg   6540
```

-continued

```
actgggcaca acagacaatc ggctgctctg atgccgccgt gttccggctg tcagcgcagg   6600
ggcgcccggt tctttttgtc aagaccgacc tgtccggtgc cctgaatgaa ctgcaggacg   6660
aggcagcgcg gctatcgtgg ctggccacga cgggcgttcc ttgcgcagct gtgctcgacg   6720
ttgtcactga agcgggaagg gactggctgc tattgggcga agtgccgggg caggatctcc   6780
tgtcatctcg ccttgctcct gccgagaaag tatccatcat ggctgatgca atgcggcggc   6840
tgcatacgct tgatccggct acctgcccat tcgaccacca agcgaaacat cgcatcgagc   6900
gagcacgtac tcggatggaa gccggtcttg tcgatcagga tgatctggac gaagagcatc   6960
aggggctcgc gccagccgaa ctgttcgcca ggctcaaggc gcgcatgccc gacggcgagg   7020
atctcgtcgt gatccatggc gatgcctgct tgccgaatat catggtggaa aatggccgct   7080
tttctggatt caacgactgt ggccggctgg gtgtggcgga ccgctatcag gacatagcgt   7140
tggatacccg tgatattgct gaagagcttg gcggcgaatg ggctgaccgc ttcctcgtgc   7200
tttacggtat cgccgctccc gattcgcagc gcatcgcctt ctatcgcctt cttgacgagt   7260
tcttctgaat tgaaaaaggt accaagttta ctcatatata ctttagattg atttaaaact   7320
tcatttttaa tttaaaagga tctaggtgaa gatccttttt gataatctca tgaccaaaat   7380
cccttaacgt gagttttcgt tccactgagc gtcagacccc gtagaaaaga tcaaaggatc   7440
ttcttgagat cctttttttc tgcgcgtaat ctgctgcttg caaacaaaaa aaccaccgct   7500
accagcggtg gtttgtttgc cggatcaaga gctaccaact ctttttccga aggtaactgg   7560
cttcagcaga gcgcagatac caaatactgt ccttctagtg tagccgtagt taggccacca   7620
cttcaagaac tctgtagcac cgcctacata cctcgctctg ctaatcctgt taccagtggc   7680
tgctgccagt ggcgataagt cgtgtcttac cgggttggac tcaagacgat agttaccgga   7740
taaggcgcag cggtcgggct gaacgggggg ttcgtgcaca cagcccagct tggagcgaac   7800
gacctacacc gaactgagat acctacagcg tgagcattga gaaagcgcca cgcttcccga   7860
agggagaaag gcggacaggt atccggtaag cggcagggtc ggaacaggag agcgcacgag   7920
ggagcttcca gggggaaacg cctggtatct ttatagtcct gtcgggtttc gccacctctg   7980
acttgagcgt cgatttttgt gatgctcgtc aggggggcgg agcctatgga aaaacgccag   8040
caacgcggcc tttttacggt tcctggcctt ttgctggcct tttgctcaca tgttctttcc   8100
tgcgttatcc cctgattctg tggataaccg tattaccgcc tttgagtgag ctgataccgc   8160
tcgccgcagc cgaacgaccg agcgcagcga g                                   8191
```

```
<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12

gaattcaaaa caaaatgtgt gcaacctcct cccagtttac tcagattacc gagcataatt     60
ctcgacgatc tgctaactac cagccgaacc tttggaactt tgagtttctc cagtctctcg    120
aaaatgacct gaaggtggaa aagctcgagg agaaggcgac caaactcgag gaggaggtgc    180
gatgtatgat caacagagtt gacacccaac ccctgtcttt gctggagctg atcgacgatg    240
tgcagcggtt gggtttgact tataaattcg agaaggacat tatcaaggca ctggagaaca    300
ttgtgctcct cgacgagaac aagaagaaca agtctgatct tcacgctacc gctctctctt    360
```

-continued

```
tccgacttct tcgacaacac ggcttcgagg tgtcgcagga cgtcttcgag agatttaagg    420
acaaggaggg aggatttagc ggcgagctga agggagacgt tcagggtctt ctctccttgt    480
acgaggcgtc ctacctggga ttcgagggag agaacctcct ggaggaagct cgtacatttt    540
ccatcactca ccttaagaat aaccttaagg agggaattaa caccaaggtg gccgagcagg    600
tttctcacgc cctggagctc ccctaccacc aacggctcca tagactggag gctcgttggt    660
tcctggacaa atatgagcca aaggagcctc atcatcagtt gctgttggag ttggccaagc    720
tggacttcaa tatggttcag acgctgcacc aaaaggagtt gcaggacctg tctcgatggt    780
ggaccgagat gggattggcc tcgaagctgg attttgtccg tgaccgactt atggaggtct    840
atttttgggc ccttggaatg gcgcctgacc cccagttcgg agagtgccgg aaggcggtga    900
cgaagatgtt cggtcttgtg actatcatcg acgacgtcta cgatgtctac ggcacactcg    960
acgagttgca gctgttcact gacgccgtcg agcgatggga tgtgaacgcc attaatactc   1020
tccctgacta tatgaagctg tgcttcctgg ctctgtacaa cactgtcaac gatacctcgt   1080
actctatcct caaggagaag ggacacaaca atctctccta cttgaccaaa tcctggcgag   1140
aactgtgcaa ggcttttctg caggaggcta aatggtccaa taacaagatc attcctgctt   1200
tttctaaata cctggaaaat gcctcggtgt cgagctctgg cgtcgccctt ctggcccctt   1260
cctacttctc cgtctgccag cagcaggagg atatttccga tcatgctctt agatcgctga   1320
ccgattttca cggcctcgtg cgatcttcct gcgtgatttt tcggttgtgt aatgaccttg   1380
cgacctctgc tgctgagctg gaacgaggcg agactacaaa ttccattatt tcttacatgc   1440
acgaaaacga tggaacatct gaagaacagg ctagagagga actgcgaaag ttgatcgacg   1500
ccgagtggaa gaagatgaac agagagcggg tgtccgactc taccctgctt cccaaggcct   1560
tcatggagat cgccgtgaac atggctcgag tttcccattg tacttaccag tacggtgacg   1620
gcctgggtcg tccggactac gctacagaga accgaatcaa gctgctgctc atcgacccct   1680
tccctatcaa ccaattgatg tacgtgtaat agtctagagg atcc                    1724
```

```
<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 13

gaattcaaca aaaatgtgct ctgtttccac tgagaacgtg tcctttactg agactgagac     60
tgaagcacgt agaagcgcca actacgaacc caactcctgg gattatgact ttctgctgtc    120
ttctgacacc gacgagtcga tcgaggttta taaggataag gccaagaaac ttgaggccga    180
ggtcagacga gagattaaca acgagaaggc cgagttcctg acccttcttg agctgatcga    240
caacgttcaa cgacttggtc ttggttaccg tttcgaatcc gatatccgac gtgcattgga    300
tcgatttgtc tcgtccggag gtttcgatgg tgtgactaag acgtcgctgc acgccacagc    360
tctttccttc agactgttgc ggcagcatgg atttgaggtt tcccaggaag ccttttctgg    420
tttcaaggat cagaacggaa actttttgga gaatctcaag gaggacacca aggccatcct    480
gtcgttgtat gaggcctcgt tcctggctct tgagggcgag aatattctgg atgaggctcg    540
ggttttcgct atttcgcacc tgaaggagtt gtcggaggaa aagatcggaa aggaactggc    600
cgagcaggtc aaccatgcac ttgaacttcc cctgcatcga cgtacccagc gactggaggc    660
cgtgtggagc atcgaggcgt acagaaaaaa ggaggatgct aatcaggttc tgctcgaact    720
```

-continued

```
cgctatcctc gactataaca tgattcagag cgtgtaccag cgtgacttgc gagagacaag    780
ccggtggtgg cgacgggtgg gactggccac gaagctccac tttgctaaag atcgattgat    840
tgagtcgttc tactgggcag tgggtgtggc ctttgagcct cagtactccg actgccgaaa    900
ctccgttgca aagatgtttt cttttgtcac tatcatcgac gacatctacg atgtttacgg    960
cactctcgat gaactcgaac tcttcacgga cgctgtcgag cgatgggatg tgaatgccat   1020
taatgatctg ccagattata tgaagttgtg tttcttggcg ctctacaaca caattaatga   1080
aattgcctac gacaacctca aggacaaggg agagaacatt ctgccctacc ttactaaagc   1140
ctgggccgac ctgtgtaacg cctttttgca ggaagccaag tggctctata acaaatctac   1200
tcctacattt gatgactact tcggcaacgc ttggaagtct tccagcggcc ctctccagtt   1260
gatcttcgct tactttgcag tggtccagaa catcaagaaa gaggagattg agaacctcca   1320
gaagtatcac gacatcatct cccgaccttc gcacatcttt cgactgtgca atgaccttgc   1380
ctccgcatcc gctgagattg cccgaggaga aacagccaat tctgtgtcgt gttacatgcg   1440
tacaaagggc atctccgagg agctggctac cgagtctgtg atgaacctga tcgatgaaac   1500
ctgtaagaag atgaacaaag agaaactggg cggttctctg ttcgccaaac catttgttga   1560
aaccgcgatc aatctggctc gtcagtctca ttgtacttac cataacggtg acgcgcacac   1620
ttcgccggac gaattgaccc gtaagcgtgt gctttcggtg attaccgagc cgatcctgcc   1680
gttcgaaaga taataggatc c                                             1701
```

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14

```
gatcaagctt aaccggaatt gccagctg                                        28
```

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15

```
gatccgatcg tcagaagaac tcgtcaagaa ggc                                  33
```

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16

```
catcaatgca tcgcccttag gaggtaaaaa aaaatgac                             38
```

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
ccttctgcag gacgcgttgt tatagc 26

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg 60

<210> SEQ ID NO 19
<211> LENGTH: 30
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga 30

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc 60
tgaatagcgc cgtcgaccat catcatcatc atcattgagt ttaaacggtc tccagcttgg 120
ctgttttggc ggatgagaga agattttcag cctgatacag attaaatcag aacgcagaag 180
cggtctgata aaacagaatt tgcctggcgg cagtagcgcg gtggtcccac ctgaccccat 240
gccgaactca gaagtgaaac gccgtagcgc cgatggtagt gtggggtctc cccatgcgag 300
agtagggaac tgccaggcat caaataaaac gaaaggctca gtcgaaagac tgggcctttc 360
gttttatctg ttgtttgtcg gtgaacgctc tcctgagtag gacaaatccg ccgggagcgg 420
atttgaacgt tgcgaagcaa cggcccggag ggtggcgggc aggacgcccg ccataaactg 480
ccaggcatca aattaagcag aaggccatcc tgacggatgg cctttttgcg tttctacaaa 540
ctctttttgt ttatttttct aaatacattc aaatatgtat ccgcttaacc ggaattgcca 600
gctggggcgc cctctggtaa ggttgggaag ccctgcaaag taaactggat ggctttctcg 660
ccgccaagga tctgatggcg caggggatca agctctgatc aagagacagg atgaggatcg 720
tttcgcatga ttgaacaaga tggattgcac gcaggttctc cggccgcttg ggtggagagg 780
ctattcggct atgactgggc acaacagaca atcggctgct ctgatgccgc cgtgttccgg 840
ctgtcagcgc aggggcgccc ggttcttttt gtcaagaccg acctgtccgg tgccctgaat 900
gaactgcaag acgaggcagc gcggctatcg tggctggcca cgacgggcgt tccttgcgca 960
gctgtgctcg acgttgtcac tgaagcggga agggactggc tgctattggg cgaagtgccg 1020
gggcaggatc tcctgtcatc tcaccttgct cctgccgaga aagtatccat catggctgat 1080
gcaatgcggc ggctgcatac gcttgatccg gctacctgcc cattcgacca ccaagcgaaa 1140
catcgcatcg agcgagcacg tactcggatg gaagccggtc ttgtcgatca ggatgatctg 1200
gacgaagagc atcaggggct cgcgccagcc gaactgttcg ccaggctcaa ggcgagcatg 1260

-continued cccgacggcg aggatctcgt cgtgacccat ggcgatgcct gcttgccgaa tatcatggtg 1320
gaaaatggcc gcttttctgg attcatcgac tgtggccggc tgggtgtggc ggaccgctat 1380
caggacatag cgttggctac ccgtgatatt gctgaagagc ttggcggcga atgggctgac 1440
cgcttcctcg tgctttacgg tatcgccgct cccgattcgc agcgcatcgc cttctatcgc 1500
cttcttgacg agttcttctg acatgaccaa aatcccttaa cgtgagtttt cgttccactg 1560
agcgtcagac cccgtagaaa agatcaaagg atcttcttga gatccttttt ttctgcgcgt 1620
aatctgctgc ttgcaaacaa aaaaaccacc gctaccagcg gtggtttgtt tgccggatca 1680
agagctacca actctttttc cgaaggtaac tggcttcagc agagcgcaga taccaaatac 1740
tgtccttcta gtgtagccgt agttaggcca ccacttcaag aactctgtag caccgcctac 1800
atacctcgct ctgctaatcc tgttaccagt ggctgctgcc agtggcgata agtcgtgtct 1860
taccgggttg gactcaagac gatagttacc ggataaggcg cagcggtcgg gctgaacggg 1920
gggttcgtgc acacagccca gcttggagcg aacgacctac accgaactga gatacctaca 1980
gcgtgagcta tgagaaagcg ccacgcttcc cgaagggaga aaggcggaca ggtatccggt 2040
aagcggcagg gtcggaacag gagagcgcac gagggagctt ccagggggaa acgcctggta 2100
tctttatagt cctgtcgggt ttcgccacct ctgacttgag cgtcgatttt tgtgatgctc 2160
gtcagggggg cggagcctat ggaaaaacgc cagcaacgcg gcctttttac ggttcctggc 2220
cttttgctgg ccttttgctc acatgttctt tcctgcgtta tcccctgatt ctgtggataa 2280
ccgtattacc gcctttgagt gagctgatac cgctcgccgc agccgaacga ccgagcgcag 2340
cgagtcagtg agcgaggaag cggaagagcg cctgatgcgg tattttctcc ttacgcatct 2400
gtgcggtatt tcacaccgca tatggtgcac tctcagtaca atctgctctg atgccgcata 2460
gttaagccag tatacactcc gctatcgcta cgtgactggg tcatggctgc gccccgacac 2520
ccgccaacac ccgctgacgc gccctgacgg gcttgtctgc tcccggcatc cgcttacaga 2580
caagctgtga ccgtctccgg gagctgcatg tgtcagaggt tttcaccgtc atcaccgaaa 2640
cgcgcgaggc agcagatcaa ttcgcgcgcg aaggcgaagc ggcatgcatt tacgttgaca 2700
ccatcgaatg gtgcaaaacc tttcgcggta tggcatgata gcgcccggaa gagagtcaat 2760
tcagggtggt gaatgtgaaa ccagtaacgt tatacgatgt cgcagagtat gccggtgtct 2820
cttatcagac cgtttcccgc gtggtgaacc aggccagcca cgtttctgcg aaaacgcggg 2880
aaaaagtgga agcggcgatg gcggagctga attacattcc caaccgcgtg gcacaacaac 2940
tggcgggcaa acagtcgttg ctgattggcg ttgccacctc cagtctggcc ctgcacgcgc 3000
cgtcgcaaat tgtcgcggcg attaaatctc gcgccgatca actgggtgcc agcgtggtgg 3060
tgtcgatggt agaacgaagc ggcgtcgaag cctgtaaagc ggcggtgcac aatcttctcg 3120
cgcaacgcgt cagtgggctg atcattaact atccgctgga tgaccaggat gccattgctg 3180
tggaagctgc ctgcactaat gttccggcgt tatttcttga tgtctctgac cagacaccca 3240
tcaacagtat tattttctcc catgaagacg gtacgcgact gggcgtggag catctggtcg 3300
cattgggtca ccagcaaatc gcgctgttag cgggcccatt aagttctgtc tcggcgcgtc 3360
tgcgtctggc tggctggcat aaatatctca ctcgcaatca aattcagccg atagcggaac 3420
gggaaggcga ctggagtgcc atgtccggtt ttcaacaaac catgcaaatg ctgaatgagg 3480
gcatcgttcc cactgcgatg ctggttgcca acgatcagat ggcgctgggc gcaatgcgcg 3540
ccattaccga gtccgggctg cgcgttggtg cggatatctc ggtagtggga tacgacgata 3600

-continued

```
ccgaagacag ctcatgttat atcccgccgt caaccaccat caaacaggat tttcgcctgc   3660
tggggcaaac cagcgtggac cgcttgctgc aactctctca gggccaggcg gtgaagggca   3720
atcagctgtt gcccgtctca ctggtgaaaa gaaaaaccac cctggcgccc aatacgcaaa   3780
ccgcctctcc ccgcgcgttg gccgattcat taatgcagct ggcacgacag gtttcccgac   3840
tggaaagcgg gcagtgagcg caacgcaatt aatgtgagtt agcgcgaatt gatctggttt   3900
gacagcttat catcgactgc acggtgcacc aatgcttctg gcgtcaggca gccatcggaa   3960
gctgtggtat ggctgtgcag gtcgtaaatc actgcataat tcgtgtcgct caaggcgcac   4020
tcccgttctg gataatgttt tttgcgccga catcataacg gttctggcaa atattctgaa   4080
atgagctgtt gacaattaat catccggctc gtataatgtg tggaattgtg agcggataac   4140
aatttcacac aggaaacagc gccgctgaga aaaagcgaag cggcactgct ctttaacaat   4200
ttatcagaca atctgtgtgg gcactcgacc ggaattatcg attaacttta ttattaaaaa   4260
ttaaagaggt atatattaat gtatcgatta aataaggagg aataaaccat gtgtgcgacc   4320
tcttctcaat ttactcagat taccgagcat aattcccgtc gttccgcaaa ctatcagcca   4380
aacctgtgga atttcgaatt cctgcaatcc ctggagaacg acctgaaagt ggaaaagctg   4440
gaggagaaag cgaccaaact ggaggaagaa gttcgctgca tgatcaaccg tgtagacacc   4500
cagccgctgt ccctgctgga gctgatcgac gatgtgcagc gcctgggtct gacctacaaa   4560
tttgaaaaag acatcattaa agccctggaa aacatcgtac tgctggacga aaacaaaaag   4620
aacaaatctg acctgcacgc aaccgctctg tctttccgtc tgctgcgtca gcacggtttc   4680
gaggtttctc aggatgtttt tgagcgtttc aaggataaag aaggtggttt cagcggtgaa   4740
ctgaaaggtg acgtccaagg cctgctgagc ctgtatgaag cgtcttacct gggtttcgag   4800
ggtgagaacc tgctggagga ggcgcgtacc ttttccatca cccacctgaa gaacaacctg   4860
aaagaaggca ttaataccaa ggttgcagaa caagtgagcc acgccctgga actgccatat   4920
caccagcgtc tgcaccgtct ggaggcacgt tggttcctgg ataaatacga accgaaagaa   4980
ccgcatcacc agctgctgct ggagctggcg aagctggatt ttaacatggt acagaccctg   5040
caccagaaag agctgcaaga tctgtcccgc tggtggaccg agatgggcct ggctagcaaa   5100
ctggattttg tacgcgaccg cctgatggaa gtttatttct gggcactggg tatggcgcca   5160
gacccgcagt ttggtgaatg tcgcaaagct gttactaaaa tgtttggtct ggtgacgatc   5220
atcgatgacg tgtatgacgt ttatggcact ctggacgaac tgcaactgtt caccgatgct   5280
gtagagcgct gggacgttaa cgctattaac accctgccgg actatatgaa actgtgtttc   5340
ctggcactgt acaacaccgt taacgacacg tcctattcta ttctgaaaga gaaaggtcat   5400
aacaacctgt cctatctgac gaaaagctgg cgtgaactgt gcaaagcctt tctgcaagag   5460
gcgaaatggt ccaacaacaa aattatcccg gctttctcca agtacctgga aaacgccagc   5520
gtttcctcct ccggtgtagc gctgctggcg ccgtcttact tttccgtatg ccagcagcag   5580
gaagacatct ccgaccacgc gctgcgttcc ctgaccgact tccatggtct ggtgcgttct   5640
agctgcgtta tcttccgcct gtgcaacgat ctggccacct ctgcggcgga gctggaacgt   5700
ggcgagacta ccaattctat cattagctac atgcacgaaa acgatggtac cagcgaggaa   5760
caggcccgcg aagaactgcg taaactgatc gacgccgaat ggaaaaagat gaatcgtgaa   5820
cgcgttagcg actccaccct gctgcctaaa gcgttcatgg aaatcgcagt taacatggca   5880
cgtgtttccc actgcaccta ccagtatggc gatggtctgg gtcgcccaga ctacgcgact   5940
gaaaaccgca tcaaactgct gctgattgac cctttcccga ttaaccagct gatgtatgtc   6000
```

-continued

```
taactgcatc gcccttagga ggtaaaaaaa aatgactgcc gacaacaata gtatgcccca   6060
tggtgcagta tctagttacg ccaaattagt gcaaaaccaa acacctgaag acattttgga   6120
agagtttcct gaaattattc cattacaaca aagacctaat acccgatcta gtgagacgtc   6180
aaatgacgaa agcggagaaa catgtttttc tggtcatgat gaggagcaaa ttaagttaat   6240
gaatgaaaat tgtattgttt tggattggga cgataatgct attggtgccg gtaccaagaa   6300
agtttgtcat ttaatggaaa atattgaaaa gggtttacta catcgtgcat tctccgtctt   6360
tattttcaat gaacaaggtg aattactttt acaacaaaga gccactgaaa aaataacttt   6420
ccctgatctt tggactaaca catgctgctc tcatccacta tgtattgatg acgaattagg   6480
tttgaagggt aagctagacg ataagattaa gggcgctatt actgcggcgg tgagaaaact   6540
agatcatgaa ttaggtattc cagaagatga aactaagaca aggggtaagt ttcacttttt   6600
aaacagaatc cattacatgg caccaagcaa tgaaccatgg ggtgaacatg aaattgatta   6660
catcctattt tataagatca acgctaaaga aaacttgact gtcaacccaa acgtcaatga   6720
agttagagac ttcaaatggg tttcaccaaa tgatttgaaa actatgtttg ctgacccaag   6780
ttacaagttt acgccttggt ttaagattat ttgcgagaat tacttattca actggtggga   6840
gcaattagat gacctttctg aagtggaaaa tgacaggcaa attcatagaa tgctataaca   6900
acgcgtcctg cattcgccct taggaggtaa aaaaacatga gttttgatat tgccaaatac   6960
ccgaccctgg cactggtcga ctccacccag gagttacgac tgttgccgaa agagagttta   7020
ccgaaactct gcgacgaact gcgccgctat ttactcgaca gcgtgagccg ttccagcggg   7080
cacttcgcct ccgggctggg cacggtcgaa ctgaccgtgg cgctgcacta tgtctacaac   7140
accccgtttg accaattgat ttgggatgtg gggcatcagg cttatccgca taaaattttg   7200
accggacgcc gcgacaaaat cggcaccatc cgtcagaaag gcggtctgca cccgttcccg   7260
tggcgcggcg aaagcgaata tgacgtatta agcgtcgggc attcatcaac ctccatcagt   7320
gccggaattg gtattgcggt tgctgccgaa aaagaaggca aaaatcgccg caccgtctgt   7380
gtcattggcg atggcgcgat taccgcaggc atggcgtttg aagcgatgaa tcacgcgggc   7440
gatatccgtc ctgatatgct ggtgattctc aacgacaatg aaatgtcgat ttccgaaaat   7500
gtcggcgcgc tcaacaacca tctggcacag ctgctttccg gtaagcttta ctcttcactg   7560
cgcgaaggcg ggaaaaaagt tttctctggc gtgccgccaa ttaaagagct gctcaaacgc   7620
accgaagaac atattaaagg catggtagtg cctggcacgt tgtttgaaga gctgggcttt   7680
aactacatcg gcccggtgga cggtcacgat gtgctggggc ttatcaccac gctaaagaac   7740
atgcgcgacc tgaaaggccc gcagttcctg catatcatga ccaaaaaagg tcgtggttat   7800
gaaccggcag aaaaagaccc gatcactttc cacgccgtgc ctaaatttga tccctccagc   7860
ggttgtttgc cgaaaagtag cggcggtttg ccgagctatt caaaaatctt tggcgactgg   7920
ttgtgcgaaa cggcagcgaa agacaacaag ctgatggcga ttactccggc gatgcgtgaa   7980
ggttccggca tggtcgagtt ttcacgtaaa ttcccggatc gctacttcga cgtggcaatt   8040
gccgagcaac acgcggtgac ctttgctgcg ggtctggcga ttggtgggta caaacccatt   8100
gtcgcgattt actccacttt cctgcaacgc gcctatgatc aggtgctgca tgacgtggcg   8160
attcaaaagc ttccggtcct gttcgccatc gaccgcgcgg gcattgttgg tgctgacggt   8220
caaacccatc agggtgcttt tgatctctct tacctgcgct gcataccgga aatggtcatt   8280
atgaccccga gcgatgaaaa cgaatgtcgc cagatgctct ataccggcta tcactataac   8340
```

gatggcccgt cagcggtgcg ctacccgcgt ggcaacgcgg tcggcgtgga actgacgccg 8400
ctggaaaaac taccaattgg caaaggcatt gtgaagcgtc gtggcgagaa actggcgatc 8460
cttaactttg gtacgctgat gccagaagcg gcgaaagtcg ccgaatcgct gaacgccacg 8520
ctggtcgata tgcgttttgt gaaaccgctt gatgaagcgt taattctgga aatggccgcc 8580
agccatgaag cgctggtcac cgtagaagaa aacgccatta tgggcggcgc aggcagcggc 8640
gtgaacgaag tgctgatggc ccatcgtaaa ccagtacccg tgctgaacat tggcctgccg 8700
gacttcttta ttccgcaagg aactcaggaa gaaatgcgcg ccgaactcgg cctcgatgcc 8760
gctggtatgg aagccaaaat caaggcctgg ctggcataac tgca 8804

<210> SEQ ID NO 21
<211> LENGTH: 41
<212> TYPE: DNA
<213> ORGANISM: Artificial Sequence
<220> FEATURE:
<223> OTHER INFORMATION: Synthetic Construct

<400> SEQUENCE: 21
aggaggtaaa aaaacatgtc attaccgttc ttaacttctg c 41

<210> SEQ ID NO 22
<211> LENGTH: 52
<212> TYPE: DNA
<213> ORGANISM: Artificial Sequence
<220> FEATURE:
<223> OTHER INFORMATION: Synthetic Construct

<400> SEQUENCE: 22
atggctgcag gcctatcgca aattagctta tgaagtccat ggtaaattcg tg 52

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23
gaattcgccc ttctgcagct acc 23

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct

<400> SEQUENCE: 24
cgactggtgc acccttaagg aggaaaaaaa catgtcag 38

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
gtgctggaat tcgcccttct gcagc 25

<210> SEQ ID NO 26
<211> LENGTH: 32

<212> TYPE: DNA
<213> ORGANISM: Artificial Sequence
<220> FEATURE:
<223> OTHER INFORMATION: Synthetic Construct

<400> SEQUENCE: 26
gtagatgcat gcagaattcg cccttaagga gg 32

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ccttctgcag gacgcgttgt tatagc 26

<210> SEQ ID NO 28
<211> LENGTH: 38
<212> TYPE: DNA
<213> ORGANISM: Artificial Sequence
<220> FEATURE:
<223> OTHER INFORMATION: Synthetic Construct

<400> SEQUENCE: 28
catcaatgca tcgcccttag gaggtaaaaa aaaatgac 38

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
gtgtgatgga tatctgcaga attcg 25

<210> SEQ ID NO 30
<211> LENGTH: 36
<212> TYPE: DNA
<213> ORGANISM: Artificial Sequence
<220> FEATURE:
<223> OTHER INFORMATION: Synthetic Construct

<400> SEQUENCE: 30
catcaatgca tcgcccttag gaggtaaaaa aacatg 36

<210> SEQ ID NO 31
<211> LENGTH: 60
<212> TYPE: DNA
<213> ORGANISM: Artificial Sequence
<220> FEATURE:
<223> OTHER INFORMATION: Synthetic Construct

<400> SEQUENCE: 31
gatcatgcat tcgcccttag gaggtaaaaa aacatgtgtg cgacctcttc tcaatttact 60

<210> SEQ ID NO 32
<211> LENGTH: 38
<212> TYPE: DNA
<213> ORGANISM: Artificial Sequence
<220> FEATURE:
<223> OTHER INFORMATION: Synthetic Construct

<400> SEQUENCE: 32

-continued

```
cggtcgacgg atccctgcag ttagacatac atcagctg                           38


<210> SEQ ID NO 33
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33

gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gtttttttgcg ccgacatcat aacggttctg gcaaatattc    180

tgaaatgagc tgttgacaat taatcatccg gctcgtataa tgtgtggaat tgtgagcgga    240

taacaatttc acacaggaaa cagcgccgct gagaaaaagc gaagcggcac tgctctttaa    300

caatttatca gacaatctgt gtgggcactc gaccggaatt atcgattaac tttattatta    360

aaaattaaag aggtatatat taatgtatcg attaaataag gaggaataaa ccatggatcc    420

gagctcggat ccactagtaa cggccgccag tgtgctggaa ttcgccctta ggaggtaaaa    480

aaacatgtca ttaccgttct taacttctgc accgggaaag gttattattt ttggtgaaca    540

ctctgctgtg tacaacaagc ctgccgtcgc tgctagtgtg tctgcgttga gaacctacct    600

gctaataagc gagtcatctg caccagatac tattgaattg gacttcccgg acattagctt    660

taatcataag tggtccatca atgatttcaa tgccatcacc gaggatcaag taaactccca    720

aaaattggcc aaggctcaac aagccaccga tggcttgtct caggaactcg ttagtctttt    780

ggatccgttg ttagctcaac tatccgaatc cttccactac catgcagcgt tttgtttcct    840

gtatatgttt gtttgcctat gcccccatgc caagaatatt aagttttctt taaagtctac    900

tttacccatc ggtgctgggt tgggctcaag cgcctctatt tctgtatcac tggccttagc    960

tatggcctac ttgggggggt taataggatc taatgacttg gaaaagctgt cagaaaacga   1020

taagcatata gtgaatcaat gggccttcat aggtgaaaag tgtattcacg gtaccccttc   1080

aggaatagat aacgctgtgg ccacttatgg taatgccctg ctatttgaaa aagactcaca   1140

taatggaaca ataaacacaa acaattttaa gttcttagat gatttcccag ccattccaat   1200

gatcctaacc tatactagaa ttccaaggtc tacaaaagat cttgttgctc gcgttcgtgt   1260

gttggtcacc gagaaatttc ctgaagttat gaagccaatt ctagatgcca tgggtgaatg   1320

tgccctacaa ggcttagaga tcatgactaa gttaagtaaa tgtaaaggca ccgatgacga   1380

ggctgtagaa actaataatg aactgtatga acaactattg gaattgataa gaataaatca   1440

tggactgctt gtctcaatcg gtgtttctca tcctggatta gaacttatta aaaatctgag   1500

cgatgatttg agaattggct ccacaaaact taccggtgct ggtggcggcg gttgctcttt   1560

gactttgtta cgaagagaca ttactcaaga gcaaattgac agcttcaaaa agaaattgca   1620

agatgatttt agttacgaga catttgaaac agacttgggt gggactggct gctgtttgtt   1680

aagcgcaaaa aatttgaata aagatcttaa aatcaaatcc ctagtattcc aattatttga   1740

aaataaaact accacaaagc aacaaattga cgatctatta ttgccaggaa acacgaattt   1800

accatggact tcataagcta atttgcgata ggcctgcacc cttaaggagg aaaaaaacat   1860

gtcagagttg agagccttca gtgccccagg gaaagcgtta ctagctggtg gatatttagt   1920

tttagataca aaatatgaag catttgtagt cggattatcg gcaagaatgc atgctgtagc   1980

ccatccttac ggttcattgc aagggtctga taagtttgaa gtgcgtgtga aaagtaaaca   2040
```

atttaaagat ggggagtggc tgtaccatat aagtcctaaa agtggcttca ttcctgtttc 2100
gataggcgga tctaagaacc ctttcattga aaaagttatc gctaacgtat ttagctactt 2160
taaacctaac atggacgact actgcaatag aaacttgttc gttattgata ttttctctga 2220
tgatgcctac cattctcagg aggatagcgt taccgaacat cgtggcaaca gaagattgag 2280
ttttcattcg cacagaattg aagaagttcc caaaacaggg ctgggctcct cggcaggttt 2340
agtcacagtt ttaactacag ctttggcctc ctttttttgta tcggacctgg aaaataatgt 2400
agacaaatat agagaagtta ttcataattt agcacaagtt gctcattgtc aagctcaggg 2460
taaaattgga agcgggtttg atgtagcggc ggcagcatat ggatctatca gatatagaag 2520
attcccaccc gcattaatct ctaatttgcc agatattgga agtgctactt acggcagtaa 2580
actggcgcat ttggttgatg aagaagactg gaatattacg attaaaagta accatttacc 2640
ttcgggatta actttatgga tgggcgatat taagaatggt tcagaaacag taaaactggt 2700
ccagaaggta aaaaattggt atgattcgca tatgccagaa agcttgaaaa tatatacaga 2760
actcgatcat gcaaattcta gatttatgga tggactatct aaactagatc gcttacacga 2820
gactcatgac gattacagcg atcagatatt tgagtctctt gagaggaatg actgtacctg 2880
tcaaaagtat cctgaaatca cagaagttag agatgcagtt gccacaatta gacgttcctt 2940
tagaaaaata actaaagaat ctggtgccga tatcgaacct cccgtacaaa ctagcttatt 3000
ggatgattgc cagaccttaa aaggagttct tacttgctta atacctggtg ctggtggtta 3060
tgacgccatt gcagtgatta ctaagcaaga tgttgatctt agggctcaaa ccgctaatga 3120
caaaagattt tctaaggttc aatggctgga tgtaactcag gctgactggg gtgttaggaa 3180
agaaaaagat ccggaaactt atcttgataa ataacttaag gtagctgcat gcagaattcg 3240
cccttaagga ggaaaaaaaa atgaccgttt acacagcatc cgttaccgca cccgtcaaca 3300
tcgcaaccct taagtattgg gggaaaaggg acacgaagtt gaatctgccc accaattcgt 3360
ccatatcagt gactttatcg caagatgacc tcagaacgtt gacctctgcg gctactgcac 3420
ctgagtttga acgcgacact ttgtggttaa atggagaacc acacagcatc gacaatgaaa 3480
gaactcaaaa ttgtctgcgc gacctacgcc aattaagaaa ggaaatggaa tcgaaggacg 3540
cctcattgcc cacattatct caatggaaac tccacattgt ctccgaaaat aactttccta 3600
cagcagctgg tttagcttcc tccgctgctg gctttgctgc attggtctct gcaattgcta 3660
agttatacca attaccacag tcaacttcag aaatatctag aatagcaaga aaggggtctg 3720
gttcagcttg tagatcgttg tttggcggat acgtggcctg ggaaatggga aaagctgaag 3780
atggtcatga ttccatggca gtacaaatcg cagacagctc tgactggcct cagatgaaag 3840
cttgtgtcct agttgtcagc gatattaaaa aggatgtgag ttccactcag ggtatgcaat 3900
tgaccgtggc aacctccgaa ctatttaaag aaagaattga acatgtcgta ccaaagagat 3960
ttgaagtcat gcgtaaagcc attgttgaaa aagatttcgc cacctttgca aaggaaacaa 4020
tgatggattc caactctttc catgccacat gtttggactc tttccctcca atattctaca 4080
tgaatgacac ttccaagcgt atcatcagtt ggtgccacac cattaatcag ttttacggag 4140
aaacaatcgt tgcatacacg tttgatgcag gtccaaatgc tgtgttgtac tacttagctg 4200
aaaatgagtc gaaactcttt gcatttatct ataaattgtt tggctctgtt cctggatggg 4260
acaagaaatt tactactgag cagcttgagg ctttcaacca tcaatttgaa tcatctaact 4320
ttactgcacg tgaattggat cttgagttgc aaaaggatgt tgccagagtg attttaactc 4380

-continued

```
aagtcggttc aggcccacaa gaaacaaacg aatctttgat tgacgcaaag actggtctac   4440
caaaggaata agatcaattc gctgcatcgc ccttaggagg taaaaaaaaa tgactgccga   4500
caacaatagt atgccccatg gtgcagtatc tagttacgcc aaattagtgc aaaaccaaac   4560
acctgaagac attttggaag agtttcctga aattattcca ttacaacaaa gacctaatac   4620
ccgatctagt gagacgtcaa atgacgaaag cggagaaaca tgtttttctg gtcatgatga   4680
ggagcaaatt aagttaatga atgaaaattg tattgttttg gattgggacg ataatgctat   4740
tggtgccggt accaagaaag tttgtcattt aatggaaaat attgaaaagg gtttactaca   4800
tcgtgcattc tccgtcttta ttttcaatga acaaggtgaa ttacttttac aacaaagagc   4860
cactgaaaaa ataactttcc ctgatctttg gactaacaca tgctgctctc atccactatg   4920
tattgatgac gaattaggtt tgaagggtaa gctagacgat aagattaagg gcgctattac   4980
tgcggcggtg agaaaactag atcatgaatt aggtattcca gaagatgaaa ctaagacaag   5040
gggtaagttt cactttttaa acagaatcca ttacatggca ccaagcaatg aaccatgggg   5100
tgaacatgaa attgattaca tcctatttta taagatcaac gctaaagaaa acttgactgt   5160
caacccaaac gtcaatgaag ttagagactt caaatgggtt tcaccaaatg atttgaaaac   5220
tatgtttgct gacccaagtt acaagtttac gccttggttt aagattattt gcgagaatta   5280
cttattcaac tggtgggagc aattagatga cctttctgaa gtggaaaatg acaggcaaat   5340
tcatagaatg ctataacaac gcgtcctgca ttcgccctta ggaggtaaaa aaacatgtgt   5400
gcgacctctt ctcaatttac tcagattacc gagcataatt cccgtcgttc cgcaaactat   5460
cagccaaacc tgtggaattt cgaattcctg caatccctgg agaacgacct gaaagtggaa   5520
aagctggagg agaaagcgac caaactggag gaagaagttc gctgcatgat caaccgtgta   5580
gacacccagc cgctgtccct gctggagctg atcgacgatg tgcagcgcct gggtctgacc   5640
tacaaatttg aaaaagacat cattaaagcc ctggaaaaca tcgtactgct ggacgaaaac   5700
aaaaagaaca aatctgacct gcacgcaacc gctctgtctt tccgtctgct gcgtcagcac   5760
ggtttcgagg tttctcagga tgtttttgag cgtttcaagg ataaagaagg tggtttcagc   5820
ggtgaactga aaggtgacgt ccaaggcctg ctgagcctgt atgaagcgtc ttacctgggt   5880
ttcgagggtg agaacctgct ggaggaggcg cgtacctttt ccatcaccca cctgaagaac   5940
aacctgaaag aaggcattaa taccaaggtt gcagaacaag tgagccacgc cctggaactg   6000
ccatatcacc agcgtctgca ccgtctggag gcacgttggt tcctggataa atacgaaccg   6060
aaagaaccgc atcaccagct gctgctggag ctggcgaagc tggattttaa catggtacag   6120
accctgcacc agaaagagct gcaagatctg tcccgctggt ggaccgagat gggcctggct   6180
agcaaactgg attttgtacg cgaccgcctg atggaagttt atttctgggc actgggtatg   6240
gcgccagacc cgcagtttgg tgaatgtcgc aaagctgtta ctaaaatgtt tggtctggtg   6300
acgatcatcg atgacgtgta tgacgtttat ggcactctgg acgaactgca actgttcacc   6360
gatgctgtag agcgctggga cgttaacgct attaacaccc tgccggacta tatgaaactg   6420
tgtttcctgg cactgtacaa caccgttaac gacacgtcct attctattct gaaagagaaa   6480
ggtcataaca acctgtccta tctgacgaaa agctggcgtg aactgtgcaa agcctttctg   6540
caagaggcga aatggtccaa caacaaaatt atcccggctt tctccaagta cctggaaaac   6600
gccagcgttt cctcctccgg tgtagcgctg ctggcgccgt cttacttttc cgtatgccag   6660
cagcaggaag acatctccga ccacgcgctg cgttccctga ccgacttcca tggtctggtg   6720
cgttctagct gcgttatctt ccgcctgtgc aacgatctgg ccacctctgc ggcggagctg   6780
```

-continued

```
gaacgtggcg agactaccaa ttctatcatt agctacatgc acgaaaacga tggtaccagc   6840
gaggaacagg cccgcgaaga actgcgtaaa ctgatcgacg ccgaatggaa aaagatgaat   6900
cgtgaacgcg ttagcgactc caccctgctg cctaaagcgt tcatggaaat cgcagttaac   6960
atggcacgtg tttcccactg cacctaccag tatggcgatg gtctgggtcg cccagactac   7020
gcgactgaaa accgcatcaa actgctgctg attgaccctt tcccgattaa ccagctgatg   7080
tatgtctaac tgcagctggt accatatggg aattcgaagc tttctagaac aaaaactcat   7140
ctcagaagag gatctgaata gcgccgtcga ccatcatcat catcatcatt gagtttaaac   7200
ggtctccagc ttggctgttt tggcggatga gagaagattt tcagcctgat acagattaaa   7260
tcagaacgca gaagcggtct gataaaacag aatttgcctg gcggcagtag cgcggtggtc   7320
ccacctgacc ccatgccgaa ctcagaagtg aaacgccgta gcgccgatgg tagtgtgggg   7380
tctccccatg cgagagtagg gaactgccag gcatcaaata aaacgaaagg ctcagtcgaa   7440
agactgggcc tttcgtttta tctgttgttt gtcggtgaac gctctcctga gtaggacaaa   7500
tccgccggga gcggatttga acgttgcgaa gcaacggccc ggagggtggc gggcaggacg   7560
cccgccataa actgccaggc atcaaattaa gcagaaggcc atcctgacgg atggcctttt   7620
tgcgtttcta caaactcttt ttgtttattt ttctaaatac attcaaatat gtatccgctt   7680
aaccggaatt gccagctggg gcgccctctg gtaaggttgg gaagccctgc aaagtaaact   7740
ggatggcttt ctcgccgcca aggatctgat ggcgcagggg atcaagctct gatcaagaga   7800
caggatgagg atcgtttcgc atgattgaac aagatggatt gcacgcaggt tctccggccg   7860
cttgggtgga gaggctattc ggctatgact gggcacaaca gacaatcggc tgctctgatg   7920
ccgccgtgtt ccggctgtca gcgcaggggc gcccggttct ttttgtcaag accgacctgt   7980
ccggtgccct gaatgaactg caagacgagg cagcgcggct atcgtggctg gccacgacgg   8040
gcgttccttg cgcagctgtg ctcgacgttg tcactgaagc gggaagggac tggctgctat   8100
tgggcgaagt gccggggcag gatctcctgt catctcacct tgctcctgcc gagaaagtat   8160
ccatcatggc tgatgcaatg cggcggctgc atacgcttga tccggctacc tgcccattcg   8220
accaccaagc gaaacatcgc atcgagcgag cacgtactcg gatggaagcc ggtcttgtcg   8280
atcaggatga tctggacgaa gagcatcagg ggctcgcgcc agccgaactg ttcgccaggc   8340
tcaaggcgag catgcccgac ggcgaggatc tcgtcgtgac ccatggcgat gcctgcttgc   8400
cgaatatcat ggtggaaaat ggccgctttt ctggattcat cgactgtggc cggctgggtg   8460
tggcggaccg ctatcaggac atagcgttgg ctacccgtga tattgctgaa gagcttggcg   8520
gcgaatgggc tgaccgcttc ctcgtgcttt acggtatcgc cgctcccgat tcgcagcgca   8580
tcgccttcta tcgccttctt gacgagttct tctgacgcat gaccaaaatc ccttaacgtg   8640
agttttcgtt ccactgagcg tcagaccccg tagaaaagat caaaggatct tcttgagatc   8700
cttttttttct gcgcgtaatc tgctgcttgc aaacaaaaaa accaccgcta ccagcggtgg   8760
tttgtttgcc ggatcaagag ctaccaactc tttttccgaa ggtaactggc ttcagcagag   8820
cgcagatacc aaatactgtc cttctagtgt agccgtagtt aggccaccac ttcaagaact   8880
ctgtagcacc gcctacatac ctcgctctgc taatcctgtt accagtggct gctgccagtg   8940
gcgataagtc gtgtcttacc gggttggact caagacgata gttaccggat aaggcgcagc   9000
ggtcgggctg aacggggggt tcgtgcacac agcccagctt ggagcgaacg acctacaccg   9060
aactgagata cctacagcgt gagctatgag aaagcgccac gcttcccgaa gggagaaagg   9120
```

-continued cggacaggta tccggtaagc ggcagggtcg gaacaggaga gcgcacgagg gagcttccag 9180
ggggaaacgc ctggtatctt tatagtcctg tcgggtttcg ccacctctga cttgagcgtc 9240
gatttttgtg atgctcgtca ggggggcgga gcctatggaa aaacgccagc aacgcggcct 9300
ttttacggtt cctggccttt tgctggcctt ttgctcacat gttctttcct gcgttatccc 9360
ctgattctgt ggataaccgt attaccgcct ttgagtgagc tgataccgct cgccgcagcc 9420
gaacgaccga gcgcagcgag tcagtgagcg aggaagcgga agagcgcctg atgcggtatt 9480
ttctccttac gcatctgtgc ggtatttcac accgcatatg gtgcactctc agtacaatct 9540
gctctgatgc cgcatagtta agccagtata cactccgcta tcgctacgtg actgggtcat 9600
ggctgcgccc cgacacccgc caacacccgc tgacgcgccc tgacgggctt gtctgctccc 9660
ggcatccgct tacagacaag ctgtgaccgt ctccgggagc tgcatgtgtc agaggttttc 9720
accgtcatca ccgaaacgcg cgaggcagca gatcaattcg cgcgcgaagg cgaagcggca 9780
tgcatttacg ttgacaccat cgaatggtgc aaaacctttc gcggtatggc atgatagcgc 9840
ccggaagaga gtcaattcag ggtggtgaat gtgaaaccag taacgttata cgatgtcgca 9900
gagtatgccg gtgtctctta tcagaccgtt tcccgcgtgg tgaaccaggc cagccacgtt 9960
tctgcgaaaa cgcgggaaaa agtggaagcg gcgatggcgg agctgaatta cattcccaac 10020
cgcgtggcac aacaactggc gggcaaacag tcgttgctga ttggcgttgc cacctccagt 10080
ctggccctgc acgcgccgtc gcaaattgtc gcggcgatta aatctcgcgc cgatcaactg 10140
ggtgccagcg tggtggtgtc gatggtagaa cgaagcggcg tcgaagcctg taaagcggcg 10200
gtgcacaatc ttctcgcgca acgcgtcagt gggctgatca ttaactatcc gctggatgac 10260
caggatgcca ttgctgtgga agctgcctgc actaatgttc cggcgttatt tcttgatgtc 10320
tctgaccaga cacccatcaa cagtattatt ttctcccatg aagacggtac gcgactgggc 10380
gtggagcatc tggtcgcatt gggtcaccag caaatcgcgc tgttagcggg cccattaagt 10440
tctgtctcgg cgcgtctgcg tctggctggc tggcataaat atctcactcg caatcaaatt 10500
cagccgatag cggaacggga aggcgactgg agtgccatgt ccggttttca acaaaccatg 10560
caaatgctga atgagggcat cgttcccact gcgatgctgg ttgccaacga tcagatggcg 10620
ctgggcgcaa tgcgcgccat taccgagtcc gggctgcgcg ttggtgcgga tatctcggta 10680
gtgggatacg acgataccga agacagctca tgttatatcc cgccgtcaac caccatcaaa 10740
caggattttc gcctgctggg gcaaaccagc gtggaccgct tgctgcaact ctctcagggc 10800
caggcggtga agggcaatca gctgttgccc gtctcactgg tgaaaagaaa aaccaccctg 10860
gcgcccaata cgcaaaccgc ctctccccgc gcgttggccg attcattaat gcagctggca 10920
cgacaggttt cccgactgga aagcgggcag tgagcgcaac gcaattaatg tgagttagcg 10980
cgaattgatc tg 10992

<210> SEQ ID NO 34
<211> LENGTH: 49
<212> TYPE: DNA
<213> ORGANISM: Artificial Sequence
<220> FEATURE:
<223> OTHER INFORMATION: Synthetic Construct

<400> SEQUENCE: 34
gagacatgag ctcaggaggt aaaaaaacat gaaaacagta gttattatt 49

<210> SEQ ID NO 35
<211> LENGTH: 54

<212> TYPE: DNA
<213> ORGANISM: Artificial Sequence
<220> FEATURE:
<223> OTHER INFORMATION: Synthetic Construct

<400> SEQUENCE: 35
tttatcaatc ccaattgtca tgttttttta cctcctttat tgttttctta aatc 54

<210> SEQ ID NO 36
<211> LENGTH: 54
<212> TYPE: DNA
<213> ORGANISM: Artificial Sequence
<220> FEATURE:
<223> OTHER INFORMATION: Synthetic Construct

<400> SEQUENCE: 36
gatttaagaa aacaataaag gaggtaaaaa aacatgacaa ttgggattga taaa 54

<210> SEQ ID NO 37
<211> LENGTH: 40
<212> TYPE: DNA
<213> ORGANISM: Artificial Sequence
<220> FEATURE:
<223> OTHER INFORMATION: Synthetic Construct

<400> SEQUENCE: 37
gacatgacat agatctttag tttcgataag aacgaacggt 40

<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38
atgaaaacag tagttattat tgatgc 26

<210> SEQ ID NO 39
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
atgttattgt tttcttaaat catttaaaat agc 33

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

<400> SEQUENCE: 40
atgacaattg ggattgataa aattag 26

<210> SEQ ID NO 41
<211> LENGTH: 24
<212> TYPE: DNA
<213> ORGANISM: Artificial Sequence
<220> FEATURE:
<223> OTHER INFORMATION: Synthetic Construct

<400> SEQUENCE: 41
ttagtttcga taagaacgaa cggt 24

<210> SEQ ID NO 42
<211> LENGTH: 23
<212> TYPE: DNA
<213> ORGANISM: Artificial Sequence
<220> FEATURE:
<223> OTHER INFORMATION: Synthetic Construct

<400> SEQUENCE: 42
gaaatagccc cattagaagt atc 23

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
ttgccaatca tatgattgaa aatc 24

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
gctatgcttc attagatcct tatcg 25

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45
gaaacctaca tccaatcttt tgccc 25

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46
cccgtcttac tgtcgggaat tcgcgttggc cgattcatta atgcagattc tgaaatgagc 60
tgttgacaat taatcatccg gctcgtataa tgtgtggaat tgtgagcgga taacaatttc 120
acacaggaaa cagcgccgct gagaaaaagc gaagcggcac tgctctttaa caatttatca 180
gacaatctgt gtgggcactc gaccggaatt atcgattaac tttattatta aaaattaaag 240
aggtatatat taatgtatcg attaaataag gaggaataaa ccatggatcc gagctcagga 300
ggtaaaaaaa catgaaaaca gtagttatta ttgatgcatt acgaacacca attggaaaat 360
ataaaggcag cttaagtcaa gtaagtgccg tagacttagg aacacatgtt acaacacaac 420
ttttaaaaag acattccact atttctgaag aaattgatca agtaatcttt ggaaatgttt 480
tacaagctgg aaatggccaa aatcccgcac gacaaatagc aataaacagc ggtttgtctc 540
atgaaattcc cgcaatgacg gttaatgagg tctgcggatc aggaatgaag gccgttattt 600

-continued

```
tggcgaaaca attgattcaa ttaggagaag cggaagtttt aattgctggc gggattgaga    660
atatgtccca agcacctaaa ttacaacgtt ttaattacga aacagaaagc tacgatgcgc    720
ctttttctag tatgatgtat gatggattaa cggatgcctt tagtggtcag gcaatgggct    780
taactgctga aaatgtggcc gaaaagtatc atgtaactag agaagagcaa gatcaatttt    840
ctgtacattc acaattaaaa gcagctcaag cacaagcaga agggatattc gctgacgaaa    900
tagccccatt agaagtatca ggaacgcttg tggagaaaga tgaagggatt cgccctaatt    960
cgagcgttga gaagctagga acgcttaaaa cagtttttaa agaagacggt actgtaacag   1020
cagggaatgc atcaaccatt aatgatgggg cttctgcttt gattattgct tcacaagaat   1080
atgccgaagc acacggtctt ccttatttag ctattattcg agacagtgtg gaagtcggta   1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaaagaa aagaaatatg gagtggcttc tttatgtatc ggcggtggct   1440
taggactcgc tatgctacta gagagacctc agcaaaaaaa aaacagccga ttttatcaaa   1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga aacagaagtg ccgatgggcg ttggcttaca tttaacagtg gacgaaactg   1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800
ttttttacga tgttgcagat cccgagtcat tgattgataa actacaagta agagaagcgg   1860
aagtttttca acaagcagag ttaagttatc catctatcgt taaacggggc ggcggcttaa   1920
gagatttgca atatcgtact tttgatgaat catttgtatc tgtcgacttt ttagtagatg   1980
ttaaggatgc aatgggggca aatatcgtta acgctatgtt ggaaggtgtg gccgagttgt   2040
tccgtgaatg gtttgcggag caaaagattt tattcagtat tttaagtaat tatgccacgg   2100
agtcggttgt tacgatgaaa acggctattc cagtttcacg tttaagtaag gggagcaatg   2160
gccgggaaat tgctgaaaaa attgttttag cttcacgcta tgcttcatta gatccttatc   2220
gggcagtcac gcataacaaa ggaatcatga atggcattga agctgtagtt ttagctacag   2280
gaaatgatac acgcgctgtt agcgcttctt gtcatgcttt tgcggtgaag gaaggtcgct   2340
accaaggctt gactagttgg acgctggatg gcgaacaact aattggtgaa atttcagttc   2400
cgcttgcttt agccacggtt ggcggtgcca caaaagtctt acctaaatct caagcagctg   2460
ctgatttgtt agcagtgacg gatgcaaaag aactaagtcg agtagtagcg gctgttggtt   2520
tggcacaaaa tttagcggcg ttacgggcct tagtctctga aggaattcaa aaaggacaca   2580
tggctctaca agcacgttct ttagcgatga cggtcggagc tactggtaaa gaagttgagg   2640
cagtcgctca acaattaaaa cgtcaaaaaa cgatgaacca agaccgagcc atggctattt   2700
taaatgattt aagaaaacaa taaaggaggt aaaaaaacat gacaattggg attgataaaa   2760
ttagtttttt tgtgccccct tattatattg atatgacggc actggctgaa gccagaaatg   2820
tagaccctgg aaaatttcat attggtattg ggcaagacca aatggcggtg aacccaatca   2880
gccaagatat tgtgacattt gcagccaatg ccgcagaagc gatcttgacc aaagaagata   2940
```

-continued

```
aagaggccat tgatatggtg attgtcggga ctgagtccag tatcgatgag tcaaaagcgg   3000
ccgcagttgt cttacatcgt ttaatgggga ttcaaccttt cgctcgctct ttcgaaatca   3060
aggaagcttg ttacggagca acagcaggct tacagttagc taagaatcac gtagccttac   3120
atccagataa aaaagtcttg gtcgtagcgg cagatattgc aaaatatggc ttaaattctg   3180
gcggtgagcc tacacaagga gctggggcgg ttgcaatgtt agttgctagt gaaccgcgca   3240
ttttggcttt aaaagaggat aatgtgatgc tgacgcaaga tatctatgac ttttggcgtc   3300
caacaggcca cccgtatcct atggtcgatg gtcctttgtc aaacgaaacc tacatccaat   3360
cttttgccca agtctgggat gaacataaaa aacgaaccgg tcttgatttt gcagattatg   3420
atgctttagc gttccatatt ccttacacaa aaatgggcaa aaaagcctta ttagcaaaaa   3480
tctccgacca aactgaagca gaacaggaac gaattttagc ccgttatgaa gaaagtatcg   3540
tctatagtcg tcgcgtagga aacttgtata cgggttcact ttatctggga ctcatttccc   3600
ttttagaaaa tgcaacgact ttaaccgcag gcaatcaaat tggtttattc agttatggtt   3660
ctggtgctgt cgctgaattt ttcactggtg aattagtagc tggttatcaa aatcatttac   3720
aaaaagaaac tcatttagca ctgctggata atcggacaga actttctatc gctgaatatg   3780
aagccatgtt tgcagaaact ttagacacag acattgatca aacgttagaa gatgaattaa   3840
aatatagtat ttctgctatt aataataccg ttcgttctta tcgaaactaa gagatctgca   3900
gctggtacca tatgggaatt cgaagcttgg gcccgaacaa aaactcatct cagaagagga   3960
tctgaatagc gccgtcgacc atcatcatca tcatcattga gtttaaacgg tctccagctt   4020
ggctgttttg gcggatgaga gaagattttc agcctgatac agattaaatc agaacgcaga   4080
agcggtctga taaaacagaa tttgcctggc ggcagtagcg cggtggtccc acctgacccc   4140
atgccgaact cagaagtgaa acgccgtagc gccgatggta gtgtggggtc tccccatgcg   4200
agagtaggga actgccaggc atcaaataaa acgaaaggct cagtcgaaag actgggcctt   4260
tcgttttatc tgttgtttgt cggtgaacgc tctcctgagt aggacaaatc cgccgggagc   4320
ggatttgaac gttgcgaagc aacggcccgg agggtggcgg gcaggacgcc cgccataaac   4380
tgccaggcat caaattaagc agaaggccat cctgacggat ggcctttttg cgtttctaca   4440
aactcttttt gtttattttt ctaaatacat tcaaatatgt atccgctcat gagacaataa   4500
ccctgataaa tgcttcaata atctggcgta atagcgaaga ggcccgcacc gatcgccctt   4560
cccaacagtt gcgcagcctg aatggcgaat ggcgcctgat gcggtatttt ctccttacgc   4620
atctgtgcgg tatttcacac cgcatatggt gcactctcag tacaatctgc tctgatgccg   4680
catagttaag ccagccccga cacccgccaa cacccgctga cgagcttagt aaagccctcg   4740
ctagatttta atgcggatgt tgcgattact tcgccaacta ttgcgataac aagaaaaagc   4800
cagcctttca tgatatatct cccaatttgt gtagggctta ttatgcacgc ttaaaaataa   4860
taaaagcaga cttgacctga tagtttggct gtgagcaatt atgtgcttag tgcatctaac   4920
gcttgagtta agccgcgccg cgaagcggcg tcggcttgaa cgaattgtta gacattattt   4980
gccgactacc ttggtgatct cgcctttcac gtagtggaca aattcttcca actgatctgc   5040
gcgcgaggcc aagcgatctt cttcttgtcc aagataagcc tgtctagctt caagtatgac   5100
gggctgatac tgggccggca ggcgctccat tgcccagtcg gcagcgacat ccttcggcgc   5160
gattttgccg gttactgcgc tgtaccaaat gcgggacaac gtaagcacta catttcgctc   5220
atcgccagcc cagtcgggcg gcgagttcca tagcgttaag gtttcattta gcgcctcaaa   5280
tagatcctgt tcaggaaccg gatcaaagag ttcctccgcc gctggaccta ccaaggcaac   5340
```

-continued

```
gctatgttct cttgcttttg tcagcaagat agccagatca atgtcgatcg tggctggctc   5400
gaagatacct gcaagaatgt cattgcgctg ccattctcca aattgcagtt cgcgcttagc   5460
tggataacgc cacggaatga tgtcgtcgtg cacaacaatg gtgacttcta cagcgcggag   5520
aatctcgctc tctccagggg aagccgaagt ttccaaaagg tcgttgatca aagctcgccg   5580
cgttgtttca tcaagcctta cggtcaccgt aaccagcaaa tcaatatcac tgtgtggctt   5640
caggccgcca tccactgcgg agccgtacaa atgtacggcc agcaacgtcg gttcgagatg   5700
gcgctcgatg acgccaacta cctctgatag ttgagtcgat acttcggcga tcaccgcttc   5760
cctcatgatg tttaactttg ttttagggcg actgccctgc tgcgtaacat cgttgctgct   5820
ccataacatc aaacatcgac ccacggcgta acgcgcttgc tgcttggatg cccgaggcat   5880
agactgtacc ccaaaaaaac agtcataaca agccatgaaa accgccactg cgccgttacc   5940
accgctgcgt tcggtcaagg ttctggacca gttgcgtgag cgcatacgct acttgcatta   6000
cagcttacga accgaacagg cttatgtcca ctgggttcgt gccttcatcc gtttccacgg   6060
tgtgcgtcac ccggcaacct tgggcagcag cgaagtcgag gcatttctgt cctggctggc   6120
gaacgagcgc aaggtttcgg tctccacgca tcgtcaggca ttggcggcct tgctgttctt   6180
ctacggcaag gtgctgtgca cggatctgcc ctggcttcag gagatcggaa gacctcggcc   6240
gtcgcggcgc ttgccggtgg tgctgacccc ggatgaagtg gttcgcatcc tcggttttct   6300
ggaaggcgag catcgtttgt tcgcccagct tctgtatgga acgggcatgc ggatcagtga   6360
gggtttgcaa ctgcgggtca aggatctgga tttcgatcac ggcacgatca tcgtgcggga   6420
gggcaagggc tccaaggatc gggccttgat gttacccgag agcttggcac ccagcctgcg   6480
cgagcagggg aattaattcc cacgggtttt gctgcccgca aacgggctgt tctggtgttg   6540
ctagtttgtt atcagaatcg cagatccggc ttcagccggt ttgccggctg aaagcgctat   6600
ttcttccaga attgccatga tttttcccc acgggaggcg tcactggctc ccgtgttgtc   6660
ggcagctttg attcgataag cagcatcgcc tgtttcaggc tgtctatgtg tgactgttga   6720
gctgtaacaa gttgtctcag gtgttcaatt tcatgttcta gttgctttgt tttactggtt   6780
tcacctgttc tattaggtgt tacatgctgt tcatctgtta cattgtcgat ctgttcatgg   6840
tgaacagctt tgaatgcacc aaaaactcgt aaaagctctg atgtatctat cttttttaca   6900
ccgttttcat ctgtgcatat ggacagtttt ccctttgata tgtaacggtg aacagttgtt   6960
ctacttttgt ttgttagtct tgatgcttca ctgatagata caagagccat aagaacctca   7020
gatccttccg tatttagcca gtatgttctc tagtgtggtt cgttgttttt gcgtgagcca   7080
tgagaacgaa ccattgagat catacttact ttgcatgtca ctcaaaaatt ttgcctcaaa   7140
actggtgagc tgaatttttg cagttaaagc atcgtgtagt gtttttctta gtccgttatg   7200
taggtaggaa tctgatgtaa tggttgttgg tattttgtca ccattcattt ttatctggtt   7260
gttctcaagt tcggttacga gatccatttg tctatctagt tcaacttgga aaatcaacgt   7320
atcagtcggg cggcctcgct tatcaaccac caatttcata ttgctgtaag tgtttaaatc   7380
tttacttatt ggtttcaaaa cccattggtt aagcctttta aactcatggt agttattttc   7440
aagcattaac atgaacttaa attcatcaag gctaatctct atatttgcct tgtgagtttt   7500
cttttgtgtt agttctttta ataaccactc ataaatcctc atagagtatt tgttttcaaa   7560
agacttaaca tgttccagat tatattttat gaattttttt aactggaaaa gataaggcaa   7620
tatctcttca ctaaaaacta attctaattt ttcgcttgag aacttggcat agtttgtcca   7680
```

-continued

```
ctggaaaatc tcaaagcctt taaccaaagg attcctgatt tccacagttc tcgtcatcag   7740

ctctctggtt gctttagcta atacaccata agcattttcc ctactgatgt tcatcatctg   7800

agcgtattgg ttataagtga acgataccgt ccgttctttc cttgtagggt tttcaatcgt   7860

ggggttgagt agtgccacac agcataaaat tagcttggtt tcatgctccg ttaagtcata   7920

gcgactaatc gctagttcat ttgctttgaa aacaactaat tcagacatac atctcaattg   7980

gtctaggtga ttttaatcac tataccaatt gagatgggct agtcaatgat aattactagt   8040

ccttttcctt tgagttgtgg gtatctgtaa attctgctag acctttgctg gaaaacttgt   8100

aaattctgct agaccctctg taaattccgc tagacctttg tgtgtttttt ttgtttatat   8160

tcaagtggtt ataatttata gaataaagaa agaataaaaa aagataaaaa gaatagatcc   8220

cagccctgtg tataactcac tactttagtc agttccgcag tattacaaaa ggatgtcgca   8280

aacgctgttt gctcctctac aaaacagacc ttaaaaccct aaaggcttaa gtagcaccct   8340

cgcaagctcg ggcaaatcgc tgaatattcc ttttgtctcc gaccatcagg cacctgagtc   8400

gctgtctttt tcgtgacatt cagttcgctg cgctcacggc tctggcagtg aatgggggta   8460

aatggcacta caggcgcctt ttatggattc atgcaaggaa actacccata atacaagaaa   8520

agcccgtcac gggcttctca gggcgtttta tggcgggtct gctatgtggt gctatctgac   8580

tttttgctgt tcagcagttc ctgccctctg attttccagt ctgaccactt cggattatcc   8640

cgtgacaggt cattcagact ggctaatgca cccagtaagg cagcggtatc atcaacaggc   8700

tta                                                                 8703
```

```
<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47

tgtaaccttt gctttcaaat gagtagaaat aatgcacatc catgtttgta tcgtgcaaat     60

aaagtgtttc atccgtagga aaaaatgact ttagtatctg ttccgctttt tctgatgaaa    120

tgtgctcccc gacaaaattg aatgaatcat ggacatttgc tggctttgat acagcgaaag    180

cagccgttcc tatgttatat atcggattta acagcaggac aaaaaaacacc atgacagcca    240

tcgtcaccca cttattcaca cgcacataaa cctttcctga cttttggaac agatgatagc    300

tcatcaaaaa tcccgccatt gccaaataaa tcgtatatgg cattactgca ccataatctt    360

ttgagatttg attgggatat ggcgcaagca gcaagacaag cagtccgata atcagcgtat    420

aaaataagcc tagtaagatc ttatccgttc tccaatacag cttgaaaaac actacattca    480

acgcaatggg aagagtgatg atgaaaaaca gaaacacgaa tgcaatcggc tccatcccat    540

ccgggtattc cttccaatac gaaaagaaac taaaaatcat ttgtacgatc ggcaaactga    600

caacagcaag gtcgaacgta taaaacttac cctttccgcc atgatcacgc ggcatcagca    660

tatagtgaaa agccgtcagc agcacatatc cgtataacaa aaaatgcagc agcggcagca    720

gttcttttcc gtcctctctt aagtaagcgc tggtgaagtt tgttgattgc acctggtgaa    780

taagttcaac agacactccc gccagcagca caatccgcaa tataacaccc gccaagaaca    840

ttgtgcgctg ccggtttatt ttgggatgat gcaccaaaag atataagccc gccagaacaa    900

caattgacca ttgaatcagc agggtgcttt gtctgcttaa tataaaataa cgttcgaaat    960

gcaatacata atgactgaat aactccaaca cgaacaacaa ctccattttc ttctgctatc   1020
```

aaaataacag actcgtgatt ttccaaacga gctttcaaaa aagcctctgc cccttgcaaa 1080
tcggatgcct gtctataaaa ttcccgatat tggttaaaca gcggcgcaat ggcggccgca 1140
tctgatgtct ttgcttggcg aatgttcatc ttatttcttc ctccctctca ataatttttt 1200
cattctatcc cttttctgta aagtttattt ttcagaatac ttttatcatc atgctttgaa 1260
aaaatatcac gataaatatcc attgttctca cggaagcaca cgcaggtcat ttgaacgaat 1320
tttttcgaca ggaatttgcc gggactcagg agcatttaac ctaaaaaagc atgacatttc 1380
agcataatga acatttactc atgtctattt tcgttctttt ctgtatgaaa atagttattt 1440
cgagtctcta cggaaatagc gagagatgat atacctaaat agagataaaa tcatctcaaa 1500
aaaatgggtc tactaaaata ttattccatc tattacaata aattcacaga atagtctttt 1560
aagtaagtct actctgaatt tttttaaaag gagagggtaa agagtgtcat taccgttctt 1620
aacttctgca ccgggaaagg ttattatttt tggtgaacac tctgctgtgt acaacaagcc 1680
tgccgtcgct gctagtgtgt ctgcgttgag aacctacctg ctaataagcg agtcatctgc 1740
accagatact attgaattgg acttcccgga cattagcttt aatcataagt ggtccatcaa 1800
tgatttcaat gccatcaccg aggatcaagt aaactcccaa aaattggcca aggctcaaca 1860
agccaccgat ggcttgtctc aggaactcgt tagtcttttg gatccgttgt tagctcaact 1920
atccgaatcc ttccactacc atgcagcgtt ttgtttcctg tatatgtttg tttgcctatg 1980
cccccatgcc aagaatatta agttttcttt aaagtctact ttacccatcg gtgctgggtt 2040
gggctcaagc gcctctattt ctgtatcact ggccttagct atggcctact tggggggtt 2100 aataggatct aatgacttgg aaaagctgtc agaaaacgat aagcatatag tgaatcaatg 2160
ggccttcata ggtgaaaagt gtattcacgg taccccttca ggaatagata acgctgtggc 2220
cacttatggt aatgccctgc tatttgaaaa agactcacat aatggaacaa taaacacaaa 2280
caattttaag ttcttagatg atttcccagc cattccaatg atcctaacct atactagaat 2340
tccaaggtct acaaaagatc ttgttgctcg cgttcgtgtg ttggtcaccg agaaatttcc 2400
tgaagttatg aagccaattc tagatgccat gggtgaatgt gccctacaag gcttagagat 2460
catgactaag ttaagtaaat gtaaaggcac cgatgacgag gctgtagaaa ctaataatga 2520
actgtatgaa caactattgg aattgataag aataaatcat ggactgcttg tctcaatcgg 2580
tgtttctcat cctggattag aacttattaa aaatctgagc gatgatttga gaattggctc 2640
cacaaaactt accggtgctg gtggcggcgg ttgctctttg actttgttac gaagagacat 2700
tactcaagag caaattgaca gcttcaaaaa gaaattgcaa gatgatttta gttacgagac 2760
atttgaaaca gacttgggtg ggactggctg ctgtttgtta agcgcaaaaa atttgaataa 2820
agatcttaaa atcaaatccc tagtattcca attatttgaa aataaaacta ccacaaagca 2880
acaaattgac gatctattat tgccaggaaa cacgaattta ccatggactt cataaaagga 2940
gagggtgtca gagttgagag ccttcagtgc cccagggaaa gcgttactag ctggtggata 3000
tttagtttta gatacaaaat atgaagcatt tgtagtcgga ttatcggcaa gaatgcatgc 3060
tgtagcccat ccttacggtt cattgcaagg gtctgataag tttgaagtgc gtgtgaaaag 3120
taaacaattt aaagatgggg agtggctgta ccatataagt cctaaaagtg gcttcattcc 3180
tgtttcgata ggcggatcta agaacccttt cattgaaaaa gttatcgcta acgtatttag 3240
ctactttaaa cctaacatgg acgactactg caatagaaac ttgttcgtta ttgatatttt 3300
ctctgatgat gcctaccatt ctcaggagga tagcgttacc gaacatcgtg gcaacagaag 3360

-continued

```
attgagtttt cattcgcaca gaattgaaga agttcccaaa acagggctgg gctcctcggc   3420
aggtttagtc acagttttaa ctacagcttt ggcctccttt tttgtatcgg acctggaaaa   3480
taatgtagac aaatatagag aagttattca taatttagca caagttgctc attgtcaagc   3540
tcagggtaaa attggaagcg ggtttgatgt agcggcggca gcatatggat ctatcagata   3600
tagaagattc ccacccgcat taatctctaa tttgccagat attggaagtg ctacttacgg   3660
cagtaaactg gcgcatttgg ttgatgaaga agactggaat attacgatta aaagtaacca   3720
tttaccttcg ggattaactt tatggatggg cgatattaag aatggttcag aaacagtaaa   3780
actggtccag aaggtaaaaa attggtatga ttcgcatatg ccagaaagct tgaaaatata   3840
tacagaactc gatcatgcaa attctagatt tatggatgga ctatctaaac tagatcgctt   3900
acacgagact catgacgatt acagcgatca gatatttgag tctcttgaga ggaatgactg   3960
tacctgtcaa aagtatcctg aaatcacaga agttagagat gcagttgcca caattagacg   4020
ttcctttaga aaaataacta aagaatctgg tgccgatatc gaacctcccg tacaaactag   4080
cttattggat gattgccaga ccttaaaagg agttcttact tgcttaatac ctggtgctgg   4140
tggttatgac gccattgcag tgattactaa gcaagatgtt gatcttaggg ctcaaaccgc   4200
taatgacaaa agattttcta aggttcaatg gctggatgta actcaggctg actggggtgt   4260
taggaaagaa aaagatccgg aaacttatct tgataaataa aaggagaggg tgaccgttta   4320
cacagcatcc gttaccgcac ccgtcaacat cgcaaccctt aagtattggg ggaaaaggga   4380
cacgaagttg aatctgccca ccaattcgtc catatcagtg actttatcgc aagatgacct   4440
cagaacgttg acctctgcgg ctactgcacc tgagtttgaa cgcgacactt tgtggttaaa   4500
tggagaacca cacagcatcg acaatgaaag aactcaaaat tgtctgcgcg acctacgcca   4560
attaagaaag gaaatggaat cgaaggacgc ctcattgccc acattatctc aatggaaact   4620
ccacattgtc tccgaaaata actttcctac agcagctggt ttagcttcct ccgctgctgg   4680
ctttgctgca ttggtctctg caattgctaa gttataccaa ttaccacagt caacttcaga   4740
aatatctaga atagcaagaa aggggtctgg ttcagcttgt agatcgttgt ttggcggata   4800
cgtggcctgg gaaatgggaa aagctgaaga tggtcatgat tccatggcag tacaaatcgc   4860
agacagctct gactggcctc agatgaaagc ttgtgtccta gttgtcagcg atattaaaaa   4920
ggatgtgagt tccactcagg gtatgcaatt gaccgtggca acctccgaac tatttaaaga   4980
aagaattgaa catgtcgtac caaagagatt tgaagtcatg cgtaaagcca ttgttgaaaa   5040
agatttcgcc acctttgcaa aggaaacaat gatggattcc aactctttcc atgccacatg   5100
tttggactct ttccctccaa tattctacat gaatgacact tccaagcgta tcatcagttg   5160
gtgccacacc attaatcagt tttacggaga aacaatcgtt gcatacacgt ttgatgcagg   5220
tccaaatgct gtgttgtact acttagctga aaatgagtcg aaactctttg catttatcta   5280
taaattgttt ggctctgttc ctggatggga caagaaattt actactgagc agcttgaggc   5340
tttcaaccat caatttgaat catctaactt tactgcacgt gaattggatc ttgagttgca   5400
aaaggatgtt gccagagtga ttttaactca agtcggttca ggcccacaag aaacaaacga   5460
atctttgatt gacgcaaaga ctggtctacc aaaggaataa aaggagaggg tgactgccga   5520
caacaatagt atgccccatg gtgcagtatc tagttacgcc aaattagtgc aaaaccaaac   5580
acctgaagac attttggaag agtttcctga aattattcca ttacaacaaa gacctaatac   5640
ccgatctagt gagacgtcaa atgacgaaag cggagaaaca tgtttttctg gtcatgatga   5700
ggagcaaatt aagttaatga atgaaaattg tattgttttg gattgggacg ataatgctat   5760
```

```
tggtgccggt accaagaaag tttgtcattt aatggaaaat attgaaaagg gtttactaca   5820
tcgtgcattc tccgtcttta ttttcaatga acaaggtgaa ttacttttac aacaaagagc   5880
cactgaaaaa ataactttcc ctgatctttg gactaacaca tgctgctctc atccactatg   5940
tattgatgac gaattaggtt tgaagggtaa gctagacgat aagattaagg gcgctattac   6000
tgcggcggtg agaaaactag atcatgaatt aggtattcca gaagatgaaa ctaagacaag   6060
gggtaagttt cactttttaa acagaatcca ttacatggca ccaagcaatg aaccatgggg   6120
tgaacatgaa attgattaca tcctatttta taagatcaac gctaaagaaa acttgactgt   6180
caacccaaac gtcaatgaag ttagagactt caaatgggtt tcaccaaatg atttgaaaac   6240
tatgtttgct gacccaagtt acaagtttac gccttggttt aagattattt gcgagaatta   6300
cttattcaac tggtgggagc aattagatga cctttctgaa gtggaaaatg acaggcaaat   6360
tcatagaatg ctataaaaaa aaccggcctt ggccccgccg gttttttatt atttttcttc   6420
ctccgcatgt tcaatccgct ccataatcga cggatggctc cctctgaaaa ttttaacgag   6480
aaacggcggg ttgacccggc tcagtcccgt aacggccaag tcctgaaacg tctcaatcgc   6540
cgcttcccgg tttccggtca gctcaatgcc gtaacggtcg gcggcgtttt cctgataccg   6600
ggagacggca ttcgtaattt gaatacatac gaacaaatta ataaagtgaa aaaaatactt   6660
cggaaacatt taaaaaataa ccttattggt acttacatgt ttggatcagg agttgagagt   6720
ggactaaaac caaatagtga tcttgacttt ttagtcgtcg tatctgaacc attgacagat   6780
caaagtaaag aaatacttat acaaaaaatt agacctattt caaaaaaaat aggagataaa   6840
agcaacttac gatatattga attaacaatt attattcagc aagaaatggt accgtggaat   6900
catcctccca aacaagaatt tatttatgga gaatggttac aagagcttta tgaacaagga   6960
tacattcctc agaaggaatt aaattcagat ttaaccataa tgctttacca agcaaaacga   7020
aaaaataaaa gaatatacgg aaattatgac ttagaggaat tactacctga tattccattt   7080
tctgatgtga gaagagccat tatggattcg tcagaggaat taatagataa ttatcaggat   7140
gatgaaacca actctatatt aactttatgc cgtatgattt taactatgga cacgggtaaa   7200
atcataccaa aagatattgc gggaaatgca gtggctgaat cttctccatt agaacatagg   7260
gagagaattt tgttagcagt tcgtagttat cttggagaga atattgaatg gactaatgaa   7320
aatgtaaatt taactataaa ctatttaaat aacagattaa aaaaattata atgtaacctt   7380
tgctttcaaa tgagtagaaa taatgcacat ccatgtttgt atcgtgcaaa taaagtgttt   7440
catccgtagg aaaaaatgac tttagtatct gttccgcttt ttctgatgaa atgtgctccc   7500
cgacaaaatt gaatgaatca tggacatttg ctggctttga tacagcgaaa gcagccgttc   7560
ctatgttata tatcggattt aacagcagga caaaaaacac catgacagcc atcgtcaccc   7620
acttattcac acgcacataa acctttcctg acttttggaa cagatgatag ctcatcaaaa   7680
atcccgccat tgccaaataa atcgtatatg gcattactgc accataatct tttgagattt   7740
gattgggata tggcgcaagc agcaagacaa gcagtccgat aatcagcgta taaaataagc   7800
ctagtaagat cttatccgtt ctccaataca gcttgaaaaa cactacattc aacgcaatgg   7860
gaagagtgat gatgaaaaac agaaacacga atgcaatcgg ctccatccca tccgggtatt   7920
ccttccaata cgaaaagaaa ctaaaaatca tttgtacgat cggcaaactg acaacagcaa   7980
ggtcgaacgt ataaaactta ccctttccgc catgatcacg cggcatcagc atatagtgaa   8040
aagccgtcag cagcacatat ccgtataaca aaaaatgcag cagcggcagc agttcttttc   8100
```

cgtcctctct taagtaagcg ctggtgaagt ttgttgattg cacctggtga ataagttcaa 8160
cagacactcc cgccagcagc acaatccgca atataacacc cgccaagaac attgtgcgct 8220
gccggtttat tttgggatga tgcaccaaaa gatataagcc cgccagaaca acaattgacc 8280
attgaatcag cagggtgctt tgtctgctta atataaaata acgttcgaaa tgcaatacat 8340
aatgactgaa taactccaac acgaacaaca aaagtgcgca ttttataaaa gctaatgatt 8400
cagtccacat aattgataga cgaattctgc tacaggtcac gtggctatgt gaaggatcgc 8460
gcgtccagtt aagagcaaaa acattgacaa aaaaatttat ttatgctaaa atttactatt 8520
aatatatttg tatgtataat aagattctcc tggccagggg aatcttattt tttgtggagg 8580
atcatttcat gaggaaaaat gagtccagct taacgtctct aatttcagct tttgcccgtg 8640
catatcacag ccgatatgac acacctctta tttttgatga ttttatcgca aaagatctca 8700
ttaacgaaaa agagtttatc gacatcagta aaaatatgat tcaagaaata tcgtttttca 8760
acaaagagat cgccgaacgt cttcaaaatg atcctgaaaa aatattaaaa tgggttgcac 8820
aaatccagct gtctccaacg cccctagcac gtgcttctta ttgtgaaaaa gtcttgcaca 8880
acgaattaat cctgggggca aaacagtatg tcattcttgg agcgggactg gatactttct 8940
gctttcggca tccagaatta gaaaacagct tacaggtttt cgaggttgat catccggcca 9000
cacagcaatt gaaaaaaaat aagctgaagg atgcaaatct gacaattccg ggtcatcttc 9060
attttgttcc tatggatttc accaaaacgt tttcgtatga tcctctctta gatgaaggat 9120
ttaaaaacac aaaaacattc ttcagccttc tcggagtgtc ttattatgta acacgggaag 9180
aaaatgcaag cttgatcagc aatttatttt ctcatgtccc gcctggaagc tctattgttt 9240
ttgattatgc ggacgaaaca ctttttacag caaaagggac gtcgaatcga gttgaacata 9300
tggtgaagat ggctgccgca agcggggaac cgatgaaatc atgtttcact tatcaagaga 9360
ttgaacatct g 9371

<210> SEQ ID NO 48
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 48
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900
ataggggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttta gtcgctgaac atgtgctctg 1200
tttctaccga gaacgtttcc ttcactgaga cggaaaccga ggcacgtcgt agcgcgaact 1260
acgagccgaa tagctgggac tacgatttcc tgctgtcttc cgatactgac gaatctattg 1320
aggtgtacaa agacaaagca aagaaactgg aggctgaagt gcgccgcgaa attaacaacg 1380
agaaagctga attcctgact ctgctggagc tgatcgataa cgtacagcgc ctgggtctgg 1440
gttaccgctt cgaatctgat atccgtcgcg cactggatcg tttcgtaagc agcggcggtt 1500
tcgatggcgt gaccaaaacg agcctgcacg ctaccgcgct gtccttccgt ctgctgcgtc 1560
agcacggctt cgaagtttct caggaagcat tctccggttt caaagatcaa aacggtaact 1620
tcctggaaaa cctgaaagaa gacactaagg cgatcctgag cctgtatgag gcaagctttc 1680
tggccctgga gggtgagaac atcctggatg aggcgcgcgt attcgccatc tcccatctga 1740
aagagctgtc tgaagagaaa atcggtaagg aactggcaga gcaggttaat cacgcactgg 1800
aactgccgct gcatcgtcgt acccagcgtc tggaggcggt ttggtccatc gaagcgtacc 1860
gcaaaaagga ggatgctaac caggttctgc tggaactggc catcctggac tacaacatga 1920
tccagtccgt ttaccagcgt gatctgcgtg aaacctcccg ttggtggcgc cgtgtgggcc 1980
tggcgaccaa actgcacttc gctaaggacc gcctgattga gtctttttac tgggcagtcg 2040
gcgttgcgtt cgaacctcag tattctgact gccgtaacag cgttgcgaaa atgttcagct 2100
tcgttactat tatcgacgac atctacgacg tttacggtac tctggacgag ctggaactgt 2160
ttaccgacgc tgtcgaacgt tgggatgtta acgccatcaa cgatctgcct gactacatga 2220
aactgtgctt cctggcactg tataacacga tcaacgaaat tgcatacgac aacctgaaag 2280
acaaaggtga aaacatcctg ccgtacctga ctaaagcgtg ggcggatctg tgtaacgctt 2340
ttctgcaaga agcgaaatgg ctgtataaca aatccactcc gacctttgac gattatttcg 2400
gcaatgcctg gaaatccagc tctggcccgc tgcaactgat cttcgcttat tttgcggttg 2460
tccaaaacat caaaaaggag gaaattgaaa acctgcaaaa ataccacgat atcattagcc 2520
gtccttctca tatctttcgc ctgtgcaacg acctggcaag cgcgtccgca gagatcgcac 2580
gtggcgaaac cgctaactct gtttcctgct acatgcgcac caagggcatt tccgaagagc 2640
tggcaaccga gagcgtaatg aatctgatcg acgaaacctg taagaaaatg aacaaagaaa 2700
aactgggtgg ctccctgttc gctaaaccgt tcgtagagac tgctattaac ctggcacgtc 2760
agagccactg cacctaccac aatggtgacg cacatactag cccggatgaa ctgactcgta 2820
aacgtgtact gtctgttatc accgaaccga ttctgccgtt cgaacgttaa ctgcagcgtc 2880
aatcgaaagg gcgacacaaa atttattcta aatgcataat aaatactgat aacatcttat 2940
agtttgtatt atattttgta ttatcgttga catgtataat tttgatatca aaaactgatt 3000
ttccctttat tattttcgag atttattttc ttaattctct ttaacaaact agaaatattg 3060
tatatacaaa aaatcataaa taatagatga atagtttaat tataggtgtt catcaatcga 3120

-continued aaaagcaacg tatcttattt aaagtgcgtt gcttttttct catttataag gttaaataat 3180
tctcatatat caagcaaagt gacaggcgcc cttaaatatt ctgacaaatg ctctttccct 3240
aaactccccc cataaaaaaa cccgccgaag cgggtttttta cgttatttgc ggattaacga 3300
ttactcgtta tcagaaccgc ccagggggcc cgagcttaag actggccgtc gttttacaac 3360
acagaaagag tttgtagaaa cgcaaaaagg ccatccgtca ggggccttct gcttagtttg 3420
atgcctggca gttccctact ctcgccttcc gcttcctcgc tcactgactc gctgcgctcg 3480
gtcgttcggc tgcggcgagc ggtatcagct cactcaaagg cggtaatacg gttatccaca 3540
gaatcagggg ataacgcagg aaagaacatg tgagcaaaag gccagcaaaa ggccaggaac 3600
cgtaaaaagg ccgcgttgct ggcgtttttc cataggctcc gcccccctga cgagcatcac 3660
aaaaatcgac gctcaagtca gaggtggcga aacccgacag gactataaag ataccaggcg 3720
tttccccctg gaagctccct cgtgcgctct cctgttccga ccctgccgct taccggatac 3780
ctgtccgcct ttctcccttc gggaagcgtg gcgctttctc atagctcacg ctgtaggtat 3840
ctcagttcgg tgtaggtcgt tcgctccaag ctgggctgtg tgcacgaacc ccccgttcag 3900
cccgaccgct gcgccttatc cggtaactat cgtcttgagt ccaacccggt aagacacgac 3960
ttatcgccac tggcagcagc cactggtaac aggattagca gagcgaggta tgtaggcggt 4020
gctacagagt tcttgaagtg gtgggctaac tacggctaca ctagaagaac agtatttggt 4080
atctgcgctc tgctgaagcc agttaccttc ggaaaaagag ttggtagctc ttgatccggc 4140
aaacaaacca ccgctggtag cggtggtttt tttgtttgca agcagcagat tacgcgcaga 4200
aaaaaaggat ctcaagaaga tcctttgatc ttttctacgg ggtctgacgc tcagtggaac 4260
gacgcgcgcg taactcacgt taagggattt tggtcatgag cttgcgccgt cccgtcaagt 4320
cagcgtaatg ctctgcttt 4339

<210> SEQ ID NO 49
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 49
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatgtgctc 420
tgtttctacc gagaacgttt ccttcactga gacggaaacc gaggcacgtc gtagcgcgaa 480
ctacgagccg aatagctggg actacgattt cctgctgtct tccgatactg acgaatctat 540
tgaggtgtac aaagacaaag caaagaaact ggaggctgaa gtgcgccgcg aaattaacaa 600
cgagaaagct gaattcctga ctctgctgga gctgatcgat aacgtacagc gcctgggtct 660
gggttaccgc ttcgaatctg atatccgtcg cgcactggat cgtttcgtaa gcagcggcgg 720
tttcgatggc gtgaccaaaa cgagcctgca cgctaccgcg ctgtccttcc gtctgctgcg 780
tcagcacggc ttcgaagttt ctcaggaagc attctccggt ttcaaagatc aaaacggtaa 840

-continued

```
cttcctggaa aacctgaaag aagacactaa ggcgatcctg agcctgtatg aggcaagctt    900
tctggccctg gagggtgaga acatcctgga tgaggcgcgc gtattcgcca tctcccatct    960
gaaagagctg tctgaagaga aaatcggtaa ggaactggca gagcaggtta atcacgcact   1020
ggaactgccg ctgcatcgtc gtacccagcg tctggaggcg gtttggtcca tcgaagcgta   1080
ccgcaaaaag gaggatgcta accaggttct gctggaactg gccatcctgg actacaacat   1140
gatccagtcc gtttaccagc gtgatctgcg tgaaacctcc cgttggtggc gccgtgtggg   1200
cctggcgacc aaactgcact tcgctaagga ccgcctgatt gagtcttttt actgggcagt   1260
cggcgttgcg ttcgaacctc agtattctga ctgccgtaac agcgttgcga aaatgttcag   1320
cttcgttact attatcgacg acatctacga cgtttacggt actctggacg agctggaact   1380
gtttaccgac gctgtcgaac gttgggatgt taacgccatc aacgatctgc ctgactacat   1440
gaaactgtgc ttcctggcac tgtataacac gatcaacgaa attgcatacg acaacctgaa   1500
agacaaaggt gaaaacatcc tgccgtacct gactaaagcg tgggcggatc tgtgtaacgc   1560
ttttctgcaa gaagcgaaat ggctgtataa caaatccact ccgacctttg acgattattt   1620
cggcaatgcc tggaaatcca gctctggccc gctgcaactg atcttcgctt attttgcggt   1680
tgtccaaaac atcaaaaagg aggaaattga aaacctgcaa aaataccacg atatcattag   1740
ccgtccttct catatctttc gcctgtgcaa cgacctggca agcgcgtccg cagagatcgc   1800
acgtggcgaa accgctaact ctgtttcctg ctacatgcgc accaagggca tttccgaaga   1860
gctggcaacc gagagcgtaa tgaatctgat cgacgaaacc tgtaagaaaa tgaacaaaga   1920
aaaactgggt ggctccctgt tcgctaaacc gttcgtagag actgctatta acctggcacg   1980
tcagagccac tgcacctacc acaatggtga cgcacatact agcccggatg aactgactcg   2040
taaacgtgta ctgtctgtta tcaccgaacc gattctgccg ttcgaacgtt aactgcagct   2100
ggtaccatat gggaattcga agctttctag aacaaaaact catctcagaa gaggatctga   2160
atagcgccgt cgaccatcat catcatcatc attgagttta aacggtctcc agcttggctg   2220
ttttggcgga tgagagaaga ttttcagcct gatacagatt aaatcagaac gcagaagcgg   2280
tctgataaaa cagaatttgc ctggcggcag tagcgcggtg gtcccacctg accccatgcc   2340
gaactcagaa gtgaaacgcc gtagcgccga tggtagtgtg gggtctcccc atgcgagagt   2400
agggaactgc caggcatcaa ataaaacgaa aggctcagtc gaaagactgg gcctttcgtt   2460
ttatctgttg tttgtcggtg aacgctctcc tgagtaggac aaatccgccg ggagcggatt   2520
tgaacgttgc gaagcaacgg cccggagggt ggcgggcagg acgcccgcca taaactgcca   2580
ggcatcaaat taagcagaag gccatcctga cggatggcct ttttgcgttt ctacaaactc   2640
tttttgttta tttttctaaa tacattcaaa tatgtatccg ctcatgagac aataaccctg   2700
ataaatgctt caataatatt gaaaaaggaa gagtatgagt attcaacatt tccgtgtcgc   2760
ccttattccc ttttttgcgg cattttgcct tcctgttttt gctcacccag aaacgctggt   2820
gaaagtaaaa gatgctgaag atcagttggg tgcacgagtg ggttacatcg aactggatct   2880
caacagcggt aagatccttg agagttttcg ccccgaagaa cgttttccaa tgatgagcac   2940
ttttaaagtt ctgctatgtg gcgcggtatt atcccgtgtt gacgccgggc aagagcaact   3000
cggtcgccgc atacactatt ctcagaatga cttggttgag tactcaccag tcacagaaaa   3060
gcatcttacg gatggcatga cagtaagaga attatgcagt gctgccataa ccatgagtga   3120
taacactgcg gccaacttac ttctgacaac gatcggagga ccgaaggagc taaccgcttt   3180
```

-continued

```
tttgcacaac atgggggatc atgtaactcg ccttgatcgt tgggaaccgg agctgaatga   3240
agccatacca aacgacgagc gtgacaccac gatgcctgta gcaatggcaa caacgttgcg   3300
caaactatta actggcgaac tacttactct agcttcccgg caacaattaa tagactggat   3360
ggaggcggat aaagttgcag gaccacttct gcgctcggcc cttccggctg gctggtttat   3420
tgctgataaa tctggagccg gtgagcgtgg gtctcgcggt atcattgcag cactggggcc   3480
agatggtaag ccctcccgta tcgtagttat ctacacgacg gggagtcagg caactatgga   3540
tgaacgaaat agacagatcg ctgagatagg tgcctcactg attaagcatt ggtaactgtc   3600
agaccaagtt tactcatata tactttagat tgatttaaaa cttcattttt aatttaaaag   3660
gatctaggtg aagatccttt ttgataatct catgaccaaa atcccttaac gtgagttttc   3720
gttccactga gcgtcagacc ccgtagaaaa gatcaaagga tcttcttgag atcctttttt   3780
tctgcgcgta atctgctgct tgcaaacaaa aaaaccaccg ctaccagcgg tggtttgttt   3840
gccggatcaa gagctaccaa ctctttttcc gaaggtaact ggcttcagca gagcgcagat   3900
accaaatact gtccttctag tgtagccgta gttaggccac cacttcaaga actctgtagc   3960
accgcctaca tacctcgctc tgctaatcct gttaccagtg gctgctgcca gtggcgataa   4020
gtcgtgtctt accgggttgg actcaagacg atagttaccg gataaggcgc agcggtcggg   4080
ctgaacgggg ggttcgtgca cacagcccag cttggagcga acgacctaca ccgaactgag   4140
atacctacag cgtgagctat gagaaagcgc cacgcttccc gaagggagaa aggcggacag   4200
gtatccggta agcggcaggg tcggaacagg agagcgcacg agggagcttc cagggggaaa   4260
cgcctggtat ctttatagtc ctgtcgggtt tcgccacctc tgacttgagc gtcgattttt   4320
gtgatgctcg tcaggggggc ggagcctatg gaaaaacgcc agcaacgcgg cctttttacg   4380
gttcctggcc ttttgctggc cttttgctca catgttcttt cctgcgttat cccctgattc   4440
tgtggataac cgtattaccg cctttgagtg agctgatacc gctcgccgca gccgaacgac   4500
cgagcgcagc gagtcagtga gcgaggaagc ggaagagcgc ctgatgcggt attttctcct   4560
tacgcatctg tgcggtattt cacaccgcat atggtgcact ctcagtacaa tctgctctga   4620
tgccgcatag ttaagccagt atacactccg ctatcgctac gtgactgggt catggctgcg   4680
ccccgacacc cgccaacacc cgctgacgcg ccctgacggg cttgtctgct cccggcatcc   4740
gcttacagac aagctgtgac cgtctccggg agctgcatgt gtcagaggtt ttcaccgtca   4800
tcaccgaaac gcgcgaggca gcagatcaat tcgcgcgcga aggcgaagcg gcatgcattt   4860
acgttgacac catcgaatgg tgcaaaacct ttcgcggtat ggcatgatag cgcccggaag   4920
agagtcaatt cagggtggtg aatgtgaaac cagtaacgtt atacgatgtc gcagagtatg   4980
ccggtgtctc ttatcagacc gtttcccgcg tggtgaacca ggccagccac gtttctgcga   5040
aaacgcggga aaaagtggaa gcggcgatgg cggagctgaa ttacattccc aaccgcgtgg   5100
cacaacaact ggcgggcaaa cagtcgttgc tgattggcgt tgccacctcc agtctggccc   5160
tgcacgcgcc gtcgcaaatt gtcgcggcga ttaaatctcg cgccgatcaa ctgggtgcca   5220
gcgtggtggt gtcgatggta gaacgaagcg gcgtcgaagc ctgtaaagcg gcggtgcaca   5280
atcttctcgc gcaacgcgtc agtgggctga tcattaacta tccgctggat gaccaggatg   5340
ccattgctgt ggaagctgcc tgcactaatg ttccggcgtt atttcttgat gtctctgacc   5400
agacacccat caacagtatt attttctccc atgaagacgg tacgcgactg ggcgtggagc   5460
atctggtcgc attgggtcac cagcaaatcg cgctgttagc gggcccatta agttctgtct   5520
cggcgcgtct gcgtctggct ggctggcata aatatctcac tcgcaatcaa attcagccga   5580
```

```
tagcggaacg ggaaggcgac tggagtgcca tgtccggttt tcaacaaacc atgcaaatgc   5640
tgaatgaggg catcgttccc actgcgatgc tggttgccaa cgatcagatg gcgctgggcg   5700
caatgcgcgc cattaccgag tccgggctgc gcgttggtgc ggatatctcg gtagtgggat   5760
acgacgatac cgaagacagc tcatgttata tcccgccgtc aaccaccatc aaacaggatt   5820
ttcgcctgct ggggcaaacc agcgtggacc gcttgctgca actctctcag ggccaggcgg   5880
tgaagggcaa tcagctgttg cccgtctcac tggtgaaaag aaaaaccacc ctggcgccca   5940
atacgcaaac cgcctctccc cgcgcgttgg ccgattcatt aatgcagctg gcacgacagg   6000
tttcccgact ggaaagcggg cagtgagcgc aacgcaatta atgtgagtta gcgcgaattg   6060
atctg                                                               6065
```

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50

```
ttgtctgctc ccggcatccg cttacagaca agctgtgacc gtctccggga gctgcatgtg     60
tcagaggttt tcaccgtcat caccgaaacg cgcgaggcag cagatcaatt cgcgcgcgaa    120
ggcgaagcgg catgcattta cgttgacacc atcgaatggt gcaaaacctt tcgcggtatg    180
gcatgatagc gcccggaaga gagtcaattc agggtggtga atgtgaaacc agtaacgtta    240
tacgatgtcg cagagtatgc cggtgtctct tatcagaccg tttcccgcgt ggtgaaccag    300
gccagccacg tttctgcgaa aacgcgggaa aaagtggaag cggcgatggc ggagctgaat    360
tacattccca accgcgtggc acaacaactg gcgggcaaac agtcgttgct gattggcgtt    420
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
tgtaaagcgg cggtgcacaa tcttctcgcg caacgcgtca gtgggctgat cattaactat    600
ccgctggatg accaggatgc cattgctgtg gaagctgcct gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca aacaggattt tcgcctgctg gggcaaacca gcgtggaccg cttgctgcaa   1140
ctctctcagg gccaggcggt gaagggcaat cagctgttgc ccgtctcact ggtgaaaaga   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
```

-continued

```
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aaagaggtat atattaatgt atcgattaaa   1740
taaggaggaa taaaccatgt gtgcgacctc ttctcaattt actcagatta ccgagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgtttttg agcgtttcaa   2160
ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga acaacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcatcgc ccttaggagg taaaaaaaaa   3480
tgactgccga caacaatagt atgccccatg gtgcagtatc tagttacgcc aaattagtgc   3540
aaaaccaaac acctgaagac attttggaag agtttcctga aattattcca ttacaacaaa   3600
gacctaatac ccgatctagt gagacgtcaa atgacgaaag cggagaaaca tgtttttctg   3660
gtcatgatga ggagcaaatt aagttaatga atgaaaattg tattgttttg gattgggacg   3720
ataatgctat tggtgccggt accaagaaag tttgtcattt aatggaaaat attgaaaagg   3780
gtttactaca tcgtgcattc tccgtcttta ttttcaatga acaaggtgaa ttacttttac   3840
aacaaagagc cactgaaaaa ataactttcc ctgatctttg gactaacaca tgctgctctc   3900
```

-continued atccactatg tattgatgac gaattaggtt tgaagggtaa gctagacgat aagattaagg 3960
gcgctattac tgcggcggtg agaaaactag atcatgaatt aggtattcca gaagatgaaa 4020
ctaagacaag ggtaagttt cactttttaa acagaatcca ttacatggca ccaagcaatg 4080
aaccatgggg tgaacatgaa attgattaca tcctatttta taagatcaac gctaaagaaa 4140
acttgactgt caacccaaac gtcaatgaag ttagagactt caaatgggtt tcaccaaatg 4200
atttgaaaac tatgtttgct gacccaagtt acaagtttac gccttggttt aagattattt 4260
gcgagaatta cttattcaac tggtgggagc aattagatga cctttctgaa gtggaaaatg 4320
acaggcaaat tcatagaatg ctataacaac gcgtcctgca gctggtacca tatgggaatt 4380
cgaagctttc tagaacaaaa actcatctca gaagaggatc tgaatagcgc cgtcgaccat 4440
catcatcatc atcattgagt ttaaacggtc tccagcttgg ctgttttggc ggatgagaga 4500
agattttcag cctgatacag attaaatcag aacgcagaag cggtctgata aaacagaatt 4560
tgcctggcgg cagtagcgcg gtggtcccac ctgaccccat gccgaactca gaagtgaaac 4620
gccgtagcgc cgatggtagt gtggggtctc cccatgcgag agtagggaac tgccaggcat 4680
caaataaaac gaaaggctca gtcgaaagac tgggcctttc gttttatctg ttgtttgtcg 4740
gtgaacgctc tcctgagtag gacaaatccg ccgggagcgg atttgaacgt tgcgaagcaa 4800
cggcccggag ggtggcgggc aggacgcccg ccataaactg ccaggcatca aattaagcag 4860
aaggccatcc tgacggatgg cctttttgcg tttctacaaa ctctttttgt ttatttttct 4920
aaatacattc aaatatgtat ccgcttaacc ggaattgcca gctggggcgc cctctggtaa 4980
ggttgggaag ccctgcaaag taaactggat ggctttctcg ccgccaagga tctgatggcg 5040
caggggatca agctctgatc aagagacagg atgaggatcg tttcgcatga ttgaacaaga 5100
tggattgcac gcaggttctc cggccgcttg ggtggagagg ctattcggct atgactgggc 5160
acaacagaca atcggctgct ctgatgccgc cgtgttccgg ctgtcagcgc aggggcgccc 5220
ggttcttttt gtcaagaccg acctgtccgg tgccctgaat gaactgcaag acgaggcagc 5280
gcggctatcg tggctggcca cgacgggcgt tccttgcgca gctgtgctcg acgttgtcac 5340
tgaagcggga agggactggc tgctattggg cgaagtgccg gggcaggatc tcctgtcatc 5400
tcaccttgct cctgccgaga aagtatccat catggctgat gcaatgcggc ggctgcatac 5460
gcttgatccg gctacctgcc cattcgacca ccaagcgaaa catcgcatcg agcgagcacg 5520
tactcggatg gaagccggtc ttgtcgatca ggatgatctg gacgaagagc atcaggggct 5580
cgcgccagcc gaactgttcg ccaggctcaa ggcgagcatg cccgacggcg aggatctcgt 5640
cgtgacccat ggcgatgcct gcttgccgaa tatcatggtg gaaaatggcc gcttttctgg 5700
attcatcgac tgtggccggc tgggtgtggc ggaccgctat caggacatag cgttggctac 5760
ccgtgatatt gctgaagagc ttggcggcga atgggctgac cgcttcctcg tgctttacgg 5820
tatcgccgct cccgattcgc agcgcatcgc cttctatcgc cttcttgacg agttcttctg 5880
acatgaccaa aatcccttaa cgtgagtttt cgttccactg agcgtcagac cccgtagaaa 5940
agatcaaagg atcttcttga gatccttttt ttctgcgcgt aatctgctgc ttgcaaacaa 6000
aaaaaccacc gctaccagcg gtggtttgtt tgccggatca agagctacca actctttttc 6060
cgaaggtaac tggcttcagc agagcgcaga taccaaatac tgtccttcta gtgtagccgt 6120
agttaggcca ccacttcaag aactctgtag caccgcctac atacctcgct ctgctaatcc 6180
tgttaccagt ggctgctgcc agtggcgata agtcgtgtct taccgggttg gactcaagac 6240

```
gatagttacc ggataaggcg cagcggtcgg gctgaacggg gggttcgtgc acacagccca   6300

gcttggagcg aacgacctac accgaactga gatacctaca gcgtgagcta tgagaaagcg   6360

ccacgcttcc cgaagggaga aaggcggaca ggtatccggt aagcggcagg gtcggaacag   6420

gagagcgcac gagggagctt ccagggggaa acgcctggta tctttatagt cctgtcgggt   6480

ttcgccacct ctgacttgag cgtcgatttt tgtgatgctc gtcagggggg cggagcctat   6540

ggaaaaacgc cagcaacgcg gcctttttac ggttcctggc cttttgctgg ccttttgctc   6600

acatgttctt tcctgcgtta tcccctgatt ctgtggataa ccgtattacc gcctttgagt   6660

gagctgatac cgctcgccgc agccgaacga ccgagcgcag cgagtcagtg agcgaggaag   6720

cggaagagcg cctgatgcgg tattttctcc ttacgcatct gtgcggtatt tcacaccgca   6780

tatggtgcac tctcagtaca atctgctctg atgccgcata gttaagccag tatacactcc   6840

gctatcgcta cgtgactggg tcatggctgc gccccgacac ccgccaacac ccgctgacgc   6900

gccctgacgg gc                                                       6912
```

<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 51

```
ttgtctgctc ccggcatccg cttacagaca agctgtgacc gtctccggga gctgcatgtg     60

tcagaggttt tcaccgtcat caccgaaacg cgcgaggcag cagatcaatt cgcgcgcgaa    120

ggcgaagcgg catgcattta cgttgacacc atcgaatggt gcaaaacctt tcgcggtatg    180

gcatgatagc gcccggaaga gagtcaattc agggtggtga atgtgaaacc agtaacgtta    240

tacgatgtcg cagagtatgc cggtgtctct tatcagaccg tttcccgcgt ggtgaaccag    300

gccagccacg tttctgcgaa aacgcgggaa aaagtggaag cggcgatggc ggagctgaat    360

tacattccca accgcgtggc acaacaactg gcgggcaaac agtcgttgct gattggcgtt    420

gccacctcca gtctggccct gcacgcgccg tcgcaaattg tcgcggcgat taaatctcgc    480

gccgatcaac tgggtgccag cgtggtggtg tcgatggtag aacgaagcgg cgtcgaagcc    540

tgtaaagcgg cggtgcacaa tcttctcgcg caacgcgtca gtgggctgat cattaactat    600

ccgctggatg accaggatgc cattgctgtg gaagctgcct gcactaatgt tccggcgtta    660

tttcttgatg tctctgacca gacacccatc aacagtatta ttttctccca tgaagacggt    720

acgcgactgg gcgtggagca tctggtcgca ttgggtcacc agcaaatcgc gctgttagcg    780

ggcccattaa gttctgtctc ggcgcgtctg cgtctggctg gctggcataa atatctcact    840

cgcaatcaaa ttcagccgat agcggaacgg gaaggcgact ggagtgccat gtccggtttt    900

caacaaacca tgcaaatgct gaatgagggc atcgttccca ctgcgatgct ggttgccaac    960

gatcagatgg cgctgggcgc aatgcgcgcc attaccgagt ccgggctgcg cgttggtgcg   1020

gatatctcgg tagtgggata cgacgatacc gaagacagct catgttatat cccgccgtca   1080

accaccatca aacaggattt tcgcctgctg gggcaaacca gcgtggaccg cttgctgcaa   1140

ctctctcagg gccaggcggt gaagggcaat cagctgttgc ccgtctcact ggtgaaaaga   1200

aaaaccaccc tggcgcccaa tacgcaaacc gcctctcccc gcgcgttggc cgattcatta   1260

atgcagctgg cacgacaggt ttcccgactg gaaagcgggc agtgagcgca acgcaattaa   1320

tgtgagttag cgcgaattga tctggtttga cagcttatca tcgactgcac ggtgcaccaa   1380
```

-continued

```
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aaagaggtat atattaatgt atcgattaaa   1740
taaggaggaa taaaccatgt gtgcgacctc ttctcaattt actcagatta ccgagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgtttttg agcgtttcaa   2160
ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga acaacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcattcg cccttaggag gtaaaaaaac   3480
atgagttttg atattgccaa atacccgacc ctggcactgg tcgactccac ccaggagtta   3540
cgactgttgc cgaaagagag tttaccgaaa ctctgcgacg aactgcgccg ctatttactc   3600
gacagcgtga gccgttccag cgggcacttc gcctccgggc tgggcacggt cgaactgacc   3660
gtggcgctgc actatgtcta caacaccccg tttgaccaat tgatttggga tgtggggcat   3720
```

-continued

```
caggcttatc cgcataaaat tttgaccgga cgccgcgaca aaatcggcac catccgtcag   3780
aaaggcggtc tgcacccgtt cccgtggcgc ggcgaaagcg aatatgacgt attaagcgtc   3840
gggcattcat caacctccat cagtgccgga attggtattg cggttgctgc cgaaaaagaa   3900
ggcaaaaatc gccgcaccgt ctgtgtcatt ggcgatggcg cgattaccgc aggcatggcg   3960
tttgaagcga tgaatcacgc gggcgatatc cgtcctgata tgctggtgat tctcaacgac   4020
aatgaaatgt cgatttccga aaatgtcggc gcgctcaaca accatctggc acagctgctt   4080
tccggtaagc tttactcttc actgcgcgaa ggcgggaaaa aagttttctc tggcgtgccg   4140
ccaattaaag agctgctcaa acgcaccgaa gaacatatta aaggcatggt agtgcctggc   4200
acgttgtttg aagagctggg ctttaactac atcggcccgg tggacggtca cgatgtgctg   4260
gggcttatca ccacgctaaa gaacatgcgc gacctgaaag gcccgcagtt cctgcatatc   4320
atgaccaaaa aaggtcgtgg ttatgaaccg gcagaaaaag acccgatcac tttccacgcc   4380
gtgcctaaat ttgatccctc cagcggttgt ttgccgaaaa gtagcggcgg tttgccgagc   4440
tattcaaaaa tctttggcga ctggttgtgc gaaacggcag cgaaagacaa caagctgatg   4500
gcgattactc cggcgatgcg tgaaggttcc ggcatggtcg agttttcacg taaattcccg   4560
gatcgctact tcgacgtggc aattgccgag caacacgcgg tgacctttgc tgcgggtctg   4620
gcgattggtg ggtacaaacc cattgtcgcg atttactcca ctttcctgca acgcgcctat   4680
gatcaggtgc tgcatgacgt ggcgattcaa aagcttccgg tcctgttcgc catcgaccgc   4740
gcgggcattg ttggtgctga cggtcaaacc catcagggtg cttttgatct ctcttacctg   4800
cgctgcatac cggaaatggt cattatgacc ccgagcgatg aaaacgaatg tcgccagatg   4860
ctctataccg gctatcacta taacgatggc ccgtcagcgg tgcgctaccc gcgtggcaac   4920
gcggtcggcg tggaactgac gccgctggaa aaactaccaa ttggcaaagg cattgtgaag   4980
cgtcgtggcg agaaactggc gatccttaac tttggtacgc tgatgccaga agcggcgaaa   5040
gtcgccgaat cgctgaacgc cacgctggtc gatatgcgtt ttgtgaaacc gcttgatgaa   5100
gcgttaattc tggaaatggc cgccagccat gaagcgctgg tcaccgtaga agaaaacgcc   5160
attatgggcg gcgcaggcag cggcgtgaac gaagtgctga tggcccatcg taaaccagta   5220
cccgtgctga acattggcct gccggacttc tttattccgc aaggaactca ggaagaaatg   5280
cgcgccgaac tcggcctcga tgccgctggt atggaagcca aaatcaaggc ctggctggca   5340
taactgcagc tggtaccata tgggaattcg aagctttcta gaacaaaaac tcatctcaga   5400
agaggatctg aatagcgccg tcgaccatca tcatcatcat cattgagttt aaacggtctc   5460
cagcttggct gttttggcgg atgagagaag attttcagcc tgatacagat taaatcagaa   5520
cgcagaagcg gtctgataaa acagaatttg cctggcggca gtagcgcggt ggtcccacct   5580
gaccccatgc cgaactcaga agtgaaacgc cgtagcgccg atggtagtgt ggggtctccc   5640
catgcgagag tagggaactg ccaggcatca aataaaacga aaggctcagt cgaaagactg   5700
ggcctttcgt tttatctgtt gtttgtcggt gaacgctctc ctgagtagga caaatccgcc   5760
gggagcggat ttgaacgttg cgaagcaacg gcccggaggg tggcgggcag gacgcccgcc   5820
ataaactgcc aggcatcaaa ttaagcagaa ggccatcctg acggatggcc tttttgcgtt   5880
tctacaaact ctttttgttt atttttctaa atacattcaa atatgtatcc gcttaaccgg   5940
aattgccagc tggggcgccc tctggtaagg ttgggaagcc ctgcaaagta aactggatgg   6000
ctttctcgcc gccaaggatc tgatggcgca ggggatcaag ctctgatcaa gagacaggat   6060
gaggatcgtt tcgcatgatt gaacaagatg gattgcacgc aggttctccg gccgcttggg   6120
```

tggagaggct attcggctat gactgggcac aacagacaat cggctgctct gatgccgccg 6180
tgttccggct gtcagcgcag gggcgcccgg ttctttttgt caagaccgac ctgtccggtg 6240
ccctgaatga actgcaagac gaggcagcgc ggctatcgtg gctggccacg acgggcgttc 6300
cttgcgcagc tgtgctcgac gttgtcactg aagcgggaag ggactggctg ctattgggcg 6360
aagtgccggg gcaggatctc ctgtcatctc accttgctcc tgccgagaaa gtatccatca 6420
tggctgatgc aatgcggcgg ctgcatacgc ttgatccggc tacctgccca ttcgaccacc 6480
aagcgaaaca tcgcatcgag cgagcacgta ctcggatgga agccggtctt gtcgatcagg 6540
atgatctgga cgaagagcat caggggctcg cgccagccga actgttcgcc aggctcaagg 6600
cgagcatgcc cgacggcgag gatctcgtcg tgacccatgg cgatgcctgc ttgccgaata 6660
tcatggtgga aaatggccgc ttttctggat tcatcgactg tggccggctg ggtgtggcgg 6720
accgctatca ggacatagcg ttggctaccc gtgatattgc tgaagagctt ggcggcgaat 6780
gggctgaccg cttcctcgtg ctttacggta tcgccgctcc cgattcgcag cgcatcgcct 6840
tctatcgcct tcttgacgag ttcttctgac gcatgaccaa aatcccttaa cgtgagtttt 6900
cgttccactg agcgtcagac cccgtagaaa agatcaaagg atcttcttga gatccttttt 6960
ttctgcgcgt aatctgctgc ttgcaaacaa aaaaaccacc gctaccagcg gtggtttgtt 7020
tgccggatca agagctacca actctttttc cgaaggtaac tggcttcagc agagcgcaga 7080
taccaaatac tgtccttcta gtgtagccgt agttaggcca ccacttcaag aactctgtag 7140
caccgcctac atacctcgct ctgctaatcc tgttaccagt ggctgctgcc agtggcgata 7200
agtcgtgtct taccgggttg gactcaagac gatagttacc ggataaggcg cagcggtcgg 7260
gctgaacggg gggttcgtgc acacagccca gcttggagcg aacgacctac accgaactga 7320
gatacctaca gcgtgagcta tgagaaagcg ccacgcttcc cgaagggaga aaggcggaca 7380
ggtatccggt aagcggcagg gtcggaacag gagagcgcac gagggagctt ccagggggaa 7440
acgcctggta tctttatagt cctgtcgggt ttcgccacct ctgacttgag cgtcgatttt 7500
tgtgatgctc gtcagggggg cggagcctat ggaaaaacgc cagcaacgcg gcctttttac 7560
ggttcctggc cttttgctgg ccttttgctc acatgttctt tcctgcgtta tcccctgatt 7620
ctgtggataa ccgtattacc gcctttgagt gagctgatac cgctcgccgc agccgaacga 7680
ccgagcgcag cgagtcagtg agcgaggaag cggaagagcg cctgatgcgg tattttctcc 7740
ttacgcatct gtgcggtatt tcacaccgca tatggtgcac tctcagtaca atctgctctg 7800
atgccgcata gttaagccag tatacactcc gctatcgcta cgtgactggg tcatggctgc 7860
gccccgacac ccgccaacac ccgctgacgc gccctgacgg gc 7902

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52
ctggcgtaat agcgaagagg cccgcaccga tcgcccttcc caacagttgc gcagcctgaa 60
tggcgaatgg cgcctgatgc ggtattttct ccttacgcat ctgtgcggta tttcacaccg 120
catatggtgc actctcagta caatctgctc tgatgccgca tagttaagcc agccccgaca 180
cccgccaaca cccgctgacg agcttagtaa agccctcgct agattttaat gcggatgttg 240

-continued

```
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgtttttgc gtgagccatg agaacgaacc attgagatca   2580
tacttacttt gcatgtcact caaaaatttt gcctcaaaac tggtgagctg aatttttgca   2640
```

```
gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttcttttaat   3000
aaccactcat aaatcctcat agagtatttg ttttcaaaag acttaacatg ttccagatta   3060
tattttatga attttttaa ctggaaaaga taaggcaata tctcttcact aaaaactaat   3120
tctaattttt cgcttgagaa cttggcatag tttgtccact ggaaaatctc aaagccttta   3180
accaaaggat tcctgatttc cacagttctc gtcatcagct ctctggttgc tttagctaat   3240
acaccataag cattttccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gacctttgtg tgtttttttt gtttatattc aagtggttat aatttataga   3660
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtctttttc gtgacattca   3900
gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat tttccagtct gaccacttcg gattatcccg tgacaggtca ttcagactgg   4140
ctaatgcacc cagtaaggca gcggtatcat caacaggctt acccgtctta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta acaatttatc agacaatctg tgtgggcact   4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaaagacatc attaaagccc   4740
tggaaaacat cgtactgctg gacgaaaaca aaaagaacaa atctgacctg cacgcaaccg   4800
ctctgtcttt ccgtctgctg cgtcagcacg gtttcgaggt ttctcaggat gtttttgagc   4860
gtttcaagga taaagaaggt ggtttcagcg gtgaactgaa aggtgacgtc caaggcctgc   4920
tgagcctgta tgaagcgtct tacctgggtt tcgagggtga gaacctgctg gaggaggcgc   4980
```

```
gtaccttttc catcacccac ctgaagaaca acctgaaaga aggcattaat accaaggttg   5040

cagaacaagt gagccacgcc ctggaactgc catatcacca gcgtctgcac cgtctggagg   5100

cacgttggtt cctggataaa tacgaaccga aagaaccgca tcaccagctg ctgctggagc   5160

tggcgaagct ggattttaac atggtacaga ccctgcacca gaaagagctg caagatctgt   5220

cccgctggtg gaccgagatg ggcctggcta gcaaactgga ttttgtacgc gaccgcctga   5280

tggaagttta tttctgggca ctgggtatgg cgccagaccc gcagtttggt gaatgtcgca   5340

aagctgttac taaaatgttt ggtctggtga cgatcatcga tgacgtgtat gacgtttatg   5400

gcactctgga cgaactgcaa ctgttcaccg atgctgtaga gcgctgggac gttaacgcta   5460

ttaacaccct gccggactat atgaaactgt gtttcctggc actgtacaac accgttaacg   5520

acacgtccta ttctattctg aaagagaaag gtcataacaa cctgtcctat ctgacgaaaa   5580

gctggcgtga actgtgcaaa gcctttctgc aagaggcgaa atggtccaac aacaaaatta   5640

tcccggcttt ctccaagtac ctggaaaacg ccagcgtttc ctcctccggt gtagcgctgc   5700

tggcgccgtc ttacttttcc gtatgccagc agcaggaaga catctccgac cacgcgctgc   5760

gttccctgac cgacttccat ggtctggtgc gttctagctg cgttatcttc cgcctgtgca   5820

acgatctggc cacctctgcg gcggagctgg aacgtggcga gactaccaat tctatcatta   5880

gctacatgca cgaaaacgat ggtaccagcg aggaacaggc ccgcgaagaa ctgcgtaaac   5940

tgatcgacgc cgaatggaaa aagatgaatc gtgaacgcgt tagcgactcc accctgctgc   6000

ctaaagcgtt catggaaatc gcagttaaca tggcacgtgt ttcccactgc acctaccagt   6060

atggcgatgg tctgggtcgc ccagactacg cgactgaaaa ccgcatcaaa ctgctgctga   6120

ttgacccttt cccgattaac cagctgatgt atgtctaact gcagctggta ccatatggga   6180

attcgaagct ttctagaaca aaaactcatc tcagaagagg atctgaatag cgccgtcgac   6240

catcatcatc atcatcattg agtttaaacg gtctccagct tggctgtttt ggcggatgag   6300

agaagatttt cagcctgata cagattaaat cagaacgcag aagcggtctg ataaaacaga   6360

atttgcctgg cggcagtagc gcggtggtcc cacctgaccc catgccgaac tcagaagtga   6420

aacgccgtag cgccgatggt agtgtggggt ctccccatgc gagagtaggg aactgccagg   6480

catcaaataa aacgaaaggc tcagtcgaaa gactgggcct ttcgttttat ctgttgtttg   6540

tcggtgaacg ctctcctgag taggacaaat ccgccgggag cggatttgaa cgttgcgaag   6600

caacggcccg gagggtggcg ggcaggacgc ccgccataaa ctgccaggca tcaaattaag   6660

cagaaggcca tcctgacgga tggccttttt gcgtttctac aaactctttt tgtttatttt   6720

tctaaataca ttcaaatatg tatccgctca tgagacaata accctgataa atgcttcaat   6780

aat                                                                 6783
```

<210> SEQ ID NO 53
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 53

```
cccgtcttac tgtcgggaat tcgcgttggc cgattcatta atgcagatta ttgaagcatt     60

tatcagggtt attgtctcat gagcggatac atatttgaat gtatttagaa aaataaacaa    120

aaagagtttg tagaaacgca aaaaggccat ccgtcaggat ggccttctgc ttaatttgat    180

gcctggcagt ttatggcggg cgtcctgccc gccaccctcc gggccgttgc ttcgcaacgt    240
```

-continued tcaaatccgc tcccggcgga tttgtcctac tcaggagagc gttcaccgac aaacaacaga 300
taaaacgaaa ggcccagtct ttcgactgag cctttcgttt tatttgatgc ctggcagttc 360
cctactctcg catggggaga ccccacacta ccatcggcgc tacggcgttt cacttctgag 420
ttcggcatgg ggtcaggtgg gaccaccgcg ctactgccgc caggcaaatt ctgttttatc 480
agaccgcttc tgcgttctga tttaatctgt atcaggctga aaatcttctc tcatccgcca 540
aaacagccaa gctggagacc gtttaaactc aatgatgatg atgatgatgg tcgacggcgc 600
tattcagatc ctcttctgag atgagttttt gttctagaaa gcttcgaatt cccatatggt 660
accagctgca gttagacata catcagctgg ttaatcggga aagggtcaat cagcagcagt 720
ttgatgcggt tttcagtcgc gtagtctggg cgacccagac catcgccata ctggtaggtg 780
cagtgggaaa cacgtgccat gttaactgcg atttccatga acgctttagg cagcagggtg 840
gagtcgctaa cgcgttcacg attcatcttt ttccattcgg cgtcgatcag tttacgcagt 900
tcttcgcggg cctgttcctc gctggtacca tcgttttcgt gcatgtagct aatgatagaa 960
ttggtagtct cgccacgttc cagctccgcc gcagaggtgg ccagatcgtt gcacaggcgg 1020
aagataacgc agctagaacg caccagacca tggaagtcgg tcagggaacg cagcgcgtgg 1080
tcggagatgt cttcctgctg ctggcatacg gaaaagtaag acggcgccag cagcgctaca 1140
ccggaggagg aaacgctggc gttttccagg tacttggaga aagccgggat aattttgttg 1200
ttggaccatt tcgcctcttg cagaaaggct ttgcacagtt cacgccagct tttcgtcaga 1260
taggacaggt tgttatgacc tttctctttc agaatagaat aggacgtgtc gttaacggtg 1320
ttgtacagtg ccaggaaaca cagtttcata tagtccggca gggtgttaat agcgttaacg 1380
tcccagcgct ctacagcatc ggtgaacagt tgcagttcgt ccagagtgcc ataaacgtca 1440
tacacgtcat cgatgatcgt caccagacca aacattttag taacagcttt gcgacattca 1500
ccaaactgcg ggtctggcgc catacccagt gcccagaaat aaacttccat caggcggtcg 1560
cgtacaaaat ccagtttgct agccaggccc atctcggtcc accagcggga cagatcttgc 1620
agctctttct ggtgcagggt ctgtaccatg ttaaaatcca gcttcgccag ctccagcagc 1680
agctggtgat gcggttcttt cggttcgtat ttatccagga accaacgtgc ctccagacgg 1740
tgcagacgct ggtgatatgg cagttccagg gcgtggctca cttgttctgc aaccttggta 1800
ttaatgcctt ctttcaggtt gttcttcagg tgggtgatgg aaaaggtacg cgcctcctcc 1860
agcaggttct caccctcgaa acccaggtaa gacgcttcat acaggctcag caggccttgg 1920
acgtcacctt tcagttcacc gctgaaacca ccttctttat ccttgaaacg ctcaaaaaca 1980
tcctgagaaa cctcgaaacc gtgctgacgc agcagacgga aagacagagc ggttgcgtgc 2040
aggtcagatt tgttcttttt gttttcgtcc agcagtacga tgttttccag ggctttaatg 2100
atgtcttttt caaatttgta ggtcagaccc aggcgctgca catcgtcgat cagctccagc 2160
agggacagcg gctgggtgtc tacacggttg atcatgcagc gaacttcttc ctccagtttg 2220
gtcgctttct cctccagctt ttccactttc aggtcgttct ccagggattg caggaattcg 2280
aaattccaca ggtttggctg atagtttgcg gaacgacggg aattatgctc ggtaatctga 2340
gtaaattgag aagaggtcgc acacatggtt tattcctcct tatttaatcg atacattaat 2400
atatacctct ttaattttta ataataaagt taatcgataa ttccggtcga gtgcccacac 2460
agattgtctg ataaattgtt aaagagcagt gccgcttcgc tttttctcag cggcgctgtt 2520
tcctgtgtga aattgttatc cgctcacaat tccacacatt atacgagccg gatgattaat 2580

-continued

```
tgtcaacagc tcatttcaga atctggcgta atagcgaaga ggcccgcacc gatcgccctt   2640
cccaacagtt gcgcagcctg aatggcgaat ggcgcctgat gcggtatttt ctccttacgc   2700
atctgtgcgg tatttcacac cgcatatggt gcactctcag tacaatctgc tctgatgccg   2760
catagttaag ccagccccga cacccgccaa cacccgctga cgagcttagt aaagccctcg   2820
ctagatttta atgcggatgt tgcgattact tcgccaacta ttgcgataac aagaaaaagc   2880
cagcctttca tgatatatct cccaatttgt gtagggctta ttatgcacgc ttaaaaataa   2940
taaaagcaga cttgacctga tagtttggct gtgagcaatt atgtgcttag tgcatctaac   3000
gcttgagtta agccgcgccg cgaagcggcg tcggcttgaa cgaattgtta gacattattt   3060
gccgactacc ttggtgatct cgcctttcac gtagtggaca aattcttcca actgatctgc   3120
gcgcgaggcc aagcgatctt cttcttgtcc aagataagcc tgtctagctt caagtatgac   3180
gggctgatac tgggccggca ggcgctccat tgcccagtcg gcagcgacat ccttcggcgc   3240
gattttgccg gttactgcgc tgtaccaaat gcgggacaac gtaagcacta catttcgctc   3300
atcgccagcc cagtcgggcg gcgagttcca tagcgttaag gtttcattta gcgcctcaaa   3360
tagatcctgt tcaggaaccg gatcaaagag ttcctccgcc gctggaccta ccaaggcaac   3420
gctatgttct cttgcttttg tcagcaagat agccagatca atgtcgatcg tggctggctc   3480
gaagatacct gcaagaatgt cattgcgctg ccattctcca aattgcagtt cgcgcttagc   3540
tggataacgc cacggaatga tgtcgtcgtg cacaacaatg gtgacttcta cagcgcggag   3600
aatctcgctc tctccagggg aagccgaagt ttccaaaagg tcgttgatca aagctcgccg   3660
cgttgtttca tcaagcctta cggtcaccgt aaccagcaaa tcaatatcac tgtgtggctt   3720
caggccgcca tccactgcgg agccgtacaa atgtacggcc agcaacgtcg gttcgagatg   3780
gcgctcgatg acgccaacta cctctgatag ttgagtcgat acttcggcga tcaccgcttc   3840
cctcatgatg tttaactttg ttttagggcg actgccctgc tgcgtaacat cgttgctgct   3900
ccataacatc aaacatcgac ccacggcgta acgcgcttgc tgcttggatg cccgaggcat   3960
agactgtacc ccaaaaaaac agtcataaca agccatgaaa accgccactg cgccgttacc   4020
accgctgcgt tcggtcaagg ttctggacca gttgcgtgag cgcatacgct acttgcatta   4080
cagcttacga accgaacagg cttatgtcca ctgggttcgt gccttcatcc gtttccacgg   4140
tgtgcgtcac ccggcaacct tgggcagcag cgaagtcgag gcatttctgt cctggctggc   4200
gaacgagcgc aaggtttcgg tctccacgca tcgtcaggca ttggcggcct tgctgttctt   4260
ctacggcaag gtgctgtgca cggatctgcc ctggcttcag gagatcggaa gacctcggcc   4320
gtcgcggcgc ttgccggtgg tgctgacccc ggatgaagtg gttcgcatcc tcggttttct   4380
ggaaggcgag catcgtttgt tcgcccagct tctgtatgga acgggcatgc ggatcagtga   4440
gggtttgcaa ctgcgggtca aggatctgga tttcgatcac ggcacgatca tcgtgcggga   4500
gggcaagggc tccaaggatc gggccttgat gttacccgag agcttggcac ccagcctgcg   4560
cgagcagggg aattaattcc cacgggtttt gctgcccgca aacgggctgt tctggtgttg   4620
ctagtttgtt atcagaatcg cagatccggc ttcagccggt ttgccggctg aaagcgctat   4680
ttcttccaga attgccatga tttttcccc acgggaggcg tcactggctc ccgtgttgtc   4740
ggcagctttg attcgataag cagcatcgcc tgtttcaggc tgtctatgtg tgactgttga   4800
gctgtaacaa gttgtctcag gtgttcaatt tcatgttcta gttgctttgt tttactggtt   4860
tcacctgttc tattaggtgt tacatgctgt tcatctgtta cattgtcgat ctgttcatgg   4920
tgaacagctt tgaatgcacc aaaaactcgt aaaagctctg atgtatctat ctttttaca   4980
```

ccgttttcat ctgtgcatat ggacagtttt ccctttgata tgtaacggtg aacagttgtt 5040
ctacttttgt ttgttagtct tgatgcttca ctgatagata caagagccat aagaacctca 5100
gatccttccg tatttagcca gtatgttctc tagtgtggtt cgttgttttt gcgtgagcca 5160
tgagaacgaa ccattgagat catacttact ttgcatgtca ctcaaaaatt ttgcctcaaa 5220
actggtgagc tgaatttttg cagttaaagc atcgtgtagt gtttttctta gtccgttatg 5280
taggtaggaa tctgatgtaa tggttgttgg tattttgtca ccattcattt ttatctggtt 5340
gttctcaagt tcggttacga gatccatttg tctatctagt tcaacttgga aaatcaacgt 5400
atcagtcggg cggcctcgct tatcaaccac caatttcata ttgctgtaag tgtttaaatc 5460
tttacttatt ggtttcaaaa cccattggtt aagcctttta aactcatggt agttattttc 5520
aagcattaac atgaacttaa attcatcaag gctaatctct atatttgcct tgtgagtttt 5580
cttttgtgtt agttctttta ataaccactc ataaatcctc atagagtatt tgttttcaaa 5640
agacttaaca tgttccagat tatattttat gaattttttt aactggaaaa gataaggcaa 5700
tatctcttca ctaaaaacta attctaattt ttcgcttgag aacttggcat agtttgtcca 5760
ctggaaaatc tcaaagcctt taaccaaagg attcctgatt tccacagttc tcgtcatcag 5820
ctctctggtt gctttagcta atacaccata agcattttcc ctactgatgt tcatcatctg 5880
agcgtattgg ttataagtga acgataccgt ccgttctttc cttgtagggt tttcaatcgt 5940
ggggttgagt agtgccacac agcataaaat tagcttggtt tcatgctccg ttaagtcata 6000
gcgactaatc gctagttcat ttgctttgaa aacaactaat tcagacatac atctcaattg 6060
gtctaggtga ttttaatcac tataccaatt gagatgggct agtcaatgat aattactagt 6120
ccttttcctt tgagttgtgg gtatctgtaa attctgctag acctttgctg gaaaacttgt 6180
aaattctgct agaccctctg taaattccgc tagacctttg tgtgtttttt ttgtttatat 6240
tcaagtggtt ataatttata gaataaagaa agaataaaaa aagataaaaa gaatagatcc 6300
cagccctgtg tataactcac tactttagtc agttccgcag tattacaaaa ggatgtcgca 6360
aacgctgttt gctcctctac aaaacagacc ttaaaaccct aaaggcttaa gtagcaccct 6420
cgcaagctcg ggcaaatcgc tgaatattcc ttttgtctcc gaccatcagg cacctgagtc 6480
gctgtctttt tcgtgacatt cagttcgctg cgctcacggc tctggcagtg aatgggggta 6540
aatggcacta caggcgcctt ttatggattc atgcaaggaa actacccata atacaagaaa 6600
agcccgtcac gggcttctca gggcgtttta tggcgggtct gctatgtggt gctatctgac 6660
tttttgctgt tcagcagttc ctgccctctg attttccagt ctgaccactt cggattatcc 6720
cgtgacaggt cattcagact ggctaatgca cccagtaagg cagcggtatc atcaacaggc 6780
tta 6783

<210> SEQ ID NO 54
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 54
ctggcgtaat agcgaagagg cccgcaccga tcgcccttcc caacagttgc gcagcctgaa 60
tggcgaatgg cgcctgatgc ggtattttct ccttacgcat ctgtgcggta tttcacaccg 120
catatggtgc actctcagta caatctgctc tgatgccgca tagttaagcc agccccgaca 180

-continued

```
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cggctgttc tggtgttgct agtttgttat cagaatcgca    2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgtttttgc gtgagccatg agaacgaacc attgagatca   2580
```

tacttacttt gcatgtcact caaaaatttt gcctcaaaac tggtgagctg aatttttgca 2640
gttaaagcat cgtgtagtgt ttttcttagt ccgttatgta ggtaggaatc tgatgtaatg 2700
gttgttggta ttttgtcacc attcattttt atctggttgt tctcaagttc ggttacgaga 2760
tccatttgtc tatctagttc aacttggaaa atcaacgtat cagtcgggcg gcctcgctta 2820
tcaaccacca atttcatatt gctgtaagtg tttaaatctt tacttattgg tttcaaaacc 2880
cattggttaa gccttttaaa ctcatggtag ttattttcaa gcattaacat gaacttaaat 2940
tcatcaaggc taatctctat atttgccttg tgagttttct tttgtgttag ttcttttaat 3000
aaccactcat aaatcctcat agagtatttg ttttcaaaag acttaacatg ttccagatta 3060
tattttatga attttttaa ctggaaaaga taaggcaata tctcttcact aaaaactaat 3120
tctaattttt cgcttgagaa cttggcatag tttgtccact ggaaaatctc aaagccttta 3180
accaaaggat tcctgatttc cacagttctc gtcatcagct ctctggttgc tttagctaat 3240
acaccataag cattttccct actgatgttc atcatctgag cgtattggtt ataagtgaac 3300
gataccgtcc gttctttcct tgtagggttt tcaatcgtgg ggttgagtag tgccacacag 3360
cataaaatta gcttggtttc atgctccgtt aagtcatagc gactaatcgc tagttcattt 3420
gctttgaaaa caactaattc agacatacat ctcaattggt ctaggtgatt ttaatcacta 3480
taccaattga gatgggctag tcaatgataa ttactagtcc ttttcctttg agttgtgggt 3540
atctgtaaat tctgctagac ctttgctgga aaacttgtaa attctgctag accctctgta 3600
aattccgcta gacctttgtg tgtttttttt gtttatattc aagtggttat aatttataga 3660
ataaagaaag aataaaaaaa gataaaaaga atagatccca gccctgtgta taactcacta 3720
ctttagtcag ttccgcagta ttacaaaagg atgtcgcaaa cgctgtttgc tcctctacaa 3780
aacagacctt aaaaccctaa aggcttaagt agcaccctcg caagctcggg caaatcgctg 3840
aatattcctt ttgtctccga ccatcaggca cctgagtcgc tgtctttttc gtgacattca 3900
gttcgctgcg ctcacggctc tggcagtgaa tgggggtaaa tggcactaca ggcgcctttt 3960
atggattcat gcaaggaaac tacccataat acaagaaaag cccgtcacgg gcttctcagg 4020
gcgttttatg gcgggtctgc tatgtggtgc tatctgactt tttgctgttc agcagttcct 4080
gccctctgat tttccagtct gaccacttcg gattatcccg tgacaggtca ttcagactgg 4140
ctaatgcacc cagtaaggca gcggtatcat caacaggctt acccgtctta ctgtcgggaa 4200
ttcgcgttgg ccgattcatt aatgcagatt ctgaaatgag ctgttgacaa ttaatcatcc 4260
ggctcgtata atgtgtggaa ttgtgagcgg ataacaattt cacacaggaa acagcgccgc 4320
tgagaaaaag cgaagcggca ctgctcttta acaatttatc agacaatctg tgtgggcact 4380
cgaccggaat tatcgattaa ctttattatt aaaaattaaa gaggtatata ttaatgtatc 4440
gattaaataa ggaggaataa accatgtgtg cgacctcttc tcaatttact cagattaccg 4500
agcataattc ccgtcgttcc gcaaactatc agccaaacct gtggaatttc gaattcctgc 4560
aatccctgga gaacgacctg aaagtggaaa agctggagga gaaagcgacc aaactggagg 4620
aagaagttcg ctgcatgatc aaccgtgtag acacccagcc gctgtccctg ctggagctga 4680
tcgacgatgt gcagcgcctg ggtctgacct acaaatttga aaaagacatc attaaagccc 4740
tggaaaacat cgtactgctg gacgaaaaca aaaagaacaa atctgacctg cacgcaaccg 4800
ctctgtcttt ccgtctgctg cgtcagcacg gtttcgaggt ttctcaggat gtttttgagc 4860
gtttcaagga taaagaaggt ggtttcagcg gtgaactgaa aggtgacgtc caaggcctgc 4920
tgagcctgta tgaagcgtct tacctgggtt tcgagggtga gaacctgctg gaggaggcgc 4980
gtaccttttc catcacccac ctgaagaaca acctgaaaga aggcattaat accaaggttg 5040
cagaacaagt gagccacgcc ctggaactgc catatcacca gcgtctgcac cgtctggagg 5100
cacgttggtt cctggataaa tacgaaccga aagaaccgca tcaccagctg ctgctggagc 5160
tggcgaagct ggattttaac atggtacaga ccctgcacca gaaagagctg caagatctgt 5220
cccgctggtg gaccgagatg ggcctggcta gcaaactgga ttttgtacgc gaccgcctga 5280
tggaagttta tttctgggca ctgggtatgg cgccagaccc gcagtttggt gaatgtcgca 5340
aagctgttac taaaatgttt ggtctggtga cgatcatcga tgacgtgtat gacgtttatg 5400
gcactctgga cgaactgcaa ctgttcaccg atgctgtaga gcgctgggac gttaacgcta 5460
ttaacaccct gccggactat atgaaactgt gtttcctggc actgtacaac accgttaacg 5520
acacgtccta ttctattctg aaagagaaag gtcataacaa cctgtcctat ctgacgaaaa 5580
gctggcgtga actgtgcaaa gcctttctgc aagaggcgaa atggtccaac aacaaaatta 5640
tcccggcttt ctccaagtac ctggaaaacg ccagcgtttc ctcctccggt gtagcgctgc 5700
tggcgccgtc ttacttttcc gtatgccagc agcaggaaga catctccgac cacgcgctgc 5760
gttccctgac cgacttccat ggtctggtgc gttctagctg cgttatcttc cgcctgtgca 5820
acgatctggc cacctctgcg gcggagctgg aacgtggcga gactaccaat tctatcatta 5880
gctacatgca cgaaaacgat ggtaccagcg aggaacaggc ccgcgaagaa ctgcgtaaac 5940
tgatcgacgc cgaatggaaa aagatgaatc gtgaacgcgt tagcgactcc accctgctgc 6000
ctaaagcgtt catggaaatc gcagttaaca tggcacgtgt ttcccactgc acctaccagt 6060
atggcgatgg tctgggtcgc ccagactacg cgactgaaaa ccgcatcaaa ctgctgctga 6120
ttgacccttt cccgattaac cagctgatgt atgtctaact gcatcgccct taggaggtaa 6180
aaaaaaatga ctgccgacaa caatagtatg ccccatggtg cagtatctag ttacgccaaa 6240
ttagtgcaaa accaaacacc tgaagacatt ttggaagagt ttcctgaaat tattccatta 6300
caacaaagac ctaatacccg atctagtgag acgtcaaatg acgaaagcgg agaaacatgt 6360
ttttctggtc atgatgagga gcaaattaag ttaatgaatg aaaattgtat tgttttggat 6420
tgggacgata atgctattgg tgccggtacc aagaaagttt gtcatttaat ggaaaatatt 6480
gaaaagggtt tactacatcg tgcattctcc gtctttattt tcaatgaaca aggtgaatta 6540
cttttacaac aaagagccac tgaaaaaata actttccctg atctttggac taacacatgc 6600
tgctctcatc cactatgtat tgatgacgaa ttaggtttga agggtaagct agacgataag 6660
attaagggcg ctattactgc ggcggtgaga aaactagatc atgaattagg tattccagaa 6720
gatgaaacta agacaagggg taagtttcac tttttaaaca gaatccatta catggcacca 6780
agcaatgaac catggggtga acatgaaatt gattacatcc tattttataa gatcaacgct 6840
aaagaaaact tgactgtcaa cccaaacgtc aatgaagtta gagacttcaa atgggtttca 6900
ccaaatgatt tgaaaactat gtttgctgac ccaagttaca agtttacgcc ttggtttaag 6960
attatttgcg agaattactt attcaactgg tgggagcaat tagatgacct ttctgaagtg 7020
gaaaatgaca ggcaaattca tagaatgcta taacgacgcg tcctgcagct ggtaccatat 7080
gggaattcga agctttctag aacgaaaact catctcagaa gaggatctga atagcgccgt 7140
cgaccatcat catcatcatc attgagttta aacggtctcc agcttggctg ttttggcgga 7200
tgagagaaga ttttcagcct gatacagatt aaatcagaac gcagaagcgg tctgataaaa 7260
cagaatttgc ctggcggcag tagcgcggtg gtcccacctg accccatgcc gaactcagaa 7320
gtgaaacgcc gtagcgccga tggtagtgtg gggtctcccc atgcgagagt agggaactgc 7380
caggcatcaa ataaaacgaa aggctcagtc gaaagactgg gcctttcgtt ttatctgttg 7440
tttgtcggtg aacgctctcc tgagtaggac aaatccgccg ggagcggatt tgaacgttgc 7500
gaagcaacgg cccggagggt ggcgggcagg acgcccgcca taaactgcca ggcatcaaat 7560
taagcagaag gccatcctga cggatggcct ttttgcgttt ctacaaactc tttttgttta 7620
tttttctaaa tacattcaaa tatgtatccg ctcatgagac aataaccctg ataaatgctt 7680
caataat 7687

<210> SEQ ID NO 55
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55
cccgtcttac tgtcgggaat tcgcgttggc cgattcatta atgcagatta ttgaagcatt 60
tatcagggtt attgtctcat gagcggatac atatttgaat gtatttagaa aaataaacaa 120
aaagagtttg tagaaacgca aaaaggccat ccgtcaggat ggccttctgc ttaatttgat 180
gcctggcagt ttatggcggg cgtcctgccc gccaccctcc gggccgttgc ttcgcaacgt 240
tcaaatccgc tcccggcgga tttgtcctac tcaggagagc gttcaccgac aaacaacaga 300
taaaacgaaa ggcccagtct ttcgactgag cctttcgttt tatttgatgc ctggcagttc 360
cctactctcg catggggaga ccccacacta ccatcggcgc tacggcgttt cacttctgag 420
ttcggcatgg ggtcaggtgg gaccaccgcg ctactgccgc caggcaaatt ctgttttatc 480
agaccgcttc tgcgttctga tttaatctgt atcaggctga aaatcttctc tcatccgcca 540
aaacagccaa gctggagacc gtttaaactc aatgatgatg atgatgatgg tcgacggcgc 600
tattcagatc ctcttctgag atgagttttt gttctagaaa gcttcgaatt cccatatggt 660
accagctgca gttatgccag ccaggccttg attttggctt ccataccagc ggcatcgagg 720
ccgagttcgg cgcgcatttc ttcctgagtt ccttgcggaa taaagaagtc cggcaggcca 780
atgttcagca cgggtactgg tttacgatgg gccatcagca cttcgttcac gccgctgcct 840
gcgccgccca taatggcgtt ttcttctacg gtgaccagcg cttcatggct ggcggccatt 900
tccagaatta acgcttcatc aagcggtttc acaaaacgca tatcgaccag cgtggcgttc 960
agcgattcgg cgactttcgc cgcttctggc atcagcgtac caaagttaag gatcgccagt 1020
ttctcgccac gacgcttcac aatgcctttg ccaattggta gtttttccag cggcgtcagt 1080
tccacgccga ccgcgttgcc acgcgggtag cgcaccgctg acgggccatc gttatagtga 1140
tagccggtat agagcatctg gcgacattcg ttttcatcgc tcggggtcat aatgaccatt 1200
tccggtatgc agcgcaggta agagagatca aaagcaccct gatgggtttg accgtcagca 1260
ccaacaatgc ccgcgcggtc gatggcgaac aggaccggaa gcttttgaat cgccacgtca 1320
tgcagcacct gatcataggc gcgttgcagg aaagtggagt aaatcgcgac aatgggtttg 1380
tacccaccaa tcgccagacc cgcagcaaag gtcaccgcgt gttgctcggc aattgccacg 1440
tcgaagtagc gatccgggaa tttacgtgaa aactcgacca tgccggaacc ttcacgcatc 1500
gccggagtaa tcgccatcag cttgttgtct ttcgctgccg tttcgcacaa ccagtcgcca 1560
aagatttttg aatagctcgg caaaccgccg ctacttttcg gcaaacaacc gctggaggga 1620

-continued

```
tcaaatttag gcacggcgtg gaaagtgatc gggtcttttt ctgccggttc ataaccacga   1680
cctttttgg tcatgatatg caggaactgc gggcctttca ggtcgcgcat gttctttagc   1740
gtggtgataa gccccagcac atcgtgaccg tccaccgggc cgatgtagtt aaagcccagc   1800
tcttcaaaca acgtgccagg cactaccatg cctttaatat gttcttcggt gcgtttgagc   1860
agctctttaa ttggcggcac gccagagaaa actttttcc cgccttcgcg cagtgaagag   1920
taaagcttac cggaaagcag ctgtgccaga tggttgttga gcgcgccgac attttcggaa   1980
atcgacattt cattgtcgtt gagaatcacc agcatatcag gacggatatc gcccgcgtga   2040
ttcatcgctt caaacgccat gcctgcggta atcgcgccat cgccaatgac acagacggtg   2100
cggcgatttt tgccttcttt ttcggcagca accgcaatac caattccggc actgatggag   2160
gttgatgaat gcccgacgct taatacgtca tattcgcttt cgccgcgcca cgggaacggg   2220
tgcagaccgc ctttctgacg gatggtgccg attttgtcgc ggcgtccggt caaaatttta   2280
tgcggataag cctgatgccc cacatcccaa atcaattggt caaacggggt gttgtagaca   2340
tagtgcagcg ccacggtcag ttcgaccgtg cccagcccgg aggcgaagtg cccgctggaa   2400
cggctcacgc tgtcgagtaa atagcggcgc agttcgtcgc agagtttcgg taaactctct   2460
ttcggcaaca gtcgtaactc ctgggtggag tcgaccagtg ccagggtcgg gtatttggca   2520
atatcaaaac tcatgttttt ttacctccta agggcgaatg cagttagaca tacatcagct   2580
ggttaatcgg gaaagggtca atcagcagca gtttgatgcg gttttcagtc gcgtagtctg   2640
ggcgacccag accatcgcca tactggtagg tgcagtggga aacacgtgcc atgttaactg   2700
cgatttccat gaacgcttta ggcagcaggg tggagtcgct aacgcgttca cgattcatct   2760
ttttccattc ggcgtcgatc agtttacgca gttcttcgcg ggcctgttcc tcgctggtac   2820
catcgttttc gtgcatgtag ctaatgatag aattggtagt ctcgccacgt tccagctccg   2880
ccgcagaggt ggccagatcg ttgcacaggc ggaagataac gcagctagaa cgcaccagac   2940
catggaagtc ggtcagggaa cgcagcgcgt ggtcggagat gtcttcctgc tgctggcata   3000
cggaaaagta agacggcgcc agcagcgcta caccggagga ggaaacgctg gcgttttcca   3060
ggtacttgga gaaagccggg ataattttgt tgttggacca tttcgcctct tgcagaaagg   3120
ctttgcacag ttcacgccag cttttcgtca gataggacag gttgttatga cctttctctt   3180
tcagaataga ataggacgtg tcgttaacgg tgttgtacag tgccaggaaa cacagtttca   3240
tatagtccgg cagggtgtta atagcgttaa cgtcccagcg ctctacagca tcggtgaaca   3300
gttgcagttc gtccagagtg ccataaacgt catacacgtc atcgatgatc gtcaccagac   3360
caaacatttt agtaacagct ttgcgacatt caccaaactg cgggtctggc gccataccca   3420
gtgcccagaa ataaacttcc atcaggcggt cgcgtacaaa atccagtttg ctagccaggc   3480
ccatctcggt ccaccagcgg gacagatctt gcagctcttt ctggtgcagg gtctgtacca   3540
tgttaaaatc cagcttcgcc agctccagca gcagctggtg atgcggttct ttcggttcgt   3600
atttatccag gaaccaacgt gcctccagac ggtgcagacg ctggtgatat ggcagttcca   3660
gggcgtggct cacttgttct gcaaccttgg tattaatgcc ttctttcagg ttgttcttca   3720
ggtgggtgat ggaaaaggta cgcgcctcct ccagcaggtt ctcaccctcg aaacccaggt   3780
aagacgcttc atacaggctc agcaggcctt ggacgtcacc tttcagttca ccgctgaaac   3840
caccttcttt atccttgaaa cgctcaaaaa catcctgaga aacctcgaaa ccgtgctgac   3900
gcagcagacg gaaagacaga gcggttgcgt gcaggtcaga tttgttcttt ttgttttcgt   3960
ccagcagtac gatgttttcc agggctttaa tgatgtcttt ttcaaatttg taggtcagac   4020
```

ccaggcgctg cacatcgtcg atcagctcca gcagggacag cggctgggtg tctacacggt 4080
tgatcatgca gcgaacttct tcctccagtt tggtcgcttt ctcctccagc ttttccactt 4140
tcaggtcgtt ctccagggat tgcaggaatt cgaaattcca caggtttggc tgatagtttg 4200
cggaacgacg ggaattatgc tcggtaatct gagtaaattg agaagaggtc gcacacatgg 4260
tttattcctc cttatttaat cgatacatta atatatacct ctttaatttt taataataaa 4320
gttaatcgat aattccggtc gagtgcccac acagattgtc tgataaattg ttaaagagca 4380
gtgccgcttc gctttttctc agcggcgctg tttcctgtgt gaaattgtta tccgctcaca 4440
attccacaca ttatacgagc cggatgatta attgtcaaca gctcatttca gaatctggcg 4500
taatagcgaa gaggcccgca ccgatcgccc ttcccaacag ttgcgcagcc tgaatggcga 4560
atggcgcctg atgcggtatt ttctccttac gcatctgtgc ggtatttcac accgcatatg 4620
gtgcactctc agtacaatct gctctgatgc cgcatagtta agccagcccc gacacccgcc 4680
aacacccgct gacgagctta gtaaagccct cgctagattt taatgcggat gttgcgatta 4740
cttcgccaac tattgcgata acaagaaaaa gccagccttt catgatatat ctcccaattt 4800
gtgtagggct tattatgcac gcttaaaaat aataaaagca gacttgacct gatagtttgg 4860
ctgtgagcaa ttatgtgctt agtgcatcta acgcttgagt taagccgcgc cgcgaagcgg 4920
cgtcggcttg aacgaattgt tagacattat ttgccgacta ccttggtgat ctcgcctttc 4980
acgtagtgga caaattcttc caactgatct gcgcgcgagg ccaagcgatc ttcttcttgt 5040
ccaagataag cctgtctagc ttcaagtatg acgggctgat actgggccgg caggcgctcc 5100
attgcccagt cggcagcgac atccttcggc gcgattttgc cggttactgc gctgtaccaa 5160
atgcgggaca acgtaagcac tacatttcgc tcatcgccag cccagtcggg cggcgagttc 5220
catagcgtta aggtttcatt tagcgcctca aatagatcct gttcaggaac cggatcaaag 5280
agttcctccg ccgctggacc taccaaggca acgctatgtt ctcttgcttt tgtcagcaag 5340
atagccagat caatgtcgat cgtggctggc tcgaagatac ctgcaagaat gtcattgcgc 5400
tgccattctc caaattgcag ttcgcgctta gctggataac gccacggaat gatgtcgtcg 5460
tgcacaacaa tggtgacttc tacagcgcgg agaatctcgc tctctccagg ggaagccgaa 5520
gtttccaaaa ggtcgttgat caaagctcgc cgcgttgttt catcaagcct tacggtcacc 5580
gtaaccagca aatcaatatc actgtgtggc ttcaggccgc catccactgc ggagccgtac 5640
aaatgtacgg ccagcaacgt cggttcgaga tggcgctcga tgacgccaac tacctctgat 5700
agttgagtcg atacttcggc gatcaccgct tccctcatga tgtttaactt tgttttaggg 5760
cgactgccct gctgcgtaac atcgttgctg ctccataaca tcaaacatcg acccacggcg 5820
taacgcgctt gctgcttgga tgcccgaggc atagactgta ccccaaaaaa acagtcataa 5880
caagccatga aaaccgccac tgcgccgtta ccaccgctgc gttcggtcaa ggttctggac 5940
cagttgcgtg agcgcatacg ctacttgcat tacagcttac gaaccgaaca ggcttatgtc 6000
cactgggttc gtgccttcat ccgtttccac ggtgtgcgtc acccggcaac cttgggcagc 6060
agcgaagtcg aggcatttct gtcctggctg gcgaacgagc gcaaggtttc ggtctccacg 6120
catcgtcagg cattggcggc cttgctgttc ttctacggca aggtgctgtg cacggatctg 6180
ccctggcttc aggagatcgg aagacctcgg ccgtcgcggc gcttgccggt ggtgctgacc 6240
ccggatgaag tggttcgcat cctcggtttt ctggaaggcg agcatcgttt gttcgcccag 6300
cttctgtatg gaacgggcat gcggatcagt gagggtttgc aactgcgggt caaggatctg 6360

-continued

```
gatttcgatc acggcacgat catcgtgcgg gagggcaagg gctccaagga tcgggccttg   6420
atgttacccg agagcttggc acccagcctg cgcgagcagg ggaattaatt cccacgggtt   6480
ttgctgcccg caaacgggct gttctggtgt tgctagtttg ttatcagaat cgcagatccg   6540
gcttcagccg gtttgccggc tgaaagcgct atttcttcca gaattgccat gatttttcc    6600
ccacgggagg cgtcactggc tcccgtgttg tcggcagctt tgattcgata agcagcatcg   6660
cctgtttcag gctgtctatg tgtgactgtt gagctgtaac aagttgtctc aggtgttcaa   6720
tttcatgttc tagttgcttt gttttactgg tttcacctgt tctattaggt gttacatgct   6780
gttcatctgt tacattgtcg atctgttcat ggtgaacagc tttgaatgca ccaaaaactc   6840
gtaaaagctc tgatgtatct atcttttta caccgttttc atctgtgcat atggacagtt    6900
ttccctttga tatgtaacgg tgaacagttg ttctactttt gtttgttagt cttgatgctt   6960
cactgataga tacaagagcc ataagaacct cagatccttc cgtatttagc cagtatgttc   7020
tctagtgtgg ttcgttgttt ttgcgtgagc catgagaacg aaccattgag atcatactta   7080
ctttgcatgt cactcaaaaa ttttgcctca aaactggtga gctgaatttt tgcagttaaa   7140
gcatcgtgta gtgtttttct tagtccgtta tgtaggtagg aatctgatgt aatggttgtt   7200
ggtattttgt caccattcat ttttatctgg ttgttctcaa gttcggttac gagatccatt   7260
tgtctatcta gttcaacttg gaaaatcaac gtatcagtcg ggcggcctcg cttatcaacc   7320
accaatttca tattgctgta agtgtttaaa tctttactta ttggtttcaa aacccattgg   7380
ttaagccttt taaactcatg gtagttattt tcaagcatta acatgaactt aaattcatca   7440
aggctaatct ctatatttgc cttgtgagtt ttcttttgtg ttagttcttt taataaccac   7500
tcataaatcc tcatagagta tttgttttca aaagacttaa catgttccag attatatttt   7560
atgaattttt ttaactggaa aagataaggc aatatctctt cactaaaaac taattctaat   7620
ttttcgcttg agaacttggc atagtttgtc cactggaaaa tctcaaagcc tttaaccaaa   7680
ggattcctga tttccacagt tctcgtcatc agctctctgg ttgctttagc taatacacca   7740
taagcatttt ccctactgat gttcatcatc tgagcgtatt ggttataagt gaacgatacc   7800
gtccgttctt tccttgtagg gttttcaatc gtggggttga gtagtgccac acagcataaa   7860
attagcttgg tttcatgctc cgttaagtca tagcgactaa tcgctagttc atttgctttg   7920
aaaacaacta attcagacat acatctcaat tggtctaggt gattttaatc actataccaa   7980
ttgagatggg ctagtcaatg ataattacta gtccttttcc tttgagttgt gggtatctgt   8040
aaattctgct agacctttgc tggaaaactt gtaaattctg ctagaccctc tgtaaattcc   8100
gctagacctt tgtgtgtttt ttttgtttat attcaagtgg ttataattta tagaataaag   8160
aaagaataaa aaaagataaa aagaatagat cccagccctg tgtataactc actactttag   8220
tcagttccgc agtattacaa aaggatgtcg caaacgctgt ttgctcctct acaaaacaga   8280
ccttaaaacc ctaaaggctt aagtagcacc ctcgcaagct cgggcaaatc gctgaatatt   8340
ccttttgtct ccgaccatca ggcacctgag tcgctgtctt tttcgtgaca ttcagttcgc   8400
tgcgctcacg gctctggcag tgaatggggg taaatggcac tacaggcgcc ttttatggat   8460
tcatgcaagg aaactaccca taatacaaga aaagcccgtc acgggcttct cagggcgttt   8520
tatggcgggt ctgctatgtg gtgctatctg actttttgct gttcagcagt tcctgccctc   8580
tgattttcca gtctgaccac ttcggattat cccgtgacag gtcattcaga ctggctaatg   8640
cacccagtaa ggcagcggta tcatcaacag gctta                              8675
```

```
<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56

tcgctgcgct cggtcgttcg gctgcggcga gcggtatcag ctcactcaaa ggcggtaata     60

cggttatcca cagaatcagg ggataacgca ggaaagaaca tgtgagcaaa aggccagcaa    120

aaggccagga accgtaaaaa ggccgcgttg ctggcgtttt tccataggct ccgcccccct    180

gacgagcatc acaaaaatcg acgctcaagt cagaggtggc gaaacccgac aggactataa    240

agataccagg cgtttccccc tggaagctcc ctcgtgcgct ctcctgttcc gaccctgccg    300

cttaccggat acctgtccgc ctttctccct tcgggaagcg tggcgctttc tcatagctca    360

cgctgtaggt atctcagttc ggtgtaggtc gttcgctcca agctgggctg tgtgcacgaa    420

ccccccgttc agcccgaccg ctgcgcctta tccggtaact atcgtcttga gtccaacccg    480

gtaagacacg acttatcgcc actggcagca gccactggta acaggattag cagagcgagg    540

tatgtaggcg gtgctacaga gttcttgaag tggtggccta actacggcta cactagaaga    600

acagtatttg gtatctgcgc tctgctgaag ccagttacct tcggaaaaag agttggtagc    660

tcttgatccg gcaaacaaac caccgctggt agcggtggtt tttttgtttg caagcagcag    720

attacgcgca gaaaaaaagg atctcaagaa gatcctttga tcttttctac ggggtctgac    780

gctcagtgga acgaaaactc acgttaaggg attttggtca tgagattatc aaaaaggatc    840

ttcacctaga tccttttaaa ttaaaaatga agttttaaat caatctaaag tatatatgag    900

taaacttggt ctgacagtta ccaatgctta atcagtgagg cacctatctc agcgatctgt    960

ctatttcgtt catccatagt tgcctgactc cccgtcgtgt agataactac gatacgggag   1020

ggcttaccat ctggccccag tgctgcaatg ataccgcgag acccacgctc accggctcca   1080

gatttatcag caataaacca gccagccgga agggccgagc gcagaagtgg tcctgcaact   1140

ttatccgcct ccatccagtc tattaattgt tgccgggaag ctagagtaag tagttcgcca   1200

gttaatagtt tgcgcaacgt tgttgccatt gctacaggca tcgtggtgtc acgctcgtcg   1260

tttggtatgg cttcattcag ctccggttcc caacgatcaa ggcgagttac atgatccccc   1320

atgttgtgca aaaaagcggt tagctccttc ggtcctccga tcgttgtcag aagtaagttg   1380

gccgcagtgt tatcactcat ggttatggca gcactgcata attctcttac tgtcatgcca   1440

tccgtaagat gcttttctgt gactggtgag tactcaacca agtcattctg agaatagtgt   1500

atgcggcgac cgagttgctc ttgcccggcg tcaatacggg ataataccgc gccacatagc   1560

agaactttaa aagtgctcat cattggaaaa cgttcttcgg ggcgaaaact ctcaaggatc   1620

ttaccgctgt tgagatccag ttcgatgtaa cccactcgtg cacccaactg atcttcagca   1680

tcttttactt tcaccagcgt ttctgggtga gcaaaaacag gaaggcaaaa tgccgcaaaa   1740

aagggaataa gggcgacacg gaaatgttga atactcatac tcttcctttt tcaatattat   1800

tgaagcattt atcagggtta ttgtctcatg agcggataca tatttgaatg tatttagaaa   1860

aataaacaaa taggggttcc gcgcacattt ccccgaaaag tgccacctga cgtctaagaa   1920

accattatta tcatgacatt aacctataaa aataggcgta tcacgaggcc ctttcgtctc   1980

gcgcgtttcg gtgatgacgg tgaaaacctc tgacacatgc agctcccgga gacggtcaca   2040

gcttgtctgt aagcggatgc cgggagcaga caagcccgtc agggcgcgtc agcgggtgtt   2100
```

-continued ggcgggtgtc ggggctggct taactatgcg gcatcagagc agattgtact gagagtgcac 2160
catagatctg gagctgtaat ataaaaacct tcttcaacta acggggcagg ttagtgacat 2220
tagaaaaccg actgtaaaaa gtacagtcgg cattatctca tattataaaa gccagtcatt 2280
aggcctatct gacaattcct gaatagagtt cataaacaat cctgcatgat aaccatcaca 2340
aacagaatga tgtacctgta aagatagcgg taaatatatt gaattacctt tattaatgaa 2400
ttttcctgct gtaataatgg gtagaaggta attactatta ttattgatat ttaagttaaa 2460
cccagtaaat gaagtccatg gaataataga aagagaaaaa gcattttcag gtataggtgt 2520
tttgggaaac aatttccccg aaccattata tttctctaca tcagaaaggt ataaatcata 2580
aaactctttg aagtcattct ttacaggagt ccaaatacca gagaatgttt tagatacacc 2640
atcaaaaatt gtataaagtg gctctaactt atcccaataa cctaactctc cgtcgctatt 2700
gtaaccagtt ctaaaagctg tatttgagtt tatcaccctt gtcactaaga aaataaatgc 2760
agggtaaaat ttatatcctt cttgttttat gtttcggtat aaaacactaa tatcaatttc 2820
tgtggttata ctaaaagtcg tttgttggtt caaataatga ttaaatatct cttttctctt 2880
ccaattgtct aaatcaattt tattaaagtt catttgatat gcctcctaaa tttttatcta 2940
aagtgaattt aggaggctta cttgtctgct ttcttcatta gaatcaatcc tttttttaaaa 3000 gtcaatatta ctgtaacata aatatatatt ttaaaaatat cccactttat ccaattttcg 3060
tttgttgaac taatgggtgc tttagttgaa gaataaaaga cctatgcggt gtgaaatacc 3120
gcacagatgc gtaaggagaa aataccgcat caggcgccat tcgccattca ggctgcgcaa 3180
ctgttgggaa gggcgatcgg tgcgggcctc ttcgctatta cgccagctgg cgaaaggggg 3240
atgtgctgca aggcgattaa gttgggtaac gccagggttt tcccagtcac gacgttgtaa 3300
aacgacggcc agtgccaagc ttgcatgcct gcactccatt ttcttctgct atcaaaataa 3360
cagactcgtg attttccaaa cgagctttca aaaaagcctc tgccccttgc aaatcggatg 3420
cctgtctata aaattcccga tattggttaa acagcggcgc aatggcggcc gcatctgatg 3480
tctttgcttg gcgaatgttc atcttatttc ttcctccctc tcaataattt tttcattcta 3540 tccctttttct gtaaagttta tttttcagaa tacttttatc atcatgcttt gaaaaaatat 3600
cacgataata tccattgttc tcacggaagc acacgcaggt catttgaacg aatttttttcg 3660 acaggaattt gccgggactc aggagcattt aacctaaaaa agcatgacat ttcagcataa 3720
tgaacattta ctcatgtcta ttttcgttct tttctgtatg aaaatagtta tttcgagtct 3780
ctacggaaat agcgagagat gatataccta aatagagata aaatcatctc aaaaaaatgg 3840
gtctactaaa atattattcc atctattaca ataaattcac agaatagtct tttaagtaag 3900
tctactctga atttttttaa aaggagaggg taaagagtga aaacagtagt tattattgat 3960
gcattacgaa caccaattgg aaaatataaa ggcagcttaa gtcaagtaag tgccgtagac 4020
ttaggaacac atgttacaac acaactttta aaaagacatt ccactatttc tgaagaaatt 4080
gatcaagtaa tctttggaaa tgttttacaa gctggaaatg gccaaaatcc cgcacgacaa 4140
atagcaataa acagcggttt gtctcatgaa attcccgcaa tgacggttaa tgaggtctgc 4200
ggatcaggaa tgaaggccgt tattttggcg aaacaattga ttcaattagg agaagcggaa 4260
gttttaattg ctggcgggat tgagaatatg tcccaagcac ctaaattaca acgttttaat 4320
tacgaaacag aaagctacga tgcgcctttt tctagtatga tgtatgatgg attaacggat 4380
gcctttagtg gtcaggcaat gggcttaact gctgaaaatg tggccgaaaa gtatcatgta 4440
actagagaag agcaagatca attttctgta cattcacaat taaaagcagc tcaagcacaa 4500

-continued

```
gcagaaggga tattcgctga cgaaatagcc ccattagaag tatcaggaac gcttgtggag   4560
aaagatgaag ggattcgccc taattcgagc gttgagaagc taggaacgct taaaacagtt   4620
tttaaagaag acggtactgt aacagcaggg aatgcatcaa ccattaatga tggggcttct   4680
gctttgatta ttgcttcaca agaatatgcc gaagcacacg gtcttcctta tttagctatt   4740
attcgagaca gtgtggaagt cggtattgat ccagcctata tgggaatttc gccgattaaa   4800
gccattcaaa aactgttagc gcgcaatcaa cttactacgg aagaaattga tctgtatgaa   4860
atcaacgaag catttgcagc aacttcaatc gtggtccaaa gagaactggc tttaccagag   4920
gaaaaggtca acatttatgg tggcggtatt tcattaggtc atgcgattgg tgccacaggt   4980
gctcgtttat taacgagttt aagttatcaa ttaaatcaaa aagaaaagaa atatggagtg   5040
gcttctttat gtatcggcgg tggcttagga ctcgctatgc tactagagag acctcagcaa   5100
aaaaaaaaca gccgatttta tcaaatgagt cctgaggaac gcctggcttc tcttcttaat   5160
gaaggccaga tttctgctga tacaaaaaaa gaatttgaaa atacggcttt atcttcgcag   5220
attgccaatc atatgattga aaatcaaatc agtgaaacag aagtgccgat gggcgttggc   5280
ttacatttaa cagtggacga aactgattat ttggtaccaa tggcgacaga agagccctca   5340
gttattgcgg ctttgagtaa tggtgcaaaa atagcacaag gatttaaaac agtgaatcaa   5400
caacgcttaa tgcgtggaca aatcgttttt tacgatgttg cagatcccga gtcattgatt   5460
gataaactac aagtaagaga agcggaagtt tttcaacaag cagagttaag ttatccatct   5520
atcgttaaac ggggcggcgg cttaagagat ttgcaatatc gtacttttga tgaatcattt   5580
gtatctgtcg actttttagt agatgttaag gatgcaatgg gggcaaatat cgttaacgct   5640
atgttggaag gtgtggccga gttgttccgt gaatggtttg cggagcaaaa gattttattc   5700
agtattttaa gtaattatgc cacggagtcg gttgttacga tgaaaacggc tattccagtt   5760
tcacgtttaa gtaaggggag caatggccgg gaaattgctg aaaaaattgt tttagcttca   5820
cgctatgctt cattagatcc ttatcgggca gtcacgcata acaaaggaat catgaatggc   5880
attgaagctg tagttttagc tacaggaaat gatacacgcg ctgttagcgc ttcttgtcat   5940
gcttttgcgg tgaaggaagg tcgctaccaa ggcttgacta gttggacgct ggatggcgaa   6000
caactaattg gtgaaatttc agttccgctt gctttagcca cggttggcgg tgccacaaaa   6060
gtcttaccta aatctcaagc agctgctgat ttgttagcag tgacggatgc aaaagaacta   6120
agtcgagtag tagcggctgt tggtttggca caaaatttag cggcgttacg ggccttagtc   6180
tctgaaggaa ttcaaaaagg acacatggct ctacaagcac gttctttagc gatgacggtc   6240
ggagctactg gtaaagaagt tgaggcagtc gctcaacaat taaaacgtca aaaaacgatg   6300
aaccaagacc gagccatggc tattttaaat gatttaagaa aacaataaaa ggagagggtg   6360
acaattggga ttgataaaat tagttttttt gtgccccctt attatattga tatgacggca   6420
ctggctgaag ccagaaatgt agaccctgga aaatttcata ttggtattgg gcaagaccaa   6480
atggcggtga acccaatcag ccaagatatt gtgacatttg cagccaatgc cgcagaagcg   6540
atcttgacca aagaagataa agaggccatt gatatggtga ttgtcgggac tgagtccagt   6600
atcgatgagt caaaagcggc cgcagttgtc ttacatcgtt taatggggat tcaacctttc   6660
gctcgctctt tcgaaatcaa ggaagcttgt tacggagcaa cagcaggctt acagttagct   6720
aagaatcacg tagccttaca tccagataaa aaagtcttgg tcgtagcggc agatattgca   6780
aaatatggct taaattctgg cggtgagcct acacaaggag ctggggcggt tgcaatgtta   6840
```

-continued gttgctagtg aaccgcgcat tttggcttta aaagaggata atgtgatgct gacgcaagat 6900
atctatgact tttggcgtcc aacaggccac ccgtatccta tggtcgatgg tcctttgtca 6960
aacgaaacct acatccaatc ttttgcccaa gtctgggatg aacataaaaa acgaaccggt 7020
cttgattttg cagattatga tgctttagcg ttccatattc cttacacaaa aatgggcaaa 7080
aaagccttat tagcaaaaat ctccgaccaa actgaagcag aacaggaacg aattttagcc 7140
cgttatgaag aaagtatcgt ctatagtcgt cgcgtaggaa acttgtatac gggttcactt 7200
tatctgggac tcatttccct tttagaaaat gcaacgactt taaccgcagg caatcaaatt 7260
ggtttattca gttatggttc tggtgctgtc gctgaatttt tcactggtga attagtagct 7320
ggttatcaaa atcatttaca aaaagaaact catttagcac tgctggataa tcggacagaa 7380
ctttctatcg ctgaatatga agccatgttt gcagaaactt tagacacaga cattgatcaa 7440
acgttagaag atgaattaaa atatagtatt tctgctatta ataataccgt tcgttcttat 7500
cgaaactaaa aaaaaccggc cttggccccg ccggtttttt attattttc ttcctccgca 7560 tgttcaatcc gctccataat cgacggatgg ctccctctga aaattttaac gagaaacggc 7620
gggttgaccc ggctcagtcc cgtaacggcc aagtcctgaa acgtctcaat cgccgcttcc 7680
cggtttccgg tcagctcaat gccgtaacgg tcggcggcgt tttcctgata ccgggagacg 7740
gcattcgtaa tcgggatccc cgggtaccga gctcgaattc gtaatcatgt catagctgtt 7800
tcctgtgtga aattgttatc cgctcacaat tccacacaac atacgagccg gaagcataaa 7860
gtgtaaagcc tggggtgcct aatgagtgag ctaactcaca ttaattgcgt tgcgctcact 7920
gcccgctttc cagtcgggaa acctgtcgtg ccagctgcat taatgaatcg gccaacgcgc 7980
ggggagaggc ggtttgcgta ttgggcgctc ttccgcttcc tcgctcactg ac 8032

<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57
gaattgctcc attttcttct gctatcaaaa taacagactc gtgattttcc aaacgagctt 60
tcaaaaaagc ctctgcccct tgcaaatcgg atgcctgtct ataaaattcc cgatattggt 120
taaacagcgg cgcaatggcg gccgcatctg atgtctttgc ttggcgaatg ttcatcttat 180
ttcttcctcc ctctcaataa ttttttcatt ctatcccttt tctgtaaagt ttatttttca 240
gaatactttt atcatcatgc tttgaaaaaa tatcacgata atatccattg ttctcacgga 300
agcacacgca ggtcatttga acgaattttt tcgacaggaa tttgccggga ctcaggagca 360
tttaacctaa aaaagcatga catttcagca taatgaacat ttactcatgt ctattttcgt 420
tcttttctgt atgaaaatag ttatttcgag tctctacgga aatagcgaga gatgatatac 480
ctaaatagag ataaaatcat ctcaaaaaaa tgggtctact aaaatattat tccatctatt 540
acaataaatt cacagaatag tcttttaagt aagtctactc tgaatttttt taaaaggaga 600
gggtaaagag tgtgtgcgac ctcttctcaa tttactcaga ttaccgagca taattcccgt 660
cgttccgcaa actatcagcc aaacctgtgg aatttcgaat tcctgcaatc cctggagaac 720
gacctgaaag tggaaaagct ggaggagaaa gcgaccaaac tggaggaaga agttcgctgc 780
atgatcaacc gtgtagacac ccagccgctg tccctgctgg agctgatcga cgatgtgcag 840
cgcctgggtc tgacctacaa atttgaaaaa gacatcatta aagccctgga aaacatcgta 900

```
ctgctggacg aaaacaaaaa gaacaaatct gacctgcacg caaccgctct gtctttccgt    960
ctgctgcgtc agcacggttt cgaggtttct caggatgttt ttgagcgttt caaggataaa   1020
gaaggtggtt tcagcggtga actgaaaggt gacgtccaag gcctgctgag cctgtatgaa   1080
gcgtcttacc tgggtttcga gggtgagaac ctgctggagg aggcgcgtac cttttccatc   1140
acccacctga agaacaacct gaaagaaggc attaatacca aggttgcaga acaagtgagc   1200
cacgccctgg aactgccata tcaccagcgt ctgcaccgtc tggaggcacg ttggttcctg   1260
gataaatacg aaccgaaaga accgcatcac cagctgctgc tggagctggc gaagctggat   1320
tttaacatgg tacagaccct gcaccagaaa gagctgcaag atctgtcccg ctggtggacc   1380
gagatgggcc tggctagcaa actggatttt gtacgcgacc gcctgatgga agtttatttc   1440
tgggcactgg gtatggcgcc agacccgcag tttggtgaat gtcgcaaagc tgttactaaa   1500
atgtttggtc tggtgacgat catcgatgac gtgtatgacg tttatggcac tctggacgaa   1560
ctgcaactgt tcaccgatgc tgtagagcgc tgggacgtta acgctattaa caccctgccg   1620
gactatatga aactgtgttt cctggcactg tacaacaccg ttaacgacac gtcctattct   1680
attctgaaag agaaaggtca taacaacctg tcctatctga cgaaaagctg gcgtgaactg   1740
tgcaaagcct ttctgcaaga ggcgaaatgg tccaacaaca aaattatccc ggctttctcc   1800
aagtacctgg aaaacgccag cgtttcctcc tccggtgtag cgctgctggc gccgtcttac   1860
ttttccgtat gccagcagca ggaagacatc tccgaccacg cgctgcgttc cctgaccgac   1920
ttccatggtc tggtgcgttc tagctgcgtt atcttccgcc tgtgcaacga tctggccacc   1980
tctgcggcgg agctggaacg tggcgagact accaattcta tcattagcta catgcacgaa   2040
aacgatggta ccagcgagga acaggcccgc gaagaactgc gtaaactgat cgacgccgaa   2100
tggaaaaaga tgaatcgtga acgcgttagc gactccaccc tgctgcctaa agcgttcatg   2160
gaaatcgcag ttaacatggc acgtgtttcc cactgcacct accagtatgg cgatggtctg   2220
ggtcgcccag actacgcgac tgaaaaccgc atcaaactgc tgctgattga ccctttcccg   2280
attaaccagc tgatgtatgt ctaaaaaaaa ccggccttgg ccccgccggt tttttattat   2340
ttttcttcct ccgcatgttc aatccgctcc ataatcgacg gatggctccc tctgaaaatt   2400
ttaacgagaa acggcgggtt gacccggctc agtcccgtaa cggccaagtc ctgaaacgtc   2460
tcaatcgccg cttcccggtt tccggtcagc tcaatgccgt aacggtcggc ggcgttttcc   2520
tgataccggg agacggcatt cgtaatcgga tcctctagag tcgacctgca ggcatgcaag   2580
ctttgcctcg cgcgtttcgg tgatgacggt gaaaacctct gacacatgca gctcccggag   2640
acggtcacag cttgtctgta agcggatgcc gggagcagac aagcccgtca gggcgcgtca   2700
gcgggtgttg gcgggtgtcg gggcgcagcc atgacccagt cacgtagcga tagcggagtg   2760
tatactggct taactatgcg gcatcagagc agattgtact gagagtgcac catatgcggt   2820
gtgaaatacc gcacagatgc gtaaggagaa aataccgcat caggcgctct tccgcttcct   2880
cgctcactga ctcgctgcgc tcggtcgttc ggctgcggcg agcggtatca gctcactcaa   2940
aggcggtaat acggttatcc acagaatcag gggataacgc aggaaagaac atgtgagcaa   3000
aaggccagca aaaggccagg aaccgtaaaa aggccgcgtt gctggcgttt ttccataggc   3060
tccgcccccc tgacgagcat cacaaaaatc gacgctcaag tcagaggtgg cgaaacccga   3120
caggactata aagataccag gcgtttcccc ctggaagctc cctcgtgcgc tctcctgttc   3180
cgaccctgcc gcttaccgga tacctgtccg cctttctccc ttcgggaagc gtggcgcttt   3240
```

-continued ctcaatgctc acgctgtagg tatctcagtt cggtgtaggt cgttcgctcc aagctgggct 3300
gtgtgcacga acccccgtt cagcccgacc gctgcgcctt atccggtaac tatcgtcttg 3360
agtccaaccc ggtaagacac gacttatcgc cactggcagc agccactggt aacaggatta 3420
gcagagcgag gtatgtaggc ggtgctacag agttcttgaa gtggtggcct aactacggct 3480
acactagaag gacagtattt ggtatctgcg ctctgctgaa gccagttacc ttcggaaaaa 3540
gagttggtag ctcttgatcc ggcaaacaaa ccaccgctgg tagcggtggt ttttttgttt 3600
gcaagcagca gattacgcgc agaaaaaaag gatctcaaga agatcctttg atcttttcta 3660
cggggtctga cgctcagtgg aacgaaaact cacgttaagg gattttggtc atgagattat 3720
caaaaaggat cgaagtcggt tcagaaaaag aaggatatgg atctggagct gtaatataaa 3780
aaccttcttc aactaacggg gcaggttagt gacattagaa aaccgactgt aaaaagtaca 3840
gtcggcatta tctcatatta taaaagccag tcattaggcc tatctgacaa ttcctgaata 3900
gagttcataa acaatcctgc atgataacca tcacaaacag aatgatgtac ctgtaaagat 3960
agcggtaaat atattgaatt acctttatta atgaattttc ctgctgtaat aatgggtaga 4020
aggtaattac tattattatt gatatttaag ttaaacccag taaatgaagt ccatggaata 4080
atagaaagag aaaaagcatt ttcaggtata ggtgttttgg gaaacaattt aaaagaacca 4140
ttatatttct ctacatcaga aaggtataaa tcataaaact ctttgaagtc attctttaca 4200
ggagtccaaa taccagagaa tgttttagat acaccatcaa aaattgtata aagtggctct 4260
aacttatccc aataacctaa ctctccgtcg ctattgtaac cagttctaaa agctgtattt 4320
gagtttatca cccttgtcac taagaaaata aatgcagggt aaaatttata tccttcttgt 4380
tttatgtttc ggtataaaac actaatatca atttctgtgg ttatactaaa agtcgtttgt 4440
tggttcaaat aatgattaaa tatctctttt ctcttccaat tgtctaaatc aattttatta 4500
aagttcattt gatatgcctc ctaaattttt atctaaagtg aatttaggag gcttacttgt 4560
ctgctttctt cattagaatc aatccttttt taaagtcaat attactgtaa cataaatata 4620
tattttaaaa atatcccact ttatccaatt ttcgtttgtt gaactaatgg gtgctttagt 4680
tgaagaataa agaccacatt aaaaaatgtg gtcttttgtg tttttttaaa ggatttgagc 4740
gtacgcgaaa aatccttttc tttctttctt atcttgataa taagggtaac tattgccggt 4800
tgtccattca tggctgaact ctgcttcctc tgttgacatg acacacatca tctcaatatc 4860
cgaatagggc ccatcagtct gacgaccaag agagccataa acaccaatag ccttaacatc 4920
atccccatat ttatccaata ttcgttcctt aatttcatga acaatcttca ttctttcttc 4980
tctagtcatt attattggtc cattcactat tctcattccc ttttcagata attttagatt 5040
tgcttttcta aataagaata tttggagagc accgttctta ttcagctatt aataactcgt 5100
cttcctaagc atccttcaat ccttttaata acaattatag catctaatct tcaacaaact 5160
ggcccgtttg ttgaactact ctttaataaa ataatttttc cgttcccaat tccacattgc 5220
aataatagaa aatccatctt catcggcttt ttcgtcatca tctgtatgaa tcaaatcgcc 5280
ttcttctgtg tcatcaaggt ttaatttttt atgtatttct tttaacaaac caccatagga 5340
gattaacctt ttacggtgta aaccttcctc caaatcagac aaacgtttca aattcttttc 5400
ttcatcatcg gtcataaaat ccgtatcctt tacaggatat tttgcagttt cgtcaattgc 5460
cgattgtata tccgatttat atttattttt cggtcgaatc atttgaactt ttacatttgg 5520
atcatagtct aatttcattg ccttttttcca aaattgaatc cattgttttt gattcacgta 5580
gttttctgtt attctaaaat aagttggttc cacacatacc attacatgca tgtgctgatt 5640
ataagaatta tctttattat ttattgtcac atccgttgca cgcataaaac caacaagatt 5700
tttattaatt tttttatatt gcatcattcg gcgaaatcct tgagccatat ctgtcaaact 5760
cttatttaat tcttcgccat cataaacatt tttaactgtt aatgtgagaa acaaccaacg 5820
aactgttggc ttttgtttaa taacttcagc aacaaccttt tgtgactgaa tgccatgttt 5880
cattgctctc ctccagttgc acattggaca aagcctggat ttgcaaaacc acactcgata 5940
ccactttctt tcgcctgttt cacgattttg tttatactct aatatttcag cacaatcttt 6000
tactctttca gccttttttaa attcaagaat atgcagaagt tcaaagtaat caacattagc 6060
gattttcttt tctctccatg gtctcacttt tccacttttt gtcttgtcca ctaaaaccct 6120
tgatttttca tctgaataaa tgctactatt aggacacata atattaaaag aaaccccccat 6180 ctatttagtt atttgtttag tcacttataa ctttaacaga tggggttttt ctgtgcaacc 6240
aattttaagg gttttcaata ctttaaaaca catacatacc aacacttcaa cgcacctttc 6300
agcaactaaa ataaaaatga cgttatttct atatgtatca agataagaaa gaacaagttc 6360
aaaaccatca aaaaaagaca ccttttcagg tgcttttttt attttataaa ctcattccct 6420
gatctcgact tcgttctttt tttacctctc ggttatgagt tagttcaaat tcgttctttt 6480
taggttctaa atcgtgtttt tcttggaatt gtgctgtttt atcctttacc ttgtctacaa 6540 acccccttaaa aacgttttta aaggctttta agccgtctgt acgttcctta ag 6592

<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58
gacatcaatt gctccatttt cttctgctat c 31

<210> SEQ ID NO 59
<211> LENGTH: 39
<212> TYPE: DNA
<213> ORGANISM: Artificial Sequence
<220> FEATURE:
<223> OTHER INFORMATION: Synthetic Construct

<400> SEQUENCE: 59
attgagaaga ggtcgcacac actctttacc ctctccttt 39

<210> SEQ ID NO 60
<211> LENGTH: 41
<212> TYPE: DNA
<213> ORGANISM: Artificial Sequence
<220> FEATURE:
<223> OTHER INFORMATION: Synthetic Construct

<400> SEQUENCE: 60
taaaaggaga gggtaaagag tgtgtgcgac ctcttctcaa t 41

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61

-continued ccaaggccgg ttttttttag acatacatca gctggttaat c 41

<210> SEQ ID NO 62
<211> LENGTH: 41
<212> TYPE: DNA
<213> ORGANISM: Artificial Sequence
<220> FEATURE:
<223> OTHER INFORMATION: Synthetic Construct

<400> SEQUENCE: 62
gattaaccag ctgatgtatg tctaaaaaaa accggccttg g 41

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63
gacatgacgg atccgattac gaatgccgtc tc 32

<210> SEQ ID NO 64
<211> LENGTH: 31
<212> TYPE: DNA
<213> ORGANISM: Artificial Sequence
<220> FEATURE:
<223> OTHER INFORMATION: Synthetic Construct

<400> SEQUENCE: 64
gacatcaatt gctccatttt cttctgctat c 31

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65
gacatgaatt cctccatttt cttctgc 27

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct

<400> SEQUENCE: 66
aggagagggt aaagagtgag 20

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67
cttttccatc acccacctga ag 22

<210> SEQ ID NO 68
<211> LENGTH: 28
<212> TYPE: DNA
<213> ORGANISM: Artificial Sequence

```
<220> FEATURE:
<223> OTHER INFORMATION: Synthetic Construct

<400> SEQUENCE: 68

ggcgaaatgg tccaacaaca aaattatc                                          28


<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69

ggtgaattca gtctactggg gattcccaaa tctatatata ctgcaggtga c                51


<210> SEQ ID NO 70
<211> LENGTH: 23
<212> TYPE: DNA
<213> ORGANISM: Artificial Sequence
<220> FEATURE:
<223> OTHER INFORMATION: Synthetic Construct

<400> SEQUENCE: 70

gcaggtggga aactatgcac tcc                                               23


<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71

cctgaattct gttggattgg aggattggat agtggg                                 36


<210> SEQ ID NO 72
<211> LENGTH: 30
<212> TYPE: DNA
<213> ORGANISM: Artificial Sequence
<220> FEATURE:
<223> OTHER INFORMATION: Synthetic Construct

<400> SEQUENCE: 72

ggtgtcgacg tacggtcgag cttattgacc                                        30


<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73

ggtgggcccg cattttgcca cctacaagcc ag                                     32


<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74

ggtgaattct agaggatccc aacgctgttg cctacaacgg                             40
```

<210> SEQ ID NO 75
<211> LENGTH: 36
<212> TYPE: DNA
<213> ORGANISM: Artificial Sequence
<220> FEATURE:
<223> OTHER INFORMATION: Synthetic Construct

<400> SEQUENCE: 75
ggtgcggccg ctgtctggac ctggtgagtt tccccg 36

<210> SEQ ID NO 76
<211> LENGTH: 37
<212> TYPE: DNA
<213> ORGANISM: Artificial Sequence
<220> FEATURE:
<223> OTHER INFORMATION: Synthetic Construct

<400> SEQUENCE: 76
ggtgggccca ttaaatcagt tatcgtttat ttgatag 37

<210> SEQ ID NO 77
<211> LENGTH: 35
<212> TYPE: DNA
<213> ORGANISM: Artificial Sequence
<220> FEATURE:
<223> OTHER INFORMATION: Synthetic Construct

<400> SEQUENCE: 77
ggtgaccagc aagtccatgg gtggtttgat catgg 35

<210> SEQ ID NO 78
<211> LENGTH: 35
<212> TYPE: DNA
<213> ORGANISM: Artificial Sequence
<220> FEATURE:
<223> OTHER INFORMATION: Synthetic Construct

<400> SEQUENCE: 78
ggtgcggccg cctttggagt acgactccaa ctatg 35

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
gcggccgcag actaaattta tttcagtctc c 31

<210> SEQ ID NO 80
<211> LENGTH: 7
<212> TYPE: DNA
<213> ORGANISM: Artificial Sequence
<220> FEATURE:
<223> OTHER INFORMATION: Synthetic Construct

<400> SEQUENCE: 80 aggaggt 7

<210> SEQ ID NO 81
<211> LENGTH: 7
<212> TYPE: DNA
<213> ORGANISM: Artificial Sequence
<220> FEATURE:
<223> OTHER INFORMATION: Synthetic Construct

<400> SEQUENCE: 81 aaggagg 7

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
gacatctgca gctccatttt cttctgc 27

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct

<400> SEQUENCE: 83
caataataac tactgttttc actctttacc ctctcctttt aa 42

<210> SEQ ID NO 84
<211> LENGTH: 42
<212> TYPE: DNA
<213> ORGANISM: Artificial Sequence
<220> FEATURE:
<223> OTHER INFORMATION: Synthetic Construct

<400> SEQUENCE: 84
ttaaaaggag agggtaaaga gtgaaaacag tagttattat tg 42

<210> SEQ ID NO 85
<211> LENGTH: 45
<212> TYPE: DNA
<213> ORGANISM: Artificial Sequence
<220> FEATURE:
<223> OTHER INFORMATION: Synthetic Construct

<400> SEQUENCE: 85
cggggccaag gccggttttt tttagtttcg ataagaacga acggt 45

<210> SEQ ID NO 86
<211> LENGTH: 45
<212> TYPE: DNA
<213> ORGANISM: Artificial Sequence
<220> FEATURE:
<223> OTHER INFORMATION: Synthetic Construct

<400> SEQUENCE: 86
accgttcgtt cttatcgaaa ctaaaaaaaa ccggccttgg ccccg 45

<210> SEQ ID NO 87
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 87
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120

-continued

```
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
```

```
gttttcaccg tcatcaccga aacgcgcgag gcagctgcgg taaagctcat cagcgtggtc    2580

gtgaagcgat tcacagatgt ctgcctgttc atccgcgtcc agctcgttga gtttctccag    2640

aagcgttaat gtctggcttc tgataaagcg ggccatgtta agggcggttt tttcctgttt    2700

ggtcactgat gcctccgtgt aagggggatt tctgttcatg ggggtaatga taccgatgaa    2760

acgagagagg atgctcacga tacgggttac tgatgatgaa catgcccggt tactggaacg    2820

ttgtgagggt aaacaactgg cggtatggat gcggcgggac cagagaaaaa tcactcaggg    2880

tcaatgccag cgcttcgtta atacagatgt aggtgttcca cagggtagcc agcagcatcc    2940

tgcgatgcag atccggaaca taatggtgca gggcgctgac ttccgcgttt ccagacttta    3000

cgaaacacgg aaaccgaaga ccattcatgt tgttgctcag gtcgcagacg ttttgcagca    3060

gcagtcgctt cacgttcgct cgcgtatcgg tgattcattc tgctaaccag taaggcaacc    3120

ccgccagcct agccgggtcc tcaacgacag gagcacgatc atgcgcaccc gtggggccgc    3180

catgccggcg ataatggcct gcttctcgcc gaaacgtttg gtggcgggac cagtgacgaa    3240

ggcttgagcg agggcgtgca agattccgaa taccgcaagc gacaggccga tcatcgtcgc    3300

gctccagcga aagcggtcct cgccgaaaat gacccagagc gctgccggca cctgtcctac    3360

gagttgcatg ataaagaaga cagtcataag tgcggcgacg atagtcatgc cccgcgccca    3420

ccggaaggag ctgactgggt tgaaggctct caagggcatc ggtcgagatc ccggtgccta    3480

atgagtgagc taacttacat taattgcgtt gcgctcactg cccgctttcc agtcgggaaa    3540

cctgtcgtgc cagctgcatt aatgaatcgg ccaacgcgcg gggagaggcg gtttgcgtat    3600

tgggcgccag ggtggttttt cttttcacca gtgagacggg caacagctga ttgcccttca    3660

ccgcctggcc ctgagagagt tgcagcaagc ggtccacgct ggtttgcccc agcaggcgaa    3720

aatcctgttt gatggtggtt aacggcggga tataacatga gctgtcttcg gtatcgtcgt    3780

atcccactac cgagatatcc gcaccaacgc gcagcccgga ctcggtaatg gcgcgcattg    3840

cgcccagcgc catctgatcg ttggcaacca gcatcgcagt gggaacgatg ccctcattca    3900

gcatttgcat ggtttgttga aaaccggaca tggcactcca gtcgccttcc cgttccgcta    3960

tcggctgaat ttgattgcga gtgagatatt tatgccagcc agccagacgc agacgcgccg    4020

agacagaact taatgggccc gctaacagcg cgatttgctg gtgacccaat gcgaccagat    4080

gctccacgcc cagtcgcgta ccgtcttcat gggagaaaat aatactgttg atgggtgtct    4140

ggtcagagac atcaagaaat aacgccggaa cattagtgca ggcagcttcc acagcaatgg    4200

catcctggtc atccagcgga tagttaatga tcagcccact gacgcgttgc gcgagaagat    4260

tgtgcaccgc cgctttacag gcttcgacgc cgcttcgttc taccatcgac accaccacgc    4320

tggcacccag ttgatcggcg cgagatttaa tcgccgcgac aatttgcgac ggcgcgtgca    4380

gggccagact ggaggtggca acgccaatca gcaacgactg tttgcccgcc agttgttgtg    4440

ccacgcggtt gggaatgtaa ttcagctccg ccatcgccgc ttccactttt tcccgcgttt    4500

tcgcagaaac gtggctggcc tggttcacca cgcgggaaac ggtctgataa gagacaccgg    4560

catactctgc gacatcgtat aacgttactg gtttcacatt caccaccctg aattgactct    4620

cttccgggcg ctatcatgcc ataccgcgaa aggttttgcg ccattcgatg gtgtccggga    4680

tctcgacgct ctcccttatg cgactcctgc attaggaagc agcccagtag taggttgagg    4740

ccgttgagca ccgccgccgc aaggaatggt gcatgcaagg agatggcgcc caacagtccc    4800

ccggccacgg ggcctgccac catacccacg ccgaaacaag cgctcatgag cccgaagtgg    4860
```

-continued

```
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgttgt agcgtgtcca ccgaaaatgt   5100
gtctttcacc gaaactgaaa ccgaagctcg tcgttctgcg aactacgaac ctaacagctg   5160
ggactatgat tacctgctgt cctccgacac ggacgagtcc atcgaagtat acaaagacaa   5220
agcgaaaaag ctggaagccg aagttcgtcg cgagattaat aacgaaaaag cagaatttct   5280
gaccctgctg gaactgattg acaacgtcca gcgcctgggc ctgggttacc gtttcgagtc   5340
tgatatccgt ggtgcgctgg atcgcttcgt ttcctccggc ggcttcgatg cggtaaccaa   5400
gacttccctg cacggtacgg cactgtcttt ccgtctgctg cgtcaacacg gttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gaaccatgca ctggaactgc cactgcatcg   5700
ccgtactcag cgtctggaag cagtatggtc tatcgaggcc taccgtaaaa aggaggacgc   5760
gaatcaggtt ctgctggagc tggcaattct ggattacaac atgatccagt ctgtatacca   5820
gcgtgatctg cgtgaaacgt cccgttggtg gcgtcgtgtg ggtctggcga ccaaactgca   5880
ctttgctcgt gaccgcctga ttgagagctt ctactgggcc gtgggtgtag cattcgaacc   5940
gcaatactcc gactgccgta actccgtcgc aaaaatgttt tctttcgtaa ccattatcga   6000
cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgacctt tgacgactac ttcggcaacg catggaaatc   6300
ctcttctggc ccgctgcaac tggtgttcgc ttacttcgct gtcgtgcaga acattaaaaa   6360
ggaagagatc gaaaacctgc aaaaatacca tgacaccatc tctcgtcctt cccatatctt   6420
ccgtctgtgc aatgacctgg ctagcgcgtc tgcggaaatt gcgcgtggtg aaaccgcaaa   6480
tagcgtttct tgttacatgc gcactaaagg tatctccgaa gaactggcta ccgaaagcgt   6540
gatgaatctg atcgatgaaa cctggaaaaa gatgaacaag gaaaaactgg gtggtagcct   6600
gttcgcgaaa ccgttcgtgg aaaccgcgat caacctggca cgtcaatctc actgcactta   6660
tcataacggc gacgcgcata cctctccgga tgagctgacc cgcaaacgcg ttctgtctgt   6720
aatcactgaa ccgattctgc cgtttgaacg ctaaggatcc gaattcgagc tccgtcgaca   6780
agcttgcggc cgcactcgag caccaccacc accaccactg agatccggct gctaacaaag   6840
cccgaaagga agctgagttg gctgctgcca ccgctgagca ataactagca taaccccttg   6900
gggcctctaa acgggtcttg aggggttttt tgctgaaagg aggaactata tccggat      6957
```

<210> SEQ ID NO 88
<211> LENGTH: 6068
<212> TYPE: DNA
<213> ORGANISM: Artificial Sequence
<220> FEATURE:
<223> OTHER INFORMATION: Synthetic Construct

<400> SEQUENCE: 88

-continued

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gtttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgagatg    420
tagcgtgtcc accgaaaatg tgtctttcac cgaaactgaa accgaagctc gtcgttctgc    480
gaactacgaa cctaacagct gggactatga ttacctgctg tcctccgaca cggacgagtc    540
catcgaagta tacaaagaca aagcgaaaaa gctggaagcc gaagttcgtc gcgagattaa    600
taacgaaaaa gcagaatttc tgaccctgct ggaactgatt gacaacgtcc agcgcctggg    660
cctgggttac cgtttcgagt ctgatatccg tggtgcgctg gatcgcttcg tttcctccgg    720
cggcttcgat gcggtaacca agacttccct gcacggtacg gcactgtctt tccgtctgct    780
gcgtcaacac ggttttgagg tttctcagga agcgttcagc ggcttcaaag accaaaacgg    840
caacttcctg gagaacctga aggaagatat caaagctatc ctgagcctgt acgaggccag    900
cttcctggct ctggaaggcg aaaacatcct ggacgaggcg aaggttttcg caatctctca    960
tctgaaagaa ctgtctgaag aaaagatcgg taaagagctg gcagaacagg tgaaccatgc   1020
actggaactg ccactgcatc gccgtactca gcgtctggaa gcagtatggt ctatcgaggc   1080
ctaccgtaaa aaggaggacg cgaatcaggt tctgctggag ctggcaattc tggattacaa   1140
catgatccag tctgtatacc agcgtgatct gcgtgaaacg tcccgttggt ggcgtcgtgt   1200
gggtctggcg accaaactgc actttgctcg tgaccgcctg attgagagct tctactgggc   1260
cgtgggtgta gcattcgaac cgcaatactc cgactgccgt aactccgtcg caaaaatgtt   1320
ttctttcgta accattatcg acgatatcta cgatgtatac ggcaccctgg acgaactgga   1380
gctgtttact gatgcagttg agcgttggga cgtaaacgcc atcaacgacc tgccggatta   1440
catgaaactg tgctttctgg ctctgtataa cactattaac gaaatcgcct acgacaacct   1500
gaaagataaa ggtgagaaca tcctgccgta tctgaccaaa gcctgggctg acctgtgcaa   1560
cgctttcctg caagaagcca agtggctgta caacaaatct actccgacct ttgacgacta   1620
cttcggcaac gcatggaaat cctcttctgg cccgctgcaa ctggtgttcg cttacttcgc   1680
tgtcgtgcag aacattaaaa aggaagagat cgaaaacctg caaaaatacc atgacaccat   1740
ctctcgtcct tcccatatct tccgtctgtg caatgacctg gctagcgcgt ctgcggaaat   1800
tgcgcgtggt gaaaccgcaa atagcgtttc ttgttacatg cgcactaaag gtatctccga   1860
agaactggct accgaaagcg tgatgaatct gatcgatgaa acctggaaaa agatgaacaa   1920
ggaaaaactg ggtggtagcc tgttcgcgaa accgttcgtg gaaaccgcga tcaacctggc   1980
acgtcaatct cactgcactt atcataacgg cgacgcgcat acctctccgg atgagctgac   2040
ccgcaaacgc gttctgtctg taatcactga accgattctg ccgtttgaac gctaactgca   2100
gctggtacca tatgggaatt cgaagctttc tagaacaaaa actcatctca gaagaggatc   2160
tgaatagcgc cgtcgaccat catcatcatc atcattgagt ttaaacggtc tccagcttgg   2220
ctgttttggc ggatgagaga agattttcag cctgatacag attaaatcag aacgcagaag   2280
cggtctgata aaacagaatt tgcctggcgg cagtagcgcg gtggtcccac ctgaccccat   2340
```

-continued

```
gccgaactca gaagtgaaac gccgtagcgc cgatggtagt gtggggtctc cccatgcgag   2400
agtagggaac tgccaggcat caaataaaac gaaaggctca gtcgaaagac tgggcctttc   2460
gttttatctg ttgtttgtcg gtgaacgctc tcctgagtag gacaaatccg ccgggagcgg   2520
atttgaacgt tgcgaagcaa cggcccggag ggtggcgggc aggacgcccg ccataaactg   2580
ccaggcatca aattaagcag aaggccatcc tgacggatgg cctttttgcg tttctacaaa   2640
ctctttttgt ttattttct aaatacattc aaatatgtat ccgctcatga gacaataacc   2700
ctgataaatg cttcaataat attgaaaaag gaagagtatg agtattcaac atttccgtgt   2760
cgcccttatt cccttttttg cggcattttg ccttcctgtt tttgctcacc cagaaacgct   2820
ggtgaaagta aaagatgctg aagatcagtt gggtgcacga gtgggttaca tcgaactgga   2880
tctcaacagc ggtaagatcc ttgagagttt tcgccccgaa gaacgttttc caatgatgag   2940
cacttttaaa gttctgctat gtggcgcggt attatcccgt gttgacgccg ggcaagagca   3000
actcggtcgc cgcatacact attctcagaa tgacttggtt gagtactcac cagtcacaga   3060
aaagcatctt acggatggca tgacagtaag agaattatgc agtgctgcca taaccatgag   3120
tgataacact gcggccaact tacttctgac aacgatcgga ggaccgaagg agctaaccgc   3180
ttttttgcac aacatggggg atcatgtaac tcgccttgat cgttgggaac cggagctgaa   3240
tgaagccata ccaaacgacg agcgtgacac cacgatgcct gtagcaatgg caacaacgtt   3300
gcgcaaacta ttaactggcg aactacttac tctagcttcc cggcaacaat taatagactg   3360
gatggaggcg gataaagttg caggaccact tctgcgctcg gcccttccgg ctggctggtt   3420
tattgctgat aaatctggag ccggtgagcg tgggtctcgc ggtatcattg cagcactggg   3480
gccagatggt aagccctccc gtatcgtagt tatctacacg acggggagtc aggcaactat   3540
ggatgaacga aatagacaga tcgctgagat aggtgcctca ctgattaagc attggtaact   3600
gtcagaccaa gtttactcat atatacttta gattgattta aaacttcatt tttaatttaa   3660
aaggatctag gtgaagatcc tttttgataa tctcatgacc aaaatccctt aacgtgagtt   3720
ttcgttccac tgagcgtcag accccgtaga aaagatcaaa ggatcttctt gagatccttt   3780
ttttctgcgc gtaatctgct gcttgcaaac aaaaaaacca ccgctaccag cggtggtttg   3840
tttgccggat caagagctac caactctttt tccgaaggta actggcttca gcagagcgca   3900
gataccaaat actgtccttc tagtgtagcc gtagttaggc caccacttca agaactctgt   3960
agcaccgcct acatacctcg ctctgctaat cctgttacca gtggctgctg ccagtggcga   4020
taagtcgtgt cttaccgggt tggactcaag acgatagtta ccggataagg cgcagcggtc   4080
gggctgaacg gggggttcgt gcacacagcc cagcttggag cgaacgacct acaccgaact   4140
gagataccta cagcgtgagc tatgagaaag cgccacgctt cccgaaggga gaaaggcgga   4200
caggtatccg gtaagcggca gggtcggaac aggagagcgc acgagggagc ttccaggggg   4260
aaacgcctgg tatctttata gtcctgtcgg gtttcgccac ctctgacttg agcgtcgatt   4320
tttgtgatgc tcgtcagggg ggcggagcct atggaaaaac gccagcaacg cggccttttt   4380
acggttcctg gccttttgct ggccttttgc tcacatgttc tttcctgcgt tatcccctga   4440
ttctgtggat aaccgtatta ccgcctttga gtgagctgat accgctcgcc gcagccgaac   4500
gaccgagcgc agcgagtcag tgagcgagga agcggaagag cgcctgatgc ggtattttct   4560
ccttacgcat ctgtgcggta tttcacaccg catatggtgc actctcagta caatctgctc   4620
tgatgccgca tagttaagcc agtatacact ccgctatcgc tacgtgactg ggtcatggct   4680
gcgccccgac acccgccaac acccgctgac gcgccctgac gggcttgtct gctcccggca   4740
```

tccgcttaca gacaagctgt gaccgtctcc gggagctgca tgtgtcagag gttttcaccg 4800
tcatcaccga aacgcgcgag gcagcagatc aattcgcgcg cgaaggcgaa gcggcatgca 4860
tttacgttga caccatcgaa tggtgcaaaa cctttcgcgg tatggcatga tagcgcccgg 4920
aagagagtca attcagggtg gtgaatgtga aaccagtaac gttatacgat gtcgcagagt 4980
atgccggtgt ctcttatcag accgtttccc gcgtggtgaa ccaggccagc cacgtttctg 5040
cgaaaacgcg ggaaaaagtg gaagcggcga tggcggagct gaattacatt cccaaccgcg 5100
tggcacaaca actggcgggc aaacagtcgt tgctgattgg cgttgccacc tccagtctgg 5160
ccctgcacgc gccgtcgcaa attgtcgcgg cgattaaatc tcgcgccgat caactgggtg 5220
ccagcgtggt ggtgtcgatg gtagaacgaa gcggcgtcga agcctgtaaa gcggcggtgc 5280
acaatcttct cgcgcaacgc gtcagtgggc tgatcattaa ctatccgctg gatgaccagg 5340
atgccattgc tgtggaagct gcctgcacta atgttccggc gttatttctt gatgtctctg 5400
accagacacc catcaacagt attattttct cccatgaaga cggtacgcga ctgggcgtgg 5460
agcatctggt cgcattgggt caccagcaaa tcgcgctgtt agcgggccca ttaagttctg 5520
tctcggcgcg tctgcgtctg gctggctggc ataaatatct cactcgcaat caaattcagc 5580
cgatagcgga acgggaaggc gactggagtg ccatgtccgg ttttcaacaa accatgcaaa 5640
tgctgaatga gggcatcgtt cccactgcga tgctggttgc caacgatcag atggcgctgg 5700
gcgcaatgcg cgccattacc gagtccgggc tgcgcgttgg tgcggatatc tcggtagtgg 5760
gatacgacga taccgaagac agctcatgtt atatcccgcc gtcaaccacc atcaaacagg 5820
attttcgcct gctggggcaa accagcgtgg accgcttgct gcaactctct cagggccagg 5880
cggtgaaggg caatcagctg ttgcccgtct cactggtgaa aagaaaaacc accctggcgc 5940
ccaatacgca aaccgcctct ccccgcgcgt tggccgattc attaatgcag ctggcacgac 6000
aggtttcccg actggaaagc gggcagtgag cgcaacgcaa ttaatgtgag ttagcgcgaa 6060
ttgatctg 6068

<210> SEQ ID NO 89
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 89
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatgagatg 420
tagcgtgtcc accgaaaatg tgtctttcac cgaaactgaa accgaagctc gtcgttctgc 480
gaactacgaa cctaacagct gggactatga ttacctgctg tcctccgaca cggacgagtc 540
catcgaagta tacaaagaca aagcgaaaaa gctggaagcc gaagttcgtc gcgagattaa 600
taacgaaaaa gcagaatttc tgaccctgct ggaactgatt gacaacgtcc agcgcctggg 660

-continued

```
cctgggttac cgtttcgagt ctgatatccg tggtgcgctg gatcgcttcg tttcctccgg    720
cggcttcgat gcggtaacca agacttccct gcacggtacg gcactgtctt tccgtctgct    780
gcgtcaacac ggttttgagg tttctcagga agcgttcagc ggcttcaaag accaaaacgg    840
caacttcctg gagaacctga aggaagatat caaagctatc ctgagcctgt acgaggccag    900
cttcctggct ctggaaggcg aaaacatcct ggacgaggcg aaggttttcg caatctctca    960
tctgaaagaa ctgtctgaag aaaagatcgg taaagagctg gcagaacagg tgaaccatgc   1020
actggaactg ccactgcatc gccgtactca gcgtctggaa gcagtatggt ctatcgaggc   1080
ctaccgtaaa aaggaggacg cgaatcaggt tctgctggag ctggcaattc tggattacaa   1140
catgatccag tctgtatacc agcgtgatct gcgtgaaacg tcccgttggt ggcgtcgtgt   1200
gggtctggcg accaaactgc actttgctcg tgaccgcctg attgagagct tctactgggc   1260
cgtgggtgta gcattcgaac cgcaatactc cgactgccgt aactccgtcg caaaaatgtt   1320
ttctttcgta accattatcg acgatatcta cgatgtatac ggcaccctgg acgaactgga   1380
gctgtttact gatgcagttg agcgttggga cgtaaacgcc atcaacgacc tgccggatta   1440
catgaaactg tgctttctgg ctctgtataa cactattaac gaaatcgcct acgacaacct   1500
gaaagataaa ggtgagaaca tcctgccgta tctgaccaaa gcctgggctg acctgtgcaa   1560
cgctttcctg caagaagcca agtggctgta caacaaatct actccgacct ttgacgacta   1620
cttcggcaac gcatggaaat cctcttctgg cccgctgcaa ctggtgttcg cttacttcgc   1680
tgtcgtgcag aacattaaaa aggaagagat cgaaaacctg caaaaatacc atgacaccat   1740
ctctcgtcct tcccatatct tccgtctgtg caatgacctg gctagcgcgt ctgcggaaat   1800
tgcgcgtggt gaaaccgcaa atagcgtttc ttgttacatg cgcactaaag gtatctccga   1860
agaactggct accgaaagcg tgatgaatct gatcgatgaa acctggaaaa agatgaacaa   1920
ggaaaaactg ggtggtagcc tgttcgcgaa accgttcgtg gaaaccgcga tcaacctggc   1980
acgtcaatct cactgcactt atcataacgg cgacgcgcat acctctccgg atgagctgac   2040
ccgcaaacgc gttctgtctg taatcactga accgattctg ccgtttgaac gctaactgca   2100
taaaggaggt aaaaaaacat ggtatcctgt tctgcgccgg gtaagattta cctgttcggt   2160
gaacacgccg tagtttatgg cgaaactgca attgcgtgtg cggtggaact gcgtacccgt   2220
gttcgcgcgg aactcaatga ctctatcact attcagagcc agatcggccg caccggtctg   2280
gatttcgaaa agcaccctta tgtgtctgcg gtaattgaga aaatgcgcaa atctattcct   2340
attaacggtg ttttcttgac cgtcgattcc gacatcccgg tgggctccgg tctgggtagc   2400
agcgcagccg ttactatcgc gtctattggt gcgctgaacg agctgttcgg ctttggcctc   2460
agcctgcaag aaatcgctaa actgggccac gaaatcgaaa ttaaagtaca gggtgccgcg   2520
tccccaaccg atacgtatgt ttctaccttc ggcggcgtgg ttaccatccc ggaacgtcgc   2580
aaactgaaaa ctccggactg cggcattgtg attggcgata ccggcgtttt ctcctccacc   2640
aaagagttag tagctaacgt acgtcagctg cgcgaaagct acccggattt gatcgaaccg   2700
ctgatgacct ctattggcaa aatctctcgt atcggcgaac aactggttct gtctggcgac   2760
tacgcatcca tcggccgcct gatgaacgtc aaccagggtc tcctggacgc cctgggcgtt   2820
aacatcttag aactgagcca gctgatctat tccgctcgtg cggcaggtgc gtttggcgct   2880
aaaatcacgg gcgctggcgg cggtggctgt atggttgcgc tgaccgctcc ggaaaaatgc   2940
aaccaagtgg cagaagcggt agcaggcgct ggcggtaaag tgactatcac taaaccgacc   3000
gagcaaggtc tgaaagtaga ttaaagtcta gttaaagttt aaacggtctc cagcttggct   3060
```

-continued

```
gttttggcgg atgagagaag attttcagcc tgatacagat taaatcagaa cgcagaagcg   3120
gtctgataaa acagaatttg cctggcggca gtagcgcggt ggtcccacct gaccccatgc   3180
cgaactcaga agtgaaacgc cgtagcgccg atggtagtgt ggggtctccc catgcgagag   3240
tagggaactg ccaggcatca aataaaacga aaggctcagt cgaaagactg ggcctttcgt   3300
tttatctgtt gtttgtcggt gaacgctctc ctgagtagga caaatccgcc gggagcggat   3360
ttgaacgttg cgaagcaacg gcccggaggg tggcgggcag gacgcccgcc ataaactgcc   3420
aggcatcaaa ttaagcagaa ggccatcctg acggatggcc tttttgcgtt tctacaaact   3480
ctttttgttt atttttctaa atacattcaa atatgtatcc gctcatgaga caataaccct   3540
gataaatgct tcaataatat tgaaaaagga agagtatgag tattcaacat ttccgtgtcg   3600
cccttattcc cttttttgcg gcattttgcc ttcctgtttt tgctcaccca gaaacgctgg   3660
tgaaagtaaa agatgctgaa gatcagttgg gtgcacgagt gggttacatc gaactggatc   3720
tcaacagcgg taagatcctt gagagttttc gccccgaaga acgttttcca atgatgagca   3780
cttttaaagt tctgctatgt ggcgcggtat tatcccgtgt tgacgccggg caagagcaac   3840
tcggtcgccg catacactat tctcagaatg acttggttga gtactcacca gtcacagaaa   3900
agcatcttac ggatggcatg acagtaagag aattatgcag tgctgccata accatgagtg   3960
ataacactgc ggccaactta cttctgacaa cgatcggagg accgaaggag ctaaccgctt   4020
ttttgcacaa catgggggat catgtaactc gccttgatcg ttgggaaccg gagctgaatg   4080
aagccatacc aaacgacgag cgtgacacca cgatgcctgt agcaatggca acaacgttgc   4140
gcaaactatt aactggcgaa ctacttactc tagcttcccg gcaacaatta atagactgga   4200
tggaggcgga taaagttgca ggaccacttc tgcgctcggc ccttccggct ggctggttta   4260
ttgctgataa atctggagcc ggtgagcgtg ggtctcgcgg tatcattgca gcactggggc   4320
cagatggtaa gccctcccgt atcgtagtta tctacacgac ggggagtcag gcaactatgg   4380
atgaacgaaa tagacagatc gctgagatag gtgcctcact gattaagcat tggtaactgt   4440
cagaccaagt ttactcatat atactttaga ttgatttaaa acttcatttt taatttaaaa   4500
ggatctaggt gaagatcctt tttgataatc tcatgaccaa aatcccttaa cgtgagtttt   4560
cgttccactg agcgtcagac cccgtagaaa agatcaaagg atcttcttga gatccttttt   4620
ttctgcgcgt aatctgctgc ttgcaaacaa aaaaaccacc gctaccagcg gtggtttgtt   4680
tgccggatca agagctacca actctttttc cgaaggtaac tggcttcagc agagcgcaga   4740
taccaaatac tgtccttcta gtgtagccgt agttaggcca ccacttcaag aactctgtag   4800
caccgcctac atacctcgct ctgctaatcc tgttaccagt ggctgctgcc agtggcgata   4860
agtcgtgtct taccgggttg gactcaagac gatagttacc ggataaggcg cagcggtcgg   4920
gctgaacggg gggttcgtgc acacagccca gcttggagcg aacgacctac accgaactga   4980
gatacctaca gcgtgagcta tgagaaagcg ccacgcttcc cgaagggaga aaggcggaca   5040
ggtatccggt aagcggcagg gtcggaacag gagagcgcac gagggagctt ccagggggaa   5100
acgcctggta tctttatagt cctgtcgggt ttcgccacct ctgacttgag cgtcgatttt   5160
tgtgatgctc gtcagggggg cggagcctat ggaaaaacgc cagcaacgcg gcctttttac   5220
ggttcctggc cttttgctgg ccttttgctc acatgttctt tcctgcgtta tcccctgatt   5280
ctgtggataa ccgtattacc gcctttgagt gagctgatac cgctcgccgc agccgaacga   5340
ccgagcgcag cgagtcagtg agcgaggaag cggaagagcg cctgatgcgg tattttctcc   5400
```

ttacgcatct gtgcggtatt tcacaccgca tatggtgcac tctcagtaca atctgctctg 5460
atgccgcata gttaagccag tatacactcc gctatcgcta cgtgactggg tcatggctgc 5520
gccccgacac ccgccaacac ccgctgacgc gccctgacgg gcttgtctgc tcccggcatc 5580
cgcttacaga caagctgtga ccgtctccgg gagctgcatg tgtcagaggt tttcaccgtc 5640
atcaccgaaa cgcgcgaggc agcagatcaa ttcgcgcgcg aaggcgaagc ggcatgcatt 5700
tacgttgaca ccatcgaatg gtgcaaaacc tttcgcggta tggcatgata gcgcccggaa 5760
gagagtcaat tcagggtggt gaatgtgaaa ccagtaacgt tatacgatgt cgcagagtat 5820
gccggtgtct cttatcagac cgtttcccgc gtggtgaacc aggccagcca cgtttctgcg 5880
aaaacgcggg aaaaagtgga agcggcgatg gcggagctga attacattcc caaccgcgtg 5940
gcacaacaac tggcgggcaa acagtcgttg ctgattggcg ttgccacctc cagtctggcc 6000
ctgcacgcgc cgtcgcaaat tgtcgcggcg attaaatctc gcgccgatca actgggtgcc 6060
agcgtggtgg tgtcgatggt agaacgaagc ggcgtcgaag cctgtaaagc ggcggtgcac 6120
aatcttctcg cgcaacgcgt cagtgggctg atcattaact atccgctgga tgaccaggat 6180
gccattgctg tggaagctgc ctgcactaat gttccggcgt tatttcttga tgtctctgac 6240
cagacaccca tcaacagtat tattttctcc catgaagacg gtacgcgact gggcgtggag 6300
catctggtcg cattgggtca ccagcaaatc gcgctgttag cgggcccatt aagttctgtc 6360
tcggcgcgtc tgcgtctggc tggctggcat aaatatctca ctcgcaatca aattcagccg 6420
atagcggaac gggaaggcga ctggagtgcc atgtccggtt ttcaacaaac catgcaaatg 6480
ctgaatgagg gcatcgttcc cactgcgatg ctggttgcca acgatcagat ggcgctgggc 6540
gcaatgcgcg ccattaccga gtccgggctg cgcgttggtg cggatatctc ggtagtggga 6600
tacgacgata ccgaagacag ctcatgttat atcccgccgt caaccaccat caaacaggat 6660
tttcgcctgc tggggcaaac cagcgtggac cgcttgctgc aactctctca gggccaggcg 6720
gtgaagggca atcagctgtt gcccgtctca ctggtgaaaa gaaaaaccac cctggcgccc 6780
aatacgcaaa ccgcctctcc ccgcgcgttg gccgattcat taatgcagct ggcacgacag 6840
gtttcccgac tggaaagcgg gcagtgagcg caacgcaatt aatgtgagtt agcgcgaatt 6900
gatctg 6906

<210> SEQ ID NO 90
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 90
aagggcgagc tcaacgatcc ggctgctaac aaagcccgaa aggaagctga gttggctgct 60
gccaccgctg agcaataact agcataaccc cttggggcct ctaaacgggt cttgaggagt 120
tttttgctga aaggaggaac tatatccgga tatcccgcaa gaggcccggc agtaccggca 180
taaccaagcc tatgcctaca gcatccaggg tgacggtgcc gaggatgacg atgagcgcat 240
tgttagattt catacacggt gcctgactgc gttagcaatt taactgtgat aaactaccgc 300
attaaagctt atcgatgata agctgtcaaa catgagaatt aattcttgaa gacgaaaggg 360
cctcgtgata cgcctatttt tataggttaa tgtcatgata ataatggttt cttagacgtc 420
aggtggcact tttcggggaa atgtgcgcgg aacccctatt tgtttatttt tctaaataca 480
ttcaaatatg tatccgctca tgagacaata accctgataa atgcttcaat aatattgaaa 540

```
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
```

-continued

```
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
acaatttgcg acggcgcgtg cagggccaga ctggaggtgg caacgccaat cagcaacgac   4980
tgtttgcccg ccagttgttg tgccacgcgg ttgggaatgt aattcagctc cgccatcgcc   5040
gcttccactt tttcccgcgt tttcgcagaa acgtggctgg cctggttcac cacgcgggaa   5100
acggtctgat aagagacacc ggcatactct gcgacatcgt ataacgttac tggtttcaca   5160
ttcaccaccc tgaattgact ctcttccggg cgctatcatg ccataccgcg aaaggttttg   5220
cgccattcga tggtgtccgg gatctcgacg ctctccctta tgcgactcct gcattaggaa   5280
```

-continued gcagcccagt agtaggttga ggccgttgag caccgccgcc gcaaggaatg gtgcatgcaa 5340
ggagatggcg cccaacagtc ccccggccac ggggcctgcc accataccca cgccgaaaca 5400
agcgctcatg agcccgaagt ggcgagcccg atcttcccca tcggtgatgt cggcgatata 5460
ggcgccagca accgcacctg tggcgccggt gatgccggcc acgatgcgtc cggcgtagag 5520
gatcgagatc tcgatcccgc gaaattaata cgactcacta taggggaatt gtgagcggat 5580
aacaattccc ctctagaaat aattttgttt aactttaaga aggagatata catatgaatt 5640
aaccctcact aaagggcggc cgcgaagttc ctattctcta gaaagtatag gaacttcatt 5700
ctaccgggta ggggaggcgc ttttcccaag gcagtctgga gcatgcgctt tagcagcccc 5760
gctgggcact tggcgctaca caagtggcct ctggcctcgc acacattcca catccaccgg 5820
taggcgccaa ccggctccgt tctttggtgg ccccttcgcg ccaccttcca ctcctcccct 5880
agtcaggaag ttcccccccg ccccgcagct cgcgtcgtgc aggacgtgac aaatggaagt 5940
agcacgtctc actagtctcg tgcagatgga cagcaccgct gagcaatgga agcgggtagg 6000
cctttggggc agcggccaat agcagctttg ctccttcgct ttctgggctc agaggctggg 6060
aaggggtggg tccgggggcg ggctcagggg cgggctcagg ggcggggcgg gcgcccgaag 6120
gtcctccgga ggcccggcat tctgcacgct tcaaaagcgc acgtctgccg cgctgttctc 6180
ctcttcctca tctccgggcc tttcgacctg cagcagcacg tgttgacaat taatcatcgg 6240
catagtatat cggcatagta taatacgaca aggtgaggaa ctaaaccatg gagaaaaaaa 6300
tcactggata taccaccgtt gatatatccc aatggcatcg taaagaacat tttgaggcat 6360
ttcagtcagt tgctcaatgt acctataacc agaccgttca gctggatatt acggcctttt 6420
taaagaccgt aaagaaaaat aagcacaagt tttatccggc ctttattcac attcttgccc 6480
gcctgatgaa tgctcatccg gaattccgta tggcaatgaa agacggtgag ctggtgatat 6540
gggatagtgt tcacccttgt tacaccgttt tccatgagca aactgaaacg ttttcatcgc 6600
tctggagtga ataccacgac gatttccggc agtttctaca catatattcg caagatgtgg 6660
cgtgttacgg tgaaaacctg gcctatttcc ctaaagggtt tattgagaat atgtttttcg 6720
tctcagccaa tccctgggtg agtttcacca gttttgattt aaacgtggcc aatatggaca 6780
acttcttcgc ccccgttttc accatgggca aatattatac gcaaggcgac aaggtgctga 6840
tgccgctggc gattcaggtt catcatgccg tttgtgatgg cttccatgtc ggcagaatgc 6900
ttaatgaatt acaacagtac tgcgatgagt ggcagggcgg ggcgtaagcg ggactctggg 6960
gttcgaataa agaccgacca agcgacgtct gagagctccc tggcgaattc ggtaccaata 7020
aaagagcttt attttcatga tctgtgtgtt ggtttttgtg tgcggcgcgg aagttcctat 7080
tctctagaaa gtataggaac ttcctcgagc cctatagtga gtcgtattag atcgcggccg 7140
cgcccttgac aatgccacat cctgagcaaa taattcaacc actaattgtg agcggataac 7200
aaaggaggta aaaaaacatg gtatcctgtt ctgcgccggg taagatttac ctgttcggtg 7260
aacacgccgt agtttatggc gaaactgcaa ttgcgtgtgc ggtggaactg cgtacccgtg 7320
ttcgcgcgga actcaatgac tctatcacta ttcagagcca gatcggccgc accggtctgg 7380
atttcgaaaa gcacccttat gtgtctgcgg taattgagaa aatgcgcaaa tctattccta 7440
ttaacggtgt tttcttgacc gtcgattccg acatcccggt gggctccggt ctgggtagca 7500
gcgcagccgt tactatcgcg tctattggtg cgctgaacga gctgttcggc tttggcctca 7560
gcctgcaaga aatcgctaaa ctgggccacg aaatcgaaat taaagtacag ggtgccgcgt 7620
ccccaaccga tacgtatgtt tctaccttcg gcggcgtggt taccatcccg gaacgtcgca 7680
aactgaaaac tccggactgc ggcattgtga ttggcgatac cggcgttttc tcctccacca 7740
aagagttagt agctaacgta cgtcagctgc gcgaaagcta cccggatttg atcgaaccgc 7800
tgatgacctc tattggcaaa atctctcgta tcggcgaaca actggttctg tctggcgact 7860
acgcatccat cggccgcctg atgaacgtca accagggtct cctggacgcc ctgggcgtta 7920
acatcttaga actgagccag ctgatctatt ccgctcgtgc ggcaggtgcg tttggcgcta 7980
aaatcacggg cgctggcggc ggtggctgta tggttgcgct gaccgctccg gaaaaatgca 8040
accaagtggc agaagcggta gcaggcgctg gcggtaaagt gactatcact aaaccgaccg 8100
agcaaggtct gaaagtagat taa 8123

<210> SEQ ID NO 91
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 91
aagggcgagc tcaacgatcc ggctgctaac aaagcccgaa aggaagctga gttggctgct 60
gccaccgctg agcaataact agcataaccc cttggggcct ctaaacgggt cttgaggagt 120
tttttgctga aaggaggaac tatatccgga tatcccgcaa gaggcccggc agtaccggca 180
taaccaagcc tatgcctaca gcatccaggg tgacggtgcc gaggatgacg atgagcgcat 240
tgttagattt catacacggt gcctgactgc gttagcaatt taactgtgat aaactaccgc 300
attaaagctt atcgatgata agctgtcaaa catgagaatt aattcttgaa gacgaaaggg 360
cctcgtgata cgcctatttt tataggttaa tgtcatgata ataatggttt cttagacgtc 420
aggtggcact tttcggggaa atgtgcgcgg aacccctatt tgtttatttt tctaaataca 480
ttcaaatatg tatccgctca tgagacaata accctgataa atgcttcaat aatattgaaa 540
aaggaagagt atgattgaac aagatggatt gcacgcaggt tctccggccg cttgggtgga 600
gaggctattc ggctatgact gggcacaact gacaatcggc tgctctgatg ccgccgtgtt 660
ccggctgtca gcgcaggggc gcccggttct ttttgtcaag accgacctgt ccggtgccct 720
gaatgaactg caggacgagg cagcgcggct atcgtggctg gccacgacgg gcgttccttg 780
cgcagctgtg ctcgacgttg tcactgaagc gggaagggac tggctgctat tgggcgaagt 840
gccggggcag gatctcctgt catctcacct tgctcctgcc gagaaagtat ccatcatggc 900
tgatgcaatg cggcggctgc atacgcttga tccggctacc tgcccattcg accaccaagc 960
gaaacatcgc atcgagcggg cacgtactcg gatggaagcc ggtcttgtcg atcaggatga 1020
tctggacgaa gagcatcagg ggctcgcgcc agccgaactg ttcgccaggc tcaaggcgcg 1080
catgcccgac ggcgaggatc tcgtcgtgac acatggcgat gcctgcttgc cgaatatcat 1140
ggtggaaaat ggccgctttt ctggattcat cgactgtggc cggctgggtg tggcggaccg 1200
ctatcaggac atagcgttgg ctacccgtga tattgctgaa gagcttggcg gcgaatgggc 1260
tgaccgcttc ctcgtgcttt acggtatcgc cgctcccgat tcgcagcgca tcgccttcta 1320
tcgccttctt gacgagttct tctgagcggg actctggggt tcgaaatgac cgaccaagcg 1380
acgcctaact gtcagaccaa gtttactcat atatacttta gattgattta aaacttcatt 1440
tttaatttaa aaggatctag gtgaagatcc tttttgataa tctcatgacc aaaatccctt 1500
aacgtgagtt ttcgttccac tgagcgtcag accccgtaga aaagatcaaa ggatcttctt 1560

-continued

```
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
```

-continued

```
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
acaatttgcg acggcgcgtg cagggccaga ctggaggtgg caacgccaat cagcaacgac   4980
tgtttgcccg ccagttgttg tgccacgcgg ttgggaatgt aattcagctc cgccatcgcc   5040
gcttccactt tttcccgcgt tttcgcagaa acgtggctgg cctggttcac cacgcgggaa   5100
acggtctgat aagagacacc ggcatactct gcgacatcgt ataacgttac tggtttcaca   5160
ttcaccaccc tgaattgact ctcttccggg cgctatcatg ccataccgcg aaaggttttg   5220
cgccattcga tggtgtccgg gatctcgacg ctctccctta tgcgactcct gcattaggaa   5280
gcagcccagt agtaggttga ggccgttgag caccgccgcc gcaaggaatg gtgcatgcaa   5340
ggagatggcg cccaacagtc ccccggccac ggggcctgcc accataccca cgccgaaaca   5400
agcgctcatg agcccgaagt ggcgagcccg atcttcccca tcggtgatgt cggcgatata   5460
ggcgccagca accgcacctg tggcgccggt gatgccggcc acgatgcgtc cggcgtagag   5520
gatcgagatc tcgatcccgc gaaattaata cgactcacta taggggaatt gtgagcggat   5580
aacaattccc ctctagaaat aattttgttt aactttaaga aggagatata catatgaatt   5640
aaccctcact aaagggcggc cgcgaagttc ctattctcta gaaagtatag gaacttcatt   5700
ctaccgggta ggggaggcgc ttttcccaag gcagtctgga gcatgcgctt tagcagcccc   5760
gctgggcact tggcgctaca caagtggcct ctggcctcgc acacattcca catccaccgg   5820
taggcgccaa ccggctccgt tctttggtgg ccccttcgcg ccaccttcca ctcctcccct   5880
agtcaggaag ttcccccccg ccccgcagct cgcgtcgtgc aggacgtgac aaatggaagt   5940
agcacgtctc actagtctcg tgcagatgga cagcaccgct gagcaatgga agcgggtagg   6000
cctttggggc agcggccaat agcagctttg ctccttcgct ttctgggctc agaggctggg   6060
aaggggtggg tccgggggcg ggctcagggg cgggctcagg ggcggggcgg gcgcccgaag   6120
gtcctccgga ggcccggcat tctgcacgct tcaaaagcgc acgtctgccg cgctgttctc   6180
ctcttcctca tctccgggcc tttcgacctg cagcagcacg tgttgacaat taatcatcgg   6240
catagtatat cggcatagta taatacgaca aggtgaggaa ctaaaccatg gagaaaaaaa   6300
```

-continued tcactggata taccaccgtt gatatatccc aatggcatcg taaagaacat tttgaggcat 6360
ttcagtcagt tgctcaatgt acctataacc agaccgttca gctggatatt acggcctttt 6420
taaagaccgt aaagaaaaat aagcacaagt tttatccggc ctttattcac attcttgccc 6480
gcctgatgaa tgctcatccg gaattccgta tggcaatgaa agacggtgag ctggtgatat 6540
gggatagtgt tcacccttgt tacaccgttt tccatgagca aactgaaacg ttttcatcgc 6600
tctggagtga ataccacgac gatttccggc agtttctaca catatattcg caagatgtgg 6660
cgtgttacgg tgaaaacctg gcctatttcc ctaaagggtt tattgagaat atgtttttcg 6720
tctcagccaa tccctgggtg agtttcacca gttttgattt aaacgtggcc aatatggaca 6780
acttcttcgc ccccgttttc accatgggca aatattatac gcaaggcgac aaggtgctga 6840
tgccgctggc gattcaggtt catcatgccg tttgtgatgg cttccatgtc ggcagaatgc 6900
ttaatgaatt acaacagtac tgcgatgagt ggcagggcgg ggcgtaagcg ggactctggg 6960
gttcgaataa agaccgacca agcgacgtct gagagctccc tggcgaattc ggtaccaata 7020
aaagagcttt attttcatga tctgtgtgtt ggtttttgtg tgcggcgcgg aagttcctat 7080
tctctagaaa gtataggaac ttcctcgagc cctatagtga gtcgtattag atcgcggccg 7140
cgcccttgac catgccacat cctgagcaaa taattcaacc actaattgtg agcggataac 7200
aaaggaggta aaaaaacatg gtatcctgtt ctgcgccggg taagatttac ctgttcggtg 7260
aacacgccgt agtttatggc gaaactgcaa ttgcgtgtgc ggtggaactg cgtacccgtg 7320
ttcgcgcgga actcaatgac tctatcacta ttcagagcca gatcggccgc accggtctgg 7380
atttcgaaaa gcacccttat gtgtctgcgg taattgagaa aatgcgcaaa tctattccta 7440
ttaacggtgt tttcttgacc gtcgattccg acatcccggt gggctccggt ctgggtagca 7500
gcgcagccgt tactatcgcg tctattggtg cgctgaacga gctgttcggc tttggcctca 7560
gcctgcaaga aatcgctaaa ctgggccacg aaatcgaaat taaagtacag ggtgccgcgt 7620
ccccaaccga tacgtatgtt tctaccttcg gcggcgtggt taccatcccg gaacgtcgca 7680
aactgaaaac tccggactgc ggcattgtga ttggcgatac cggcgttttc tcctccacca 7740
aagagttagt agctaacgta cgtcagctgc gcgaaagcta cccggatttg atcgaaccgc 7800
tgatgacctc tattggcaaa atctctcgta tcggcgaaca actggttctg tctggcgact 7860
acgcatccat cggccgcctg atgaacgtca accagggtct cctggacgcc ctgggcgtta 7920
acatcttaga actgagccag ctgatctatt ccgctcgtgc ggcaggtgcg tttggcgcta 7980
aaatcacggg cgctggcggc ggtggctgta tggttgcgct gaccgctccg gaaaaatgca 8040
accaagtggc agaagcggta gcaggcgctg gcggtaaagt gactatcact aaaccgaccg 8100
agcaaggtct gaaagtagat taa 8123

<210> SEQ ID NO 92
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 92
aagggcgagc tcaacgatcc ggctgctaac aaagcccgaa aggaagctga gttggctgct 60
gccaccgctg agcaataact agcataaccc cttggggcct ctaaacgggt cttgaggagt 120
tttttgctga aaggaggaac tatatccgga tatcccgcaa gaggcccggc agtaccggca 180

-continued

```
taaccaagcc tatgcctaca gcatccaggg tgacggtgcc gaggatgacg atgagcgcat    240
tgttagattt catacacggt gcctgactgc gttagcaatt taactgtgat aaactaccgc    300
attaaagctt atcgatgata agctgtcaaa catgagaatt aattcttgaa gacgaaaggg    360
cctcgtgata cgcctatttt tataggttaa tgtcatgata ataatggttt cttagacgtc    420
aggtggcact tttcggggaa atgtgcgcgg aacccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
```

-continued

```
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
```

acaatttgcg acggcgcgtg cagggccaga ctggaggtgg caacgccaat cagcaacgac 4980
tgtttgcccg ccagttgttg tgccacgcgg ttgggaatgt aattcagctc cgccatcgcc 5040
gcttccactt tttcccgcgt tttcgcagaa acgtggctgg cctggttcac cacgcgggaa 5100
acggtctgat aagagacacc ggcatactct gcgacatcgt ataacgttac tggtttcaca 5160
ttcaccaccc tgaattgact ctcttccggg cgctatcatg ccataccgcg aaaggttttg 5220
cgccattcga tggtgtccgg gatctcgacg ctctccctta tgcgactcct gcattaggaa 5280
gcagcccagt agtaggttga ggccgttgag caccgccgcc gcaaggaatg gtgcatgcaa 5340
ggagatggcg cccaacagtc ccccggccac ggggcctgcc accataccca cgccgaaaca 5400
agcgctcatg agcccgaagt ggcgagcccg atcttcccca tcggtgatgt cggcgatata 5460
ggcgccagca accgcacctg tggcgccggt gatgccggcc acgatgcgtc cggcgtagag 5520
gatcgagatc tcgatcccgc gaaattaata cgactcacta taggggaatt gtgagcggat 5580
aacaattccc ctctagaaat aattttgttt aactttaaga aggagatata catatgaatt 5640
aaccctcact aaagggcggc cgcgaagttc ctattctcta gaaagtatag gaacttcatt 5700
ctaccgggta ggggaggcgc ttttcccaag gcagtctgga gcatgcgctt tagcagcccc 5760
gctgggcact tggcgctaca caagtggcct ctggcctcgc acacattcca catccaccgg 5820
taggcgccaa ccggctccgt tctttggtgg ccccttcgcg ccaccttcca ctcctcccct 5880
agtcaggaag ttcccccccg ccccgcagct cgcgtcgtgc aggacgtgac aaatggaagt 5940
agcacgtctc actagtctcg tgcagatgga cagcaccgct gagcaatgga agcgggtagg 6000
cctttggggc agcggccaat agcagctttg ctccttcgct ttctgggctc agaggctggg 6060
aaggggtggg tccgggggcg ggctcagggg cgggctcagg ggcggggcgg gcgcccgaag 6120
gtcctccgga ggcccggcat tctgcacgct tcaaaagcgc acgtctgccg cgctgttctc 6180
ctcttcctca tctccgggcc tttcgacctg cagcagcacg tgttgacaat taatcatcgg 6240
catagtatat cggcatagta taatacgaca aggtgaggaa ctaaaccatg gagaaaaaaa 6300
tcactggata taccaccgtt gatatatccc aatggcatcg taaagaacat tttgaggcat 6360
ttcagtcagt tgctcaatgt acctataacc agaccgttca gctggatatt acggcctttt 6420
taaagaccgt aaagaaaaat aagcacaagt tttatccggc ctttattcac attcttgccc 6480
gcctgatgaa tgctcatccg gaattccgta tggcaatgaa agacggtgag ctggtgatat 6540
gggatagtgt tcacccttgt tacaccgttt tccatgagca aactgaaacg ttttcatcgc 6600
tctggagtga ataccacgac gatttccggc agtttctaca catatattcg caagatgtgg 6660
cgtgttacgg tgaaaacctg gcctatttcc ctaaagggtt tattgagaat atgtttttcg 6720
tctcagccaa tccctgggtg agtttcacca gttttgattt aaacgtggcc aatatggaca 6780
acttcttcgc ccccgttttc accatgggca aatattatac gcaaggcgac aaggtgctga 6840
tgccgctggc gattcaggtt catcatgccg tttgtgatgg cttccatgtc ggcagaatgc 6900
ttaatgaatt acaacagtac tgcgatgagt ggcagggcgg ggcgtaagcg ggactctggg 6960
gttcgaataa agaccgacca agcgacgtct gagagctccc tggcgaattc ggtaccaata 7020
aaagagcttt attttcatga tctgtgtgtt ggtttttgtg tgcggcgcgg aagttcctat 7080
tctctagaaa gtataggaac ttcctcgagc cctatagtga gtcgtattag atcgcggccg 7140
cgcccttgac gatgccacat cctgagcaaa taattcaacc actaattgtg agcggataac 7200
aaaggaggta aaaaaacatg gtatcctgtt ctgcgccggg taagatttac ctgttcggtg 7260
aacacgccgt agtttatggc gaaactgcaa ttgcgtgtgc ggtggaactg cgtacccgtg 7320
ttcgcgcgga actcaatgac tctatcacta ttcagagcca gatcggccgc accggtctgg 7380
atttcgaaaa gcacccttat gtgtctgcgg taattgagaa aatgcgcaaa tctattccta 7440
ttaacggtgt tttcttgacc gtcgattccg acatcccggt gggctccggt ctgggtagca 7500
gcgcagccgt tactatcgcg tctattggtg cgctgaacga gctgttcggc tttggcctca 7560
gcctgcaaga aatcgctaaa ctgggccacg aaatcgaaat taaagtacag ggtgccgcgt 7620
ccccaaccga tacgtatgtt tctaccttcg gcggcgtggt taccatcccg gaacgtcgca 7680
aactgaaaac tccggactgc ggcattgtga ttggcgatac cggcgttttc tcctccacca 7740
aagagttagt agctaacgta cgtcagctgc gcgaaagcta cccggatttg atcgaaccgc 7800
tgatgacctc tattggcaaa atctctcgta tcggcgaaca actggttctg tctggcgact 7860
acgcatccat cggccgcctg atgaacgtca accagggtct cctggacgcc ctgggcgtta 7920
acatcttaga actgagccag ctgatctatt ccgctcgtgc ggcaggtgcg tttggcgcta 7980
aaatcacggg cgctggcggc ggtggctgta tggttgcgct gaccgctccg gaaaaatgca 8040
accaagtggc agaagcggta gcaggcgctg gcggtaaagt gactatcact aaaccgaccg 8100
agcaaggtct gaaagtagat taa 8123

<210> SEQ ID NO 93
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 93
aagggcgagc tcaacgatcc ggctgctaac aaagcccgaa aggaagctga gttggctgct 60
gccaccgctg agcaataact agcataaccc cttggggcct ctaaacgggt cttgaggagt 120
tttttgctga aaggaggaac tatatccgga tatcccgcaa gaggcccggc agtaccggca 180
taaccaagcc tatgcctaca gcatccaggg tgacggtgcc gaggatgacg atgagcgcat 240
tgttagattt catacacggt gcctgactgc gttagcaatt taactgtgat aaactaccgc 300
attaaagctt atcgatgata agctgtcaaa catgagaatt aattcttgaa gacgaaaggg 360
cctcgtgata cgcctatttt tataggttaa tgtcatgata ataatggttt cttagacgtc 420
aggtggcact tttcggggaa atgtgcgcgg aacccctatt tgtttatttt tctaaataca 480
ttcaaatatg tatccgctca tgagacaata accctgataa atgcttcaat aatattgaaa 540
aaggaagagt atgattgaac aagatggatt gcacgcaggt tctccggccg cttgggtgga 600
gaggctattc ggctatgact gggcacaact gacaatcggc tgctctgatg ccgccgtgtt 660
ccggctgtca gcgcaggggc gcccggttct ttttgtcaag accgacctgt ccggtgccct 720
gaatgaactg caggacgagg cagcgcggct atcgtggctg gccacgacgg gcgttccttg 780
cgcagctgtg ctcgacgttg tcactgaagc gggaagggac tggctgctat tgggcgaagt 840
gccggggcag gatctcctgt catctcacct tgctcctgcc gagaaagtat ccatcatggc 900
tgatgcaatg cggcggctgc atacgcttga tccggctacc tgcccattcg accaccaagc 960
gaaacatcgc atcgagcggg cacgtactcg gatggaagcc ggtcttgtcg atcaggatga 1020
tctggacgaa gagcatcagg ggctcgcgcc agccgaactg ttcgccaggc tcaaggcgcg 1080
catgcccgac ggcgaggatc tcgtcgtgac acatggcgat gcctgcttgc cgaatatcat 1140
ggtggaaaat ggccgctttt ctggattcat cgactgtggc cggctgggtg tggcggaccg 1200

-continued

```
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
```

-continued ggtcgtcatc tacctgcctg gacagcatgg cctgcaacgc gggcatcccg atgccgccgg 3660
aagcgagaag aatcataatg gggaaggcca tccagcctcg cgtcgcgaac gccagcaaga 3720
cgtagcccag cgcgtcggcc gccatgccgg cgataatggc ctgcttctcg ccgaaacgtt 3780
tggtggcggg accagtgacg aaggcttgag cgagggcgtg caagattccg aataccgcaa 3840
gcgacaggcc gatcatcgtc gcgctccagc gaaagcggtc ctcgccgaaa atgacccaga 3900
gcgctgccgg cacctgtcct acgagttgca tgataaagaa gacagtcata agtgcggcga 3960
cgatagtcat gccccgcgcc caccggaagg agctgactgg gttgaaggct ctcaagggca 4020
tcggtcgaga tcccggtgcc taatgagtga gctaacttac attaattgcg ttgcgctcac 4080
tgcccgcttt ccagtcggga aacctgtcgt gccagctgca ttaatgaatc ggccaacgcg 4140
cggggagagg cggtttgcgt attgggcgcc agggtggttt ttcttttcac cagtgagacg 4200
ggcaacagct gattgccctt caccgcctgg ccctgagaga gttgcagcaa gcggtccacg 4260
ctggtttgcc ccagcaggcg aaaatcctgt ttgatggtgg ttaacggcgg gatataacat 4320
gagctgtctt cggtatcgtc gtatcccact accgagatat ccgcaccaac gcgcagcccg 4380
gactcggtaa tggcgcgcat tgcgcccagc gccatctgat cgttggcaac cagcatcgca 4440
gtgggaacga tgccctcatt cagcatttgc atggtttgtt gaaaaccgga catggcactc 4500
cagtcgcctt cccgttccgc tatcggctga atttgattgc gagtgagata tttatgccag 4560
ccagccagac gcagacgcgc cgagacagaa cttaatgggc ccgctaacag cgcgatttgc 4620
tggtgaccca atgcgaccag atgctccacg cccagtcgcg taccgtcttc atgggagaaa 4680
ataatactgt tgatgggtgt ctggtcagag acatcaagaa ataacgccgg aacattagtg 4740
caggcagctt ccacagcaat ggcatcctgg tcatccagcg gatagttaat gatcagccca 4800
ctgacgcgtt gcgcgagaag attgtgcacc gccgctttac aggcttcgac gccgcttcgt 4860
tctaccatcg acaccaccac gctggcaccc agttgatcgg cgcgagattt aatcgccgcg 4920
acaatttgcg acggcgcgtg cagggccaga ctggaggtgg caacgccaat cagcaacgac 4980
tgtttgcccg ccagttgttg tgccacgcgg ttgggaatgt aattcagctc cgccatcgcc 5040
gcttccactt tttcccgcgt tttcgcagaa acgtggctgg cctggttcac cacgcgggaa 5100
acggtctgat aagagacacc ggcatactct gcgacatcgt ataacgttac tggtttcaca 5160
ttcaccaccc tgaattgact ctcttccggg cgctatcatg ccataccgcg aaaggttttg 5220
cgccattcga tggtgtccgg gatctcgacg ctctccctta tgcgactcct gcattaggaa 5280
gcagcccagt agtaggttga ggccgttgag caccgccgcc gcaaggaatg gtgcatgcaa 5340
ggagatggcg cccaacagtc ccccggccac ggggcctgcc accataccca cgccgaaaca 5400
agcgctcatg agcccgaagt ggcgagcccg atcttcccca tcggtgatgt cggcgatata 5460
ggcgccagca accgcacctg tggcgccggt gatgccggcc acgatgcgtc cggcgtagag 5520
gatcgagatc tcgatcccgc gaaattaata cgactcacta taggggaatt gtgagcggat 5580
aacaattccc ctctagaaat aattttgttt aactttaaga aggagatata catatgaatt 5640
aaccctcact aaagggcggc cgcgaagttc ctattctcta gaaagtatag gaacttcatt 5700
ctaccgggta ggggaggcgc ttttcccaag gcagtctgga gcatgcgctt tagcagcccc 5760
gctgggcact tggcgctaca caagtggcct ctggcctcgc acacattcca catccaccgg 5820
taggcgccaa ccggctccgt tctttggtgg ccccttcgcg ccaccttcca ctcctcccct 5880
agtcaggaag ttcccccccg ccccgcagct cgcgtcgtgc aggacgtgac aaatggaagt 5940
agcacgtctc actagtctcg tgcagatgga cagcaccgct gagcaatgga agcgggtagg 6000
cctttggggc agcggccaat agcagctttg ctccttcgct ttctgggctc agaggctggg 6060
aaggggtggg tccgggggcg ggctcagggg cgggctcagg ggcggggcgg gcgcccgaag 6120
gtcctccgga ggcccggcat tctgcacgct tcaaaagcgc acgtctgccg cgctgttctc 6180
ctcttcctca tctccgggcc tttcgacctg cagcagcacg tgttgacaat taatcatcgg 6240
catagtatat cggcatagta taatacgaca aggtgaggaa ctaaaccatg gagaaaaaaa 6300
tcactggata taccaccgtt gatatatccc aatggcatcg taaagaacat tttgaggcat 6360
ttcagtcagt tgctcaatgt acctataacc agaccgttca gctggatatt acggcctttt 6420
taaagaccgt aaagaaaaat aagcacaagt tttatccggc ctttattcac attcttgccc 6480
gcctgatgaa tgctcatccg gaattccgta tggcaatgaa agacggtgag ctggtgatat 6540
gggatagtgt tcacccttgt tacaccgttt tccatgagca aactgaaacg ttttcatcgc 6600
tctggagtga ataccacgac gatttccggc agtttctaca catatattcg caagatgtgg 6660
cgtgttacgg tgaaaacctg gcctatttcc ctaaagggtt tattgagaat atgtttttcg 6720
tctcagccaa tccctgggtg agtttcacca gttttgattt aaacgtggcc aatatggaca 6780
acttcttcgc ccccgttttc accatgggca aatattatac gcaaggcgac aaggtgctga 6840
tgccgctggc gattcaggtt catcatgccg tttgtgatgg cttccatgtc ggcagaatgc 6900
ttaatgaatt acaacagtac tgcgatgagt ggcagggcgg ggcgtaagcg ggactctggg 6960
gttcgaataa agaccgacca agcgacgtct gagagctccc tggcgaattc ggtaccaata 7020
aaagagcttt attttcatga tctgtgtgtt ggtttttgtg tgcggcgcgg aagttcctat 7080
tctctagaaa gtataggaac ttcctcgagc cctatagtga gtcgtattag atcgcggccg 7140
cgcccttgac tatgccacat cctgagcaaa taattcaacc actaattgtg agcggataac 7200
aaaggaggta aaaaaacatg gtatcctgtt ctgcgccggg taagatttac ctgttcggtg 7260
aacacgccgt agtttatggc gaaactgcaa ttgcgtgtgc ggtggaactg cgtacccgtg 7320
ttcgcgcgga actcaatgac tctatcacta ttcagagcca gatcggccgc accggtctgg 7380
atttcgaaaa gcacccttat gtgtctgcgg taattgagaa aatgcgcaaa tctattccta 7440
ttaacggtgt tttcttgacc gtcgattccg acatcccggt gggctccggt ctgggtagca 7500
gcgcagccgt tactatcgcg tctattggtg cgctgaacga gctgttcggc tttggcctca 7560
gcctgcaaga aatcgctaaa ctgggccacg aaatcgaaat taaagtacag ggtgccgcgt 7620
ccccaaccga tacgtatgtt tctaccttcg gcggcgtggt taccatcccg gaacgtcgca 7680
aactgaaaac tccggactgc ggcattgtga ttggcgatac cggcgttttc tcctccacca 7740
aagagttagt agctaacgta cgtcagctgc gcgaaagcta cccggatttg atcgaaccgc 7800
tgatgacctc tattggcaaa atctctcgta tcggcgaaca actggttctg tctggcgact 7860
acgcatccat cggccgcctg atgaacgtca accagggtct cctggacgcc ctgggcgtta 7920
acatcttaga actgagccag ctgatctatt ccgctcgtgc ggcaggtgcg tttggcgcta 7980
aaatcacggg cgctggcggc ggtggctgta tggttgcgct gaccgctccg gaaaaatgca 8040
accaagtggc agaagcggta gcaggcgctg gcggtaaagt gactatcact aaaccgaccg 8100
agcaaggtct gaaagtagat taa 8123

<210> SEQ ID NO 94
<211> LENGTH: 19
<212> TYPE: DNA
<213> ORGANISM: Artificial Sequence
<220> FEATURE:
<223> OTHER INFORMATION: Synthetic Construct

<400> SEQUENCE: 94
accaattgca cccggcaga 19

<210> SEQ ID NO 95
<211> LENGTH: 21
<212> TYPE: DNA
<213> ORGANISM: Artificial Sequence
<220> FEATURE:
<223> OTHER INFORMATION: Synthetic Construct

<400> SEQUENCE: 95
gctaaagcgc atgctccaga c 21

<210> SEQ ID NO 96
<211> LENGTH: 20
<212> TYPE: DNA
<213> ORGANISM: Artificial Sequence
<220> FEATURE:
<223> OTHER INFORMATION: Synthetic Construct

<400> SEQUENCE: 96
gactggcctc agatgaaagc 20

<210> SEQ ID NO 97
<211> LENGTH: 20
<212> TYPE: DNA
<213> ORGANISM: Artificial Sequence
<220> FEATURE:
<223> OTHER INFORMATION: Synthetic Construct

<400> SEQUENCE: 97
caaacatgtg gcatggaaag 20

<210> SEQ ID NO 98
<211> LENGTH: 52
<212> TYPE: DNA
<213> ORGANISM: Artificial Sequence
<220> FEATURE:
<223> OTHER INFORMATION: Synthetic Construct

<400> SEQUENCE: 98
gggcccgttt aaactttaac tagactctgc agttagcgtt caaacggcag aa 52

<210> SEQ ID NO 99
<211> LENGTH: 38
<212> TYPE: DNA
<213> ORGANISM: Artificial Sequence
<220> FEATURE:
<223> OTHER INFORMATION: Synthetic Construct

<400> SEQUENCE: 99
cgcatgcatg tcatgagatg tagcgtgtcc accgaaaa 38

<210> SEQ ID NO 100
<211> LENGTH: 22
<212> TYPE: DNA
<213> ORGANISM: Artificial Sequence
<220> FEATURE:
<223> OTHER INFORMATION: Synthetic Construct

<400> SEQUENCE: 100
acaatttcac acaggaaaca gc 22

<210> SEQ ID NO 101
<211> LENGTH: 23
<212> TYPE: DNA
<213> ORGANISM: Artificial Sequence
<220> FEATURE:
<223> OTHER INFORMATION: Synthetic Construct

<400> SEQUENCE: 101
ccaggcaaat tctgttttat cag 23

<210> SEQ ID NO 102
<211> LENGTH: 22
<212> TYPE: DNA
<213> ORGANISM: Artificial Sequence
<220> FEATURE:
<223> OTHER INFORMATION: Synthetic Construct

<400> SEQUENCE: 102
gcactgtctt tccgtctgct gc 22

<210> SEQ ID NO 103
<211> LENGTH: 66
<212> TYPE: DNA
<213> ORGANISM: Artificial Sequence
<220> FEATURE:
<223> OTHER INFORMATION: Synthetic Construct

<400> SEQUENCE: 103
gcgaacgatg cataaaggag gtaaaaaaac atggtatcct gttctgcgcc gggtaagatt 60
tacctg 66

<210> SEQ ID NO 104
<211> LENGTH: 48
<212> TYPE: DNA
<213> ORGANISM: Artificial Sequence
<220> FEATURE:
<223> OTHER INFORMATION: Synthetic Construct

<400> SEQUENCE: 104
gggcccgttt aaactttaac tagactttaa tctactttca gaccttgc 48

<210> SEQ ID NO 105
<211> LENGTH: 24
<212> TYPE: DNA
<213> ORGANISM: Artificial Sequence
<220> FEATURE:
<223> OTHER INFORMATION: Synthetic Construct

<400> SEQUENCE: 105
gatagtaacg gctgcgctgc tacc 24

<210> SEQ ID NO 106
<211> LENGTH: 23
<212> TYPE: DNA
<213> ORGANISM: Artificial Sequence
<220> FEATURE:
<223> OTHER INFORMATION: Synthetic Construct

<400> SEQUENCE: 106
gacagcttat catcgactgc acg 23

<210> SEQ ID NO 107
<211> LENGTH: 22
<212> TYPE: DNA
<213> ORGANISM: Artificial Sequence
<220> FEATURE:
<223> OTHER INFORMATION: Synthetic Construct

<400> SEQUENCE: 107
caccatggta tcctgttctg cg 22

<210> SEQ ID NO 108
<211> LENGTH: 22
<212> TYPE: DNA
<213> ORGANISM: Artificial Sequence
<220> FEATURE:
<223> OTHER INFORMATION: Synthetic Construct

<400> SEQUENCE: 108
ttaatctact ttcagacctt gc 22

<210> SEQ ID NO 109
<211> LENGTH: 81
<212> TYPE: DNA
<213> ORGANISM: Artificial Sequence
<220> FEATURE:
<223> OTHER INFORMATION: Synthetic Construct

<400> SEQUENCE: 109
aaagtagccg aagatgacgg tttgtcacat ggagttggca ggatgtttga ttaaaagcaa 60
ttaaccctca ctaaagggcg g 81

<210> SEQ ID NO 110
<211> LENGTH: 31
<212> TYPE: DNA
<213> ORGANISM: Artificial Sequence
<220> FEATURE:
<223> OTHER INFORMATION: Synthetic Construct

<400> SEQUENCE: 110
gatatacata tgaattaacc ctcactaaag g 31

<210> SEQ ID NO 111
<211> LENGTH: 125
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 80
<223> OTHER INFORMATION: n = A,T,C or G

<400> SEQUENCE: 111
gcatgcatga catgtttttt tacctccttt gttatccgct cacaattagt ggttgaatta 60
tttgctcagg atgtggcatn gtcaagggcg cggccgcgat ctaatacgac tcactatagg 120
gctcg 125

<210> SEQ ID NO 112
<211> LENGTH: 87
<212> TYPE: DNA
<213> ORGANISM: Artificial Sequence
<220> FEATURE:
<223> OTHER INFORMATION: Synthetic Construct

<400> SEQUENCE: 112
aggctctcaa ctctgacatg tttttttcct ccttaagggt gcaggcctat cgcaaattag 60
cttaatctac tttcagacct tgctcgg 87

<210> SEQ ID NO 113
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 113
gcggccgcgc ccttgacgat gccacatcct gagcaaataa ttcaaccact aattgtgagc 60
ggataacaca aggaggaaac agccatggta tcctgttctg cgccgggtaa gatttacctg 120
ttcggtgaac acgccgtagt ttatggcgaa actgcaattg cgtgtgcggt ggaactgcgt 180
acccgtgttc gcgcggaact caatgactct atcactattc agagccagat cggccgcacc 240
ggtctggatt tcgaaaagca cccttatgtg tctgcggtaa ttgagaaaat gcgcaaatct 300
attcctatta acggtgtttt cttgaccgtc gattccgaca tcccggtggg ctccggtctg 360
ggtagcagcg cagccgttac tatcgcgtct attggtgcgc tgaacgagct gttcggcttt 420
ggcctcagcc tgcaagaaat cgctaaactg ggccacgaaa tcgaaattaa agtacagggt 480
gccgcgtccc caaccgatac gtatgtttct accttcggcg gcgtggttac catcccggaa 540
cgtcgcaaac tgaaaactcc ggactgcggc attgtgattg gcgataccgg cgttttctcc 600
tccaccaaag agttagtagc taacgtacgt cagctgcgcg aaagctaccc ggatttgatc 660
gaaccgctga tgacctctat tggcaaaatc tctcgtatcg gcgaacaact ggttctgtct 720
ggcgactacg catccatcgg ccgcctgatg aacgtcaacc agggtctcct ggacgccctg 780
ggcgttaaca tcttagaact gagccagctg atctattccg ctcgtgcggc aggtgcgttt 840
ggcgctaaaa tcacgggcgc tggcggcggt ggctgtatgg ttgcgctgac cgctccggaa 900
aaatgcaacc aagtggcaga agcggtagca ggcgctggcg gtaaagtgac tatcactaaa 960
ccgaccgagc aaggtctgaa agtagattaa gccttgactt aatagctgct tatttcgccc 1020
ttatggtacc tagtaggagg aaaaaaacat ggaaatgcgt caaccggctg tcgcaggtca 1080
attctaccca ctgcgttgcg agaacctgga aaacgaactg aaacgctgct tcgaaggcct 1140
ggagatccgc gaacaagaag tgctgggcgc agtctgtccg cacgccggtt atatgtactc 1200
tggcaaagtt gcggcgcacg tctatgccac tctgccggaa gctgatacct acgtaatctt 1260
cggcccgaac cacaccggct acggtagccc tgtctctgtg agccgtgaaa cttggaagac 1320
cccgttgggc aatatcgatg ttgacctgga actggcggac ggcttcctgg gttccatcgt 1380
agatgcggat gaactcggtc acaaatacga acactctatc gaagttcagc tgccgtttct 1440
gcaataccgt tttgaacgcg atttcaaaat tctgccaatc tgcatgggta tgcaagacga 1500
agaaaccgcg gtcgaagtag gtaacctgct ggcggatctg atcagcgagt ccggtaaacg 1560
tgctgtgatc atcgcaagct ctgatttcac ccactatgag acggctgaac gtgccaaaga 1620
aatcgattcc gaagttattg attctatcct gaactttgac atctctggca tgtacgatcg 1680
cctgtatcgc cgtaacgcct ctgtttgcgg ttacggcccg atcaccgcta tgctgacggc 1740
aagcaaaaag ctgggcggct ctcgtgcgac tttgctgaaa tacgcaaaca gcggtgacgt 1800
gtccggtgat aaagacgctg tggtgggcta cgccgccatc atcgttgagt aagctgatta 1860
aaggttgaac agataggatt tcgtcatgga tcctacaagg aggaaaaaaa catgaatgct 1920
tctaatgaac cggtgattct gaaactgggt ggctctgcta ttaccgacaa aggtgcctac 1980
gaaggcgtag ttaaggaagc tgatttgctg cgcatcgcac aggaagttag cggtttccgt 2040
ggcaagatga tcgtggttca tggtgctggt agcttcggcc atacgtacgc gaagaaatac 2100
ggcctggacc gtaccttcga cccagagggc gcaattgtta ctcatgaatc tgttaaaaag 2160
ctcgcctcca aagttgtagg tgctctgaat agcttcggcg tgcgtgctat cgcggtgcat 2220
cctatggact gcgcagtatg ccgtaacggt cgtatcgaaa cgatgtatct ggactccatc 2280
aagttaatgc tggaaaaagg tctggtgccg gttctgcacg gcgacgtcgc aatggatatt 2340
gaactgggca cttgtatcct gtccggtgat caaatcgttc cttacctggc caaagaactg 2400
ggtatctccc gcctcggcct gggcagcgca gaggatggtg tgctggatat ggagggcaaa 2460
cctgtaccgg aaatcacccc agaaactttc gaagagttcc gccactgcat cggtggttct 2520
ggttctactg atgtaaccgg tggcatgctg ggcaaagtgc tggaacttct ggaattgagc 2580
aaaaattctt ccattactag ctacattttc aacgctggta aagcagacaa catctaccgc 2640
tttctgaatg gtgagtccat cggcactcgc atcagcccgg acaagcgtgt ttaagctagt 2700
tattaaccta aatgctctaa accagttatg agctctacaa ggaggaaaaa aacatgatta 2760
acactaccag ccgccgcaaa attgaacacc tgaaactctg cgcagaatcc ccggttgaag 2820
cgcgtcaggt atctgccggc tttgaagacg ttactctgat ccaccgcgct ttaccggagc 2880
tgaacatgga tgaactggac ctcagcgttg atttcctggg taaacgcatc aaagcgccgt 2940
tcctgattgc gtctatcacg ggtggtcacc cagataccat cccggttaac gctgcgctgg 3000
cagctgctgc tgaggagctg ggtgttggca tcggcgttgg ctctcagcgc gcggccattg 3060
atgatccgag ccaggaagac agcttccgtg tagtgcgtga tgaagcccca gatgcgtttg 3120
tttatggcaa cgtcggcgca gcacagatcc gtcagtatgg tgttgaaggt gttgaaaaac 3180
tgatcgaaat gattgacgca gatgccttgg caatccacct gaactttctg caagaagcgg 3240
tccaaccgga aggtgaccgc gacgcgaccg gttgcctgga catgattacc gaaatttgct 3300
ctcagattaa aactccggta atcgtgaaag aaaccggtgc aggcattagc cgtgaagatg 3360
cgattctgtt ccagaaagct ggcgtgagcg caatcgacgt tggcggcgcg ggcggcacct 3420
cctgggctgg cgtcgaggtc taccgtgcta aagaaagccg tgactctgtt agcgagcgtt 3480
taggtgagct gttttgggat ttcggcattc cgacggtagc ttctctgatt gaatcccgcg 3540
tttccttgcc gctgatcgca accggcggta tccgtaacgg tctggacatt gctaaaagca 3600
ttgctctcgg cgcaagcgct gccagcgccg ctctgccgtt cgttggtccg tccctggagg 3660
gcaaagaatc cgttgtacgt gtgctgagct gcatgctgga agaatttaaa gcagcaatgt 3720
ttttgtgcgg ttgcggcaac atcaaagacc tgcacaactc tccagtagtg gtaactggtt 3780
ggacccgcga atacctggag cagcgcggtt ttaacgttaa ggacctctcc ctgccgggca 3840
acgctctgta agcttcaacg cgtctacaaa taaaaaaggc acgtcagatg acgtgccttt 3900
tttcttgtct aga 3913

<210> SEQ ID NO 114
<211> LENGTH: 6648
<212> TYPE: DNA
<213> ORGANISM: Artificial Sequence
<220> FEATURE:
<223> OTHER INFORMATION: Synthetic Construct

<400> SEQUENCE: 114
aagggcgagc tcaacgatcc ggctgctaac aaagcccgaa aggaagctga gttggctgct 60
gccaccgctg agcaataact agcataaccc cttggggcct ctaaacgggt cttgaggagt 120
tttttgctga aaggaggaac tatatccgga tatcccgcaa gaggcccggc agtaccggca 180

-continued

```
taaccaagcc tatgcctaca gcatccaggg tgacggtgcc gaggatgacg atgagcgcat    240
tgttagattt catacacggt gcctgactgc gttagcaatt taactgtgat aaactaccgc    300
attaaagctt atcgatgata agctgtcaaa catgagaatt aattcttgaa gacgaaaggg    360
cctcgtgata cgcctatttt tataggttaa tgtcatgata ataatggttt cttagacgtc    420
aggtggcact tttcggggaa atgtgcgcgg aacccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
```

-continued

```
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
```

acaatttgcg acggcgcgtg cagggccaga ctggaggtgg caacgccaat cagcaacgac 4980
tgtttgcccg ccagttgttg tgccacgcgg ttgggaatgt aattcagctc cgccatcgcc 5040
gcttccactt tttcccgcgt tttcgcagaa acgtggctgg cctggttcac cacgcgggaa 5100
acggtctgat aagagacacc ggcatactct gcgacatcgt ataacgttac tggtttcaca 5160
ttcaccaccc tgaattgact ctcttccggg cgctatcatg ccataccgcg aaaggttttg 5220
cgccattcga tggtgtccgg gatctcgacg ctctccctta tgcgactcct gcattaggaa 5280
gcagcccagt agtaggttga ggccgttgag caccgccgcc gcaaggaatg gtgcatgcaa 5340
ggagatggcg cccaacagtc ccccggccac ggggcctgcc accataccca cgccgaaaca 5400
agcgctcatg agcccgaagt ggcgagcccg atcttcccca tcggtgatgt cggcgatata 5460
ggcgccagca accgcacctg tggcgccggt gatgccggcc acgatgcgtc cggcgtagag 5520
gatcgagatc tcgatcccgc gaaattaata cgactcacta taggggaatt gtgagcggat 5580
aacaattccc ctctagaaat aattttgttt aactttaaga aggagatata catatgcggg 5640
gttctcatca tcatcatcat catggtatgg ctagcatgac tggtggacag caaatgggtc 5700
gggatctgta cgacgatgac gataaggatc atcccttcac catggtatcc tgttctgcgc 5760
cgggtaagat ttacctgttc ggtgaacacg ccgtagttta tggcgaaact gcaattgcgt 5820
gtgcggtgga actgcgtacc cgtgttcgcg cggaactcaa tgactctatc actattcaga 5880
gccagatcgg ccgcaccggt ctggatttcg aaaagcaccc ttatgtgtct gcggtaattg 5940
agaaaatgcg caaatctatt cctattaacg gtgttttctt gaccgtcgat tccgacatcc 6000
cggtgggctc cggtctgggt agcagcgcag ccgttactat cgcgtctatt ggtgcgctga 6060
acgagctgtt cggctttggc ctcagcctgc aagaaatcgc taaactgggc cacgaaatcg 6120
aaattaaagt acagggtgcc gcgtccccaa ccgatacgta tgtttctacc ttcggcggcg 6180
tggttaccat cccggaacgt cgcaaactga aaactccgga ctgcggcatt gtgattggcg 6240
ataccggcgt tttctcctcc accaaagagt tagtagctaa cgtacgtcag ctgcgcgaaa 6300
gctacccgga tttgatcgaa ccgctgatga cctctattgg caaaatctct cgtatcggcg 6360
aacaactggt tctgttctgg cgactacgca tccatcggcc gcctgatgaa cgtcaaccag 6420
ggtctcctgg acgccctggg cgttaacatc ttagaactga gccagctgat ctattccgct 6480
cgtgcggcag gtgcgtttgg cgctaaaatc acgggcgctg gcggcggtgg ctgtatggtt 6540
gcgctgaccg ctccggaaaa atgcaaccaa gtggcagaag cggtagcagg cgctggcggt 6600
aaagtgacta tcactaaacc gaccgagcaa ggtctgaaag tagattaa 6648

<210> SEQ ID NO 115
<211> LENGTH: 67
<212> TYPE: DNA
<213> ORGANISM: Artificial Sequence
<220> FEATURE:
<223> OTHER INFORMATION: Synthetic Construct

<400> SEQUENCE: 115
accgccaaaa gcgactaatt ttagctgtta cagtcagttg aattaaccct cactaaaggg 60
cggccgc 67

<210> SEQ ID NO 116
<211> LENGTH: 152
<212> TYPE: DNA
<213> ORGANISM: Artificial Sequence
<220> FEATURE:
<223> OTHER INFORMATION: Synthetic Construct

<400> SEQUENCE: 116
gctggcgata taaactgttt gcttcatgaa tgctcctttg ggttacctcc gggaaacgcg 60
gttgatttgt ttagtggttg aattatttgc tcaggatgtg gcatagtcaa gggcgtgacg 120
gctcgctaat acgactcact atagggctcg ag 152

<210> SEQ ID NO 117
<211> LENGTH: 30
<212> TYPE: DNA
<213> ORGANISM: Artificial Sequence
<220> FEATURE:
<223> OTHER INFORMATION: Synthetic Construct

<400> SEQUENCE: 117
cttgatatct tagtgtgcgt taaccaccac 30

<210> SEQ ID NO 118
<211> LENGTH: 21
<212> TYPE: DNA
<213> ORGANISM: Artificial Sequence
<220> FEATURE:
<223> OTHER INFORMATION: Synthetic Construct

<400> SEQUENCE: 118
cgtgaatttg ctggctctca g 21

<210> SEQ ID NO 119
<211> LENGTH: 21
<212> TYPE: DNA
<213> ORGANISM: Artificial Sequence
<220> FEATURE:
<223> OTHER INFORMATION: Synthetic Construct

<400> SEQUENCE: 119
ggtttagttc ctcaccttgt c 21

<210> SEQ ID NO 120
<211> LENGTH: 21
<212> TYPE: DNA
<213> ORGANISM: Artificial Sequence
<220> FEATURE:
<223> OTHER INFORMATION: Synthetic Construct

<400> SEQUENCE: 120
actgaaacgt tttcatcgct c 21

<210> SEQ ID NO 121
<211> LENGTH: 26
<212> TYPE: DNA
<213> ORGANISM: Artificial Sequence
<220> FEATURE:
<223> OTHER INFORMATION: Synthetic Construct

<400> SEQUENCE: 121
accgccaaaa gcgactaatt ttagct 26

<210> SEQ ID NO 122
<211> LENGTH: 7519
<212> TYPE: DNA
<213> ORGANISM: Artificial Sequence
<220> FEATURE:
<223> OTHER INFORMATION: Synthetic Construct

<400> SEQUENCE: 122

-continued

```
ctcgggccgt ctcttgggct tgatcggcct tcttgcgcat ctcacgcgct cctgcggcgg     60
cctgtagggc aggctcatac ccctgccgaa ccgcttttgt cagccggtcg gccacggctt    120
ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg ccccgttgca    300
gccctagatc ggccacagcg gccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctggcagc aactcgcgca gtcggcccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg gacaagctga   1080
tggacaggct gcgcctgccc acgagcttga ccacagggat tgcccaccgg ctacccagcc   1140
ttcgaccaca tacccaccgg ctccaactgc gcggcctgcg gccttgcccc atcaattttt   1200
ttaattttct ctggggaaaa gcctccggcc tgcggcctgc gcgcttcgct tgccggttgg   1260
acaccaagtg gaaggcgggt caaggctcgc gcagcgaccg cgcagcggct tggccttgac   1320
gcgcctggaa cgacccaagc ctatgcgagt gggggcagtc gaaggcgaag cccgcccgcc   1380
tgccccccga gcctcacggc ggcgagtgcg gggggttccaa gggggcagcg ccaccttggg   1440
caaggccgaa ggccgcgcag tcgatcaaca agccccggag gggccacttt ttgccggagg   1500
gggagccgcg ccgaaggcgt gggggaaccc cgcaggggtg cccttctttg ggcaccaaag   1560
aactagatat agggcgaaat gcgaaagact taaaaatcaa caacttaaaa aagggggggta   1620
cgcaacagct cattgcggca ccccccgcaa tagctcattg cgtaggttaa agaaaatctg   1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacggcgcg ggcagcagcg cctgccgatg cccgatgagc cgtgttttct   2400
```

ggacgatggc gagccgttgg agccgccgac acgggtcacg ctgccgcgcc ggtagcactt 2460
gggttgcgca gcaacccgta agtgcgctgt tccagactat cggctgtagc cgcctcgccg 2520
ccctatacct tgtctgcctc cccgcgttgc gtcgcggtgc atggagccgg gccacctcga 2580
cctgaatgga agccggcggc acctcgctaa cggattcacc gtttttatca ggctctggga 2640
ggcagaataa atgatcatat cgtcaattat tacctccacg gggagagcct gagcaaactg 2700
gcctcaggca tttgagaagc acacggtcac actgcttccg gtagtcaata aaccggtaaa 2760
ccagcaatag acataagcgg ctatttaacg accctgccct gaaccgacga ccgggtcgaa 2820
tttgctttcg aatttctgcc attcatccgc ttattatcac ttattcaggc gtagcaccag 2880
gcgtttaagg gcaccaataa ctgccttaaa aaaattacgc cccgccctgc cactcatcgc 2940
agtcggccta ttggttaaaa aatgagctga tttaacaaaa atttaacgcg aattttaaca 3000
aaatattaac gcttacaatt tccattcgcc attcaggctg cgcaactgtt gggaagggcg 3060
atcggtgcgg gcctcttcgc tattacgcca gctggcgaaa gggggatgtg ctgcaaggcg 3120
attaagttgg gtaacgccag ggttttccca gtcacgacgt tgtaaaacga cggccagtga 3180
gcgcgcgtaa tacgactcac tatagggcga attggagctc caccgcggtg gcggccgctc 3240
tagaactagt ggatcccccg ggctgcatgc tcgagcggcc gccagtgtga tggatatctg 3300
cagaattcgc ccttcttgat atcttagtgt gcgttaacca ccacccacat tggtccctgc 3360
ccgaccgcat agcggccttt ttcatgcagt agcccctgct cgccaacaat ttcgtatacc 3420
gagatgtggt gagatttttg cccggcggca atcagatact tgccgctgtg atcaacattg 3480
aagccgcgcg gctgggtttc cgttggctgg aagccttctt tactcaacac gctgccatct 3540
tccgaaacgc tgaaaacggt aatcaggctg gcggtacggt cgcaggcgta taaatggcga 3600
ccatccgggg tgatatgaat atcagccgcc caacgggtgt cggagaagtt ttccggcatc 3660
atatccagcg tctggacaca ttcgatatta ccgtgcggat ctttcagttc ccagacatcc 3720
actgagctgt ttaactcatt gacgcaatac gcatattgtt cgtttggatg gaataccata 3780
tgacgcgggc cggccccttc aacggtggtc acttccgcag ggtcctgcgc cacgagatga 3840
ccatcatcgc tgaccgtaaa caggcaaatg cgatcctgct ttaatgccgg aacccacagc 3900
gtacggttgt ccggtgagat attggcggaa tggcaaccgt ccagcccctc gaccacatcg 3960
acgacgccca ctggcaggcc atcttccaga cgcgttacgc tcacgttacc cgcattgtaa 4020
gaacctacaa agacaaactg cccctggtga tcggtggaaa tatgcgtcgg actacccggc 4080
agcgcagact ctgcggcaaa ggtcagtgcg ccatcgtccg ggcgatacgg atacgccagg 4140
acgcgaaact cagggcgaac accaacatag agataacgtt tgtccgggct gaccaccatc 4200
ggctgcacct gccccggcac atcgacaacc tgtgtcagcg tcagtgcgcc ttcatgattc 4260
agattccaga cgtgaatttg ctggctctca gggctggcga tataaactgt ttgcttcatg 4320
aatgctcctt tgggttacct ccgggaaacg cggttgattt gtttagtggt tgaattattt 4380
gctcaggatg tggcatagtc aagggcgtga cggctcgcta atacaactca ctatagggct 4440
cgaggaagtt cctatacttt ctagagaata ggaacttccg cgccgcacac aaaaaccaac 4500
acacagatca tgaaaataaa gctcttttat tggtaccgaa ttcgccaggg agctctcaga 4560
cgtcgcttgg tcggtcttta ttcgaacccc agagtcccgc ttacgccccg ccctgccact 4620
catcgcagta ctgttgtaat tcattaagca ttctgccgac atggaagcca tcacaaacgg 4680
catgatgaac ctgaatcgcc agcggcatca gcaccttgtc gccttgcgta taatatttgc 4740

-continued

```
ccatggtgaa aacgggggcg aagaagttgt ccatattggc cacgtttaaa tcaaaactgg   4800
tgaaactcac ccagggattg gctgagacga aaaacatatt ctcaataaac cctttaggga   4860
aataggccag gttttcaccg taacacgcca catcttgcga atatatgtgt agaaactgcc   4920
ggaaatcgtc gtggtattca ctccagagcg atgaaaacgt ttcagtttgc tcatggaaaa   4980
cggtgtaaca agggtgaaca ctatcccata tcaccagctc accgtctttc attgccatac   5040
ggaattccgg atgagcattc atcaggcggg caagaatgtg aataaaggcc ggataaaact   5100
tgtgcttatt tttctttacg gtctttaaaa aggccgtaat atccagctga acggtctggt   5160
tataggtaca ttgagcaact gactgaaatg cctcaaaatg ttctttacga tgccattggg   5220
atatatcaac ggtggtatat ccagtgattt ttttctccat ggtttagttc ctcaccttgt   5280
cgtattatac tatgccgata tactatgccg atgattaatt gtcaacacgt gctgctgcag   5340
gtcgaaaggc ccggagatga ggaagaggag aacagcgcgg cagacgtgcg cttttgaagc   5400
gtgcagaatg ccgggcctcc ggaggacctt cgggcgcccg ccccgcccct gagcccgccc   5460
ctgagcccgc ccccggaccc accccttccc agcctctgag cccagaaagc gaaggagcaa   5520
agctgctatt ggccgctgcc ccaaaggcct acccgcttcc attgctcagc ggtgctgtcc   5580
atctgcacga gactagtgag acgtgctact tccatttgtc acgtcctgca cgacgcgagc   5640
tgcggggcgg gggggaactt cctgactagg ggaggagtgg aaggtggcgc gaaggggcca   5700
ccaaagaacg gagccggttg gcgcctaccg gtggatgtgg aatgtgtgcg aggccagagg   5760
ccacttgtgt agcgccaagt gcccagcggg gctgctaaag cgcatgctcc agactgcctt   5820
gggaaaagcg cctcccctac ccggtagaat gaagttccta tactttctag agaataggaa   5880
cttcgcggcc gccctttagt gagggttaat tcaactgact gtaacagcta aaattagtcg   5940
cttttggcgg taagggcgaa ttccagcaca ctggcggccg ttactagtgg atccgagctc   6000
ggtaccaagc ttgatgcagg aattcgatat caagcttatc gataccgtcg acctcgaggg   6060
ggggcccggt acccagcttt tgttcccttt agtgagggtt aattgcgcgc ttggcgtaat   6120
catggtcata gctgtttcct gtgtgaaatt gttatccgct cacaattcca cacaacatac   6180
gagccggaag cataaagtgt aaagcctggg gtgcctaatg agtgagctaa ctcacattaa   6240
ttgcgttgcg ctcactgccc gctttccagt cgggaaacct gtcgtgccag ctgcattaat   6300
gaatcggcca acgcgcgggg agaggcggtt tgcgtattgg gcgcatgcat aaaaactgtt   6360
gtaattcatt aagcattctg ccgacatgga agccatcaca aacggcatga tgaacctgaa   6420
tcgccagcgg catcagcacc ttgtcgcctt gcgtataata tttgcccatg gacgcacacc   6480
gtggaaacgg atgaaggcac gaacccagtt gacataagcc tgttcggttc gtaaactgta   6540
atgcaagtag cgtatgcgct cacgcaactg gtccagaacc ttgaccgaac gcagcggtgg   6600
taacggcgca gtggcggttt tcatggcttg ttatgactgt ttttttgtac agtctatgcc   6660
tcgggcatcc aagcagcaag cgcgttacgc cgtgggtcga tgtttgatgt tatggagcag   6720
caacgatgtt acgcagcagc aacgatgtta cgcagcaggg cagtcgccct aaaacaaagt   6780
taggtggctc aagtatgggc atcattcgca catgtaggct cggccctgac caagtcaaat   6840
ccatgcgggc tgctcttgat cttttcggtc gtgagttcgg agacgtagcc acctactccc   6900
aacatcagcc ggactccgat tacctcggga acttgctccg tagtaagaca ttcatcgcgc   6960
ttgctgcctt cgaccaagaa gcggttgttg gcgctctcgc ggcttacgtt ctgcccaggt   7020
ttgagcagcc gcgtagtgag atctatatct atgatctcgc agtctccggc gagcaccgga   7080
ggcagggcat tgccaccgcg ctcatcaatc tcctcaagca tgaggccaac gcgcttggtg   7140
```

```
cttatgtgat ctacgtgcaa gcagattacg gtgacgatcc cgcagtggct ctctatacaa   7200

agttgggcat acgggaagaa gtgatgcact ttgatatcga cccaagtacc gccacctaac   7260

aattcgttca agccgagatc ggcttcccgg ccgcggagtt gttcggtaaa ttgtcacaac   7320

gccgccaggt ggcacttttc ggggaaatgt gcgcgcccgc gttcctgctg gcgctgggcc   7380

tgtttctggc gctggacttc ccgctgttcc gtcagcagct tttcgcccac ggccttgatg   7440

atcgcggcgg ccttggcctg catatcccga ttcaacggcc ccagggcgtc cagaacgggc   7500

ttcaggcgct cccgaaggt                                                 7519
```

<210> SEQ ID NO 123
<211> LENGTH: 4395
<212> TYPE: DNA
<213> ORGANISM: Artificial Sequence
<220> FEATURE:
<223> OTHER INFORMATION: Synthetic Construct

<400> SEQUENCE: 123

```
tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240

gaatccggtg agaatggcaa aagtttatgc atttctttcc agacttgttc aacaggccag    300

ccattacgct cgtcatcaaa atcactcgca tcaaccaaac cgttattcat tcgtgattgc    360

gcctgagcga ggcgaaatac gcgatcgctg ttaaaaggac aattacaaac aggaatcgag    420

tgcaaccggc gcaggaacac tgccagcgca tcaacaatat tttcacctga atcaggatat    480

tcttctaata cctggaacgc tgtttttccg gggatcgcag tggtgagtaa ccatgcatca    540

tcaggagtac ggataaaatg cttgatggtc ggaagtggca taaattccgt cagccagttt    600

agtctgacca tctcatctgt aacatcattg gcaacgctac ctttgccatg tttcagaaac    660

aactctggcg catcgggctt cccatacaag cgatagattg tcgcacctga ttgcccgaca    720

ttatcgcgag cccatttata cccatataaa tcagcatcca tgttggaatt taatcgcggc    780

ctcgacgttt cccgttgaat atggctcata ttcttccttt ttcaatatta ttgaagcatt    840

tatcagggtt attgtctcat gagcggatac atatttgaat gtatttagaa aaataaacaa    900

ataggggtca gtgttacaac caattaacca attctgaaca ttatcgcgag cccatttata    960

cctgaatatg gctcataaca ccccttgttt gcctggcggc agtagcgcgg tggtcccacc   1020

tgaccccatg ccgaactcag aagtgaaacg ccgtagcgcc gatggtagtg tggggactcc   1080

ccatgcgaga gtagggaact gccaggcatc aaataaaacg aaaggctcag tcgaaagact   1140

gggcctttcg cccgggctaa ttagggggtg tcgcccttcg attgacggtt acgggatcct   1200

cacacgtaca tcagctggtt gatggggaac gggtcgatga gcagcagctt gatgcggttc   1260

tcggtggcgt aatccgggcg gcccagcccg tccccatatt ggtaggtgca gtggctcacg   1320

cgggccatgt tcacggcgat ctccatgaac gccttcggca gcagggtgct gtccgacacg   1380

cgctcgcggt tcattttctt ccactcggcg tcgatcagct tgcgcagctc ttcgcgggcc   1440

tgttcctcgc tcgtgccgtc gttctcgtgc atgtagctga tgatgctgtt ggtggtttcg   1500

ccgcgttcga gttccgccgc cgaggtcgcc agatcgttgc acagccgaaa gatcacgcag   1560

gacgagcgca ccaggccgtg gaagtcggtc agggagcgga gggcgtggtc cgagatatct   1620
```

```
tcctgctgct ggcagaccga gaagtagctc ggcgccagca gcgcgacccc gctggaggac   1680
acgctggcgt tctccaggta cttgctgaag gcggggatga tcttgttatt gctccacttg   1740
gcttcttgca ggaaggcctt gcacagttcg cgccagcttt tggtcagata gctcaggtta   1800
ttgtggccct tctccttcag gatggagtag gacgtgtcgt tcacggtgtt gtacagggcc   1860
aggaagcaca gcttcatata gtcgggcagc gtgttgatgg cgttcacgtc ccagcgttcc   1920
accgcgtcgg tgaagagctg cagttcgtcc agggtaccgt acacgtcata gacgtcatcg   1980
ataatggtga ccagaccgaa catcttggtg acggccttgc ggcattcgcc gaactgcggg   2040
tccggcgcca tgcccagcgc ccagaagtac acttccatca ggcggtcccg cacgaaatcc   2100
agcttgctgg cgaggcccat ctcggtccac caccggctca ggtcctgcag ctctttttgg   2160
tgcagggtct ggaccatgtt gaaatcgagt ttggccagtt ccagcagcag ctggtgatgc   2220
ggctccttgg gttcgtactt gtccagaaac caccgcgcct ccaggcggtg caggcgttga   2280
tgatacggca gctccagcgc gtgggacacc tgctcggcca ccttcgtgtt gatcccctcc   2340
ttgaggttgt tcttcagatg ggtgatgctg aaggtacggg cctcctccag cagattttcg   2400
ccttcgaaac cgagatagct ggcctcgtac aggctcagca ggccctgcac gtcacccttc   2460
agttccccgg agaagccccc ttctttgtcc ttgaagcgct cgaacacgtc ctggctcacc   2520
tcaaagccat gctgccgcag caggcggaag ctcagggcgg tcgcgtgcag atcgcttttg   2580
ttcttcttat tctcgtccag caggacgatg ttctccagcg ccttgatgat atctttctca   2640
aacttgtagg tcaggcccag gcgctgcacg tcgtcgatga gctccagcag gctcaggggc   2700
tgggtgtcca cccggttgat catgcaacgc acctcctcct ccagcttggt ggccttctct   2760
tcgagcttct ccaccttcag gtcgttttcc aggctctgca ggaactcgaa gttccacagg   2820
ttgggctggt agttcgcgga ccgacggcta ttatgctcgg tgatctgggt gaactggctg   2880
ctggtggcgc acatatgtat atctccttct taaagttaaa caagcttaag atgttcagcg   2940
acaagggcga cacaaaattt attctaaatg cataataaat actgataaca tcttatagtt   3000
tgtattatat tttgtattat cgttgacatg tataattttg atatcaaaaa ctgattttcc   3060
ctttattatt ttcgagattt attttcttaa ttctctttaa caaactagaa atattgtata   3120
tacaaaaaat cataaataat agatgaatag tttaattata ggtgttcatc aatcgaaaaa   3180
gcaacgtatc ttatttaaag tgcgttgctt ttttctcatt tataaggtta aataattctc   3240
atatatcaag caaagtgaca ggcgccctta aatattctga caaatgctct ttccctaaac   3300
tccccccata aaaaaacccg ccgaagcggg tttttacgtt atttgcggat taacgattac   3360
tcgttatcag aaccgcccag ggggcccgag cttaagactg gccgtcgttt tacaacacag   3420
aaagagtttg tagaaacgca aaaaggccat ccgtcagggg ccttctgctt agtttgatgc   3480
ctggcagttc cctactctcg ccttccgctt cctcgctcac tgactcgctg cgctcggtcg   3540
ttcggctgcg gcgagcggta tcagctcact caaaggcggt aatacggtta tccacagaat   3600
caggggataa cgcaggaaag aacatgtgag caaaaggcca gcaaaaggcc aggaaccgta   3660
aaaaggccgc gttgctggcg tttttccata ggctccgccc ccctgacgag catcacaaaa   3720
atcgacgctc aagtcagagg tggcgaaacc cgacaggact ataaagatac caggcgtttc   3780
cccctggaag ctccctcgtg cgctctcctg ttccgaccct gccgcttacc ggatacctgt   3840
ccgcctttct cccttcggga agcgtggcgc tttctcatag ctcacgctgt aggtatctca   3900
gttcggtgta ggtcgttcgc tccaagctgg gctgtgtgca cgaacccccc gttcagcccg   3960
accgctgcgc cttatccggt aactatcgtc ttgagtccaa cccggtaaga cacgacttat   4020
```

-continued

```
cgccactggc agcagccact ggtaacagga ttagcagagc gaggtatgta ggcggtgcta    4080

cagagttctt gaagtggtgg gctaactacg gctacactag aagaacagta tttggtatct    4140

gcgctctgct gaagccagtt accttcggaa aaagagttgg tagctcttga tccggcaaac    4200

aaaccaccgc tggtagcggt ggtttttttg tttgcaagca gcagattacg cgcagaaaaa    4260

aaggatctca agaagatcct ttgatctttt ctacggggtc tgacgctcag tggaacgacg    4320

cgcgcgtaac tcacgttaag ggattttggt catgagcttg cgccgtcccg tcaagtcagc    4380

gtaatgctct gcttt                                                     4395
```